(12) United States Patent
Barbero Calzado et al.

(10) Patent No.: US 12,214,033 B2
(45) Date of Patent: *Feb. 4, 2025

(54) VIRUS PURIFICATION

(71) Applicant: Valneva SE, Nantes (FR)

(72) Inventors: Jana Barbero Calzado, Vienna (AT); Mario Nebenführ, Vienna (AT); Robert Schlegl, Siegenfield (AT); Michael Weber, Vienna (AT); Jürgen Heindl-Wruss, Vienna (AT)

(73) Assignee: Valneva SE, Nantes (FR)

( * ) Notice: Subject to any disclaimer, the term of this patent is extended or adjusted under 35 U.S.C. 154(b) by 0 days.

This patent is subject to a terminal disclaimer.

(21) Appl. No.: 17/811,059

(22) Filed: Jul. 6, 2022

(65) Prior Publication Data

US 2023/0056142 A1    Feb. 23, 2023

Related U.S. Application Data

(63) Continuation of application No. 16/840,760, filed on Apr. 6, 2020, now Pat. No. 11,406,700, which is a continuation of application No. 15/781,959, filed as application No. PCT/EP2016/082663 on Dec. 23, 2016, now Pat. No. 10,660,950.

(30) Foreign Application Priority Data

| Dec. 23, 2015 | (EP) | .................................... | 15202585 |
| Mar. 18, 2016 | (EP) | .................................... | 16161068 |
| Jun. 23, 2016 | (EP) | .................................... | 16176025 |
| Jun. 23, 2016 | (EP) | .................................... | 16176049 |
| Aug. 4, 2016 | (EP) | .................................... | 16182845 |

(51) Int. Cl.
| A61K 39/12 | (2006.01) |
| A61K 39/39 | (2006.01) |
| A61P 31/14 | (2006.01) |
| C07K 14/18 | (2006.01) |
| C12N 7/00 | (2006.01) |
| C12N 7/02 | (2006.01) |
| C12N 7/06 | (2006.01) |
| A61K 39/00 | (2006.01) |

(52) U.S. Cl.
CPC ............. *A61K 39/12* (2013.01); *A61K 39/39* (2013.01); *A61P 31/14* (2018.01); *C07K 14/18* (2013.01); *C07K 14/1825* (2013.01); *C12N 7/00* (2013.01); *C12N 7/02* (2013.01); *C12N 7/06* (2013.01); *A61K 2039/5252* (2013.01); *A61K 2039/5254* (2013.01); *A61K 2039/5258* (2013.01); *A61K 2039/55505* (2013.01); *C12N 2770/24134* (2013.01); *C12N 2770/24151* (2013.01); *C12N 2770/24163* (2013.01); *Y02A 50/30* (2018.01)

(58) Field of Classification Search
CPC .... A61K 2039/5252; A61K 2039/5254; A61K 2039/5258; A61K 39/12; A61K 2039/55505; A61K 39/39; A61P 31/14; C12N 2770/36151; C12N 7/02; C12N 7/06; C12N 2770/24151; C12N 2770/24163; C12N 7/00; C12N 2770/24134; Y02A 50/30; C07K 14/1825; C07K 14/18

See application file for complete search history.

(56) References Cited

U.S. PATENT DOCUMENTS

| 6,309,650 | B1 | 10/2001 | Kim et al. |
| 7,871,814 | B2 | 1/2011 | Andino-Pavlovsky et al. |
| 8,765,148 | B2 | 7/2014 | Wizel et al. |
| 8,865,184 | B2 | 10/2014 | Ella et al. |
| 9,353,353 | B2 | 5/2016 | Nabel et al. |
| 9,499,588 | B2 | 11/2016 | Mason et al. |
| 10,086,061 | B2 | 10/2018 | Thomas et al. |
| 10,537,630 | B2* | 1/2020 | Barbero Calzado ... A61K 39/12 |
| 10,660,950 | B2* | 5/2020 | Barbero Calzado ... A61K 39/12 |
| 10,744,194 | B2* | 8/2020 | Barbero Calzado ... C07K 14/18 |
| 11,207,397 | B2* | 12/2021 | Barbero Calzado .... A61P 31/14 |
| 11,357,846 | B2 | 6/2022 | Fritzer et al. |
| 11,406,700 | B2* | 8/2022 | Barbero Calzado ... A61K 39/39 |
| 11,484,587 | B2 | 11/2022 | Fritzer et al. |
| 11,524,064 | B2* | 12/2022 | Barbero Calzado ..... C12N 7/00 |
| 2011/0171249 | A1 | 7/2011 | Frolov et al. |
| 2012/0003266 | A1 | 1/2012 | Nabel et al. |
| 2018/0362936 | A1 | 12/2018 | Barbero Calzado et al. |
| 2018/0362937 | A1 | 12/2018 | Barbero Calzado et al. |
| 2018/0369359 | A1 | 12/2018 | Barbero Calzado et al. |
| 2018/0371027 | A1 | 12/2018 | Barbero Calzado et al. |
| 2019/0008945 | A1 | 1/2019 | Barbero Calzado et al. |
| 2020/0197506 | A1 | 6/2020 | Barbero Calzado et al. |
| 2020/0368342 | A1 | 11/2020 | Barbero Calzado et al. |

(Continued)

FOREIGN PATENT DOCUMENTS

| CN | 105749268 A | 7/2016 |
| WO | WO 1999/011762 A1 | 3/1999 |

(Continued)

OTHER PUBLICATIONS

[No Author Listed], Centers for Disease Control and Prevention. Ingredients of vaccines fact sheet; continuously updated; https://www.cdc.gov/vaccines/vac-gen/additives.htm.

[No Author Listed], Japanese Encephalitis Vaccine. Centers for Disease Control and Prevention, 2016. Retrieved from https://www.cdc.gov/japaneseencephalitis/vaccine/ on Jun. 16, 2016.

[No Author Listed], Pan-American Health Organization, 2015. Number of Reported Cases of Chikungunya Fever in the Americas, by Country or Territory 2013-2014. Cumulative Cases (Updated Oct. 23, 2015).

[No Author Listed], Protamine sulfate. Wikimedia Foundation, Inc., 2015. Retrieved from https://en.wikipedia.org/wiki/Protamine_sulfate; updated Sep. 30, 2015 on Nov. 26, 2015.

(Continued)

*Primary Examiner* — Bao Q Li

(74) *Attorney, Agent, or Firm* — Wolf, Greenfield & Sacks, P.C.

(57) ABSTRACT

Described herein are processes for purifying infectious virus particles and uses of protamine in such processes.

14 Claims, 35 Drawing Sheets

Specification includes a Sequence Listing.

(56) References Cited

U.S. PATENT DOCUMENTS

| | | |
|---|---|---|
| 2021/0322534 A1 | 10/2021 | Fritzer et al. |
| 2022/0016230 A1 | 1/2022 | Fritzer et al. |
| 2023/0226165 A1 | 7/2023 | Calzado et al. |

FOREIGN PATENT DOCUMENTS

| | | |
|---|---|---|
| WO | WO 2001/092552 A2 | 12/2001 |
| WO | WO 2008/026225 A2 | 3/2008 |
| WO | WO 2010/062396 A2 | 6/2010 |
| WO | WO 2013/083726 A1 | 6/2013 |
| WO | WO 2016/145149 A1 | 9/2016 |
| WO | WO 2017/109225 A1 | 6/2017 |

OTHER PUBLICATIONS

[No Author Listed], Valneva Reports Excellent Final Phase 1 Results for its Chikungunya Vaccine Candidate, Confirms Plans. Press release. Nov. 18, 2019.

[No Author Listed], World Health Organization, 2016 Zika Situation Report Feb. 5, 2016.

[No Author Listed], World Health Organization, 2016 Zika Virus Fact Sheet 2016. Retrieved from http://www.who.int/mediacentre/factsheets/zika/en/ on Mar. 11, 2016.

[No Author Listed], Zika virus, strain H/PF/2013. European virus archive, 2016.

[No Author Listed], Valneva Announces Successful Generation of a Highly-purified Zika Vaccine Candidate Using its FDA-EMA Approved Japanese Encephalitis Platform. Press release. Jul. 7, 2016.

[No. Author Listed], Valneva Reports Further Positive Results for Its Chikungunya Vaccine Candidate. Saint Herblain, France. May 2, 20192. 4 pages.

[No Author Listed], Valneva Reports Positive Phase 1 Interim Results for Its Chikungunya Vaccine Candidate. Saint Herblain, France. Jan. 7, 2019. 4 pages.

Abbink et al., Durability and correlates of vaccine protection against Zika virus in rhesus monkeys. Sci. Transl. Med. 2017;9:eaao4163.

Altschul et al., Basic Local Alignment Search Tool. J. Mol. Biol. 1990;215:403-410.

Altschul et al., Gapped BLAST and PSI-BLAST: a new generation of protein database search programs. Nuc. Acids Res. 1997;25(17):3389-3402.

Anez et al, Passage of dengue virus type 4 vaccine candidates in fetal rhesus lung cells selects heparin-sensitive variants that result in loss of infectivity and immunogenicity in rhesus macaques. J Virol. Oct. 2009;83(20):10384-94. doi: 10.1128/JVI.01083-09. Epub Aug. 5, 2009.

Athmaram et al., A two step purification strategy for Chikungunya virions purification using sucrose buoyant density gradient separation. J Virology Res. 2013;2(1):18-21.

Aubry et al., Inactivation of Zika virus in plasma with amotosalen and ultraviolet A illumination. Transfusion. Jan. 2016;56(1):33-40. doi: 10.1111/trf.13271. Epub Aug. 18, 2015.

Baronti et al., Complete Coding Sequence of Zika Virus from a French Polynesia Outbreak in 2013. Genome Announc. May-Jun. 2014; 2(3):e00500-14. Abstract.

Bender et al., Zika Virus Vaccine Candidate VLA1601: Cooperation VALNEVA & EMERGENT. Presentation at World Vaccine Congress Apr. 4, 2018.

Bender, Chikungunya Virus Vaccine Candidate Valneva's VLA1553. World Vaccine Conference 2019. Washington, D.C . . . Apr. 16, 2019. 43 pages.

Chroboczek et al., Virus-like particles as vaccine. Acta Biochim Pol. 2014;61(3):531-9. Epub Sep. 18, 2014.

Cohen, Infectious Disease. The race for a Zika vaccine is on. Science. Feb. 5, 2016;351(6273):543-4. doi: 10.1126/science.351.6273.543.

Cox et al., Predicting Zika virus structural biology: Challenges and opportunities for intervention. Antivir Chem Chemother. Aug. 2015;24(3-4):118-26. doi: 10.1177/2040206616653873. Epub Jun. 13, 2016.

Dowall et al., A susceptible mouse model for Zika virus infection. PLOS Neglected Tropical Diseases.10(5):e0004658. May 5, 2016. DOI:10.1371/journal.pntd.0004658.

Eckels et al., Chikungunya virus vaccine prepared by Tween-ether extraction. Appl Microbiol. Feb. 1970;19(2):321-5.

Edelman et al., Phase II safety and immunogenicity study of live chikungunya virus vaccine TSI-GSD-218. Am J Trop Med Hyg. Jun. 2000;62(6):681-5. doi: 10.4269/ajtmh.2000.62.681.

Fritsche et al., Vaccine hypersensitivity—update and overview. Swiss Med Wkly. 2010;140(17-18):238-246.

Garcia-Arriaza et al., A novel poxvirus-based vaccine, MVA-CHIKV, is highly immunogenic and protects mice against chikungunya infection. J Virol. Mar. 2014;88(6):3527-47. doi: 10.1128/JVI.03418-13. Epub Jan. 8, 2014.

Gardner et al., Deliberate Attenuation of Chikungunya Virus by Adaptation to Heparan Sulfate-Dependent Infectivity: A Model of Rational Arboviral Vaccine Design. PLOS Neglected Tropical Diseases. 2014;8(2):e2719.
Geradin et al., Chikungunya virus-associated encephalitis: A cohort study on La Réunion Island. 2005-2009. Neurology. 86(1):94-102.
Gubler et al., Fields Virology. Knipe DM, Howley PM, editors. Lippincott-Raven Publishers; Philadelphia: 2007:1153-1252.
Haddow et al., Genetic Characterization of Zika Virus Strains: Geographic Expansion of the Asian Lineage. PLoS Negl Trop Dis 6(2): e1477. doi:10.1371/journal.pntd.0001477.
Hallengard et al., Novel Attenuated Chikungunya Vaccine Candidates Elicit Protective Immunity in C57BL/6 mice. J. Virology 88(5):2858-2866.
Hallengard et al., Prime-Boost Immunization Strategies against Chikungunya Virus. J. Virology. 88(22):13333-13343.
Hombach et al., Report on a WHO consultation on immunological endpoints for evaluation of new Japanese encephalitis vaccines, WHO, Geneva, Sep. 2-3, 2004. Vaccine. 2005; 23(45):5205-5211.
Hutornojs et al., Comparison of ultracentrifugation methods for concentration of recombinant alphaviruses: sucrose and iodixanol cushions. Environmental Experimental Biology. 2012;10:117-123.
Katoh et al., Recent developments in the MAFFT multiple sequence alignment program. Briefings in Bioinformatics. 2008;9(4):286-298.
Kim et al., Design of Chimeric Alphaviruses with a Programmed, Attenuated, Cell Type-Restricted Phenotype. J Virol. 2011;85(9):4363-4376.
Konishi et al., Studies on structural proteins of Chikungunya Virus. I. Separation of three species of proteins and their preliminary characterization. Microbiol Immunol. 1980;24(5):419-28.
Larkin et al., Clustal W and Clustal X version 2.0. Bioinformatics. 2007;23(21):2947-2948.
Larocca et al., Vaccine protection against Zika virus from Brazil. Nature. 2016;536:474-478. doi:10.1038/nature18952. Methods.
Liljestrom et al., A new generation of animal cell expression vectors based on the Semliki Forest virus replicon. Biotechnology (N Y). Dec. 1991;9(12):1356-61. doi: 10.1038/nbt1291-1356.
Lindenbach et al., Fields Virology. Knipe DM, Howley PM, editors. Lippincott-Raven Publishers; Philadelphia: 2007;1101-1152.
Malone et al., Zika Virus: Medical Countermeasure Development Challenges. PLoS Negl Trop Dis. 2016;10(3):e0004530. doi:10.1371/journal.pntd.0004530.
Modjarrad et al., Preliminary aggregate safety and immunogenicity results from three trials of a purified inactivated Zika virus vaccine candidate: phase 1, randomised, double-blind, placebo-controlled clinical trials. Dec. 4, 2017.
Monath, Yellow fever: an update. Lancet Infect Dis. 2001;1(1):11-20.
Needleman et al., A general method applicable to the search for similarities in the amino acid sequence of two proteins. J. Mol. Biol. 1970;48(3):443-453.
Patkar et al., Yellow Fever virus NS3 plays an essential role in virus assembly independent of its known enzymatic functions. J Virol. Apr. 2008;82(7):3342-52. doi: 10.1128/JVI.02447-07. Epub Jan. 16, 2008.
Pearson et al., Improved tools for biological sequence comparison. Proc. Natl. Acad. Sci. USA. 1988;85(8):2444-8.

(56) References Cited

OTHER PUBLICATIONS

Pellerin, Walter Reed Scientists Test Zika Vaccine Candidate. U.S. Department of Defense. Jun. 9, 2016.

Pinto et al., A Temporal Role of Type I Interferon Signaling in CD8+ T Cell Maturation during Acute West Nile Virus Infection. PLoS Pathog. Dec. 2011;7(12):e1002407.

Plevka et al., Maturation of flaviviruses starts from one or more icosahedrally independent nucleation centres. EMBO reports. 2011;12(6):602-606.

Pohjala et al., Inhibitors of alphavirus entry and replication identified with a stable Chikungunya replicon cell line and virus-based assays. PLoS One. 2011;6(12):e28923. doi: 10.1371/journal.pone. 0028923. Epub Dec. 19, 2011. 13 pages.

Powers et al., Re-emergence of Chikungunya and O'nyong-nyong viruses: evidence for distinct geographical lineages and distant evolutionary relationships. J Gen Virol. Feb. 2000;81(Pt 2):471-9. doi: 10.1099/0022-1317-81-2-471.

Reed et al., A simple method of estimating fifty percent endpoints. American J Hygiene. May 1938;27:493-497.

Rocha et al., Microcephaly: normality parameters and its determinants in northeastern Brazil: a multicentre prospective cohort study. Bull World Health Organ, E-pub: Feb. 8, 2016. doi:http://dx.doi.org/10.2471/BLT.16.171215.

Roques et al., Attenuated and vectored vaccines protect nonhuman primates against Chikungunya virus. JCI Insight. Mar. 23, 2017;2(6):e83527. doi: 10.1172/jci.insight.83527.

Rozen-Gagnon et al., Alphavirus Mutator Variants Present Host-Specific Defects and Attenuation in Mammalian and Insect Models, PLOS Pathogens, 10(1):e1003877.

Schlegl et al., Influence of elemental impurities in aluminum hydroxide adjuvant on the stability of inactivated Japanese Encephalitis vaccine, IXIARO®. Vaccine. 2015;33(44):5989-5996.

Shustov et al., Efficient, trans-complementing packaging systems for chimeric, pseudoinfectious dengue 2/yellow fever viruses. Virology. Apr. 25, 2010;400(1):8-17. doi: 10.1016/j.virol.2009.12.015.

Simizu et al., Structural Proteins of Chikungunya Virus, J Virol. 1984;51(1): 254-258.

Smith et al., Comparison of Biosequences. Adv. Appl. Math. 1981;2:482-489.

Srivastava et al., A purified inactivated Japanese encephalitis virus vaccine made in vero cells. Vaccine. 2001;19:4557-4565.

Tiwari et al., Assessment of immunogenic potential of Vero adapted formalin inactivated vaccine derived from novel ECSA genotype of Chikungunya virus. Vaccine. Apr. 21, 2009;27(18):2513-22. doi: 10.1016/j.vaccine.2009.02.062. Epub Feb. 27, 2009.

Vega-Rua et al., Chikungunya Virus Transmission Potential by Local Aedes Mosquitoes in the Americas and Europe. PLOS Neglected Tropical Diseases. 2015;9(5):e0003780.

Waterhouse et al., Jalview Version 2—a multiple sequence alignment editor and analysis workbench. Bioinformatics. 2009;25(9):1189-1191.

Way et al., Comparative Studies of some African Arboviruses in Cell Culture and in Mice, J Gen. Virol. 1976;30:123-130.

Weaver, Arrival of Chikungunya Virus in the New Word: Prospects for Spread and Impact on Public Health. PLoS Negl Trop Dis. 2014;8(6):e2921. doi:10.1371/journal.pntd.0002921.

No Author Listed, Valneva Reports Positive 24-Month Antibody Persistence Data for its Single-Shot Chikungunya Vaccine IXCHIQ®. VALNEVA SE. Dec. 4, 2023. 5 pages.

U.S. Appl. No. 17/935,490, filed Sep. 26, 2022, Fritzer et al.

PCT/EP2016/082662, Jul. 5, 2018, International Preliminary Report and Patentability.

PCT/EP2016/082662, Apr. 18, 2017, International Search Report and Written Opinion.

PCT/EP2016/082663, Jul. 5, 2018, International Preliminary Report and Patentability.

PCT/EP2016/082663, Apr. 19, 2017, International Search Report and Written Opinion.

PCT/EP2016/075392, Nov. 20, 2018, International Preliminary Report and Patentability.

PCT/EP2016/075392, Apr. 2, 2020, International Search Report and Written Opinion.

\* cited by examiner

TEV_virus.NC_001672.1
YFV_ASIBI.AY640589.1
YFV_17D_vaccine_strain.NC_002031.1
YFV_virus_isol-Pasteur_17D-204_yellow_fever_vaccine.X15062.1
YFV_vaccine_strain_17D-213.U17067.1
JEV_SA14.D90194.1
JEV_virus.M55506.1
JEV_SA14-14-2.AF315119.1
JEV_SA14-14-2.D90195.1
JEV_virus.NC_001437.1
WNV_956.NC_001563.2
WNV_NY99_isol-385-99.NC_009942.1
WNV_Chin-01.AY490240.2
ZVV_MR766-NIID.LC002520.1
ZVV_MR_766.NC_012532.1
ZVV_MR_766.AY632535.2
ZVV_ZikaSPH2015.KU321639.1
DVV_1.NC_001477.1
DVV_3_isol-D3%H%IMTSSA-SRI%2000%1266.NC_001475.2
DVV_16681.NC_001474.2
DVV_4.NC_002640.1

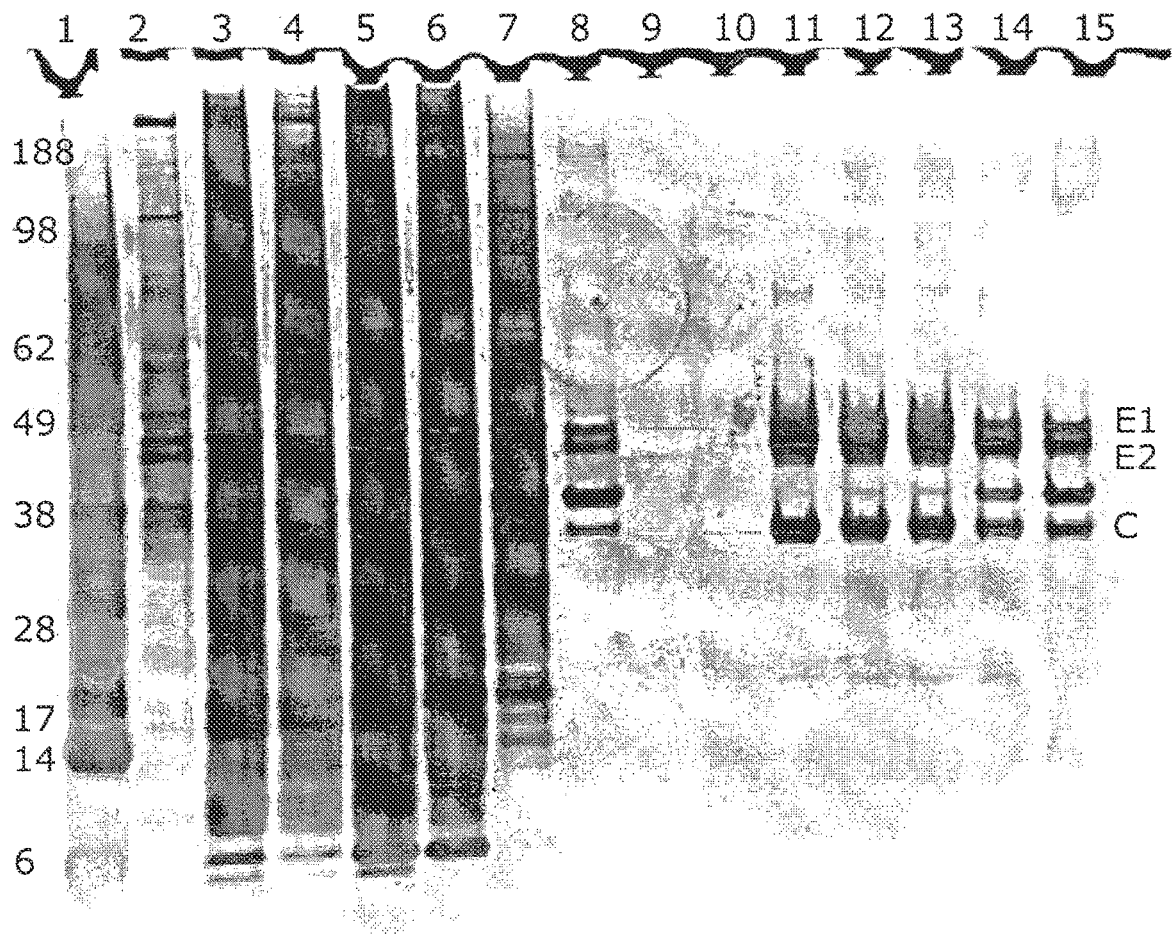

| Lane | Sample |
|------|--------|
| 1 | Marker Seeblueplus2 |
| 2 | CHIKV lot20150812_WVB2015-01_Filtered harvest0.2μ_24hpi |
| 3 | CHIKV lot20150812_WVB2015-01_Filtered harvest0.2μ_48hpi |
| 4 | 20150812_CHIKV_DSP_UF/DF_Load |
| 5 | 20150812_CHIKV_DSP_UF/DF_conc.10x |
| 6 | 20150813_CHIKV_DSP_UF/DF_conc.&dia. 11x |
| 7 | 20150813_CHIKV_DSP_PStreatment |
| 8 | 20150813_CHIKV_DSP_PS&CC700treatment |
| 9 | 20150813_CHIKV_DSP_SGCFrac F5 |
| 10 | 20150813_CHIKV_DSP_SGCFrac F6 |
| 11 | 20150813_CHIKV_DSP_SGCPoolF7-F10 |
| 12 | 20150813_CHIKV_DSP_SGCPoolF7-F11 (final pool) |
| 13 | 20150813_CHIKV_DSP_SGCPoolF7-F12 |
| 14 | 20150813_CHIKV_DSP_SGCFrac F13 |
| 15 | 20150813_CHIKV_DSP_SGCFrac F14 |

VIRUS PURIFICATION

RELATED APPLICATIONS

This application is a continuation of U.S. application Ser. No. 16/840,760, filed Apr. 6, 2020, which is a continuation of U.S. application Ser. No. 15/781,959, filed Jun. 6, 2018, now issued as U.S. Pat. No. 10,660,950, which is a national stage filing under 35 U.S.C. § 371 of International Patent Application Serial No. PCT/EP2016/082663, filed Dec. 23, 2016, the contents of each of which is incorporated herein by reference in its entirety.

REFERENCE TO AN ELECTRONIC SEQUENCE LISTING

The contents of the electronic sequence listing (1042270124US02-SEQ-NTJ.xml; Size: 364,761 bytes; and Date of Creation: Jul. 5, 2022) is herein incorporated by reference in its entirety.

FIELD OF THE INVENTION

The disclosure relates to methods for the purification of viruses for use in vaccines.

BACKGROUND OF THE INVENTION

Regulatory agencies such as the World Health Organization establish standards and guidelines for the production of pharmaceutical compositions administered to humans, such as vaccines, that limit quantity and components of the compositions. Meeting these standards is particularly challenging with regard to production of vaccines containing biological agents, such as viruses, which must be propagated on cell substrates. Such vaccine preparations must be sterile (i.e., free from independently replicating organisms) and may contain no more than 10 ng of host cell DNA per human dose, among other requirements. These standards are in place in order to ensure safety of the composition for human administration, but may introduce challenges in the development of processes used to produce such compositions.

Protamine was originally isolated from the sperm of salmon and other species of fish but is now produced primarily through recombinant biotechnology. It is a highly cationic peptide that binds to negatively charged molecules such as nucleic acids to form a stable ion pair. Its use in removing host cell nucleic acid is well document.

SUMMARY

During the course of routine virus purification, it was observed that addition of protamine sulfate to a virus harvest produced on a cell substrate removed not only contaminating DNA derived from host cells, as expected, but surprisingly also virtually eliminated immature and otherwise non-infectious virus particles from the preparation. This finding provides a streamlined, gentle, reproducible and broadly-applicable process for obtaining highly-purified infectious virus particles for applications such as vaccine preparation; furthermore, the process is not dependent on the charge of the virus particle.

Disclosed herein are downstream processes for purifying virus particles from a crude preparation. The downstream process can be applied to either a virus which has not adapted for propagation on a particular cell substrate or for a partial/fully cell substrate adapted virus particle.

Aspects of the invention provide processes for the purification of infectious virus particles comprising the steps of (a) providing a crude harvest (a) comprising virus particles and impurities, wherein the impurities are generated from growing said virus particles on a cell substrate; (b) reducing impurities from the crude harvest (a) by precipitation with an agent comprising a protamine salt, preferably a protamine sulphate, to obtain a virus preparation (b); and further purifying the virus preparation (b) by method or methods selecting for size of the virus particles, such as e.g. a sucrose density gradient centrifugation to obtain a virus preparation (c) comprising the infectious virus particles.

In some embodiments, the concentration of protamine sulphate in step (b) is about 1 to 10 mg/ml, more preferably about 1 to 5 mg/ml, more preferably about 1 to 2 mg/ml. In one embodiment, the concentration of protamine sulphate in step (b) is about 2 mg/mL. In one embodiment, the concentration of protamine sulphate is 1.2 to 1.8 mg/ml, more preferably 1.4 to 1.6 mg/ml. In a preferred embodiment, the concentration of protamine sulphate in step (b) is about 1.6 mg/ml or about 2 mg/ml.

In some embodiments, the residual host cell DNA of the virus preparation (e) is less than 1 µg/mL, especially less than 900, 800, 700, 600, 500, 400, 300 or 200 ng/mL, preferably less than 100 ng/mL. In a preferred embodiment, the residual host cell DNA of the virus preparation (c) is less than 10 ng/mL. In some embodiments, the residual host cell protein of the final virus preparation (c) is less than 10 µg/mL, especially less than 9, 8, 7, 6, 5, 4, 3 or 2 µg/mL, preferably less than 1 µg/mL. In a preferred embodiment, the residual host cell protein of the virus preparation (c) is less than 100 ng/mL. In some embodiments, the residual non-infectious virus particles of the final virus preparation (c) is less than 10 µg/mL, especially less than 9, 8, 7, 6, 5, 4, 3 or 2 µg/mL, preferably less than 1 µg/mL. In a preferred embodiment, the residual non-infectious virus particles of the virus preparation (c) is less than 100 ng/mL.

In some embodiments, the residual protamine is less than 1 µg/mL, especially less than 900, 800, 700, 600, 500, 400, 300 or 200 ng/mL, preferably less than 100 ng/mL, more preferably is below the detection limit of HPLC, in particular below the detection limit in the final drug substance. In some embodiments, the PS content is tested by HPLC or size exclusion chromatography (SEC). For example, HPLC is validated for PS determination in JEV sucrose gradient pool samples as a routine release assay and is very sensitive (i.e., LOQ 3 µg/mL; LOD 1 µg/mL). In the current invention, PS content in in virus DS samples was <LOD. In one embodiment, the HPLC assessment of PS content can be performed on a Superdex Peptide 10/300GL column (GE: 17-5176-01) using 30% Acetonitrile, 0.1% Trifluoroacetic acid as solvent with a flow rate of 0.6 ml/min at 25° C. and detection at 214 nm. A more sensitive method of measurement for residual protamine in a purified virus preparation is mass spectrometry (MS). In some embodiments, the residual PS levels in a virus preparation are tested by MS or other such highly sensitive method, e.g., nuclear magnetic resonance (NMR). With this method, residual PS, as well as fragments and/or break-down products of PS, can be detected at trace amounts, such as levels as low as, for example, $10^6$, $10^7$ or $10^8$ molecules per typical sample load. In some embodiments, the PS levels are tested in the sucrose gradient pool. In some embodiments, the PS levels are tested in the drug product. In some embodiments, the PS levels are tested in the drug substance.

In some embodiments, the crude harvest (a) comprising the virus particles and impurities is subjected to one or more pre-purification step(s) prior to step (b). In some embodiments, the one or more pre-purification step(s) comprises digesting host cell genomic DNA in the crude harvest (a) comprising the virus particles and impurities by enzymatic treatment. In some embodiments, the one or more pre-purification step(s) comprises filtration, ultrafiltration, concentration, buffer exchange and/or diafiltration. In some embodiments, the one or more pre-purification steps is filtration using a filter having a pore size equal to or less than 1 μm. In some embodiments, the filter has a pore size equal to or less than 0.2 μm. In a preferred embodiment, the filter has a pore size of 0.2 μm. In some embodiments, the concentration and/or ultra/diafiltration and/or buffer exchange is performed by tangential flow filtration (TFF). In some embodiments, ultra/diafiltration of the crude harvest (a) comprising the virus particles and impurities is performed using a hollow fiber membrane having a cut-off of equal to or less than 300 kDa. In a preferred embodiment, the hollow fiber membrane has a cut-off of 100 kDa.

In some embodiments, the virus particle is a live virus, a chimeric virus, an attenuated live virus, a modified live virus, or a recombinant live virus. In a further step, the virus particles of the invention may by optionally inactivated. In some embodiments, the virus particle is an attenuated form of the virus particle. For example, the virus may have reduced infectivity, virulence, and/or replication in a host, as compared to a wild-type virus. In some embodiments, the virus is a mutated or modified virus, for example the nucleic acid of the virus may contain at least one mutation relative to the wild-type virus. In some embodiments, the virus is a recombinant live virus, meaning a virus that is generated recombinantly and may contain nucleic acid from different sources.

In some embodiments, the virus particle is a live virus, an attenuated live virus, a modified live virus, or a recombinant live virus. In some embodiments, the virus belongs to a virus family selected from the group consisting of Paramyxoviridae, Orthomyxoviridae, Flaviviridae, Filoviridae, Arenaviridae, Rhabdoviridae, and Coronaviridae. In some embodiments, the virus belongs to a virus family selected from the group consisting of Togaviridae (being live or inactivated), such as alphaviruses, or Flaviviridae (being live or inactivated). In some embodiments, the virus is a virus of the family Flaviviridae, i.e. a flavivirus. In other embodiments, the virus is a Zika virus or Yellow Fever virus. In preferred embodiments, the virus is a Zika virus. In a most preferred embodiment, the Zika virus is a Zika virus from the Asian lineage.

In some embodiments, the relative reduction of impurity of the final virus preparation relative to the liquid medium (a) comprising the virus particles and impurities is in a range from 60 to 95%. In some embodiments, the residual impurity of the final virus preparation is less than 1%. We observed a decrease in the HCP peaks and the non-infectious aggregate peaks in the HPLC-SEC or SDS-PAGE. An exact quantification is difficult but one can measure the density of the SDS-PAGE bands and other methods.

In some embodiments, the filtration of step in (b)(ii) of claim 1 is performed using a filter having a pore size equal to or greater than 1 μm. In some embodiments, the filter has a pore size equal to or greater than 0.2 μm. In a preferred embodiment, the filter has a pore size of 0.2 μm.

In some embodiments, the virus is propagated in a cell line selected from the group consisting of an EB66 cell line, a Vero cell line, a Vero-αHis cell line, a HeLa cell line, a HeLa-S3 cell line, a 293 cell line, a PC12 cell line, a CHO cell line, a 3T3 cell line, a PerC6 cell line, a MDSK cell line, a chicken embryonic fibroblast cell line, a duck cell line, and a diploid avian cell line. In some embodiments, said cell line is a duck cell line. In some embodiments, said cell line is a diploid avian cell line. In some embodiments, said cell line is EB66 cell line. In a preferred embodiment, said cell line is a Vero cell line.

Aspects of the invention provide a use of any of the processes described herein for manufacturing a composition for immunization against a viral infection. In a preferred embodiment, the composition is a vaccine. In one embodiment, the composition or vaccine is directed against Chikungunya virus. In one embodiment, the composition or vaccine is directed against a flavivirus. In one embodiment, the composition or vaccine is directed against Yellow Fever virus. In one embodiment, the composition or vaccine is directed against Zika virus such as e.g. a Zika virus of the Asian lineage.

Other aspects provide compositions comprising the virus particles obtainable by any of the processes described herein for treating and/or preventing a viral infection. In one embodiment, the viral infection is caused by Chikungunya virus. In one embodiment, the viral infection is caused by a flavivirus. In one embodiment, the viral infection is caused by Yellow Fever virus. In one embodiment, the viral infection is caused by Zika virus such as e.g. a Zika virus of the Asian lineage.

In some embodiments, the attenuated form of ChikV is derived from the LR2006-OPY1 ChikV infectious clone (La Reunion isolate). In some embodiments, the attenuated form of ChikV is the Δ5nsP3 mutant as described by Hallengärd et al. (Novel Attenuated Chikungunya Vaccine Candidates Elicit Protective Immunity in C57BL/6 mice (2014) Journal of Virology 88(5):2858-2866) or an immunogenic variant thereof. The immunogenic variant of the Δ5nsP3 ChikV mutant is herein defined as having at least 80% sequence identity to the nucleotide sequence of the Δ5nsP3 mutant sequence as provided by SEQ ID NO: 77, especially at least 81%, 82%, 83%, 84%, 85%, 86%, 87%, 88% 89%, 90%, 91%, 92%, 93%, 94%, 95%, 96%, 97%, 98% or at least 99% sequence identity to SEQ ID NO: 77.

In some embodiments, the Zika virus is derived from the Asian lineage. In some embodiments, the Zika virus is a Zika virus as described partially or fully in Sequence section of this application, i.e. any of sequences SEQ ID Nos 2 to 69 or 78, in particular all partly or fully described Zika viruses of the Asian lineages or an immunogenic variant thereof. The immunogenic variants of the Zika virus or Zika virus of the Asian lineages are herein defined as having at least 80% sequence identity to the nucleotide sequence of the sequences described in any of sequences SEQ ID Nos 2 to 69 or 78, especially at least 81%, 82%, 83%, 84%, 85%, 86%, 87%, 88% 89%, 90%, 91%, 92%, 93%, 94%, 95%, 96%, 97%, 98% or at least 99% sequence identity.

In some embodiments, the process of the invention results in an enrichment of infectious virus particles from the crude harvest comprising infectious virus particles and non-infectious virus particles and other virus products such that the enrichment of the infectious virus particles is at least 50%, at least 60%, at least 70%, at least 80%, at least 90%, at least 95%, preferably at least 80%, especially 85% relative to the total virus particle content of the crude harvest (a) comprising the virus particles and impurities.

In some embodiments, the residual impurity of the final virus preparation with respect to all impurities in the crude harvest is less than 10%, 9%, 8%, 7%, 6%, 5%, 4%, 3%, 2%, 1%, preferably less than 5% as determined by SEC-HPLC (Size Exclusion Chromatography—HPLC).

In some embodiments, the filtration step of the virus preparation (b) after contact with the solid-phase matrix is performed using a filter having a pore size equal to or greater than 1 µm. In some embodiments, the filter has a pore size equal to or greater than 0.2 µm. In a preferred embodiment, the filter has a pore size of about 0.2 µm, such as 0.22 µm.

In some embodiments, the Zika virus, or Chikungunya virus is propagated in a cell line selected from the group consisting of an EB66 cell line, a Vero cell line, a Vero-αHis cell line, a HeLa cell line, a HeLa-S3 cell line, a 293 cell line, a PC12 cell line, a CHO cell line, a 3T3 cell line, a PerC6 cell line, a MDSK cell line, a chicken embryonic fibroblast cell line, a duck cell line, and a diploid avian cell line. In some embodiments, said cell line is a duck cell line. In some embodiments, said cell line is a diploid avian cell line. In some embodiments, said cell line is EB66 cell line. In a preferred embodiment, said cell line is a Vero cell line.

Aspects of the invention provide a use of any of the processes described herein for manufacturing a composition for immunization against a Zika virus, Yellow Fever, or Chikungunya virus infection. In a preferred embodiment, the composition is a vaccine. In preferred embodiments, the vaccine is administered to the subject once, twice or three or more times. In a preferred embodiment, the vaccine is administered once or twice. In a preferred embodiment, the vaccine is administered only once.

The herein disclosed in vivo data regarding immunogenicity of the inactivated Zika virus vaccine of the current invention indicates that the virus is surprisingly potently immunogenic and also highly cross-protective (very similar immunogenicity in African and Asian strains). Data indicate that immunogenicity was unexpectedly higher than the recently reported inactivated Zika virus vaccine candidate (Larocca, et. al, 2016, Nature doi:10.1038/nature18952.). Inactivated viruses are among the safest vaccines and especially preferred for delivery to populations where safety is especially concerning, such as pregnant women, children and immunocompromised individuals, which makes the herein disclosed inactivated Zika virus particularly suitable. Obtaining a high titer of inactivated virus is a challenge in the field. The herein disclosed process for purifying inactivated Zika virus results in not only a high yield, but also a very pure drug substance.

Other aspects provide compositions comprising the virus particles obtainable by any of the processes described herein for treating and/or preventing a Chikungunya virus infection.

BRIEF DESCRIPTION OF THE DRAWINGS

The accompanying drawings are not intended to be drawn to scale. The figures are illustrative only and are not required for enablement of the disclosure. For purposes of clarity, not every component may be labeled in every drawing, alignments were performed with the multi alignment package Jalview (Waterhouse et al., 2009, Bioinformatics 25 (9) 1189-1191). In the drawings:

FIG. 1: Average distance tree (by % identity, nt), complete genomes.

Figure 7A:
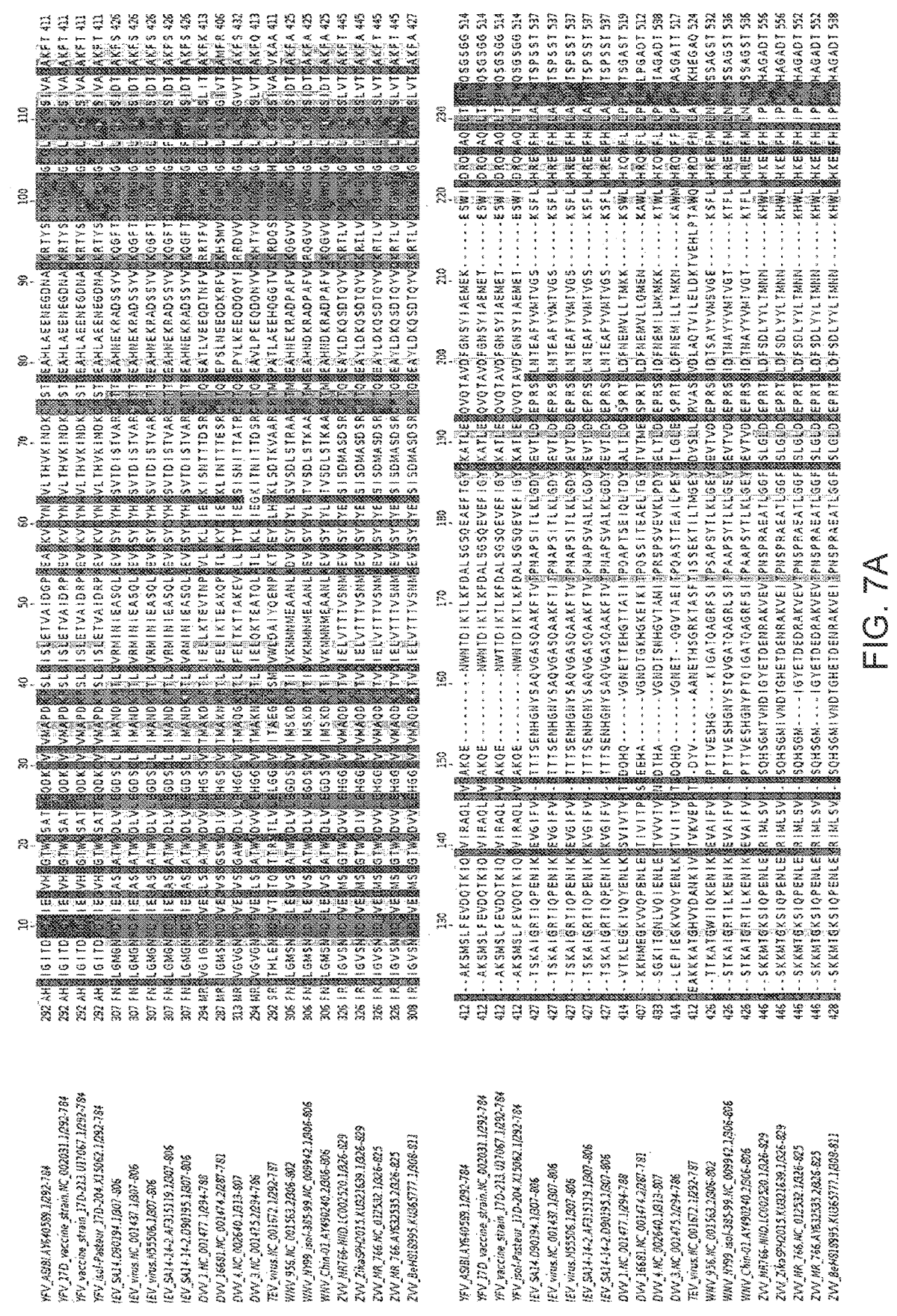
Figure 7B:
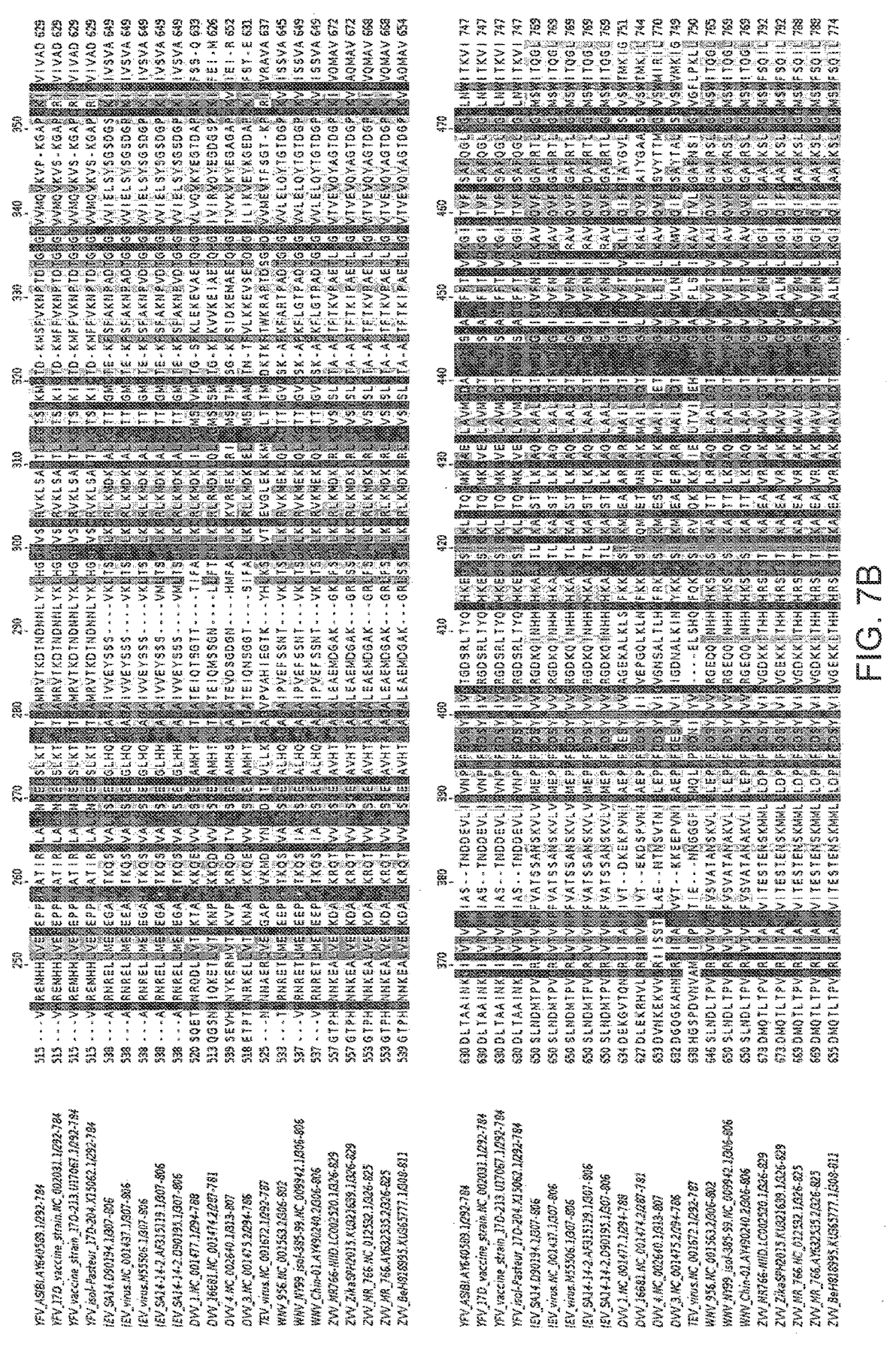
Figure 7C:
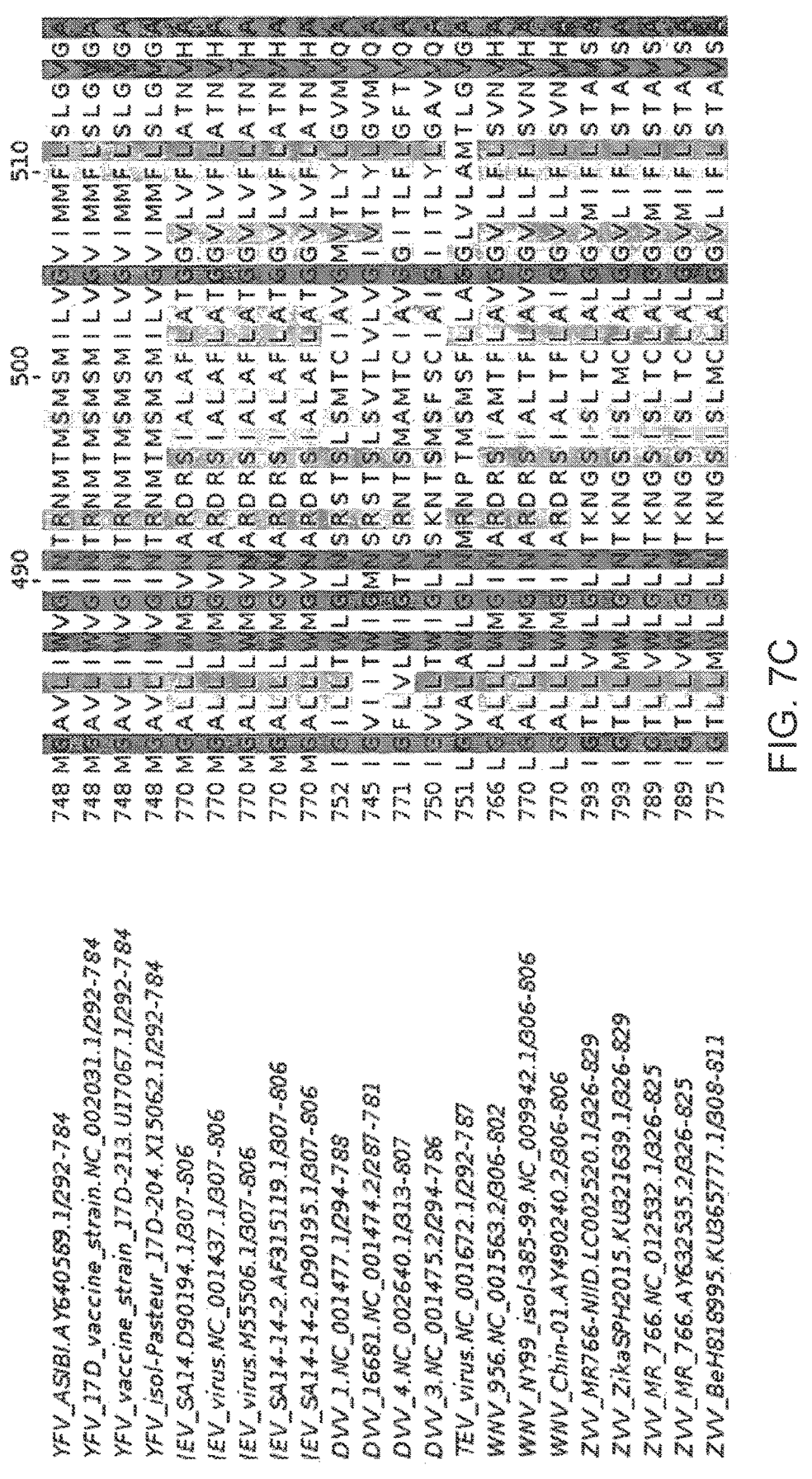

FIGS. 7A-7C: Alignment (shading: % identity, aa), E-protein.

FIGS. 11A-11C: Absorbance at 214 nm, 260 nm and 280 nm of individual sucrose gradient centrifugation (SGC) fractions of a representative purification run of the process of the invention (FIG. 11A); the SEC-HPLC analysis of the final pooled fractions containing purified infectious attenuated Δ5nsP3 ChikV virus particles (FIG. 11B); and a silver-stained SDS-PAGE gel showing the protein content of the virus preparation following different steps of the process of the invention (defined in the table below the figure) (FIG. 11C). The SGC purified pool consisting of SGC fractions F7-F11 is shown in lane 12.

FIG. 15A: CHIKV load material containing 10% sucrose was loaded on top of one 50 (w/w) sucrose layer. Determination of sucrose content in the fractions showed the formation of a linear gradient. SEC showed concentration of CHIKV within a sucrose concentration range from 40-30% (w/w) sucrose. PS SEC showed insufficient separation of PS from CHIKV. FIG. 15B: CHIKV load material containing 10% sucrose was loaded on top of a two layer system consisting of a 50% (w/w) sucrose bottom layer and a second 35% (w/w) sucrose layer. Determination of sucrose content in the fractions showed the formation of a linear gradient. SEC showed concentration of CHIKV within a sucrose concentration range from 40-30% (w/w) sucrose. PS SEC showed acceptable separation of PS from CHIKV, however a slight overlap is still present. FIG. 15C: CHIKV load material containing 10% sucrose was loaded on top of a two layer system consisting of a 50 (w/w) sucrose bottom layer and a second 25 (w/w) sucrose layer. Determination of sucrose content in the fractions showed the formation of a linear gradient. SEC showed concentration of CHIKV within a sucrose concentration range from 40-30% (w/w) sucrose. PS SEC showed a good separation of PS from CHIKV. D: CHIKV load material containing 10% sucrose was loaded on top of a three layer system consisting of a 50 (w/w) sucrose bottom layer as well as a 35% and a 15 (w/w) sucrose layer. Determination of sucrose content in the fractions showed the formation of a linear gradient and SEC showed concentration of CHIKV within a sucrose concentration range from 40-30% (w/w) sucrose. PS SEC showed a very good separation of PS and residual contaminants from CHIKV. Of the four tested sucrose layer systems the combination of 3 layers (shown in FIG. 15D) showed the best separation of the virus particles from residual contaminants and was therefore used for further DSP development.

Figure 16A:
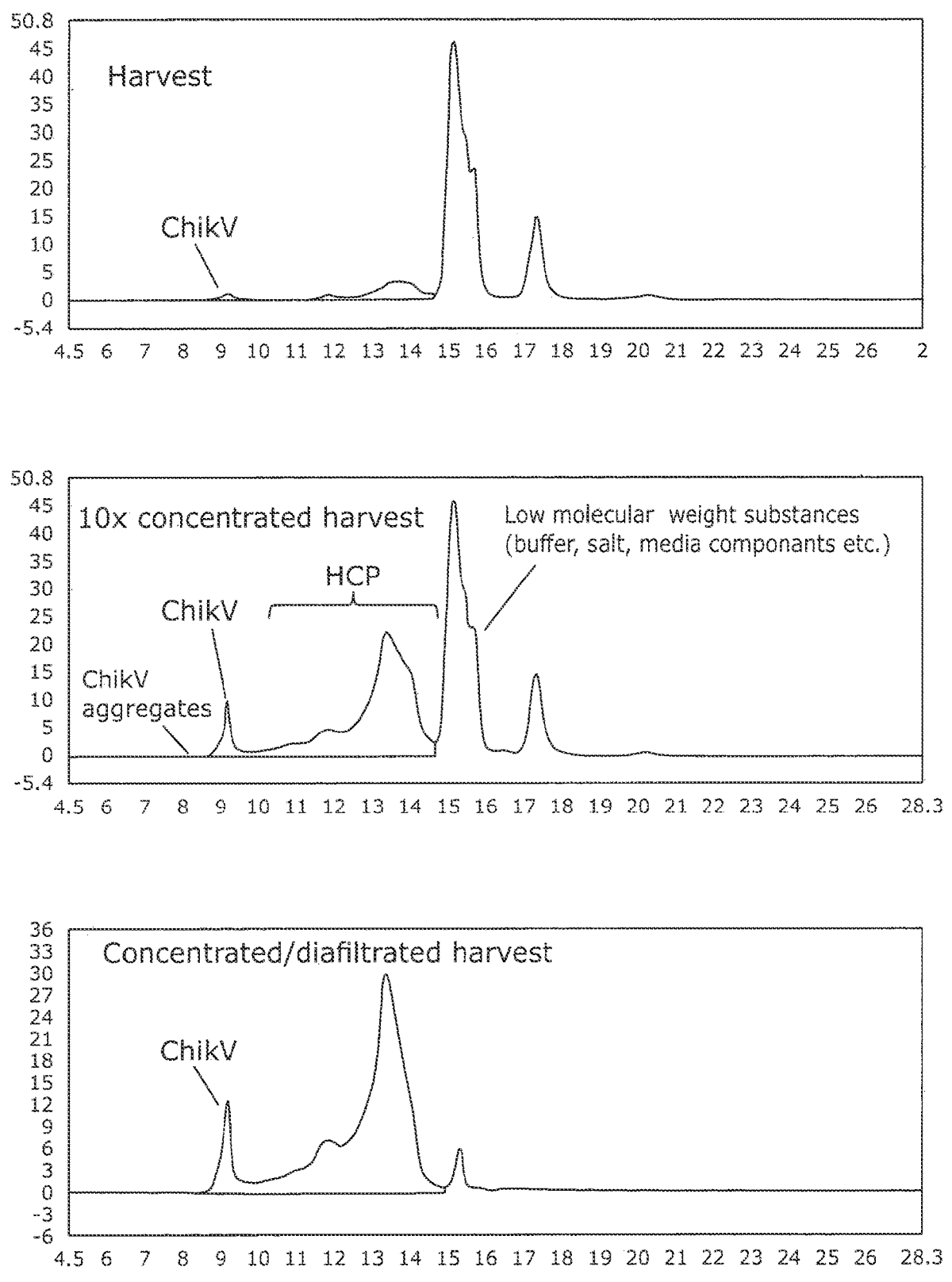
Figure 16B:
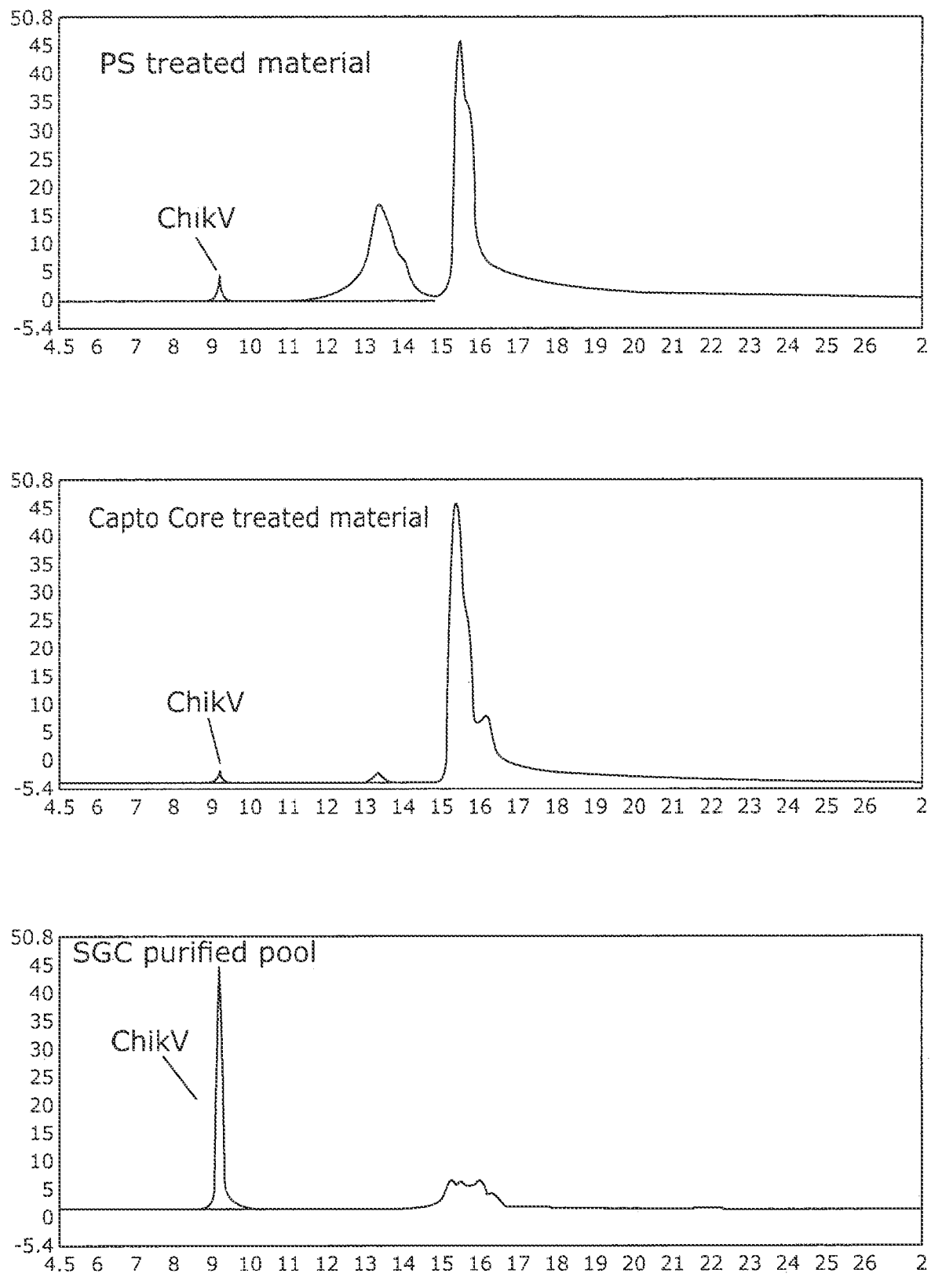

FIGS. 16A-16B: Relative amounts of attenuated Δ5nsP3 ChikV particles and other components by SEC-HPLC analysis at the different steps of the process of the invention including, from top to bottom: crude harvest (a); 10× concentrated harvest; diafiltrated concentrated harvest; PS treated material; CC700-treated material and SGC purified pool.

FIGS. 17A-17B: An exemplary downstream virus purification process from the crude harvest to formulation of the drug substance (vaccine), a preferred embodiment of the process of the invention (FIG. 17 A). A flow-chart of an exemplary virus inactivation process is shown in (FIG. 17 B).

FIG. 18: PS treatment results in selective removal of Zika virus aggregates and Vero HCP and LMW impurities (SEC-HPLC of 30× concentrated Zika Virus harvest day 5).

FIG. 19: SEC-HPLC of individual 30× concentrated Zika harvest prior PS treatment at different time points.

FIG. 20: SEC-HPLC of individual 30× concentrated Zika harvest post PS treatment at different time points.

FIG. 21: Representative SDS-PAGE from the sucrose gradient harvest of a Zika purification is shown.

FIG. 22: Correlation between JEV Antigen content in NIV analysed by ELISA and SEC-HPLC (Dionex Ultimate 3000, Superose 6 column).

FIG. 23: Comparison of JEV and ZikaV harvest schedules/yields.

FIG. 24: SEC-HPLC elution profile of ZikaV NIV. Data were processed on Dionex Ultimate 3000/Superose 6 Increase column. Both panels are from the same chromatogram. The upper graph is the complete elution profile; the lower graph is an enlargement of the ZIKAV elution peak.

FIG. 25: SEC-MALLS analysis of inactivated ZikaV.

FIG. 26: Cumulative particle size distribution of Zika NIV.

FIG. 27: Graphical representation of the neutralization of the Zika virus H/PF/2013 with pooled mouse sera. The number of plaques without serum was set to 100%. The EC50 was calculated with the 3-parameter method.

FIG. 28: Graphical representation of the neutralization of the Zika virus MR766 with pooled mouse sera. The number of plaques without serum was set to 100%. The EC50 was calculated with the 3-parameter method.

FIG. 29: Change in SEC profile of Yellow fever virus peak after PS addition according to the invention showing a complete removal of large size aggregates and LMW impurities.

DETAILED DESCRIPTION OF THE INVENTION

Disclosed herein are processes for the purification of infectious virus particles, i.e., mature, functional virus particles, e.g. flavivirus particles (Yellow Fever, Zika Virus, Japanese Encephalitis virus, Dengue virus) and/or alphavirus particles (Chikungunya virus). The processes disclosed are characterized by the removal of undesired by-products of virus production on host cells, such as non-infectious virus particles and aggregated and immature virus by-products. The processes provided herein allow the production of highly-purified virus preparations comprising mostly infectious virus particles. During the course of the invention, it was observed that protamine sulphate (PS), added to remove contaminating DNA during virus purification, resulted not only in removal of contaminating DNA, but also in the loss of a high percentage of total virus particles present in the preparation. Surprisingly, however, quantification of total infectious virus particles by TCID50 before and after PS treatment revealed that the absolute number of infectious virus particles did not change following this loss of total virus particles. This observation clearly shows that treatment with PS can facilitate selective removal of non-infectious, aggregated and immature viral by-products, leaving behind the infectious Chikungunya virus particles or other infectious virus particles. Because by-products produced during virus growth on host cells may have different (and undesirable) immunological properties or other unwanted side-effects or safety issues, a simple and robust way to remove these by-products is of high importance for the quality and safety of the final product.

Protamines are small arginine-rich nuclear proteins, present in high amounts in the sperm of fish, which have an important role in DNA packaging during spermatogenesis. Protamine sulfate (or "protamine" or "PS") can form a stable ion pair with heparin and is thus commonly used during certain surgeries when the anti-coagulation effect of heparin is no longer needed. In large doses, protamine sulfate administered alone can also have a weak anticoagulant effect ("Protamine sulfate". Wikipedia: The Free Encyclopedia. Wikimedia Foundation, Inc. 30 Sep. 2015 Web. 26 Nov. 2015<https://en.wikipedia.org/wiki/Protamine_sulfate>). Protamine_Sulphate is additionally routinely used in biotechnology applications such as DNA precipitation (e.g., removal of host cell DNA from cell culture processes), purification of DNA binding proteins and retroviral-mediated gene transfer.

Protamine is obtained from salmon sperm or produced recombinantly and is used as a sulphate salt. The four major peptides, which constitute almost the entire nitrogen-containing material in salmon protamine, have been fully characterized and found to be polypeptides of 30-32 amino acids in length, of which 21-22 residues are arginine. The average molecular mass is in the range of 4250 Da for the following sequence: PRRRRSSSRP VRRRRRPRVS RRRRRRGGRR RR (SEQ ID NO: 1). Herein, protamine is also referred to as protamine salt, or preferably protamine sulphate.

Figure 2:
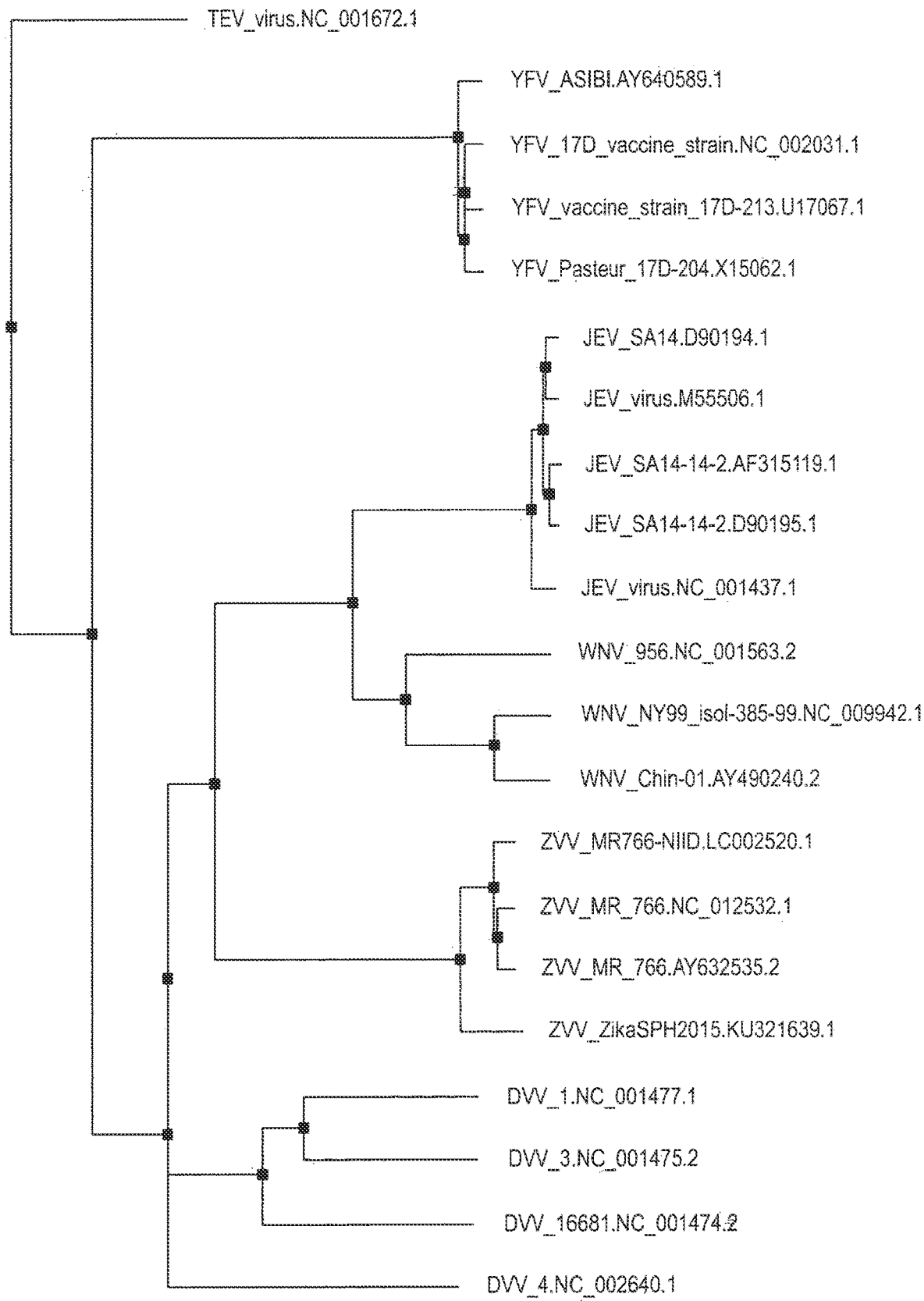
FIG. 2: Neighbor joining tree (by % identity, nt), complete genomes.
Figure 3:
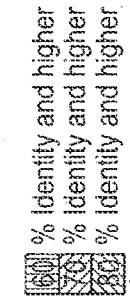
FIG. 3: Pairwise alignment-Jalview (% identity, nt), complete genomes.
Figure 4:
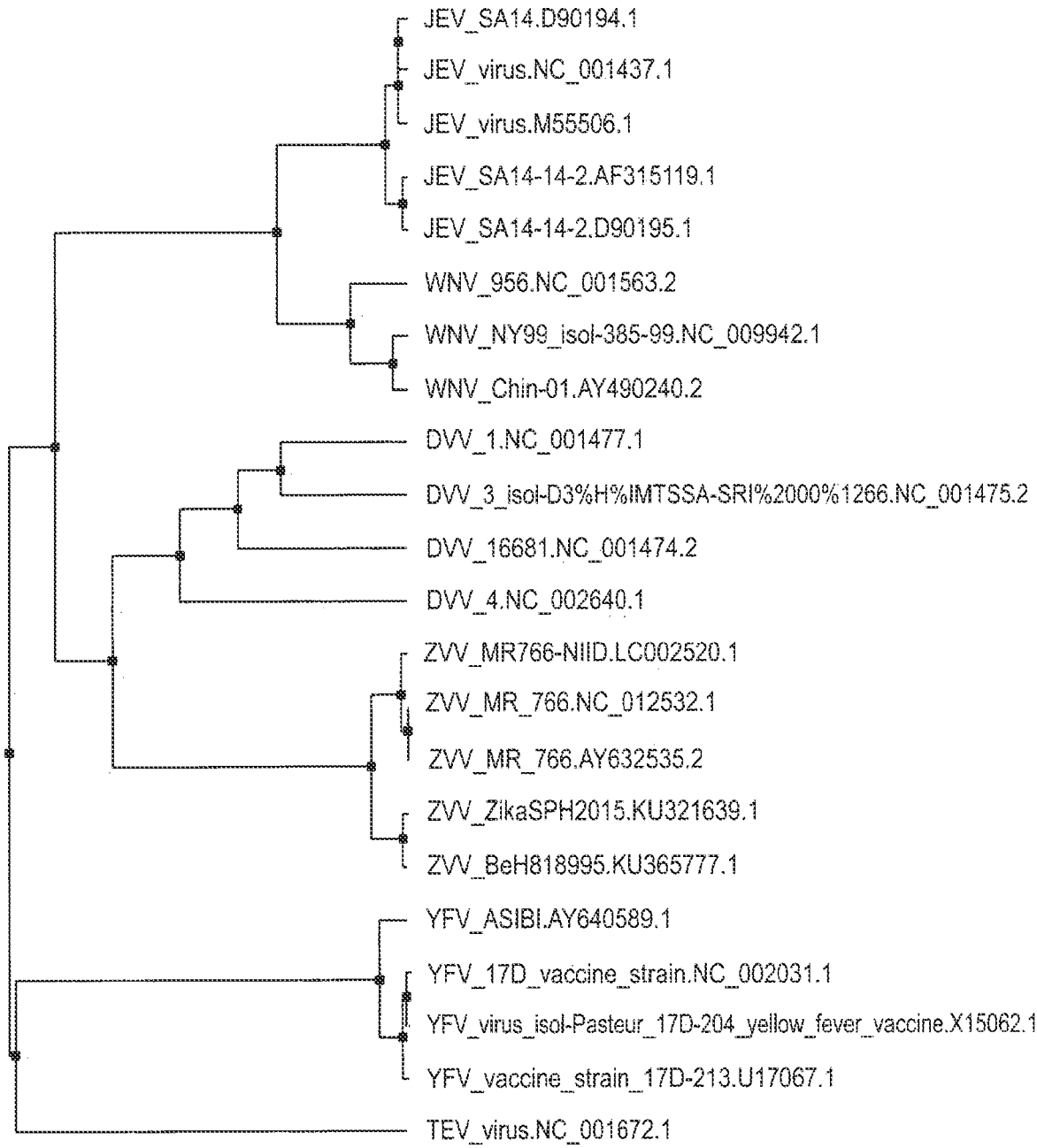
FIG. 4: Average distance tree (by % identity, aa), E-protein.
Figure 5:
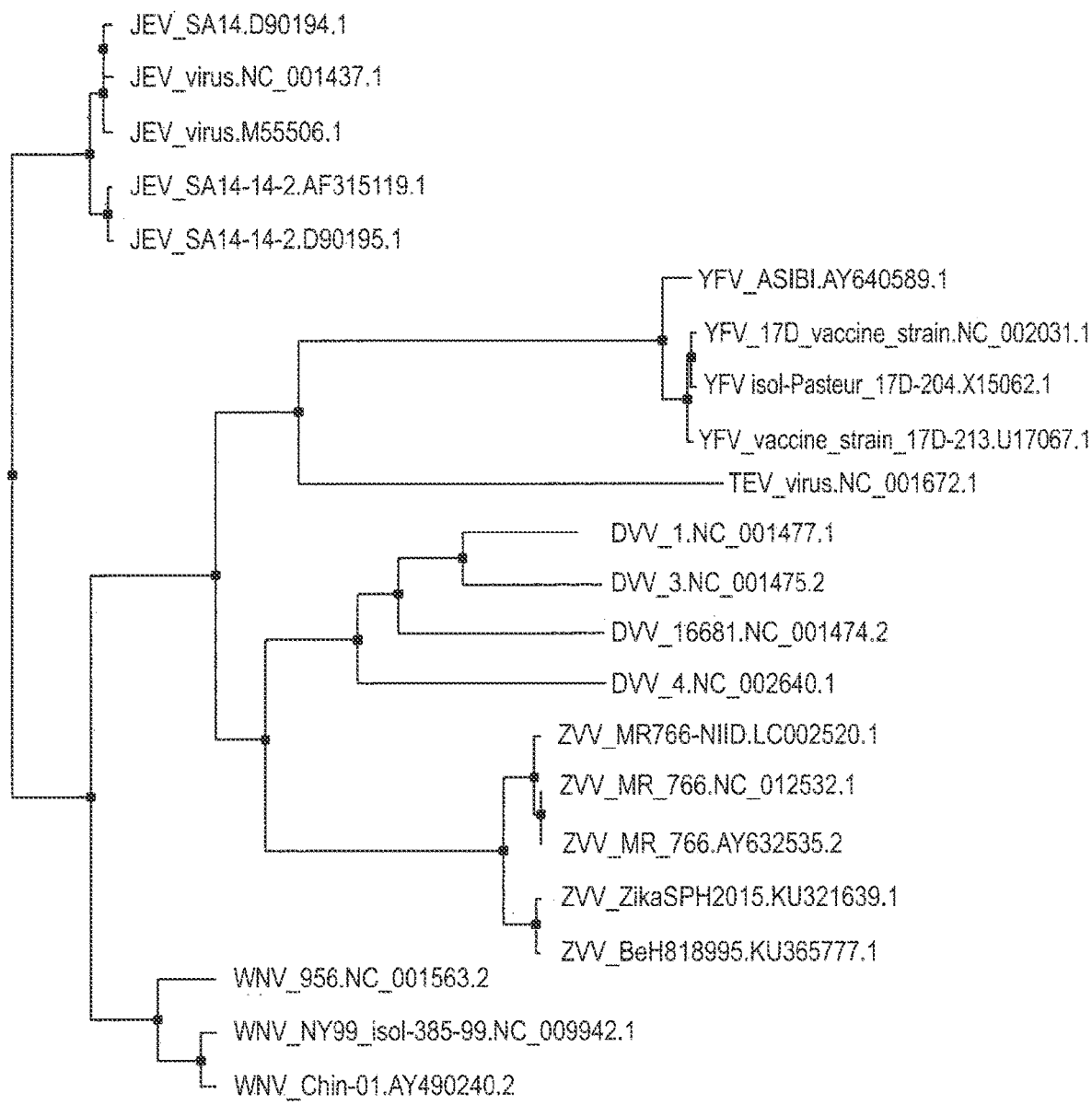
FIG. 5: Neighbor joining tree (by % identity. aa), E-protein.
Figure 6:
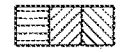
FIG. 6: Pairwise alignment-Jalview (% identity, aa), E-protein.
Figure 8:
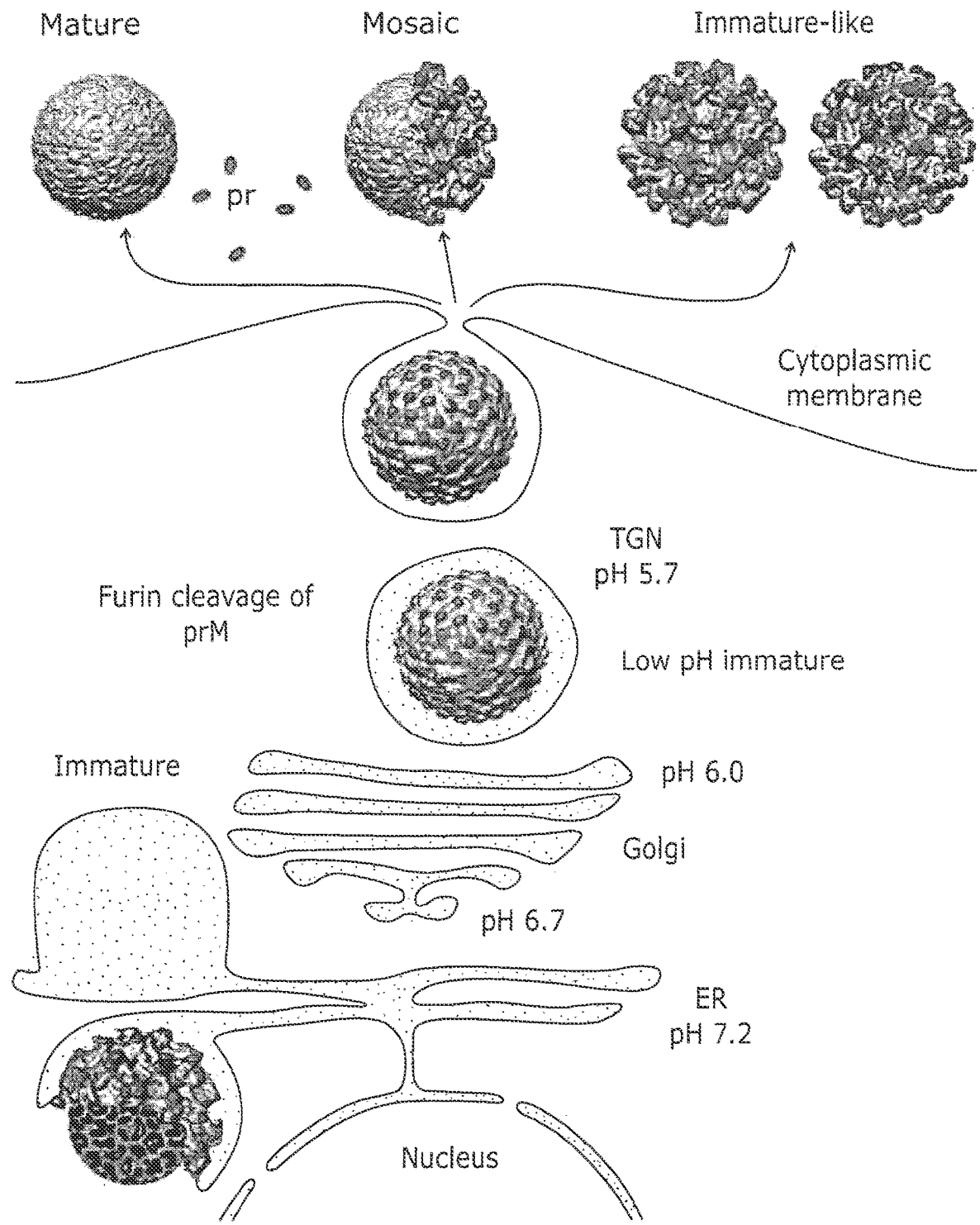
FIG. 8: An example of virus particle maturation in the host cell. As observed in flaviviruses, full maturation of the particles requires proteolytic cleavage of the precursor membrane glycoprotein (prM) by the host protease furin. Not all prM molecules are cleaved, resulting in the release of mature, mosaic or immature-like conformations from the cells. Mosaic and immature forms are generally not infectious—only mature virions are infective and have hemagglutinin (HA)/TCID50 activity. (Figure adapted from Plevka, et al., Maturation of flaviviruses starts from one or more icosahedrally independent nucleation centres, EMBO reports (2011) 12, 602-606).

The present invention relates to the use of protamine sulphate (PS) in a process of purification of a live virus, wherein the protamine sulphate facilitates the removal of impurities from a crude virus harvest, including non-infectious virus particles and aggregates. As seen in FIG. 8 using flaviviruses as an example, virus production in the host cell can result in the release of virus products which are not mature, and non-infectious particles, which can also be considered impurities according to the present invention. As such, the present invention also relates to the enrichment of infectious virus particles from a crude harvest containing a mixture of virus particles and other viral products in various stages of maturation.

The use of protamine sulphate can follow crude cell lysis or any further step after cell lysis (e.g. including after a pre-purification with filtration, chromatography etc) wherein the virus particles are further enriched or concentrated and/or other impurities are removed and/or buffer components are exchanged. The further steps may comprise filtration or concentration of the crude cell lysate.

The protamine sulphate may comprise the sequence PRRRRSSSRP VRRRRRPRVS RRRRRRGGRR RR (SEQ ID NO: 1) or a variant thereof wherein the amino acid sequence comprises from 28-35 amino acids, preferably 29-34, more preferably 30-33 amino acids, most preferably 31 or 32 amino acids. The protamine sulphate preferably comprises at least 19 arginine residues, more preferably at least 20 arginine residues, more preferably at least 21 arginine residues, even more preferably at least 22 residues, most preferably 20 or 21 arginine residues. Further, other protamine sulphate-like compounds or variants thereof may be used. Therefore, the use of the term "protamine salt" herein shall serve to encompass natural variations on SEQ ID NO: 1, preferably, but not limited to, the protamine sulphate forms.

The process according to the current invention may also comprise the use of a sucrose gradient, preferably an optimized sucrose gradient. The sucrose gradient is preferably optimized for the removal of protamine sulfate, also for the removal of immature viral particles or other viral particles which are non-infectious or host cell proteins or nucleic acids (DNA, RNA, mRNA, etc) or other host cell debris. In the current invention the optimized sucrose gradient comprises at least two, at least three, at least four layers of sucrose solutions with different densities. In one embodiment, the virus preparation to be purified is provided in a sucrose solution which has a density of about 8%, about 9%, about 10%, about 11%, about 12% sucrose (w/w), preferably about 10%. In one embodiment, one sucrose solution in the gradient has a density of about 45%, about 46%, about 47%, about 48%, about 49%, about 50%, about 51%, about 52%, about 53%, about 54%, about 55% sucrose (w/w), preferably about 50%. In one embodiment, one sucrose solution in the gradient has a density of about 30%, about 31%, about 32%, about 33%, about 34%, about 35%, about 36%, about 37%, about 38%, about 39%, about 40% sucrose (w/w), preferably about 35%. In one embodiment, one sucrose solution in the gradient has a density of about 10%, about 11%, about 12%, about 13%, about 14%, about 15%, about 16%, about 17%, about 18%, about 19%, about 20% sucrose (w/w), preferably about 15% sucrose. In a preferred embodiment, the sucrose gradient comprises three layers of sucrose solutions of about 50%, about 35% and about 15% (w/w) sucrose and the virus composition to be purified is contained in about 10% (w/w) sucrose. Because the invention provided for means to not only test for host cell DNA but also immature viral particles, the skilled person in the art is able to more precisely optimize the sucrose gradient for most efficient purification and include additional tools such as PRNT assay to monitor purification success.

The process comprising the use of protamine sulphate of the invention can be applied to purification of any virus for use in pharmaceutical compositions, for example, for a pharmaceutical composition such as a vaccine where it is important that the virus is in its infectious form. The virus to be purified may be any live virus, any live attenuated virus or any live chimeric virus, preferably a live wild type virus such as a Zika virus of the Asian lineage. In one embodiment, the virus particle is also be later inactivated. In a preferred embodiment, the virus is inactivated with formaldehyde.

In a preferred embodiment, the produced Zika virus is derived from the Asian lineage (which includes the strains found in South America and all strains derived from any Asian lineage). In some other embodiments, the produced Zika virus is a Zika virus as described in the Sequence section of this application (SEQ ID NO: 2 to 69 or 78).

Figure 9:
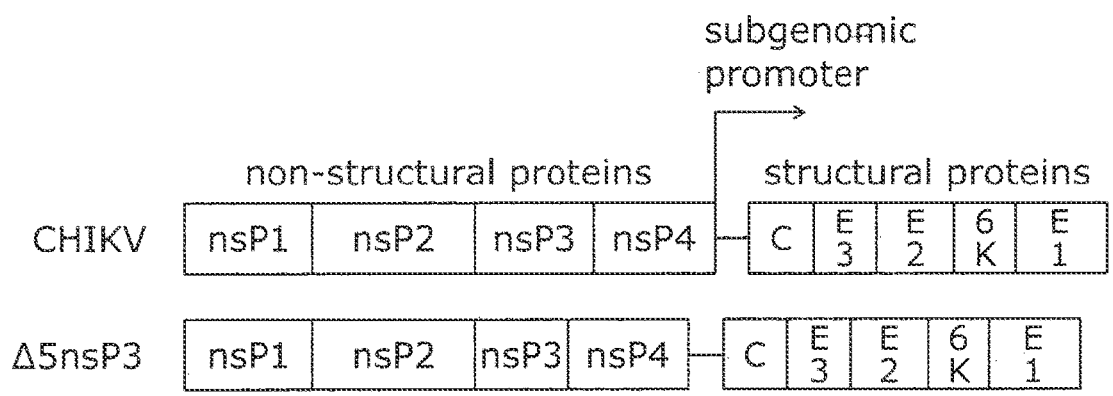
FIG. 9: CHIKV schematic genome, including non-structural and structural proteins (labeled "CHIKV") as well as a schematic representation of the Δ5nsP3 attenuated Chikungunya virus used to exemplify the purification process of the current invention (labeled "Δ5nsP3"). The black triangle indicates the approximate location of the deletion in the nsP3 coding region. (Figure adapted from Hallengärd et al. 2014, supra.)

In another preferred embodiment, the live attenuated Chikungunya virus is the protective ChikV-ICRES1-Δ5nsP3 described by Hallengärd et al. (Novel Attenuated Chikungunya Vaccine Candidates Elicit Protective Immunity in C57BL/6 mice (2014) J. Virology, 88(5):2858-2866). Briefly, the ChikV genome carries a positive-sense single-stranded RNA genome of 11 Kb containing two open reading frames encoding nonstructural proteins (nsP1 to nsP4) and structural proteins (C, E3, E2, 6K, and E1), respectively (see FIG. 9, top construct). The attenuated virus Δ5nsP3, based on the La Reunion ChikV strain LR2006-OPY1, was obtained by the substitution of amino acid residues 1656 to 1717 of the P1234 polyprotein with a small linker (aa sequence AYRAAAG) in the hypervariable region of the nsP3 protein (see FIG. 9, bottom construct). The Δ5nsP3 ChikV mutant was shown to be infectious, highly immunogenic and protective against challenge with wild type ChikV (Hallengärd, et al., supra and Hallengärd, et al., Prime-Boost Immunization Strategies against Chikungunya Virus (2014) J. Virology, 88(22):13333-13343). In one embodiment, the live attenuated Chikungunya virus may be a variant of the ChikV-ICRES1-Δ5nsP3 attenuated mutant virus.

Figure 10:
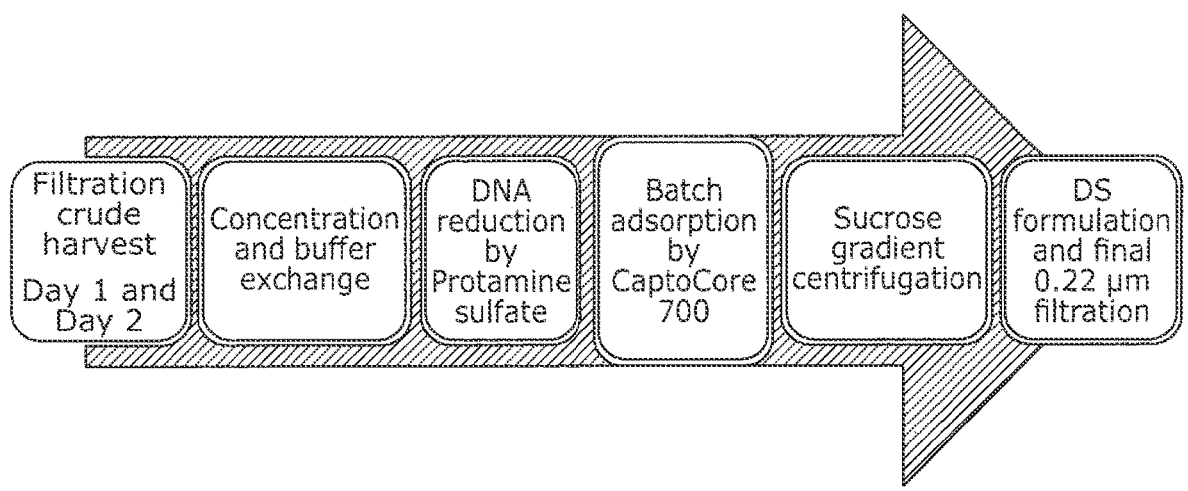
FIG. 10: How-chart showing an exemplary downstream Δ5nsP3 CHIK virus purification process from the crude harvest to formulation of the (vaccine) drug substance, a preferred embodiment of the process of the invention.
Figure 11A:
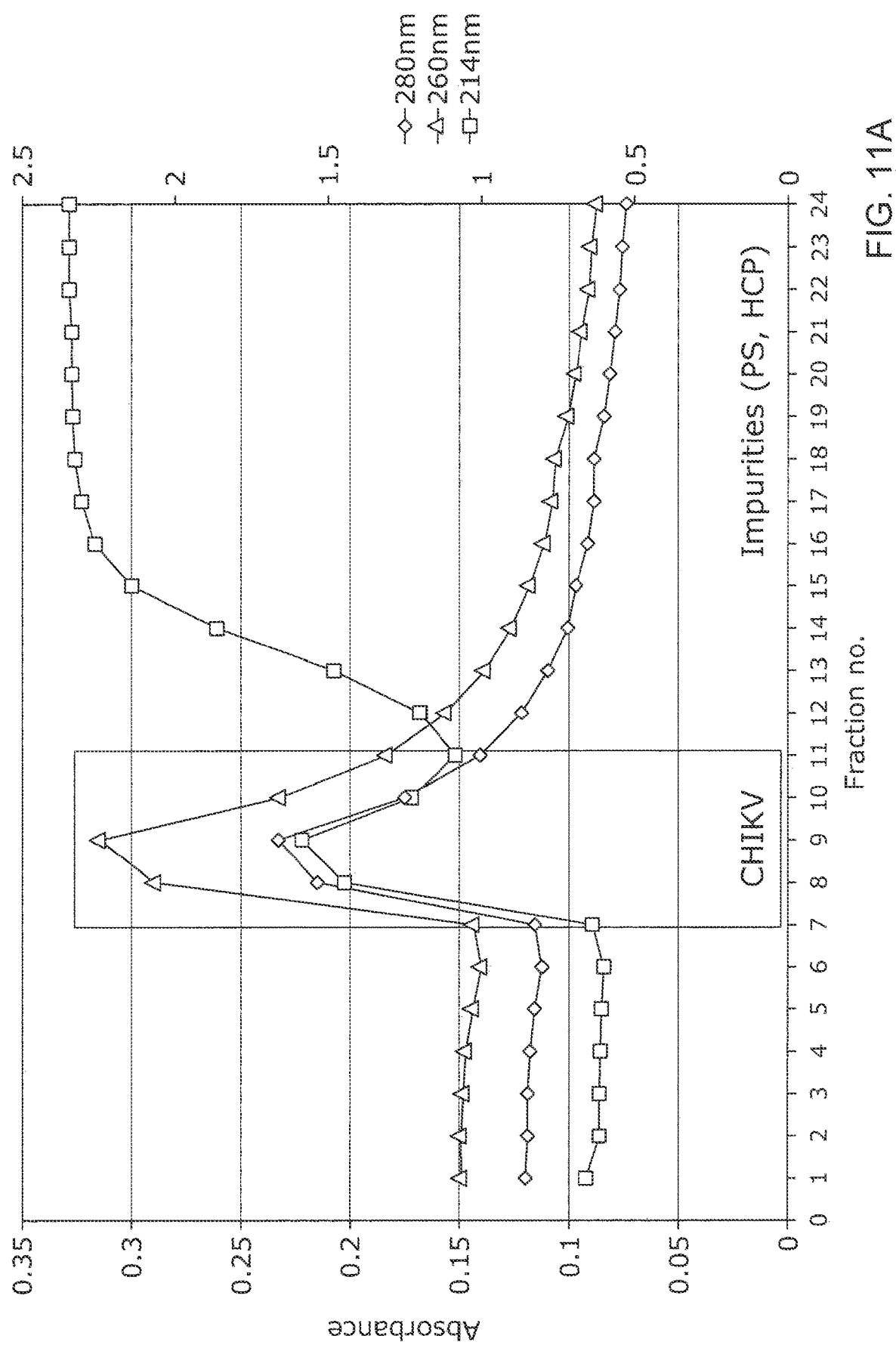
Figure 11B:
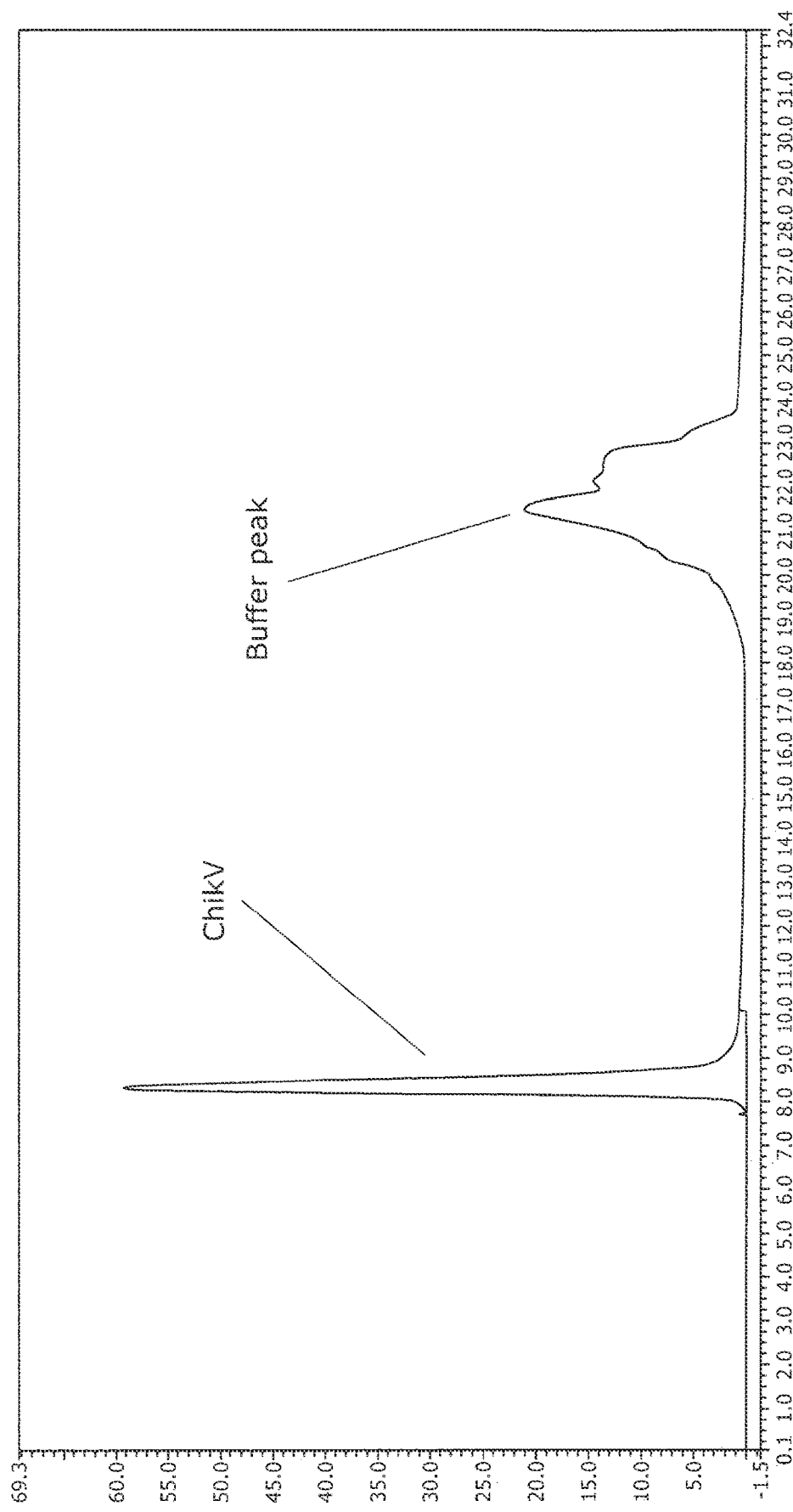
Figure 17A:
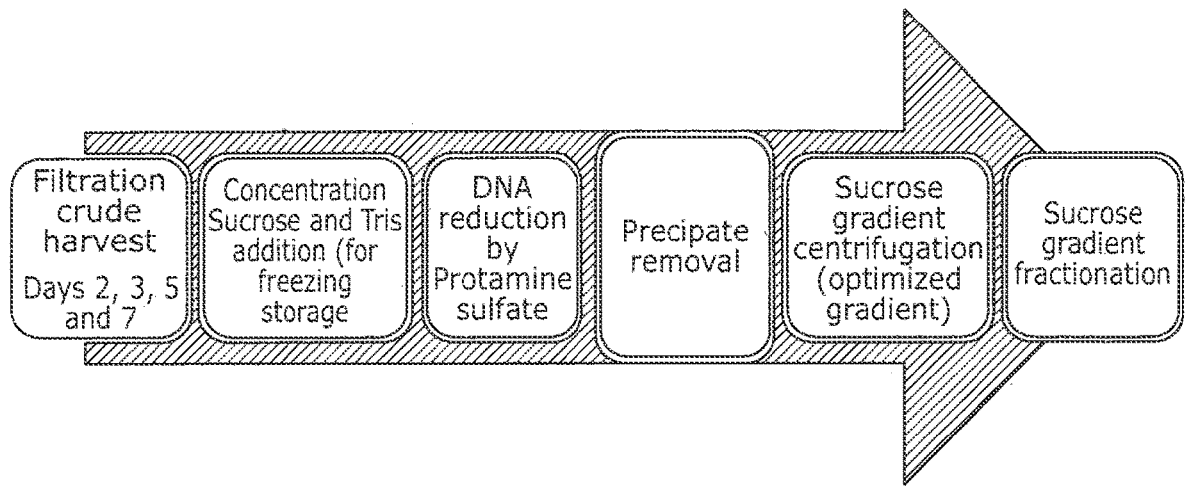
Figure 17B:
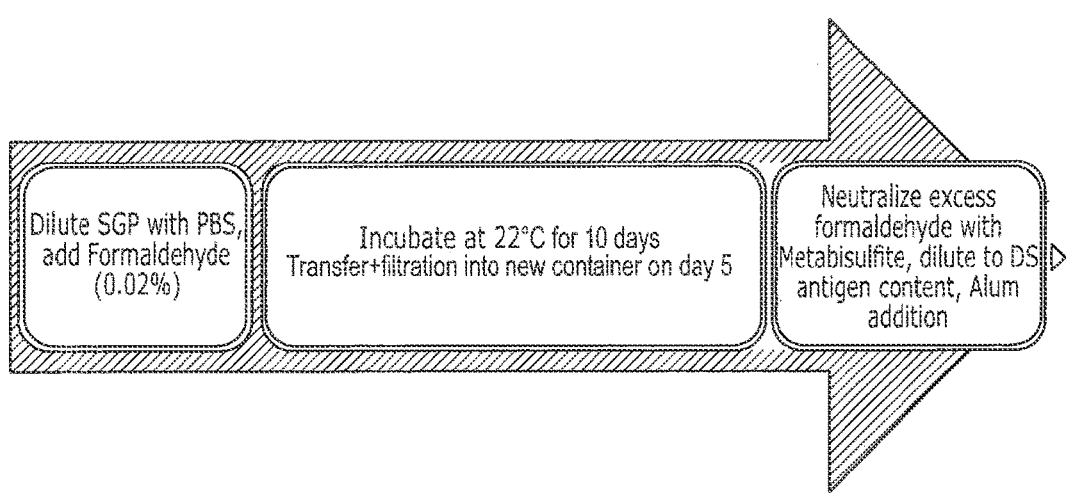

A preferred embodiment of the process of the current invention is shown in FIG. 10 (Chikungunya virus) and FIG. 17A (Zika virus).

TABLE 1

Overview of process buffers and stock solutions

| Buffer | Composition | Final pH | Final conductivity [mS/cm] |
|---|---|---|---|
| A | 0.5M NaOH | | n.a. |
| B | 0.1M NaOH | | n.a. |
| C | 25 mM Tris, 150 mM NaCl | 7.4 ± 0.2 | 16.5 |
| D | 1M Tris | 7.4 ± 0.2 | n.a. |
| E | 4.5M NaCl | n.a. | n.a. |
| F | 1M NaCl | n.a. | n.a. |
| G | 1% SDS | n.a. | n.a. |
| H | 50% (w/w) Sucrose in 25 mM Tris, 150 mM NaCl | 7.4 ± 0.2 | n.a. |
| I | 35% (w/w) Sucrose in 25 mM Tris, 150 mM NaCl | 7.4 ± 0.2 | n.a. |
| J | 15% (w/w) Sucrose in 25 mM Tris, 150 mM NaCl | 7.4 ± 0.2 | n.a. |
| K | 10 x PBS | 7.4 ± 0.2 | n.a. |
| L | 50 mg/mL Protamine sulphate | 7.4 ± 0.2 | n.a. |
| M | Drug substance formulation buffer (10 mM Tris(hydroxymethyl)-aminomethan, 5% Sucrose, 1% (10 mg/mL) rHSA) | 7.4 ± 0.2 | 1.3 |

TABLE 2

Abbreviations

| | |
|---|---|
| °Bx | Degrees Brix = sugar content (w/w) of an aqueous solution |
| BSA | Bovine serum albumin |
| CC700 | Capto ™ Core 700 |
| ChikV | Chikungunya virus |
| CPE | Cytopathic effect |
| EtOH | Ethanol |
| EU | Endotoxin units |
| DS | Drug Substance |
| DP | Drug Product |
| DSP | Downstream Process |
| HCP | Host cell protein |
| hcDNA | Host cell DNA |
| hpi | Hours post infection |
| HPLC | High Performance Liquid Chromatography |
| ID | Inner diameter |
| JEV | Japanese Encephalitis virus |
| LAL | Limulus amebocyte lysate |
| LDS buffer | Lithium dodecyl sulfate sample loading buffer |
| LOD | Limit of detection |
| LOQ | Limit of quantitation |
| MALLS | Multiangle light scattering |
| mAU | Milli absorbance units |
| MS | Mass spectroscopy |
| NIV | Neutralized inactivated virus |
| PBS | Phosphate buffered saline |
| PD | Process development |
| PFU | Plaque forming units |
| p.i. | Post-infection |
| PS | Protamine sulphate or protamine sulfate |
| ref | Relative centrifugal force |
| rHSA | Recombinant human serum albumin |
| Rms radius | Root mean square radius |
| rMSB | Research master seed bank |
| RSD | Relative standard deviation |
| SEC | Size exclusion chromatography |
| SGC | Sucrose gradient centrifugation |
| SGP | Sucrose gradient purified |
| SDS | Sodium dodecyl sulphate |
| TBS | Tris buffered saline |
| TFF | Tangential flow filtration |
| TCID50 | Tissue culture infectious dose 50% |
| UF/DF | Ultrafiltration/diafiltration |
| WFI | Water for injection |
| ZikaV | Zika virus |

Brix

Degrees Brix (° Bx) is the sugar content of an aqueous solution. One degree Brix is 1 gram of sucrose in 100 grams of solution and represents the strength of the solution as percentage by mass. ° Bx corresponds to the sucrose content in % (w/w), eg. 45° Bx equals 45% (w/w) sucrose.

TABLE A

Primers for Zika virus sequencing: lower case letters indicate bases not included in ZIKA but containing restriction sites for later cloning when needed (therefore, two Tms provided).

| Primer Pair | Oligoname | Primer sequence (5'-3') restriction sites (lower case) | Tm (gene-specific) | Tm (entire primer) | Amplicon size [bp] |
|---|---|---|---|---|---|
| 1 | 9320_Zika_PF_1F | SEQ ID NO: 80 ttaggatccGTTGTTGATCTGTGTGAAT | 69.9 | 74.6 | 707 |
| | 9321_Zika_PF_1R | SEQ ID NO: 81 taactcgagCGTACACAACCCAAGTT | 69.3 | 75.6 | |
| 2 | 9322_Zika_PF_2F | SEQ ID NO: 82 ttaggatccTCACTAGACGTGGGAGTG | 70 | 73.9 | 704 |
| | 9323_Zika_PF_2R | SEQ ID NO: 83 taactcgagAAGCCATGTCYGATATTGAT | 69.8 | 73.7 | |

TABLE A-continued

Primers for Zika virus sequencing: lower case letters indicate bases not included in ZIKA but containing restriction sites for later cloning when needed (therefore, two Tms provided).

| Primer Pair | Oligoname | Primer sequence (5'-3') restriction sites (lower case) | Tm (gene-specific) | Tm (entire primer) | Amplicon size [bp] |
|---|---|---|---|---|---|
| 3 | 9324_Zika_PF_3F | SEQ ID NO: 84<br>ttaggatccGCATACAGCATCAGGTG | 72.3 | 74.5 | 712 |
|   | 9325_Zika_PF_3R | SEQ ID NO: 85<br>taactcgagTGTGGAGTTCCGGTGTCT | 72 | 76.4 |   |
| 4 | 9326_Zika_PF_4F | SEQ ID NO: 86<br>ttaggatccGAATAGAGCGAARGTTGAGATA | 70.9 | 74 | 712 |
|   | 9327_Zika_PF_4R | SEQ ID NO: 87<br>taactcgAGTGGTGGGTGATCTTCTTCT | 70.5 | 73.7 |   |
| 5 | 9328_Zika_PF_5F | SEQ ID NO: 88<br>ttaggatcCAGTCACAGTGGAGGTACAGTAC | 70.3 | 75 | 704 |
|   | 9329_Zika_PF_5R | SEQ ID NO: 89<br>taactcgagCRCAGATACCATCTTCCC | 71.5 | 77.3 |   |
| 6 | 9330_Zika_PF_6F | SEQ ID NO: 90<br>ttaggatCCCTTATGTGCTTGGCCTTAG | 70.7 | 72.7 | 698 |
|   | 9331_Zika_PF_6R | SEQ ID NO: 91<br>taactcgagTCTTCAGCCTCCATGTG | 70.4 | 76.9 |   |
| 7 | 9332_Zika_PF_7F | SEQ ID NO: 92<br>ttaggatccAATGCCCACTCAAACATAGA | 71.9 | 75 | 716 |
|   | 9333_Zika_PF_7R | SEQ ID NO: 93<br>taactcgagTCATTCTCTTCTTCAGCCCTT | 71 | 74 |   |
| 8 | 9334_Zika_PF_8F | SEQ ID NO: 94<br>ttaggatccAAGGGTGATCGAGGAAT | 70.9 | 75.2 | 703 |
|   | 9335_Zika_PF_8R | SEQ ID NO: 95<br>taactcgagTTCCCTTCAGAGAGAGGAGC | 71.9 | 73.4 |   |
| 9 | 9336_Zika_PF_9F | SEQ ID NO: 96<br>ttaggatccTCTTTTGCAAACTGCGATC | 71.9 | 75 | 699 |
|   | 9337_Zika_PF_9R | SEQ ID NO: 97<br>taactcgagTCCAGCTGCAAAGGGTAT | 71 | 74.9 |   |
| 10 | 9338_Zika_PF_10F | SEQ ID NO: 98<br>ttaggatccGTGTGGACATGTACATTGA | 71.4 | 75.8 | 706 |
|   | 9339_Zika_PF_10R | SEQ ID NO: 99<br>taactcgagCCCATTGCCATAAAGTC | 70.4 | 75.8 |   |
| 11 | 9340_Zika_PF_11F | SEQ ID NO: 100<br>ttaggatccTCATACTGTGGTCCATGGA | 71.6 | 78.1 | 692 |
|   | 9341_Zika_PF_11R | SEQ ID NO: 101<br>taactcgagGCCCATCTCAACCCTTG | 74 | 78 |   |
| 12 | 9342_Zika_PF_12F | SEQ ID NO: 102<br>ttaggatccTAGAGGGCTTCCAGTGC | 70.9 | 74 | 707 |
|   | 9343_Zika_PF_12R | SEQ ID NO: 103<br>taactcgAGATACTCATCTCCAGGTTTGTTG | 70.2 | 72.2 |   |
| 13 | 9344_Zika_PF_13F | SEQ ID NO: 104<br>ttaggatccGAAAACAAAACATCAAGAGTG | 70.6 | 75.4 | 726 |
|   | 9345_Zika_PF_13R | SEQ ID NO: 105<br>taactcgagGAATCTCTCTGTCATGTGTCCT | 71.9 | 75.6 |   |
| 14 | 9346_Zika_PF_14F | SEQ ID NO: 106<br>ttaggatccTTGATGGCACGACCAAC | 73.1 | 75.6 | 715 |
|   | 9347_Zika_PF_14R | SEQ ID NO: 107<br>ttaggatccGTTGTTGATCTGTGTGAAT | 70.8 | 77.9 |   |
| 15 | 9348_Zika_PF_15F | SEQ ID NO: 108<br>taactcgagCAGGTCAATGTCCATTG | 71.9 | 75.4 | 719 |
|   | 9349_Zika_PF_15R | SEQ ID NO: 109<br>ttaggatccTGTTGTGTTCCTATTGCTGGT | 73.9 | 77.2 |   |
| 16 | 9350_Zika_PF_16F | SEQ ID NO: 110<br>taactcgaGTGATCAGRGCCCCAGC | 72.3 | 75.4 | 703 |
|   | 9351_Zika_PF_16R | SEQ ID NO: 111<br>ttaggatccTGCTGCCCAGAAGAGAA | 72 | 76.3 |   |
| 17 | 9352_Zika_PF_17F | SEQ ID NO: 112<br>taactcgaGCACCAACAYGGGTTCTT | 73.6 | 76 | 705 |

TABLE A-continued

Primers for Zika virus sequencing: lower case letters indicate bases not included in ZIKA but containing restriction sites for later cloning when needed (therefore, two Tms provided).

| Primer Pair | Oligoname | Primer sequence (5'-3') restriction sites (lower case) | Tm (gene-specific) | Tm (entire primer) | Amplicon size [bp] |
|---|---|---|---|---|---|
|  | 9353_Zika_PF_17R | SEQ ID NO: 113<br>ttaggatcCTCAAGGACGGTGTGGC | 72 | 75.5 |  |
| 18 | 9354_Zika_PF_18F | SEQ ID NO: 114<br>taactcgagCAATGATCTTCATGTTGGG | 71.7 | 75.8 | 699 |
|  | 9355_Zika_PF_18R | SEQ ID NO: 115<br>ttaggatccTATGGGGGAGGACTGGT | 71 | 74.1 |  |
| 19 | 9356_Zika_PF_19F | SEQ ID NO: 116<br>taactcGAGCCCAGAACCTTGGATC | 73.3 | 75.5 | 711 |
|  | 9357_Zika_PF_19R | SEQ ID NO: 117<br>ttaggatcCAGACCCCCAAGAAGGC | 71.3 | 76.9 |  |
| 20 | 9358_Zika_PF_20F | SEQ ID NO: 118<br>taactcgagCCCCTTTGGTCTTGTCT | 71.7 | 75 | 706 |
|  | 9359_Zika_PF_20R | SEQ ID NO: 119<br>ttaggatccAGGAAGGATGTATGCAGATG | 71.9 | 73.9 |  |
| 21 | 9360_Zika_PF_21F | SEQ ID NO: 120<br>taactcgagACATTTGCGCATATGATTTTG | 70.4 | 75.7 | 709 |
|  | 9361_Zika_PF_21R | SEQ ID NO: 121<br>ttaggatccAGGAAGGACACACAAGAGT | 71.8 | 75 |  |
| 22 | 9362_Zika_PF_22F | SEQ ID NO: 122<br>taactcgagACAGGCTGCACAGCTTT | 70 | 79.1 | 581 |
|  | 9363_Zika_PF_22R | SEQ ID NO: 123<br>ttaggatccTCTCTCATAGGGCACAGAC | 74.8 | 81.1 |  |

SEQUENCES

SEQ ID NO: 1
A typical form of protamine
PRRRRSSSRP VRRRRPRVS RRRRRRGGRR RR

Provided below are examples of nucleic acid sequences of the genomes of Zika viruses that may be used in the methods, compositions, and/or vaccines described herein.

SEQ ID NO: 2
KU321639.1 Zika virus strain ZikaSPH2015, Brazil, complete genome (SEQ ID NO: 2)
GTTGTTACTGTTGCTGACTCAGACTGCGACAGTTCGAGTTTGAAGCGAAAGCTAGCAACAGTATCAACAGGTTTTATTTGGATT
TGGAAACGAGAGTTTCTGGTCATGAAAAACCCAAAAAGAAATCCGGAGGATTCCGGATTGTCAATATGCTAAAACGCGGAG
TAGCCCGTGTGAGCCCCTTTGGGGGCTTGAAGAGGCTGCCAGCCGGACTTCTGCTGGGTCATGGGCCCATCAGGATGGTCTTG
GCAATTCTAGCCTTTTTGAGATTCACGGCAATCAAGCCATCACTGGGTCTCATCAATAGATGGGGTTCAGTGGGAAAAAGA
GGCTATGGAAATAATAAAGAAGTTCAAGAAAGATCTGGCTGCCATGCTTCCATAATCAATGCTAGGAAGGAGAAGAAGAG
ACGGGGCGCAGATACTAGTGTCGGAATTGTTGGCCTCCTGCTGACCACAGCTATGGCAGCGGAGGTCACTAGACGTGGGAGT
GCATACTATATGTACTTGGACAGAAACGATGCTGGGGAGGCCATATCTTTTCCAACCACATTGGGGATGAATAAGTGTTATAT
ACAGATCATGGATCTTGGACACATGTGTGATGCCACCATGAGCTATGAATGCCCTATGCTGGATGAGGGGGTGGAACCAGAT
GACGTCGATTGTTGGTGCAACACGACGTCAACTTGGGTTGTGTACGGAACCTGCCATCACAAAAAGGTGAAGCACGGAGAT
CTAGAAGAGCTGTGACGCTCCCCTCCCATTCCACTAGGAAGCTGCAAACGCGGTCGCAAACCTGGTTGGAATCAAGAGAATAC
ACAAAGCACTTGATTAGAGTCGAAAATTGGATATTCAGGAACCCTGGCTTCGCGTTAGCAGCAGCTGCCATCGCTTGGCTTTTG
GGAAGCTCAACGAGCCAAAAGTCATATACTTGGTCATGATACTGCTGATTGCCCCGGCATACAGCATCAGGTGCATAGGAGT
CAGCAATAGGGACTTTGTGGAAGGTATGTCAGGTGGGACTTGGGTTGATATTGTCTTGGAACATGGAGGTTGTGTCACCGTA
ATGGCACAGGACAAACCGACTGTCGACATAGAGCTGGTTACAACAACAGTCAGCAACATGGCGGAGGTAAGATCCTACTGCT
ATGAGGCATCAATATCAGACATGGCTTCGGACAGCCGCTGCCCAACACAAGGTGAAGCCTACCTTGACAAGCAATCAGACACT
CAATATGTCTGCAAAAGAACGTTAGTGGACAGAGGCTGGGGAAATGGATGTGGACTTTTTGGCAAAGGGAGTCTGGTGACAT
GCGCTAAGTTTGCATGCTCCAAGAAAATGACCGGGAAGAGCATCCAGCCAGAGAATCTGGAGTACCGGATAATGCTGTCAGT
TCATGGCTCCCAGCACAGTGGGATGATCGTTAATGACACAGGACATGAAACTGATGAGAATAGAGCGAAGGTTGAGATAACG
CCCAATTCACCAAGAGCCGAAGCCACCCTGGGGGGTTTTGGAAGCCTAGGACTTGATTGTGAACCGAGGACAGGCCTTGACTT
TTCAGATTTGTATTACTTGACTATGAATAACAAGCACTGGTTGGTTCACAAGGAGTGGTTCCACGACATTCCATTACCTTGGCAC
GCTGGGGCAGACACCGGAACTCCACACTGGAACAACAAAGAAGCACTGGTAGAGTTCAAGGACGCACATGCCAAAAGGCAA
ACTGTCGTGGTTCTAGGGAGTCAAGAAGGAGCAGTTCACACGGCCCTTGCTGGAGCTCTGGAGGCTGAGATGGATGGTGCAA
AGGGAAGGCTGTCCTCTGGCCACTTGAAATGTCGCCTGAAATGGATAAACTTAGATTGAAGGGCGTGTCATACTCCTTGTGT
ACCGCAGCGTTCACATTCACCAAGATCCCGGCTGAAACACTGCACGGGACAGTCACAGTGGAGGTACAGTACGCAGGGACAG
ATGGACCTTGCAAGGTTCCAGCTCAGATGGCGGTGGACATGCAAACTCTGACCCCAGTTGGGAGGTTGATAACCGCTAACCCC
GTAATCACTGAAAGCACTGAGAACTCTAAGATGATGCTGGAACTTGATCCACCATTTGGGGATGTCTTACATTGTCATAGGAGTC
GGGGAGAAGAAGATCACCCACCACTGGCACAGGAGTGGCAGCACCATTGGAAAAGCATTTGAAGCCACTGTGAGAGGTGCC
AAGAGAATGGCAGTCTTGGGAGACACAGCCTGGGACTTTGGATCAGTTGGAGGCGCTCTCAACTCATTGGGCAAGGGCATCC
ATCAAATTTTTGGAGCAGCTTTCAAATCATTGTTTGGAGGAATGTCCTGGTTCTCACAAATTCTCATTGGAACGTTGCTGATGTG
GTTGGGTCTGAACACAAAGAATGGATCTATTTCCCTTATGTGCTTGGCCTAGGGGAGTGTTGATCTTCTTATCCACAGCCGT -continued

| SEQUENCES |
|---|
| CTCTGCTGATGTGGGGTGCTCGGTGGACTTCTCAAAGAAGGAGACGAGATGCGGTACAGGGGTGTTCGTCTATAACGACGTT |
| GAAGCCTGGAGGGACAGGTACAAGTACCATCCTGACTCCCCCCGTAGATTGGCAGCAGCAGTCAAGCAAGCCTGGGAAGATG |
| GTATCTGCGGGATCTCCTCTGTTTCAAGAATGGAAAACATCATGTGGAGATCAGTAGAAGGGGAGCTCAACGCAATCCTGGAA |
| GAGAATGGAGTTCAACTGACGGTCGTTGTGGGATCTGTAAAAAACCCCATGTGGAGAGGTCCACAGAGATTGCCCGTGCCTG |
| TGAACGAGCTGCCCCACGGCTGGAAGGCTTGGGGGAAATCGCACTTCGTCAGAGCAGCAAAGACAAATAACAGCTTTGTCGT |
| GGATGGTGACACACTGAAGGAATGCCCACTCAAACATAGAGCATGGAACAGCTTTCTTGTGGAGGATCATGGGTTCGGGGTA |
| TTTCACACTAGTGTCTGGCTCAAGGTTAGAGAAGATTATTCATTAGAGTGTGATCCAGCCGTTATTGGAACAGCTGTTAAGGGA |
| AAGGAGGCTGTACACAGTGATCTAGGCTACTGGATTGAGAGTGAGAAGAATGACACATGGAGGCTGAAGAGGGCCCATCTG |
| ATCGAGATGAAAACATGTGAATGGCCAAAGTCCCACACATTGTGGACAGATGGAATAGAAGAGAGTGATCTGATCATACCCA |
| AGTCTTTAGCTGGGCCACTCAGCCATCACAATACCAGAGAGGGCTACAGGACCCAAATGAAAGGGCCATGGCACAGTGAAGA |
| GCTTGAAATTCGGTTTGAGGAATGCCCAGGCACTAAGGTCCACGTGGAGGAAACATGTGGAACAAGAGGACCATCTCTGAGA |
| TCAACCACTGCAAGCGGAAGGGTGATCGAGGAATGGTGCTGCAGGGAGTGCACAATGCCCCACTGTCGTTCCGGGCTAAAG |
| ATGGCTGTTGGTATGGAATGGAGATAAGGCCCAGGAAAGAACCAGAAAGCAACTTAGTAAGGTCAATGGTGACTGCAGGATC |
| AACTGATCACATGGATCACTTCTCCCTTGGAGTGCTTGTGATTCTGCTCATGGTGCAGGAAGGGCTGAAGAAGAGAATGACCA |
| CAAAGATCATCATAAGCACATCAATGGCAGTGCTGGTAGCTATGATCTCTGGGAGGATTTTCAATGAGTGACCTGGCTAAGCTT |
| GCAATTTTGATGGGTGCCACCTTCGCGGAAATGAACACTGGAGGAGATGTAGCTCATCTGGCGCTGATAGCGGCATTCAAAGT |
| CAGACCAGCGTTGCTGGTATCTTTCATCTTCAGAGCTAATTGGACACCCCGTGAAAGCATGCTGCTGGCCTTGGCCTCGTGTCT |
| TTTGCAAACTGCGATCTCCGCTTGGAAGGCGACCTGATGGTTCTCATCAATGGTTTTGCTTTGGCCTGGTTGGCAATACGAGC |
| GATGGTTGTTCCACGCACTGATAACATCACCTTGGCAATCCTGGCTGCTCTGACACCACTGGCCCGGGGCACACTGCTTGTGGC |
| GTGGAGACAGGCCTTGCTACTTGCGGGGGGTTTATGCTCCTCTCTGAAGGGAAAAGGCAGTGTGAAGAAGAACTTACCA |
| TTTGTCATGGCCCTGGGACTAACCGCTGTGAGGCTGGTCGACCCCATCAACGTGGTGGGGCTGCTGTTGCTCACAAGGAGTGG |
| GAAGCGGAGCTGGCCCCCTAGCGAAGTACTCACAGCTGTTGGCCTGATATGCGCATTGGCTGGAGGGTTCGCCAAGGCAGAT |
| ATAGAGATGGCTGGGCCCATGGCCGCGGTCGGTCTGCTAATTGTCAGTTACGTGGTCTCAGGAAAGAGTGTGGACATGTACA |
| TTGAAAGAGCAGGTGACATCACATGGGAAAAAGATGCGGAAGTCACTGGAAACAGTCCCCGGCTCGATGTGGCGCTAGATGA |
| GAGTGGTGATTTCICCCTGGTGGAGGATGACGGTCCCCCCATGAGAGAGATCATACTCAAGGTGGTCCTGATGACCATCTGTG |
| GCATGAACCCAATAGCCATACCCTTTGCAGCTGGAGCGTGGTACGTATACGTGAAGACTGGAAAAAGGAGTGGTGCTCTATG |
| GGATGTGCCTGCTCCCAAGGAAGTAAAAAAGGGGGAGACCACAGATGGAGTGTACAGAGTAATGACTCGTAGACTGCTAGG |
| TTCAACACAAGTTGGAGTGGGAGTTATGCAAGAGGGGGTCTTTCACACTATGTGGCACGTCACAAAAGGATCCGCGCTGAGA |
| AGCGGTGAAGGGAGACTTGATCCATACTGGGGAGATGTCAAGCAGGATCTGGTGTCATACTGTGGTCCATGGAAGCTAGATG |
| CCGCCTGGGACGGGCACAGCGAGGTGCAGCTCTTGGCCGTGCCCCCCGGAGAGAGAGCGAGGAACATCCAGACTCTGCCCG |
| GAATATTTAAGACAAAGGATGGGGACATTGGAGCGGTTGCGCTGGATTACCCAGCAGGAACTTCAGGATCTCCAATCCTAGA |
| CAAGTGTGGGAGAGTGATAGGACTTTATGGCAATGGGGTCGTGATCAAAAATGGAGGTTATGTTAGTGCCATCACCCAAGGG |
| AGGAGGGAGGAAGAGACTCCTGTTGAGTGCTTCGAGCCTTCGATGCTGAAGAAGAAGCAGCTAACTGTCTTAGACTTGCATC |
| CTGGAGCTGGGAAAACCAGGAGAGTTCTTCCTGAAATAGTCCGTGAAGCCATAAAAACAAGACTCCGTACTGTGATCTTAGCT |
| CCAACCCAGGGTTGTCGCTGCTGAAATGGAGGAAGCCCTTAGGGGCTTCCAGTGCGTTATATGACAACAGCAGTCAATGTCAC |
| CCACTCTGGAACAGAAATCGTCGACTTAATGTGCCATGCCACCTTCACTTCACGTCTACTACAGCCAATCAGAGTCCCCAACTAT |
| AATCTGTATATTATGGATGAGGCCCACTTCACAGATCCCTCAAGTATAGCAGCAAGAGGATACATTTCAACAAGGGTTGAGAT |
| GGGCGAGGCGGCTGCCATCTTCATGACCGCCACGCCACCAGGAACCCGTGACGCATTTCCGGACTCCAACTCACCAATTATGG |
| ACACCGAAGTGGAAGTCCCAGAGAGAGCCTGGAGCTCAGGCTTTGATTGGGTGACGGATTATTCTGGAAAAACAGTTTGGTT |
| TGTTCCAAGCGTGAGGAACGGCAATGAGATCGCAGCTTGTCTGACAAAGGCTGGAAAACGGGTCATACAGCTCAGCAGAAG |
| ACTTTTTGAGACAGAGTTCCAGAAAACAAAACATCAAGAGTGGGACTTTGTCGTGACAACTGACATTTCAGAGATGGGCGCCAA |
| CTTTAAAGCTGACCGTGTCATAGATTCCAGGAGATGCCTAAAGCCGGTCATACTTGATGGCGAGAGAGTCATTCTGGCTGGAC |
| CCATGCCTGTCACACATGCCAGCGCTGCCCAGAGGAGGGGGCGCATAGGCAGGAATCCCAACAAACCTGGAGATGAGTATCT |
| GTATGGAGGTGGGTGCGCAGAGACTGACGAAGACCATGCACACTGGCTTGAAGCAAGAATGCTCCTTGACAATATTTACCTCC |
| AAGATGGCCTCATAGCCTCGCTCTATCGACCTGAGGCCGACAAAGTAGCAGCCATTGAGGGAGAGTTCAAGCTTAGGACGGA |
| GCAAAGGAAGACCTTTGTGGAACTCATGAAAAGAGGAGATCTTCCTGTTTGGCTGGCCTATCAGGTTGCATCTGCCGGAATAA |
| CCTACACAGATAGAAGATGGTGCTTTGATGGCACGACCAACAACACCATAATGGAAGACAGTGTGCCGGCAGAGGTGTGGAC |
| CAGACACGGAGAGAAAGAGTGCTCAAACCGAGGTGGATGGACGCCAGAGTTTGTTCAGATCATGCGGCCCTGAAGTCATTC |
| AAGGAGTTTGCCGCTGGGAAAAGAGGAGCGGCTTTTGGAGTGATGGAGGCCCTGGAACACTGCCAGGACACATGACAGAG |
| AGATTCCAGGAAGCCATTGACAACCTCGCTGTGCTCATGCGGGCAGAGACTGGAAGCAGGCCCTTACAAAGCCGCGGCGGCCC |
| AATTGCCGGAGACCCTAGAGACCATTATGCTTTTGGGGTTGCTGGGAACAGTCTCGCTGGGAATCTTTTCGTCTTGATGAGG |
| AACAAGGGCATAGGGAAGATGGGCTTTGGAATGGTGACTCTTGGGGCCAGCGCATGGCTCATGTGGCTCTCGGAAATTGAGC |
| CAGCCAGAATTGCATGTGTCCTCATTGTTGTGTTCCTATTGCTGGTCGTGCTCATACCTGAGCCAGAAAAGCAAAGATCTCCCC |
| AGGACAACCAAATGGCAATCATCATCATGGTAGCAGTAGGTCTTCTGGGCTTGATTACCGCCAATGAACTCGGATGGTTGGAG |
| AGAACAAAGAGTGACCTAAGCCATCTAATGGGAAGGAGAGAGGAGGGGGCAACCATGGGATTCTCAATGGACATTGACCTG |
| CGGCCAGCCTCAGCTTGGGCCATCTATGCTGCCTTGACAACTTTCATTACCCCAGCCGTCCAACATGCAGTGACCACTTCATACA |
| ACAACTACTCCTTAATGGCGATGGCCACGCAAGCTGGAGTGTTTTGGTATGGGGATGGCCATTCTACGCATGGAA |
| TTTGGAGTCCCGCTGCTAATGATAGGTTGCTACTCACAATTAACGCCCTGACCCTAATAGTGGCCATCATTTTGCTCGTGGCG |
| CACTACATGTACTTGATCCCAGGGCTGCAGGCAGCAGCTGCGCGTGCTGCCCAGAAGAGAACGGCAGCTGGCATCATGAAGA |
| ACCCTGTTGTGGATGGAATAGTGGTGACTGACATTGACACAATGACAATTGACCCCCAAGTGGAGAAAAAGATGGGACAGGT |
| GCTACTCATGGCAGTAGCCGTCTCCAGCGCCCATACTGTCGCGGACCGCCTGGGGGTGGGGGAGGCTGGGGCCTGATCACA |
| GCCGCAACTTCCACTTTGTGGGAAGGCTCTCCGAACAAGTACTGGAACTCCTCTACAACCACTTCACTGTGTAACATTTTTAGG |
| GGAAGTTACTTGGCTGGAGCTTCTCTAATCTACACAGTAACAAGAAACGCTGGCTTGGTCAAGAGACGTGGGGGTGGAACAG |
| GAGAGACCCTGGGAGAGAAATGGAAGGCCCGCTTGAACCAGATGTCGGCCCTGGAGTTCTACTCCTACAAAAAGTCAGGCAT |
| CACCGAGGTGTGCAGAGAAGAGGCCCGCCGCGCCCTCAAGGACGGTGTGGCAACGGGAGGCCATGCTGTGTCCCGAGGAAG |
| TGCAAAGCTGAGATGGTTGGTGGAGCGGGGATACCTGCAGCCCTATGGAAAAGTCATTGATCTTGGATGTGGCAGAGGGGG |
| CTGGAGTTACTACGCCGCCACCATCCGCAAAGTTCAAGAAGTGAAAGGATACACAAAAGGAGGCCCTGGTCATGAAGAACCC |
| GTGTTGGTGCAAAGCTATGGGTGGAACATAGTCCGTCTTAAGAGTGGGGTGGACGTCTTTCATATGGCGGCTGAGCCGTGTG |
| ACACGTTGCTGTGTGACATAGGTGAGTCATCATCTAGTCCTGAAGTGGAAGAAGCACGGACGCTCAGAGTCCTCTCCATGGTG |
| GGGGATTGGCTTGAAAAAGACCAGGAGCCTTTTGTATAAAAGTGTTGTGCCCATACACCAGCACTATGATGGAAACCCTGGA |
| GCGACTGCAGCGTAGGTATGGGGGAGGACTGGTCAGAGTGCCACTCTCCCGCAACTCTACACATGAGATGTACTGGGTCTCT |
| GGAGCGAAAAGCAACACCATAAAAAGTGTGTCCACCACGAGCCAGCTCCTCTTGGGGCGCATGGACGGCCTAGGAGGCCA |
| GTGAAATATGAGGAGGATGTGAATCTCGGCTCTGGCACGCGGGCTGTGGTAAGCTGCGCTGAAGCTCCCAACATGAAGATCA |
| TTGGTAACCGCATTGAAAGGATCCGCAGTGAGCACGCGGAAACGTGGTTCTTTGACGAGAACCACCCATATAGGACATGGGC |
| TTACCATGGAAGCTATGAGGCCCCCACACAAGGGTCAGCGTCCTCTCTAATAAACGGGGTTGTCAGGCTCCTGTCAAAACCCT |
| GGGATGTGGTGACTGGAGTCACAGGAATAGCCATGACCGACACCACACCGTATGGTCAGCAAAGAGTTTTCAAGGAAAAAGT |
| GGACACTAGGGTGCCAGACCCCCAAGAAGGTACTCGTCAGGTTATGAGCATGGTCTCTTCCTGGTTGTGAAAGAGCTAGGC |

-continued

SEQUENCES

AAACACAAACGGCCACGAGTCTGTACCAAAGAAGAGTTCATCAACAAGGTTCGTAGCAATGCAGCATTAGGGGCAATATTTGA
AGAGGAAAAAGAGTGGAAGACTGCAGTGGAAGCTGTGAACGATCCAAGGTTCTGGGCTCTAGTGGACAAGGAAAGAGAGCA
CCACCTGAGAGGAGAGTGCCAGAGTTGTGTGTACAACATGATGGGAAAAAGAGAAAAGAAACAAGGGGAATTTGGAAAGGC
CAAGGGCAGCCGCGCCATCTGGTATATGTGGCTAGGGGCTAGATTTCTAGAGTTCGAAGCCCTTGGATTCTTGAACGAGGATC
ACTGGATGGGGAGAGAGAACTCAGGAGGTGGTGTTGAAGGGCTGGGATTACAAAGACTCGGATATGTCCTAGAAGAGATGA
GTCGCATACCAGGAGGAAGGATGTATGCAGATGACACTGCTGGCTGGGACACCCGCATCAGCAGGTTTGATCTGGAGAATGA
AGCTCTAATCACCAACCAAATGGAGAAAGGGCACAGGGCCTTGGCATTGGCCATAATCAAGTACACATACCAAAACAAAGTG
GTAAAGGTCCTTAGACCAGCTGAAAAAGGGAAAACAGTTATGGACATTATTTCGAGACAAGACCAAAGGGGGAGCGGACAA
GTTGTCACTTACGCTCTTAACACATTTACCAACCTAGTGGTGCAACTCATTCGGAATATGGAGGCTGAGGAAGTCCTAGAGATG
CAAGACTTGTGGCTGCTGCGGAGGTCAGAGAAAGTGACCAACTGGTTGCAGAGCAACGGATGGGATAGGCTCAAACGAATG
GCAGTCAGTGGAGATGATTGCGTTGTGAAGCCAATTGATGATAGGTTTGCACATGCCCTCAGGTTCTTGAATGATATGGGAAA
AGTTAGGAAGGACACACAAGAGTGGAAACCCTCAACTGGATGGGACAACTGGGAAGAAGTTCCGTTTTGCTCCCACCACTTCA
ACAAGCTCCATCTCAAGGACGGGAGGTCCATTGTGGTTCCCTGCCGCCACCAAGATGAACTGATTGGCCGGGCCCGCGTCTCT
CCAGGGGCGGGATGGAGCATCCGGGAGACTGCTTGCCTAGCAAAATCATATGCGCAAATGTGGCAGCTCCTTTATTTCCACAG
AAGGGACCTCCGACTGATGGCCAATGCCATTTGTTCATCTGTGCCAGTTGACTGGGTTCCAACTGGGAGAACTACCTGGTCAAT
CCATGGAAAGGGAGAATGGATGACCACTGAAGACATGCTTGTGGTGTGGAACAGAGTGTGGATTGAGGAGAACGACCACAT
GGAAGACAAGACCCCAGTTACGAAATGGACAGACATTCCCTATTTGGGAAAAAGGGAAGACTTGTGGTGTGGATCTCTCATA
GGGCACAGACCGCGCACCACCTGGGCTGAGAACATTAAAAACACAGTCAACATGGTGCGCAGGATCATAGGTGATGAAGAA
AGTACATGGACTACCTATCCACCCAAGTTCGCTACTTGGGTGAAGAAGGGTCTACACCTGGAGTGCTGTAAGCACCAATCTTA
ATGTTGTCAGGCCTGCTAGTCAGCCACAGCTTGGGGAAAGCTGTGCAGCCTGTGACCCCCCCAGGAGAAGCTGGGAAACCAA
GCCTATAGTCAGGCCGAGAACGCCATGGCACGGAAGAAGCCATGCTGCCTGTGAGCCCCTCAGAGGACACTGAGTCAAAAAA
CCCCACGCGCTTGGAGGCGCAGGATGGGAAAAGAAGGTGGCGACCTTCCCCACCCTTCAATCTGGGGCCTGAACTGGAGATC
AGCTGTGGATCTCCAGAAGAGGGACTAGTGGTTAGAGGAGA

SEQ ID NO: 3
KU497555.1 Zika virus isolate Brazil-ZKV2015, Brazil, complete genome
CCAATCTGTGAATCAGACTGCGACAGTTCGAGTTTGAAGCGAAAGCTAGCAACAGTATCAACAGGTTTTATTTTGGATTTGGA
AACGAGAGTTTCTGGTCATGAAAAACCCAAAAAAGAAATCCGGAGGATTCCGGATTGTCAATATGCTAAAACGCGGAGTAGC
CCGTGTGAGCCCCTTTGGGGGCTTGAAGAGGCTGCCAGCCGGACTTCTGCTGGGTCATGGGCCCATCAGGATGGTCTTGGCG
ATTCTAGCCTTTTTGAGATTCACGGCAATCAAGCCATCACTGGGTCTCATCAATAGATGGGGTTCAGTGGGGAAAAAAGAGGC
TATGGAAATAATAAAGAAGTTCAAGAAAGATCTGGCTGCCATGCTGAGAATAATCAATGCCAGGAAGGAGAAGAAGAGACG
AGGCGCAGATACTAGTGTCGGAATCGTTGGCCTCCTGCTGACCACAGCTATGGCAGCGGAGGTCACTAGACGTGGGAGTGCA
TACTATATGTACTTGGACAGAAACGATGCTGGGGAGGCCATATCTTTTCCAACCACATTGGGGATGAATAAGTGTTATATACA
GATCATGGATCTTGGACACATGTGTGATGCCACCATGAGCTATGAATGCCCTATGCTGGATGAGGGGGTGGAACCAGATGAC
GTCGATTGTTGGTGCAACACGACGTCAACTTGGGTTGTGTACGGAACCTGCCATCACAAAAAAGGTGAAGCACGGAGATCTA
GAAGAGCTGTGACGCTCCCCTCCCATTCCACTAGGAAGCTGCAAACGCGGTCGCAAACCTGGTTGGAATCAAGAGAATACACA
AAGCACTTGATTAGAGTCGAAAATTGGATATTCAGGAACCCTGGCTTCGCGTTAGCAGCAGCTGCCATCGCTTGGCTTTTGGG
AAGCTCAACGAGCCAAAAGTCATATACTTGGTCATGATACTGCTGATTGCCCCGGCATACAGCATCAGGTGCATAGGAGTCA
GCAATAGGGACTTTGTGGAAGGTATGTCAGGTGGGACTTGGGTTGATGTTGTCTTGGAACATGGGGGTTGTGTCACCGTAAT
GGCACAGGACAAACCGACTGTCGACATAGAGCTGGTTACAACAACAGTCAGCAACATGGCGGAGGTAAGATCCTACTGCTAT
GAGGCATCAATATCAGACATGGCTTCGGACAGCCGCTGCCCAACACAAGGTGAAGCCTACCTTGACAAGCAATCAGACACTCA
ATATGTCTGCAAAAGAACGTTAGTGGACAGAGGCTGGGGAAATGGATGTGGACTTTTTGGCAAAGGGAGCCTGGTGACATGC
GCTAAGTTTGCATGCTCCAAGAAAATGACCGGGAAGAGCATCCAGCCAGAGAATCTGGAGTACCGGATAATGCTGTCAGTTC
ATGGCTCCCAGCACAGTGGGATGATCGTTAATGACACAGGACATGAAACTGATGAGAATAGAGCGAAGGTTGAGATAACGCC
CAATTCACCAAGAGCCGAAGCCACCCTGGGGGTTTTGGAAGCTTAGGACTTGATTGTGAACCGAGGACAGGCCTTGACTTTT
CAGATTTGTATTACTTGACTATGAATAACAAGCACTGGTTGGTTCACAAGGAGTGGTTCCACGACATTCCATTACCTTGGCACG
CTGGGGCAGACACCGGAACTCCACACTGGAACAACAAAGAAGCACTGGTAGAGTTCAAGGACGCACATGCCAAAAGGCAAA
CTGTCGTGGTTCTAGGGACTCAAGAAGGAGCAGTTCACACGCGCCCTTGCTGGAGCTCTGGAGGCTGAGATGGATGGTGCAAA
GGGAAGGCTGTCCTCTGCCACTTGAAATGTCGCCTGAAAATGGATAAACATAGGTTGAAGGCGTGTCATACTCCTTGTGTA
CCGCAGCGTTCACATTCACCAAGATCCCGGCTGAAACACTGCACGGGACAGTCACAGTGGAGGTACAGTACGCAGGGACAGA
TGGACCTTGCAAGGTTCCAGCTCAGATGGCGGTGGACATGCAAACTCTGACCCCAGTTGGGAGGTTGATAACCGCTAACCCCG
TAATCACTGAAAGCACTGAGAACTCTAAGATGATGCTGGAACTTGATCCACCATTTGGGGACTCTTACATTGTCATAGGAGTCG
GGGAGAAGAAGATCACCCACCACTGGCACAGGAGTGGCAGCCACCATTGGAAACAGCATTTGAAGCCACTGTGAGAGGTGCCA
AGAGAATGGCAGTCTTGGGAGACACAGCCTGGGACTTTGGATCAGTTGGAGGCGCTCTCAACTCATTGGGCAAGGGCATCCA
TCAAATTTTTGGAGCAGCTTTCAAATCATTGTTTGGAGGAATGTCCTGGTTCTCACAAATTCTCATTGGAACGTTGCTGATGTGG
TTGGGTCTGAACACAAAGAATGGATCTATTTCCCTTATGTGCTTGGCCTTAGGGGGAGTGTTGATCTTCTTATCCACAGCCGTC
TCTGCTGATGTGGGGTGCTCGGTGGACTTCTCAAAGAAGGAGACGAGATGTGGTCACAGGGGTGTTCGTCTACAACGATGTTG
AAGCCTGGAGGGACAGGTACAAGTACCATCCTGACTCTCCCCGTAGATTGGCAGCAGCAGTCAAGCAAGCCTGGGAAGATGG
TATCTGCGGGATCTCCTCTGTTTCAAGAATGGAAAACATCATGTGGAGATCAGTAGAAGGGGAGCTTAACGCAATCCTGGAAG
AGAATGGAGTTCAACTGACGGTCGTTGTGGGATCTGTAAAAAACCCCATGTGGAGAGGTCCACAGAGATTGCCCGTGCCTGT
GAACGAGCTGCCCCACGCTGGAAGGCTTGGGGGGAAATCGTACTTCGTCAGACAGCAAAGACAAATAACAGCTTTGTCGTG
GATGGTGACACACTGAAGGAATGCCCACTCAAACATAGAGCATGGAACAGCTTTCTTGTGGAGGATCATGGTTTCGGGGTAT
TTCACACTAGTGTCTGCTCAAGGTTAGAAGATTATTCATTAGAGTGTGATCCAGCCGTTATTGGAACAGCTGTTAAGGGA
AAGGAGGCTGTACACAGTGATCTAGGCTACTGGATTGAGAGTGAGAAGAATGACACATGGAGGCTGAAGAGGGCCCATCTG
ATCGAGATGAAAACATGTGAATGGCCAAAGTCCCACACATTGTGGACAGATGGAATAGAAGAGAGTGATCTGATCATACCCA
AGTCTTTAGCTGGGCCATCAGCCATCACAATACAGAGAGGGCTACAGGACCCAAATGAAGGGCCATGGCACAGTGAAGA
GCTTGAAATTCGGTTTGAGGAATGCCCAGGCACTAAGGTCCACGTGGAGGAAACATGTGGAACAAGAGGACCATCTCTGAGA
TCAACCACTGCAAGCGGAAGGGTGATCGAGGAATGGTGCTGCAGGGAGTGCACAATGCCCCACTGTCGTTCCGGGCTAAAG
ATGGCTGTTGGTATGGAATGGAGATAAGGCCCAGGAAAGAACCAGAAAGCAACTTAGTAAGGTCAATGGTGACTGCAGGATC
AACTGATCACATGGATCACTTCTCCCTTGGAGTGCTTGTGATTCTGCTCATGGTGCAGGAAGGGCTGAAGAAGAGAATGACCA
CAAAGATCATCATAAGCACATCAATGGCAGTGCTGGTAGCTATGATTCTGGGAGGATTTTCAATGAGTGACCTGGCTAAGCTT
GCAATTTTGATGGGTGCCACCTTCGCGGAAATGAACACTGGAGGAGATGTAGCTCATCTGGCGCTGATAGCGGCATTCAAAGT
CAGACCAGCGTTGCTGGTATCTTTCATCTTCAGAGCTAATTGGACACCCCGTGAAAGCATGCTGCTGGCCTTGGCCTCGTGTTT
TTTGCAAACTGCGATCTCCGCCTTGGAAGGCGACCTGATGGTTCTCATCAATGGTTTTGCTTTGGCCTGGTTGGCAATACGAGC
GATGGTTGTTCCACGCACTGACAACATCACCTTGGCAATCCTGGCTGCTCTGACACCACTGGCCCGGGGCACACTGCTTGTGGC
GTGGAGAGCAGGCCTTGCTACTTGCGGGGGGTTTATGCTCCTCTCTCTGAAGGGAAAGGCAGTGTGAAGAAGAACTTACCA
TTTGTCATGGCCCTGGGACTAACCGCTGTGAGGCTGGTCGACCCCATCAACGTGGTGGGACTGCTGTTGCTCACAAGGAGTGG -continued

SEQUENCES

```
GAAGCGGAGCTGGCCCCCTAGCGAAGTACTCACAGCTGTTGGCCTGATATGCGCATTGGCTGGAGGGTTCGCCAAGGCAGAT
ATAGAGATGGCTGGGCCCATGGCCGCGGTCGGTCTGCTAATTGTCAGTTACGTGGTCTCAGGAAAGAGTGTGGACATGTACA
TTGAAAGAGCAGGTGACATCACATGGGAAAAAGATGCGGAAGTCACTGGAAACAGTCCCCGGCTCGATGTGGCGCTAGATGA
GAGTGGTGACTTCTCCCTGGTGGAGGATGACGGTCCCCCCATGAGAGAGATCATACTCAAGGTGGTCCTGATGACCATCTGT
GCATGAACCCAATAGCCATACCCTTTGCAGCTGGAGCGTGGTACGTATACGTGAAGACTGGAAAAAGGAGTGGTGCTCTATG
GGATGTGCCTGCTCCCAAGGAAGTAAAAAAGGGGGAGACCACAGATGGAGTGTACAGAGTAATGACTCGTAGACTGCTAGG
TTCAACACAAGTTGGAGTGGGAGTTATGCAAGAGGGGGTCTTTCACACTATGTGGCACGTCACAAAAGGATCCGCGCTGAGA
AGCGGTGAAGGGAGACTTGATCCATACTGGGGAGATGTCAAGCAGGATCTGGTGTCATACTGTGGTCCATGGAAGCTAGATG
CCGCCTGGGACGGGCACAGCGAGGTGCAGCTCTTGGCCGTGCCCCCCGGAGAGAGAGCGAGGAACATCCAGACTCTGCCCG
GAATATTTAAGACAAAGGATGGGGACATTGGAGCGGTTGCGCTGGATTACCCAGCAGGAACTTCAGGATCTCCAATCCTAGA
CAAGTGTGGGAGAGTGATAGGACTTTATGGCAATGGGGTCGTGATAAAAAATGGGAGTTATGTTAGTGCCATCACCCAAGGG
AGGAGGGAGGAAGAGACTCCTGTTGAGTGCTTCGAGCCTTCGATGCTGAAGAAGAAGCAGCTAACTGTCTTAGACTTGCATC
CTGGAGCTGGGAAAACCAGGAGAGTTCTTCCTGAAATAGTCCGTGAAGCCATAAAAACAAGACTCCGTACTGTGATCTTAGCT
CCAACCAGGGTTGTCGCTGCTGAAATGGAGGAAGCCCTTAGAGGGCTTCCAGTGCGTTATATGACAACAGCAGTCAATGTCAC
CCACTCTGGAACAGAAATCGTCGACTTAATGTGCCATGCCACCTTCACTTCACGTCTACTACAGCCAATCAGAGTCCCCAACTAT
AATCTGTATATTATGGATGAGGCCCACTTCACAGATCCCTCAAGCATAGCAGCAAGAGGATACATTTCAACAAGGGTTGAGAT
GGGCGAGGCGGCTGCCATCTTCATGACCGCCACGCCACCAGGAACCCGTGACGCATTTCCGGACTCCAACTCACCAATTATGG
ACACCGAAGTGGAAGTCCCAGAGAGAGCCTGGAGCTCAGGCTTTGATTGGGTGACGGATCATTCTGGAAAAACAGTTTGGTT
TGTTCCAAGCGTGAGGAACGGCAATGAGATCGCAGCTTGTCTGACAAAGGCTGGAAAACGGGTCATACAGCTCAGCAGAAAG
ACTTTTGAGACAGAGTTCCAGAAAACAAAACATCAAGAGTGGGACTTTGTCGTGACAACTGACATTTCAGAGATGGGCGCCAA
CTTTAAAGCTGACCGTGTCATAGATTCCAGGAGATGCCTAAAGCCGGTCATACTTGATGGCGAGAGAGTCATTCTGGCTGGAC
CCATGCCTGTCACACATGCCAGCGCTGCCCAGAGGAGGGGCGCATAGGCAGGAATCCCAACAAACCTGGAGATGAGTACCT
GTATGGAGGTGGGTGCGCAGAGACTGACGAAGACCATGCACACTGGCTTGAAGCAAGAATGCTCCTTGACAATATTTACCTCC
AAGATGGCCTCATAGCCTCGCTCTATCGACCTGAGGCCGACAAGATAGCAGCCATTGAGGGAGAGTTCAAGCTTAGGACGGA
GCAAAGGAAGACCTTTGTGGAACTCATGAAAAGAGGAGATCTTCCTGTTTGGCTGGCCTATCAGGTTGCATCTGCCGGAATAA
CCTACACAGATAGAAGATGGTGCTTTGATGGCACGACCAACAACACCATAATGGAAGACAGTGTGCCGGCAGAGGTGTGGAC
CAGACACGGAGAGAAAGAGTGCTCAAACCGAGGTGGATGGACGCCAGATTTGTTCAGATCATGCGGCCCTGAAGTCATTC
AAGGAGTTTGCCGCTGGGAAAAGAGGAGCGGCTTTTGGAGTGAGTGAAGCCCTGGGAACACTGCCAGGACACATGACAGAG
AGATTCCAGGAAGCCATTGACAACCTCGCTGTGCTCATGCGGGCAGAGACTGGAAGCAGGCCTTACAAAGCCGCGGCGGCCC
AATTGCCGGAGACCCTAGAGACCATTATGCTTTTGGGGTTGCTGGGAACAGTCTCGCTGGGAATCTTTTTGCTCTTGATGAGG
AACAAGGGCATAGGGAAGATGGGCTTTGGAATGGTGACTCTTGGGGCAGCGCATGGCTCATGTGGCTCTCGGAAATTGAGC
CAGCCAGAATTGCATGTGTCCTCATTGTTGTGTTCCTATTGCTGGATTGTGCTCATACCTGAGCCAGAAAAGCAAAGATCTCCC
AGGACAACCAAATGGCAATCATCATCATGGTAGCAGTAGGTCTTCTGGGCTTGATTACCGCCAATGAACTCGGATGGTTGGAG
AGAACAAAGAGTGACCTAAGCCATCTAATGGGAAGGAGAGAGGAGGGGGCAACCATAGGATTCTCAATGGACATTGACCTG
CGGCCAGCCTCAGCTTGGGCCATCTATGCTGCCTTGACAACTTTCATTACCCCAGCCGTCCAACATGCAGTGACCACTTCATACA
ACAACTACTCCTTAATGGCGATGGCCACGCAAGCTGGAGTGTTGTTTGGTATGGGCAAAGGGATGCCATTCTACGCATGGGAN
TTTGGAGTCCCGCTGCTAATGATAGGTTGCTACTCACAATTAACACCCCTGACCCTAATAGTGGCCATCATTTTGCTCGTGGCGC
ACTACATGTACTTGATCCCAGGGCTGCAGGCAGCAGCTGCGCGTGCTGCCCAGAAGAGAACGGCAGCTGGCATCATGAAGAA
CCCTGTTGTGGATGGAATAGTGGTGACTGACATTGACACAATGACAATTGACCCCCCAAGTGGAGAAAAAGATGGGACAGGTG
CTACTCATAGCAGTAGCCGTCTCCAGCGCCATACTGTCGCGGACCGCCTGGGGGTGGGGGAGGCTGGGGCCTGATCACAG
CCGCAACTTCCACTTTGTGGGAAGGCTCTCCGAACAAGTACTGGAACTCCTCTACAGCGCACTTCACTGTGTAACATTTTAGGG
GAAGTTACTTGGCTGGAGCTTCTCTAATCTACACAGTAACAAGAAACGCTGGCTTGGTCAAGAGACGTGGGGGTGGAACAGG
AGAGACCCTGGGAGAGAAATGGAAGGCCCGCTTGAACACAGATGTCGGCCCTGGAGTTCTACTCCTACAAAAAGTCAGGCATC
ACCGAGGTGTGCAGAGAAGAGGCCCGCGCGCCCTCAAGGACGGTGTGGCAACGGGAGGCCATGCTGTGTCCCGAGGAAGT
GCAAAGCTGAGATGGTTGGTGGAGCGGGGATACCTGCAGCCCTATGGAAAGGTCATTGATCTTGGATGTGGCAGAGGGGC
TGGAGTTACTACGCCGCCACCATCCGCAAAGTTCAAGAAGTGAAAGGATACACAAAAGGAGGCCCTGGTCATGAAGAACCCG
TGTTGGTGCAAAGCTATGGGTGGAACATAGTCCGTCTTAAGAGTGGGGTGGACGTCTTTCATATGGCGGCTGAGCCGTGTGA
CACGTTGCTGTGTGACATAGGTGAGTCATCATCTAGTCCTGAAGTGGAAGAAGCACGGACGCTCAGAGTCCTCTCCATGGTGG
GGGATTGGCTTGAAAAAAGACCAGGAGCCTTTTGCATAAAAGTGTTGTGCCCATACATGCCACCTATGATGGAAAACCCTGGAG
CGACTGCAGCGTAGGTATGGGGAGGACTGGTCAGAGTGCCACTCTCCCGCAACTCTACACATGAGATGTACTGGGTCTCTG
GAGCGAAAAGCAACACCATAAAAAGTGTGTCCACCACGAGCCAGCTCCTCTTGGGGCGCATGGACGGGCCTAGGAGGCCAGT
GAAATATGAGGAGGATGTGAATCTCGGCTCTGGCACGCGGGCTGTGGTAAGCTGCGCTGAAGCTCCCAACATGAAGATCATT
GGTAACCGCATTGAAAGGATCCGCAGTGAGCACGCGGAAACGGATCTTCTTTGACGAAAACACCCATATAGGACATGGGCTT
ACCATGGAAGCTATGTGGCCCCCACACAAGGGTCAGCGTCCTCTCTAATAAACGGGGTTGTCAGGCTCCTGTCAAAACCCTGG
GATGTGGTGACTGGAGTCACAGGAATAGCCATGACCGACACCACACCGTATGGTCAGCAAAGAGTTTTCAAGGAAAAAGTGG
ACACTAGGGTGCCAGACCCCCAAGAAGGCACTCGTCAGGTTATGAGCATGGTCTCTTCCTGGTTGTGGAAAGAGCTAGGCAA
ACACAAACGACCACGAGTCTGTACCAAAGAAGAGTTCATCAACAAGGTTCGTAGCAATGCAGCATTAGGGGCAATATTTGAAG
AGGAAAAAGAGTGGAAGACTGCAGTGGAAGCTGTGAACGATCCAAGGTTCTGGGCTCTAGTGGACAAGGAAAGAGAGCACC
ACCTGAGAGGAGAGTGCCAGAGTTGTGTGTACAACATGATGGGAAAAAGAGAAAAGAAACAAGGGGAATTTGGAAAGGCCA
AGGGCAGCCGCGCCATCTGGTATATGTGGCTAGGGGCTAGATTTCTAGAGTTCGAAGCCCTTGGATTCTTGAACGAGGATCAC
TGGATGGGAGAGAGAACTCAGGAGGTGGTGTTGAAGGCTGGATTACAAAGACTCGGATATGTCCTAGAAGAGATGAGT
CGCATACCAGGAGGAAGGATGTATGCAGATGACACTGCTGGCTGGGACACCCGCATCAGCAGGTTTGATCTGGAGAATGAAG
CTCTAATCACCAACCAAATGGAGAAAGGGCACAGGGCCTTGGCATTGGCCATAATCAAGTACACATACCAAAACAAAGTGGTA
AAGGTCCTTAGACCAGCTGAAAAAGGGAAAACAGTTATGGACATTATTCGAGACAAGACCAAAGGGGAGCGGACAAGTT
GTCACTTACGCTCTTAACACATTTACCAACCTAGTGGTGCAACTCATTCGGAATATGGAGGCTGAGGAAGTTCTAGAGATGCAA
GACTTGTGGCTGCTGCGGAGGTCAGAGAAAGTGACCAACTGGTTGCAGGCAACGGATGGTAGGCTCAAACGAATGGCA
GTCAGTGGAGATGATTGCGTTGTGAAGCCAATTGATGATAGGTTTGCACATGCCCTCAGGTTCTTGAATGATATGGGAAAGT
TAGGAAGGACACACAAGAGTGGAAACCCTCAACTGGATGGGACAACTGGGAAGAAGTTCCGTTTTGCTCCCACCACTTCAACA
AGCTCCATCTCAAGGACGGGAGGTCCATTGTGGTTCCCTGCCGCCACCAAGATGAACTGATTGGCCGGGCCCGCGTCTCTCCA
GGGGCGGGATGGAGCATCCGGGAGACTGCTTGCCTAGCAAAATCATATGCGCAAATGTGGCAGCTCCTTTATTTCCACAGAA
GGGACCTCCGACTGATGGCCAATGCCATTTGTTCATCTGTGCCAGTTGGACTGGGTCAACTGGGAGAACTACCTGGTCAATCC
ATGGAAAGGAGAATGGATGACCACTGAAGACATGCTTGTGGTGTGGAACAGAGTGTGGATTGAGGAGAACGACCACATGG
AAGACAAGACCCCAGTTACGAAATGGACAGACATTCCCTATTTGGGAAAAAGGGAAGACTTGTGGTGTGGATCTCTCATAGG
GCACAGACCGCGCACCACCTGGGCTGAGAACATTAAAAATACAGTCAACATGGTGCGCAGGATCATAGGTGATGAAGAAAG
TACATGGACTACCTATCCACCCAAGTTCGCTACTTGGGTGAAGAAGGGTCTACACCTGGAGTGCTGTGAGCACCAATCTTAATG
TTGTCAGGCCTGCTAGTCAGCCACAGCTTGGGGAAAGCTGTGCAGCCTGTGACCCCTCCAGGAGAAGCTGGGTAACCAAGCCT
ATAGTCAGGCCGAGAACGCCATGGCACGGAAGAAGCCATGCTGCCTGTGAGCCCCTCAGAGGACACTGAGTCAAAAACCCC
```

ACGCGCTTGGAGGCGCAGGATGGGAAAAGAAGGTGGCGACCTTCCCCACCCTTCAATCTGGGGCCTGAACTGGAGATCAGCT
GTGGATCTCCAGAAGAGGGACTAGTGGTTAGAGGAGACCCCCCGGAAAACGCAAAACAGCATATTGACGCTGGGAAAGACC
AGAGACTCCATGAGTTTCCACCACGCTGGCCGCCAGGCACAGATCGCCGAATAGCGGCGGCCGGTGTGGGGAAATCCA

SEQ ID NO: 4
KU501215.1 Zika virus strain PRVABC59, Puerto Rico, complete genome
GTTGTTGATCTGTGTGAATCAGACTGCGACAGTTCGAGTTTGAAGCGAAAGCTAGCAACAGTATCAACAGGTTTTATTTTGGAT
TTGGAAACGAGAGTTTCTGGTCATGAAAAACCCAAAAAAGAAATCCGGAGGATTCCGGATTGTCAATATGCTAAAACGCGGA
GTAGCCCGTGTGAGCCCCTTTGGGGGCTTGAAGAGGCTGCCAGCCGGACTTCTGCTGGGTCATGGGCCCATCAGGATGGTCTT
GGCGATTCTAGCCTTTTTGAGATTCACGGCAATCAAGCCATCACTGGGTCTCATCAATAGATGGGGTTCAGTGGGGAAAAAAG
AGGCTATGGAAACAATAAAGAAGTTCAAGAAGATCTGGCTGCCATGCTGAGAATAATCAATGCTAGGAAGGAGAAGAAGA
GACGAGGCGCAGATACTAGTGTCGGAATTGTTGGCCTCCTGCTGACCACAGCTATGGCAGCGGAGGTCACTAGACGTGGGAG
TGCATACTATATGTACTTGGACAGAAACGATGCTGGGGAGGCCATATCTTTTCCAACCACATTGGGGATGAATAAGTGTTATAT
ACAGATCATGGATCTTGGACACATGTGTGATGCCACCATGAGCTATGAATGCCCTATGCTGGATGAGGGGGTGGAACCAGAT
GACGTCGATTGTTGGTGCAACACGACGTCAACTTGGGTTGTGTACGGAACCTGCCATCACAAAAAAGGTGAAGCACGGAGAT
CTAGAAGAGCTGTGACGCTCCCCTCCCATTCCACCAGGAAGCTGCAAACGCGGTCGCAAACCTGGTTGGAATCAAGAGAATAC
ACAAAGCACTTGATTAGAGTCGAAAATTGGATATTCAGGAACCCTGGCTTCGCGTTAGCAGCAGCTGCCATCGCTTGGCTTTTG
GGAAGCTCAACGAGCCAAAAAGTCATATACTTGGTCATGATACTGCTGATTGCCCCGGCATACAGCATCAGGTGCATAGGAGT
CAGCAATAGGGACTTTGTGGAAGGTATGTCAGGTGGGACTTGGGTTGATGTTGTCTTGGAACATGGAGGTTGTGTCACCGTA
ATGGCACAGGACAAACCGACTGTCGACATAGAGCTGGTTACAACAACAGTCAGCAACATGGCGGAGGTAAGATCCTACTGCT
ATGAGGCATCAATATCAGACATGGCTTCTGACAGCCGCTGCCCAACACAAGGTGAAGCCTACCTTGACAAGCAATCAGACACT
CAATATGTCTGCAAAAGAACGTTAGTGGACAGAGGCTGGGGAAATGGATGTGGACTTTTTGGCAAAGGGAGCCTGGTGACAT
GCGCTAAGTTTGCATGCTCCAAGAAAATGACCGGGAAGAGCATCCAGCCAGAGAATCTGGAGTACCGGATAATGCTGTCAGT
TCATGGCTCCCAGCACAGTGGGATGATCGTTAATGACCAGAGTGAAACTGATGAGAATAGAGCGAAAGTTGAGATAACG
CCCAATTCACCGAGAGCCGAAGCCACCCTGGGGGGTTTTGGAAGCCTAGGACTTGATTGTGAACGAGGACAGGCCTTGACTT
TTCAGATTTGTATTACTTGACTATGAATAACAAGCACTGGTTGGTTCACAAGGAGTGGTTCCACGACATTCCATTACCTTGGCAC
GCTGGGGCAGACACCGGAACTCCACACTGGAACAACAAAGAAGCACTGGTAGAGTTCAAGGACGCACATGCCAAAAGGCAA
ACTGTCGTGGTTCTAGGGAGTCAAGAAGGAGCAGTTCACACGGCCCTTGCTGGAGGCTCTGGAGGCTGGAGATGGATGGTGCAA
AGGGAAGGCTGTCCTCTGGCCACTTGAAATGTCGCCTGAAAATGGATAAACTTAGATTGAAGGCGTGTCATACTCCTTGTGT
ACTGCAGCGTTCACATTCACCAAGATCCCGGCTGAAACACTGCACGGGACAGTCACAGTGGAGGTACAGTACGCAGGGACAG
ATGGGACCTTGCAAGGTTCCAGCTCAGATGGCGGTGGACATGCAAACTCTGACCCCAGTTGGGAGGTTGATAACCGCTAACCCC
GTAATCACTGAAAGCACTGAGAACTCTAAGATGATGCTGGAACTTGATCCACCATTTGGGGACTCTTACATTGTCATAGGAGTC
GGGGAGAAGAAGATCACCCACCACTGGCACAGGAGTGGCAGCACCATTGGAAAAGCATTTGAAGCCACTGTGAGAGGTGCC
AAGAGAATGGCAGTCTTGGGAGACACAGCCTGGGACTTTGGATCAGTTGGAGGCGCTCTCAACTCATTGGGCAAGGGCATCC
ATCAAATTTTTGGAGCAGCTTTCAAATCATTGTTTGGAGGAATGTCCTGGTTCTCACAAATTCTCATTGGAACGTTGCTGATGTG
GTTGGGTCTGAACACAAAGAATGGATCTATTTCCCTTATGTGCTTGGCCTTAGGGGGAGTGTTGATCTTCTTATCCACAGCCGT
CTCTGCTGATGTGGGGTGCTCGGTGGACTTCTCAAAGAAGGAGACGAGATGCGGGTACAGGGGTCTTGTCTATAACGACGTT
GAAGCCTGGAGGGACAGGTACAAGTACCATCCTGACTCCCCCCGTAGATTGGCAGCAGCAGTCAAGCAAGCCTGGGAAGATG
GTATCTGCGGGATCCTCTGTTTCAAGAATGGAAAACATCATGTGGAGATCAGTAGAAGGGGAGCTCAACGCAATCCTGGAA
GAGAATGGAGTTCAACTGACGGTCGTTGTGGGATCTGTAAAAAACCCCATGTGGAGAGGTCCACAGAGATTGCCCGTGCCTG
TGAACGAGCTGCCCCACGGCTGGAAGGCTTGGGGGAAATCGTATTTCGTCAGAGCAGCAAAGACAAATAACAGCTTTGTCGT
GGATGGTGACACACTGAAGGAATGCCCACTCAAACATAGAGCATGGAACAGCTTTCTTGTGGAGGATCATGGGTTCGGGGTA
TTTCACACTAGTGTCTGGCTCAAGGTTAGAGAAGATTATTCATTAGAGTGTGATCAGCCGTTATTGGAACAGCTGTTAAGGGA
AAGGAGGCTGTACACAGTGATCTAGGCTACTGGATTGAGAGTGAGAAGAATGACACATGGAGGCTGAAGAGGGCCCATCTG
ATCGAGATGAAAACATGTGAATGGCCAAAGTCCCACACATTGGACAGATGGAATAGAAGGATGATCTGATCATACCCA
AGTCTTTAGCTGGGCCACTCAGCCATCACAATACCAGAGAGGGCTACAGGACCCAAATGAAAGGGCCATGGCACAGTGAAGA
GCTTGAAATTCGGTTTGAGGAATGCCCAGGCACTAAGGTCCACGTGGAGGAAACATGTGGAACAAGAGGACCATCTCTGAGA
TCAACCACTGCAAGCGGAAGGGTGATCGAGGAATGGTGCTGCAGGGAGTGCACAATGCCCCACTGTCGTTCCGGGCTAAAG
ATGGCTGTTGGTATGAATGAGATAAGGCCCAGGAAGAACCAGAAAGCAACTTAGTAAGGTCAATGGTGACTGCAGGATC
AACTGATCACATGGACCACTTCTCCCTTGGAGTGCTTGTGATCCTGCTCATGGTGCAGGAAGGGCTGAAGAAGAGAATGACCA
CAAAGATCATCATAAGCACATCAATGGCAGTGCTGGTAGCTATGATCCTGGGAGGATTTTCAATGAGTGACCTGGCTAAGCTT
GCAATTTTGATGGGTGCCACCTTCGCGGAAATGAACACTGGAGGAGATGTAGCTCATCTGGCGCTGATAGCGGCATTCAAAGT
CAGACCAGCCGTTGCTGGTATCTTTCATCTTCAGAGCTAATTGGACAACCCGTGAAAAGCATCGCTGCTGGCCTTGGCCTCTGTGTCT
TTTGCAAACTGCGATCTCCGCCTTGGAAGGCGACCTGATGGTTCTCATCAATGGTTTTGCTTTGGCCTGGTTGGCAATACGAGC
GATGGTTGTTCCACGCACTGATAACATCACCTTGGCAATCCTGGCTGCTCTGACACCACTGGCCCGGGGCACACTGCTTGTGGC
GTGGAGAGCAGGCCTTGCTACTTGCGGGGGGTTTATGCTCCTCTCTCTGAAGGGAAAAGGCAGTGTGAAGAAGAACTTACCA
TTTGTCATGGCTCTGGGACTAACCGCTGTGAGGCTGGTCGACCCCATCAACGTGGTGGGACTGCTGTTGCTCACAAGGAGTGG
GAAGCGGAGCTGGCCCCCTAGCGAAGTACTCACAGCTGTTGGCCTGATATGCGCATTGGCTGGAGGGTTCGCCAAGGCAGAT
ATAGAGATGGCTGGGCCCATGGCCGCGGTCGGTCTGCTAATTGTCAGTTACGTGGTCTCAGGAAAGAGTGTGGACATGTACA
TTGAAAGAGCAGGTGACATCACATGGGAAAAGATGCGGAAGTCACTGGAAACAGTCCCCGGCTCGATGGCGCTAGATGA
GAGTGGTGATTTCTCCTGGTGGAGGATGACGGTCCCCCCATGAGAGGATCATACTCAAGGTGGTCCTGATGACCATCTGTG
GCATGAACCCAATAGCCATACCCTTTGCAGCTGGAGCGTGGTACGTATACGTGAAGACTGGAAAAAGGAGTGGTGCTCTATG
GGATGTGCCTGCTCCCAAGGAAGTAAAAAAGGGGGAGACCACAGATGGAGTGTACAGAGTAATGACTCGTAGACTGCTAGG
TTCAACACAAGTTGGAGTGGGAGTTATGCAAGAGGGGGTCTTTCACACTATGTGGCACGTCACAAAAGGATCCGCGCTGAGA
AGCGGTGAAGGGAGACTTGATCCATACTGGGGAGATGTCAAGCAGGATCTGGTGTCATACTGTGGTCCATGGAAGCTAGATG
CCGCCTGGGATGGGCACAGCGAGGTGCAGCTCTTGGCCGTGCCCCCGGGAGAGAGAGCGAGGAACATCCAGACTCTGCCCG
GAATATTTAAGACAAAGGATGGGGACATTGGAGCGGTTGCGCTGGATTACCCAGCAGGAACTTCAGGATCTCCAATCCTAGA
CAAGTGTGGGAGAGTGATAGGACTTTATGGCAATGGGGTCGTGATCAAAAACGGGAGTTATGTTAGTGCCATCACCCAAGGG
AGGAGGGAGGAAGAGACTCCTGTTGAGTGCTTCGAGCCCTCGATGCTGAAGAAGAAGCAGCTAACTGTCTTAGACTTGCATC
CTGGAGCTGGGAAACCAGGAGAGTTCTTCCTGAAATAGTCCGTGAAGCCATAAAACAAGACTCCGTACTGTGATCTTAGCT
CCAACCAGGGTTGTCGCTGCTGAAATGGAGGAGGCCCTTAGAGGGCTTCCAGTGCGTTATATGACAACAGCAGTCAATGTCAC
CCACTCTGGAACAGAAATCGTCGACTTAATGTGCCATGCCACCTTCACTTCACGTCTACTACAGCCAATCAGATTCCCAACTAT
AATCTGTATATTATGGATGAGGCCCACTTCACAGATCCCTCAAGTATAGCAGCAAGAGGATACATTTCAACAAGGGTTGAGAT
GGGCGAGGCGGCTGCCATCTTCATGACCGCCACGCCACCAGGAACCCGTGACGCATTTCCGGACTCCAACTCACCAATTATGG
ACACCGAAGTGGAAGTCCCAGAGAGAGCCTGGAGCTCAGGCTTTGATTGGGTGACGGATCATTCTGGAAAAACAGTTTGGTT
TGTTCCAAGCGTGAGGAACGGCAATGAGATCGCAGCTTGTCTGACAAAGGCTGGAAAACGGGTCATACAGCTCAGCAGAAAG
ACTTTTGAGACAGAGTTCCAGAAAACAAAACATCAAGAGTGGGACTTTGTCGTGACAACTGACATTTCAGAGATGGGCGCCAA

| SEQUENCES |
|---|
| CTTTAAAGCTGACCGTGTCATAGATTCCAGGAGATGCCTAAAGCCGGTCATACTTGATGGCGAGAGAGTCATTCTGGCTGGAC |
| CCATGCCTGTCACACATGCCAGCGCTGCCCAGAGGAGGGGGCGCATAGGCAGGAATCCCAACAAACCTGGAGATGAGTATCT |
| GTATGGAGGTGGGTGCGCAGAGACTGACGAAGACCATGCGACTGCTTGAAGCAAGAATGCTCCTTGACAATATTTACCTCC |
| AAGATGGCCTCATAGCCTCGCTCTATCGACCTGAGGCCGACAAAGTAGCAGCCATTGAGGGAGAGTTCAAGCTTAGGACGGA |
| GCAAAGGAAGACCTTTGTGGAACTCATGAAAAGAGGAGATCTTCCTGTTTGGCTGGCCTATCAGGTTGCATCTGCCGGAATAA |
| CCTACACAGATAGAAGATGGTGCTTTGATGGCACGACCAACAACACCATAATGGAAGACAGTGTGCCGGCAGAGGTGTGGAC |
| CAGACACGGAGAGAAAAGAGTGCTCAAACCGAGGTGGATGGACGCCAGAGTTTGTTCAGATCATGCGGCCCTGAAGTCATTC |
| AAGGAGTTTGCCGCTGGGAAAGAGGAGCGGCTTTTGGAGTGATGGAAGCCCTGGGAACACTGCCAGGACACATGACAGAG |
| AGATTCCAGGAAGCCATTGACAACCTCGCTGTGCTCATGCGGGCAGAGACTGGAAGCAGGCCTTACAAAGCGCGGCGGCCC |
| AATTGCCGGAGACCCTAGAGACCATAATGCTTTTGGGGTTGCTGGGAACAGTCTCGCTGGGAATCTTCTTCGTCTTGATGAGG |
| AACAAGGGCATAGGGAAGATGGGCTTTGGAATGGTGACTCTTGGGGCCAGCGCATGGCTCATGTGGCTCTCGGAAATTGAGC |
| CAGCCAGAATTGCATGTGTCCTCATTGTTGTGTTCCTATTGCTGGTGGTGCTCATACCTGAGCCAGAAAAGCAAAGATCTCCCC |
| AGGACAACCAAATGGCAATCATCATCATGGTAGCAGTAGGTCTTCTGGGCTTGATTACCGCCAATGAACTCGGATGGTTGGAG |
| AGAACAAAGAGTGACCTAAGCCATCTAATGGGAAGGAGAGAGGAGGGGGCAACCATAGGATTCTCAATGGACATTGACCTG |
| CGGCCAGCCTCAGCTTGGGCCATCTATGCTGCCTTGACAACTTTCATTACCCCAGCCGTCCAACATGCAGTGACCACCTCATACA |
| ACAACTACTCCTTAATGGCGATGGCCACGCAAGCTGGAGTGTTGTTTGGCATGGGCAAAGGGATGCCATTCTACGCATGGGAC |
| TTTGGAGTCCCGCTGCTAATGATAGGTTGCTACTCACAATTAACACCCCTGACCCTAATAGTGGCCATCATTTTGCTCGTGGCGC |
| ACTACATGTACTTGATCCCAGGGCTGCAGGCAGCAGCTGCGCGTGCTGCCCAGAAGAGAACGGCAGCTGGCATCATGAAGAA |
| CCCTGTTGTGGATGGAATAGTGGTGACTGACATTGACACAATGACAATTGACCCCCAAGTGGAGAAAAAGATGGGACAGGTG |
| CTACTCATAGCAGTAGCCGTCTCCAGCGCCATACTGTCGCGGACCGCCTGGGGTTGGGGAGGCTGGGGTCTGATCACAG |
| CCGCAACTTCCACTTTGTGGGAAGGCTCTCCGAACAAGTACTGGAACTCCTCTACACCACTTCACTGTGTAACATTTTTAGGG |
| GAAGTTACTTGGCTGGAGCTTCTCTAATCTACACAGTAACAAGAAACGCTGGCTTGGTCAAGAGACGTGGGGGTGGAACAGG |
| AGAGACCCTGGGAGAGAAATGGAAGGCCCGCTTGAACCAGATGTCGGCCCTGGAGTTCTACTCCTACAAAAAGTCAGGCATC |
| ACCGAGGTGTGCAGAGAAGAGGCCCGCCGCAAGCTCAAGGACGGTGTGGCAACGGTGCATGCTGTTCTGTCCGAGGAAGT |
| GCAAAGCTGAGATGGTTGGTGGAGCGGGGATACCTGCAGCCCATGAAAGGTCATTGATCTTGGATGTGGCAGAGGGGGC |
| TGGAGTTACTACGTCGCCACCATCCGCAAAGTTCAAGAAGTGAAAGGATACACAAAAGGAGGCCCTGGTCATGAAGAACCCG |
| TGTTGGTGCAAAGCTATGGGTGGAACATAGTCCGTCTTAAGAGTGGGGTGGACGTCTTTCATATGGCGGCTGAGCCGTGTGA |
| CACGTTGCTGTGTGACATAGGTGAGTCATCATCTAGTCCTGAAGTGGAAGAAGCACGGACGCTCAGAGTCCTCTCCATGGTGG |
| GGGATTGGCTTGAAAAAAGACCAGGAGCCTTTTGTATAAAAGTGTTGTGCCCATACACCAGCACTATGATGGAAACCCTGGAG |
| CGACTGCAGCGTAGGTATGGGGAGGACTGGTCAGAGTGCCACTCTCCCGCAACTCTACACATGAGATGTACTGGGTCTCTG |
| GAGCGAAAAGCAACACCATAAAAAGTGTGTCCACCACGAGCCAGCTCCTCTTGGGGCGCATGGACGGGCCTAGGAGGCCAGT |
| GAAATATGAGGAGGATGTGAATCTCGGCTCTGGCACGCGGGCTGTGGTAAGCTGCGTGGCTGAAGCTCCCAACATGAAGATCATT |
| GGTAACCGCATTGAAAGGATCCGCAGTGAGCACGCGGAAACGTGGTTCTTTGACGAGAACCACCCATATAGGACATGGGCTT |
| ACCATGGAAGCTATGAGGCCCCCACACAAGGGTCAGCGTCCTCTCTAATAAACGGGGTTGTCAGGCTCCTGTCAAACCCTGG |
| GATGTGGTGACTGGAGTCACAGGAATAGCCATGACCGACACCACACCGTATGGTCAGCAAAGAGTTTTCAAGGAAAAAGTGG |
| ACACTAGGGTGCCAGACCCCCAAGAAGGCACTCGTCAGGTTATGAGCATGGTCTCTTCCTGGTTGTGGAAAGAGCTAGGCAA |
| ACACAAACGGCCACGAGTCTGCACCAAAGAAGAGTTCATCAACAAGGTTCGTAGCAATGCAGCATTAGGGGCAATATTTGAA |
| GAGGAAAAAGAGTGGAAGACTGCAGTGGAAGCTGTGAACGATCCAAGGTTCTGGGCTCTAGTGGACAAGGAAAGAGAGCAC |
| CACCTGAGAGGAGAGTGCCAGAGCTGTGTGTACAACATGATGGGAAAAAGAGAAAAGAAACAAGGGGAATTTGGAAAGGCC |
| AAGGGCAGCCGCCGCCATCTGGTATATGTGGCTAGGGGCTAGATTTCTAGAGTTCGAAGCCCTTGGATTCTTGAACGAGGATCA |
| CTGGATGGGAGAGAACTCAGGAGGTGGTGTTGAAGGGCTGGGATTACAAAGACTCGGATATGTCCTAGAAGAGATGAG |
| TCGTATACCAGGAGGAAGGATGTATGCAGATGACACTGCTGGCTGGGACACCCGCATTAGCAGGTTTGATCTGGAGAATGAA |
| GCTCTAATCACCAACCAAATGGAGAAAGGGCACAGGGCCTTGGCATTGGCCATAATCAAGTACACATACCAAAACAAAGTGGT |
| AAAGGTCCTTAGACCAGCTGAAAAAGGGAAAACAGTTATGGACATTATTCGAGACAAGACCAAAGGGGGAGCGGACAAGTT |
| GTCACTTACGCTCTTAACACATTTACCAACCTAGTGGTGCAACTCATTCGGAACTCATCGGATATGGAGGCTGAGGAAGTTCTAGAGATGCAA |
| GACTTGTGGCTGCTGCGGAGGTCAGAGAAAGTGACCAACTGGTTGCAGAGCAACGGATGGGATAGGCTCAAACGAATGGCA |
| GTCAGTGGAGATGATTGCGTTGTGAAGCCAATTGATGATAGGTTTGCACATGCCCTCAGGTTCTTGAATGATATGGGAAAGT |
| TAGGAAGGACACACAAGAGTGGAAACCCTCAACTGGATGGGACAACTGGGAAGAAGTTCCGTTTTGCTCCCACCACTTCAACA |
| AGCTCCATCTCAAGGACGGGAGGTCCATTGTGGTTCCTGCCACCAAGATGAACTGATTGGCCGGGCCCGCGTCTCTCCA |
| GGGGCGGGATGGAGCATCCGGGAGACTGCTTGCCTAGCAAAATCATATGCGCAAATGTGGCAGCTCCTTTATTTCCACAGAA |
| GGGACCTCCGACTGATGGCCAATGCCATTTGTTCATCTGTGCCAGTTGACTGGGTTCCAACTGGGAGAACTACCTGGTCAATCC |
| ATGGAAAGGGAGAATGGATGACCACTGAAGACATGCTTGGTGTGGAACAGAGTGTGGATTGAGGAGAACGACCACATGG |
| AAGACAAGACCCAGTTACGAAATGGACAGACATTCCCTATTTGGGAAAAAGGGAAGACTTGTGGTGTGGATCTCTCATAGG |
| GCACAGACCGCGCACCACCTGGGCTGAGAACATTAAAAACACAGTCAACATGGTGCGCAGGATCATAGGTGATGAAGAAAAG |
| TACATGGACTACCTATCCACCCAAGTTCGCTACTTGGGTGAAGAAGGGTCTACACCTGGAGTGCTGTAAGCACCAATCTTAATG |
| TTGTCAGGCCTGCTAGTCAGCCACAGCTTGGGGAAAGCTGTGCAGCCTGTGACCCCCCAGGAGAAGCTGGGAAACCAAGCC |
| TATAGTCAGGCCGAGAACGCCATGGCACGGAAGAAGCCATGCTGCCTGTGAGCCCCTCAGAGGACACTGAGTCAAAAACCC |
| CACGCGCTTGGAGGCGCAGGATGGGAAAGAAGGTGGCGACCTTCCCCACCCTTCAATCTGGGGCCTGAACTGGAGATCAGC |
| TGTGGATCTCCAGAAGAGGGACTAGTGGTTAGAGGA |

SEQ ID NO: 5
KU509998.1 Zika virus strain Haiti/1225/2014, Haiti, complete genome
GTTGTTACTGTTGCTGACTCAGACTGCGCACAGTTCGAGTTTGAAGCGAAAGCTAGCAACAGTATCAACAGGTTTTATTTGGATT
TGGAAACGAGAGTTTcTGGTCATGAAAAACCCAAAAAAGAAATCCGGAGGGTTCCGGATTGTCAATATGCTAAAACGCGGAG
TAGCCCGTGTGAGCCCCTTTGGGGGCTTGAAGAGGCTGCCAGCCGGACTTCTGCTGGGTCATGGGCCCATCAGGATGGTCTTG
GCAATTCTAGCCTTTTTGAGATTCACGGCAATCAAGCCATCACTGGGTCTCATAAATAGATGGGGTTCAGTGGGGAAAAAAGA
GGCTATGGAAATAATAAAGAAGTTCAAGAAAGATCTGGCTGCCATGCTGAGAATAATCAATGCTAGGAAGGAGAAGAAGAG
ACGAGGCGCAGATACTAGTGTCGGAATTGTTGGCCTCCTGCTGACCACAGCTATGGCAGCGGAGGTCACTAGACGTGGGAGT
GCATACTATATGTACTTGGACAGAAACGATGCTGGGGAGGCCATATCTTTTCCAACCACATTGGGGATGAATAAGTGTTATAT
ACAGATCATGGATCTTGGACACATGTGTGATGCCACCATGAGCTATGAATGCCCTATGCTGGATGAGGGGTGGAACCAGAT
GACGTCGATTGTTGGTGCAACACGACGTCAACTTGGGTTGTACGGAACCTGCAAAAAAAGGTGAAGATCCTCTGCATGGAT
CTAGAAGAGCTGTGACGCTCCCCTCCCATTCCACTAGGAAGCTGCAAACGCGGTCGCAAACCTGGTTGGAATCAAGAGAATAC
ACAAAGCACTTGATTAGAGTCGAAAATTGGATATTCAGGAACCCTGGCTTCGCGTTAGCAGCAGCTGCCATCGCTTGGCTTTTG
GGAAGCTCAACGAGCCAAAAAGTCATATACTTGGTCATGATACTGCTGATTGCCCCGGCATACAGCATCAGGTGCATAGGAGT
CAGCAATAGGGACTTTGTGGAAGGTATGTCAGGTGGGACTTGGGTTGATGTTGTCTTGGAACATGGAGGTTGTGTCACCGTA
ATGGCACAGGACAAACCGACTGTCGACATAGAGCTGGTTACAACAACAGTCAGCAACATGGCGGAGGTAAGATCCTACTGCT
ATGAGGCATCAATATCAGACATGGCTTCGGACAGCCGCTGCCCAACACAAGGTGAAGCCTACCTTGACAAGCAATCAGACACT

| SEQUENCES |
|---|
| CAATATGTCTGCAAAAGAACGTTAGTGGACAGAGGCTGGGGAAATGGATGTGGACTTTTTGGCAAAGGGAGTCTGGTGACAT |
| GCGCTAAGTTTGCATGCTCCAAGAAAATGACCGGGAAGAGCATCCAGCCAGAGAATCTGGAGTACCGGATAATGCTGTCAGT |
| TCATGGCTCCCAGCACAGTGGGATGATCGTTAATGACACAGGACATGAAACTGATGAGAATAGAGCGAAGGTTGAGATAACG |
| CCCAATTCACCAAGAGCCGAAGCCACCCTGGGGGGTTTTGGAAGCCTAGGACTTGATTGTGAACCGAGGACAGGCCTTGACTT |
| TTCAGATTTGTATTACTTGACTATGAATAACAAGCACTGGTTGGTTCACAAGGAGTGGTTCCACGACATTCCATTCCTTGGCAC |
| GCTGGGGCAGACACCGGAACTCCACACTGGAACAACAAAGAAGCACTGGTAGAGTTCAAGGACGCACATGCCAAAAGGCAA |
| ACTGTCGTGGTTCTAGGGAGTCAAGAAGGAGCAGTTCACACGGCCCTTGCTGGAGCTCTGGAGGCTGAGATGGATGGTGCAA |
| AGGGAAGGCTGTCCTCTGGCCACTTGAAATGTCGCCTGAAAATGGATAAACTTAGATTGAAGGGCGTGTCATACTCCTTGTGT |
| ACCGCAGCGTTCACATTCACCAAGATCCCGGCTGAAACACTGCACGGGACAGTCACAGTGGAGGTACAGTACGCAGGGACAG |
| ATGGACCTTGCAAGGTTCCAGCTCAGATGGCGGTGGACATGCAAACTCTGACCCCAGTTGGGAGGTTGATAACCGCTAACCCC |
| GTAATCACTGAAAGCACTGAGAACTCTAAGATGATGCTGGAACTTGATCCCACCATTTGGGGACTCTTACATTGTCATAGGAGTC |
| GGGGAGAAGAAGATCACCCACCACTGGCACAGGAGTGGCAGCACCATTGGAAAAGCATTTGAAGCCACTGTGAGAGGTGCC |
| AAGAGAATGGCAGTCTTGGAGACACAGCCTGGGACTTTGGATCAGTTGGAGGCGCTCTCAACTCATTGGGCAAGGGCATCC |
| ATCAAATTTTTGGAGCAGCTTTCAAATCATTGTTTGGAGGAATGTCCTGGTTCTCACAAATTCTCATTGGAACGTTGCTGATGTG |
| GTTGGGTCTGAACACAAAGAATGGATCTATTTCCCTTATGTGCTTGGCCTTAGGGGGAGTGTTGATCTTCTTATCCACAGCCGT |
| CTCTGCTGATGTGGGGTGCTCGGTGGACTTCTCAAAGAAGGAGACGAGATGCGGTACAGGGGTGTTCGTCTATAACGACGTT |
| GAAGCCTGGAGGGACAGGTACAAGTACCATCCTGACTCCCCCCGTAGATTGGCAGCAGCAGTCAAGCAAGCCTGGGAAGATG |
| GTATCTGCGGGATCTCCTCTGTTTCAAGAATGGAAAACATCATGTGGAGATCAGTAGAAGGGGAGCTCAACGCAATCCTGGAA |
| GAGAATGGAGTTCAACTGACGGTCGTTGTGGGATCTGTAAAAAACCCCATGTGGAGAGGTCCACAGAGATTGCCCGTGCCTG |
| TGAACGAGCTGCCCCCACGGCTGGAAGGCTTGGGGGAAATCGCACTTCGTCAGACGCGACAAAGACAAATAACAGCTTTGTCGT |
| GGATGGTGACACACTGAAGGAATGCCCACTCAAACATAGAGCATGGAACAGCTTTCTTGTGGAGGATCATGGGTTCGGGGTA |
| TTTCACACTAGTGTCTGGCTCAAGGTTAGAGAAGATTATTCATTAGAGTGTGATCCAGCCGTTATTGGAACAGCTGTTAAGGGA |
| AAGGAGGCTGTACACAGTGATCTAGGCTACTGGATTGAGAGTGAGAAGAATGACACATGGAGGCTGAAGAGGGCCCATCTG |
| ATCGAGATGAAAACATGTGAATGGCCAAAGTCCCACACATTGTGGACAGATGGAATAGAAGAGAGTGATCTGATCATACCCA |
| AGTCTTTAGCTGGGCCACTCAGCCATCACAATACCAGAGAGGGCTACAGGACCCAAATGAAAGGGCCATGGCACAGTGAAGA |
| GCTTGAAATTCGGTTTGAGGAATGCCCAGGCACTAAGGTCCACGTGGAGGAAACATGTGGAACAAGAGGACCATCTCTGAGA |
| TCAACCACTGCAAGCGGAAGGGTGATCGAGGAATGGTGCTGCAGGGAGTGCACAATGCCCCACTGTCGTTCCGGGCTAAAG |
| ATGGCTGTTGGTATGGAATGGAGATAAGGCCCAGGAAAGAACCAGAAAGCAACTTAGTAAGGTCAATGGTGACTGCAGGATC |
| AACTGATCACATGGATCACTTCTCCCTTGGAGTGCTTGTGATTCTGCTCATGGTGCAGGAAGGGCTGAAGAAGAGAATGACCA |
| CAAAGATCATCATAAGCACATCAATGGCAGTGCTGGTAGCTATGATCCTGGGAGGATTTTCAATGAGTGACCTGGCTAAGCTT |
| GCAATTTTGATGGGTGCCACCTTCGCGGAAATGAACACTGGAGGAGATGTAGCTCATCTGGCGCTGATAGCGGCATTCAAAGT |
| CAGACCAGCGTTGCTGGTATCTTTTCATCTTCAGAGCTAATTGGACACCCCGTGAAAGCATGCTGCTGGCCTTGGCCTCGTGTCT |
| TTTGCAAACTGCGATCTCCGCCTTGGAAGGCGACCTGATGGTTCTCATCAATGGTTTTGCTTTGGCCTGGTTGGCAATACGAGC |
| GATGGTTGTTCCACGCACTGATAACATCACCTTGGCAATCCTGGCTGCTCTGACACCACTGGCCCGGGGCACACTGCTTGTGGC |
| GTGGAGAGCAGGCCTTGCTACTTGCGGGGGGTTTATGCTCCTCTCTCTGAAGGGAAAAGGCAGTGTGAAGAAGAACTTACCA |
| TTTGTCATGGCCCTGGGACTAACCGCTGTGAGGCTGGTCGACCCCATCAACGTGGTGGGCTGCTGTTGCTCACAAGGAGTGG |
| GAAGCGGAGCTGGCCCCCTAGCGAAGTACTCACAGCTGTTGGCCTGATATGCGCATTGGCTGGAGGGTTCGCCAAGGCAGAT |
| ATAGAGATGGCTGGGCCCATGGCCGCGGTCGGTCTGCTAATTGTCAGTTACGTGGTCTCAGGAAAGAGTGTGGACATGTACA |
| TTGAAAGAGCAGGTGACATCACATGGGAAAAAGATGCGGAAGTCACTGGAAACAGTCCCCGGCTCGATGTGGCGCTAGATGA |
| GAGTGGTGATTTCTCCCTGGTGGAGGATGACGGTCCCCCCATGAGAGAGATCATACTCAAGGTGGTCCTGATGACCATCTGTG |
| GCATGAACCCAATAGCCATACCCTTTGCAGCTGGAGCGTGGTACGTATACGTGAAGACTGGAAAAAGGAGTGGTGCTCTATG |
| GGATGTGCCTGCTCCCAAGGAAGTAAAAAAGGGGGAGACCCACAGATGGAGTGTACAGAGTAATGACTCGTAGACTGCTAGG |
| TTCAACACAAGTTGGAGTGGGAGTTATGCAAGAGGGGGTCTTTCACACTATGTGGCACGTCACAAAAGGATCCGCGCTGAGA |
| AGCGGTGAAGGGAGACTTGATCCATACTGGGGAGATGTCAAGCAGGATCTGGTGTCATACTGTGGTCCATGGAAGCTAGATG |
| CCGCCTGGGACGGGCACAGCGAGGTGCAGCTCTTGGCCGTGCCCCCCGGAGAGGAGGCGAGGAACATCCAGACTCTGCCCG |
| GAATATTTAAGACAAAGGATGGGGACATTGGAGCGGTTGCGCTGGATTACCCAGCAGGAACTTCAGGATCTCCAATCCTAGA |
| CAAGTGTGGGAGAGTGATAGGACTTTATGGCAATGGGGTCGTGATCAAAAATGGGAGTTATGTTAGTGCCATCACCCAAGGG |
| AGGAGGGAGGAAGAGACTCCTGTTGAGTGCTTCGAGCCTTCGATGCTGAAGAAGAAGCAGCTAACTGTCTTAGACTTGCATC |
| CTGGAGCTGGGAAAACCAGGAGAGTTCTTCCTGAAATAGTCCGTGAAGCCATAAAAACAAGACTCCGTACTGTGATCTTAGCT |
| CCAACCAGGGTTGTCGCTGCTGAAATGGAGGAAGCCCTTAGAGGGCTTCCAGTGCGTTATATGACAACAGCAGTCAATGTCAC |
| CCACTCTGGAACAGAAATCGTCGACTTAATGTGCCATGCCACCTTCACTTCACGTCTACTACAGCCAATCAGAGTCCCCAACTAT |
| AATCTGTATATTATGGATGAGGCCCACTTCACAGATCCCTCAAGTATAGCAGCAAGAGGATACATTTCAACAAGGGTTGAGAT |
| GGGCGAGGCGGCTGCCATCTTCATGACCGCCACGCCACCAGGAACCCGTGACGCATTTCCGGACTCCAACTCACCAATTATGG |
| ACACCGAAGTGGAAGTCCCAGAGAGAGCCTGGAGCTCAGGCTTTGATTGGGTGACGGATTATTCTGGAAAAACAGTTTGGTT |
| TGTTCCAAGCGTGAGGAACGGCAATGAGATCGCAGCTTGTCTGACAAAGGCTGGAAAACGGGTCATACAGCTCAGCAGAAAG |
| ACTTTTGAGACAGAGTTCCAGAAAACAAAACATCAAGAGTGGGACTTTGTCGTGACAACTGACATTTCAGAGATGGGCGCCAA |
| CTTTAAAGCTGACCGTGTCATAGATTCCAGGAGATGCCTAAAGCCCGTCATACTTGATGGCGAGAGAGTCATTCTGGCTGGAC |
| CCATGCCTGTCACACATGCCAGCGCTGCCCAGAGGAGGGGCGCATAGGCAGGAATCCCAACAAACCTGGAGATGAGTATCT |
| GTATGGAGGTGGGTGCGCAGAGACTGACGAAGACCATGCACACTGGCTTGAAGCAAGAATGCTCCTTGACAATATTTACCTCC |
| AAGATGGCCTCATAGCCTCGCTCTATCGACCTGAGGCCGACAAAGTAGCAGCCATTGAGGGAGAGTTCAAGCTTAGGACGGA |
| GCAAAGGAAGACCTTTGTGGAACTCATGAAAAGAGGAGATCTTCCTGTTTGGCTGGCCTATCAGGTTGCATCTGCCGGAATAA |
| CCTACACAGATAGAAGATGGTGCTTTGATGGCACGACCAACAACACCATAATGGAAGACAGTGTGCCGGCAGAGGTGTGGAC |
| CAGACACGGAGAGAAAGAGTGCTCAAACCGAGGTGGATGGACGCCAGAGTTTGTTCAGATCATGCGGCCCTGAAGTCATTC |
| AAGGAGTTTGCCGCTGGGAAAAGAGGAGCGGCTTTTGGAGTGATGGAAGCCCTGGGAACACTGCCAGGACACATGACAGAG |
| AGATTCCAGGAAGCCATTGACAACCTCGCTGTGCTCATGCGGGCAGAGACTGGAAGCAGGCCTTACAAAGCCGCGGCGGCCC |
| AATTGCCGGAGACCCTAGAGACCATTATGCTTTTGGGGTTGCTGGGAACAGTCTCTCTGGGGATCTTTTTGCTCTTGATGAGG |
| AACAAGGGCATAGGGAAGATGGGCTTTGGAATGGTGACTCTTGGGGCCAGCGCATGGCTCATGTGGCTCTCGGAAATTGAGC |
| CAGCCAGAATTGCATGTGTCCTCATTGTTGTGTTCCTATTGCTGGTGGTGCTCATACCTGAGCCAGAAAAGCAAAGATCTCCCC |
| AGGACAACCAAATGGCAATCATCATCATGGTAGCAGTAGGTCTTCTGGGCTTGATTACCGCAATGAACTCGGATGGTTGGAG |
| AGAACAAAGAGTGACCTAAGCCATCTAATGGGAAGGAGAGGAGGGGCAACCATGGGATTCTCAATGGACATTGACCTG |
| CGGCCAGCCTCAGCTTGGGCCATCTATGCTGCCTTGACAACTTTCATTACCCCAGCCGTCCAACATGCAGTGACCACTTCATACA |
| ACAACTACTCCTTAATGGCGATGGCCACGCAAGCTGGAGTGTTGTTTGGTATGGGCAAAGGATGCCATTCTACGCATGGGAC |
| TTTGAGTCCCGCTGCTAATGATAGGTTGCTACTCACAATTAACGCCCCTGACCCTAATAGTGGCCATCATTTTGCTCGTGGCG |
| CACTACATGTACTTGATCCCAGGGCTGCAGGCAGCAGCTGCGCGTGCTGCCCAGAAAGAGAACGGCAGCTGGCATCATGAAGA |
| ACCCTGTTGTGGATGGAATAGTGGTGACTGACATTGACACAATGACAATTGACCCCCAAGTGGAGAAAAAGATGGGACAGGT |
| GCTACTCATGGCAGTAGCCGTCTCCAGCGCCATACTGTCGCGGACCGCCTGGGGTGGGGGAGGCTGGGGCCCTGATCACA |
| GCCGCAACTTCCACTTTGTGGGAAGGCTCTCCGAACAAGTACTGGAACTCCTCTACAGCCACTTCACTGTGTAACATTTTAGG |

-continued

SEQUENCES

GGAAGTTACTTGGCTGGAGCTTCTCTAATCTACACAGTAACAAGAAACGCTGGCTTGGTCAAGAGACGTGGGGGTGGAACAG
GAGAGACCCTGGGAGAGAAATGGAAGGCCCGCTTGAACCAGATGTCGGCCCTGGAGTTCTACTCCTACAAAAAGTCAGGCAT
CACCGAGGTGTGCAGAGAAGAGGCCCGCCGCGCCCTCAAGGACGGTGTGGCAACGGGAGGCCATGCTGTGTCCCGAGGAAG
TGCAAAGCTGAGATGGTTGGTGGAGCGGGGATACCTGCAGCCCTATGGAAAGGTCATTGATCTTGGATGTGGCAGAGGGGG
CTGGAGTTACTACGCCGCCACCATCCGCAAAGTTCAAGAAGTGAAAGGATACACAAAAGGAGGCCCTGGTCATGAAGAACCC
GTGTTGGTGCAAAGCTATGGGTGGAACATAGTCCGTCTTAAGAGTGGGGTGGACGTCTTTCATATGGCGGCTGAGCCGTGTG
ACACGTTGCTGTGTGACATAGGTGAGTCATCATCTAGTCCTGAAGTGGAAGAAGCACGGACGCTCAGAGTCCTCTCCATGGTG
GGGGATTGGCTTGAAAAAAGACCAGGAGCCTTTTGTATAAAAGTGTTGTGCCCATACACCAGCACTATGATGGAAACCCTGGA
GCGACTGCAGCGTAGGTATGGGGGAGGACTGGTCAGAGTGCCACTCTCCCGCAACTCTACACATGAGATGTACTGGGTCTCT
GGAGCGAAAAGCAACACCATAAAAAGTGTGTCCACCACGAGCCAGCTCCTCTTGGGGCGCATGGACGGGCCTAGGAGGCCA
GTGAAATATGAGGAGGATGTGAATCTCGGCTCTGGCACGCGGGCTGTGGTAAGCTGCGCTGAAGCTCCCAACATGAAGATCA
TTGGTAACCGCATTGAAAGGATCCGCAGTGAGCACGCGGAAACGTGGTTCTTTGACGAGAACCACCCATATAGGACATGGGC
TTACCATGGAAGCTATGAGGCCCCCACACAAGGGTCAGCGTCCTCTCTAATAAACGGGGTTGTCAGGCTCCTGTCAAAACCCT
GGGATGTGGTGACTGGAGTCACAGGAATAGCCATGACCGACACCACACCGTATGGTCAGCAAAGAGTTTTCAAGGAAAAAGT
GGACACTAGGGTGCCAGACCCCCAAGAAGGCACTCGTCAGGTTATGAGCATGGTCTCTTCCTGGTTGTGGAAAGAGCTAGGC
AAACACAAACGGCCACGAGTCTGTACCAAAGAAGAGTTCATCAACAAGGTTCGTAGCAATGCAGCATTAGGGGCAATATTTGA
AGAGGAAAAAGAGTGGAAGACTGCAGTGGAAGCTGTGAACGATCCAAGGTTCTGGGCTCTAGTGGACAAGGAAAGAGAGCA
CCACCTGAGAGGAGAGTGCCAGAGTTGTGTGTACAACATGATGGGAAAAAGAGAAAAGAAACAAGGGGAATTTGGAAAGGC
CAAGGGCAGCCGCGCCATCTGGTATATGTGGCTAGGGGCTAGATTTCTAGAGTTCGAAGCCCTTGGATTCTTGAACGAGGATC
ACTGGATGGGGAGAGAGAACTCAGGAGGTGGTGTTGAAGGGCTGGGATTACAAAGACTCGGATATGTCCTAGAAGAGATGA
GTCGCATACCAGGAGGAAGGATGTATGCAGATGACACTGCTGGCTGGGACACCCGCATCAGCAGGTTTGATCTGGAGAATGA
AGCTCTAATCACCAACCAAATGGAGAAAGGGCACAGGGCCTTGGCATTGGCCATAATCAAGTACACATACCAAAACAAAGTG
GTAAAGGTCCTTAGACCAGCTGAAAAAGGGAAGACAGTTATGGACATTATTTCGAGACAAGACCAAAGGGGGAGCGGACAA
GTTGTCACTTACGCTCTTAACACATTTACCAACCTAGTGGTGCAACTCATTCGGAATATGGAGGCTGAGGAAGTTCTAGAGATG
CAAGACTTGTGGCTGCTGCGGAGGTCAGAGAAAGTGACCAACTGGTTGCAGAGCAACGGATGGGATAGGCTCAAACGAATG
GCAGTCAGTGGAGATGATTGCGTTGTGAAGCCAATTGATGATAGGTTTGCACATGCCCTCAGGTTCTTGAATGATATGGGAAA
AGTTAGGAAGGACACACAAGAGTGGAAACCCTCAACTGGATGGGACAACTGGGAAGAAGTTCCGTTTTGCTCCCACCACTTCA
ACAAGCTCCATCTCAAGGACGGGAGGTCCATTGTGGTTCCCTGCCGCCACCAAGATGAACTGATTGGCCGGGCCCGCGTCTCT
CCAGGGGCGGGATGGAGCATCCGGGAGACTGCTTGCCTAGCAAAATCATATGCGCAAATGTGGCAGCTCCTTTATTTCCACAG
AAGGGACCTCCGACTGATGGCCAATGCCATTTGTTCATCTGTGCCAGTTGACTGGGTTCCAACTGGGAGAACTACCTGGTCAAT
CCATGGAAAGGGAGAATGGATGACCACTGAAGACATGCTTGTGGTGTGGAACAGAGTGTGGATTGAGGAGAACGACCACAT
GGAAGACAAGACCCCAGTTACGAAATGGACAGACATTCCCTATTTGGGAAAAAGGGAAGACTTGTGGTGTGGATCTCTCATA
GGGCACAGACCGCGCACCACCTGGGCTGAGAACATTAAAAACACAGTCAACATGGTGCGCAGGATCATAGGTGATGAAGAAA
AGTACATGGACTACCTATCCACCCAAGTTCGCTACTTGGGTGAAGAAGGGTCTACACCTGGAGTGCTGTAAGCACCAATCTTA
ATGTTGTCAGGCCTGCTAGTCAGCCACAGCTTGGGGAAAGCTGTGCAGCCTGTGACCCCCCCAGGAGAAGCTGGGAAACCAA
GCCTATAGTCAGGCCGAGAACGCCATGGCACGGAAGAAGCCATGCTGCCTGTGAGCCCCTCAGAGGACACTGAGTCAAAAAA
CCCCACGCGCTTGGAGGCGCAGGATGGGAAAAGAAGGTGGCGACCTTCCCCACCCTTCAATCTGGGGCCTGAACTGGAGATC
AGCTGTGGATCTCCAGAAGAGGGACTAGTGGTTAGAGGAGA

SEQ ID NO: 6
KU527068.1 Zika virus strain Natal RGN, Brazil: Rio Grande do Norte, Natal, complete genome
AGTTGTTGATCTGTGTGAATCAGACTGCGACAGTTCGAGTTTGAAGCGAAAGCTAGCAACAGTATCAACAGGTTTTATTTTGG
ATTTGGAAACGAGAGTTTCTGGTCATGAAAAACCCAAAAAAGAAATCCGGAGGATTCCGGATTGTCAATATGCTAAAACGCGG
AGTAGCCCGTGTGAGCCCCTTTGGGGGCTTGAAGAGGCTGCCAGCCGGACTTCTGCTGGGTCATGGGCCCATCAGGATGGTC
TTGGCAATTCTAGCCTTTTTGAGATTCACGGCAATCAAGGCATCACTGGGTGTGATGAATAGATGGGGTTGAGTGGGGAAAAA
AGAGGCTATGGAAATAATAAAGAAGTTCAAGAAAGATCTGGCTGCCATGCTGAGAATAATCAATGCTAGGAAGGAGAAGAA
GAGACGAGGCGCAGATACTAGTGTCGGAATTGTTGGCCTCCTGCTGACCACAGCTATGGCAGCGGAGGTCACTAGACGTGGG
AGTGCATACTATATGTACTTGGACAGAAACGATGCTGGGGAGGCCATATCTTTTCCAACCACATTGGGGATGAATAAGTGTTA
TATACAGATCATGGATCTTGGACACATGTGTGATGCCACCATGAGCTATGAATGCCCTATGCTGGATGAGGGGGTGGAACCAG
ATGACGTCGATTGTTGGTGCAACACGACGTCAACTTGGGTTGTGTACGGAACCTGCCATCACAAAAAAGGTGAAGCACGGAG
ATCTAGAAGAGCTGTGACGCTCCCCTCCCATTCCACTAGGAAGCTGCAAACGCGGTCGCAAACCTGGTTGGAATCAAGAGAAT
ACACAAAGCACTTGATTAGAGTCGAAAATTGGATATTCAGGAACCCTGGCTTCGCGTTAGCAGCAGCTGCCATCGCTTGGCTTT
TGGGAAGCTCAACGAGCCAAAAAGTCATATACTTGGTCATGATACTGCTGATTGCCCCGGCATACAGCATCAGGTGCATAGGA
GTCAGCAATAGGGACTTTGTGGAAGGTATGTCAGGTGGGACTTGGGTTGATGTTGTCTTGGAACATGGAGGTTGTGTCACCG
TAATGGCACAGGACAAACCGACTGTCGACATAGAGCTGGTTACAACAACAGTCAGCAACATGGCGGAGGTAAGATCCTACTG
CTATGAGGCATCAATATCAGACATGGCTTCGGACAGCCGCTGCCCAACACAAGGTGAAGCCTACCTTGACAAGCAATCAGACA
GTGAATATGTGTGGAAAAGAAGGTTAGTGGAGAGAGGGTGGGGAAATGGATGTGGAGTTTTTGGGAAAGGGAGGGTGGTGAG
ATGCGCTAAGTTTGCATGCTCCAAGAAAATGACCGGGAAGAGCATCCAGCCAGAGAATCTGGAGTACCGGATAATGCTGTCA
GTTCATGGCTCCCAGCACAGTGGGATGATCGTTAATGACACAGGACATGAAACTGATGAGAATAGAGCGAAGGTTGAGATAA
CGCCCAATTCACCAAGAGCCGAAGCCACCCTGGGGGGTTTTGGAAGCCTAGGACTTGATTGTGAACCGAGGACAGGCCTTGA
CTTTTCAGATTTGTATTACTTGACTATGAATAACAAGCACTGGTTGGTCCACAAGGAGTGGTTCCACGACATTCCATTACCTTGG
CACGCTGGGGCAGACACCGGAACTCCACACTGGAACAACAAAGAAGCACTGGTAGAGTTCAAGGACGCACATGCCAAAAGG
CAAACTGTCGTGGTTCTAGGGAGTCAAGAAGGAGCAGTTCACACGGCCCTTGCTGGAGCTCTGGAGGCTGAGATGGATGGTG
CAAAGGGAAGGCTGTCCTCTGGCCACTTGAAATGTCGCCTGAAAATGGATAAACTTAGATTGAAGGGCGTGTCATACTCCTTG
TGTACCGCAGCGTTCACATTCACCAAGATCCCGGCTGAAACACTGCACGGGACAGTCACAGTGGAGGTACAGTACGCAGGGA
CAGATGGACCTTGCAAGGTTCCAGCTCAGATGGCGGTGGACATGCAAACTCTGACCCCAGTTGGGAGGTTGATAACCGCTAAC
CCCGTAATCACTGAAAGCACTGAGAACTCTAAGATGATGCTGGAACTTGATCCACCATTTGGGGACTCTTACATTGTCATAGGA
GTCGGGGAGAAGAAGATCACCCACCACTGGCACAGGAGTGGCAGCACCATTGGAAAAGCATTTGAAGCCACTGTGAGAGGT
GCCAAGAGAATGGCAGTCTTGGGAGACACAGCCTGGGACTTTGGATCAGTTGGAGGCGCTCTCAACTCATTGGGCAAGGGCA
TCCATCAAATTTTTGGAGCAGCTTTCAAATCATTGTTTGGAGGAATGTCCTGGTTCTCACAAATCCTCATTGGAACGTTGCTGAT
GTGGTTGGGTCTGAACACAAAGAATGGATCTATTTCCCTTATGTGCTTGGCCTTAGGGGGAGTGTTGATCTTCTTATCCACAGC
CGTCTCTGCTGATGTGGGGTGCTCGGTGGACTTCTCAAAGAAGGAGACGAGATGCGGTACAGGGGTGTTCGTCTATAACGAC
GTTGAAGCCTGGAGGGACAGGTACAAGTACCATCCTGACTCCCCCCGTAGATTGGCAGCAGCAGTCAAGCAAGCCTGGGAAG
ATGGTATCTGCGGGATCTCCTCTGTTTCAAGAATGGAGAACATCATGTGGAGATCAGTAGAAGGGGAGCTCAACGCAATCTTG
GAAGAGAATGGAGTTCAACTGACGGTCGTTGTGGGATCTGTAAAAAACCCCATGTGGAGAGGTCCACAGAGATTGCCCGTGC
CTGTGAACGAGCTGCCCCACGGCTGGAAGGCTTGGGGGAAATCGTACTTCGTCAGAGCAGCAAAGACAAATAACAGCTTTGT
CGTGGATGGTGACACACTGAAGGAATGCCCACTCGAACATAGAGCATGGAACAGCTTTCTTGTGGAGGATCATGGGTTCGG

| SEQUENCES |
|---|
| GTATTTCACACTAGTGTCTGGCTCAAGGTTAGAGAAGATTATTCATTAGAGTGTGATCCAGCCGTTATTGGAACAGCTGTTAAG |
| GGGAAGGAGGCTGTACACAGTGATCTAGGCTACTGGATTGAGAGTGAGAAGAATGACACATGGAGGCTGAAGAGGGCCCAT |
| CTAATCGAGATGAAAACATGTGAATGGCCAAAGTCCCACACATTGTGGGCAGATGGAATAGAAGAGGAGTGATCTGATCATTCC |
| CAAGTCTTTAGCTGGGCCACTCAGCCATCACAATACCAGAGAGGGCTACAGGACCCAAATGAAAGGGCCATGGCACAGTGAA |
| GAGCTTGAAATTCGGTTTGAGGAATGCCCGGGCACTAAGGTCCACGTGGAGGAAACATGTGAACAAGAGGACCATCTCTGA |
| GATCAACCACTGCAAGCGGAAGGGTGATCGAGGAATGGTGCTGCAGGGAGTGCACAATGCCCCCACTGTCGTTCCGGGCTAA |
| AGATGGCTGTTGGTATGGAATGGAGATAAGGCCCAGGAAAGAACCAGAAAGCAACTTAGTAAGGTCAGTGGTGACTGCAGG |
| ATCAACTGATCACATGGATCACTTCTCCCTTGGAGTGCTTGTGATTCTGCTCATGGTGCAGGAAGGGCTGAAGAAGAGAATGA |
| CCACAAAGATCATCATAAGCACATCAATGGCAGTGCTGGTAGCTATGATCCTGGGAGGATTTTCAATGAGTGACCTGGCTAAG |
| CTTGCAATTTTGATGGGCGCCACCTTCGCGGAAATGAACACTGGAGGAGATGTAGCTCATCGGCGCTGATAGCGGCATTCAA |
| AGTCAGACCAGCGTTGCTGGTATCTTTCATCTTCAGAGCTAATTGGACACCCCGTGAAAGCATGCTGCTGGCCTTGGCCTCGTG |
| TCTTTTGCAAACTGCGATCTCCGCCTTGGAAGGCGACCTGATGGTTCTCATCAATGGTTTTGCTTTGGCCTGGTTGGCAATACG |
| AGCGATGGTTGTTCCACGCACTGATAACATCACCTTGGCAATCCTGGCTGCTCTGACACCACTGGCCCGGGGCACACTGCTTGT |
| GGCGTGGAGAGCAGGCCTTGCTACTTGCGGGGGGTTTATGCTCCTCTCTCTGAAGGGAAAAGGCAGTGTGAAGAAGAACTTA |
| CCATTTGTCATGGCCCTGGGACTAACCGCTGTGAGGCTGGTCGACCCCATCAACGTGGTGGGACTGCTGTTGCTCACAAGGAG |
| TGGGAAGCGGAGCTGGCCCCCTAGCGAAGTACTCACAGCTGTTGGCCTGATATGCGCATTGGCTGGAGGGTTCGCCAAGGCA |
| GATATAGAGATGGCTGGGCCCATGGCCGCGGTCGGTCTGCTAATTGTCAGTTACGTGGTCTCAGGAAAGAGTGTGGACATGT |
| ACATTGAAAGAGCAGGTGACATCACATGGGAAAAAGATGCGGAAGTCACTGGAAACAGTCCCCGGCTCGATGTGGCGCTAGA |
| TGAGAGTGGTGATTTCTCCCTGGTGGAGGATGACGGTCCCCCCATGAGAGAGATCATACTCAAGGTGGTCCTGATGACCATCT |
| GTGGCATGAACCCAATAGCCATACCCTTTGCAGCTGGAGCGTGGTACGTATACGTGGAAGACTGGAAAAAGGAGTGGTGCTCT |
| ATGGGATGTGCCTGCTCCCAAGGAAGTAAAAAAGGGGGAGACCACAGATGGAGTGTACAGAGTAATGACTCGTAGACTGCTA |
| GGTTCAACACAAGTTGGAGTGGGAGTTATGCAAGAGGGGTCTTTCACACTATGTGGCACGTCACAAAAGGATCCGCGCTGA |
| GAAGCGGTGAAGGGAGACTTGATCCATACTGGGGAGATGTCAAGCAGGATCTGGTGTCATACTGTGGTCCATGGAAGCTAGA |
| TGCCGCCTGGGACGGGCACAGCGAGGTGCAGCTCTTGGCCGTGCCCCCCGGAGAGAGAGCGAGGAACATCCAGACTCTGCCC |
| GGAATATTTAAGACAAAGGATGGGGACATTGGAGCGGTTGCGCTGGATTACCCAGCAGGAACTTCAGGATCTCCAATCCTAG |
| ACAAGTGTGGGAGAGTGATAGGACTTTATGGCAATGGGGTCGTGATCAAAAATGGGAGTTATGTTAGTGCCATCACCCAAGG |
| GAGGAGGGAGGAAGAGACTCCTGTTGAGTGCTTCGAGCCTTCGATGCTGAAGAAGAAGCAGCTAACTGTCTTAGACTTGCAT |
| CCTGGAGCTGGGAAAACCAGGAGAGTTCTTCCTGAAATAGTCCGTGAAGCCATAAAAACAAGACTCCGTACTGTGATCTTAGC |
| TCCAACCAGGGTTGTCGCTGCTGAAATGGAGGAAGCCCTTAGAGGGCTTCCAGTGCGTTATATGACAACAGCAGTCAATGTCA |
| CCCACTCTGGAACAGAAATCGTCGACTTAATGTGCCATGCCACCTTCACTTCACGTCTACTACAGCCAATCAGAGTCCCAACTA |
| TAATCTGTATATTATGGATGAGGCCCACTTCACAGATCCCTCAAGTATAGCAGCAAGAGGATACATTTCAACAAGGGTTGAGA |
| TGGGCGAGGCGGCTGCCATCTTCATGACCGCCACGCCCACCAGGAACCCGTGACGCATTTCCGGACTCCAACTCACCAATTATG |
| GACACCGAAGTGGAAGTCCCAGAGAGAGCCTGGAGCTCAGGCTTTGATTGGGTGACGGATCATTCTGGAAAAACAGTTTGGT |
| TTGTTCCAAGCGTGAGGAACGGCAATGAGATCGCAGCTTGTCTGACAAAGGCTGGAAAACGGGTCATACAGCTCAGCAGAAA |
| GACTTTTGAGACAGAGTTCCAGAAAACAAAACATCAAGAGTGGGACTTTGTCGTGACAACTGACATTTCAGAGATGGGCGCCA |
| ACTTTAAAGCTGACCGTGTCATAGATTCCAGGAGATGCCTAAAGCCGGTCATACTTGATGGCGAGAGAGTCATTTTGGCTGGA |
| CCCATGCCTGTCACACATGCCAGCGCTGCCCAGAGGAGGGGCGCATAGGCAGGAATCCCAACAAACCTGGAGATGAGTATC |
| TGTATGGAGGTGGGTGCGCAGAGACTGACGAAGACCATGCACACTGGCTTGAAGCAAGAATGCTCCTTGACAATATTTACCTC |
| CAAGATGGCCTCATAGCCTCGCTCTATCGACCTGAGGCCGACAAAGTAGCAGCCATTGAGGGAGAGTTCAAGCTTAGGACGG |
| AGCAAAGGAAGACCTTTGTGGAACTCATGAAAAGAGGAGATCTTCCTGTTTGGCTGGCCTATCAGGTTGCATCTGCCGGAATA |
| ACCTACACAGATAGAAGATGGTGCTTTGATGGCACGACCAACAACACCATAATGGAAGACAGTGTGCCGCAGAGGTGTGGA |
| CCAGACACGGAGAGAAAAGAGTGCTCAAACCGAGGTGGATGGACGCCAGAGTTTGTTCAGATCATGCGGCCCTGAAGTCATT |
| CAAGGAGTTTGCCGCTGGGAAAAGAGGAGCGGCTTTTGGAGTGATGGAAGCCCTGGGAACACTGCCAGGACACATGACAGA |
| GAGATTCCAGGAAGCCATTGACAACCTCGCTGTGCTCATGCGGGCAGAGACTGGAAGCAGGCCTTACAAAGCCGCGGCGGCC |
| CAATTGCCGGAGACCCTAGAGACCATTATGCTTTTGGGGTTGCTGGGAACAGTCTCGCTGGGAATCTTTTTGCTCTTGATGAGG |
| AACAAGGGCATAGGGAAGATGGGCTTTGGAATGGTGACTCTTGGGGCCAGCGCATGGCTCATGTGGCTCTCGGAAATTGAGC |
| CAGCCAGAATTGCATGTGTCCTCATTGTTGTGTTCCTATTGCTGGTGGTGCTCATACCTGAGCCAGAAAAGCAAAGATCTCCCC |
| AGGACAACCAAATGGCAATCATCATCATGGTAGCAGTAGGTCTTCTGGGCTTGATTACCGCCAATGAACTCGGATGGTTGGAG |
| AGAACAAAGAGTGACCTAAGCCATCTAATGGGAAGGAGAGAGGAAGGAACCATAGGATTCTCAATGGACATTGACCTG |
| CGGCCAGCCTCAGCTTGGGCCATCTATGCTGCCTTGACAACTTTCATTACCCCAGCCGTCCAACATGCAGTGACCACTTCATACA |
| ACAACTACTCCTTAATGGCGATGGCCACGCAAGCTGGAGTGTTGTTTGGTATGGGCAAAGGGATGCCATTCTACGCATGGGAC |
| TTTGGAGTCCCGCTGCTAATGATAGGTTGCTACTCACAATTAACACCCCTGACCCTAATAGTGGCCATCATTTTGCTCGTGGCGC |
| ACTACATGTACTTGATCCCAGGGCTGCAGGCACAGCTGCCGCGTGCTGCCCAGAAGAACAGCCAGCTGGCATCATGAAGAA |
| CCCTGTTGTGGATGGAATAGTGGTGACTGACATTGACACAATGACAATTGACCCCCAAGTGGAGAAAAAGATGGGACAGGTG |
| CTACTCATAGCAGTAGCAGTCTCCAGCGCCATACTGTCGCGACCGCCTGGGGGTGGGGGAGGCTGGGCCCTGATCACAG |
| CCGCAACTTCCACTTTGTGGGAAGGCTCTCCGAACAAGTACTGGAACTCCTCTACAGCCACTTCACTGTGTAACATTTTTAGGG |
| GAAGTTACTTGGCTGGACTTCTCTAATCTACATAGTAACAAGAACGCTGGCTTGGTTGGTCAAGGACATGTGGGGGTGGAACAGG |
| AGAGACCCTGGGAGAGAAATTGGAAGGCCCGCTTGAACCAGATGTCGGCCCTGGAGTTCTACTCCTACAAAAAGTCAGGCATC |
| ACCGAGGTGTGCAGAGAAGAGGCCCGCCGCGCCCTCAAGGATGGTGTGGCAACGGGAGGCCATGCTGTGTCCCGAGGAAGT |
| GCAAAGCTGAGATGGTTGGTGGAGCGGGGATACCTGCAGCCCATGAAAGGTCATTGATCTTGGATGTGGCAGAGGGGC |
| TGGAGTTACTACGCCGCCACCATCCGCAAAGTTCAAGAAGTGAAAGGATACAACAAAAGGAGCCCTGGCTGATGAAGAACCCG |
| TGTTGGTGCAAAGCTATGGGTGGAACATAGTCCGTCTTAAGAGTGGGGTGGACGTCTTTCATATGGCGGCTGAGCCGTGTGA |
| CACGTTGCTGTGTGACATAGGTGAGTCATCATCTAGTCCTGAAGTGGAAGAAGCACGGACGCTCAGAGTCCTCTCCATGGTGG |
| GGGATTGGCTTGAAAAAAGACCAGGAGCCTTTTGTATAAAAGTGTTGTGCCCATACACCAGCACTATGATGGAAACCCTGGAG |
| CGACTGCAGCGTAGGTATGGGGGAGGACTGGTCAGAGTGCCACTCTCCCGCAACTCTACACATGAGATGTACTGGGTCTCTG |
| GAGCGAAAAGCAACACCATAAAAAGTGTGTCCACCACGAGCCAGCTCCTCTTGGGGCGCATGGACGGGCCTAGGAGGCCAGT |
| GAAATATGAGGAGGATGTGAATCTCGGCTCTGGCACGCGGGCTGTGGTAAGCTGCGCTGAAGCTCCCAACATGAAGATCATT |
| GGTAACCGCATTGAAAGGATCCGCAGTGAGCACGCGGAAACGTGGTTCTTTGACGAGAACCACCCATATAGGACATGGGCTT |
| ACCATGGAAGCTATGAGGCCCCCACACAAGGGTCAGCGTCCTCTCTAATAAACGGGTTGTCAGGCTCCTGTCAAACCCTGG |
| GATGTGGCTGACTGGAGTCACAGGAATAGCCATGACCGACACCACACCGTATGGTCAGCAAAGAGTTTTCAAGGAAAAGTGG |
| ACACTAGGGTGCCAGACCCCAAGAAGGCACTCGTCAGGTTATGAGCATGGTCTTCTCCTGGTTGTGGAAAGAGCTAGGCAA |
| ACACAAAACGGCCACGAGTCTGTACCAAAGAAGAGTTCATCAACAAGGTTCGTAGCAATGCAGCATTAGGGGCAATATTTGAA |
| GAGGAAAAAGAGTGGAAGACTGCAGTGGAAGCTGTGAACGATCCAAGGTTCTGGGCTCTAGTGGACAAGGAAAGAGAGCAC |
| CACCTGAGAGGAGAGTGCCAGAGTTGTGTGTACAACATGATGGGAAAAAGAGAAAAGAAACAAGGGGAATTTGGAAAGGCC |
| AAGGGCAGCCGCGCCATCTGGTATATGTGGCTAGGGGCTAGATTTCTAGAGTTCGAAGCCCTTGGATTCTTGAACGAGGATCA |
| CTGGATGGGAGAGAGAACTCAGGAGGTGGTGTTGAAGGGCTGGATTACAAAGACTCGGATATGTCCTAGAAGAGATGAG |
| TCGCATACCAGGAGGAAGGATGTATGCAGATGACACTGCTGGCTGGGACACCCGCATCAGCAGGTTCGATCTGGAGAATGAA |

| SEQUENCES |
|---|
| GCTCTAATCACCAACCAAATGGAGAAAGGGCATAGGGCCTTGGCATTGGCCATAATCAAGTACACATACCAAACAAAGTGGT<br>AAAGGTCCTTAGACCAGCTGAAAAAGGGAAAACAGTTATGGACATTATTTCGAGACAAGACCAAAGGGGGAGCGGACAAGTT<br>GTCACTTACGCTCTTAACACATTTACCAACCTAGTGGTGCAACTCATTCGGAATATGGAGGCTGAGGAAGTTCTAGAGATGCAA<br>GACTTGTGGCTGCTGCGGAGGTCAGAGAAAGTGACCAACTGGTTGCAGAGCAACGGATGGGATAGGCTCAAACGAATGGCA<br>GTCAGTGGAGATGATTGCGTTGTGAAGCCAATTGATGATAGGTTTGCACATGCCCTCAGGTTCTTGAATGATATGGGAAAGT<br>TAGGAAGGACACACAAGAGTGGAAACCCTCAACTGGATGGGACAACTGGGAAGAAGTTCCGTTTTGCTCCCACCACTTCAACA<br>AGCTCCATCTCAAGGACGGGAGGTCCATTGTGGTTCCCTGCCGCCACCAAGATGAACTGATTGGCCGGGCCCGCGTCTCTCCA<br>GGGGCGGGATGGAGCATCCGGGAGACTGCTTGCCTAGCAAAATCATATGCGCAAATGTGGCAGCTCCTTTATTTCCACAGAA<br>GGGACCTCCGACTGATGGCCAATGCCATTTGTTCATCTGTGCCAGTTGACTGGGTTCCAACTGGGAGAACTACCTGGTCAATCC<br>ATGGAAAGGGAGAATGGATGACCACTGAAGACATGCTTGTGGTGTGAACAGAGTGTGGATTGAGGAGAACGACCACATGG<br>AAGACAAGACCCCAGTTACGAAATGGACAGACATTCCCTATTTGGGAAAAAGGGAAGACTTGTGGTGTGGATCTCTCATAGG<br>GCACAGACCGCGCACCACCTGGGCTGAGAACATTAAAAACACAGTCAACATGGTGCGCAGGATCATAGGTGATGAAGAAAG<br>TACATGGACTACCTATCCACCCAAGTTCGCTACTTGGGTGAAGAAGGGTCTACACCTGGAGTGCTGTAAGCACCAATCTTAATG<br>TTGTCAGGCCTGCTAGTCAGCCACAGCTTGGGGAAAGCTGTGCAGCCTGTGACCCCCCAGGAGAAGCTGGGAAACCAAGCC<br>TATAGTCAGGCCGAGAACGCCATGGCACGGAAGAAGCCATGCTGCCTGTGAGCCCCTCAGAGGACACTGAGTCAAAAACCC<br>CATGCGCTTGGAGGCGCAGGATGGGAAAAGAAGGTGGCGACCTTCCCCACCCTTCAATCTGGGGCCTGAACTGGAGATCAGC<br>TGTGGATCTCCAGAAGAGGGACTAGTGGTTAGAGGAGACCCCCCGGAAAACGCAAAACAGCATATTGACGCTGGGAAAGAC<br>CAGAGACTCCATGAGTTTCCACCACGCTGGCCGCCAGGCACAGATCGCCGAATAGCGGCGGCCGGTGTGGGGAAATCCATGG<br>GTCTT |

SEQ ID NO: 7
KU681081.3 Zika virus isolate Zika virus/H.sapiens-tc/THA/2014/SV0127-14, Thailand, complete genome
AGTTGTTGATCTGTGTGAATCAGAC

SEQUENCES

```
ATGAGAGTGGTGATTTCTCCCTGGTGGAGGATGACGGTCCCCCCATGAGAGAGATCATACTCAAAGTGGTCCTGATGACCATC
TGTGGCATGAACCCAATAGCCATACCCTTTGCAGCTGGAGCGTGGTACGTATACGTGAAAACTGGAAAAAGGAGTGGTGCTCT
ATGGGATGTGCCTGCTCCCAAGGAAGTAAAAAAGGGGGAGACCACAGATGGAGTGTACAGAGTAATGACTCGTAGACTGCTA
GGTTCAACACAAGTTGGAGTGGGAGTTATGCAAGAGGGGGTCTTTCACACTATGTGGCATGTCACAAAAGGATCCGCGCTGA
GAAGCGGTGAAGGGAGACTTGATCCATACTGGGGAGATGTCAAGCAGGATCTGGTGTCATACTGTGGTCCATGGAAGCTAGA
TGCCGCCTGGGACGGGCACAGCGAGGTGCAGCTCTTGGCCGTGCCCCCCGGAGAGAGAGCGAGGAACATCCAGACTCTGCCC
GGAATATTTAAGACAAAGGATGGGGACATTGGAGCGGTTGCGCTGGACTATCCAGCAGGAACTTCAGGATCTCCAATCCTAG
ACAAGTGTGGGAGAGTGATAGGACTCTATGGCAATGGGGTCGTGATCAAGAATGGGAGTTATGTCAGTGCCATCACCCAAGG
GAGGAGGGAGGAAGAGACTCCTGTTGAGTGCTTCGAGCCTTCGATGCTGAAGAAGAAGCAGCTAACTGTCTTAGACTTGCAT
CCTGGAGCTGGGAAAACCAGGAGAGTTCTTCCTGAAATAGTCCGTGAAGCCATAAAAACGAGACTCCGTACTGTGATCTTAGC
TCCAACCAGGGTTGTCGCTGCTGAAATGGAGGAAGCCCTTAGAGGGCTTCCAGTGCGTTATATGACAACAGCAGTCAATGTCA
CCCATTCTGGGACAGAAATCGTTGACTTAATGTGCCATGCCACCTTCACTTCACGTCTACTACAGCCAATCAGAGTCCCCAACTA
TAATCTGTATATTATGGATGAGGCCCACTTCACAGATCCCTCAAGTATAGCAGCAAGAGGATACATTTCAACAAGGGTTGAGA
TGGGCGAGGCAGCTGCCATCTTCATGACCGCCACGCCACCAGGAACCCGTGACGCATTCCCGGACTCCAACTCACCAATTATG
GACACCGAAGTGGAAGTCCCAGAGAGAGCCTGGAGCTCAGGCTTTGATTGGGTGACGGATCATTCTGGAAAAACAGTTTGGT
TTGTCCCAAGCGTGAGGAACGGCAATGAGATCGCAGCTTGTCTGACAAAGGCTGGAAAACGGGTCATACAGCTCAGCAGAAA
GACTTTTGAGACAGAGTTCCAGAAAACAAAACATCAAGAGTGGGACTTCGTCGTGACAACTGACATTTCAGAGATGGGCGCCA
ACTTTAAAGCTGACCGTGTCATAGATTCCAGGAGATGCCTAAAGCCGGTCATACTTGATGGCGAGAGAGTCATTCTGGCTGGA
CCCATGCCTGTCACACATGCCAGCGCTGCCCAGAGGAGGGGGCGCATAGGCAGGAATCCCAACAAACCTGGAGATGAGTATC
TGTATGGAGGTGGGTGCGCAGAGACTGATGAAGAACCATGCACACTGGCTTGAAGCAGAATGCTCCTTGACAATATTTACCTC
CAAGATGGCCTCATAGCCTCGCTCTATCGACCTGAGGCCGACAAAGTAGCAGCCATTGAGGGAGAGTTCAAGCTTAGGACGG
AGCAAAGGAAGACCTTTGTGGAACTCATGAAAAGAGGGAGATCTTCCTGTTTGGCTGGCCTATCAGGTTGCATCTGCCGGAATA
ACCTACACAGATAGAAGATGGTGCTTTGATGGCATGACCAACAACACCATAATGGAAGACAGTGTGCCGGCAGAGGTGTGGA
CCAGACACGGAGAGAAAAGAGTGCTCAAACCGAGGTGGATGACGCCAGAGTTTGTTCAGATCATGCGGCCCTGAAGTCATT
CAAGGAGTTTGCCGCTGGGAAAAGAGGAGCGGCTTTTGGAGTGATGGAAGCCCTGGGAACACTGCCAGGACACATGACGGA
GAGATTCCAGGAAGCCATTGACAACCTCGCTGTGCTCATGCGGGCAGAGACTGGAAGCAGGCCTTACAAAGCCGCGGCGGCC
CAATTGCCGGAGACCCTAGAGACCATTATGCTTTTGGGGTTGCTGGGAACAGTCTCGCTGGGAATCTTTTTGCTCTTGATGCGG
AACAAGGGCATAGGGAAGATGGGCTTTGGAATGGTGACTCTTGGGGCCAGCGCATGGCTCATGTGGCTCTCGGAAATTGAGC
CAGCCAGAATTGCATGCGTCCTCCATTGTTGTGTTCCTATTGCTGGTGGTGCTCATACCTGAGCCAGAAAAGCAAAGATCCCCCC
AGGACAACCAAATGGCAATCATCATCATGGTAGCAGTAGGTCTTCTGGGCTTGATTACCGCCAATGAACTCGGATGGTTGGAG
AGAACAAAGAGTGACCTAAGCCATCTAATGGGAAGGAGAGAGGAGGGGGCAACCATAGGATTCTCAATGGACATTGACCTG
CGGCCAGCCTCGGCCTGGGCCATCTATGCTGCCCTGACAACTTTCATTACCCCAGCCGTCCAACATGCAGTGACCACTTCATAC
AACAACTACTCCTTAATGGCGATGGCCACGCAAGCTGGAGTGTTGTTTGGTATGGGCAAAGGGATGCCATTCTACGCATGGGA
CTTTGGAGTCCCGCTGCTAATGATAGGTTGCTACTCACAATTAACACCCCTGACCCTAATAGTGGCTATCATTTTGCTCGTGGCG
CACTACATGTACTTGATCCCAGGGCTGCAGGCAGCAGCTGCGCGTGCTGCCCAGAAGAGAACGGCAGCTGGCATCATGAAGA
ACCCTGTTGTGGATGGAATAGTGGTGACTGACATTGACACAATGACTATTGACCCCAAGTGGAGAAAAAGATGGGACAGGT
GCTACTCATAGCAGTAGCCGTCTCCAGCGCCATACTGTCGCGGACCGCCTGGGGTGGGGGGAAGCTGGGGCCCTGATCACA
GCTGCAACTTCCACTTTGTGGGAAGGCTCTCCGAACAAGTACTGGATCCTCTACAGCCCACTTCACTGTGCAACATTTTTAGG
GGAAGTTACTTGGCTGGAGCTTCTCTAATCTACACAGTAACAAGAAACGCTGGCTTGGTCAAGAGACGTGGGGGTGGAACAG
GAGAGACCCTGGGAGAAATGGAAGGCCCGCTTGAACCAGATGTCGGCCCTGGAGTTCTACTCCTACAAAAAGTCAGGCAT
CACCGAGGTGTGCAGAGAAGAGGCCCGCCGCGCCCTCAAGGACGGTGTGGCAACGGGAGGCCATGCTGTGTCCCGAGGAAG
TGCAAAGCTGAGATGGTTGGTGGAGCGGGGATACCTGCAGCCCTATGGAAAGGTCATTGATCTTGGATGTGGCAGAGGGGG
CTGGAGTTACTACGCCGCCACCATCCGCAAAGTTCAAGAAGTGAAAGGATACACAAAAGGAGGCCCTGGTCATGAAGAACCC
ATGTTGGTGCAAAGCTATGGGTGGAACATAGTCCGTCTTAAGAGTGGGGTGGACGTCTTTCATATGGCGGCTGAGCCGTGTG
ACACGTTGCTGTGTGACATAGGTGAGTCATCATCTAGTCCTGAAGTGGAAGAAGCACGGACGCTCAGAGTCCTCTCCATGGTG
GGGGATTGGCTTGAAAAAGACCAGGAGCCTTTTGTGTAAAAGTGTTGTGCCCATACACCAGCACTATGATGGAAACCCTGGA
GCGACTGCAGCGTAGGTATGGGGAGGACTGGTCAGAGTGCCACTCTCCCGCAACTCTACACATGAGATGTACTGGGTCTCT
GGAGCGAAAAGCAACACCATAAAAAGTGTGTCCACCACGAGCCAGCTCCTCTTGGGGCGCATGGACGGGCCCAGGAGGCCA
GTGAAATATGAGGAGGATGTGAATCTCGGCTCTGGCACGCGGGCTGTGGTAAGCTGCGCTGAAGCTCCCAACATGAAGATCA
TTGGTAACCGCATTGAAAGGATCCGCAGTGAGCACGCGGAAACGTGGTTCTTTGACGAGAACCACCCATATAGGACATGGGC
TTACCATGGAAGCTATGAGGCCCCTACACAAGGGTCAGCGTCCTCTCTAATAAACGGGGTTGTCAGGCTCCTGTCAAACCCT
GGGATGGTGACTGGAGTCACAGGAATAGCCATGACCGACACCACACCGTATGGTCAGCAAAGAGTTTTCAAGGAAAAAGT
GGACACCAGGGTGCCAGACCCCCAAGAAGGCACTCGTCAGGTTATGAGCATGGTCTCTTCCTGGTTGTGAAAGAGCTAGGC
AAACACAAACGGCCACGAGTCTGTACCAAAGAAGAGTTCATCAACAAGGTTCGTAGCAATGCAGCATTAGGGGCAATATTTGA
AGAGGAAAAAGAGTGGAAGACCGCAGTGGAAGCTGTGAACGATCCAAGGTTCTGGGCTCTAGTGGACAAGGAAAGAGAGC
ACCACCTGAGAGGAGAGTGCCAGAGCTGTGTGTACAACATGATGGGAAAAAGAGAAAAGAAACAAGGGGAATTTGGAAAG
GCCAAGGGCAGCCGCGCCATCTGGTATATGTGGCTAGGGCTAGATTTCTAGAGTTCGAAGCCCTTGGATTCTTAAATGAGGA
TCACTGGATGGGAGAGAGAACTCAGGAGGTGGTGTTGAAGGGCTGGATTACAAAGACTCGGATATGTCCTAGAAGAGAT
GAGTCGCATACCAGGAGGAAGGATGTATGCAGATGACACTGCTGGCTGGGACACCCGCATCAGCAGGTTTGATCTGGAGAAT
GAAGCTTTAATCACCAACCAAATGGAGAAAGGGCACAGGGCCTTAGCATTGCATAATCAAGTACACATACCAAACAAAGT
GGTAAAGGTCCTTAGACCAGCTGAAAAGGGAAGACAGTTATGGACATTATTTCAAGACAAGACCAAAGGGGAGCGGACA
AGTTGTCACTTACGCTCTTAACACATTTACCAACCTAGTGGTGCAACTCATTCGGAATATGGAGGCTGAGGAAGTTCTAGAT
GCAAGACTTGTGGCTGCTGCGGAGGTCAGAGAAAGTGACCAACTGGTTGCAGAGCAACGGATGGGATAGGCTCAAACGAAT
GGCAGTCAGTGGAGATGATTGCGTTGTGAAGCCAATTGATGATAGGTTTGCAACATGCCTCAGTTCTTGAATGATATGGGAA
AAGTTAGGAAGGACACACAAGAGTGGAAACCCTCAACTGGATGGGACAACTGGGAAGAAGTTCGTTTTTGTTCCCACCACTTC
AACAAGCTCCATCTCAAGGACGGGAGGTCCATTGTGGTTCCCTGCCGCCACCAAGATGAACTGATTGGCCGGGCCCGTGTCTC
TCCAGGGCGGGATGGAGCATCCGGGAGACTGCTTGCCTAGCAAAGTCATATGCGCAAATGTGGCAGCTCCTTTATTTCCACA
GAAGGGACCTCCGACTGATGGCCAATGCCATCTGTTCATCTGTGCCAGTTGACTGGGTTCCAACTGGGAGAACTACCTGGTCA
ATCCATGGAAAGGGAGAATGGATGACCACTGAAGACATGCTTGTGGTGAACAGAGTGGATGGAGAACGACCAC
ATGGAAGACAAGACCCCAGTTACGAAATGGACAGACATTCCCTATCTGGGAAAAAGGGAAGACTTGGTGGTGGATCTCTCA
TAGGGCACAGACCGCGCACCACCTGGGCTGAGAACATTAAAAACACAGTCAACATGGTGCGCAGGATCATAGGTGATGAAGA
AAAGTACATGGACTACCTATCCACCCAAGTTCGCTACTTGGGTGAAGAAGGGTCTACACCTGGAGTGCTATAAGCACCAATCTT
AGTGTTGTCAGGCCTGCTAGTCAGCCACAGCTTGGGGAAAGCTGTGCAGCCTGTGACCCCCCAGGAGAGGCTGGGAAACCA
AGCCCATAGTCAGGCCGAGAACGCCATGGCACGGAAGAAGCCATGCTGCCTGTGAGCCCCTCAGAGGACACTGAGTCAAAAA
ACCCCACGCGCTTGGAGGCGCAGGATGGGAAAAGAAGGTGGCGACCTTCCCCACCCTTCAATCTGGGGCCTGAACTGGAGAT
```

```
                                      SEQUENCES
CAGCTGTGGATCTCCAGAAGAGGGACTAGTGGTTAGAGGAGACCCCCCGGAAAACGCAAAACAGCATATTGACGCTGGGAA
AGACCAGAGACTCCATGAGTTTCCACCACGCTGGCCGCCAGGCACAGATCGCCGAATAGCGGCGGCCGGTGTGGGGAAATCC
ATGGGTCT

SEQ ID NO: 8
KU681082.3 Zika virus isolate Zika virus/H.sapiens-tc/PHL/2012/CPC-0740, Philippines, complete
genome
AGTTGTTGATCTGTGTGAATCAGACTGCGACAGTTCGAGTTTGAAGCGAAAGCTAGCAACAGTATCAACAGGTTTTATTTTGG
ATTTGGAAACGAGAGTTTCTGGTCATGAAAAACCCAAAAAAGAAATCCGGAGGATTCCGGATTGTCAATATGCTAAAACGCGG
AGTAGCCCGTGTGAGCCCCTTTGGGGGCTTGAAGAGGCTGCCAGCCGGACTTCTGCTGGGCATGGGCCCATCAGGATGGTC
TTGGCGATACTAGCCTTTTTGAGATTCACGGCAATCAAGCCATCACTGGGTCTCATCAATAGATGGGGTTCAGTGGGGAAAAA
AGAGGCTATGGAAATAATAAAGAAGTTCAAGAAAGATCTGGCTGCCATGCTGAGAATAATCAATGCTAGGAAGGAGAAGAA
GAGACGAGGCGCAGATACTAGCGTCGGAATTGTTGGCCTCCTCCTGACCACAGCCATGGCAGTAGAGGTCACTAGACGTGGG
AGTGCATACTATATGTACTTGGACAGAAGCGATGCTGGGGAGGCCATATCTTTTCCAACCACACTGGGGATGAATAAGTGTTA
CATACAAATCATGGATCTTGGACACATGTGTGATGCCACCATGAGCTATGAATGCCCTATGTTGGATGAGGGGGTAGAACCAG
ATGACGTCGATTGCTGGTGCAACACGACATCAACTTGGGTTGTGTATGGAACCTGCCACCACAAAAAAGGTGAAGCACGGAG
ATCTAGAAGAGCTGTGACGCTCCCCTCCCATTCCACTAGGAAGCTGCAAACGCGGTCGCAGACCTGGTTGGAATCAAGAGAAT
ACACAAAGCACCTGATTAGAGTTGAAAATTGGATATTCAGGAACCCTGGCTTCGCGTTAGCAGCAGCTGTCATCGCTTGGCTTT
TGGGAAGTTCAACGAGCCAAAAAGTCATATATCTGGTCATGATACTGCTGATTGCCCCGGCATACAGCATCAGGTGCATAGGA
GTCAGCAATAGGGACTTTGTGGAAGGTATGTCAGGTGGGACTTGGGTTGATGTTGTCTTGGAACATGGAGGTTGTGTTACCGT
AATGGCACAGGACAAACCGACTGTCGACATAGAGCTGGTTACAACAACAGTCAGCAACATGGCGGAGGTAAGATCCTACTGC
TATGAGGCATCAATATCGGATATGGCTTCGGACAGCCGCTGCCCAACACAAGGTGAGGCCTACCTTGACAAGCAGTCAGACAC
TCAATATGTCTGCAAAAGAACGTTAGTGGACAGAGGCTGGGGAAATGGATGTGGACTTTTTGGCAAAGGGAGCCTGGTGACA
TGCGCTAAGTTTGCATGCTCCAAGAAAATGACCGGGAAGAGCATCCAGCCAGAGAATCTGGAGTACCGGATAATGCTGTCAG
TTCATGGCTCCCAGCACAGTGGGATGATCGTTAATGACACAGGACATGAAACTGATGAGAATAGAGCGAAGGTTGAGATAAC
GCCCAATTCACCAAGAGCCGAAGCCCACCCTGGGGGGTTTTGGGAGCCTAGGACTTGATTGTGAACCGAGGACAGGCCTTGAC
TTTTCAGATTTGTATTACCTGACTATGAATAACAAGCACTGGTTGGTTCACAAGGAGTGGTTCCACGACATTCCATTACCTTGGC
ATGCTGGGGCAGACACTGGAACTCCACATTGGAACAACAAAGAAGCACTGGTAGAGTTCAAGGACGCACATGCAAAAAGGCA
AACTGTCGTGGTTCTAGGGAGTCAAGAAGGAGCAGTTCACACGCCCCTTGCTGGAGCTCTGGAGGCTGAGATGGATGGAGCC
AAGGGAAGGCTGTCCTCTGGCCACTTGAAATGTCGCCTGAAAATGGATAAACTTAGATTGAAGGGCGTGTCATACTCCTTGTG
CACTGCAGCGTTCACATTCACCAAGATCCCGGCTGAAACACTGCACGGGACAGTCACAGTGGAGGTACAGTACGCAGGGACA
GATGGACCTTGCAAGGTTCCAGCTCAGATGGCCGTTGGATATGCAAACTCTGACCCCAGTTGGGAGGTTGATAACCGCTAACCC
TGTAATCACTGAAAGCACCGAGAACTCTAAGATGATGCTGGAACTTGATCCACCATTTGGGGACTCTTACATTGTCATAGGAGT
CGGGGAGAAGAAGATCACCCATCACTGGCACAGGAGTGGCAGCACCATTGGAAAAGCATTTGAAGCCACTGTGAGAGGTGC
CAAGAGAATGGCAGTCTTGGGAGACACAGCCTGGACTTTGGATCAGTTGGGGGTGCTCTCAACTCATTGGGCAAGGGCATC
ATCAAATTTTTGGAGCAGCTTTCAAATATTGTTCGGAGGAATGTCCTGGTTCTCACAAATTCTATTGGAACGTToCTGGTGT
GGTTGGGTCTGAATACAAAGAATGGATCTATTTCCCTTACGTGCTTGGCCTTAGGGGGAGTGTTGATCTTCTTATCCACAGCCG
TTTCTGCTGATGTGGGGTGCTCGGTGGACTTCTCAAAGAAGGAAACGAGATGCGGTACAGGGGTGTTCGTCTATAACGACGTT
GAAGCCTGGAGGGACAGGTACAAGTACCATCCTGACTCCCCTCGTAGATTGGCAGCAGCAGTCAAGCAAGCCTGGGAAGATG
GGATCTGTGGGATCTCCTCTGTCTCAAGAATGGAAAACATCATGTGGAGATCAGTAGAAGGGGAGCTCAACGCAATCCTGGA
AGAGAATGGAGTTCAACTGACGGTCGTTGTGGGATCTGTAAAAAACCCCATGTGGAGAGGTCCACAGAGATTGCCCGTGCCT
GTGAACGAGCTGCCCCACGGCTGGAAGGCTTGGGGGAAATCGTACTTCGTCAGAGCAGCAAAGACAAATAACAGCTTTGTCG
TGGATGGTGACACACTGAAGGAATGCCCACTCAAACATAGAGCATGGAACAGCTTTCTTGTGGAGGATCATGGGTTTGGGT
ATTTCACACTAGTGTCTGGCTCAAGGTTAGAGAAGATTATTCATTAGAGTGTGATCCAGCCGTCATTGGAACAGCTGCTAAGG
GAAAGGAGGCTGTGCACAGCGATCTAGGCTACTGGATTGAGTGAGAAGAACACATGGAGGCTGAAGAGGGCCCACC
TGATCGAGATGAAAACATGTGAATGGCCAAAGTCCCACACATTGTGGACAGATGGAGTAGAAGAAAGTGATCGATCATACC
CAAGTCTTTAGCTGGGCCACTCAGCCATCACAACACCAGAGAGGGCTACAGGACTCAAATGAAAGGGCCATGGCACAGTGAA
GAGCTTGAAATTCGGTTTGAGGAATGCCCAGGCACTAAGGTCCACGTGGAGGAAACATGTGGACAAGAGGACCATCCCTGA
GATCAACCACTGCAAGCGGAAAGGGTGATCGAGGAATGGTGCTGCAGGGAATGCACAATGCCCCCCACTGTCGTTCCGAACTAA
AGATGGCTGTTGGTATGGAATGGAGATAAGGCCCAGGAAAGAACCAGAAAGTAACTTAGTAAGGTCAATGGTGACTGCAGG
ATCAACTGATCACATGGATCACTTCTCTCTTGGAGTGCTTGTGATTTTGCTCATGGTGCAGGAAGGGCTGAAGAAGAGAATGA
CCACAAAGATCATCATAAGCACATCAATGGCAGTGCTGGTAGCCATGATCCTGGGAGGATTTTCAATGAGTGACCTGGCTAAG
CTTGCAATTTTGATGGGTGCCACCTTCGCGGAAATGAACACTGGAGGAGATGTAGCTCATCTGGCGCTCATAGCTGCATTCAA
AGTCAGACCTGCGTTGCTGGTATCTTTCATCTTCAGAGCTAATTGGACACCCCGTGAGAGCATGCTGCTGGCCTTGGCCTCGTG
TCTTCTGCAAACTGCGATCTCCGCCTTGGAAGGCGACCTGATGGTTCTCATCAATGGTTTTGCTTTGGCCTGGTTGGCAATACG
AGCGATGGTTGTTCCACGCACTGACAACATCACCTTGGCAATCCTGGCTGCTCTGACACCACTGGCCCGGGGCACACTGCTTGT
GGCGTGGAGAGCAGGCCTTGCTACTTGCGGGGGGTTCATGCTCCTCTCTCTGAAGGGGAAAGGCAGTGTGAAGAAGAACCTA
CCATTTGTCATGGCCTTGGGACTAACTGCTGTGAGGCTGGTCGACCCCATCAACGTGGTGGGACTGCTGTTGCTCACAAGGAG
TGGGAAGCGGAGCTGGCCCCCTAGTGAAGTACTCACAGCTGTTGGCCTGATATGCGCATTGGCTGGAGGGTTCGCCAAGGCG
GATATAGAGATGGCTGGGCCCATGGCCGCGGTCGGTCTGCTAATTGTCAGTTACGTGGTCTCAGGAAAGAGTGTGGACATGT
ACATTGAAAGAGCAGGTGACATCACATGGGAAAAAGATGCGGAAATCACTGGGAACAGTCCCCGGCTCGATGTGGCACTAGA
TGAGAGTGGTGATTTCTCCCTAGTGGAGGATGATGGTCCACCCATGAGAGAGATCATACTCAAAGTGGTCCTGATGACCATCT
GCGGCATGAACCCAATAGCCATACCCTTTGCAGCTGGAGCGTGGTACGTGTATGTGAAGACTGGAAAAAGGAGTGGTGCTCT
ATGGGATGTGCCTGCTCCCAAGGAAGTAAAAAGGGGGAGACCACAGATGGAGTGTACAGAGTAATGACTCGTAGAGCTGCTT
GGTTCAACACAAGTTGGAGTGGGAGTCATGCAAGAGGGGGTCTTCCACACTATGTGGCACGTCACAAAAGGATCCGCGCTGA
GAAGCGGTGAAGGGAGACTTGATCCATACTGGGGAGATGTCAAGCAGGATCTGGTGTCATATTGTGGTCCGTGGAAGCTAGA
CGCCGCCTGGGACGGGCACAGCGAGGTGCAGCTCTTGGCCGTGCCCCCCGGAGAGAGAGCGAGGAACATCCAGACTCTGCC
CGGAACATTTAAGACAAAGGATGGGGACATTGGAGCAGTTGCGCTGGACTACCCAGCAGGAACTTCAGGATCTCCAATCCTA
GACAAGTGTGGGAGAGTGATAGGACTCTATGGTAATGGGGTCGTGATAAAAAATGGGAGTTATGTTAGTGCCATCACCCAAG
GGAGGAGGGAGGAAGAGACTCCTGTTGAGTGCTTCGAGCCTTCGATGCTGAAGAAGAAGCAGCTAACTGTCTTAGACCTGCA
TCCTGAGCCGGGAAACCAGGAGAGTTCTTCCTGAAATAGTCCGTGAAGCCATAAAAAACAAGACTCCGTACTGTGATCTTAG
CTCCAACCAGGGTCGTCGCTGCTGAAATGGAGGAAGCCCTTAGAGGGCTTCCAGTTCGTTATATGCAACAGCAGTCAATGTC
ACCCATTCTGGGACAGAAATCGTTGACTTAATGTGCCATGCTACCTTCACTTCACGCCTACTACAACCAATCAGAGTCCCCAACT
ATAATTTGTATATTATGGATGAGGCCCACTTCACAGATCCCTCAAGTATAGCAGCAAGAGGATACATTTCAACAAGGGTTGAG
ATGGGCGAGGCGGCTGCCATCTTCATGACCGCCACGCCACCAGGAACCCGTGACGCATTCCCGGACTCCAACTCACCAATTAT
GGACACCGAGGTGGAAGTCCCAGAGAGAGCCTGGAGCACAGGCTTTGATTGGGTGACGGATCATTCTGGGAAACAGTCTG
GTTTGTTCCAAGCGTGAGGAACGGCAATGAGATCGCAGCTTGTCTGACAAAGGCTGGAAAACGGGTCATACAGCTCAGCAGA
```

| SEQUENCES |
|---|
| AAGACTTTTGAGACAGAGTTCCAGAAAACGAAAAATCAAGAGTGGGACTTCGTCGTGACAACCGACATTTCAGAGATGGGCG |
| CCAACTTTAAAGCTGACCGTGTCATAGATTCCAGGAGATGCTTAAAGCCGGTCATACTTGATGGCGAGAGAGTCATTTTGGCT |
| GGACCCATGCCTGTCACACATGCCAGCGCTGCTCAGAGGAGGGGGCGCATAGGCAGGAATCCCAACAAACCTGGAGATGAGT |
| ATCTGTATGGAGGTGGGTGCGCAGAGACTGATGAAGATCACGCACACTGGCTTGAAGCAAGAATGCTTCTTGACAACATTTAC |
| CTCCAAGATGGCCTCATAGCTTCGCTCTATCGACCTGAGGCCGACAAAGTAGCAGCTATTGAGGGAGAGTTCAAGCTTAGGAC |
| GGAGCAAAGGAAGACCTTTGTGGAACTCATGAAAAGAGGGAGATCTTCCGGTTTGGTTGGCCTATCAGGTTGCATCTGCCGGA |
| ATAACCTACACAGATAGAAGATGGTGCTTTGATGGCATGACCAACAACACCATAATGGAAGACAGTGTGCCGGCAGAGGTGT |
| GGACCAGATACGGAGAGAAAAGAGTGCTCAAACCGAGGTGGATGGACGCCAGAGTTTGTTCAGATCATGCGGCCCTGAAGT |
| CATTCAAAGAGTTTGCCGCTGGGAAAAGAGGAGCGGCCTTTGGAGTGATAGAAGCCCTGGGAACACTGCCAGGACACATGAC |
| AGAGAGATTCCAGGAAGCCATTGACAACCTCGCTGTGCTCATGCGGGCAGAGACTGGAAGCAGGCCTTACAAAGCCGCGGCG |
| GCCCAATTGCCGGAGACCCTAGAGACCATTATGCTTTTGGGGTTGCTGGGAACAGTCTCGCTGGGAATCTTTTTTGCTCTTGATG |
| CGGAACAAGGGCATGGGGAAGATGGGCTTTGGAATGGTGACTCTTGGGGCCAGCGCATGGCTTATGTGGCTCTCGGAAATTG |
| AGCCAGCCAGAATTGCATGTGTCCTCATTGTCGTGTTCCTATTGCTGGTGGTGCTCATACCTGAGCCAGAAAAGCAAAGATCTC |
| CTCAGGACAACCAAATGGCAATCATCATCATGGTAGCAGTGGGTCTTCTGGGCTTGATTACCGCCAATGAACTCGGATGGTTG |
| GAGAGAACAAAAAGTGACCTAAGCCATCTAATGGGAAGGAGAGGAGGAGGGGGCAACCACAGGATTCTCAATGGACATTGAC |
| CTGCGGCCAGCCTCAGCTTGGGCTATCTATGCTGCTCTGACAACTTTCATCACCCCAGCCGTCCAACATGCGGTGACCACTTCAT |
| ACAACAACTACTCCTTAATGGCGATGGCCACGCAAGCTGGGGTGTTGTTTGGTATGGGCAAAGGGATGCCATTCTACGCATGG |
| GACTTTGGAGTCCCGCTGCTAATGATGGGTTGCTACTCACAATTAACACCTCTGACCCTAATAGTGGCCATCATTTTGCTCGTG |
| GCGCACTACATGTACTTGATCCCAGGGCTGCAGGCAGCAGCTGCGCGGGCTGCCCAGAAGAGAACGGCAGCTGGCATCATGA |
| AGAACCCTGTTGTGGATGGAATAGTGGTGACTGACATTGACACAATGACAATTGACCCCCAAGTGGAAAAAAAGATGGGGCA |
| GGTGCTACTCATAGCAGTAGCCGTCTCCAGCGCCATACTGTCGCGGACCGCCTGGGGGTGGGGGGAGGCTGGGGCCCTGATC |
| ACAGCTGCAACTTCCACCTTGTGGGAAGGCTCTCCGAACAAGTACTGGAACTCCTCCACAGCCACTTCACTGTGTAACATTTTTA |
| GGGGAAGTTACTTGGCTGGAGCTTCTCTAATCTACACAGTAACAAGAAACGCTGGCTTGGTCAAGAGACGTGGGGGTGGAAC |
| GGGAGAGACCCTGGGAGGAGAAATGGAAGGCCCGCCTGAACCAGATGTCGGCCCTGGAGTTTCTACTCCTACAAAAAGTCAGGC |
| ATCACCGAGGTGTGCAGAGAAGAGGCCCGCCGTGCCCTCAAGGACGGTGTGGCAACAGGAGGCCATGCTGTGTCCCGAGGA |
| AGTGCAAAGCTTAGATGGCTGGTGGAGAGAGGATACCTGCAGCCCTATGAAAGGTCATTGATCTTGGATGTGGCAGAGGG |
| GGCTGGAGTTACTATGCCGCCACCATCCGCAAAGTTCAGGAAGTGAAAGGATACACAAAAGGAGGCCCTGGTCATGAAGAAC |
| CCATGTTGGTGCAAAGCTATGGGTGGACACATAGTCCGTCTTAAGGATGGGGTGGACGTTCTTTCACATGGCGGCTGAGCCGTG |
| TGACACTTTGCTGTGTGATATAGGTGAGTCATCATCTAGTCCTGAAGTGGAAGAGCACGGACGCTCAGAGTCCTCTCCATGG |
| TGGGGGATTGGCTTGAAAAAAGACCAGGAGCCTTTTGTATAAAAGTGTTGTGCCCATACACCAGCACTATGATGGAAACCCTG |
| GAGCGACTGCAGCGTAGGTATGGGGGAGGACTGGTCAGGGTGCCACTCTCCCGCAACTCTACACATGAGATGTACTGGGTCT |
| CTGGAGCGAAAAGCAACACCATAAAAAGTGTGTCCACCACGACCAGCTCCTCTTGGGGCGCATGGACGGGCCCAGGAGGCC |
| AGTGAAATATGAGGAGGATGTGAATCTCGGCTCTGGCACGCGGGCTGTGGTAAGCTGCGCTGAAGCTCCCAACATGAAGATC |
| ATTGGTAACCGCATTGAGAGGATCCGCAGTGAGCACGCGGAAACGTGGTTCTTTGACGAGAACCACCCATATAGGACATGGG |
| CTTACCATGGAAGCTATGAGGCCCCTACACAAGGGTCAGCGTCCTCTCTAATAAACGGGGTTGTCAGGCTCCTGTCAAACCCT |
| GGGATGTGGTGACTGGAGTCACAGGAATAGCCATGACTGACACCACACCGTATGGTCAGCAAGAGTTTTCAAGGAAAAAGT |
| GGACACTAGGGTGCCAGACCCCCAAGAAGGCACTCGTCAGGTTATGAGCATGGTCTCTTCCTGGTTATGGAAGGAGCTAGGC |
| AAACACAAACGGCCACGAGTCTGTACCAAAGAAGAGTTCATCAACAAGGTTCGTAGCAATGCAGCATTAGGGGCAATATTTGA |
| AGAGGAAAAGAGTGGAAGACTGCAGTGGAAGCTGTGAATGATCCAAGGTTCTGGGCTCTAGTGGACAAGGAAAGAGAGCA |
| TCACCTGAGAGGAGAGTGTCAGAGCTGTGTGTACAACATGATGGGAAAAAGAGAAAAGAAACAAGGGGAATTTGGAAAGGC |
| CAAGGGCAGCCGCCGCCATCTGGTATATGTGGCTAGGGGCTAGATTCCTAGAGTTCGAAGCCCTTGGATTCTTGAATGAGGATC |
| ATTGGATGGGGAGAGAATTCAGGAGGTGGTGTTGAAGGACTGGGATTACAAAGACTCGGATATGTCCTAGAAGATGA |
| GTCGCATACCAGGAGGAAGGATGTATGCAGATGATACTGCTGGCTG

| SEQUENCES |
|---|
| TGTCAGGTGGGACCTGGGTTGATGTTGTCTTGGAACATGGAGGTTGTGTCACCGTAATGGCACAGGACAAACCGACTGTCGA |
| CATAGAGCTGGTTACAACAACAGTCAGCAACATGGCGGAGGTAAGATCCTACTGCTATGAGGCATCAATATCAGACATGGCTT |
| CGGACAGCCGCTGCCCAACACAAGGTGAAGCCTACCTTGACAAGCAATCAGACACTCAATATGTCTGCAAAAGAACGTTAGTG |
| GACAGAGGCTGGGGAAATGGATGTGGACTTTTTGGCAAAGGGAGCCTGGTGACAToCGCTAAGTTTGCATGCTCCAAGAAAA |
| TGACCGGGAAGAGCATCCAGCCAGAGAATCTGGAGTACCGGATAATGCTGTCAGTTCATGGCTCCCAGCACAGTGGGATGAT |
| TGTTAATGACACAGGACATGAAACTGATGAGAATAGAGCGAAAGTTGAGATAACGCCCAATTCACCAAGAGCCGAAGCCACC |
| CTGGGGGGTTTTGGAAGCCTAGGACTTGATTGTGAACCGAGGACAGGCCTTTGACTTTTCAGATTTGTATTACTTGACTATGAAT |
| AACAAGCACTGGTTGGTTCACAAGGAGTGGTTCCACGACATTCCATTACCTTGGCACGCTGGGGCAGACACCGGAACTCCACA |
| CTGGAACAACAAAGAAGCACTGGTAGAGTTCAAGGACGCACATGCCAAAAGGCAAACTGTCGTGGTTCTAGGGAGTCAAGAA |
| GGAGCAGTTCACACGGCCCTTGCTGGAGCTCTGGAGGCTGAGATGGATGGTGCAAAGGGAAGGCTGTCCTCTGGCCACTTGA |
| AATGTCGCCTGAAAATGGATAAACTTAGATTGAAGGGCGTGTCATACTCCTTGTGTACTGCAGCGTTCACATTCACCAAGATCC |
| CGGCTGAAACACTGCACGGGACAGTCACAGTGGAGGTACAGTACGCAGGGACAGATGGACCTTGCAAGGTTCCAGCTCAGAT |
| GGCGGTGGACATGCAAACTCTGACCCCAGTTGGGAGGTTGATAACCGCTAACCCCGTAATCACTGAAAGCACTGAGAACTCTA |
| AGATGATGCTGGAACTTGATCCACCATTTGGGGACTCTTACATTGTCATAGGAGTCGGGGAGAAGAAGATCACCCACCACTGG |
| CACAGGAGTGGCAGCACCATTGGAAAAGCATTTGAAGCCACTGTGAGAGGTGCCAAGAGAATGGCAGTCTTGGGAGACACA |
| GCCTGGGACTTTGGATCACTTGGAGGCGCTCTCAACTCATTGGGCAAGGGCATCCATCAAATTTTTGGAGCAGCTTTCAAATCA |
| TTGTTTGGAGGAATGTCCTGGTTCTCACAAATTCTCATTGGAACGTTGCTGATGTGGTTGGGTCTGAACACAAAGAATGGATCT |
| ATTTCCCTTATGTGCTTGGCCTTAGGGGGAGTGTTGATCTTCTTATCCACAGCCGTCTCTGCTGATGTGGGGTGCTCGGTGGAC |
| TTCTCAAAGAAGGAGACGAGATGCGGTACAGGGGTGTTCGTCTATAACGACGTTGAAGCCTGGAGGGACAGGTACAAGTACC |
| ATCCTGACTCCCCCCGTAGATTGGCAGCAGCAGTCAAGCAAGCCTGGGAAGATGGTATCTGCGGGATCTCCTCTGTTTCAAGA |
| ATGGAAAACATCATGTGGAGATCAGTAGAAGGGGAGCTCAACGCAATCCTGGAAGAGAATGGAGTTCAACTGACGGTCGTTG |
| TGGGATCTGTAAAAAACCCCATGTGGAGAGGTCCACAGAGATTGCCCGTGCCTGTGAACGAGCTGCCCCACGGCTGGAAGGC |
| TTGGGGGAAATCGTACTTCGTCAGAGCAGCAAAGACAAATAACAGCTTTGTCGTGGATGGTGACACACTGAAGGAATGCCCA |
| CTCAAACATAGAGCATGGAACAGCTTTCTTGTGGAGGATCATGGGTTCGGGGTATTTCACACTAGTGTCTGGCTCAAGGTTAG |
| AGAAGATTATTCATTAGAGTGTGATCCAGCCGTTATTGGAACAGCTGTTAAGGGAAAGGAGGCTGTACACAGTGATCTAGGCT |
| ACTGGATTGAGAGTGAGAAGAATGACACATGGAGGCTGAAGAGGGCCCATCTGATCGAGATGAAAACATGTGAATGGCCAA |
| AGTCCCACACATTGTGGACAGATGGAATAGAAGAGAGTGATCTGATCATACCCAAGTCTTTAGCTGGGCCACTCAGCCATCAC |
| AATACCAGAGAGGGCTACAGGACCCAAATGAAAGGGCCATGGCACAGTGAAGAGCTTGAAATTCGGTTTGAGGAATGCCCA |
| GGCACTAAGGTCCACGTGGAGGAAACATGTGGAACAAGAGGACCATCTCTGAGATCAACCACTGCAAGCGGAAGGGTGATC |
| GAGGAATGGTGCTGCAGGGAGTGCACAATGCCCCCACTGTCGTTCCGGGCTAAAGATGGCTGTTGGTATGGAATGGAGATAA |
| GGCCCAGGAAAGAACCAGAAAGCAACTTAGTAAGGTCAATGGTGACTGCAGGATCAACTGATCACATGGACCACTTCTCCCTT |
| GGAGTGCTTGTGATTCTGCTCATGGTGCAGGAAGGGCTGAAGAAGAGAATGACCAAAGATCATCATAAGCACATCAATGG |
| CAGTGCTGGTAGCTATGATCCTGGGAGGATTTTCAATGAGTGACCTGGCTAAGCTTGCAATTTTGATGGGTGCCACCTTCGCG |
| GAAATGAACACTGGAGGAGATGTAGCTCATCGGCGCTGATAGCGGCATTCAAAGTCAGACCAGCGTTGCTGGTATCTTTCAT |
| CTTCAGAGCTAATTGGACACCCCGTGAAAGCATGCTGCTGGCCTTGGCCTCGTGTCTTTGCAAACTGCGATCTCCGCCTTGGA |
| AGGCGACCTGATGGTTCTCATCAATGGTTTTGCTTTGGCCTGGTTGGCAATACGAGCGATGGTTGTTCCACGCACTGATAACAT |
| CACCTTGGCAATCCTGGCTGCTCTGACACCACTGGCCGCGGGACACACTGCTTGTGGCGTGGAGAGCAGGCCTTGCTACTTGCG |
| GGGGGTTTATGCTCCTCTCTCTGAAGGGAAAAGGCAGTGTGAAGAAGAACTTACCATTTGTCATGGCCCTGGGACTAACCGCT |
| GTGAGGCTGGTCGACCCCATCAACGTGGTGGGACTGCTGTTGCTCACAAGGAGTGGGAAGCGGAGCTGGCCCCCTAGCGAA |
| GTACTCCAGCTGTTGGCCTGATATGCGCATTGGCTGGAGGGTTCGCCAAGGCAGATATAGAGATGGCTGGGCCCATGGCCG |
| CGGTCGGTCTGCTAATTGTCAGTTACGTGGTCTCAGGAAAGAGTGGACATGTACATTGAAAGAGCAGGTGACATCACATG |
| GGAAAAAGATGCGGAAGTCACTGGAAACAGTCCCCGGCTCGATGTGGCGCTAGATGAGAGTGGTGATTTCTCCCTGGTGGAG |
| GATGACGGTCCCCCCATGAGAGAGATCATACTCAAGGTGGTCCTGATGACCATCTGTGGCATGAACCCAATAGCCATACCCTTT |
| GCAGCTGGAGCGTGGTACGTATACGTGAAGACTGGAAAAAGGAGTGGTGCTCTATGGGATGTGCCTGCTCCCAAGGAAGTAA |
| AAAAGGGGGAGACCACAGATGGAGTGTACAGAGTAATGACTCGTAGACTGCTAGGTTCAACACAAGTTGGAGTGGGAGTTA |
| TGCAAGAGGGGGTCTTTCACACTATGTGGCACGTCACAAAAGGATCCGCGCTGAGAAGCGGTGAAGGGAGACTTGATCCATA |
| CTGGGGAGATGTCAAGCAGGATCTGGTGTCATACTGTGGTCCATGGAAGCTAGATGCCGCTGGGACGGGCACAGCGAGGT |
| GCAGCTCTTGGCCGTGCCCCCGGAGAGAGAGCGAGGAACATCCAGACTCTGCCCGGAATATTTAAGACAAAGGATGGGGAC |
| ATTGGAGCGGTTGCGCTGGATTACCCAGCAGGAACTTCAGGATCTCCAATCCTAGACAAGTGTGGGAGGGTGATAGGACTTTA |
| TGGCAATGGGTCGTGATCAAAAATGGGAGTTATGTTAGTGCCATCACCCAAGGGAGGAGGGAGGAAGAGACTCCTGTTGA |
| GTGCTTCGAGCCTTCGATGCTGAAGAAGAAGCAGCTAACTGTCTTAGACTTGCATCCTGGAGCTGGGAAACCAGGAGAGTTC |
| TTCCTGAAATAGTCCGTGAAGCCATAAAAACAAGACTCCGTACTGTGATCTTAGCTCCAACCAGGGTTGTCGCTGCTGAAATGG |
| AGGAGGCCCTTAGAGGGCTTCCAGTGCGTTATATGACAACAGCAGTCAATGTCACCCACTCTGGAACAGAAATCGTCGACTTA |
| ATGTGCCATGCCACCTTCACTTCACGTCTACTACAGCCAATCAGAGTCCCCAACTATAATCTGTATATTATGGATGAGGCCCACT |
| TCACAGATCCCTCAAGTATAGCAGCAAGAGGATACATTTCAACAAGGGTTGAGATGGGCGAGGCGGCTGCCATCTTCATGACC |
| GCCACGCCACCAGGAACCCGTGACGCATTTCCGGACTCCAACTCACCAATTATGGACACCGAAGTGGAAGTCCCAGAGAGC |
| CTGGAGCTCAGGCTTTGATTGGGTGACGGATCATTCTGGAAAAACAGTTTGGTTTGTTCCAAGCGTGAGGAACGGCAATGAG |
| ATCGCAGCTTGTCTGACAAAGGCTGGAAAACGGGTCATACAGCTCAGCAGAAAGACTTTTGAGACAGAGTTCCAGAAACAA |
| AACATCAAGAGTGGGACTTTGTCGTGACAACTGACATTTCAGAGATGGGCGCCAACTTTAAAGCTGACCGTGTCATAGATTCC |
| AGGAGATGCCTAAAGCCGGTCATACTTGATGGCGAGAGAGTCATTCTGGCTGGACCCATGCCTGTCACACATGCCAGCGCTGC |
| CCAGAGGAGGGGGCGTATAGGCAGGAATCCCAACAAACCTGGAGATGAGTATCTGTATGGGGGTGCGCAGACTGA |
| CGAAGACCATGCACACTGGCTTGAAGCAAGAATGCTCCTTGACAATATTTACCTCCAAGATGGCCTCATAGCCTCGCTCTATCG |
| ACCTGAGGCCGACAAAGTAGCAGCCATTGAGGGAGAGTTCAAGCTTAGGACGGAGCAAAGGAAGACCTTTGTGGAACTCATG |
| AAAAGAGGAGATCTTCCTGTTTGGCTGGCCTATCAGGTTGCATCTGCCGAATAACCTACACAGATAGAAGATGGTGCTTTGA |
| TGGCACGACCAACAACACCATAATGGAAGACAGTGTGCCGGCAGAGGTGTGGACCAGACACGGAGAGAAAGAGTGCTCAA |
| ACCGAGGTGGATGGACGCCAGAGTTGTTCAGATCATGCGGCCCTGAAGTCATTCAAGGAGTTTGCCGCTGGGAAAAGAGGA |
| GCGGCTTTTGGAGTGATGGAAGCCCTGGGAACACTGCCAGGACACATGACAGAGAGATTCCAGGAAGCCATTGACAACCTCG |
| CTGTGCTCATGCGGGCAGAGACTGGAAGCAGGCCTTACAAAGCCGCGGCGGCCCAATTGCCGGAGACCCTAGAGACCATTAT |
| GCTTTTGGGGTTGCTGGGAACAGTCTCGCTGGGAATCTTCTTCGTCTTGATGAGGAACAAGGGCATAGGGAAGATGGGCTTT |
| GGAATGGTGACTCTTGGGGCCAGCGCATGGCTCATGTGGCTCTCGGAAATTGAGCCAGCCAGAATTGCATGTGTCCTCATTGT |
| TGTGTTTCTATTGCTGGTGGTGCTCATACCTGAGCCAGAAAAGCAAAGATCTCCCCAGGACAACCAAATGGCAATCATCATCAT |
| GGTAGCAGTAGGTCTTCTGGGCTTGATTACCGCCAATGAACTCGGATGGTTGGAGAGGAACAAAGAGTGACCTAAGCATCA |
| ATGGGAAGGAGAGGAGGAGGGGCAACCATAGGATTCTCAATGGACATTGACCTGCGGCCAGCCTCAGCTTGGGCCATCTATG |
| CTGCCTTGACAACTTTCATTACCCCAGCCGTCCAACATGCAGTGACCACTTCATCAACAACTACTCCTTAATGGCGATGGCCAC |
| GCAAGCTGGAGTGTTGTTTGGTATGGGCAAAGGGATGCCATTCTACGCATGGGACTTTGGAGTCCCGCTGCTAATGATAGGTT |
| GCTACTCACAATTAACACCCCTGACCCTAATAGTGGCCATCATTTTGCTCGTGGCGCACTACATGTACTTGATCCCAGGGCTGCA |
| GGCAGCAGCTGCGCGTGCTGCCCAGAAGAGAACGGCGCAGCTGGCATCATGAAGAACCCTGTTGTGGATGGAATAGTGGTGACT |

| SEQUENCES |
|---|
| GACATTGACACAATGACAATTGACCCCCAAGTGGAGAAAAAGATGGGACAGGTGCTACTCATAGCAGTAGCCGTCTCCAGCG
CCATACTGTCGCGGACCGCCTGGGGGTGGGGGAGGCTGGGGCCCTGATCACAGCCGCAACTTCCACTTTGTGGGAAGGCTC
TCCGAACAAGTACTGGGAACTCCTCTACAGCCACTTCACTGTGTAACATTTTTAGGGGAAGTTACTTGGCTGGAGCTTCTCTAATC
TACACAGTAACAAGAAACGCTGGCTTGGTCAAGAGACGTGGGGGTGGAACAGGAGAGACCCTGGGAGAGAAATGGAAGGC
CCGCTTGAACCAGATGTCGGCCCTGGAGTTCTACTCCTACAAAAAGTCAGGCATCACCGAGGTGTGCAGAGAAGAGGCCCGC
CGCGCCCTCAAGGACGGTGTGGCAACGGGAGGCCATGCTGTGTCCCGAGGAAGTGCAAAGCTGAGATGGTTGGTGGAGCGG
GGATACCTGCAGCCCTATGGAAAGGTCATTGATCTTGGATGTGGCAGAGGGGGCTGGAGTTACTACGCCGCCACCATCCGCA
AAGTTCAAGAAGTGAAAGGATACACAAAAGGAGGCCCTGGTCATGAAGAACCCGTGTTGGTGCAAAGCTATGGGTGGAACAT
AGTCCGTCTTAAGAGTGGGGTGGACGTCTTTCATATGGCGGCTGAGCCGTGTGACACGTTGCTGTGTGACATAGGTGAGTCAT
CATCTAGTCCTGAAGTGGAAGAAGCACGGACGCTCAGAGTCCTCTCCATGGTGGGGATTGGCTTGAAAAAAGACCAGGAGC
CTTTTGTATAAAGGTGTTGTGCCCATACACCAGCACTATGATGGAAACCCTGGAGCGACTGCAGCGTAGGTATGGGGGAGGA
CTGGTCAGAGTGCCACTCTCCCGCAACTCTACACATGAGATGTATTGGGTCTCTGGAGCGAAAAGCAACACCATAAAAAGTGT
GTCCACCACGAGCCAGCTCCTCTTGGGGCGCATGGACGGGCCTAGGAGGCCAGTGAAATATGAGGAGGATGTGAATCTCGGC
TCTGGCACGCGGGCTGTGGTAAGCTGCGCTGAAGCTCCCAACATGAAGATCATTGGTAACCGCATTGAAAGGATCCGCAGTG
AGCACGCGGAAACGTGGTTCTTTGACGAGAACCACCCATATAGGACATGGGCTTACCATGGAAGCTATGAGGCCCCCACACA
GGGTCAGCGTCCTCTCTAATAAACGGGGTTGTCAGGCTCCTGTCAAAACCCTGGGATGTGGTGACTGGAGTCACAGGAATAGC
CATGACCGACACCACACCGTATGGTCAGCAAAGAGTTTTCAAGGAAAAAGTGGACACTAGGGTGCCAGACCCCCAAGAAGGC
ACTCGTCAGGTTATGAGCATGGTCTCTTCCTGGTTGTGGAAAGAGCTAGGCAAACACAAACGGCCACGAGTCTGTACCAAAGA
AGAGTTCATCAACAAGGTTCGTAGCAATGCAGCATTAGGGGCAATATTTGAAGAGGAAAAAGAGTGGAAGACTGCAGTGGA
AGCTGTGAACGATCCAAGGTTCTGGGCTCTAGTGGATAAGGAAAGAGGCACCACCTGAGAGGGAGAGTGCCAGAGTTGTGT
GTACAACATGATGGGAAAAAGAGAAAAGAAACAAGGGGAATTTGGAAAGGCCAAGGGCAGCCGCGCCATCTGGTATATGTG
GCTAGGGGCTAGATTTCTAGAGTTCGAAGCCCTTGGATTCTTGAACGAGGATCACTGGATGGGAGAGAGAACTCAGGAGGT
GGTGTTGAAGGGCTGGGATTACAAAGACTCGGATATGTCCTAGAAGAGATGAGTCGTATACCAGGAGGAAGGATGTATGCA
GATGACACTGCTGGCTGGGACACCCGCATCAGCAGGTTTGATCTGGAGAATGAAGCTCTAATCACCAACCAAATGGAAAAAG
GGCACAGGGCCTTGGCATTGGCCATAATCAAGTACACATACCAAAACAAAGTGGTAAAGGTCCTTAGACCAGCTGAAAAAGG
GAAAACAGTTATGGACATTATTTGAGACAAGACCAAAGGGGGAGCGGACAAGTTGTCACTTACGCTCTTAACACATTTACCA
ACCTAGTGGTGCAACTCATTCGGAATATGGAGGCTGAGGAAGTTCTAGAGATGCAAGACTTGTGGCTGCTGCGGAGGTCAGA
GAAAGTGACCAACTGGTTGCAGAGCAACGGATGGGATAGGCTCAAACGAATGGCAGTCAGTGGAGATGATTGCGTTGTGAA
GCCAATTGATGATAGGTTTGCACATGCCCTCAGGTTCTTGAATGATATGGGAAAAGTTAGGAAGGACACACAAGAGTGGAAA
CCCTCAACTGGATGGGACAACTGGGAAGAAGTTCCGTTTTGCTCCCACCACTTCAACAAGCTCCATCTCAAGGACGGGAGGTC
CATTGTGGTTCCCTGCCGCCACCAAGATGAACTGATTGGCCGGGCCCGCGTCTCTCAGGGGCGGGATGGAGCATCCGGGAG
ACTGCTTGCCTAGCAAAATCATATGCGCAAATGTGGCAGCTCCTTTATTTCCACAGAAGGGACCTCCGACTGATGGCCAATGCC
ATTTGTTCATCTGTGCCAGTTGACTGGGTTCCAACTGGGAGAACTACCTGGTCAATCCATGGAAAGGGAGAATGGATGACCAC
TGAAGACATGCTTGTGGTGTGAACAGAGTGTGGATTGAGGAGAACGACCACATGGAAGACAAGACCCCAGTTACGAAATG
GACAGACATCCCCTATTTGGGAAAAAGGGAAGACTTGTGGTGTGGATCTCTCATAGGGCACAGACCGCGCACCACCTGGGCT
GAGAACATTAAAAACACAGTCAACATGGTGCGCAGGATCATAGGTGATGAAGAAAGGTACATGGACTACCTATCCACCCAAG
TTCGCTACTTGGGTGAAGAAGGGTCTACACCTGGAGTGCTGTAAGCACCAGTCTTAATGTTGTCAGGCCTGCTAGTCAGCCAC
AGCTTGGGGAAAGCTGTGCAGCCTGTGACCCCCCAGGAGAAGCTGGGAAACCAAGCCTATAGTCAGGCCGAGAACGCCATG
GCACGGAAGAAGCCATGCTGCCTGTGAGCCCTCAGAGGACACTGAGTCAAAAAACCCCACGCGCTTGGAGGCGCAGGATG
GGAAAAGAAGGTGGCGACCTTCCCCACCCTTCAATCTGGGGCCTGAACTGGAGATCAGCTGTGGATCTCCAGAAGAGGGACT
AGTGGTTAGAGGAG |

SEQ ID NO: 10
KU744693.1 Zika virus isolate VE_Ganxian, China, complete genome
GTTGTTACTGTTGCTGACTCAGACTGCGACAGTTCGAGTTTGAAGCGAAAGCTAGCAACAGTATCAACAGGTTTTATTTGGATT
TGGAAACGAGAGTTTCTGGTCATGAAAAACCCAAAAAAGAAATCCGGAGGGTTCCGGATTGTCAATATGCTAAAACGCGGAG
TAGCCCGTGTGAGCCCCTTTGGGGGCTTGAAGAGGCTGCCAGCCGGACTTCTGCTGGGTCATGGGCCCATCAGGATGGTCTTG
GCAATTCTAGCCTTTTTGAGATTCACGGCAATCAAGCCATCACTGGGTCTCATCAATAGATGGGGTTCAGTGGGAAAAAAGA
TGCTATGGAAATAATAAAGAAGTTCAAGAAAGATCTGGCTGCCATGCTGAGAATAATCAATTCTAGGAAGGAGAAGAAGAGA
CGAGGCGCAGATACTAGTGTCGGAATTGTTGGCCTCCTGCTGACCAGCTATGGCAGCGGAGGTCACTAGACGTGGGAGTG
CATACTATATGTACTTGGACAGAAACGATGCTGGGGAGGCCATATCTTTTCCAACCACATTGGGGATGAATAAGTGTTATATAC
AGATCATGGATCTTGGACACATGTGTGATGCCACCATGAGCTATGAATGCCCTATGCTGGATGAGGGGGTGGAACCAGATGA
CGTCGATTGTTGGTGCAACACGACGTCAACTTGGGTTGTGTACGGAACCTGCCATCACAAAAAGGTGAAGCAGGAGATCTA
GAAGAGCTGTGACGCTCCCTTCCCATTCCACTAGGAAGCTGCAAACGCGGTCGCAAACCTGGTTGGAATCAAGAGAATACACA
AAGCACTTGATTAGAGTCGAAAATTGGATATTCAGGAACCCTGGCTTCGCGTTAGCAGCAGCTGCCATCGCTTGGCTTTTGGG
AAGCTCAACGAGCCAAAAAGTCATATACTTGGTCATGATACTGCTGATTGCCCCGGCATACAGCATCAGGTGCATAGGAGTCA
GCAATAGGGACTTTGTGGAAGGTATGTCAGGTGGGACTTGGGTTGATGTTGTCTTGGAACATGGAGGTTGTGTCACCGCAAT
GGCACAGGACAAACCGACTGTCGACATAGAGCTGGTTACAACAACAGTCAGCAACATGGCGGAGGTAAGATCCTACTGCTAT
GAGGCATCAATATCAGACATGGCTTCGGACAGCCGCTGCCCAACACAAGGTGAAGCCTACCTTGACAAGCAATCAGACACTCA
ATATGTTTGCAAAAGAACGTTAGTGGACAGAGGCTGGGGAAATGGATGTGGACTTTTTGGCAAAGGGAGTCTGGTGACATGC
GCTAAGTTTGCATGCTCCAAGAAAATGACCGGGAAGAGCATCCAGCCAGAGAATCTGGATACCGGATAATGCTGTCAGTTC
ATGGCTCCCAGCACAGTGGGATGCTCGTTAATGACAACAGGACATGAAACTGATGAGAATAGAGCGAAGGTTGAGATAACGCC
CAATTCACCAAGAGCCGAAGCCACCCTGGGGGTTTTGGAAGCCTAGGACTTGATTGTGAACCGAGGACAGGCCTTGACTTTT
CAGATTTGTATTACTTGACTATGAATAACAAGCACTGGTTGGCTCACAAGGAGTGGTTCCACGACATTCCATTACCTTGGCACG
CTGGGGCAGCCACCGGAACTCCACACTGGAACAACAAAGAAGCACTGGTAGAGTTCAAGGACGCACATGCCAAAAGGCAAAC
TGTCGTGGTTCTAGGGAGTCAAGAAGGAGCAGTTCACACAGCCCTTGCTGGAGCCTGAGATGGATGGTGCAAAG
GGAAGGCTGTCCTCTGGCCACTTGAAATGTCGCCTGAAAATGGATAAACTTAGATTGAAGGCGTGTCATACTCCTTGTGTAC
CGCAGCGTTCACATTCACCAAGATCCCGGCTGAAACAGTGGACGGGACAGTCACAGTGGAGGGACAGTACGAGGGACAGA
TGGACCTTGCAAGGTTCCAGCTCAGATGGCGGTGGACATGCAGACTCTGACCCCAGTTGGGAGGTTGATAACCGCTAACCCCG
TAATCACTGAAAGCACTGAGAACTCTAAGATGATGCTGGAACTTGATCCACCATTTGGGACTCTTACATTGTCATAGGAGTCG
GGGAGAAGATCACCACCAACCACTGGCACAGGAGTGGCAGCATTGGAAAACATTTGAAAGCACGTGAGAGGTGCCA
AGAGAATGGCAGTCTTGGGAGACACAGCCTGGGACTTTGATCAGTTGGAGGCGCTCTCAACTCATTGGGCAAGGGCATCCA
TCAAATTATTGGAGCAGCTTTCAAATCATTGTTTGGAGGAATGTCCTGGTTCTCACAAATTCTCATTGGGACGTTGCTGATGTG
GTTGGGTCTGAACACAAAGAATGGATCTATTTCCCTTATGTGCTTGGCCTTAGGGGAGTGTTGATCTTCTTATCCACAGCCGT
CTCAGGTGGTGTGGGGTGCTCGGTGGACTTCTCAAAGAAGGAGACGAGATGCGGTACAGGGGTGTTCGTCTATAACGATGTT
GAAGCCTGGAGGGACAGGTACAAGTACCATCCTGACTCCCCCCGTAGATTGGCAGCAGCAGTCAAGCAAGCCTGGGAAGATG
GTATCTGCGGGATCTCCTCTGTTTCAAGAATGGAAAACATCATGTGGAGATCAGTAGAAGGGGAGCTCAACGCAATCCTGGAA |

| SEQUENCES |
|---|
| GAGAATGGAGTTCAACTGACGGTCGTTGTGGGATCTGTAAAAAACCCCATGTGGAGAGGTCCACAGAGATTGCCCGTGCCTG |
| TGAACGAGCTGCCCCACGGCTGGAAGGCTTGGGGGAAATCGTACTTCGTCAGAGCAGCAAAGACAAATAACAGCTTTGTCGT |
| GGATGGTGACACACTGAAGGAATGCCCACTCAAACATAGAGCATGGAACAGCTTTCTTGTGGAGGATCATGGGTTCGGGGTA |
| TTTCACACTAGTGTCTGGCTCAAGGTTAGAGAAGACTATTGGTTAGAGTGTGATCCAGCCGTTATTGGAACAGCTGTTAAGGG |
| AAAGGAGGCTGTACACAGTGATCTAGGCTACTGGATTGAGAGTGAGAAGAATGACACATGGTGGCTGAAGAGGGCCCATCT |
| GATCGAGATGAAAACATGTGAATGGCCAAAGTCCCACACATTGTGGACAGATGGAATAGAAGAGAGTGATCTGATCATACCC |
| AAGTCTTTAGCTGGGCCACTCAGCCATCACAATGCCAGAGAGGGCTACAGGACCCAAATGAAAGGGCCATGGCACAGTGAAG |
| AGCTTGAAATTCGGTTTGAGGAATGCCCAGGCACTAAGGTCCACGTGGAGGAAACATGTGGAACAAGAGGACCATCTCTGAG |
| ATCAACCACTGCAAGCGGAAGGGTGATCGAGGAATGGTGCTCCAGGGAGTGCACAATGCCCCACTGTCCTTCCAGGCTAAA |
| GATGGCTGTTGGTATGGAATGGAGATAAGGCCCAGGAAAGAACCAGAAAGCAACTTAGTAAGGTCAATGGTGACTGCAGGA |
| TCAACTGATCACATGGATCACTTCTCCCTTGGAGTGCTTGTGATTCTGCTCATGGTGCAGGAAGGGCTGAAGAAGAGAATGAC |
| CACAAAGATCATCATAAGCACATCAATGGCAGTGCTGGTAGCTATGATCCTGGGAGGATTTTCAATGAGTGACCTGGCTAAGC |
| TTGCAATTTTGATGGGTGCCACCTTCGCGGAAATGAACACTGGAGGAGATGTAGCTCATCTGGCGCTGATAGCGGCATTCAAA |
| GTCAGACCAGCGTTGCTGGTATCTTTCATCTTCAGAGCTAATTGGACACCCGTGAAAGCATGCTGCTGGCCTTGGCCTCGTGT |
| CTTTTGCAAACTGCGATCTCCGCCTTGGAAGGCGACCTGATGGTTCTCATCAATGGTTTTGCTTTGGCCTGGTTGGCAATACGA |
| GCGATGGTTGTTCCACGCACTGATAACATCACCTTAGCAATCCTGGCTGCTGTGACACCACTGGCCCGGGGCACACTGCTTGTG |
| GCGTGGAGAGCAGGCCTTGCTACTTGCGGGGGGTTTATGCTCCTCTCTCTGAAGGGAAAAGGCAGTGTGAAGAAGAACTTAC |
| CATTTGTCATGGCCCTGGGACTAACCGCTGTGAGGCTGGTCGACCCCATCAACGTGGTGGGACTGCTGTTGCTCACAAGGAGT |
| GGGAAGCGGAGCTGGCCCCCTAGCGAAGTACTCACAGCTGTTGGCCTGATATGCGCATTGGCTGGAGGGTTCGCCAAGGCAG |
| ATATAGAGATGGCTGGGCCCATGGCCGCGGTCGGTCTGCTAATTGTCAGTTACGTGGTCTCAGGAAAGAGTGTGGACATGTA |
| CATTGAAAGAGCAGGTGACATCACATGGGAAAAAGATGCGGAAGTCACTGGAAACAGTCCCCGGCTCGATGTGGCGCTAGAT |
| GAGAGTGGTGATTTCTCCCTGGTGGAGGATGACGGTCCCCCCATGAGAGAGATCATACTCAAGGTGGTCCTGATGACCATCTG |
| TGGCATGAACCCAATAGCCATACCCTTTGCAGCTGGAGCGTGGTACGTATACGTGAAGACTGGAAAAAGGAGTGGTGCTCTAT |
| GGGATGTGCCTGCTCCCAAGGAAGTAAAAAAGGGGGAGACCACAGATGGAGTGTACACAGACTGCTAG |
| GTTCAACACAAGTTGGAGTGGGAGTTATGCAAGAGGGGGTCTTTCACACTATGTGGCACGTCACAAAAGGATCCGCGCTGAG |
| AAGCGGTGAAGGGAGACTTGATCCATACTGGGGAGATGTCAAGCAGGATCTGGTGTCATACTGTGGTCCATGGAAGCTAGAT |
| GCCGCCTGGGACGGGCACAGCGAGGTGCAGCTCTTGGCCGTGCCCCCGGAGAGAGAGCGAGGAACATCCAGACTCTGCCC |
| GGAATATTTAAGACAAAGGATGGGGACATTGGAGCGGTTGCACTGGATTACCCAGCAGGAACTTCAGGATCTCCAATCCTAG |
| ACAAGTGTGGGAGAGTGATAGGACTTTATGGCAATGGGGTCGTGATCAAAAATGGGAGTTATGTTAGTGCCATCACCCAAGG |
| GAGGAGGAGGAAGAGACTCCTGTTGAGTGCTTCGAGCCTTCGATGCTGAAGAAGAAGCAGCTAACTGTCTTAGACTTGCAT |
| CCTGGAGCTGGGAAAACCAGGAGAGTTCTTCCTGAAATAGTCCGTGAAGCCATAAAAACAAGACTCCGTACTGTGATCTTGGC |
| TCCAACCAGGGTTGTCGCTGCTGAAATGGAGGAGGCCCTTAGAGGGCTTCCAGTGCGTTATATGACAACAGCAGTCAATGTCA |
| CCCACTCTGGAACAGAAATCGTCGACTTAATGTGCCATGCCACCTTCACTTCACGTCTACTACAGCCAATTAGAGTCCCCAACTA |
| TAATCTGTATATTATGGATGAGGCCCACTTCACAGATCCCTCAAGTATAGCAGCAAGAGGATACATTTCAACAAGGGTTGAGA |
| TGGGCGAGGCGGCTGCCATCTTCATGACCGCCACGCCACCAGGAACCCGTGACGCATTTCCGGACTCCAACTCACCAATTATG |
| GACACCGAAGTGGAAGTCCCAGAGAGAGCCTGGAGCTCAGGCTTTGATTGGGTGACGGAGTATTCTGGAAAAACAGTTTGGT |
| TTGTTCCACGCGTGAGGAACGGCAATGAGATCGCAGCTTGTCTGACAAAGGCTGGAAAACGGGTCATACAGCTCAGCAGAAA |
| GACTTTTGAGACAGAGTTCCAGAAAACAAAACATCAAGAGTGGGACTTTGTCGTGACAACTGACATTTCAGAGATGGGCGCCA |
| ACTTTAAAGCTGACCGTGTCATAGATTCCAGGAGATGCCTAAAGCCGGTCATACTTGGTGGCGAGAGAGTCATTCTGGCTGGA |
| CCCATGCCTGTCACATGCCACGCTGCCCAGAGGAGGGGGCCATAGGCAGGAATCCCAACAAACCTGGAGATGAGTATC |
| TGTATGGAGGTGGGTGCGCAGAGACTGACGAAGACCATGCACACTGGCTTGAAGCAAGAATGCTCCTTGACAATATTTACCTC |
| CAAGATGGCCTCATAGCCTCGCTCTATCGACCTGAGGCCGACAAAGTAGCAGCCATTGAGGGAGAGTTCAAGCTTAGGACGG |
| AGCAAAGGAAGACCTTTGTGGAACTCATGAAAAGAGGAGATCTTCCTGTTTGGCTGGCCTATCAGGTTGCATCTGCCGGAATA |
| ACCTACACAGATAGAAGATGGTGCTTTGATGGCACGACCAACAACACCATAATGGAAGACAGTGTGCCGGCAGAGGTGTGGA |
| CCAGACAGGAGAGAAAAGGCTGTCAAACCGAGGTGGATGACGCCAGAGTTTGTTCAGATCATGCGGCCCTGAAGTCATT |
| CAAGGAGTTTGCCGCTGGGAAAAGAGGAGCGGCTTTTGGAGTGATGGAAGCCCTGGGAACACTGCCAGGACACATGACAGA |
| GAGATTCCAGGAAGCCATTGACAACCTCGCTGTGCTCATGCGGGCAGAGACTGGAAGCAGGCCTTACAAAGCCGCGGCGCC |
| CAATTGCCGGAGACCCTAGAGACCATTATGCTTTTGGGTTGCTGGGAACAGTCTCGCTGGGAATCTTTTTGCTCTTGATGAGG |
| AACAAGGGCATAGGGAAGATGGGCTTTGGAATGGTGACTCTTGGGCCAGCGCATGGCTCACATGGCTCTCGGAAATTGAGC |
| CAGCCAGAATTGCATGTGTCCTCATTGTTGTGTTCCTATTGCTGGTGGTGCTCATACCTGAGCCAGAAAAGCAAAGATCTCCCC |
| AGGACACCAAATGGCCATCATCATCATGGTAGCAGTAGGTCTTCTGGGCTTGATTACCGCCAATGAACTCGGATGGTTGGAG |
| AGAACAAAGAGTGACCTAAGCCATCTAATGGGAAGGAGAGAGGAGGGGGCAACCATGGGATTCTCAATGGACATTGACCTG |
| CGGCCAGCCTCAGCTTGGGCCATCTATGCAGCTCTGACATCTTTCATTACCCCAGCGTCCAACATGCAGTGACCACTTCATACA |
| ACAACTACTCCTTAATGGCGATGGCCACGCAAGCTGGAGTGTTGTTTGGTATGGGCAAAGGGATGCCATTCTACGCATGGGAC |
| TTTGGAGTCCCGCTGCTAATGATAGGTTGCTACTCACAATTAACGCCCCTGACCCTAATAGTGGCCATCATTTTGCTCGTGGCG |
| CACTACATGTACTTGATCCCAGGGCTGCAGGCAGCAGCTGCGCGTGCTGCCCAGAAGAGAACGGCAGCTGGCATCATGAAGA |
| ACCCTGTTGTGGAGGGAATAGTGGTGACTGACATTGACACAATGACCATTGACCCCCAAGTGGAGAAAAAGATGGGACAGGT |
| GCTACTCATGGCAGTAGCCGTCTCCAGCGCCATACTGTCGAGGACCGCCTGGGGGTGGGGGGAGGCTGGGCCCTGATCACA |
| GCCGCAACTTCCACTTTGTGGGAAGGCTCTCCGAACAAGTACTGGAACTCCTCTACAGCCACCTCACTGTGTAACATTTTTAGG |
| GGAAGTTACTTGGCTGGAGCTTCTCTAATCTACACAGTAACAAGAAACGCTGGCTTGGTCAAGAGACGTGGGGGTGGAACAG |
| GAGAGACCCTGGGAGAGAAATTGGAAGGCCCGTTGAACCAGATGTCGGCCCTGGAGTTCTACTCACAAAAGTCAGGCAT |
| CACCGAGGTGTGCAGAGAAGAGGCCCGCGCCCTCAAGGACGGTGGCAACGGGAGGCCATGCTGTGTCCCGAGGAAG |
| TGCAAAGCTGAGATGGTTGGTGAGCGGGATACCTGCAGCCCTATGGAAAGGTCATTGATCTTGGATGTGGCAGAGGGG |
| CTGGAGTTACTACGCCGCCACCATCCGCAAAGTTCAAGAAGTGAAAGGATACACAAAAGGAGGCCCTGGTCATGAAGAACCC |
| GTGTTGGTGCAAAGCTATGGGTGGAACATAGTCCGTCTTAAGAGTGGGGTGGACGTCTTTCATATGGCGGCTGAGCCGTGTG |
| ACACGTTGCTGTGTGACATAGGTGAGTCATCATCTAGTCCTGAAGTGGAAGAAGCACGGACGCTCAGAGTCCTCTCCATGGTG |
| GGGGATTGGCTTGAAAAAAGACCAGGAGCCTTTTGTATAAAAGTGTTGTGCCCATACACCAGCACTATGATGGAAACCCTGGA |
| GCGACTGCAGCGTAGGTATGGGGGAGGACTGGTCAGAGTGCCACTCTCCCGCAACTCTACACATGAGATGTACTGGGTCTCT |
| GGAGCGAAAAGCAACACCATAAAAAGTGTGTCCACCACGAGCCAGCTCCTCTTGGGGCGCATGGACGGGCCTAGGAGGCCA |
| GTGAAATATGAGGAGGATGTGAATCTCGGCTCTGGCACGCGGGCTGTGGTAAGCTGCGCTGAAGCTCCCAACATGAAGATCA |
| TTGGTAACCGCATTGAAAGGATCCGCAGTGAGCACGCGGAAACGTGGTTCTTTGACGAGAACCACCCATATAGGACATGGGC |
| TTACCATGGAAGCTATGATGCCGCCACACAAGGGTCAGCGTCCTCTCTAATAAACGGGGTTGTCAGGCTCCTGTCAAACCCT |
| GGGATGTGGTGACTGGAGTCACAGGAATAGCCATGACCGACACCACACCGTATGGTCAGCAAAGAGTTTTCAAGGAAAAAGT |
| GGACACTAGGGTGCCAGACCCCCAAGAGGCACTCGTCAGGTTATGAGCATGGTCTCTTCCTGGTTGTGGAAAGAGCTAGGC |
| AAACACAAACGGCCACGAGTCTGTACCAAAGAAGAGTTCATCAACAAGGTTCGTAGCAATGCAGCATTAGGGGCAATATTTGA |
| AGAGGAAAAGAGTGGAAGACTGCAGTGGAAGCTGTGAACGATCCAAGGTTCTGGGCTCTAGTGGACAAGGAAAGAGAGCA |
| CCACCTGAGAGGAGAGTGCCAGAGTTGTGTGTACATCACAATGGGAAAAAGAGAAAAGAAACAAGGGGAATTTGGAAAGGC |

| SEQUENCES |
|---|
| CAAGGGCAGCCGCGCCATCTGGTATATGTGGCTAGGGGCTAGATTTCTAGAGTTCGAAGCCCTTGGATTCTTGAACGAGGATC<br>ACTGGATGGGGAGAGAGAACTCAGGAGGTGGTGTTGAAGGGCTGGGATTACAAAGACTCGGATATGTCCTAGAAGAGATGA<br>GTCGCATACCAGGAGGAAGGATGTATGCAGATGACACTGCTGGCTGGGACACCCGCATCAGCAGGTTTGATCTGGAGAATGA<br>AGCTCTAATCACCAACCAAATGGAGAAAGGGCACAGGGCCTTGGCATTGGCCATAATCAAGTACACATACCAAACAAAGTG<br>GTAAAGGTCCTTAGACCAGCTGAAAAAGGGAAGACAGTTATGGACATTATTTCGAGACAAGACCAAAGGGGGAGCGGACAA<br>GTTGTCACTTACGCTCTCAACACATTTACCAACCTAGTGGTGCAACTCATTCGGAATATGGAGGCTGAGGAAGTTCTAGAGATG<br>CAAGACTTTGTGGCTGCTGCGGAGGTCAGAGAAAGTGACCAACTGGTTGCAGAGCAACGATGGGATAGGCTCAAACGAATG<br>GCGGTCAGTGGAGATGATTGCGTTGTGAAACCAATTGATGATAGGTTTGCACATGCCCTCAGGTTCTTGAATGATATGGGAAA<br>AGTTAGGAAGGACACACAAGAGTGGAAACCCTCAACTGGATGGGACAACTGGGAAGAAGTTCCCTTCTGCTCCCACCACTTCA<br>ACAAGCTCCATCTCAAGGACGGGAGGTCCATTGTGGTTCCCTGCCGCCACCAAGATGAACTGATTGGCCGGGCCCGCGTCTCT<br>CCAGGGGCGGGATGGAGCATCCGGGAGACTGCTTGCCTAGCAAAATCATATGCGCAAATGTGGCAGCTCCTTTATTTCCACAG<br>AAGGGACCTCCGACTGATGGCCAATGCCATTTGTTCATCTGTGCCAGTTGACTGGGTTCCAACTGGGAGAACTACCTGGTCAAT<br>CCATGGAAAGGGAGAATGGATGACCACTGAAGACATGCTTGGCGTGGAACAGAGTGTGGATTGAGGAGAACGACCACAT<br>GGAAGACAAGACCCCAGTCACGAAATGGACAGACATTCCCTATTTGGGAAAAAGGGAAGACTTGTGGTGTGGATCTCTCATA<br>GGGCACAGACCGCGCACCACCTGGGCTGAGAACATTAAAAACACAGTCAACATGGTGCGCAGGATCATAGGTGATGAAGAAA<br>AGTACATGGACTACCTATCCACCCAAGTTCGCTACTTGGGTGAAGAAGGGTCTACACCTGGAGTGCTGTAAGCACCAATCTTA<br>ATGTTGTCAGGCCTGCTAGTCAGCCACAGCTTGGGGAAAGCTGTGCAGCCTGTGACCCCCCAGGAGAAGCTGGGAAACCAA<br>GCCTATAGTCAGGCCGAGAACGCCATGGCACGGAAGAAGCCATGCTGCCTGTGAGCCCCTCAGAGGACACTGAGTCAAAAAA<br>CCCCACGCGCTTGGAGGCGCAGGATGGGAAAAGAAGGTGGCGACCTTCCCCACCCTTCAATCTGGGGCCTGAACTGGAGATC<br>AGCTGTGGATCTCCAGAAGAGGGACTAGTGGTTAGAGGAGA |
| SEQ ID NO: 11<br>LC002520.1 Zika virus genomic RNA, strain: MR7GG-NIID, Uganda, complete genome<br>AGTTGTTGATCTGTGTGAGTCAGACTGCGACAGTTCGAGTCTGAAGCGAGAGCTAACAACAGTATCAACAGGTTTAATTTGGA<br>TTTGGAAACGAGAGTTTCTGGT-ATGAAAAACCCAAAGAAGAAATCCGGAGGATTCCGGATTGTCAATATGCTAAAACGCGG<br>AGTAGCCCGTGTAAACCCCTTGGGAGGTTTGAAGAGGTTGCCAGCCGGACTTCTGCTGGGTCATGGACCCATCAGAATGGTTT<br>TGGCGATACTAGCCTTTTTGAGATTTACAGCAATCAAGCCATCACTGGGCCTTATCAACAGATGGGGTTCCGTGGGGAAAAAA<br>GAGGCTATGGAAATAATAAAGAAGTTCAAGAAAGATCTTGCTGCCATGTTGAGAATAATCAATGCTAGGAAAGAGAGGAAGA<br>GACGTGGCGCAGACACCAGCATCGGAATCATTGGCCTCCTGCTGACTACAGCCATGCAGCAGAGATCACTAGACGCGGGAG<br>TGCATACTACATGTACTTGGATAGGAGCGATGCCGGGAAGGCCATTTCGTTTGCTACCACATTGGGAGTGAACAAGTGCCACG<br>TACAGATCATGGACCTCGGGCACATGTGTGACGCCACCATGAGTTATGAGTGCCCTATGCTGGATGAGGGAGTGGAACCAGA<br>TGATGTCGATTGCTGGTGCAACACGACATCAACTTGGGTTGTGTACAGAACCTGTCATCACAAAAAAGGTGAGGCACGGCGAT<br>CTAGAAGAGCCGTGACGCTCCCTTCTCACTCTACAAGGAAGTTGCAAACGCGGTCGCAGACCTGGTTAGAATCAAGAGAATAC<br>ACGAAGCACTTGATCAAGGTTGAAAACTGGATATTCAGGAACCCCGGGTTTGCGCTAGTGGCCGTTGCCATTGCCTGGCTTTT<br>GGGAAGCTCGACGAGCCAAAAAGTCATATACTTGGTCATGATACTGCTGATTGCCCCGGCATACAGTATCAGGTGCATTGGAG<br>TCAGCAATAGAGACTTCGTCGTGGAGGGCATGTCAGGTGGGACCTGGGTTGCATGTCTTGGAACATGGAGGCTGCGTTACCGT<br>GATGGCACAGGACAAGCCAACAGTTGACATAGAGTTGGTCACGACGACGGTTAGTAACATGGCCGAGGTAAGATCCTATTGC<br>TACGAGGCATCGATATCGGACATGGCTTCGGACAGTCGTTGCCCAACACAAGGTGAAGCCTACCTTGACAAGCAATCAGACAC<br>TCAATATGTCTGCAAAAGAACATTACTGGACAGAGGTTGGGGAAACGGTTGTGGACTTTTTGGCAAAGGGAGCTTGGTGACA<br>TGTGCCAAGTTTACGTGTTCTAAGAAGATGACCGGGAAGAGCATTCAACCGGAAAATCTGGAGTATCGGATAATGCTATCAGT<br>GCATGGCTCCCAGCATAGCGGGATGACTGTCAATGATATAGGATATGAAACTGACGAAAATAGAGCGAAAGTCGAGGTTACG<br>CCTAATTCACCAAGAGCGGAAGCAACCTTGGGAGGCTTTGGAAGCTTAGGACTTGACTGTGAACCAAGGACAGGCCTTGACTT<br>TTCAGATCTGTATTACCTGACCATGAACAATAAGCATTGGTTGGTGCACAAAGAGTGGTTTCATGACATCCCATTGCCTTGGCA<br>TGCTGGGGCAGACACTGGAACTCCACACTGGAACAACAAAGAGGCATTGGTAGAATTCAAGGATGCCCACGCCAAGAGGCAA<br>ACCGTCGTCGTTCTGGGGAGCCAGGAAGGGAGCCGTTCACACGGCTCTCGCTGGGACGTCTAGAGGCTGAGATGGATGGTGCAA<br>AGGGAAAGCTGTTCTCTGGCCATTTGAAATGCCGCCTAAAAATGGACAAGCTTAGATTGAAGGGCGTGTCATATATTCCTTGTGC<br>ACTGCGGCATTCACATTCACCAAGGTCCCAGCTGAAACACTGCATGGAACAGTCACAGTGGAGGTGCAGTATGCAGGGACAG<br>ATGGACCCTGCAAGATCCCAGTCCAGATGGCGGTGGACATGCAGACCCTGACCCCAGTTGGAAGGCTGATAACCGCCAACCC<br>CGTGATTACTGAAAGCACTGAGGAACTCAAAGATGATGTTGGACATCTGACCCACCATTTGGGGATTCTTACATTGTCATAGGAG<br>TTGGGGACAAGAAAATCACCCACCACTGGCATAGGAGTGGTAGCACCATCGGAAAGGCATTTGAGGCCACTGTGAGAGGCGC<br>CAAGAGAATGGCAGTCCTGGGGGATACAGCCTGGGACTTCGGATCAGTCGGGGGTGTGTTCAACTCACTGGGTAAGGGCATT<br>CACCAGATTTTTGGAGCAGCCTTCAAATCACTGTTTGGAGGAATGTCCTGGTTCTCACAGATCCTCATAGGCACGCTGCTAGTG<br>TGGTTAGGTTTGAACACAAAGAATGGATCTATCTCCCTCACATGCTTGGCCCTGGGGGAGTGATGATCTTCCTCTCCACGGCT<br>GTTTCTGCTGACGTGGGGTGCTCAGTGGACTTCTCAAAAAAGGAAACGAGATGTGGCACGGGGGTATTCATCTATAATGATGT<br>TGAAGCTGGAGGGGACCGGTACAAGTACCATCCTGACTCCCCCGCAGATTGGCAGCAGCAGTCAAGCAGGCCTGGGAAGAG<br>GGGATCTGTGGGATCTCATCCGTTTCAAGAATGGAAAACATCATGTGGAAATCAGTAGAAGGGGAGCTCAATGCTATCCTAGA<br>GGAGAATGGAGTTCAACTGACAGTTGTTGTGGGATCTGTAAAAAACCCATGTGGAGAGGTCACAAAGATTGCCAGTGCCT<br>GTGAATGAGCTGCCCCATGGCTGGAAAGCCTGGGGGAAATCGTATTTTGTTAGGGCGGCAAAGACCAACAACAGTTTTGTTGT<br>CGACGGTGACACACTGAAGGAATGTCCGCTTGAGCACAGAGCATGGAATAGTTTTCTTGTGGAGGATCACGGGTTTGGAGTC<br>TTCCACACCAGTGTCTGGCTTAAGGTCAGAGAAGATTACTCATTAGAATGTGACCCAGCCGTCATAGGAACAGCTGTTAAGGG<br>AAGGGAGGCCGCGCACAGTGATCTGGGCTATTGGATTGAAAGTGAAAAGAATGACACATGGCGACTGGCTCGAGGCGGCCACCT<br>GATTGAGATGAAACATGTGAATGGCCAAAGTCTCACACATTGTGGACAGATGGAGTAGAAGAAAGTGATCTTATCATACCCA<br>AGTCTTTAGCTGGTCCACTCAGCCACCACAACACCAGAGAGGGTTACAGAACCCAAGTGAAAGGGCCATGGCACAGTGAAGA<br>GCTTGAAATCCGGTTTGAGGAATGTCCAGGCACCAAGGTTTACGTGGAGGAGACATGCGGAACTAGAGGACCATCTCTGAGA<br>TCAACTACTGCAAGTGGAAGGGTCATTGAGGAATGGTGCTGTAGGGAATGCACAATGCCCCACTATCGTTTCGAGCAAAAG<br>ACGGCTGCTGGTATGGAATGGAGATAAGGCCCAGGAAAGAACCAGAGAGCACTTAGTGAGGTCAATGGTGACAGCGGGGT<br>CAACCGATCATATGGACCACTTCTCTCTTGGAGTGCTTGTGATTCTACTCATGGTGCAGGAGGGTTGAAGAAGAGAATGACC<br>ACAAAGATCATCATGAGCACATCAATGGCAGTGCTGGTAGTCATGATCTTGGGAGGATTTTCAATGAGTGACCTGGCCAAGCT<br>TGTGATCCTGATGGGTGCTACTTTCGCAGAAATGAACACTGGAGGAGATGTAGCTCACTTGGCATTGGTAGCGGCATTTAAAG<br>TCAGACCAGCCTTGCTGGTCTCCTTCATTTTCAGAGCCAATTGGACACCCCGTGAGAGCATGCTGCTAGCCCTGGCTTCGTGTC<br>TTCTGCAAACTGCGATCTCTGCTCTTGAAGGTGACTTGATGGTCCTCATTAATGGATTTGCTTTGGCCTGGTTGGCAATTCGAGC<br>AATGGCCGTGCCACGCACTGACAACATCGCTCTACCAATCTTGGCTGTCTAACACCACTAGCTCGAGGCACACTGCTCGTGGC<br>ATGGAGAGCGGGCCTGGCTACTTGTGAGGGATCATGCTCCTCTCCCTGAAAGGGAAAGGTAGTGTGAAGAAGAACCTGCCA<br>TTTGTCATGGCCCTGGGATTGACAGCTGTGAGGGTAGTAGACCCTATTAATGTGGTAGGACTACTGTTACTCACAAGGAGTGG<br>GAAGCGGAGCTGGCCCCCTAGTGAAGTTCTCACAGCCGTTGGCCTGATATGTGCACTGGCCGGAGGGTTTGCCAAGGCAGAC<br>ATTGAGATGGCTGGACCCATGGCTGCAGTAGGCTTGCTAATTGTCAGCTATGTGGTCTCGGGAAAGAGTGTGGACATGTACAT<br>TGAAAGAGCAGGTGACATCACATGGGAAAAGGACGCGGAAGTCACTGGAAACAGTCCTCGGCTTGACGTGGCACTGGATGA |

| SEQUENCES |
|---|
| GAGTGGTGATTTCTCCTTGGTAGAGGAAGATGGTCCACCCATGAGAGAGATCATACTTAAGGTGGTCCTGATGGCCATCTGTG |
| GCATGAACCCAATAGCTATACCTTTTGCTGCAGGAGCGTGGTATGTGTATGTGAAGACTGGGAAAAGGAGTGGCGCCCTCTG |
| GGACGTGCCTGCTGCTCCCAAAGAAGTGAAGAAAGGAGAGACACAGATGGAGTGTACAGAGTGATGACTCGCAGACTGCTAGG |
| TTCAACACAGGTTGGAGTGGGAGTCATGCAAGAGGGAGTCTTCCACACCATGTGGCACGTTACAAAAGGAGCCGCACTGAGG |
| AGCGGTGAGGGAAGACTTGATCCATACTGGGGGGATGTCAAGCAGGACTTGGTGTCATACTGTGGGCCTTGGAAGTTGGATG |
| CAGCTTGGGATGGACTCAGCGAGGTACAGCTTTTGGCCGTACCTCCCGGAGAGAGGGCCAGAAACATTCAGACCCTGCCTGG |
| AATATTCAAGACAAAGGACGGGACATCGGAGCAGTTGCTCTGGACTACCCTGCAGGGACCTCAGGATCTCCGATCCTAGAC |
| AAATGTGGAAGAGTGATAGGACTCTATGGCAATGGGGTTGTGATCAAGAATGGAAGCTATGTTAGTGCTATAACCCAGGGAA |
| AGAGGGAGGAGGAGACTCCGGTTGAATGTTTCGAACCCTCGATGCTGAAGAAGAAGCAGCTAACTGTCTTGGATCTGCATCC |
| AGGAGCCGGAAAAACCAGGAGAGTTCTTCCTGAAATAGTCCGTGAAGCCATAAAAAAGAGACTCCGGACAGTGATCTTGGCA |
| CCAACTAGGGTTGTCGCTGCTGAGATGGAGGAGGCCTTGAGAGGACTTCCGGTGCGTTACATGACAACAGCAGTCAACGTCA |
| CCCATTCTGGGACAGAAATCGTTGATTTGATGTGCCATGCCACTTTCACTTCACGCTTACTACAACCCATCAGAGTCCCTAATTA |
| CAATCTCTACATCATGGATGAAGCCCACTTCACAGACCCCTCAAGTATAGCTGCAAGAGGATATATATCAACAAGGGTTGAAAT |
| GGGCGAGGCGGCTGCCATTTTTATGACTGCCACACCACCAGGAACCCGTGATGCGTTTCCTGACTCTAACTCACCAATCATGGA |
| CACAGAAGTGGAAGTCCCAGAGAGAGCCTGGAGCTCAGGCTTTGATTGGGTGACAGACCATTCTGGGAAAACAGTTTGGTTC |
| GTTCCAAGCGTGAGAAACGGAAATGAAATCGCAGCCTGTCTGACAAAGGCTGGAAAGCGGGTCATACAGCTCAGCAGGAAG |
| ACTTTTGAGACAGAATTTCAGAAAACAAAAATCAAGAGTGGGACTTTGTCATAACAACTGACATCTCAGAGATGGGCGCCAA |
| CTTCAAGGCTGACCGGGTCATAGACTCTAGGAGATGCCTAAAACCAGTCATACTTGATGGTGAGAGAGTCATCTTGGCTGGGC |
| CCATGCCTGTCACGCATGCTAGTGCTGCTCAGAGGAGAGGACGTATAGGCAGGAACCCTAACAAACCTGGAGATGAGTACAT |
| GTATGGAGGTGGGTGTGCAGAGACTGATGAAGGCCATGCACACTGGCTTGAGACAAGAATGCTTCTTGACAACATCTACCTCC |
| AGGATGGCCTCATAGCCTCGCTCTATCGGCCTGAGGCCGATAAGGTAGCCGCCATTGAGGGAGAGTTTAAGCTGAGGACAGA |
| GCAAAGGAAGACCTTCGTGGAACTCATGAAGAGAGGGAGACCTTCCCGTCTGGCTAGCCTATCAGGTTGCATCTGCCGGAATAA |
| CTTACACAGACAGAAGATGGTGCTTTGATGGCACAACCAACAACACCATAATGGAAGACAGCGTACCAGCAGAGGTGTGGAC |
| AAAGTATGGAGAGAAGAGAGTGCTCAAACCGAGATGGATGATCGCTAGGGTCTGTTCAGACCATGCGGCCCTGAAGTCGTTC |
| AAAGAATTCGCCGCTGGAAAAAGAGGGAGCGGCTTTGGGAGTAATGGAGGCCCTGGGAACACTGCCAGGACACATGACAGAG |
| AGGTTTCAGGAAGCCATTGACAACCTCGCCGTGCTCATGCGAGCAGAGACTGGAAGCAGGCCTTATAAGGCAGCGGCAGCCC |
| AACTGCCGGAGACCCTAGAGACCATTATGCTCTTAGGTTTGCTGGGAACAGTTTCACTGGGGATCTTCTTCGTCTTGATGCGGA |
| ATAAGGGCATCGGGAAGATGGGCTTTGGAATGGTAACCCTTGGGGCCAGTGCATGGCTCATGTGGCTTTCGGAAATTGAACC |
| AGCCAGAATTGCATGTGTCCTCATTGTTGTGTTTTATTACTGGTGGTGCTCATACCCGAGCCAGAGAAGCAAAGATCTCCCCA |
| AGATAACCAGATGGCAATTATCATCATGGTGGCAGTGGGCCTTCTAGGTTTGATAACTGCAAACGAACTTGGATGGCTGGAAA |
| GAACAAAAAATGACATAGCTCATCTAATGGGAAGGAGAGAAGAAGGAGCAACCATGGGATTCTCAATGGACATTGATCTGCG |
| GCCAGCCTCCGCCTGGGCTATCTATGCCGCATTGACAACTCTCATCACCCCAGCTGTCCAACATGCGGTAACCACTTCATACAAC |
| AACTACTCCTTAATGGCGATGGCCACACAAGCTGGAGTGCTGTTTGGCATGGCAGCAAAGGGATGCCATTTTATGCATGGGACCT |
| TGGAGTCCCGCTGCTAATGATGGGTTGCTATTCACAATTAACACCCCTGACTCTGATAGTAGCTATCATTCTGCTTGTGGCGCA |
| CTACATGTACTTGATCCCAGGCCTACAAGCGGCAGCAGCGCGTGCTGCCCAGAAAAGGACAGCAGCTGGCATCATGAAGAAT |
| CCCGTTGTGGATGGAATAGTGGTAACTGACATTGACACAATGACAATAGACCCCCAGGTGGAGAAGAAGATGGGACAAGTGT |
| TACTCATAGCAGTAGCCATCTCCAGTGCTGTGCTGCTGCGGACCGCCTGGGGATGGGGGGAGGCTGGAGCTCTGATCACAGC |
| AGCGACCTCCACCTTGTGGGAAGGCTCTCCAAACAAATACTGGAAGTTCCTCTACACCACCCACTCACTGTGCAACATCTTCAGAGG |
| AAGCTATCTGGCAGGAGCTTCCCTTATCTATACAGTGACGAGAAACGCTGGCCTGGTTAAGACGTGGAGGTGGGACGGGA |
| GAGACTCTGGGAGAGAAGTGGAAAGCTCGTCTGAATCAGATGTCGGCCCTGGAGTTCTACTCTTATAAAAAGTCAGGTATCAC |
| TGAAGTGTGTAGAGAGGAGGCTCGCCGTGCCCTCAAGGATGGAGTGGCCACAGGAGGACATGCCGTATCCCGGGGAAGTGC |
| AAAGCTCAGATGGTTGGTGGAGAGAGGATATCTGCAGCCCTATGGGAAGGTTGTTGACCTCGGATGTGGCAGAGGGGCTG |
| GAGCTATTATGCGCCACCATCCGCAAAGTGCAGGAGGTGAGAGGATACAAAAGGGAGGTCCCGGTCATGAAGAACCCATG |
| CTGGTGCAAAGCTATGGGTGGAACATAGTTCGTCTCAAGAGTGGAGTGGACGTCTTCCACATGGCGGCTGAGCCGTGTGACA |
| CTCTGCTGTGTGACATAGGTGAGTCATCATCTAGTCCTGAAGTGGAAGAGACACGAACACTCAGAGTGCTCTCTATGGTGGGG |
| GACTGGCTTGAAAAAAGACCAGGGGCCTTCTGTATAAAGGTGCTGTGCCCATACACCAGCACTATGATGGAAACCATGGAGC |
| GACTGCAACGTAGGCATGGGGAGGATTAGTCAGAGTGCCATTGTCTCGCAACTCCACACATGAGATGTACTGGGTCTCTGG |
| GGCAAAGAGCAACATCATAAAAAGTGTGTCCACCACAAGTCAGCTCCTCCTGGGACGCATGGATGGCCCCAGGAGGCCAGTG |
| AAATATGGAGGAGGATGTGAACCTCGGCTCGGGTACAGAGCTGTGGCAAGCTGTGCTGAGGCTCCTAACATGAAAATCATCG |
| GCAGGCGCATTGAGAGAATCCGCAATGAACATGCAGAAACATGGTTTCTTGATGAAAACCACCCATACAGGACATGGGCCTAC |
| CATGGGAGCTACGAAGCCCCACGCAAGGATCAGCGTCTTCCCTCGTGAACGGGGTTGTTAGACTCCTGTCAAAGCCTTGGGA |
| CGTGGTGACTGGAGTTACAGGAATAGCCATGACTGACACCACACCATACGGCCAACAAAGAGTCTTCAAAGAAAAGTGGAC |
| ACCAGGGTGCCAGATCCCCAAGAAGGCACTCGCCAGGTAATGAACATAGTCTCTTCCTGGCTGTGGAAGGAGCTGGGGAAAC |
| GCAAGCGGCCACGCGTCTGCACCAAAGAAGAGTTTATCAACAAGGTGCGCAGCAATGCAGCACTGGGAGCAATATTTTGAAGA |
| GGAAAAAGAATGGAAGACGGCTGTGGAAGCTGTGAATGATCCAAGGTTTTGGGCCCTAGTGGATAGGGAGAGAGAACACCA |
| CCTGAGAGGAGAGTGTCACAGCTGTGTGTACAACATGATGGGAAAAAGAGAAAAGAAGCAAGGAGAGTTCGGGAAAGCAA |
| AAGGTAGCCGCGCCATCTGGTACATGTGGTTGGGAGCCAGATTCTTGGAGTTTGAAGCCCTTGGATTCTTGAACGAGGACCAT |
| TGGATGGGAAGAGAAAACTCAGGAGGTGGAGTCGAAGGGTTAGGATTGCAAAGACTTGGATACATTCTAGAAGAAATGAAT |
| CGGGCACCAGGAGGAAAGATGTACGCAGATGACACTGCTGGCTGGGACACCCGCATTAGTAAGTTTGATCTGGAGAATGAAG |
| CTCTGATTACCAACCAAATGGAGAAGGGCACAGAACTCTGGCGTTGGCCGTGATTAAATACACATACAAACAAAGTGGTG |
| AAGGTTCTCAGACCAGCTGAAGGAGGAAAACAGTTATGGACATCATTTCAAGACAAGACCAGAGAGGGAGTGGACAAGTT |
| GTCACTTATGCTCTCAACACATTCACCAACTTGGTGGTGCAGCTTATCCGGAACATGGAAGCTGAGGAAGTGTTAGAGATGCA |
| AGACTTATGGTTGTTGAGGAAGCCAGAGAAAGTGACCAGATGGTTGCAGAGCAATGGATGGGATAGACTCAAACGAATGGC |
| GGTCAGTGGAGATGACTGCGTTGTGAAGCCAATCGATGATAGGTTTGCAAGCCCTCAGGTTCTTGAATGACATGGGAAAA |
| GTTAGGAAAGACACACAGGAGTGGAAACCCTCGACTGGATGGAGCAATTGGGAAGAAGTCCCGTTCTGCTCCCACCACTTCA |
| ACAAGCTGTACCTCAAGGATGGGAGATCCATTGTGGTCCCTTGCCGCCACCAAGATGAACTGATTGGCCGAGCTCGCGTCTCA |
| CCAGGGGCAGGATGGAGCATCCGGGAGACTGCCTGTCTTGCAAAATCATATGCGCAGATGTGGCAGCTCCTTTATTTCCACAG |
| AAGAGACCTTCGACTGATGGCTAATGCCATTTGCTCGGCTGTGCCAGTTGACTGGGTACCAACTGGGAGAACCACCTGGTCAA |
| TCCATGGAAAGGGAGAATGGATGACCACTGAGGACATGCTCAGTGTTGGGAACATAGAGAAGATGGCTGTCCTGACAAGTT |
| GGAGGACAAGACTCCTGTAACAAAATGGACAGACATTCCCTATCTAGGAAAAGGGAGGACTTATGGTGTGGATCCCTTATA |
| GGGCACAGACCCCGCACCACTTGGGCTGAAAACATCAAAGACACAGTCAACATGGTGCGCAGGATCATAGGTGATGAAGAA |
| AGTACATGGACTATCATCCACCCAAGTCCGCTACTTGGGTGAGGAAGGGTCCACACCCGGAGTGTTGTAAGCACCAATTTTA |
| GTGTTGTCAGGCCTGCTAGTCAGCCACAGTTTGGGGAAAGCTGTGCAGCCTGTAACCCCCCAGGAGAAGCTGGGAAACCAA |
| GCTCATAGTCAGGCCGAGAACGCCATGGCACGGAAGAAGCCATGCTGCCTGTGAGCCCCTCAGAGGACACTGAGTCAAAAAA |
| CCCCACGCGCTTGGAAGCGCAGGATGGGAAAAGAAGGTGGCGACCTTCCCCACCCTTCAATCTGGGGCCTGAACTGGAGACT |

AGCTGTGAATCTCCAGCAGAGGGACTAGTGGTTAGAGGAGACCCCCCGGAAAACGCAAAACAGCATATTGACGCTGGGAAA
GACCAGAGACTCCATGAGTTTCCACCACGCTGGCCGCCAGGCACAGATCGCCGAACAGCGGCGGCCGGTGTGGGGAAATCCA
TGGTTTCT

SEQ ID NO: 12
AY632535.2 NC_012532.1 Zika virus strain MR 766, Uganda, complete genome
AGTTGTTGATCTGTGTGAGTCAGACTGCGACAGTTCGAGTCTGAAGCGAGAGCTAACAACAGTATCAACAGGTTTAATTTGGA
TTTGGAAACGAGAGTTTCTGGTCATGAAAAACCCCAAAGAAGAAATCCGGAGGATCCGGATTGTCAATATGCTAAAACGCGG
AGTAGCCCGTGTAAACCCCTTGGGAGGTTTGAAGAGGTTGCCAGCCGGACTTCTGCTGGGTCATGGACCCATCAGAATGGTTT
TGGCGATACTAGCCTTTTTGAGATTTACAGCAATCAAGCCATCACTGGGCCTTATCAACAGATGGGGTTCCGTGGGGAAAAA
GAGGCTATGGAAATAATAAAGAAGTTCAAGAAAGATCTTGCTGCCATGTTGAGAATAATCAATGCTAGGAAAGAGAGGAAGA
GACGTGGCGCAGACACCAGCATCGGAATCATTGGCCTCCTGCTGACTACAGCCATGGCAGCAGAGATCACTAGACGCGGGAG
TGCATACTACATGTACTTGGATAGGAGCGATGCCGGGAAGGCCATTTCGTTTGCTACCACATTGGGAGTGAACAAGTGCCACG
TACAGATCATGGACCTCGGGCACATGTGTGACGCCACCATGAGTTATGAGTGCCCTATGCTGGATGAGGGAGTGGAACCAGA
TGATGTCGATTGCTGGTGCAACACGACATCAACTTGGGTTGTGTACGGAACCTGTCATCACAAAAAAGGTGAGGCACGGCGAT
CTAGAAGAGCCGTGACGCTCCCTTCTCACTCTACAAGGAAGTTGCAAACGCGGTCGCAGACCTGGTTAGAATCAAGAGAATAC
ACGAAGCACTTGATCAAGGTTGAAAACTGGATATTCAGGAACCCCGGGTTTGCGCTAGTGGCCGTTGCCATTGCCTGGCTTTT
GGGAAGCTCGACGAGCCAAAAAGTCATATACTTGGTCATGATACTGCTGATTGCCCCGGCATACAGTATCAGGTGCATTGGAG
TCAGCAATAGAGACTTCGTGGAGGGCATGTCAGGTGGGACCTGGGTTGATGTTGTCTTGGAACATGGAGGCTGCGTTACCGT
GATGGCACAGGACAAGCCAACAGTCGACATAGAGTTGGTCACGACAGGTTAGTAACATGGCCGAGGTAAGATCCTATTGC
TACGAGGCATCGATATCGGACATGGCTTCGGACAGTCGTTGCCCAACACAAGGTGAAGCCTACCTTGACAAGCAATCAGACAC
TCAATATGTCTGCAAAAGAACATTAGTGGACAGAGGTTGGGGAAACGGTTGTGGACTTTTTGGCAAAGGGAGCTTGGTGACA
TGTGCCAAGTTTACGTGTTCTAAGAAGATGACCGGGAAGAGCATTCAACCGGAAAATCTGGAGTATCGGATAATGCTATCAGT
GCATGGCTCCCAGCATAGCGGGATGATTGGATATGAAACTGACGAAGATAGAGCGAAAGTCGAGGTTACGCCTAATTCACCA
AGAGCGGAAGCAACCTTGGGAGGCTTTGGAAGCTTAGGACTTGACTGTGAACAAGGACAGGCCTTGACTTTTCAGATCTGTA
TTACCTGACCATGAACAATAAGCATTGGTTGGTGCACAAAGAGTGGTTTCATGACATCCCATTGCCTTGGCATGCTGGGGCAG
ACACCGGAACTCCACACTGGAACAACAAAGAGGCATTGGTAGAATTCAAGGATGCCCACGCCAAGAGGCAAACCGTCGTCGT
TCTGGGGAGCCAGGAAGGAGCCGTTCACACGGCTCTCGCTGGAGCTCTAGAGGCTGAGATGGATGGTGCAAAGGGAAGGCT
GTTCTCTGGCCATTTGAAATGCCGCCTAAAAATGGACAAGCTTAGATTGAAGGGCGTGTCATATTCCTTGTGCACTGCGGCATT
CACATTCACCAAGGTCCCAGCTGAAACACTGCATGGAACAGTCACAGTGGAGGTGCAGTATGCAGGGACAGATGGACCCTGC
AAGATCCCAGTCCAGATGGCGGTGGACATGCAGACCCTGACCCCAGTTGGAAGGCTGATAACCGCCAACCCCGTGATTACTGA
AAGCACTGAGAACTCAAAGATGATGTTGGAGCTTGACCCACCATTTGGATTCTTACATTTCATAGGAGTTGGGGACAAGA
AAATCACCCACCACTGGCATAGGAGTGGTAGCACCATCGGAAAGGCATTTGAGGCCACTGTGAGAGGCGCCAAGAGAATGGC
AGTCCTGGGGATACAGCCTGGGACTTCGGATCAGTCGGGGGTGTGTTCAACTCACTGGGTAAGGGCATTCACCAGATTTTTG
GAGCAGCCTTCAAATCACTGTTTGGAGGAATGTCCTGGTTCTCACAGATCCTCATAGGCACGCTGCTAGTGTGGTTAGGTTTGA
ACACAAAGAATGGATCTATCTCCTCACATGCTTGGCCTGGGGGAGTGATGATCTTCCTCTCCACGGCTGTTTCTGCTGACG
TGGGGTGCTCAGTGGACTTCTCAAAAAAGGAAACGAGATGTGGCACGGGGGTATTCATCTATAATGATGTTGAAGCCTGGAG
GGACCGGTACAAGTACCATCCTGACTCCCCCGCAGATTGGCAGCAGCAGTCAAGCAGGCCTGGGAAGAGGGGATCTGTGGG
ATCTCATCCGTTTCAAGAATGGAAAACATCATGTGGAAATCAGTAGAAGGGGAGCTCAATGCTATCCTAGAGGAGAATGGAG
TTCAACTGACAGTTGTTGTGGGATCTGTAAAAAACCCCATGTGGAGAGGTCCACAAAGATTGCCAGTGCCTGTGAATGAGCTG
CCCCATGGCTGGAAAGCCTGGGGGAAATCGTATTTTGTTAGGGCGGCAAAGACCAACAAGCAGTTTTGTTGTTGCGACGGTGACAC
ACTGAAGGAATGTCCGCTTGAGCACAGAGCATGGAATAGTTTTCTTGTGGAGGATCACGGGTTTGGAGTCTTCCACACCAGTG
TCTGGCTTAAGGTCAGAGAAGATTACTCATTAGAATGTGACCCAGCCGTCATAGGAACAGCTGTTAAGGGAAGGGAGGCCGC
GCACAGTGATCTGGGCTATTGGATTGAAAGTGAAAAGAATGACACATGGAGGCTGAAGAGGGCCCACCTGATTGAGATGAAA
ACATGTGAATGGCCAAAGTCTCACACATTGTGGACAGATGGATTAGAAGAAATTGATCTTATCATACCCAAGTCTTTAGCTGG
TCCACTCAGCCACCACAACACCAGAGAGGGTTACAGAACCCAAGTGAAAGGGCCATGGCACAGTGAAGAGCTTGAAATCCGG
TTTGAGGAATGTCCAGGCACCAAGGTTTACGTGGAGGAGACATGCGGAACTAGAGGACCATCTCTGAGATCAACTACTGCAA
GTGGAAGGGTCATTGAGAATGGTGCTGTAGGGAATGCACAATGCCCCCACTATCGTTTCGAGCAAAAGACGGCTGCTGGTA
TGGAATGGAGATAAGGCCCAGGAAAGAACCAGAGAGCAACTTAGTGGTGACAGCGGGGGTCAACCGATCATAT
GGACCACTTCTCTCTTGGAGTGCTTGTGATTCTACTCATGGTGCAGGAGGGGTTGAAGAAGAGAATGACCAAAGATCATCA
TGAGCACATCAATGGCAGTGCTGGTAGTCATGATCTTGGGAGGATTTTCAATGAGTGACCTGGCCAAGCTTGTGATCCTGATG
GGTGCTACTTTCGCAGAAATGAACACTGGAGGAGATGTAGCTCACTTGGCATTGGTAGCGGCATTTAAAGTCAGACCAGCCTT
GCTGGTCTCCTTCATTTTCAGAGCCAATTGGACACCCCGTGAGGACATGCTGCTAGCCCTGGCTTCGTGTCTTCTGCAAACTGC
GATCTCTGCTCTTGAAGGTGACTTGATGGTCCTCATTAATGGATTTGCTTTGGCCTGGTTGGCAATTCGAGCAATGGCCGTGCC
ACGCACTGACAACATCGCTCTACCAATCTTGGCTGCTCTAACACCACTAGCTCGAGGCACACTGCTCGTGGCATGGAGAGCGG
GCCTGGCTACTTGTGGAGGGATCATGCTCCTCTCCCTGAAAGGGAAAGGTAGTGTGAAGAAGAACCTGCCATTTGTCATGGCC
CTGGGATTGACAGCTGTGAGGGTAGTAGACCCTATTAATGTGGTAGGACTGCTGCTACTCACAAGGAGTGGGAAGCGGAGCT
GGCCCCCTAGTGAAGTTCTCACAGCCGTTGGCCTGATATGTGCACTGGCCGGAGGGTTTGCAAGGCAGACATTGAGATGGCT
GGACCCATGGCTGCAGTAGGCTTGCTAATTGTCAGCTATGTGGTCTCGGGAAAGAGTGTGGACATGTACATTGAAAGAGCAG
GTGACATCACATGGGAAAAGGACGCGGAAGTCACTGGAAACAGTCCTCGGCTTGACGTGGCACTGGATGAGAGTGGTGACTT
CTCCTTGGTAGAGGAAGATGGTCCACCCATGAGAGAGATACATCAAGGAGGATGTGATGGCCATCTGTGGTGACACACCTAA
TAGCTATACCTTTTGCTGCAGGAGCGTGGTATGTGTATGTGAAGACTGGGAAAAGGAGTGGCCCCTCTGGGACGTGCCTGC
TCCCAAAGAAGTGAAGAAAGGAGAGACCACAGATGGAGTGTACAGAGTGATGACTCGCAGACTGCTAGGTTCAACACAGGTT
GGGAGTGGGAGTCATGCAAGAGGGAGTCTTCCACACCATGTGGCACGTTACAAAAGGAGCCGCACTGAGGAGCGGTGAGGGA
AGACTTGATCCATACTGGGGGGATGTCAAGCAGGACTTGGTGTCATACTGTGGGCCTTGGAAGTTGGATGCAGCTTGGGATG
GACTCAGCGAGGTACAGCTTTTGGCCGTACCTCCGGAGAGAAGGGCCAGAAACATTCAGACCCTGCCTGTTACTAGACAAATGCTGGAAGA
AAGGACGGGACATCGGAGCAGTTGCTCTGGACTACCCTGCAGGGACCTCAGGATCTCCGATCCTAGACAAATGTGGAAGAG
TGATAGGACTCTATGGCAATGGGGTTGTGATCAAGAATGGAAGCTATGTTAGTGCTATAACCCAGGGAAAGAGGGAGGAGG
AGACTCCGGTTGAATGTTTCGAACCCTCGATGCTGAAGAAGAAGCAGCTAACTGTCTTGGATCTGCATCCAGGAGCCGGAAAA
ACCAGGAGAGTTCTTCCTGAAATAGTCCGTGAAGCCATAAAAAAGAGACTCCGGACAGTGATCTTGGCACCAACTAGGGTTGT
CGCTGCTGAGATGGAGGAGGCGTTCAGAGGACTTCCGGTGCGTTACATGACAACAGCAGTCAACGTCACTCACTCTGGGACAG
GAAATCGTTGATTTGATGTGCCATGCCACTTTCACTTCACGCTTACTACAACCATCAGAGTCCCTAATTACAATCTCAACATCAT
GGATGAAGCCCACTTCACAGACCCCTCAAGTATAGCTGCAAGAGGATACATATCAACAAGGGTTGAAATGGGCGAGGCGGCT
GCCATTTTTATGACTGCCACACCACCAGGAACCCGTGATGCGTTTCCTGACTCTAACTCACCAATCATGGACACAGAAGTGGAA
GTCCCAGAGAGAGCCTGGAGCTCAGGCTTTGATTGGGTGACAGACCATTCTGGGAAAACAGTTTGGTTCGTTCCAAGCGTGA
GAAACGGAAATGAAATCGCAGCCTGTCTGACAAAGGCTGGAAAGCGGGTCATACAGCTCAGCAGGAAGACTTTTGAGACAGA
ATTTCAGAAAACAAAAAATCAAGAGTGGGACTTTGTCATAACAACTGACATCTCAGAGATGGGCGCCAACTTCAAGGCTGACC

| SEQUENCES |
| --- |
| GGGTCATAGACTCTAGGAGATGCCTAAAACCAGTCATACTTGATGGTGAGAGAGTCATCTTGGCTGGGCCCATGCCTGTCACG
CATGCTAGTGCTGCTCAGAGGAGAGGACGTATAGGCAGGAACCCTAACAAACCTGGAGATGAGTACATGTATGGAGGTGGG
TGTGCAGAGACTGATGAAGGCCATGCACACTGGCTTGAAGCAACAAATGCTTGTTGACAACATCTACCTCCAGGATGGCCTCAT
AGCCTCGCTCTATCGGCCTGAGGCCGATAAGGTAGCCGCCATTGAGGGAGAGTTTAAGCTGAGGACAGAGCAAAGGAAGAC
CTTCGTGGAACTCATGAAGAGAGGAGACCTTCCCGTCTGGCTAGCCTATCAGGTTGCATCTGCCGGAATAACTTACACAGACA
GAAGATGGTGCTTTGATGGCACAACCAACAACACCATAATGGAAGACAGTGTACCAGCAGAGGTTTGGACAAAGTATGGAGA
GAAGAGAGTGCTCAAACCGAGATGGATGGATGCTAGGGTCTGTTCAGACCATGCGGCCCTGAAGTCGTTCAAAGAATTCGCC
GCTGGAAAAAGAGGAGCGGCTTTGGGAGTAATGGAGGCCCTGGGAACACTGCCAGGACACATGACAGAGAGGTTTCAGGAA
GCCATTGACAACCTCGCCGTGCTCATGCGAGCAGAGACTGGAAGCAGGCCTTATAAGGCAGCGGCAGCCCAACTGCCGGAGA
CCCTAGAGACCATTATGCTCTTAGGTTTGCTGGGAACAGTTTCACTGGGGATCTTCTTCGTCTTGATGCGGAATAAGGGCATCG
GGAAGATGGGCTTTGGAATGGTAACCCTTGGGGCCAGTGCATGGCTCATGTGGCTTTCGGAAATTGAACCAGCCAGAATTGC
ATGTGTCCTCATTGTTGTGTTTTTATTACTGGTGGTGCTCATACCCGAGCCAGAGAAGCAAAGATCTCCCCAAGATAACCAGAT
GGCAATTATCATCATGGTGGCAGTGGGCCTTCTAGGTTTGATAACTGCAAACGAACTTGGATGGCTGGAAAGAACAAAAAAT
GACATAGCTCATCTAATGGGAAGGAGAGAAGAAGGAGCAACCATGGGATTCTCAATGGACATTGATCTGCGGCCAGCCTCCG
CCTGGGCTATCTATGCCGCATTGACAACTCTCATCACCCCAGCTGTCCAACATGCGGTAACCACTTCATACAACAACTACTCCTT
AATGGCGATGGCCACACAAGCTGGAGTGCTGTTTGGCATGGGCAAAGGGATGCCATTTATGCATGGGGACCTTGGAGTCCCG
CTGCTAATGATGGGTTGCTATTCACAATTAACACCCCTGACTCTGATAGTAGCTATCATTCTGCTTGTGGCGCACTACATGTACT
TGATCCCAGGCCTACAAGCGGCAGCAGCGCGTGCTGCCCAGAAAAGGACAGCAGCTGGCATCATGAAGAATCCCGTTGTGGA
TGGAATAGTGGTAACTGACATTGACACAATGACAATAGACCCCCAGGTGGAGAAGAAGATGGGACAAGTGTTACTCATAGCA
GTAGCCATCTCCAGTGCTGTGCTGCTGCGGACCGCCTGGGGATGGGGGGAGGCTGGACTCTGATCACAGCAGCGACCTCCA
CCTTGTGGGAAGGCTCTCCAAACAAATACTGGAACTCCTCTACAGCCACCTCACTGTGCAACATCTTCAGAGGAAGCTATCTGG
CAGGAGCTTCCCTTATCTATACAGTGACGAGAAACGCTGGCCTGGTTAAGAGACGTGGAGGTGGGACGGGAGAGACTCTGG
GAGAGAAGTGGAAAGCTCGTCTGAATCAGATGTCGGCCCTGGAGTTCTACTCTTATAAAAAGTCAGGTATCACTGAAGTGTGT
AGAGAGGAGGCTCGCCGTCGCCCTCAAGGATGGAGTGGCCACAGGAGGCATGCCGTATCCCGGGGAAGTGCAAAGATCAGA
TGGTTGAGGAGAGAGGATATCTGCAGCCCTATGGGAAGGTTGTTGACCTCGGATGTGGCAGGGGGCTGGAGCTATTAT
GCCGCCACCATCCGCAAAGTGCAGGAGGTGAGAGGATACACAAAGGGAGGTCCCGGTCATGAAGAACCCATGCTGGTGCAA
AGCTATGGGTGGAACATAGTTCGTCTCAAGAGTGGAGTGGACGTCTTCCACATGGCGGCTGAGCCGTGTGACACTCTGCTGTG
TGACATAGGTGAGTCATCATCTAGTCCTGAAGTGGAAGAGACACTGAGGATTCTCTATGGTGGGGACTGGCTT
GAAAAAAGACCAGGGGCCTTCTGTATAAAGGTGCTGTGCCCATACACCAGCACTATGATGGAAACCATGGAGGCGACTGCAAC
GTAGGCATGGGGAGGATTAGTCAGAGTGCCATTGTGTCGCAACTCCACACATGAGATGTACTGGGTCTCTGGGCAAAGAG
CAACATCATAAAAGTGTGTCCACCACAAGTCAGCTCCTCCTGGGACGCATGGATGGCCCCAGGAGGCCAGTGAAATATGAG
GAGGATGTGAACCTCGGCTACGGAGCTGTGGCAAGCTGTGCTGAGGCTCCTAACATGAAAATCATCGGCAGGCGCA
TTGAGAGAATCCGCAATGAACATGCAGAAACATGGTTTCTTGATGAAAACCACCCATACAGGACATGGGCCTACCATGGGAGC
TACGAAGCCCCCACGCAAGGATCAGCGTCTTCCCTCGTGAACGGGGTTGTTAGACTCCTGTCAAAGCCTTGGGACGTGGTGAC
TGGAGTTACAGGAATAGCCATGACTGACACCACACCATACGGCCAACAAAGAGTCTTCAAAGAAAAAGTGGACACCAGGGTG
CCAGATCCCCAAGAAGGCACTCGCCAGGTAATGAACATAGTCTCTTCCTGGCTGTGGAAGGAGCTGGGGAAACGCAAGCGGC
CACGCGTCTGCACCAAAGAAGAGTTTATCAACAAGGTGCGCAGCAATGCAGCACTGGGAGCAATATTTGAAGAGGAAAAAGA
ATGGAAGACGGCTGTGGAAGCTGTGAATGATCCAAGGTTTTGGGCCCTAGTGGATAGGGAGAGAGAACACCACCTGAGAGG
AGAGTGTCACAGCTGTGTGTACAACATGATGGGAAAAAGAGAAAAGAAGCAAGGAGAGTTCGGGAAAGCAAAAGGTAGCC
GCGCCATCTGGTACATGTGGTTGGGAGCCCAGATTCTTGGAGTTTGAAGCCCTTGGATTCTTGAACGAGGACCATTGGATGGGA
AGAGAAACTCAGGAGGTGGAGTCGAAGGGTTAGGATTGCAAAGACTTGGATACATTCTTAGAGAAAATGAATCGGGCACCA
GGAGGAAAGATGTACGCAGATGACACTGCTGGCTGGGACACCCGCATTAGTAAGTTTGATCTGGAGAATGAAGCTCTGATTA
CCAACCAAATGGAGGAAGGGCACAGAACTCTGGCGTTGGCCGTGATTAAATACACATACCAAAACAAAGTGGTGAAGGTTCT
CAGACCAGCTGAAGGAGGAAAAACAGTTATGGACATCATTTCAAGACAAGACCAGAGAGGGAGTGGACAAGTTGTCACTTAT
GCTCTCAACACATTCACCAACTTGGTGGTGCAGCTTATCCGGAACATGGAAGCCGAAGTGTTAGAGATGCAAGACTTATG
GTTGTTGAGGAAGCCAGAGAAAGTGACCAGATGGTTGCAGAGCAATGGATGGGATAGACTCAAACGAATGGCGGTCAGTGG
AGATGACTGCGTTGTGAAGCCAATCGATGATAGGTTTGCACATGCCCTCAGGTTCTTGAATGACATGGGAAAAGTTAGGAAAG
ACACACAGGAGTGGAAACCCTCGACTGGATGGAGCAATTGGGAAGAAGTCCCGTTCTGCTCCCACCACTTCAACAAGCTGTAC
CTCAAGGATGGGAGATCCATTGTGGTCCCTTGCCGCCACCAAGATGAACTGATTGGCCGAGCCCGCATCAGCCCAGGGGCAG
GATGGAGCATCCGGGAGACTGCCTGTCTTGCAAAATCATATGCGCAGATGTGGCAGCTCCTTTATTTCCACAGAAGAGACCTT
CGACTGATGGCTAATGCCATTTGCTCGGCTGTGCCAGTTGACTGGGTACCAACTGGGAGAACCACCTGGTCAATCCATGGAAA
GGGAGAATGGATGACCACTGAGGACATGCTCATGGTGTGAATAGAGTGTGGATTGAGGAGAACGACCATATGGAGGACAA
GACTCCTGTAACAAAATGGACAGACATTTCCCTATCTAGGAAAAAGGGAGGACCTTATGGTGCTGATCCCTAAGGGCACAGAC
CCCGCACCACTTGGGCTGAAAACATCAAAGACACAGTCAACATGGTGCGCAGGATCATAGGTGATGAAGAAAGTACATGGA
CTATCTATCCACCCAAGTCCGCTACTTGGGTGAGGAAGGGTCCACACCCGGAGTGTTGTAAGCACCAATTTTAGTGTTGTCAGG
CCTGCTAGTCAGCCACAGTTTGGGGAAAGCTGTGCAGCCTGTAACCCCCCAGGAGAAGCTGGGAAACCAAGCTCATAGTCA
GGCCGAGAACGCCATGGCACGGAAGAAGCCATGCTGCCTGTGAGCCCCTCAGAGGACACTGAGTCAAAAACCCCACGCGCT
TGGAAGCGCAGGATGGGAAAGAAGGTGGCGACCTTCCCCACCCTTCAATCTGGGGCCTGAACTGGAGACTAGCTGTGAATC
TCCAGCAGAGGGACTAGTGGTTAGAGGAGACCCCCCGGAAAACGCAAAACAGCATATTGACGTGGGAAAGACCAGAGACTC
CATGAGTTTCCACCACGCTGGCCGCCAGGCACAGATCGCCGAACTTCGGCGGCCGGTGTGGGGAAATCCATGGTTTCT |

SEQ ID NO: 13
KJ776791.1, Zika virus strain H/PF/2013 polyprotein gene, complete cds
AGTATCAACAGGTTTTATTTTGGATTTGGAAACGAGAGTTTCTGGTCATGAAAAACCCAAAAAAGAAATCCGGAGGATTCCGG
ATTGTCAATATGCTAAAACGCGGAGTAGCCCGTGTGAGCCCCTTTGGGGGCTTGAAGAGGCTGCCAGCCGGACTTCTGCTGG
GTCATGGCCCATCAGGATGGTCTTGGCGATTCTAGCCTTTTTGAGATTCACGGCAATCAAGCCATCACTGGGTCTCATCAATA
GATGGGGTTCAGTGGGGAAAAAGAGGCTATGGAAATAATAAAGAAGTTCAAGAAAGATCTGGCTGCCATGCTGAGAATAA
TCAATGCTAGGAAGGAGAAGAAGAGACGAGGCGCAGATACTAGTGTCGGAATTGTTGGCCTCCTGCTGACCACAGCTATGGC
AGCGGAGGTCACTAGACGTGGGAGTGCATACTATATGTACTTGGACAGAAACGACGCTGGGGAGGCCATATCTTTTCCAACC
ACATTGGGGATGAATAAGTGTTATATACAGATCATGGATCTTGGACACATGTGTGATGCCACCATGAGCTATGAATGCCCTAT
GCTGGATGAGGGGGTGGAACCAGATGACGTCGATTGTTGGTGCAACACGACGTCAACTTGGGTTGTGTACGGAACCTGCCAT
CACAAAAAGGGTGAAGCACGGAGATCTAGAAGAGCTGTGACGCTCCCCTCCCATTCCACTAGGAAGCTGCAAACGCGGTCGC
AAACCTGGTTGAATCAAGAGAATACACAAAGCACTTGATTAGAGTCGAAAATTGGATATTCAGGAACCCTGGCTTCGCGTTA
GCAGCAGCTGCCATCGCTTGGCTTTTGGGAAGCTCAACGAGCCAAAAAGTCATATACTTGGTCATGATACTGCTGATTGCCCCG
GCATACAGCATCAGGTGCATAGGAGTCAGCAATAGGGACTTTGTGGAAGGTATGTCAGGTGGGACTTGGGTTGATGTTGTCT
TGGAACATGGAGGTTGTGTCACCGTAATGGCACAGGACAAACCGACTGTCGACATAGAGCTGGTTACAACAACAGTCAGCAA
CATGGCGGAGGTAAGATCCTACTGCTATGAGGCATCAATATCGGACATGGCTTCGGACAGCCGCTGCCCAACACAAGGTGAA

```
GCCTACCTTGACAAGCAATCAGACACTCAATATGTCTGCAAAAGAACGTTAGTGGACAGAGGCTGGGGAAATGGATGTGGAC
TTTTTGGCAAAGGGAGCCTGGTGACATGCGCTAAGTTTGCATGCTCCAAGAAAATGACCGGGAAGAGCATCCAGCCAGAGAA
TCTGGAGTACCGGATAATGCTGTCAGTTCATGGCTCCCAGCACAGTGGGATGATCGTTAATGACACAGGACATGAAACTGATG
AGAATAGAGCGAAGGTTGAGATAACGCCCAATTCACCAAGAGCCGAAGCCACCCTGGGGGGTTTTGGAAGCCTAGGACTTGA
TTGTGAACCGAGGACAGGCCTTGACTTTTCAGATTTGTATTACTTGACTATGAATAACAAGCACTGGTTGGTTCACAAGGAGTG
GTTCCACGACATTCCATTACCTTGGCACGCTGGGGCAGACACCGGAACTCCACACTGGAACAACAAAGAAGCACTGGTAGAGT
TCAAGGACGCACATGCCAAAAGGCAAACTGTCGTGGTTCTAGGGAGTCAAGAAGGAGCAGTTCACACGGCCCTTGCTGGAGC
TCTGGAGGCTGAGATGGATGGTGCAAAGGGAAGGCTGTCCTCTGGCCACTTGAAATGTCGCCTGAAAATGGATAAACTTAGA
TTGAAGGGCGTGTCATACTCCTTGTGTACCGCAGCGTTCACATTCACCAAGATCCCGGCTGAAACACTGCACGGGACAGTCAC
AGTGGAGGTACAGTACGCAGGGACAGATGGACCTTGCAAGGTTCCAGCTCAGATGGCGGTGGACATGCAAACTCTGACCCCA
GTTGGGAGGTTGATAACCGCTAACCCCGTAATCACTGAAAGCACTGAGAACTCTAAGATGATGCTGGAACTTGATCCACCATT
TGGGGACTCTTACATTGTCATAGGAGTCGGGGAGAAGAAGATCACCCACCACTGGCACAGGAGTGGCAGCACCATTGGAAAA
GCATTTGAAGCCACTGTGAGAGGTGCCAAGAGAATGGCAGTCTTGGGAGACACAGCCTGGGACTTTGGATCAGTTGGAGGCG
CTCTCAACTCATTGGGCAAGGGCATCCATCAAATTTTTGGAGCAGCTTTCAAATCATTGTTTGGAGGAATGTCCTGGTTCTCACA
AATTCTCATTGGAACGTTGCTGATGTGGTTGGGTCTGAACACAAAGAATGGATCTATTTCCCTTATGTGCTTGGCCTTAGGGGG
AGTGTTGATCTTCTTATCCACAGCTGTCTCTGCTGATGTGGGGTGCTCGGTGGACTTCTCAAAGAAGGAGACGAGATGCGGTA
CAGGGGTGTTCGTCTATAACGACGTTGAAGCCTGGAGGGACAGGTACAAGTACCATCCTGACTCCCCCCGTAGATTGGCAGCA
GCAGTCAAGCAAGCCTGGGAAGATGGTATCTGTGGGATCTCCTCTGTTTCAAGAATGGAAAACATCATGTGGAGATCAGTAG
AAGGGGAGCTCAACGCAATCCTGGAAGAGAATGGAGTTCAACTGACGGTCGTTGTGGGATCTGTAAAAAACCCCATGTGGAG
AGGTCCACAGAGATTGCCCGTGCCTGTGAACGAGCTGCCCCCACGGCTGGAGGCTGTGGGGGAAATCGTACTTCGTCAGAGCA
GCAAAGACAAATAACAGCTTTGTCGTGGATGGTGACACACTGAAGGAATGCCCACTCAAACATAGAGCATGGAACAGCTTTCT
TGTGGAGGATCATGGGTTCGGGTTATTTCACACTAGTGTCTGGCTCAAGGTTAGAGAAGATTATTCATTAGAGTGTGATCCAG
CCGTTATTGGAACAGCTGTTAAGGGAAAGGAGGCTGTACACAGTGATCTAGGCTACTGGATTGAGAGTGAGAAGAATGACAC
ATGGAGGCTGAAGAGGGCCCATCTGATCGAGATGAAAACATGTGAATGGCCAAAGTCCCACCACATTGTGGACAGATGGAATA
GAAGAGAGTGATCTGATCATACCCAAGTCTTTAGCTGGGCCACTCAGCCATCACAATACCAGAGAGGGCTACAGGACCCAAAT
GAAAGGGCCATGGCACAGTGAAGAGCTTGAAATTCGGTTTGAGGAATGCCCAGGCACTAAGGTCCACGTGGAGGAAACATG
TGGAACAAGAGGACCATCTCTGAGATCAACCACTGCAAGCGGAAGGGTGATCGAGGAATGGTGCTGCAGGGAGTGCACAAT
GCCCCCACTGTCGTTCCGGGCTAAAGATGGCTGTTGGTATGGAATGGAGATAAGGCCCAGGAAAGAACCAGAAAGTAACTTA
GTAAGGTCAATGGTGACTGCAGGATCAACTGATCACATGGATCACTTCTCCCTTGGAGTGCTTGTGATTCTGCTCATGGTGCAG
GAAGGGCTGAAGAAGAGAATGACCACAAAGATCATCATAAGCACATCGATGGCAGTGCTGGTAGCTATGATCCTGGGAGGAT
TTTCAATGAGTGACCTGGCTAAGCTTGCAATTTTGATGGGTGCCACCTTCGCGGAAATGAACACTGGAGGAGATGTAGCTCAT
CTGGCGCTGATAGCGGCATTCAAAGTCAGACCAGCGTTGCTGGTATCTTTCATCTTCAGAGCTAATTGGACACCCCGTGAAAGC
ATGCTGCTGGCCTTGGCCTCGTGTCTTTTGCAAACATGCGATCTCCGCCTTGGAAGGCGACCTGATGGTTCTCATCAATGGTTTT
GCTTTGGCCTGGTTGGCAATACGAGCGATGGTTGTTCCACGCACTGATAACATCACCTTGGCAATCCTGGCTGCTCTGACACCA
CTGGCCCGGGGCACACTGCTTGTGGCGTGGAGAGCAGGCCTTGCTACTTGCGGGGGTTTATGCTCCTCTCTGAAGGGAA
AAGGCAGTGTGAAGAAGAACTTACCATTTGTCATGGCCCTGGGACTAACCGCTGTGAGGCTGGTCGACCCCATCAACGTGGTG
GGACTGCTGTTGCTCACAAGGAGTGGGAAGCGGAGCTGGCCCCCTAGCGAAGTACTCACAGCTGTTGGCCTGATATGCGCAT
TGGCTGGAGGGTTCGCAAGGCAGATATAGAGATGGCTGGGCCCATGGCCGCGGTCGGTCTGCTAATTGTCAGTTACGTGGT
CTCAGGAAAGAGTGTGGACATGTACATTGAAAGAGCAGGTGACATCACATGGGAAAAAGATGCGGAAGTCACTGGAAACAG
TCCCCGGCTCGATGTGGCGCTAGATGAGAGTGGTGATTTCTCCCTGGTGGAGGATGACGGTCCCCCCATGAGAGAGATCATAC
TCAAGGTGGTCCTGATGACCATCTGTGGCATGAACCCAATAGCCATACCCTTTGCAGCTGGAGCGTGGTACGTATACGTGAAG
ACTGGAAAAAGGAGTGGTGCTCTATGGGATGCCTGCTCCCAAGGAAGTAAAAAAGGGGGAGACCACAGATGGAGTGTAC
AGAGTAATGACTCGTAGACTGCTAGGTTCAACACAAGTTGGAGTGGGAGTTATGCAAGAGGGGGTCTTTCACACTATGTGGC
ACGTCACAAAAGGATCCGCGCTGAGAAGCGGTGAAGGGAGACTTGATCCATACTGGGGAGATGTCAAGCAGGATCTGGTGT
CATACTGTGGTCCATGGAAGCTAGATGCCGCTCTGGGACGGCACAGCGAGGTGCAGCTCTTGGCCGTGCCCCCCGGAGAGAG
AGCGAGGAACATCCAGACTCTGCCCGGAATATTTAAGACAAAGGATGGGGACATTGGAGCGGTTGCGCTGGATTACCCAGCA
GGAACTTCAGGATCTCCAATCCTAGACAAGTGTGGGAGAGTGATAGGACTTTATGGCAATGGGTCGTGATCAAAAATGGGA
GTTATGTTAGTGCCATCACCCAAGGGAGGAGGGAGGAAGAGACTCCTGTTGAGTGCTTCGAGCCTTCGATGCTGAAGAAGAA
GCAGCTAACTGTCTTAGACTTGCATCCTGGAGCTGGGAAAACCAGGAGAGTTCTTCCTGAAATAGTCCGTGAAGCCATAAAAA
CAAGACTCCGTACTGTGATCTTAGCTCCAACCAGGGTTGTCGCTGCTGAAATGGAGGAAGCCCTTAGAGGGCTTCCAGTGCGT
TATATGACAACAGCAGTCAATGTCACCCACTCTGGAACAGAAATCGTCGACTTAATGTGCCATGCCACCTTCACTTCACGTCTAC
TACAGCCAATCAGAGTCCCCAACTATAATCTGTATATTATGGATGAGGCCCACTTCACAGATCCCTCAAGTATAGCAGCAAGAG
GATACATTTCAACAAGGGTTGAGATGGGCGAGGCGGCTGCCATCTTCATGACCGCCACCCCAGGAACCCGTGACGCATTT
CCGGACTCCAACTCACCAATTATGGACACCGAAGTGGAAGTCCCAGAGAGAGCCTGGAGCTCAGGCTTTGATTGGGTGACGG
ATCATTCTGGAAAAACAGTTTGGTTTGTTCCAAGCGTGAGGAACGGCAATGAGATCGCAGCTTGTCTGACAAAGGCTGGAAAA
CGGGTCATACAGCTCAGCAGAAAGACTTTTGAGACAGAGTTCCAGAAAACAAAACATCAAGAGTGGGACTTTGTCGTGACAA
CTGACATTTCAGAGATGGGCGCCAACTTTAAAGCTGACCGTGTTATCGACTCCAGGAGATGCCTAAAGCCGGTCATACTTGAT
GGCGAGAGAGTCATTCTGGCTGGACCCATGCCTGTCACACATGCCAGCGCTGCCCAGAGGAGGGGCGCATAGGCAGGAAT
CCCAACAAACCTGGAGATGAGTATCTGTATGGAGGTGGGTGCGCAGAGACTGACGAAGACCATGCACACTGGCTTGAAGCAA
GAATGCTCCTTGACAATATTTACCTCCAAGATGGCCTCATAGCCTCGCTCTATCGACCTGAGGCCGACAAAGTAGCAGCCATTG
AGGGAGAGTTCAAGCTTAGGACGGAGCAAAGGAAGACCTTTGTGGAACTCATGAAAAGAGGAGATTTCCTGTTTTGGCTGGC
CTATCAGGTTGCATCTGCCGGAATAACCTACACAGATAGAAGATGGTGCTTTGATGGCACGACCAACAACACCATAATGGAAG
ACAGTGTGCCGGCAGAGGTGTGGACCAGACACGGAGAGAAAAGAGTGCTCAAACCGAGGTGGATGGACGCCAGAGTTTGTT
CAGATCATGCGCCCTGAAGTCATTCAAGGAGTTTGCCGCTGGGAAAAGAGGAGCGGCTTTTGGAGTGATGGAAGCCCTGGG
AACACTGCCAGGACACATGACAGAGAGATTCCAGGAAGCCATTGACAACCTCGCTGTGCTCATGCGGGCAGAGACTGGAAGC
AGGCCTTACAAAGCCGCGGCGGCCCAATTGCCGGAGACCCTAGAGACACATTATGCTGTTTTGGGGTTGCTGGAACAGTCTCGCT
GGGAATCTTTTTCGTCTTGATGAGGAACAAGGCATAGGGAAGATGGGCTTTGGAATGGTGACTCTTGGGGCCAGCGCATGG
CTCATGTGGCTCTCGGAAATTGAGCCAGCCAGAATTGCATGTGTCCTCATTGTTGTGTTCCTATTGCTGGTGGTGCTCATACCTG
AGCCAGAAAAGCAAAGATCTCCCCAGGACAACCAAATGGCAATCATCATCATGGTAGCAGTAGGTCTTCTGGGCTTGATTACC
GCCAATGAACTCGGATGGTTGGAGAGAACAAAGAGTGACCTAAGCCATCTAATGGGAAGGAGAGAGGAGGGGGCAACCATA
GGATTCTCAATGGACATTGACCTGCGGCCAGCCTCAGCTTGGGCCATCTATGCTGCCTTGACAACTTTCATTACCCCAGCCGTCC
AACATGCAGTGACCACTTCATACAACAACTACTCCTTAATGGCGATGGCCACGCAAGCTGGAGTGTTGTTTGGTATGGGCAAA
GGGATGCCATTCTACGCATGGGACTTTGGAGTCCCGCTGCTAATGATAGGTTGCTACTCACAATTAACACCCCTGACCCTAATA
GTGGCCATCATTTTGCTCGTGGCGCACTACATGTACTTGATCCCAGGGCTGCAGGCAGCAGCTGCGCGTGCTGCCCAGAAGAG
AACGGCAGCTGGCATCATGAAGAACCCTGTTGTGGATGGAATAGTGGTGACTGACATTGACACAATGACAATTGACCCCCAA
GTGGAGAAAAAGATGGGACAGGTGCTACTCATAGCAGTAGCCGTCTCCAGCGCCATACTGTCGCGGACCGCCTGGGGGTGG
GGGAGGCTGGGCCCTGATCACAGCGGCAACTTCCACTTTGTGGGAAGGCTCTCCGAACAAGTACTGGAACTCCTCTACAGC
```

| SEQUENCES |
|---|
| CACTTCACTGTGTAACATTTTTAGGGGAAGTTACTTGGCTGGAGCTTCTCTAATCTACACAGTAACAAGAAACGCTGGCTTGGT
CAAGAGACGTGGGGGTGGAACAGGAGAGACCCTGGGAGAGAAATGGAAGGCCCGCTTGAACCAGATGTCGGCCCTGGAGT
TCTACTCCTACAAAAAGTCAGGCATCACCGAGGTGTGCAGAGAAGAGGCCCGCCGCGCCCTCAAGGACGGTGTGGCAACGGG
AGGCCATGCTGTGTCCCGAGGAAGTGCAAAGCTGAGATGGTTGGTGGAGCGGGGATACCTGCAGCCCTATGGAAAGGTCATT
GATCTTGGATGTGGCAGAGGGGGCTGGAGTTACTACGCCGCCACCATCCGCAAAGTTCAAGAAGTGAAAGGATACACAAAAG
GAGGGCCCTGGTCATGAAGAACCCATGTTGGTGCAAAGCTATGGGTGGAACATAGTCCGTCTTAAGAGTGGGGTGGACGTCTT
TCATATGGCGGCTGAGCCGTGTGACACGTTGCTGTGTGACATAGGTGAGTCATCATCTAGTCCTGAAGTGGAAGAAGCACGG
ACGCTCAGAGTCCTCTCCATGGTGGGGGATTGGCTTGAAAAAAGACCAGGAGCCTTTTGTATAAAAGTGTTGTGCCCATACAC
CAGCACTATGATGGAAACCCTGGAGCGACTGCAGCGTAGGTATGGGGGAGGACTGGTCAGAGTGCCACTCTCCCGCAACTCT
ACACATGAGATGTACTGGGTCTCTGGAGCGAAAAGCAACACCATAAAAAGTGTGTCCACCACGAGCCAGCTCCTCTTGGGGC
GCATGGACGGGCCCAGGAGGCCAGTGAAATATGAGGAGGATGTGAATCTCGGCTCTGGCACGCGGGCTGTGGTAAGCTGCG
CTGAAGCTCCCAACATGAAGATCATTGGTAACCGCATTGAAAGGATCCGCAGTGAGCACGCGGAAACGTGGTTCTTTGACGA
GAACCACCCATATAGGACATGGGCTTACCATGGAAGCTATGAGGCCCCCACACAAGGGTCAGCGTCCTCTCTAATAAACGGGG
TTGTCAGGCTCCTGTCAAAACCCTGGGATGTGGTGACTGGAGTCACAGGAATAGCCATGACCGACACCACACCGTATGGTCAG
CAAAGAGTTTTCAAGGAAAAAGTGGACACTAGGGTGCCAGACCCCCAAGAAGGCACTCGTCAGGTTATGAGCATGGTCTCTTC
CTGGTTGTGGAAAGAGCTAGGCAAACACAAACGGCCACGAGTCTGTACCAAAGAAGAGTTCATCAACAAGGTTCGTAGCAAT
GCAGCATTAGGGGCAATATTTGAAGAGGAAAAAGAGTGGAAGACTGCAGTGGAAGCTGTGAACGATCCAAGGTTCTGGGCT
CTAGTGGACAAGGAAAGAGAGCACCACCTGAGAGGAGAGTGCCAGAGTTGTGTGTACAACATGATGGGAAAAAGAGAAAAG
AAACAAGGGGAATTTGGAAAGGCCAAGGGCAGCCGCGCCATCTGGTATATGTGGCTAGGGGCTAGATTTCTAGAGTTCGAAG
CCCTTGGATTCTTGAACGAGGATCACTGGATGGGGAGAGAACTCAGGAGGTGGTGTTGAAGGGCTGGGATTACAAAGAC
TCGGATATGTCCTAGAAGAGATGAGTCGCATACCAGGAGGAAGGATGTATGCAGATGACACTGCTGGCTGGGACACCCGCAT
CAGCAGGTTTGATCTGGAGAATGAAGCTCTAATCACCAACCAAATGGAGAAAGGGCACAGGGCCTTGGCATTGGCCATAATC
AAGTACACATACCAAAACAAAGTGGTAAAGGTCCTTAGACCAGCTGAAAAAGGGAAGACAGTTATGGACATTATTTCGAGAC
AAGACCAAAGGGGGAGCGAACAAGTTGTCACTTACGCTCTTAACACATTTACCAACCTAGTGGTGCAACTCATTCGGAATATG
GAGGCTGAGGAAGTTCTAGAGATGCAAGACTTGTGGCTGCTGCGGAGGTCAGAGAAAGTGACCAACTGGTTGCAGAGCAAC
GGATGGGATAGGCTCAAACGAATGGCAGTCAGTGGAGATGATTGCGTTGTGAAGCCAATTGATGATAGGTTTGCACATGCCC
TCAGGTTCTTGAATGATATGGGAAAAGTTAGGAAGGACACACAAGAGTGGAAACCCTCAACTGGATGGGACAACTGGGAAG
AAGTTCCGTTTTGCTCCCACCACTTCAACAAGCTCCATCTCAAGGACGGGAGGTCCATTGTGGTTCCCTGCCGCCACCAAGATG
AACTGATTGGCCGGGCCCGCGTCTCTCCAGGGGCGGGATGGAGCATCCGGGAGACTGCTTGCCTAGCAAAATCATATGCGCA
AATGTGGCAGCTCCTTTATTTCCACAGAAGGGACCTCCGACTGATGGCCAATGCCATTTGTTCATCTGTGCCAGTTGACTGGGT
TCCAACTGGGAGAACTACCTGGTCAATCCATGGAAAGGGAGAATGGATGACCACTGAAGACATGCTTGTGGTGTGGAACAGA
GTGTGGATTGAGGAGAACGACCACATGGGAAGACAAGACCCCAGTTACGAAATGGACAGACATTCCCTATTTGGGAAAAAGGG
AAGACTTGTGGTGTGGATCTCTCATAGGGCACAGACCGCGCACCACCTGGGCTGAGAACATTAAAAACACAGTCAACATGGT
GCGCAGGATCATAGGTGATGAAGAAAGTACATGGACTACCTATCCACCCAAGTTCGCTACTTGGGTGAAGAAGGGTCTACA
CCTGGAGTGCTGTAAGCACCAATCTTAGTGTTGTCAGGCCTGCTAGTCAGCCACAGCTTGGGGAAAGCTGTGCAGCCTGTGAC
CCCCCCAGGAGAAGCTGGGAAACCAAGCCTATAGTCAGGCCGAGAACGCCATGGCACGGAAGAAGCCATGCTGCCTGTGAGC
CCCTCAGAGGACACTGAGTCAAAAAACCCCACGCGCTTGGAGGCGCAGGATGGGAAAAGAAGGTGGCGACCTTCCCCACCCT
TCAATCTGGGCCTGAACTGGAGATCAGCTGTGGATCTCCAGAAGAGGGACTAGTGGTTAGAGGAG |

In some embodiments, the Zika virus has a RNA genome corresponding to the DNA sequence provided by the nucleic acid sequence of any one of SEQ ID NOs: 2-13 or 73. In some embodiments, the Zika virus 45 has a variant genome that is at least 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8% or 99.9% identical to any one of SEQ ID NOs: 2-13 or 78.

Provided below are amino acid sequences of the E-proteins of Zika strains that may be used in the methods, compositions, and/or vaccines described herein.

isol-ARB15076.AHF49784.1.Central_African_Republic/291-788 Flavivirus envelope glycoprotein E.

SEQ ID NO: 14

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFTCSKKMTGKSIQPENLEYRIMLSVHGSQHSGMIVNDENRAKVEVTPNSPRA

EATLGGFGSLGLDCEPRTGLDFSDLYYLTMNNKHWLVHKEWFHDIPLPWHAGADTGTPHWNNKEALVEFKDAHAKRQTVVVLGS

QEGAVHTALAGALEAEMDGAKGRLFSGHLKCRLKMDKLRLKGVSYSLCTAAFTFTKVPAETLHGTVTVEVQYAGTDGPCKVPAQM

AVDMQTLTPVGRLITANPVITESTENSKMMLELDPPFGDSYIVIGVGDKKITHHWHRSGSTIGKAFEATVRGAKRMAVLGDTAWDF

GSVGGVFNSLGKGIHQIFGAAFKSLFGGMSWFSQILIGTLLVWLGLNTKNGSISLTCLALGGVMIFLSTAVSA isol-1bH_30656.AEN75265.1.Nigeria/291-788 Flavivirus envelope glycoprotein E.

SEQ ID NO: 15

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFTCSKKMTGKSIQPENLEYRIMLSVHGSQHSGMIVNDENRAKVEVTPNSPRA

EATLGGFGSLGLDCEPRTGLDFSDLYYLTMNNKHWLVHKEWFHDIPLPWHSGADTETPHWNNKEALVEFKDAHAKRQTVVVLGS

QEGAVHTALAGALEAEMDGAKGRLSSGHLKCRLKMDKLRLKGVSYSLCTAAFTFTKVPAETLHGTVTVEVQYAGRDGPCKVPAQM

-continued

AVDMQTLTPVGRLITANPVITESTENSKMMLELDPPFGDSYMGVGDKKITHHWHRSGSIIGKAFEATVRGAKRMAVLGDTAWDF

GSVGGVFNSLGKGIHQIFGAAFKSLFGGMSWFSQILIGTLLVWLGLNTKNGSISLTCLALGGVMIFLSTAVSA

ArB1362.AHL43500.1.-/291-794 Flavivirus envelope glycoprotein E.
SEQ ID NO: 16
IRCIGVSNRDFVEGMSGGTWVDVVLEHGGCVTVMAQDKPTVDIELVTTTVSNMAEVRSYCYEASISDMASDSRCPTQGEAYLDKQ SDTQYVCKRTLVDRGWGNGCGLFGKGSLVTCAKFTCSKKMTGKSIQPENLEYRIMLSVHGSQHSGMIVNDXXXXXXXNRAEVEVT PNSPRAEATLGGFGSLGLDCEPRTGLDFSDLYYLTMNNKHWLVHKEWFHDIPLPWHAGADTGTPHWNNKEALVEFKDAHAKRQT VVVLGSQEGAVHTALAGALEAEMDGAKGRLFSGHLKCRLKMDKLRLKGVSYSLCTAAFTFTKVPAETLHGTVTVEVQYAGTDGPCK VPAQMAVDMQTLTPVGRLITANPVITESTENSKMMLELDPPFGDSYIVIGVGDKKITHHWHRSGSTIGKAFEATVRGAKRMAVLG

DTAWDFGSVGGVFNSLGKGIHQIFGAAFKSLFGGMSWFSQILIGTLLVWLGLNTKNGSISLTCLALGGVMIFLSTAVSA

ArD128000.AHL43502.1.-/291-794 Flavivirus envelope glycoprotein E.
SEQ ID NO: 17
IRCIGVSNRDFVEGMSGGTWVDVVLEHGGCVTVMAQDKPTVDIELVTTTVSNMAEVRSYCYEASISDMASDSRCPTQGEAYLDKQ SDTQYVCKRTLVDRGWGNGCGLFGKGSLVTCAKFTCSKKMTGKSIQPENLEYRIMLSVHGSQHSGMXXXXXGHETDENRAKVEVT PNSPRAEATLGGFGSLGLDCEPRTGLDFSDLYYLTMNNKHRLVRKEWFHDIPLPWHAGADTGTPHWNNKEALVEFKDAHAKRQT VVVLGSQEGAVHTALAGALEAEMDGAKGRLFSGHLKCRLKMDKLRLKGVSYSLCTAAFTFTKVPAETLHGTVTVEVQYAGTDGPCK VPAQMAVDMQTLTPVGRLITANPVITESTENSKMMLELDPPFGDSYIVIGVGDKKITHHWLKKGSSIGKAFEATVRGAKRMAVLGD

TAWDFGSVGGVFNSLGKGVHQIFGAAFKSLFGGMSWFSQILIGTLLVWLGLNTKNGSISLTCLALGGVMIFLSTAVSA

ArD158095.AHL43505.1.-/291-794 Flavivirus envelope glycoprotein E.
SEQ ID NO: 18
IRCIGVSNRDFVEGMSGGTWVDVVLEHGGCVTVMAQDKPTVDIELVTTTVSNMAEVRSYCYEASISDMASDSRCPTQGEAYLDKQ SDTQYVCKRTLVDRGWGNGCGLFGKGSLVTCAKFTCSKKMTGKSIQPENLEYRIMLSVHGSQHSGMIVNDIGHETDENRAKVEVT PNSPRAEATLGGFGSLGLDCEPRTGLDFSDLYYLTMNNKHWLVHKEWFHDIPLPWHAGADTGTPHWNNKEALVEFKDAHAKRQT VVVLGSQEGAVHTALAGALEAEMDGAKGRLFSGHLKCRLKMDKLRLKGVSYSLCTAAFTFTKVPAETLHGTVTVEVQYAGTDGPCK VPAQMAVDMQTLTPVGRLITANPVITESTENSKMMLELDPPFGDSYIVIGVGDKKITHHWHRSGSTIGKAFEATVRGAKRMAVLG

DTAWDFGSVGGVFNSLGKGIHQIFGAAFKSLFGGMSWFSQILIGTLLVWLGLNTKNGSISLTCLALGGVMIFLSTAVSA

ArD158084.AHL43504.1.-/291-794 Flavivirus envelope glycoprotein E.
SEQ ID NO: 19
IRCIGVSNRDFVEGMSGGTWVDVVLEHGGCVTVMAQDKPTVDIELVTTTVSNMAEVRSYCYEASISDMASDSRCPTQGEAYLDKQ SDTQYVCKRTLVDRGWGNGCGLFGKGSLVTCAKFTCSKKMTGKSIQPENLEYRIMLSVHGSQHSGMIVNDIGHETDENRAKVEVT PNSPRAEATLGGFGSLGLDCEPRTGLDFSDLYYLTMNNKHWLVHKEWFHDIPLPWHAGADTGTPHWNNKEALVEFKDAHAKRQT VVVLGSQEGAVHTALAGALEAEMDGAKGRLFSGHLKCRLKMDKLRLKGVSYSLCTAAFTFTKVPAETLHGTVTVEVQYAGTDGPCK VPAQMAVDMQTLTPVGRLITANPVITESTENSKMMLELDPPFGDSYIVIGVGDKKITHHWHRSGSTIGKAFEATVRGAKRMAVLG

DTAWDFGSVGGVFNSLGKGIHQIFGAAFKSLFGGMSWFSQILIGTLLVWLGLNTKNGSISLTCLALGGVMIFLSTAVSA isol-ARB13565.AHF49783.1.Central_African_Republic/291-794 Flavivirus
envelope glycoprotein E.
SEQ ID NO: 20
IRCIGVSNRDFVEGMSGGTWVDVVLEHGGCVTVMAQDKPTVDIELVTTTVSNMAEVRSYCYEASISDMASDSRCPTQGEAYLDKQ SDTQYVCKRTLVDRGWGNGCGLFGKGSLVTCAKFTCSKKMTGKSIQPENLEYRIMLSVHGSQHSGMIVNDIGHETDENRAKVEVT PNSPRAEATLGGFGSLGLDCEPRTGLDFSDLYYLTMNNKHWLVHKEWFHDIPLPWHAGADTGTPHWNNKEALVEFKDAHAKRQT VVVLGSQEGAVHTALAGALEAEMDGAKGRLFSGHLKCRLKMDKLRLKGVSYSLCTAAFTFTKVPAETLHGTVTVEVQYAGTDGPCK VPAQMAVDMQTLTPVGRLITANPVITESTENSKMMLELDPPFGDSYIVIGVGDKKITHHWHRSGSTIGKAFEATVRGAKRMAVLG

DTAWDFGSVGGVFNSLGKGVHQIFGAAFKSLFGGMSWFSQILIGTLLVWLGLNTKNGSISLTCLALGGVMIFLSTAVSA isol-ARB7701.AHF49785.1.Central_African_Republic/291-794 Flavivirus
envelope glycoprotein E.
SEQ ID NO: 21
IRCIGVSNRDFVEGMSGGTWVDVVLEHGGCVTVMAQDKPTVDIELVTTTVSNMAEVRSYCYEASISDMASDSRCPTQGEAYLDKQ SDTQYVCKRTLVDRGWGNGCGLFGKGSLVTCAKFTCSKKMTGKSIQPENLEYRIMLSVHGSQHSGMIVNDIGHETDENRAKVEVT PNSPRAEATLGGFGSLGLDCEPRTGLDFSDLYYLTMNNKHWLVHKEWFHDIPLPWHAGADTGTPHWNNKEALVEFKDAHAKRQT VVVLGSQEGAVHTALAGALEAEMDGAKGRLFSGHLKCRLKMDKLRLKGVSYSLCTAAFTFTKVPAETLHGTVTVEVQYAGTDGPCK VPAQMAVDMQTLTPVGRLITANPVITESTENSKMMLELDPPFGDSYIVIGVGDKKITHHWHRSGSTIGKAFEATVRGAKRMAVLG

DTAWDFGSVGGVFNSLGKGVHQIFGAAFKSLFGGMSWFSQILIGTLLVWLGLNTKNGSISLTCLALGGVMIFLSTAVSA isol-ArD_41519.AEN75266.1.Senegal/291-794 Flavivirus envelope glycoprotein E.
SEQ ID NO: 22
IRCIGVSNRDFVEGMSGGTWVDVVLEHGGCVTVMAQDKPTVDIELVTTTVSNMAEVRSYCYEASISDMASDSRCPTQGEAYLDKQ SDTQYVCKRTLVDRGWGNGCGLFGKGSLVTCAKFTCSKKMTGKSIQPENLEYRIMLSVHGSQHSGMIVNDTGHETDENRAKVEVT PNSPRAEATLGGFGSLGLDCEPRTGLDFSDLYYLTMNNKHWLVHKEWFHDIPLPWHAGADTGTPHWNNKEALVEFKDAHAKRQT VVVLGSQEGAVHTALAGALEAEMDGAKGRLFSGHLKCRLKMDKLRLKGVSYSLCTAAFTFTKVPAETLHGTVTVEVQYAGTDGPCK VPAQMAVDMQTLTPVGRLITANPVITESTENSKMMLELDPPFGDSYIVIGVGDKKITHHWHRSGSTIGKAFEATVRGAKRMAVLG

DTAWDFGSVGGVFNSLGKGIHQIFGAAFKSLFGGMSWFSQILIGTLLVWLGLNTKNGSISLTCLALGGVMIFLSTAVSA

MR766-NHD.BAP47441.1.Uganda/291-794 Flavivirus envelope glycoprotein E.
SEQ ID NO: 23
IRCIGVSNRDFVEGMSGGTWVDVVLEHGGCVTVMAQDKPTVDIELVTTTVSNMAEVRSYCYEASISDMASDSRCPTQGEAYLDKQ SDTQYVCKRTLVDRGWGNGCGLFGKGSLVTCAKFTCSKKMTGKSIQPENLEYRIMLSVHGSQHSGMTVNDIGYETDENRAKVEVT PNSPRAEATLGGFGSLGLDCEPRTGLDFSDLYYLTMNNKHWLVHKEWFHDIPLPWHAGADTGTPHWNNKEALVEFKDAHAKRQT VVVLGSQEGAVHTALAGALEAEMDGAKGKLFSGHLKCRLKMDKLRLKGVSYSLCTAAFTFTKVPAETLHGTVTVEVQYAGTDGPCK IPVQMAVDMQTLTPVGRLITANPVITESTENSKMMLELDPPFGDSYIVIGVGDKKITHHWHRSGSTIGKAFEATVRGAKRMAVLGD

TAWDFGSVGGVFNSLGKGIHQIFGAAFKSLFGGMSWFSQILIGTLLVWLGLNTKNGSISLTCLALGGVMIFLSTAVSA

LC002520.1/326-829 Zika virus genomic RNA, strain: MR766-NIID,
Uganda, Flavivirus envelope glycoprotein E.
SEQ ID NO: 24
IRCIGVSNRDFVEGMSGGTWVDVVLEHGGCVTVMAQDKPTVDIELVTTTVSNMAEVRSYCYEASISDMASDSRCPTQGEAYLDKQ SDTQYVCKRTLVDRGWGNGCGLFGKGSLVTCAKFTCSKKMTGKSIQPENLEYRIMLSVHGSQHSGMTVNDIGYETDENRAKVEVT PNSPRAEATLGGFGSLGLDCEPRTGLDFSDLYYLTMNNKHWLVHKEWFHDIPLPWHAGADTGTPHWNNKEALVEFKDAHAKRQT VVVLGSQEGAVHTALAGALEAEMDGAKGKLFSGHLKCRLKMDKLRLKGVSYSLCTAAFTFTKVPAETLHGTVTVEVQYAGTDGPCK IPVQMAVDMQTLTPVGRLITANPVITESTENSKMMLELDPPFGDSYIVIGVGDKKITHHWHRSGSTIGKAFEATVRGAKRMAVLGD

TAWDFGSVGGVFNSLGKGIHQIFGAAFKSLFGGMSWFSQILIGTLLVWLGLNTKNGSISLTCLALGGVMIFLSTAVSA isol-MR_766.AEN75263.1.Uganda/291-794 Flavivirus envelope glycoprotein E.
SEQ ID NO: 25
IRCIGVSNRDFVEGMSGGTWVDVVLEHGGCVTVMAQDKPTVDIELVTTTVSNMAEVRSYCYEASISDMASDSRCPTQGEAYLDKQ SDTQYVCKRTLVDRGWGNGCGLFGKGSLVTCAKFTCSKKMTGKSIQPENLEYRIMLSVHGSQHSGMIVNDTGYETDENRAKVEVT PNSPRAEATLGGFGSLGLDCEPRTGLDFSDLYYLTMNNKHWLVHKEWFHDIPLPWHAGADTGTPHWNNKEALVEFKDAHAKRQT VVVLGSQEGAVHTALAGALEAEMDGAKGKLFSGHLKCRLKMDKLRLKGVSYSLCTAAFTFTKVPAETLHGTVTVEVQYAGTDGPCK IPVQMAVDMQTLTPVGRLITANPVITESTENSKMMLELDPPFGDSYIVIGVGDKKITHHWHRSGSTIGKAFEATVRGAKRMAVLGD

TAWDFGSVGGVFNSLGKGIHQIFGAAFKSLFGGMSWFSQILIGTLLVWLGLNTKNGSISLTCLALGGVMIFLSTAVSA

ArD7117.AHL43501.1.-/291-794 Flavivirus envelope glycoprotein E.
SEQ ID NO: 26
IRCIGVSNRDFVEGMSGGTWVDVVLEHGGCVTVMAQDKPTVDIELVTTTVSNMAEVRSYCYEASISDMASDSRCPTQGEAYLDKQ SDTQYVCKRTLVDRGWGNGCGLFGKGSLVTCAKFTCSKKMTGKSIQPENLEYRIMLSVHGSQHSGMIVNDIGHETDENRAKVEVT PNSPRAEATLGGFGSLGLDCEPRTGLDFSDLYYLTMNNKHWLVHKEWFHDIPLPWHAGADTGTPHWNNKEALVEFKDAHAKRQT VVVLGSQEGAVHTALAGALEAEMDGAKGRLFSGHLKCRLKMDKLRLKGVSYSLCTAVCTAAKVPAETLHGTVTVEVQYAGTDGPC KVPAQMAVDMQTLTPVGRLITANPVITESTENSKMMLELDPPFGDSYIVIGVGDKKITHHWHRSGSTIGKAFEATVRGAKRMAVL

GDTAWDFGSVGGVFNSLGKGIHQIFGAAFKSLFGGMSWFSQILIGTLLVWLGLNTKNGSISLTCLALGGVMIFLSTAVSA

AY632535.2/326-825 NC 012532.1 Zika virus strain MR 766, Uganda,
Flavivirus envelope glycoprotein E.

SEQ ID NO: 27

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFTCSKKMTGKSIQPENLEYRIMLSVHGSQHSGMIGYETDEDRAKVEVTPNSPR

AEATLGGFGSLGLDCEPRTGLDFSDLYYLTMNNKHWLVHKEWFHDIPLPWHAGADTGTPHWNNKEALVEFKDAHAKRQTVVVL

GSQEGAVHTALAGALEAEMDGAKGRLFSGHLKCRLKMDKLRLKGVSYSLCTAAFTFTKVPAETLHGTVTVEVQYAGTDGPCKIPVQ

MAVDMQTLTPVGRLITANPVITESTENSKMMLELDPPFGDSYIVIGVGDKKITHHWHRSGSTIGKAFEATVRGAKRMAVLGDTAW

DFGSVGGVFNSLGKGIHQIFGAAFKSLFGGMSWFSQILIGTLLVWLGLNTKNGSISLTCLALGGVMIFLSTAVSA

MR_766.AAV34151.1.Uganda/291-790 Flavivirus envelope glycoprotein E. | Q32ZE11Q32ZE19FL

SEQ ID NO: 28

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFTCSKKMTGKSIQPENLEYRIMLSVHGSQHSGMIGYETDEDRAKVEVTPNSPR

AEATLGGFGSLGLDCEPRTGLDFSDLYYLTMNNKHWLVHKEWFHDIPLPWHAGADTGTPHWNNKEALVEFKDAHAKRQTVVVL

GSQEGAVHTALAGALEAEMDGAKGRLFSGHLKCRLKMDKLRLKGVSYSLCTAAFTFTKVPAETLHGTVTVEVQYAGTDGPCKIPVQ

MAVDMQTLTPVGRLITANPVITESTENSKMMLELDPPFGDSYIVIGVGDKKITHHWHRSGSTIGKAFEATVRGAKRMAVLGDTAW

DFGSVGGVFNSLGKGIHQIFGAAFKSLFGGMSWFSQILIGTLLVWLGLNTKNGSISLTCLALGGVMIFLSTAVSA

MR_766.YP_009227198.1.Uganda/1-500 envelope protein E [Zika virus]

SEQ ID NO: 29

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFTCSKKMTGKSIQPENLEYRIMLSVHGSQHSGMIGYETDEDRAKVEVTPNSPR

AEATLGGFGSLGLDCEPRTGLDFSDLYYLTMNNKHWLVHKEWFHDIPLPWHAGADTGTPHWNNKEALVEFKDAHAKRQTVVVL

GSQEGAVHTALAGALEAEMDGAKGRLFSGHLKCRLKMDKLRLKGVSYSLCTAAFTFTKVPAETLHGTVTVEVQYAGTDGPCKIPVQ

MAVDMQTLTPVGRLITANPVITESTENSKMMLELDPPFGDSYIVIGVGDKKITHHWHRSGSTIGKAFEATVRGAKRMAVLGDTAW

DFGSVGGVFNSLGKGIHQIFGAAFKSLFGGMSWFSQILIGTLLVWLGLNTKNGSISLTCLALGGVMIFLSTAVSA

KU681081.3/308-811 Zika virus isolate Zika virus/H.sapiens-tc/THA/2014/SV0127-14,
Thailand, Flavivirus envelope
glycoprotein E.

SEQ ID NO: 30

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

PNSPRAEATLGGFGSLGLDCEPRTGLDFSDLYYLTMNNKHWLVHKEWFHDIPLPWHTGADTGTPHWNNKEALVEFKDAHAKRQT

VVVLGSQEGAVHTALAGALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITEGTENSKMMLELDPPFGDSYIVIGVGEKKITHHWHRSGSTIGKAFEATVRGAKRMAVLG

DTAWDFGSVGGVLNSLGKGIHQIFGAAFKSLFGGMSWFSQILIGTLLMWLGLNTKNGSISLMCLALGGVLIFLSTAVSA isol-Zika_virus%H.sapiens-tc%THA%2014%SV0127-_14.AMD61710.1.Thailand/291-794
Flavivirus envelope
glycoprotein E.

SEQ ID NO: 31

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

PNSPRAEATLGGFGSLGLDCEPRTGLDFSDLYYLTMNNKHWLVHKEWFHDIPLPWHTGADTGTPHWNNKEALVEFKDAHAKRQT

VVVLGSQEGAVHTALAGALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITEGTENSKMMLELDPPFGDSYIVIGVGEKKITHHWHRSGSTIGKAFEATVRGAKRMAVLG

DTAWDFGSVGGVLNSLGKGIHQIFGAAFKSLFGGMSWFSQILIGTLLMWLGLNTKNGSISLMCLALGGVLIFLSTAVSA

CK-ISL_2014.AIC06934.1.Cook_Islands/1-504 Flavivirus envelope glycoprotein
E. (Fragment) OS = Zika virus GN = E
PE = 4 SV = 1

SEQ ID NO: 32

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNTKNGSISLMCLALGGVLIFLSTAVSA

Natal_RGN.AMB18850.1.Brazil:_Rio_Grande_do_Norte,_Natal/291-794
Flavivirus envelope glycoprotein E.]

SEQ ID NO: 33

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNTKNGSISLMCLALGGVLIFLSTAVSA isol-Si323.AMC37200.1.Colombia/1-504 Flavivirus envelope glycoprotein E.

SEQ ID NO: 34

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNTKNGSISLMCLALGGVLIFLSTAVSA

KU707826.1/317-820 Zika virus isolate SSABRI, Brazil, Flavivirus
envelope glycoprotein E.

SEQ ID NO: 35

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNTKNGSISLMCLALGGVLIFLSTAVSA

KU509998.1/326-829 Zika virus strain Haiti/1225/2014, Haiti,
Flavivirus envelope glycoprotein E.

SEQ ID NO: 36

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNTKNGSISLMCLALGGVLIFLSTAVSA isol-GDZ16001.AML82110.1.China/291-794 Flavivirus envelope glycoprotein E.

SEQ ID NO: 37

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

-continued

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNTKNGSISLMCLALGGVLIFLSTAVSA

BeH819015.AMA12085.1.Brazil/291-794 Flavivirus envelope glycoprotein E.]
SEQ ID NO: 38

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNTKNGSISLMCLALGGVLIFLSTAVSA

MRS_OPY_Martinique_PaRi_2015.AMC33116.1.Martinique/291-794 Flavivirus
envelope glycoprotein E.
SEQ ID NO: 39

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNTKNGSISLMCLALGGVLIFLSTAVSA

KU501215.1/308-811 Zika virus strain PRVABC59, Puerto Rico, Flavivirus
envelope glycoprotein E.
SEQ ID NO: 40

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNTKNGSISLMCLALGGVLIFLSTAVSA

Haiti%1225%2014.AMB37295.1.Haiti/291-794 Flavivirus envelope glycoprotein E.
SEQ ID NO: 41

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNTKNGSISLMCLALGGVLIFLSTAVSA

KU527068.1/308-811 Zika virus strain Natal RGN, Brazil: Rio Grande
do Norte, Natal, Flavivirus envelope glycoprotein E.
SEQ ID NO: 42

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNTKNGSISLMCLALGGVLIFLSTAVSA

-continued isol-Z1106027.ALX35662.1.Suriname/5-508 Flavivirus envelope glycoprotein E.
SEQ ID NO: 43
IRCIGVSNRDFVEGMSGGTWVDVVLEHGGCVTVMAQDKPTVDIELVTTTVSNMAEVRSYCYEASISDMASDSRCPTQGEAYLDKQ
SDTQYVCKRTLVDRGWGNGCGLFGKGSLVTCAKFACSKKMTGKSIQPENLEYRIMLSVHGSQHSGMIVNDTGHETDENRAKVEIT
PNSPRAEATLGGFGSLGLDCEPRTGLDFSDLYYLTMNNKHWLVHKEWFHDIPLPWHAGADTGTPHWNNKEALVEFKDAHAKRQT
VVVLGSQEGAVHTALAGALEAEMDGAKGRLSSGHLKCRLKMDKLRLKGVSYSLCTAAFTFTKIPAETLHGTVTVEVQYAGTDGPCK
VPAQMAVDMQTLTPVGRLITANPVITESTENSKMMLELDPPFGDSYIVIGVGEKKITHHWHRSGSTIGKAFEATVRGAKRMAVLGD
TAWDFGSVGGALNSLGKGIHQIFGAAFKSLFGGMSWFSQILIGTLLMWLGLNTKNGSISLMCLALGGVLIFLSTAVSA isol-FLR.AMM39804.1.Colombia:_Barranquilla/291-794 Flavivirus envelope glycoprotein E.
SEQ ID NO: 44
IRCIGVSNRDFVEGMSGGTWVDVVLEHGGCVTVMAQDKPTVDIELVTTTVSNMAEVRSYCYEASISDMASDSRCPTQGEAYLDKQ
SDTQYVCKRTLVDRGWGNGCGLFGKGSLVTCAKFACSKKMTGKSIQPENLEYRIMLSVHGSQHSGMIVNDTGHETDENRAKVEIT
PNSPRAEATLGGFGSLGLDCEPRTGLDFSDLYYLTMNNKHWLVHKEWFHDIPLPWHAGADTGTPHWNNKEALVEFKDAHAKRQT
VVVLGSQEGAVHTALAGALEAEMDGAKGRLSSGHLKCRLKMDKLRLKGVSYSLCTAAFTFTKIPAETLHGTVTVEVQYAGTDGPCK
VPAQMAVDMQTLTPVGRLITANPVITESTENSKMMLELDPPFGDSYIVIGVGEKKITHHWHRSGSTIGKAFEATVRGAKRMAVLGD
TAWDFGSVGGALNSLGKGIHQIFGAAFKSLFGGMSWFSQILIGTLLMWLGLNTKNGSISLMCLALGGVLIFLSTAVSA PLCal_ZV_isol-From_Vero_E6_cells.AHL37808.1.Canada/254-757
Flavivirus envelope glycoprotein E.
SEQ ID NO: 45
IRCIGVSNRDFVEGMSGGTWVDVVLEHGGCVTVMAQDKPTVDIELVTTTVSNMAEVRSYCYEASISDMASDSRCPTQGEAYLDKQ
SDTQYVCKRTLVDRGWGNGCGLFGKGSLVTCAKFACSKKMTGKSIQPENLEYRIMLSVHGSQHSGMIVNDTGHETDENRAKVEIT
PNSPRAEATLGGFGSLGLDCEPRTGLDFSDLYYLTMNNKHWLVHKEWFHDIPLPWHAGADTGTPHWNNKEALVEFKDAHAKRQT
VVVLGSQEGAVHTALAGALEAEMDGAKGRLSSGHLKCRLKMDKLRLKGVSYSLCTAAFTFTKIPAETLHGTVTVEVQYAGTDGPCK
VPAQMAVDMQTLTPVGRLITANPVITESTENSKMMLELDPPFGDSYIVIGVGEKKITHHWHRSGSTIGKAFEATVRGAKRMAVLGD
TAWDFGSVGGALNSLGKGIHQIFGAAFKSLFGGMSWFSQILIGTLLMWLGLNTKNGSISLMCLALGGVLIFLSTAVSA BeH818995.AMA12084.1.Brazil/291-794 Flavivirus envelope glycoprotein E. [Zika virus].
SEQ ID NO: 46
IRCIGVSNRDFVEGMSGGTWVDVVLEHGGCVTVMAQDKPTVDIELVTTTVSNMAEVRSYCYEASISDMASDSRCPTQGEAYLDKQ
SDTQYVCKRTLVDRGWGNGCGLFGKGSLVTCAKFACSKKMTGKSIQPENLEYRIMLSVHGSQHSGMIVNDTGHETDENRAKVEIT
PNSPRAEATLGGFGSLGLDCEPRTGLDFSDLYYLTMNNKHWLVHKEWFHDIPLPWHAGADTGTPHWNNKEALVEFKDAHAKRQT
VVVLGSQEGAVHTALAGALEAEMDGAKGRLSSGHLKCRLKMDKLRLKGVSYSLCTAAFTFTKIPAETLHGTVTVEVQYAGTDGPCK
VPAQMAVDMQTLTPVGRLITANPVITESTENSKMMLELDPPFGDSYIVIGVGEKKITHHWHRSGSTIGKAFEATVRGAKRMAVLGD
TAWDFGSVGGALNSLGKGIHQIFGAAFKSLFGGMSWFSQILIGTLLMWLGLNTKNGSISLMCLALGGVLIFLSTAVSA H/PF/2013.AHZ13508.1.French_Polynesia/291-794 Flavivirus envelope glycoprotein E.
SEQ ID NO: 47
IRCIGVSNRDFVEGMSGGTWVDVVLEHGGCVTVMAQDKPTVDIELVTTTVSNMAEVRSYCYEASISDMASDSRCPTQGEAYLDKQ
SDTQYVCKRTLVDRGWGNGCGLFGKGSLVTCAKFACSKKMTGKSIQPENLEYRIMLSVHGSQHSGMIVNDTGHETDENRAKVEIT
PNSPRAEATLGGFGSLGLDCEPRTGLDFSDLYYLTMNNKHWLVHKEWFHDIPLPWHAGADTGTPHWNNKEALVEFKDAHAKRQT
VVVLGSQEGAVHTALAGALEAEMDGAKGRLSSGHLKCRLKMDKLRLKGVSYSLCTAAFTFTKIPAETLHGTVTVEVQYAGTDGPCK
VPAQMAVDMQTLTPVGRLITANPVITESTENSKMMLELDPPFGDSYIVIGVGEKKITHHWHRSGSTIGKAFEATVRGAKRMAVLGD
TAWDFGSVGGALNSLGKGIHQIFGAAFKSLFGGMSWFSQILIGTLLMWLGLNTKNGSISLMCLALGGVLIFLSTAVSA PRVABC59.AMC13911.1.Puerto_Rico/291-794 Flavivirus envelope glycoprotein E.
SEQ ID NO: 48
IRCIGVSNRDFVEGMSGGTWVDVVLEHGGCVTVMAQDKPTVDIELVTTTVSNMAEVRSYCYEASISDMASDSRCPTQGEAYLDKQ
SDTQYVCKRTLVDRGWGNGCGLFGKGSLVTCAKFACSKKMTGKSIQPENLEYRIMLSVHGSQHSGMIVNDTGHETDENRAKVEIT
PNSPRAEATLGGFGSLGLDCEPRTGLDFSDLYYLTMNNKHWLVHKEWFHDIPLPWHAGADTGTPHWNNKEALVEFKDAHAKRQT
VVVLGSQEGAVHTALAGALEAEMDGAKGRLSSGHLKCRLKMDKLRLKGVSYSLCTAAFTFTKIPAETLHGTVTVEVQYAGTDGPCK VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNTKNGSISLMCLALGGVLIFLSTAVSA

KU321639.1/326-829 Zika virus strain ZikaSPH2015, Brazil,
Flavivirus envelope glycoprotein E.

SEQ ID NO: 49

IRCIGVSNRDFVEGMSGGTWVDIVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNTKNGSISLMCLALGGVLIFLSTAVSA

ZikaSPH2015.ALU33341.1.Brazil/291-794 Flavivirus envelope glycoprotein E.

SEQ ID NO: 50

IRCIGVSNRDFVEGMSGGTWVDIVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNTKNGSISLMCLALGGVLIFLSTAVSA

103344.AMC13912.1.Guatemala/291-794 polyprotein [Zika virus].
103344.AMC13912.1.Guatemala Flavivirus
envelope glycoprotein E.

SEQ ID NO: 51

IRCIGVSNRDFVEGMSGGTWVDVVLEHGGCVTVMAQDKPTVDIELVTTTVSNMAEIRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

PNSPRAEATLGGFGSLGLDCEPRTGLDFSDLYYLTMNNKHWLVHKEWFHDIPLPWHAGADTGTPHWNNKEALVEFKDAHAKRQT

VVVLGSQEGAVHTALAGALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNTKNGSISLMCLALGGVLIFLSTAVSA isol-Brazil-ZKV2015.AMD16557.1.Brazil/291-794 Flavivirus envelope glycoprotein E.

SEQ ID NO: 52

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

PNSPRAEATLGGFGSLGLDCEPRTGLDFSDLYYLTMNNKHWLVHKEWFHDIPLPWHAGADTGTPHWNNKEALVEFKDAHAKRQT

VVVLGTQEGAVHTALAGALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNTKNGSISLMCLALGGVLIFLSTAVSA

KU497555.1/308-811 Zika virus isolate Brazil-ZKV2015,
Flavivirus envelope glycoprotein E.

SEQ ID NO: 53

IRCIGVSNRDFVEGMSGGTWVDVVLEHGGCVTVMAQDKPTVDIELVTTTVSNMAEVRSYCYEASISDMASDSRCPTQGEAYLDKQ

SDTQYVCKRTLVDRGWGNGCGLFGKGSLVTCAKFACSKKMTGKSIQPENLEYRIMLSVHGSQHSGMIVNDTGHETDENRAKVEIT

PNSPRAEATLGGFGSLGLDCEPRTGLDFSDLYYLTMNNKHWLVHKEWFHDIPLPWHAGADTGTPHWNNKEALVEFKDAHAKRQT

VVVLGTQEGAVHTALAGALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNTKNGSISLMCLALGGVLIFLSTAVSA

-continued isol-ZJ03.AMM39806.1.China/291-794 Flavivirus envelope glycoprotein E.
SEQ ID NO: 54
IRCIGVSNRDFVEGMSGGTWVDVVLEHGGCVTVMAQDKPTVDIELVTTTVSNMAEVRSYCYEASISDMASDSRCPTQGEAYLDKQ
SDTQYVCKRTLVDRGWGNGCGLFGKGSLVTCAKFACSKKMTGKSIQPENLEYRIMLSVHGSQHSGMIVNDTGHETDENRAKVEIT
PNSPRAEATLGGFGSLGLDCEPRTGLDFSDLYYLTMNNKHWLVHKEWFHDIPLPWHAGADTGTPHWNNKEALVEFKDAHAKRQT
VVVLGSQEGAVHTALAGALEAEMDGAKGRLSSGHLKCRLKMDKLRLKGVSYSLCTAAFTFTKIPAETLHGTVTVEVQYAGTDGPCK
VPAQMAVDMQTLTPVGRLITANPVITESTENSKMMLELDPPFGDSYIVIGVGEKKITHHWHRSGSTIGKAFEATVRGARRMAVLG
DTAWDFGSVGGALNSLGKGIHQIFGAAFKSLFGGMSWFSQILIGTLLMWLGLNTKNGSISLMCLALGGVLIFLSTAVSA isol-FSS13025.AFD30972.1.Cambodia/291-794 Flavivirus envelope glycoprotein E.
SEQ ID NO: 55
IRCIGVSNRDFVEGMSGGTWVDVVLEHGGCVTVMAQDKPTVDIELVTTTVSNMAEVRSYCYEASISDMASDSRCPTQGEAYLDKQ
SDTQYVCKRTLVDRGWGNGCGLFGKGSLVTCAKFACSKKMTGKSIQPENLEYRIMLSVHGSQHSGMIVNDTGHETDENRAKVEIT
PNSPRAEATLGGFGSLGLDCEPRTGLDFSDLYYLTMNNKHWLVHKEWFHDIPLPWHAGADTGTPHWNNKEALVEFKDAHAKRQT
VVVLGSQEGAVHTALAGALEAEMDGAKGRLSSGHLKCRLKMDKLRLKGVSYSLCTAAFTFTKIPAETLHGTVTVEVQYAGTDGPCK
VPAQMAVDMQTLTPVGRLITANPVITESTENSKMMLELDPPFGDSYIVIGVGEKKITHHWHRSGSTIGKAFEATVRGAKRMAVLGD
TAWDFGSVGGALNSLGKGIHQIFGAAFKSLFGGMSWFSQILIGTLLVWLGLNTKNGSISLMCLALGGVLIFLSTAVSA isol-Z1106032.ALX35660.1.Suriname/291-794 Flavivirus envelope
glycoprotein E. [Zika virus]
SEQ ID NO: 56
IRCIGVSNRDFVEGMSGGTWVDVVLEHGGCVTVMAQDKPTVDIELVTTTVSNMAEVRSYCYEASISDMASDSRCPTQGEAYLDKQ
SDTQYVCKRTLVDRGWGNGCGLFGKGSLVTCAKFACSKKMTGKSIQPENLEYRIMLSVHGSQHSGMIVNDTGHETDENRAKVEIT
PNSPRAEATLGGFGSLGLDCEPRTGLDFSDLYYLTMNNKHWLVHKEWFHDIPLPWHAGADTGTPHWNNKEALVEFKDAHAKRQT
VVVLGSQEGAVHTALAGALEAEMDGAKGRLSSGHLKCRLKMDKLRLKGVSYSLCTAAFTFTKIPAETLHGTVTVEVQYAGTDGPCK
VPAQMAVDMQTLTPVGRLITANPVITESTENSKMMLELDPPFGDSYIVIGVGEKKITHHWHRSGSTIGKAFEATVRGAKRMAVLGD
TAWDFGSVGGALNSLGKGIHQIFGAAFKSLFGGMSWFSQILIGTLLMWLGLNAKNGSISLMCLALGGVLIFLSTAVSA isol-Z1106033.ALX35659.1.Suriname/291-794 Flavivirus envelope
glycoprotein E. [Zika virus]
SEQ ID NO: 57
IRCIGVSNRDFVEGMSGGTWVDVVLEHGGCVTVMAQDKPTVDIELVTTTVSNMAEVRSYCYEASISDMASDSRCPTQGEAYLDKQ
SDTQYVCKRTLVDRGWGNGCGLFGKGSLVTCAKFACSKKMTGKSIQPENLEYRIMLSVHGSQHSGMIVNDTGHETDENRAKVEIT
PNSPRAEATLGGFGSLGLDCEPRTGLDFSDLYYLTMNNKHWLVHKEWFHDIPLPWHAGADTGTPHWNNKEALVEFKDAHAKRQT
VVVLGSQEGAVHTALAGALEAEMDGAKGRLSSGHLKCRLKMDKLRLKGVSYSLCTAAFTFTKIPAETLHGTVTVEVQYAGTDGPCK
VPAQMAVDMQTLTPVGRLITANPVITESTENSKMMLELDPPFGDSYIVIGVGEKKITHHWHRSGSTIGKAFEATVRGAKRMAVLGD
TAWDFGSVGGALNSLGKGIHQIFGAAFKSLFGGMSWFSQILIGTLLMWLGLNAKNGSISLMCLALGGVLIFLSTAVSA isol-BeH828305.AMK49165.1.Brazil/291-794 Flavivirus envelope glycoprotein E.
SEQ ID NO: 58
IRCIGVSNRDFVEGMSGGTWVDVVLEHGGCVTVMAQDKPTVDIELVTTTVSNMAEVRSYCYEASISDMASDSRCPTQGEAYLDKQ
SDTQYVCKRTLVDRGWGNGCGLFGKGSLVTCAKFACSKKMTGKSIQPENLEYRIMLSVHGSQHSGMIVNDTGHETDENRAKVEIT
PNSPRAEATLGGFGSLGLDCEPRTGLDFSDLYYLTMNNKHWLVHKEWFHDIPLPWHAGADTGTPHWNNKEALVEFKDAHAKRQT
VVVLGSQEGAVHTALAGALEAEMDGAKGRLSSGHLKCRLKMDKLRLKGVSYSLCTAAFTFTKIPAETLHGTVTVEVQYAGTDGPCK
VPAQMAVDTQTLTPVGRLITANPVITESTENSKMMLELDPPFGDSYIVIGVGEKKITHHWHRSGSTIGKAFEATVRGAKRMAVLGD
TAWDFGSVGGALNSLGKGIHQIFGAAFKSLFGGMSWFSQILIGTLLMWLGLNTKNGSISLMCLALGGVLIFLSTAVSA isol-GD01.AMK79468.1.China/291-794 Flavivirus envelope glycoprotein E.
SEQ ID NO: 59
IRCIGVSNRDFVEGMSGGTWVDVVLEHGGCVTVMAQDKPTVDIELVTTTVSNMAEVRSYCYEASISDMASDSRCPTQGEAYLDKQ
SDTQYVCKRTLVDRGWGNGCGLFGKGSLVTCAKFACSKKMTGKSIQPENLEYRIMLSVHGSQHSGMIVNGTGHETDENRAKVEIT
PNSPRAEATLGGFGSLGLDCEPRTGLDFSDLYYLTMNNKHWLVHKEWFHDIPLPWHAGADTGTPHWNNKEALVEFKDAHAKRQT -continued VVVLGSQEGAVHTALAGALEAEMDGAKGRLSSGHLKCRLKMDKLRLKGVSYSLCTAAFTFTKIPAETLHGTVTVEVQYAGTDGPCK VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNTKNGSISLMCLALGGVLIFLSTAVSA isol-Z1106031.ALX35661.1.Suriname/291-794 Flavivirus envelope glycoprotein E.
SEQ ID NO: 60
IRCIGVSNRDFVEGMSGGTWVDVVLEHGGCVTVMAQDKPTVDIELVTTTVSNMAEVRSYCYEASISDMASDSRCPTQGEAYLDKQ SDTQYVCKRTLVDRGWGNGCGLFGKGSLVTCAKFACSKKMTGKSIQPENLEYRIMLSVHGSQHSGMIVNDTGHETDENRAKVEIT PNSPRAEATLGGFGSLGLDCEPRTGLDFSDLYYLTMNNKHWLVHKEWFHDIPLPWHAGADTGTPHWNNKEALVEFKDAHAKRQT VVVLGSQEGAVHTALAGALEAEMDGAKGRLSSGHLKCRLKMDKLRLKGVSYSLCTAAFTFTKIPAETLHGTVTVEVQYAGTDGPCK VLAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNTKNGSISLMCLALGGVLIFLSTAVSA

ACD75819.1.Micronesia/291-794 Flavivirus envelope glycoprotein E.
SEQ ID NO: 61
IRCIGVSNRDFVEGMSGGTWVDVVLEHGGCVTVMAQDKPAVDIELVTTTVSNMAEVRSYCYEASISDMASDSRCPTQGEAYLDKQ SDTQYVCKRTLVDRGWGNGCGLFGKGSLVTCAKFACSKKMTGKSIQPENLEYRIMLSVHGSQHSGMIVNDTGHETDENRAKVEIT PNSPRAEATLGGFGSLGLDCEPRTGLDFSDLYYLTMNNKHWLVHKEWFHDIPLPWHAGADTGTPHWNNKEALVEFKDAHAKRQT VVVLGSQEGAVHTALAGALEAEMDGAKGRLSSGHLKCRLKMDKLRLKGVSYSLCTAAFTFTKIPAETLHGTVTVEVQYAGTDGPCK VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLVWLGLNTKNGSISLTCLALGGVLIFLSTAVSA

KU681082.3/308-811 Zika virus isolate Zika virus/*H.sapiens*-tc/PHL/2012/CPC-0740,
Philippines, Flavivirus envelope
glycoprotein E.
SEQ ID NO: 62
IRCIGVSNRDFVEGMSGGTWVDVVLEHGGCVTVMAQDKPTVDIELVTTTVSNMAEVRSYCYEASISDMASDSRCPTQGEAYLDKQ SDTQYVCKRTLVDRGWGNGCGLFGKGSLVTCAKFACSKKMTGKSIQPENLEYRIMLSVHGSQHSGMIVNDTGHETDENRAKVEIT PNSPRAEATLGGFGSLGLDCEPRTGLDFSDLYYLTMNNKHWLVHKEWFHDIPLPWHAGADTGTPHWNNKEALVEFKDAHAKRQT VVVLGSQEGAVHTALAGALEAEMDGAKGRLSSGHLKCRLKMDKLRLKGVSYSLCTAAFTFTKIPAETLHGTVTVEVQYAGTDGPCK VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLVWLGLNTKNGSISLTCLALGGVLIFLSTAVSA isol-Zika_virus%*H.sapiens*-tc%PHL%2012%CPC-0740.AMD61711.1.Philippines/291-794
Flavivirus envelope glycoprotein E.
SEQ ID NO: 63
IRCIGVSNRDFVEGMSGGTWVDVVLEHGGCVTVMAQDKPTVDIELVTTTVSNMAEVRSYCYEASISDMASDSRCPTQGEAYLDKQ SDTQYVCKRTLVDRGWGNGCGLFGKGSLVTCAKFACSKKMTGKSIQPENLEYRIMLSVHGSQHSGMIVNDTGHETDENRAKVEIT PNSPRAEATLGGFGSLGLDCEPRTGLDFSDLYYLTMNNKHWLVHKEWFHDIPLPWHAGADTGTPHWNNKEALVEFKDAHAKRQT VVVLGSQEGAVHTALAGALEAEMDGAKGRLSSGHLKCRLKMDKLRLKGVSYSLCTAAFTFTKIPAETLHGTVTVEVQYAGTDGPCK VPAQMAVDMQTLTPVGRLITANPVITESTENSKMMLELDPPFGDSYIVIGVGEKKITHHWHRSGSTIGKAFEATVRGAKRMAVLGD TAWDFGSVGGALNSLGKGIHQIFGAAFKSLFGGMSWFSQILIGTLLVWLGLNTKNGSISLTCLALGGVLIFLSTAVSA
SEQ ID NO: 64
isol-BeH823339.AMK49164.2.Brazil/291-794 Flavivirus envelope glycoprotein E.

IRCIGVSNRDFVEGMSGGTWVDVVLEHGGCVTVMAQDKPTVDIELVSTTVSNMAEVRSYCYEATISDIASDSRCPTQGEAYLDKQS

DTQYVCKRTLVDRGWGNGCGLFGKGSLVTCAKFACSKKMTGKSIQPENLEYRIMLSVHGSQHSGMIVNDTGHETDENRAKVEITP

NSPRAEATLGGFGSLGLDCEPRTGLDFSDLYYLTMNNKHWLVHKEWFHDIPLPWHAGADTGTPHWNNKEALVEFKDAHAKRQT

AVVLGSQEGAVHTALAGALEAEMDGAKGRLSSGHLKCRLKMDKLRLKGVSYSLCTAAFTFTKIPAETLHGTVTVEVQYAGTDGPCK

VPAQMAVDMQTLTPVGRLITANPVITESTENSKMMLELDPPFGDSYIVIGVGEKKITHHWHRSGSTIGKAFEATVRGAKRMAVLGD

TAWDFGSVGGALNSLGKGIHQIFGAAFKSLFGGMSWFSQILIGTLLMWLGLNTKNGSISLMCLALGGVLIFLSTAVSA

-continued isol-P6-740.AEN75264.1.Malaysia/291-794 Flavivirus envelope glycoprotein E.
SEQ ID NO: 65
IRCIGVSNRDFVEGMSGGTWVDVVLEHGGCVTVMAQDKPTVDIELVTTTVSNMAEVRSYCYEASISDMASDSRCPTQGEAYLDKQ
SDTQYVCKRTLVDRGWGNGCGLFGKGSLVTCAKFACSKKMTGKSIQPENLEYRIMLSVHGSQHSGMIVNDXGHETDENRAKVEIT
PNSPRAEATLGGFGSLGLDCEPRTGLDFSDLYYLTMNNKHWLVHKEWFHDIPLPWHAGADTGTPHWNNKEALVEFKDAHAKRQT
VVVLGSQEGAVHTALAGALEAEMDGAKGRLSSGHLKCRLKMDKLRLKGVSYSLCTAAFTFTKIPAETLHGTVTVEVQYAGTDGPCK
VPAQMAVDMQTLTPVGRLITANPVITESTENSKMMLELDPPFGDSYIVIGVGDKKITHHWXRSGSTIGKAFEATVRGAKRMAVLG
DTAWDFGSVGGALNSLGKGIHQIFGAAFKSLFGGMSWFSQILIGTLLVWLGLNTKNGSISLTCLALGGVLIFLSTAVSA KU744693.1/326-829 Zika virus isolate VE_Ganxian, China, Flavivirus
envelope glycoprotein E.
SEQ ID NO: 66
IRCIGVSNRDFVEGMSGGTWVDVVLEHGGCVTAMAQDKPTVDIELVTTTVSNMAEVRSYCYEASISDMASDSRCPTQGEAYLDKQ
SDTQYVCKRTLVDRGWGNGCGLFGKGSLVTCAKFACSKKMTGKSIQPENLEYRIMLSVHGSQHSGMLVNDTGHETDENRAKVEIT
PNSPRAEATLGGFGSLGLDCEPRTGLDFSDLYYLTMNNKHWLAHKEWFHDIPLPWHAGAATGTPHWNNKEALVEFKDAHAKRQT
VVVLGSQEGAVHTALAGALEAEMDGAKGRLSSGHLKCRLKMDKLRLKGVSYSLCTAAFTFTKIPAETVDGTVTVEGQYGGTDGPCK
VPAQMAVDMQTLTPVGRLITANPVITESTENSKMMLELDPPFGDSYIVIGVGEKKITHHWHRSGSTIGKAFEATVRGAKRMAVLGD
TAWDFGSVGGALNSLGKGIHQIIGAAFKSLFGGMSWFSQILIGTLLMWLGLNTKNGSISLMCLALGGVLIFLSTAVSG isol-VE_Ganxian.AMK79469.1.China/291-794 Flavivirus envelope glycoprotein E.
SEQ ID NO: 67
IRCIGVSNRDFVEGMSGGTWVDVVLEHGGCVTAMAQDKPTVDIELVTTTVSNMAEVRSYCYEASISDMASDSRCPTQGEAYLDKQ
SDTQYVCKRTLVDRGWGNGCGLFGKGSLVTCAKFACSKKMTGKSIQPENLEYRIMLSVHGSQHSGMLVNDTGHETDENRAKVEIT
PNSPRAEATLGGFGSLGLDCEPRTGLDFSDLYYLTMNNKHWLAHKEWFHDIPLPWHAGAATGTPHWNNKEALVEFKDAHAKRQT
VVVLGSQEGAVHTALAGALEAEMDGAKGRLSSGHLKCRLKMDKLRLKGVSYSLCTAAFTFTKIPAETVDGTVTVEGQYGGTDGPCK
VPAQMAVDMQTLTPVGRLITANPVITESTENSKMMLELDPPFGDSYIVIGVGEKKITHHWHRSGSTIGKAFEATVRGAKRMAVLGD
TAWDFGSVGGALNSLGKGIHQIIGAAFKSLFGGMSWFSQILIGTLLMWLGLNTKNGSISLMCLALGGVLIFLSTAVSG ArD157995.AHL43503.1.-/291-794 Flavivirus envelope glycoprotein E.
SEQ ID NO: 68
ISCIGVSNRDLVEGMSGGTWVDVVLEHGGCVTEMAQDKPTVDIELVTMTVSNMAEVRSYCYEASLSDMASASRCPTQGEPSLDK
QSDTQSVCKRTLGDRGWGNGCGIFGKGSLVTCSKFTCCKKMPGKSIQPENLEYRIMLPVHGSQHSGMIVNDIGHETDENRAKVEV
TPNSPRAEATLGGFGSLGLDCEPRTGLDFSDLYYLTMNNKHWLVHKEWFHDIPLPWHAGADTGTPHWNNKEALVEFKDAHAKRQ
TVVVLGSQEGAVHTALAGALEAEMDGAKGRLFSGHLKCRLKMDKLRLKGVSYSLCTAAFTFTKVPAETLHGTVTVEVQSAGTDGPC
KVPAQMAVDMQTLTPVGRLITANPVITESTENSKMMLELDPPFGDSYIVIGVGDKKITHHWHRSGSTIGKAFEATVRGAKRMAVL
GDTAWDFGSVGGVFNSLGKGIHQIFGAAFKSLFGGMSWFSQILIGTLLVWLGLNTKNGSISLTCLALGGVMIFLSTAVSA MR_766.ABI54475.1.Uganda/291-788 Flavivirus envelope glycoprotein E.
SEQ ID NO: 69
IRCIGVSNRDFVEGMSGGTWVDVVLEHGGCVTVMAQDKPTVDIELVTTTVSNMAEVRSYCYEASISDMASDSRCPTQGEAYLDKQ
SDTQYVCKRTLVDRGWGNGCGLFGKGSLVTCAKFTCSKKMTGKSIQPENLEYRIMLSVHGSQHSGMIVNDENRAKVEVTPNSPRA
EATLGGFGSLGLDCEPRTGLDFSDLYYLTMNNKHWLVHKEWFHDIPLPWHAGADTGTPHWNNKEALVEFKDAHAKRQTVVVLGS
QEGAVHTALAGALEAEMDGAKGRLFSGHLKCRLKMDKLRLKGVSYSLCTAAFTFTKVPAETLHGTVTVEVQYAGTDGPCKVPAQM
AVDMQTLTPVGRLITANPVITESTENSKMMLELDPPFGDSYIVIGVGDKKITHHWHRSGSTIGKAFEATVRGAKRMAVLGDTAWDF
GSVGGVFNSLGKGIHQIFGAAFKSLFGGMSWFSQILIGTLLVWLGLNTKNGSISLTCLALGGVMIFLSTAVSA 5'-(dldC)i3-3'
SEQ ID NO: 70
dldC dldC dldC dldC dldC dldC dldC dldC dldC dldC dldC dldC dldC KLK peptide
SEQ ID NO: 71
KLKLLLLLKLK Provided below are examples of nucleic acid sequences of the genomes of Chikungunya, Japanese Encephalitis and yellow fever viruses that may be used in the methods, compositions, and/or vaccines described herein.

```
Chikungunya virus strain LR2006_OPY1, complete genome ACCESSION: DQ443544
                                                            SEQ ID NO: 72
ATGGCTGCGTGAGACACACGTAGCCTACCAGTTTCTTACTGCTCTACTCTGCAAAGCAAGAGATTAATAACCC

ATCATGGATCCTGTGTACGTGGACATAGACGCTGACAGCGCCTTTTTGAAGGCCCTGCAACGTGCGTACCCC

ATGTTTGAGGTGGAACCAAGGCAGGTCACACCGAATGACCATGCTAATGCTAGAGCGTTCTCGCATCTAGCT

ATAAAACTAATAGAGCAGGAAATTGACCCCGACTCAACCATCCTGGATATCGGCAGTGCGCCAGCAAGGAGG

ATGATGTCGGACAGGAAGTACCACTGCGTCTGCCCGATGCGCAGTGCGGAAGATCCCGAGAGACTCGCCAAT

TATGCGAGAAAGCTAGCATCTGCCGCAGGAAAAGTCCTGGACAGAAACATCTCTGGAAAGATCGGGGACTTA

CAAGCAGTAATGGCCGTGCCAGACACGGAGACGCCAACATTCTGCTTACACACAGACGTCTCATGTAGACAG

AGAGCAGACGTCGCTATATACCAAGACGTCTATGCTGTACACGCACCCACGTCGCTATACCACCAGGCGATT

AAAGGGGTCCGAGTGGCGTACTGGGTTGGGTTCGACACAACCCCGTTCATGTACAATGCCATGGCGGGTGCC

TACCCCTCATACTCGACAAACTGGGCAGATGAGCAGGTACTGAAGGCTAAGAACATAGGATTATGTTCAACA

GACCTGACGGAAGGTAGACGAGGCAAGTTGTCTATTATGAGAGGGAAAAAGCTAAAACCGTGCGACCGTGTG

CTGTTCTCAGTAGGGTCAACGCTCTACCCGAAAGCCGCAAGCTACTTAAGAGCTGGCACCTGCCATCGGTG

TTCCATTTAAAGGGCAAACTCAGCTTCACATGCCGCTGTGATACAGTGGTTTCGTGTGAGGGCTACGTCGTT

AAGAGAATAACGATGAGCCCAGGCCTTTATGGAAAAACCACAGGGTATGCGGTAACCCACCACGCAGACGGA

TTCCTGATGTGCAAGACTACCGACACGGTTGACGGCGAAAGARTGTCATTCTCGGTGTGCACATACGTGCCG

GCGACCATTTGTGATCAAATGACCGGCATCCTTGCTACAGAAGTCACGCCGGAGGATGCACAGAAGCTGTTG

GTGGGGCTGAACCAGAGAATAGTGGTTAACGGCAGAACGCAACGGAATACGAACACCATGAAAAATTATCTG

CTTCCCGTGGTCGCCCAAGCCTTCAGTAAGTGGGCAAAGGAGTGCCGGAAAGACATGGAAGATGAAAAACTC

CTGGGGGTCAGAGAAAGAACACTGACCTGCTGCTGTCTATGGGCATTCAAGAAGCAGAAAACACACACGGTC

TACAAGAGGCCTGATACCCAGTCAATTCAGAAGGTTCAGGCCGAGTTTGACAGCTTTGTGGTACCGAGTCTG

TGGTCGTCCGGGTTGTCAATCCCTTTGAGGACTAGAATCAAATGGTTGTTAAGCAAGGTGCCAAAAACCGAC

CTGATCCCATACAGCGGAGACGCCCGAGAAGCCCGGGACGCAGAAAAGAAGCAGAGGAAGAACGAGAAGCA

GAACTGACTCGCGAAGCCCTACCACCTCTACAGGCAGCACAGGAAGATGTTCAGGTCGAAATCGACGTGGAA

CAGCTTGAGGACAGAGCGGGCGCAGGAATAATAGAGACTCCGAGAGGAGCTATCAAAGTTACTGCCCAACCA

ACAGACCACGTCGTGGGAGAGTACCTGGTACTCTCCCCGCAGACCGTACTACGTAGCCAGAAGCTCAGTCTG

ATTCACGCTTTGGCGGAGCAAGTGAAGACGTGCACGCACAACGGACGAGCAGGGAGGTATGCGGTCGAAGCG

TACGACGGCCGAGTCCTAGTGCCCTCAGGCTATGCAATCTCGCCTGAAGACTTCCAGAGTCTAAGCGAAAGC

GCAACGATGGTGTATAACGAAAGAGAGTTCGTAAACAGAAAGCTACACCATATTGCGATGCACGGACCAGCC

CTGAACACCGACGAAGAGTCGTATGAGCTGGTGAGGGCAGAGAGGACAGAACACGAGTACGTCTACGACGTG

GATCAGAGAAGATGCTGTAAGAAGGAAGAAGCCGCAGGACTGGTACTGGTGGGCGACTTGACTAATCCGCCC

TACCACGAATTCGCATATGAAGGGCTAAAAATCCGCCCTGCCTGCCCATACAAAATTGCAGTCATAGGAGTC

TTCGGAGTACCGGGATCTGGCAAGTCAGCTATTATCAAGAACCTAGTTACCAGGCAGGACCTGGTGACTAGC

GGAAAGAAAGAAAACTGCCAAGAAATCACCACCGACGTGATGAGACAGAGAGGTCTAGAGATATCTGCACGT

ACGGTTGACTCGCTGCTCTTGAATGGATGCAACAGACCAGTCGACGTGTTGTACGTAGACGAGGCGTTTGCG

TGCCACTCTGGAACGCTACTTGCTTTGATCGCCTTGGTGAGACCAAGGCAGAAAGTTGTACTTTGTGGTGAC

CCGAAGCAGTGCGGCTTCTTCAATATGATGCAGATGAAAGTCAACTATAATCACAACATCTGCACCCAAGTG

TACCACAAAAGTATCTCCAGGCGGTGTACACTGCCTGTGACCGCCATTGTGTCATCGTTGCATTACGAAGGC

AAAATGCGCACTACGAATGAGTACAACAAGCCGATTGTAGTGGACACTACAGGCTCAACAAAACCTGACCCT
```

-continued

```
GGAGACCTCGTGTTAACGTGCTTCAGAGGGTGGGTTAAACAACTGCAAATTGACTATCGTGGATACGAGGTC
ATGACAGCAGCCGCATCCCAAGGGTTAACCAGAAAAGGAGTTTACGCAGTTAGACAAAAAGTTAATGAAAAC
CCGCTCTATGCATCAACGTCAGAGCACGTCAACGTACTCCTAACGCGTACGGAAGGTAAACTGGTATGGAAG
ACACTTTCCGGCGACCCGTGGATAAAGACGCTGCAGAACCCACCGAAAGGAAACTTCAAAGCAACTATTAAG
GAGTGGGAGGTGGAGCATGCATCAATAATGGCGGGCATCTGCAGTCACCAAATGACCTTCGATACATTCCAA
AATAAAGCCAACGTTTGTTGGGCTAAGAGCTTGGTCCCTATCCTCGAAACAGCGGGGATAAAACTAAATGAT
AGGCAGTGGTCTCAGATAATTCAAGCCTTCAAAGAAGACAAAGCATACTCACCTGAAGTAGCCCTGAATGAA
ATATGTACGCGCATGTATGGGGTGGATCTAGACAGCGGGCTATTTTCTAAACCGTTGGTGTCTGTGTATTAC
GCGGATAACCACTGGGATAATAGGCCTGGAGGGAAAATGTTCGGATTTAACCCCGAGGCAGCATCCATTCTA
GAAAGAAAGTATCCATTCACAAAAGGGAAGTGGAACATCAACAAGCAGATCTGCGTGACTACCAGGAGGATA
GAAGACTTTAACCCTACCACCAACATCATACCGGCCAACAGGAGACTACCACACTCATTAGTGGCCGAACAC
CGCCCAGTAAAAGGGGAAAGAATGGAATGGCTGGTTAACAAGATAAACGGCCACCACGTGCTCCTGGTCAGT
GGCTATAACCTTGCACTGCCTACTAAGAGAGTCACTTGGGTAGCGCCGTTAGGTGTCCGCGGAGCGGACTAC
ACATACAACCTAGAGTTGGGTCTGCCAGCAACGCTTGGTAGGTATGACCTAGTGGTCATAAACATCCACACA
CCTTTTCGCATACACCATTACCAACAGTGCGTCGACCACGCAATGAAACTGCAAATGCTCGGGGTGACTCA
TTGAGACTGCTCAAACCGGGCGGCTCTCTATTGATCAGAGCATATGGTTACGCAGATAGAACCAGTGAACGA
GTCATCTGCGTATTGGGACGCAAGTTTAGATCGTCTAGAGCGTTGAAACCACCATGTGTCACCAGCAACACT
GAGATGTTTTTCCTATTCAGCAACTTTGACAATGGCAGAAGGAATTTCACAACTCATGTCATGAACAATCAA
CTGAATGCAGCCTTCGTAGGACAGGTCACCCGAGCAGGATGTGCACCGTCGTACCGGGTAAAACGCATGGAC
ATCGCGAAGAACGATGAAGAGTGCGTAGTCAACGCCGCTAACCCTCGCGGGTTACCGGGTGRCGGTGTTTGC
AAGGCAGTATACAAAAAATGGCCGGAGTCCTTTAAGAACAGTGCAACACCAGTGGGAACCGCAAAACAGTT
ATGTGCGGTACGTATCCAGTAATCCACGCTGTTGGACCAAACTTCTCTAATTATTCGGAGTCTGAAGGGGAC
CGGGAATTGGCAGCTGCCTATCGAGAAGTCGCAAAGGAAGTAACTAGGCTGGGAGTAAATAGTGTAGCTATA
CCTCTCCTCTCCACAGGTGTATACTCAGGAGGGAAAGACAGGCTGACCCAGTCACTGAACCACCTCTTTACA
GCCATGGACTCGACGGATGCAGACGTGGTCATCTACTGCCGCGACAAAGAATGGGAGAAGAAAATATCTGAG
GCCATACAGATGCGGACCCAAGTAGAGCTGCTGGATGAGCACATCTCCATAGACTGCGATATTGTTCGCGTG
CACCCTGACAGCAGCTTGGCAGGCAGAAAAGGATACAGCACCACGGAAGGCGCACTGTACTCATATCTAGAA
GGGACCCGTTTTCATCAGACGGCTGTGGATATGGCGGAGATACATACTATGTGGCCAAAGCAAACAGAGGCC
AATGAGCAAGTCTGCCTATATGCCCTGGGGGAAAGTATTGAATCGATCAGGCAGAAATGCCCGGTGGATGAT
GCAGACGCATCATCTCCCCCCAAAACTGTCCCGTGCCTTTGCCGTTACGCTATGACTCCAGAACGCGTCACC
CGGCTTCGCATGAACCACGTCACAAGCATAATTGTGTGTTCTTCGTTTCCCCTCCCAAAGTACAAAATAGAA
GGAGTGCAAAAAGTCAAATGCTCTAAGGTAATGCTATTTGACCACAACGTGCCATCGCGCGTAAGTCCAAGG
GAATATAKATCTTCCCAGGAGTCTGCACAGGAGGCGAGTACAATCACGTCACTGACGCATAGTCAATTCGAC
CTAAGCGTTGATGGCGAGATACTGCCCGTCCCGTCAGACCTGGATGCTGACGCCCCAGCCCTAGAACCAGCA
CTAGACGACGGGGCGACACACACGCTGCCATCCACAACCGGAAACCTTGCGGCCGTGTCTGATTGGGTAATG
AGCACCGTACCTGTCGCGCCGCCCAGAAGAAGGCGAGGGAGAAACCTGACTGTGACATGTGACGAGAGAGAA
GGGAATATAACACCCATGGCTAGCGTCCGATTCTTTAGGGCAGAGCTGTGTCCGGTCGTACAAGAAACAGCG
GAGACGCGTGACACAGCAATGTCTCTTCAGGCACCACCGAGTACCGCCACGGAACCGAATCATCCGCCGATC
TCCTTCGGAGCATCAAGCGAGACGTTCCCCATTACATTTGGGGACTTCAACGAAGGAGAAATCGAAAGCTTG
TCTTCTGAGCTACTAACTTTCGGAGACTTCTTACCAGGAGAAGTGGATGACTTGACAGACAGCGACTGGTCC
ACGTGCTCAGACACGGACGACGAGTTATGACTAGACAGGGCAGGTGGGTATATATTCTCGTCGGACACCGGT
```

-continued

```
CCAGGTCATTTACAACAGAAGTCAGTACGCCAGTCAGTGCTGCCGGTGAACACCCTGGAGGAAGTCCACGAG
GAGAAGTGTTACCCACCTAAGCTGGATGAAGCAAACGAGCAACTATTACTTAAGAAACTCCAGGAGAGTGCA
TCCATGGCCAACAGAAGCAGGTATCAGTCGCGCAAAGTAGAAAACATGAAAGCAGCAATCATCCAGAGACTA
AAGAGAGGCTGTAGACTATACTTAATGTCAGAGACCCCAAAAGTCCCTACTTACCGGACTACATATCCGGCG
CCTGTGTACTCGCCTCCGATCAACGTCCGATTGTCCAATCCCGAGTCCGCAGTGGCAGCATGCAATGAGTTC
TTAGCTAGAAAGTATCCAACTGTCTCATCATACCAAATTACCGACGAGTATGATGCATATCTAGACATGGTG
GACGGGTCGGAGAGTTGCCTGGACCGAGCGACATTCAATCCGTCAAAACTCAGGAGCTACCCGAAACAGCAC
GCTTACCACGCGCCCTCCATCAGAAGCGCTGTACCGTCCCCATTCCAGAACACACTACAGAATGTACTGGCA
GCAGCCACGAAAAGAAACTGCAACGTCACACAGATGAGGGAATTACCCACTTTGGACTCAGCAGTATTCAAC
GTGGAGTGTTTCAAAAAATTCGCATGCAACCAAGAATACTGGGAAGAATTTGCTGCCAGCCCTATTAGGATA
ACAACTGAGAATTTAGCAACCTATGTTACTAAACTAAAAGGGCCAAAAGCAGCAGCGCTATTCGCAAAAACC
CATAATCTACTGCCACTACAGGAAGTACCAATGGATAGGTTCACAGTAGATATGAAAAGGGACGTAAAGGTG
ACTCCTGGTACAAAGCATACAGAGGAAAGACCTAAGGTGCAGGTTATACAGGCGGCTGAACCCTTGGCGACA
GCATACCTATGTGGGATTCACAGAGAGCTGGTTAGGAGGCTGAACGCCGTCCTCCTACCCAATGTACATACA
CTATTTGACATGTCTGCCGAGGATTTCGATGCCATCATAGCCGCACACTTTAAGCCAGGAGACACTGTTTTG
GAAACGGACATAGCCTCCTTTGATAAGAGCCAAGATGATTCACTTGCGCTTACTGCTTTGATGCTGTTAGAG
GATTTAGGGGTGGATCACTCCCTGCTGGACTTGATAGAGGCTGCTTTCGGAGAGATTTCCAGCTGTCACCTA
CCGACAGGTACGCGCTTCAAGTTCGGCGCCATGATGAAATCAGGTATGTTCCTAACTCTGTTCGTCAACACA
TTGTTAAACATCACCATCGCCAGCCGAGTGCTGGAAGATCGTCTGACAAAATCCGCGTGCGCGGCCTTCATC
GGCGACGACAACATAATACATGGAGTCGTCTCCGATGAATTGATGGCAGCCAGATGTGCCACTTGGATGAAC
ATGGAAGTGAAGATCATAGATGCAGTTGTATCCTTGAAAGCCCCTTACTTTTGTGGAGGGTTTATACTGCAC
GATACTGTGACAGGAACAGCTTGCAGAGTGGCAGACCCGCTAAAAAGGCTTTTTAAACTGGGCAAACCGCTA
GCGGCAGGTGACGAACAAGATGAAGATAGAAGACGAGCGCTGGCTGACGAAGTGATCAGATGGCAACGAACA
GGGCTAATTGATGAGCTGGAGAAAGCGGTATACTCTAGGTACGAAGTGCAGGGTATATCAGTTGTGGTAATG
TCCATGGCCACCTTTGCAAGCTCCAGATCCAACTTCGAGAAGCTCAGAGGACCCGTCATAACTTTGTACGGC
GGTCCTAAATAGGTACGCACTACAGCTACCTATTTTGCAGAAGCCGACAGCAAGTATCTAAACACTAATCAG
CTACAATGGAGTTCATCCCAACCCAAACTTTTTACAATAGGAGGTACCAGCCTCGACCCTGGACTCCGCGCC
CTACTATCCAAGTCATCAGGCCCAGACCGCGCCCTCAGAGGCAAGCTGGGCAACTTGCCCAGCTGATCTCAG
CAGTTAATAAACTGACAATGCGCGCGGTACCCCAACAGAAGCCACGCAGGAATCGGAAGAATAAGAAGCAAA
AGCAAAAACAACAGGCGCCACAAAACAACACAAATCAAAAGAAGCAGCCACCTAAAAAGAAACCGGCTCAAA
AGAAAAAGAAGCCGGGCCGCAGAGAGAGGATGTGCATGAAATCGAAATGATTGTATTTTCGAAGTCAAGC
ACGAAGGTAAGGTAACAGGTTACGCGTGCCTGGTGGGGACAAAGTAATGAAACCAGCACACGTAAAGGGGA
CCATCGATAACGCGGACCTGGCCAAACTGGCCTTTAAGCGGTCATCTAAGTATGACCTTGAATGCGCGCAGA
TACCCGTGCACATGAAGTCCGACGCTTCGAAGTTCACCCATGAGAAACCGGAGGGGTACTACAACTGGCACC
ACGGAGCAGTACAGTACTCAGGAGGCCGGTTCACCATCCCTACAGGTGCTGGCAAACCAGGGGACAGCGGCA
GACCGATCTTCGACAACAAGGGACGCGTGGTGGCCATAGTCTTAGGAGGAGCTAATGAAGGAGCCCGTACAG
CCCTCTCGGTGGTGACCTGGAATAAAGACATTGTCACTAAAATCACCCCCGAGGGGGCCGAAGAGTGGAGTC
TTGCCATCCCAGTTATGTGCCTGTTGGCAAACACCACGTTCCCTGCTCCCAGCCCCTTGCACGCCCTGCT
GCTACGAAAAGGAACCGGAGGAAACCCTACGCATGCTTGAGGACAACGTCATGAGACCTGGGTACTATCAGC
TGCTACAAGCATCCTTAACATGTTCTCCCCACCGCCAGCGACGCAGCACCAAGGACAACTTCAATGTCTATA
```

-continued

```
AAGCCACAAGACCATACTTAGCTCACTGTCCCGACTGTGGAGAAGGGCACTCGTGCCATAGTCCCGTAGCAC
TAGAACGCATCAGAAATGAAGCGACAGACGGGACGCTGAAAATCCAGGTCTCCTTGCAAATCGGAATAAAGA
CGGATGACAGCCACGATTGGACCAAGCTGCGTTATATGGACAACCACATGCCAGCAGACGCAGAGAGGGCGG
GGCTATTTGTAAGAACATCAGCACCGTGTACGATTACTGGAACAATGGGACACTTCATCCTGGCCCGATGTC
CAAAAGGGGAAACTCTGACGGTGGGATTCACTGACAGTAGGAAGATTAGTCACTCATGTACGCACCCATTTC
ACCACGACCCTCCTGTGATAGGTCGGGAAAAATTCCATTCCCGACCGCAGCACGGTAAAGAGCTACCTTGCA
GCACGTACGTGCAGAGCACCGCCGCAACTACCGAGGAGATAGAGGTACACATGCCCCCAGACACCCCTGATC
GCACATTAATGTCACAACAGTCCGGCAACGTAAAGATCACAGTCAATGGCCAGACGGTGCGGTACAAGTGTA
ATTGCGGTGGCTCAAATGAAGGACTAACAACTACAGACAAAGTGATTAATAACTGCAAGGTTGATCAATGTC
ATGCCGCGGTCACCAATCACAAAAAGTGGCAGTATAACTCCCCTCTGGTCCCGCGTAATGCTGAACTTGGGG
ACCGAAAAGGAAAAATTCACATCCCGTTTCCGCTGGCAAATGTAACATGCAGGGTGCCTAAAGCAAGGAACC
CCACCGTGACGTACGGGAAAAACCAAGTCATCATGCTACTGTATCCTGACCACCCAACACTCCTGTCCTACC
GGAATATGGGAGAAGAACCAAACTATCAAGAAGAGTGGGTGATGCATAAGAAGGAAGTCGTGCTAACCGTGC
CGACTGAAGGGCTCGAGGTCACGTGGGGCAACAACGAGCCGTATAAGTATTGGCCGCAGTTATCTACAAACG
GTACAGCCCATGGCCACCCGCATGAGATAATTCTGTATTATTATGAGCTGTACCCCACTATGACTGTAGTAG
TTGTGTCAGTGGCCACGTTCATACTCCTGTCGATGGTGGGTATGGCAGCGGGGATGTGCATGTGTGCACGAC
GCAGATGCATCACACCGTATGAACTGACACCAGGAGCTACCGTCCCTTTCCTGCTTAGCCTAATATGCTGCA
TCAGAACAGCTAAAGCGGCCACATACCAAGAGGCTGCGATATACCTGTGGAACGAGCAGCAACCTTTGTTTT
GGCTACAAGCCCTTATTCCGCTGGCAGCCCTGATTGTTCTATGCAACTGTCTGAGACTCTTACCATGCTGCT
GTAAAACGTTGGCTTTTTTAGCCGTAATGAGCGTCGGTGCCCACACTGTGAGCGCGTACGAACACGTAACAG
TGATCCCGAACACGGTGGGAGTACCGTATAAGACTCTAGTCAATAGACCTGGCTACAGCCCCATGGTATTGG
AGATGGAACTACTGTCAGTCACTTTGGAGCCAACACTATCGCTTGATTACATCACGTGCGAGTACAAAACCG
TCATCCCGTCTCCGTACGTGAAGTGCTGCGGTACAGCAGAGTGCAAGGACAAAAACCTACCTGACTACAGCT
GTAAGGTCTTCACCGGCGTCTACCCATTTATGTGGGCGGCGCCTACTGCTTCTGCGACGCTGAAAACACGC
AGTTGAGCGAAGCACACGTGGAGAAGTCCGAATCATGCAAAACAGAATTTGCATCAGCATACAGGGCTCATA
CCGCATCTGCATCAGCTAAGCTCCGCGTCCTTTACCAAGGAAATAACATCACTGTAACTGCCTATGCAAACG
GCGACCATGCCGTCACAGTTAAGGACGCCAAATTCATTGTGGGCCAATGTCTTCAGCCTGGACACCTTTCG
ACAACAAAATTGTGGTGTACAAAGGTGACGTCTATAACATGGACTACCCGCCCTTTGGCGCAGGAAGACCAG
GACAATTTGGCGATATCCAAAGTCGCACACCTGAGAGTAAAGACGTCTATGCTAATACACAACTGGTACTGC
AGAGACCGGCTGTGGGTACGGTACACGTGCCATACTCTCAGGCACCATCTGGCTTTAAGTATTGGCTAAAAG
AACGCGGGGCGTCGCTGCAGCACACAGCACCATTTGGCTGCCAAATAGCAACAAACCCGGTAAGAGCGGTGA
ACTGCGCCGTAGGGAACATGCCCATCTCCATCGACATACCGGAAGCGGCCTTCACTAGGGTCGTCGACGCGC
CCTCTTTAACGGACATGTCGTGCGAGGTACCAGCCTGCACCCATTCCTCAGACTTTGGGGGCGTCGCCATTA
TTAAATATGCAGCCAGCAAGAAAGGCAAGTGTGCGGTGCATTCGATGACTAACGCCGTCACTATTCGGGAAG
CTGAGATAGAAGTTGAAGGGAATTCTCAGCTGCAAATCTCTTTCTCGACGGCCTTAGCCAGCGCCGAATTCC
GCGTACAAGTCTGTTCTACACAAGTACACTGTGCAGCCGAGTGCCACCCCCCGAAGGACCACATAGTCAACT
ACCCGGCGTCACATACCACCCTCGGGGTCCAGGACATCTCCGCTACGGCGATGTCATGGGTGCAGAAGATCA
CGGGAGGTGTGGGACTGGTTGTTGCTGTTGCCGCACTGATTCTAATCGTGGTGCTATGCGTGTCGTTCAGCA
GGCACTAACTTGACAATTAAGTATGAAGGTATATGTGTCCCCTAAGAGACACACTGTACATAGCAAATAATC
TATAGATCAAAGGGCTACGCAACCCCTGAATAGTAACAAAATACAAAATCACTAAAAATTATAAAACAGAA
AAATACATAAATAGGTATACGTGTCCCCTAAGAGACACATTGTATGTAGGTGATAAGTATAGATCAAAGGGC
```

-continued

```
CGAATAACCCCTGAATAGTAACAAAATATGAAAATCAATAAAAATCATAAAATAGAAAAACCATAAACAGAA

GTAGTTCAAAGGGCTATAAAACCCCTGAATAGTAACAAAACATAAAATTAATAAAAATCAAATGAATACCAT

AATTGGCAAACGGAAGAGATGTAGGTACTTAAGCTTCCTAAAAGCAGCCGAACTCACTTTGAGAAGTAGGCA

TAGCATACCGAACTCTTCCACGATTCTCCGAACCCACAGGGACGTAGGAGATGTTATTTTGTTTTTAATATT

TCAAAAAAAAAAAAAAAAAAAAAAAAAAAAA
```

Japanese encephalitis virus strain SA14-14-2, complete genome,
ACCESSION: KC517497

SEQ ID NO: 73

```
TTTAAACAGTTTTTTAGAACGGAAGATAACCATGACTAAAAAACCAGGAGGGCCCGGTAAAAACCGGGCTAT

CAATATGCTGAAACGCGGCCTACCCCGCGTATTCCCACTAGTGGGAGTGAAGAGGGTAGTAATGAGCTTGTTG

GACGGCAGAGGGCCAGTACGTTTCGTGCTGGCTCTTATCACGTTCTTCAAGTTTACAGCATTAGCCCCGA

CCAAGGCGCTTTTAGGCCGATGGAAAGCAGTGGAAAAGAGTGTGGCAATGAAACATCTTACTAGTTTCAA

ACGAGAACTTGGAACACTCATTGACGCCGTGAACAAGCGGGGCAGAAAGCAAAACAAAAGAGGAGGAAAT

GAAGGCTCAATCATGTGGCTCGCGAGCTTGGCAGTTGTCATAGCTTGTGCAGGAGCCATGAAGTTGTCGA

ATTTCCAGGGGAAGCTTTTGATGACCATCAACAACACGGACATTGCAGACGTTATCGTGATTCCCACCTC

AAAAGGAGAGAACAGATGCTGGGTCCGGGCAATCGACGTCGGCTACATGTGTGAGGACACTATCACGTAC

GAATGTCCTAAGCTTACCATGGGCAATGATCCAGAGGATGTGGATTGCTGGTGTGACAACCAAGAAGTCT

ACGTCCAATATGGACGGTGCACGCGGACCAGGCATTCCAAGCGAAGCAGGAGATCCGTGTCGGTCCAAAC

ACATGGGGAGAGTTCACTAGTGAATAAAAAAGAGGCTTGGCTGGATTCAACGAAAGCCACACGATATCTC

ATGAAAACTGAGAACTGGATCATAAGGAATCCTGGCTATGCTTTCCTGGCGGCGGTACTTGGCTGGATGC

TTGGCAGTAACAACGGTCAACGCGTGGTATTTACCATCCTCCTGCTGTTGGTCGCTCCGGCTTACAGTTT

TAATTGTCTGGGAATGGGCAATCGTGACTTCATAGAAGGAGCCAGTGGAGCCACTTGGGTGGACTTGGTG

CTAGAAGGAGATAGCTGCTTGACAATCATGGCAAACGACAAACCAACATTGGACGTCCGCATGATTAACA

TCGAAGCTAGCCAACTTGCTGAGGTCAGAAGTTACTGCTATCATGCTTCAGTCACTGACATCTCGACGGT

GGCTCGGTGCCCCACGACTGGAGAAGCCCACAACGAGAAGCGAGCTGATAGTAGCTATGTGTGCAAACAA

GGCTTCACTGACCGTGGGTGGGCAACGGATGTGGACTTTTCGGGAAGGGAAGCATTGACACATGTGCAA

AATTCTCCTGCACCAGTAAAGCGATTGGGAGAACAATCCAGCCAGAAAACATCAAATACGAAGTTGGCAT

TTTTGTGCATGAACCACCACTTCGGAAAACCATGGGAATTATTCAGCGCAAGTTGGGGCGTCCCAGGCG

GCAAAGTTTACAGTAACACCCAATGCTCCTTCGATAACCCTCAAACTTGGTGACTACGGAGAAGTCACAC

TGGACTGTGAGCCAAGGAGTGGACTGAACACTGAAGCGTTTTACGTCATGACCGTGGGGTCAAAGTCATT

TCTGGTCCATAGGGAGTGGTTTCATGACCTCGCTCTCCCCTGGACGTCCCCTTCGAGCACAGCGTGGAGA

AACAGAGAACTCCTCATGGAATTTGAAGGGGCGCACGCCACAAAACAGTCCGTTGTTGCTCTTGGGTCAC

AGGAAGGAGGCCTCCATCAGGCGTTGGCAGGAGCCATCGTGGTGGAGTACTCAAGCTCAGTGAAGTTAAC

ATCAGGCCACCTGAAATGTAGGCTGAAAATGGACAAACTGGCTCTGAAAGGCACAACCTATGGCATGTGT

ACAGAAAAATTCTCGTTCGCGAAAAATCCGGCGGACACTGGTCACGGAACAGTTGTCATTGAACTCTCCT

ACTCTGGGAGTGATGGCCCCTGCAAAATTCCGATTGTTTCCGTTGCGAGCCTCAATGACATGACCCCCGT

TGGGCGGCTGGTGACAGTGAACCCCTTCGTCGCGACTTCCAGTGCCAACTCAAAGGTGCTGGTCGAGATG

GAACCCCCCTTCGGAGACTCCTACATCGTAGTTGGAAGGGGAGACAAGCAGATCAACCACCATTGGCACA

AAGCTGGAAGCACGCTGGGCAAGGCCTTTTCAACAACTTTGAAGGGAGCTCAAAGACTGGCAGCGTTGGG

CGACACAGCCTGGGACTTTGGCTCTATTGGAGGGGTCTTCAACTCCATAGGAAAAGCCGTTCACCAAGTG

TTTGGTGGTGCCTTCAGAACACTCTTTGGGGGAATGTCTTGGATCACACAAGGGCTAATGGGTGCCCTAC

TGCTCTGGATGGGCGTCAACGCACGAGACCGATCAATTGCTTTGGCCTTCTTAGCCACAGGGGGTGTGCT
```

-continued

```
CGTGTTCTTAGCGACCAATGTGCATGCTGACACTGGATGTGCCATTGACATCACAAGAAAAGAGATGAGA

TGTGGAAGTGGCATCTTCGTGCACAACGACGTGGAAGCCTGGGTGGATAGGTATAAATATTTGCCAGAAA

CGCCCAGATCCCTAGCGAAGATCGTCCACAAAGCGCACAAGGAAGGCGTGTGCGGAGTCAGATCTGTCAC

TAGACTGGAGCACCAAATGTGGGAAGCCGTACGGGACGAATTGAACGTCCTGCTCAAAGAGAATGCAGTG

GACCTCAGTGTGGTTGTGAACAAGCCCGTGGGAAGATATCGCTCAGCCCCTAAACGCCTATCCATGACGC

AAGAGAAGTTTGAAATGGGCTGGAAAGCATGGGGAAAAAGCATTCTCTTTGCCCCGGAATTGGCTAACTC

CACATTTGTCGTAGATGGACCTGAGACAAAGGAATGCCCTGATGAGCACAGAGCTTGGAACAGCATGCAA

ATCGAAGACTTCGGCTTTGGCATCACATCAACCCGTGTGTGGCTGAAAATTAGAGAGGAGAGCACTGACG

AGTGTGATGGAGCGATCATAGGCACGGCTGTCAAAGGACATGTGGCAGTCCATAGTGACTTGTCGTACTG

GATTGAGAGTCGCTACAACGACACATGGAAACTTGAGAGGGCAGTCTTTGGAGAGGTCAAATCTTGCACT

TGGCCAGAGACACACACCCTTTGGGGAGATGATGTTGAGGAAAGTGAACTCATCATTCCGCACACCATAG

CCGGACCAAAAAGCAAGCACAATCGGAGGGAAGGGTATAAGACACAAAACCAGGGACCTTGGGATGAGAA

TGGCATAGTCTTGGACTTTGATTATTGCCCAGGGACAAAAGTCACCATTACAGAGGATTGTGGCAAGAGA

GGCCCTTCGGTCAGAACCACTACTGACAGTGGAAAGTTGATCACTGACTGGTGCTGTCGCAGTTGCTCCC

TTCCGCCCCTACGATTCCGGACAGAAAATGGCTGCTGGTACGGAATGGAAATCAGACCTGTTAGGCATGA

TGAAACAACACTCGTCAGATCACAGGTTGATGCTTTCAATGGTGAAATGGTTGACCCTTTTCAGCTGGGC

CTTCTGGTGATGTTTCTGGCCACCCAGGAGGTCCTTCGCAAGAGGTGGACGGCCAGATTGACCATTCCTG

CGGTTTTGGGGGCCCTACTTGTGCTGATGCTTGGGGGCATCACTTACACTGATTTGGCGAGGTATGTGGT

GCTAGTCGCTGCTGCTTTCGCAGAGGCCAACAGTGGAGGAGACGTCCTGCACCTTGCTTTGATTGCCGTT

TTTAAGATCCAACCAGCATTTCTAGTGATGAACATGCTTAGCACGAGATGGACGAACCAAGAAAACGTGG

TTCTGGTCCTAGGGGCTGCCTTTTTCCAATTGGCCTCAGTAGATCTGCAAATAGGAGTCCACGGAATCCT

GAATGCCGCCGCTATAGCATGGATGATTGTCCGAGCGATCACCTTCCCCACAACCTCCTCCGTCACCATG

CCAGTCTTAGCGCTTCTAACTCCGGGGATGAGGGCTCTATACCTAGACACTTACAGAATCATCCTCCTCG

TCATAGGGATTTGCTCCCTGCTGCACGAGAGGAAAAAGACCATGGCAAAAAGAAAGGAGCTGTACTCTT

GGGCTTAGCGCTCACATCCACTGGATGGTTCTCGCCCACCACTATAGCTGCCGGACTAATGGTCTGCAAC

CCAAACAAGAAGAGAGGGTGGCCAGCTACTGAGTTTTTGTCGGCAGTTGGATTGATGTTTGCCATCGTAG

GTGGTTTGGCCGAGTTGGATATTGAATCCATGTCAATACCCTTCATGCTGGCAGGTCTCATGGCAGTGTC

CTACGTGGTGTCAGGAAAAGCAACAGATATGTGGCTTGAACGGGCCGCCGACATCAGCTGGGAGATGGAT

GCTGCAATCACAGGAAGCAGTCGGAGGCTGGATGTGAAACTGGATGATGACGGAGATTTTCACTTGATTG

ATGATCCCGGTGTTCCATGGAAGGTCTGGGTCCTGCGCATGTCTTGCATTGGCTTAGCCGCCCTCACGCC

TTGGGCCATCGTTCCCGCCGCTTTCGGTTATTGGCTCACTTTAAAAACAACAAAAAGAGGGGCGTGTTT

TGGGACACGCCATCCCCAAAACCTTGCTCAAAAGGAGACACCACTACAGGAGTCTACCGAATTATGGCTA

GAGGGATTCTTGGCACTTACCAGGCCGGCGTCGGAGTCATGTACGAGAATGTTTTCCACACACTATGGCA

CACAACTAGAGGAGCAGCCATTATGAGTGGAGAAGGAAAATTGACGCCATACTGGGGTAGTGTGAGAGAA

GACCGCATAGCTTACGGAGGCCCATGGAGGTTTGACCGAAATGGAATGGAACAGATGACGTGCAAGTGA

TCGTGGTAGAACCGGGGAAGGCTGCAGTAAACATCCAGACAAAACCAGGAGTGTTTCGGACTCCCTTCGG

GGAGGTTGGGGCTGTTAGTCTGGATTACCCGCGAGGAACATCCGGCTCACCCATTCTGGATTCCAATGGA

GACATTATAGGCCTATACGGCAATGGAGTTGAGCTTGGCGATGGCTCATACGTCAGCGCCATCGTGCAGG

GTGACCGTCAGGAGGAACCAGTCCCAGAAGCTTACACCCCAAACATGTTGAGAAAGAGACAGATGACTGT

GCTAGATTTGCACCCTGGTTCAGGGAAAACCAGGAAAATTCTGCCACAAATAATTAAGGACGCTATCCAG
```

-continued

```
CAGCGCCTAAGAACAGCTGTGTTGGCACCGACGCGGGTGGTAGCAGCAGAAATGGCAGAAGCTTTGAGAG

GGCTCCCAGTACGATATCAAACTTCAGCAGTGCAGAGAGAGCACCAAGGGAATGAAATAGTGGATGTGAT

GTGCCACGCCACTCTGACCCATAGACTGATGTCACCGAACAGAGTGCCCAACTACAACCTATTTGTCATG

GATGAAGCTCATTTCACCGACCCAGCCAGTATAGCCGCACGAGGATACATTGCTACCAAGGTGGAATTAG

GGGAGGCAGCAGCCATCTTTATGACAGCGACCCCGCCTGGAACCACGGATCCTTTTCCTGACTCAAATGC

CCCAATCCATGATTTGCAAGATGAGATACCAGACAGGGCATGGAGCAGTGGATACGAATGGATCACAGAA

TATGCGGGTAAAACCGTGTGGTTTGTGGCGAGCGTAAAAATGGGGAATGAGATTGCAATGTGCCTCCAAA

GAGCGGGGAAAAAGGTCATCCAACTCAACCGCAAGTCCTATGACACAGAATACCCAAAATGTAAGAATGG

AGACTGGGATTTTGTCATTACCACCGACATCTCTGAAATGGGGGCCAACTTCGGTGCGAGCAGGGTCATC

GACTGTAGAAAGAGCGTGAAACCCACCATCTTAGAAGAGGGAGAAGGCAGAGTCATCCTCGGAAACCCAT

CTCCCATAACCAGTGCAAGCGCAGCTCAACGGAGGGGCAGAGTAGGCAGAAACCCCAACCAAGTTGGAGA

TGAATACCACTATGGGGGGCTACCAGTGAAGATGACAGTAACCTAGCCCATTGGACAGAGGCAAAGATC

ATGTTAGACAACATACACATGCCCAATGGACTGGTGGCCCAGCTCTATGGACCAGAGAGGGAAAAGGCTT

TCACAATGGATGGCGAATACCGTCTCAGAGGTGAAGAAAAGAAAAACTTCTTAGAGCTGCTTAGGACGGC

TGACCTCCCGGTGTGGCTGGCCTACAAGGTGGCGTCCAATGGCATTCAGTACACCGACAGAAAGTGGTGT

TTTGATGGGCCGCGTACGAATGCCATACTGGAGGACAACACCGAGGTAGAGATAGTCACCCGGATGGGTG

AGAGGAAAATCCTCAAGCCGAGATGGCTTGATGCAAGAGTTTATGCAGATCACCAAGCCCTCAAGTGGTT

CAAAGACTTTGCAGCAGGGAAGAGATCAGCCGTTAGCTTCATAGAGGTGCTCGGTCGCATGCCTGAGCAT

TTCATGGGAAAGACGCGGGAAGCTTTAGACACCATGTACTTGGTTGCAACGGCTGAGAAAGGTGGGAAAG

CACACCGAATGGCTCTCGAAGAGCTGCCAGATGCACTGGAAACCATCACACTTATTGTCGCCATTACTGT

GATGACAGGAGGATTCTTCCTACTAATGATGCAGCGAAAGGGTATAGGGAAGATGGGTCTTGGAGCTCTA

GTGCTCACGCTAGCTACCTTCTTCCTGTGGGCGGCAGAGGTTCCTGGAACCAAAATAGCAGGGACCCTGC

TGATCGCCCTGCTGCTGATGGTGGTTCTCATCCCAGAACCGGAAAAACAGAGGTCACAGACAGATAACCA

ACTGGCGGTGTTTCTCATCTGTGTCTTGACCGTGGTTGGAGTGGTGGCAGCAAACGAGTACGGGATGCTA

GAAAAAACCAAAGCAGATCTCAAGAGCATGTTTGGCGGAAAGACGCAGGCATCAGGACTGACTGGATTGC

CAAGCATGGCACTGGACCTGCGTCCAGCCACAGCCTGGGCACTGTATGGGGGAGCACAGTCGTGCTAAC

CCCTCTTCTGAAGCACCTGATCACGTCGGAATACGTCACCACATCGCTAGCCTCAATTAACTCACAAGCT

GGCTCATTATTCGTCTTGCCACGAGGCGTGCCTTTTACCGACCTAGACTTGACCGTTGGCCTCGTCTTCC

TTGGCTGTTGGGGTCAAATCACCCTCACAACGTTTCTGACAGCCATGGTTCTGGCGACACTTCACTATGG

GTACATGCTCCCTGGATGGCAAGCAGAAGCACTCAGGGCTGCCCAGAGAAGGACAGCGGCTGGAATAATG

AAGAATGCCGTTGTTGACGGAATGGTCGCCACTGATGTGCCTGAACTGGAAAGGACTACTCCTCTGATGC

AAAAGAAAGTCGGACAGGTGCTCCTCATAGGGGTAAGCGTGGCAGCGTTCCTCGTCAACCCTAATGTCAC

CACTGTGAGAGAAGCAGGGGTGTTGGTGACGGCGGCTACGCTTACTTTGTGGGACAATGGAGCCAGTGCC

GTTTGGAATTCCACCACAGCCACGGGACTCTGCCATGTCATGCGAGGTAGCTACCTGGCTGGAGGCTCCA

TTGCTTGGACTCTCATCAAGAACGCTGATAAGCCCTCCTTGAAAAGGGGAAGGCCTGGGGGCAGGACGCT

AGGGGAGCAGTGGAAGGAAAAACTAAATGCCATGAGCAGAGAAGAGTTTTTTAAATACCGGAGAGAGGCC

ATAATCGAGGTGGACCGCACTGAAGCACGCAGGGCCAGACGTGAAAATAACATAGTGGGAGGACATCCGG

TTTCGCGAGGCTCAGCAAAACTCCGTTGGCTCGTGGAGAAAGGATTTGTCTCGCCAATAGGAAAAGTCAT

TGATCTAGGGTGTGGGCGTGGAGGATGGAGCTACTACGCAGCAACCCTGAAGAAGGTCCAGGAAGTCAGA

GGATACACGAAAGGTGGGCGGACATGAAGAACCGATGCTCATGCAGAGCTACGGCTGGAACCTGGTCT

CCCTGAAGAGTGGAGTGGACGTGTTTTACAAACCTTCAGAGCCCAGTGACACCCTGTTCTGTGACATAGG
```

-continued

```
GGAATCCTCCCCAAGTCCAGAAGTAGAAGAACAACGCACACTACGCGTCCTAGAGATGACATCTGACTGG

TTGCACCGAGGACCTAGAGAGTTCTGCATTAAAGTTCTCTGCCCTTACATGCCCAAGGTTATAGAAAAAA

TGGAAGTTCTGCAGCGCCGCTTCGGAGGTGGGCTAGTGCGTCTCCCCCTGTCCCGAAACTCCAATCACGA

GATGTAT

TGGGTTAGTGGAGCCGCTGGCAATGTGGTGCACGCTGTGAACATGACCAGCCAGGTACTACTGGGGCGAA

TGGATCGCACAGTGTGGAGAGGGCCAAAGTATGAGGAAGATGTCAACCTAGGGAGCGGAACAAGAGCCGT

GGGAAAGGGAGAAGTCCATAGCAATCAGGAGAAAATCAAGAAGAGAATCCAGAAGCTTAAAGAAGAATTC

GCCACAACGTGGCACAAAGACCCTGAGCATCCATACCGCACTTGGACATACCACGGAAGCTATGAAGTGA

AGGCTACTGGCTCAGCCAGCTCTCTCGTCAACGGAGTGGTGAAGCTCATGAGCAAACCTTGGGACGCCAT

TGCCAACGTCACCACCATGGCCATGACTGACACCACCCCTTTTGGACAGCAAAGAGTTTTCAAGGAGAAA

GTTGACACGAAGGCTCCTGAGCCACCAGCTGGAGCCAAGGAAGTGCTCAACGAGACCACCAACTGGCTGT

GGGCCCACTTGTCACGGGAAAAAGACCCCGCTTGTGCACCAAGGAAGAATTCATAAAGAAAGTCAACAG

CAACGCGGCTCTTGGAGCAGTGTTCGCTGAACAGAATCAATGGAGCACGGCGCGTGAGGCTGTGGATGAC

CCGCGGTTTTGGGAGATGGTTGATGAAGAGAGGGAAAACCATCTGCGAGGAGAGTGTCACACATGTATCT

ACAACATGATGGGAAAAAGAGAGAAGAAGCCTGGAGAGTTTGGAAAAGCTAAAGGAAGCAGGGCCATTTG

GTTCATGTGGCTTGGAGCACGGTATCTAGAGTTTGAAGCTTTGGGGTTCCTGAATGAAGACCATTGGCTG

AGCCGAGAGAATTCAGGAGGTGGAGTGGAAGGCTCAGGCGTCCAAAAGCTGGATACATCCTCCGTGACA

TAGCAGGAAAGCAAGGAGGGAAAATGTACGCTGATGATACCGCCGGGTGGGACACTAGAATTACCAGAAC

TGATTTAGAAAATGAAGCTAAGGTACTGGAGCTCCTAGACGGTGAACACCGCATGCTCGCCCGAGCCATA

ATTGAACTGACTTACAGGCACAAAGTGGTCAAGGTCATGAGACCTGCAGCAGAAGGAAAGACCGTGATGG

ACGTGATATCAAGAGAAGATCAAAGGGGAGTGGACAGGTGGTCACTTATGCTCTTAACACTTTCACGAA

CATCGCTGTCCAGCTCGTCAGGCTGATGGAGGCTGAGGGGGTCATTGGACCACAACACTTGGAACAGCTA

CCTAGGAAAAACAAGATAGCTGTCAGGACCTGGCTCTTTGAGAATGGAGAGGAGAGAGTGACCAGGATGG

CGATCAGCGGAGACGACTGTGTCGTCAAGCCGCTGGACGACAGATTCGCCACAGCCCTCCACTTCCTCAA

CGCAATGTCAAAGGTCAGAAAAGACATCCAGGAATGGAAGCCTTCGCATGGCTGGCACGATTGGCAGCAA

GTTCCCTTCTGCTCTAACCATTTTCAGGAGATTGTGATGAAAGATGGAAGGAGTATAGTTGTCCCGTGCA

GAGGACAGGATGAGCTGATAGGCAGGGCTCGCATCTCTCCAGGAGCTGGATGGAATGTGAAGGACACAGC

TTGCCTGGCCAAAGCATATGCACAGATGTGGCTACTCCTATACTTCCATCGCAGGGACTTGCGTCTCATG

GCAAATGCGATTTGCTCAGCAGTGCCAGTGGATTGGGTGCCCACAGGCAGGACATCCTGGTCAATACACT

CGAAAGGAGAGTGGATGACCACGGAAGACATGCTGCAGGTCTGGAACAGAGTCTGGATTGAAGAAAATGA

ATGGATGATGGACAAGACTCCAATCACAAGCTGGACAGACGTTCCGTATGTGGGAAAGCGTGAGGACATC

TGGTGTGGCAGCCTCATCGGAACGCGATCCAGAGCAACCTGGGCTGAGAACATCTATGCGGCGATAAACC

AGGTTAGAGCTGTCATTGGGAAAGAAAATTATGTTGACTACATGACCTCACTCAGGAGATACGAAGACGT

CTTGATCCAGGAAGACAGGGTCATCTAGTGTGATTTAAGGTAGAAAAGTAGACTATGTAAATAATGTAAA

TGAGAAAATGCATGCATATGGAGTCAGGCCAGCAAAAGCTGCCACCGGATACTGGGTAGACGGTGCTGCC

TGCGTCTCAGTCCCAGGAGGACTGGGTTAACAAATCTGACAACAGAAAGTGAGAAAGCCCTCAGAACCGT

CTCGGAAGTAGGTCCCTGCTCACTGGAAGTTGAAAGACCAACGTCAGGCCACAAATTTGTGCCACTCCGC

TAGGGAGTGCGGCCTGCGCAGCCCCAGGAGGACTGGGTTACCAAAGCCGTTGAGGCCCCCACGGCCCAAG

CCTCGTCTAGGATGCAATAGACGAGGTGTAAGGACTAGAGGTTAGAGGAGACCCCGTGGAAACAACAACA
```

-continued

```
TGCGGCCCAAGCCCCCTCGAAGCTGTAGAGGAGGTGGAAGGACTAGAGGTTAGAGGAGACCCCGCATTTG

CATCAAACAGCATATTGACACCTGGGAATAGACTGGGAGATCTTCTGCTCTATCTCAACATCAGCTACTA

G
```

Japanese encephalitis virus strain SA14-14-2, complete genome,
ACCESSION: JN604986
SEQ ID NO: 74

```
AGAAGTTTATCTGTGTGAACTTCTTGGCTTAGTATCGTAGAGAAGAATCGAGAGATTAGTGCAGTTTAAA

CAGTTTTTTAGAACGGAAGATAACCATGACTAAAAAACCAGGAGGGCCCGGTAAAAACCGGGCTATCAAT

ATGCTGAAACGCGGCCTACCCCGCGTATTCCCACTAGTGGGAGTGAAGAGGGTAGTAATGAGCTTGTTGG

ACGGCAGAGGGCCAGTACGTTTCGTGCTGGCTCTTATCACGTTCTTCAAGTTTACAGCATTAGCCCCGAC

CAAGGCGCTTTCAGGCCGATGGAAAGCAGTGGAAAAGAGTGTGGCAATGAAACATCTTACTAGTTTCAAA

CGAGAACTTGGAACACTCATTGACGCCGTGAACAAGCGGGGCAGAAAGCAAAACAAAAGAGGAGGAAATG

AAGGCTCAATCATGTGGCTCGCGAGCTTGGCAGTTGTCATAGCTTGTGCAGGAGCCATGAAGTTGTCGAA

TTTCCAGGGGAAGCTTTTGATGACCATCAACAACACGGACATTGCAGACGTTATCGTGATTCCCACCTCA

AAAGGAGAGAACAGATGCTGGGTCCGGGCAATCGACGTCGGCTACATGTGTGAGGACACTATCACGTACG

AATGTCCTAAGCTTACCATGGGCAATGATCCAGAGGATGTGGATTGCTGGTGTGACAACCAAGAAGTCTA

CGTCCAATATGGACGGTGCACGCGGACCAGGCATTCCAAGCGAAGCAGGAGATCCGTGTCGGTCCAAACA

CATGGGAGAGTTCACTAGTGAATAAAAAAGAGGCTTGGCTGGATTCAACGAAAGCCACACGATATCTCA

TGAAAACTGAGAACTGGATCATAAGGAATCCTGGCTATGCTTTCCTGGCGGCGGTACTTGGCTGGATGCT

TGGCAGTAACAACGGTCAACGCGTGGTATTTACCATCCTCCTGCTGTTGGTCGCTCCGGCTTACAGTTTT

AATTGTCTGGGAATGGGCAATCGTGACTTCATAGAAGGAGCCAGTGGAGCCACTTGGGTGGACTTGGTGC

TAGAAGGAGACAGCTGCTTGACAATCATGGCAAACGACAAACCAACATTGGACGTCCGCATGATTAACAT

CGAAGCTAGCCAACTTGCTGAGGTCAGAAGTTACTGCTATCATGCTTCAGTCACTGACATCTCGACGGTG

GCTCGGTGCCCCACGACTGGAGAAGCCCACAACGAGAAGCGAGCTGATAGTAGCTATGTGTGCAAACAAG

GCTTCACTGACCGTGGGTGGGGCAACGGATGTGGATTTTTCGGGAAGGGAAGCATTGACACATGTGCAAA

ATTCTCCTGCACCAGTAAAGCGATTGGGAGAACAATCCAGCCAGAAAACATCAAATACAAAGTTGGCATT

TTTGTGCATGGAACCACCACTTCGGAAAACCATGGGAATTATTCAGCGCAAGTTGGGGCGTCCCAGGCGG

CAAAGTTTACAGTAACACCCAATGCTCCTTCGGTAGCCCTCAAACTTGGTGACTACGGAGAAGTCACACT

GGACTGTGAGCCAAGGAGTGGACTGAACACTGAAGCGTTTTACGTCATGACCGTGGGGTCAAAGTCATTT

CTGGTCCATAGGGAGTGGTTTCATGACCTCGCTCTCCCCTGGACGTCCCCTTCGAGCACAGCGTGGAGAA

ACAGAGAACTCCTCATGGAATTTGAAGGGGCGCACGCCACAAAACAGTCCGTTGTTGCTCTTGGGTCACA

GGAAGGAGGCCTCCATCATGCGTTGGCAGGAGCCATCGTGGTGGAGTACTCAAGCTCAGTGATGTTAACA

TCAGGCCACCTGAAATGTAGGCTGAAAATGGACAAACTGGCTCTGAAAGGCACAACCTATGGCATGTGTA

CAGAAAAATTCTCGTTCGCGAAAAATCCGGTGGACACTGGTCACGGAACAGTTGTCATTGAACTCTCCTA

CTCTGGGAGTGATGGCCCCTGCAAAATTCCGATTGTTTCCGTTGCGAGCCTCAATGACATGACCCCCGTT

GGGCGGCTGGTGACAGTGAACCCCTTCGTCGCGACTTCCAGTGCCAACTCAAAGGTGCTGGTCGAGATGG

AACCCCCCTTCGGAGACTCCTACATCGTAGTTGGAAGGGGAGACAAGCAGATCAACCACCATTGGCACAA

AGCTGGAAGCACGCTGGGCAAGGCCTTTTCAACAACTTTGAAGGGAGCTCAAAGACTGGCAGCGTTGGGC

GACACAGCCTGGGACTTTGGCTCTATTGGAGGGGTCTTCAACTCCATAGGAAGAGCCGTTCACCAAGTGT

TTGGTGGTGCCTTCAGAACACTCTTTGGGGGAATGTCTTGGATCACACAAGGGCTAATGGGTGCCCTACT

GCTCTGGATGGGCGTCAACGCACGAGACCGATCAATTGCTTTGGCCTTCTTAGCCACAGGAGGTGTGCTC

GTGTTCTTAGCGACCAATGTGCATGCTGACACTGGATGTGCCATTGACATCACAAGAAAAGAGATGAGAT
```

-continued

```
GTGGAAGTGGCATCTTCGTGCACAACGACGTGGAAGCCTGGGTGGATAGGTATAAATATTTGCCAGAAAC

GCCCAGATCCCTAGCGAAGATCGTCCACAAAGCGCACAAGGAAGGCGTGTGCGGAGTCAGATCTGTCACT

AGACTGGAGCACCAAATGTGGGAAGCCGTAAGGGACGAATTGAACGTCCTGCTCAAAGAGAATGCAGTGG

ACCTCAGTGTGGTTGTGAACAAGCCCGTGGGAAGATATCGCTCAGCCCCTAAACGCCTATCCATGACGCA

AGAGAAGTTTGAAATGGGCTGGAAAGCATGGGGAAAAAGCATCCTCTTTGCCCCGGAATTGGCTAACTCC

ACATTTGTCGTAGATGGACCTGAGACAAAGGAATGCCCTGATGAGCACAGAGCTTGGAACAGCATGCAAA

TCGAAGACTTCGGCTTTGGCATCACATCAACCCGTGTGTGGCTGAAAATTAGAGAGGAGAGCACTGACGA

GTGTGATGGAGCGATCATAGGCACGGCTGTCAAAGGACATGTGGCAGTCCATAGTGACTTGTCGTACTGG

ATTGAGAGTCGCTACAACGACACATGGAAACTTGAGAGGGCAGTCTTTGGAGAGGTCAAATCTTGCACTT

GGCCAGAGACACACACCCTTTGGGGAGATGATGTTGAGGAAAGTGAACTCATCATTCCGCACACCATAGC

CGGACCAAAAAGCAAGCACAATCGGAGGGAAGGGTATAAGACACAAAACCAGGGACCTTGGGATGAGAAT

GGCATAGTCTTGGACTTTGATTATTGCCCAGGGACAAAAGTCACCATTACAGAGGATTGTAGCAAGAGAG

GCCCTTCGGTCAGAACCACTACTGACAGTGGAAAGTTGATCACTGACTGGTGCTGTCGCAGTTGCTCCCT

TCCGCCCCTACGATTCCGGACAGAAAATGGCTGCTGGTACGGAATGGAAATCAGACCTGTTATGCATGAT

GAAACAACACTCGTCAGATCACAGGTTCATGCTTTCAAAGGTGAAATGGTTGACCCTTTTCAGCTGGGCC

TTCTGGTGATGTTTCTGGCCACCCAGGAAGTCCTTCGCAAGAGGTGGACGGCCAGATTGACCATTCCTGC

GGTTTTGGGGGTCCTACTTGTGCTGATGCTTGGGGGTATCACTTACACTGATTTGGCGAGGTATGTGGTG

CTAGTCGCTGCTGCTTTCGCAGAGGCCAACAGTGGAGGAGACGTCCTGCACCTTGCTTTGATTGCTGTTT

TTAAGATCCAACCAGCATTTTTAGTGATGAACATGCTTAGCACGAGATGGACGAACCAAGAAAACGTGGT

TCTGGTCCTAGGGGCTGCCTTTTTCCAATTGGCCTCAGTAGATCTGCAAATAGGAGTCCACGGAATCCTG

AATGCCGCCGCTATAGCATGGATGATTGTCCGAGCGATCACCTTCCCCACAACCTCCTCCGTCACCATGC

CAGTCTTAGCGCTTCTAACTCCGGGGATGAGGGCTCTATACCTAGACACTTACAGAATCATCCTCCTCGT

CATAGGGATTTGCTCCCTGCTGCACGAGAGGAAAAAGACCATGGCGAAAAAGAAAGGAGCTGTACTCTTG

GGCTTAGCGCTCACATCCACTGGATGGTTCTCGCCCACCACTATAGCTGCCGGACTAATGGTCTGCAACC

CAAACAAGAAGAGAGGGTGGCCAGCTACTGAGTTTTTGTCGGCAGTTGGATTGATGTTTGCCATCGTAGG

TGGTTTGGCCGAGTTGGATATTGAATCCATGTCAATACCCTTCATGCTGGCAGGTCTCATGGCAGTGTCC

TACGTGGTGTCAGGAAAAGCAACAGATATGTGGCTTGAACGGGCCGCCGACATCAGCTGGGATATGGGTG

CTGCAATCACAGGAAGCAGTCGGAGGCTGGATGTGAAACTGGATGATGACGGAGATTTTCACTTGATTGA

TGATCCCGGTGTTCCATGGAAGGTCTGGGTCCTGCGCATGTCTTGCATTGGCTTAGCCGCCCTCACGCCT

TGGGCCATCGTTCCCGCCGCTTTCGGTTATTGGCTCACTTTAAAAACAACAAAAAGAGGGGCGTGTTTT

GGGACACGCCATCCCCAAAACCTTGCTCAAAAGGAGACACCACTACAGGAGTCTACCGAATTATGGCTAG

AGGGATTCTTGGCACTTACCAGGCCGGCGTCGGAGTCATGTACGAGAATGTTTTCCACACACTATGGCAC

ACAACTAGAGGAGCAGCCATTGTGAGTGGAGAAGGAAAATTGACGCCATACTGGGGTAGTGTGAAAGAAG

ACCGCATAGCTTACGGAGGCCCATGGAGGTTTGACCGAAAATGGAATGGAACAGATGACGTGCAAGTGAT

CGTGGTAGAACCGGGGAAGGGCGCAGTAAACATCCAGACAAAACCAGGAGTGTTTCGGACTCCCTTCGGG

GAGGTTGGGGCTGTTAGTCTGGATTACCCGCGAGGAACATCCGGCTCACCCATTCTGGATTCCAATGGAG

ACATTATAGGCCTATACGGCAATGGAGTTGAGCTTGGCGATGGCTCATACGTCAGCGCCATCGTGCAGGG

TGACCGTCAGGAGGAACCAGTCCCAGAAGCTTACACCCCAAACATGTTGAGAAAGAGACAGATGACTGTG

CTAGATTTGCACCCTGGTTCAGGGAAAACCAGGAAAATTCTGCCACAAATAATTAAGGACGCTATCCAGC

AGCGCCTAAGAACAGCTGTGTTGGCACCGACGCGGGTGGTAGCAGCAGAAATGGCAGAAGCTTTGAGAGG
```

-continued

```
GCTCCCAGTACGATATCAAACTTCAGCAGTGCAGAGAGAGCACCAAGGGAATGAAATAGTGGATGTGATG

TGCCACGCCACTCTGACCCATAGACTGATGTCACCGAACAGAGTGCCCAACTACAACCTATTTGTCATGG

ATGAAGCTCATTTCACCGACCCAGCCAGTATAGCCGCACGAGGATACATTGCTACCAAGGTGGAATTAGG

GGAGGCAGCAGCCATCTTTATGACAGCGACCCCGCCTGGAACCACGGATCCTTTTCCTGACTCAAATGCC

CCAATCCATGATTTGCAAGATGAGATACCAGACAGGGCATGGAGCAGTGGATACGAATGGATCACAGAAT

ATGCGGGTAAAACCGTGTGGTTTGTGGCGAGCGTAAAAATGGGGAATGAGATTGCAATGTGCCTCCAAAG

AGCGGGGAAAAAGGTCATCCAACTCAACCGCAAGTCCTATGACACAGAATACCCAAAATGTAAGAATGGA

GACTGGGATTTTGTCATTACCACCGACATCTCTGAAATGGGGGCCAACTTCGGTGCGAGCAGGGTCATCG

ACTGTAGAAAGAGCGTGAAACCCACCATCTTAGAAGAGGGAGAAGGCAGAGTCATCCTCGGAAACCCATC

TCCCATAACCAGTGCAAGCGCAGCTCAACGGAGGGGCAGAGTAGGCAGAAACCCCAATCAAGTTGGAGAT

GAATACCACTATGGGGGGGCTACCAGTGAAGATGACAGTAACCTAGCCCATTGGACAGAGGCAAAGATCA

TGTTAGACAACATACACATGCCCAATGGACTGGTGGCCCAGCTCTATGGACCAGAGAGGGAAAAGGCTTT

CACAATGGATGGCGAATACCGTCTCAGAGGTGAAGAAAGAAAAACTTCTTAGAGCTGCTTAGGACGGCT

GACCTCCCGGTGTGGCTGGCCTACAAGGTGGCGTCCAATGGCATTCAGTACACCGACAGAAAGTGGTGTT

TTGATGGGCCGCGTACGAATGCCATACTGGAGGACAACACCGAGGTAGAGATAGTCACCCGGATGGGTGA

GAGGAAAATCCTCAAGCCGAGATGGCTTGATGCAAGAGTTTATGCAGATCACCAGGCCCTCAAGTGGTTC

AAAGACTTTGCAGCAGGGAAGAGATCAGCCGTTAGCTTCATAGAGGTGCTCGGTCGCATGCCTGAGCATT

TCATGGGAAAGACGCGGGAAGCTTTAGACACCATGTACTTGGTTGCAACGGCTGAGAAAGGTGGGAAAGC

ACACCGAATGGCTCTCGAAGAGCTGCCAGATGCACTGGAAACCATCACACTTATTGTCGCCATTACTGTG

ATGACAGGAGGATTCTTCCTACTAATGATGCAGCGAAAGGGTATAGGGAAGATGGGTCTTGGAGCTCTAG

TGCTCACACTAGCTACCTTCTTCCTGTGGGCGGCAGAGGTTCCTGGAACCAAAATAGCAGGGACCCTGCT

GATCGCCCTGCTGCTGATGGTGGTTCTCATCCCAGAACCGGAAAAACAGAGGTCACAGACAGATAACCAA

CTGGCGGTGTTTCTCATCTGTGTCTTGACCGTGGTTGGAGTGGTGGCAGCAAACGAGTACGGGATGCTAG

AAAAAACCAAAGCGGATCTCAAGAGCATGTTTGGCGGAAAGACGCAGGCATCAGGACTGACTGGATTGCC

AAGCATGGCACTGGACCTGCGTCCAGCCACAGCCTGGGCACTGTATGGGGGGAGCACAGTCGTGCTAACC

CCTCTTCTGAAGCACCTGATCACGTCGGAATACGTCACCACATCGCTAGCTTCAATTAACTCACAAGCTG

GCTCATTATTCGTCTTGCCACGAGGCGTGCCTTTTACCGACCTAGACTTGACTGTTGGCCTCGTCTTCCT

TGGCTGTTGGGGTCAAGTCACCCTCACAACGTTTCTGACAGCCATGGTTCJGGCGACACTTCACTATGGG

TACATGCTCCCTGGATGGCAAGCAGAAGCACTCAGGGCTGCCCAGAGAAGGACAGCGGCTGGAATAATGA

AGAATGCCGTTGTTGACGGAATGGTCGCCACTGATGTGCCTGAACTGGAAAGGACTACTCCTCTGATGCA

AAAGAAAGTCGGACAGGTGCTCCTCATAGGGGTAAGCGTGGCAGCGTTCCTCGTCAACCCTAATGTCACC

ACTGTGAGAGAAGCAGGGGTGTTGGTGACGGCGGCTACGCTTACTTTGTGGGACAATGGAGCCAGTGCCG

TTTGGAATTCCACCACAGCCACGGGACTCTGCCATGTCATGCGAGGTAGCTACCTGGCTGGAGGCTCCAT

TGCTTGGACTCTCATCAAGAACGCTGATAAGCCCTCCTTGAAAAGGGGAAGGCCTGGGGGCAGGACGCTA

GGGGAGCAGTGGAAGGAAAAACTAAATGCCATGAGTAGAGAAGAGTTTTTTAAATACCGGAGAGAGGCCA

TAATCGAGGTGGACCGCACTGAAGCACGCAGGGCCAGACGTGAAAATAACATAGTGGGAGGACATCCGGT

TTCGCGAGGCTCAGCAAAACTCCGTTGGCTCGTGGAGAAAGGATTTGTCTCGCCAATAGGAAAAGTCATT

GATCTAGGGTGTGGGCGTGGAGGATGGAGCTACTACGCAGCAACCCTGAAGAAGGTCCAGGAAGTCAGAG

GATACACGAAAGGTGGGCGGGACATGAAGAACCGATGCTCATGCAGAGCTACGGCTGGAACCTGGTCTC

CCTGAAGAGTGGAGTGGACGTGTTTTACAAACCTTCAGAGCCCAGTGATACCCTGTTCTGTGACATAGGG

GAATCCTCCCCAAGTCCAGAAGTAGAAGAACAACGCACACTACGCGTCCTAGAGATGACATCTGACTGGT
```

-continued

```
TGCACCGAGGACCTAGAGAGTTCTGCATTAAAGTTCTCTGCCCTTACATGCCCAAGGTTATAGAAAAAAT

GGAAGTTCTGCAGCGTCGCTTCGGAGGTGGGCTAGTGCGTCTCCCCCTGTCCCGAAACTCCAATCACGAG

ATGTATTGGGTTAGTGGACCCGCTGGCAATGTGGTGCACGCTGTGAACATGACCAGCCAGGTATTACTGG

GGCGAATGGATCGCACAGTGTGGAGAGGGCCAAAGTATGAGGAAGATGTCAACCTAGGGAGCGGAACAAG

AGCCGTGGGAAAGGGAGAAGTCCATAGCAATCAGGAGAAAATCAAGAAGAGAATCCAGAAGCTTAAAGAA

GAATTCGCCACAACGTGGCACAAAGACCCTGAGCATCCATACCGCACTTGGACATACCACGGAAGCTATG

AAGTGAAGGCTACTGGCTCAGCCAGCTCTCTCGTCAACGGAGTGGTGAAGCTCATGAGCAAACCTTGGGA

CGCCATTGCCAACGTCACCACCATGGGCCATGACTGACACCACCCCTTTTGGACAGCAAAGAGTTTTCAAG

GAGAAAGTTGACACGAAGGCTCCTGAGCCACCAGCTGGAGCCAAGGAAGTGCTCAACGAGACCACCAACT

GGCTGTGGGCCTACTTGTCACGGGAAAAAAGACCCCGCTTGTGCACCAAGGAAGAATTCATTAAGAAAGT

TAACAGCAACGCGGCTCTTGGAGCAGTGTTCGCTGAACAGAATCAATGGAGCACGGCGCGTGAGGCTGTG

GATGACCCGCGGTTTTGGGAGATGGTTGATGAAGAGAGGGAAAACCATCTGCGAGGAGAGTGTCACACAT

GTATCTACAACATGATGGGAAAAGAGAGAAGAAGCCTGGAGAGTTTGGAAAAGCTAAAGGAAGCAGGGC

CATTTGGTTCATGTGGCTTGGAGCACGGTATCTAGAGTTTGAAGCTTTGGGGTTCCTGAATGAAGACCAT

TGGCTGAGCCGAGAGAATTCAGGAGGTGGAGTGGAAGGCTCAGGCGTCCAAAAGCTGGGATACATCCTCC

GTGACATAGCAGGAAAGCAAGGAGGGAAAATGTACGCTGATGATACCGCCGGGTGGGACACTAGAATTAC

CAGAACTGATTTAGAAAATGAAGCTAAGGTACTGGAGCTCCTAGACGGTGAACACCGCATGCTCGCCCGA

GCCATAATTGAACTGACTTACAGGCACAAAGTGGTCAAGGTCATGAGACCTGCAGCAGAAGGAAAGACCG

TGATGGACGTGATATCAAGAGAAGATCAAAGGGGGAGTGGACAGGTGGTCACTTATGCTCTTAACACTTT

CACGAACATCGCTGTCCAGCTCGTCAGGCTGATGGAGGCTGAGGGGGTCATTGGACCACAACACTTGGAA

CATCTACCTAGGAAAAACAAGATAGCTGTCAGGACCTGGCTCTTTGAGAATGGAGAGGAGAGAGTGACCA

GGATGGCGATCAGCGGAGACGACTGTGCCGTCAAACCGCTGGACGACAGATTCGCCACAGCCCTCCACTT

CCTCAACGCAATGTCAAAGGTCAGAAAAGACATCCAGGAATGGAAGCCTTCGCATGGCTGGCACGATTGG

CAGCAAGTTCCCTTCTGTTCTAACCATTTTCAGGAGATTGTGATGAAAGATGGAAGGAGTATAGTTGTCC

CGTGCAGAGGACAGGATGAGCTGATAGGCAGGGCTCGCATCTCTCCTGGAGCTGGATGGAATGTGAAGGA

CACAGCTTGCCTGGCCAAAGCATATGCACAGATGTGGCTACTCCTATACTTCCATCGCAGGGACTTGCGT

CTCATGGCAAATGCGATTTGCTCAGCAGTGCCAGTAGATTGGGTGCCCACAGGCAGGACATCCTGGTCAA

TACACTCGAAAGGAGAGTGGATGACCACGGAAGACATGCTGCAGGTCTGGAACAGAGTTTGGATTGAAGA

AAATGAATGGATGATGGACAAGACTCCAATCACAAGCTGGACAGACGTTCCGTATGTGGGAAAGCGCGAG

GACATCTGGTGTGGCAGCCTCATCGGAACGCGATCCAGAGCAACCTGGGCTGAGAACATCTATGCGGCGA

TAAACCAGGTTAGAGCTGTCATTGGGAAAGAAAATTATGTTGACTACATGACCTCACTCAGGAGATACGA

AGACGTCTTGATCCAGGAAGACAGGGTCATCTAGTGTGATTTAAGGTAGAAAAGTAGACTATGTAAACAA

TGTAAATGAGAAAATGCATGCATATGGAGTCAGGCCAGCAAAAGCTGCCACCGGATACTGGGTAGACGGT

GCTGCCTGCGTCTCAGTCCCAGGAGGACTGGGTTAACAAATCTGACAACAGAAAGTGAGAAAGCCCTCAG

AACCGTCTCGGAAGTAGGTCCCTGCTCACTGGAAGTTGAAAGACCAACGTCAGGCCACAAATTTGTGCCA

CTCCGCTAGGGAGTGCGGCCTGCGCAGCCCCAGGAGGACTGGGTTACCAAAGCCGTTGAGGCCCCCACGG

CCCAAGCCTCGTCTAGGATGCAATAGACGAGGTGTAAGGACTAGAGGTTAGAGGAGACCCCGTGGAAACA

ACAACATGCGGCCCAAGCCCCCTCGAAGCTGTAGAGGAGGTGGAAGGACTAGAGGTTAGAGGAGACCCCG

CATTTGCATCAAACAGCATATTGACACCTGGGAATAGACTGGGAGATCTTCTGCTCTATCTCAACATCAG

CTACTAGGCACAGAGCGCCGAAGTATGTAGCTGGTGGTGAGGAAGAACACAGGATCT
```

-continued

Japanese encephalitis virus strain SA14-14-2, complete genome,
ACCESSION: AF315119

SEQ ID NO: 75

AGAAGTTTATCTGTGTGAACTTCTTGGCTTAGTATCGTAGAGAAGAATCGAGAGATTAGTGCAGTTTAAA

CAGTTTTTTAGAACGGAAGATAACCATGACTAAAAAACCAGGAGGGCCCGGTAAAAACCGGGCTATCAAT

ATGCTGAAACGCGGCCTACCCCGCGTATTCCCACTAGTGGGAGTGAAGAGGGTAGTAATGAGCTTGTTGG

ACGGCAGAGGGCCAGTACGTTTCGTGCTGGCTCTTATCACGTTCTTCAAGTTTACAGCATTAGCCCCGAC

CAAGGCGCTTTCAGGCCGATGGAAAGCAGTGGAAAAGAGTGTGGCAATGAAACATCTTACTAGTTTCAAA

CGAGAACTTGGAACACTCATTGACGCCGTGAACAAGCGGGGCAGAAAGCAAAACAAAAGAGGAGGAAATG

AAGGCTCAATCATGTGGCTCGCGAGCTTGGCAGTTGTCATAGCTTGTGCAGGAGCCATGAAGTTGTCGAA

TTTCCAGGGGAAGCTTTTGATGACCATCAACAACACGGACATTGCAGACGTTATCGTGATTCCCACCTCA

AAAGGAGAGAACAGATGCTGGGTCCGGGCAATCGACGTCGGCTACATGTGTGAGGACACTATCACGTACG

AATGTCCTAAGCTTACCATGGGCAATGATCCAGAGGATGTGGATTGCTGGTGTGACAACCAAGAAGTCTA

CGTCCAATATGGACGGTGCACGCGGACCAGGCATTCCAAGCGAAGCAGGAGATCCGTGTCGGTCCAAACA

CATGGGAGAGTTCACTAGTGAATAAAAAAGAGGCTTGGCTGGATTCAACGAAAGCCACACGATATCTCA

TGAAAACTGAGAACTGGATCATAAGGAATCCTGGCTATGCTTTCCTGGCGGCGGTACTTGGCTGGATGCT

TGGCAGTAACAACGGTCAACGCGTGGTATTTACCATCCTCCTGCTGTTGGTCGCTCCGGCTTACAGTTTT

AATTGTCTGGGAATGGGCAATCGTGACTTCATAGAAGGAGCCAGTGGAGCCACTTGGGTGGACTTGGTGC

TAGAAGGAGACAGCTGCTTGACAATCATGGCAAACGACAAACCAACATTGGACGTCCGCATGATTAACAT

CGAAGCTAGCCAACTTGCTGAGGTCAGAAGTTACTGCTATCATGCTTCAGTCACTGACATCTCGACGGTG

GCTCGGTGCCCCACGACTGGAGAAGCCCACAACGAGAAGCGAGCTGATAGTAGCTATGTGTGCAAACAAG

GCTTCACTGACCGTGGGTGGGGCAACGGATGTGGATTTTTCGGGAAGGGAAGCATTCACACATCTGCAAA

ATTCTCCTGCACCAGTAAAGCGATTGGGAGAACAATCCAGCCAGAAAACATCAAATACAAAGTTGGCATT

TTTGTGCATGGAACCACCACTTCGGAAAACCATGGGAATTATTCAGCGCAAGTTGGGGCGTCCCAGGCGG

CAAAGTTTACAGTAACACCCAATGCTCCTTCGGTAGCCCTCAAACTTGGTGACTACGGAGAAGTCACACT

GGACTGTGAGCCAAGGAGTGGACTGAACACTGAAGCGTTTTACGTCATGACCGTGGGGTCAAAGTCATTT

CTGGTCCATAGGGAGTGGTTTCATGACCTCGCTCTCCCCTGGACGTCCCCTTCGAGCACAGCGTGGAGAA

ACAGAGAACTCCTCATGGAATTTGAAGGGGCGCACGCCACAAAACAGTCCGTTGTTGCTCTTGGGTCACA

GGAAGGAGGCCTCCATCATGCGTTGGCAGGAGCCATCGTGGTGGAGTACTCAAGCTCAGTGATGTTAACA

TCAGGCCACCTGAAATGTAGGCTGAAAATGGACAAACTGGCTCTGAAAGGCACAACCTATGGCATGTGTA

CAGAAAAATTCTCGTTCGCGAAAAATCCGGTGGACACTGGTCACGGAACAGTTGTCATTGAACTCTCCTA

CTCTGGGAGTGATGGCCCCTGCAAAATTCCGATTGTTTCCGTTGCGAGCCTCAATGACATGACCCCCGTT

GGGCGGCTGGTGACAGTGAACCCCTTCGTCGCGACTTCCAGTGCCAACTCAAAGGTGCTGGTCGAGATGG

AACCCCCCTTCGGAGACTCCTACATCGTAGTTGGAAGGGGAGACAAGCAGATCAACCACCATTGGCACAA

AGCTGGAAGCACGCTGGGCAAGGCCTTTTCAACAACTTTGAAGGGAGCTCAAAGACTGGCAGCGTTGGGC

GACACAGCCTGGGACTTTGGCTCTATTGGAGGGGTCTTCAACTCCATAGGAAGAGCCGTTCACCAAGTGT

TTGGTGATGCCTTCAGAACACTCTTTGGGGAATGTCTTGGATCACACAAGGGCTAATGGGTGCCCTACT

GCTCTGGATGGGCGTCAACGCACGAGACCGATCAATTGCTTTGGCCTTCTTAGCCACAGGAGGTGTGCTC

GTGTTCTTAGCGACCAATGTGCATGCTGACACTGGATGTGCCATTGACATCACAAGAAAAGAGATGAGAT

GTGGAAGTGGCATCTTCGTGCACAACGACGTGGAAGCCTGGGTGGATAGGTATAAATATTTGCCAGAAAC

GCCCAGATCCCTAGCGAAGATCGTCCACAAAGCGCACAAGGAAGGCGTGTGCGGAGTCAGATCTGTCACT

AGACTGGAGCACCAAATGTGGGAAGCCGTAAGGGACGAATTGAACGTCCTGCTCAAAGAGAATGCAGTGG

-continued

ACCTCAGTGTGGTTGTGAACAAGCCCGTGGGAAGATATCGCTCAGCCCCTAAACGCCTATCCATGACGCA

AGAGAAGTTTGAAATGGGCTGGAAAGCATGGGGAAAAAGCATCCTCTTTGCCCCGGAATTGGCTAACTCC

ACATTTGTCGTAGATGGACCTGAGACAAAGGAATGCCCTGATGAGCACAGAGCTTGGAACAGCATGCAAA

TCGAAGACTTCGGCTTTGGCATCACATCAACCCGTGTGTGGCTGAAAATTAGAGAGGAGAGCACTGACGA

GTGTGATGGAGCGATCATAGGCACGGCTGTCAAAGGACATGTGGCAGTCCATAGTGACTTGTCGTACTGG

ATTGAGAGTCGCTACAACGACACATGGAAACTTGAGAGGGCAGTCTTTGGAGAGGTCAAATCTTGCACTT

GGCCAGAGACACACACCCTTTGGGGAGATGATGTTGAGGAAAGTGAACTCATCATTCCGCACACCATAGC

CGGACCAAAAAGCAAGCACAATCGGAGGGAAGGGTATAAGACACAAAACCAGGGACCTTGGGATGAGAAT

GGCATAGTCTTGGACTTTGATTATTGCCCAGGGACAAAAGTCACCATTACAGAGGATTGTAGCAAGAGAG

GCCCTTCGGTCAGAACCACTACTGACAGTGGAAAGTTGATCACTGACTGGTGCTGTCGCAGTTGCTCCCT

TCCGCCCCTACGATTCCGGACAGAAAATGGCTGCTGGTACGGAATGGAAATCAGACCTG

Japanese encephalitis virus strain SA14-14-2, complete genome,
ACCESSION: AF315119

SEQ ID NO: 75

AGAAGTTTATCTGTGTGAACTTCTTGGCTTAGTATCGTAGAGAAGAATCGAGAGATTAGTGCAGTTTAAA

CAGTTTTTTAGAACGGAAGATAACCATGACTAAAAAACCAGGAGGGCCCGGTAAAAACCGGGCTATCAAT

ATGCTGAAACGCGGCCTACCCCGCGTATTCCCACTAGTGGGAGTGAAGAGGGTAGTAATGAGCTTGTTGG

ACGGCAGAGGGCCAGTACGTTTCGTGCTGGCTCTTATCACGTTCTTCAAGTTTACAGCATTAGCCCCGAC

CAAGGCGCTTTCAGGCCGATGGAAAGCAGTGGAAAAGAGTGTGGCAATGAAACATCTTACTAGTTTCAAA

CGAGAACTTGGAACACTCATTGACGCCGTGAACAAGCGGGGCAGAAAGCAAAACAAAAGAGGAGGAAATG

AAGGCTCAATCATGTGGCTCGCGAGCTTGGCAGTTGTCATAGCTTGTGCAGGAGCCATGAAGTTGTCGAA

TTTCCAGGGGAAGCTTTTGATGACCATCAACAACACGGACATTGCAGACGTTATCGTGATTCCCACCTCA

AAAGGAGAGAACAGATGCTGGGTCCGGGCAATCGACGTCGGCTACATGTGTGAGGACACTATCACGTACG

AATGTCCTAAGCTTACCATGGGCAATGATCCAGAGGATGTGGATTGCTGGTGTGACAACCAAGAAGTCTA

CGTCCAATATGGACGGTGCACGCGGACCAGGCATTCCAAGCGAAGCAGGAGATCCGTGTCGGTCCAAACA

CATGGGAGAGTTCACTAGTGAATAAAAAAGAGGCTTGGCTGGATTCAACGAAAGCCACACGATATCTCA

TGAAAACTGAGAACTGGATCATAAGGAATCCTGGCTATGCTTTCCTGGCGGCGGTACTTGGCTGGATGCT

TGGCAGTAACAACGGTCAACGCGTGGTATTTACCATCCTCCTGCTGTTGGTCGCTCCGGCTTACAGTTTT

AATTGTCTGGGAATGGGCAATCGTGACTTCATAGAAGGAGCCAGTGGAGCCACTTGGGTGGACTTGGTGC

TAGAAGGAGACAGCTGCTTGACAATCATGGCAAACGACAAACCAACATTGGACGTCCGCATGATTAACAT

CGAAGCTAGCCAACTTGCTGAGGTCAGAAGTTACTGCTATCATGCTTCAGTCACTGACATCTCGACGGTG

GCTCGGTGCCCCACGACTGGAGAAGCCCACAACGAGAAGCGAGCTGATAGTAGCTATGTGTGCAAACAAG

GCTTCACTGACCGTGGGTGGGCAACGGATGTGGATTTTTCGGGAAGGGAAGCATTCACACATCTGCAAA

ATTCTCCTGCACCAGTAAAGCGATTGGGAGAACAATCCAGCCAGAAAACATCAAATACAAAGTTGGCATT

TTTGTGCATGGAACCACCACTTCGGAAAACCATGGGAATTATTCAGCGCAAGTTGGGCGTCCCAGGCGG

CAAAGTTTACAGTAACACCCAATGCTCCTTCGGTAGCCCTCAAACTTGGTGACTACGGAGAAGTCACACT

GGACTGTGAGCCAAGGAGTGGACTGAACACTGAAGCGTTTTACGTCATGACCGTGGGGTCAAAGTCATTT

CTGGTCCATAGGGAGTGGTTTCATGACCTCGCTCTCCCTGGACGTCCCCTTCGAGCACAGCGTGGAGAA

ACAGAGAACTCCTCATGGAATTTGAAGGGGCGCACGCCACAAAACAGTCCGTTGTTGCTCTTGGGTCACA

GGAAGGAGGCCTCCATCATGCGTTGGCAGGAGCCATCGTGGTGGAGTACTCAAGCTCAGTGATGTTAACA

TCAGGCCACCTGAAATGTAGGCTGAAAATGGACAAACTGGCTCTGAAAGGCACAACCTATGGCATGTGTA

CAGAAAAATTCTCGTTCGCGAAAAATCCGGTGGACACTGGTCACGGAACAGTTGTCATTGAACTCTCCTA

```
-continued
CTCTGGGAGTGATGGCCCCTGCAAAATTCCGATTGTTTCCGTTGCGAGCCTCAATGACATGACCCCCGTT

GGGCGGCTGGTGACAGTGAACCCCTTCGTCGCGACTTCCAGTGCCAACTCAAAGGTGCTGGTCGAGATGG

AACCCCCCTTCGGAGACTCCTACATCGTAGTTGGAAGGGGAGACAAGCAGATCAACCACCATTGGCACAA

AGCTGGAAGCACGCTGGGCAAGGCCTTTTCAACAACTTTGAAGGGAGCTCAAAGACTGGCAGCGTTGGGC

GACACAGCCTGGGACTTTGGCTCTATTGGAGGGGTCTTCAACTCCATAGGAAGAGCCGTTCACCAAGTGT

TTGGTGATGCCTTCAGAACACTCTTTGGGGGAATGTCTTGGATCACACAAGGGCTAATGGGTGCCCTACT

GCTCTGGATGGGCGTCAACGCACGAGACCGATCAATTGCTTTGGCCTTCTTAGCCACAGGAGGTGTGCTC

GTGTTCTTAGCGACCAATGTGCATGCTGACACTGGATGTGCCATTGACATCACAAGAAAAGAGATGAGAT

GTGGAAGTGGCATCTTCGTGCACAACGACGTGGAAGCCTGGGTGGATAGGTATAAATATTTGCCAGAAAC

GCCCAGATCCCTAGCGAAGATCGTCCACAAAGCGCACAAGGAAGGCGTGTGCGGAGTCAGATCTGTCACT

AGACTGGAGCACCAAATGTGGGAAGCCGTAAGGGACGAATTGAACGTCCTGCTCAAAGAGAATGCAGTGG

ACCTCAGTGTGGTTGTGAACAAGCCCGTGGGAAGATATCGCTCAGCCCCTAAACGCCTATCCATGACGCA

AGAGAAGTTTGAAATGGGCTGGAAAGCATGGGAAAAAGCATCCTCTTTGCCCCGGAATTGGCTAACTCC

ACATTTGTCGTAGATGGACCTGAGACAAAGGAATGCCCTGATGAGCACAGAGCTTGGAACAGCATGCAAA

TCGAAGACTTCGGCTTTGGCATCACATCAACCCGTGTGTGGCTGAAAATTAGAGAGGAGAGCACTGACGA

GTGTGATGGAGCGATCATAGGCACGGCTGTCAAAGGACATGTGGCAGTCCATAGTGACTTGTCGTACTGG

ATTGAGAGTCGCTACAACGACACATGGAAACTTGAGAGGGCAGTCTTTGGAGAGGTCAAATCTTGCACTT

GGCCAGAGACACACACCCTTTGGGGAGATGATGTTGAGGAAAGTGAACTCATCATTCCGCACACCATAGC

CGGACCAAAAAGCAAGCACAATCGGAGGGAAGGGTATAAGACACAAAACCAGGGACCTTGGGATGAGAAT

GGCATAGTCTTGGACTTTGATTATTGCCCAGGGACAAAAGTCACCATTACAGAGGATTGTAGCAAGAGAG

GCCCTTCGGTCAGAACCACTACTGACAGTGGAAAGTTGATCACTGACTGGTGCTGTCGCAGTTGCTCCCT

TCCGCCCCTACGATTCCGGACAGAAAATGGCTGCTGGTACGGAATGGAAATCAGACCTGGCACGCAGGGC

CAGAAGTGAAAATAACATAGTGGGAGGACATCCGGTTTCGCGAGGCTCAGCAAAACTCCGTTGGCTTGTG

GAGAAAGGATTTGTCTCGCCAATAGGAAAAGTCATTGATCTAGGGTGTGGGCGTGGAGGATGGAGCTACT

ACGCAGCAACCCTGAAGAAGGTCCAGGAAGTCAGAGGATACACGAAAGGTGGGGCGGGACATGAAGAACC

GATGCTCATGCAGAGCTACGGCTGGAACCTGGTCTCCCTGAAGAGTGGAGTGGACGTGTTTTACAAACCT

TCAGAGCCCAGTGATACCCTGTTCTGTGACATAGGGGAATCCTCCCCAAGTCCAGAAGTAGAAGAACAAC

GCACACTACGCGTCCTAGAGATGACATCTGACTGGTTGCACCGAGGACCTAGAGAGTTCTGCATTAAAGT

TCTCTGCCCTTACATGCCCAAGGTTATAGAAAAAATTGAAGTTCTGCAGCGCCGCTTCGGAGGTGGGCTA

GTGCGTCTCCCCCTGTCCCGAAACTCCAATCACGAGATGTATTGGGTTAGTGGAGCCGCTGGCAATGTGG

TGCACGCTGTGAACATGACCAGCCAGGTATTACTGGGGCGAATGGATCGCACAGTGTGGAGAGGGCCAAA

GTATGAGGAAGATGTCAACCTAGGGAGCGGAACAAGAGCCGTGGGAAAGGGAGAAGTCCATAGCAATCAG

GAGAAAATCAAGAAGAGAATCCAGAAGCTTAAAGAAGAATTCGCCACAACGTGGCACAAAGACCCTGAGC

ATCCATACCGCACTTGGACATACCACGGAAGCTATGAAGTGAAGGCTACTGGCTCAGCCAGCTCTCTCGT

CAACGGAGTGGTGAAGCTCATGAGCAAACCTTGGGACGCCATTGCCAACGTCACCACCATGGCCATGACT

GACAC

CACCCCTTTTGGACAGCAAAGAGTTTTCAAGGAGAAAGTTGACACGAAGGCTCCTGAGCCACCAGCTGGA

GCCAAGGAAGTGCTCAACGAGACCACCAACTGGCTGTGGGCCTACTTGTCACGGGAAAAAAGACCCCGCT

TGTGCACCAAGGAAGAATTCATTAAGAAAGTTAACAGCAACGCGGCTCTTGGAGCAGTGTTCGCTGAACA

GAATCAATGGAGCACGCGCGTGAGGCTGTGGATGACCCGCGGTTTTGGGAGATGGTTGATGAAGAGAGG

GAAAACCATCTGCGAGGAGAGTGTCACACATGTATCTACAACATGATGGGAAAAAGAGAGAAGAAGCCTG
```

```
GAGAGTTTGGAAAAGCTAAAGGAAGCAGGGCCATTTGGTTCATGTGGCTTGGAGCACGGTATCTAGAGTT
TGAAGCTTTGGGGTTCCTGAATGAAGACCATTGGCTGAGCCGAGAGAATTCAGGAGGTGGAGTGGAAGGC
TCAGGCGTCCAAAAGCTGGGATACATCCTCCGTGACATAGCAGGAAAGCAAGGAGGGAAAATGTACGCTG
ATGATACCGCCGGGTGGGACACTAGAATTACCAGAACTGATTTAGAAAATGAAGCTAAGGTACTGGAGCT
CCTAGACGGTGAACACCGCATGCTCGCCCGAGCCATAATTGAACTGACTTACAGGCACAAAGTGGTCAAG
GTCATGAGACCTGCAGCAGAAGGAAAGACCGTGATGGACGTGATATCAAGAGAAGATCAAAGGGGGAGTG
GACAGGTGGTCACTTATGCTCTTAACACTTTCACGAACATCGCTGTCCAGCTCGTCAGGCTGATGGAGGC
TGAGGGGGTCATTGGACCACAACACTTGGAACATCTACCTAGGAAAAACAAGATAGCTGTCAGGACCTGG
CTCTTTGAGAATGGAGAGGAGAGTGACCAGGATGGCGATCAGCGGAGACGACTGTGCCGTCAAACCGC
TGGACGACAGATTCGCCACAGCCCTCCACTTCCTCAACGCAATGTCAAAGGTCAGAAAAGACATCCAGGA
ATGGAAGCCTTCGCATGGCTGGCACGATTGGCAGCAAGTTCCCTTCTGTTCTAACCATTTTCAGGAGATT
GTGATGAAAGATGGAAGGAGTATAGTTGTCCCGTGCAGAGGACAGGATGAGCTGATAGGCAGGGCTCGCA
TCTCTCCAGGAGCTGGATGGAATGTGAAGGACACAGCTTGCCTGCCCAAAGCATATGCACAAATGTGGGT
ACTCCTATACTTCCACCGCAGGGACTTGCGTCTCATGGCAAATGCGATTTGCTCAGCAGTGCCAGTAGAT
TGGGTGCCCACAGGCAGGACATCCTGGTCAATACACTCGAAAGGAGAGTGGATGACCACGGAAGACATGC
TGCAGGTCTGGAACAGAGTTTGGATTGAAGAAAATGAATGGATGATGGACAAGACTCCAATCACAAGCTG
GACAGACGTTCCGTATGTGGGAAAGCGCGAGGACATCTGGTGTGGCAGCCTCATCGGAACGCGATCCAGA
GCAACCTGGGCTGAGAACATCTATGCGGCGATAAACCAGGTTAGAGCTGTCATTGGGAAAGAAAATTATG
TTGACTACATGACCTCACTCAGGAGATACGAAGACGTCTTGATCCAGGAAGACAGGGTCATCTAGTGTGA
TTTAAGGTAGAAAAGTAGACTATGTAAACAATGTAAATGAGAAAATGCATGCATATGGAGTCAGGCCAGC
AAAAGCTGCCACCGGATACTGGGTAGACGGTGCTGCCTGCGTCTCAGTCCCAGGAGGACTGGGTTAACAA
ATCTGACAACAGAAAGTGAGAAAGCCCTCAGAACTGTCTCGGAAGTAGGTCCCTGCTCACTGGAAGTTGA
AAGACCAACGTCAGGCCACAAATTTGTGCCACTCCGCTAGGGAGTGCGGCCTGCGCAGCCCCAGGAGGAC
TGGGTTACCAAAGCCGTTGAGCCCCCACGGCCCAAGCCTCGTCTAGGATGCAATAGACGAGGTGTAAGGA
CTAGAGGTTAGAGGAGACCCCGTGGAAACAACAACATGCGGCCCAAGCCCCCTCGAAGCTGTAGAGGAGG
TGGAAGGACTAGAGGTTAGAGGAGACCCCGCATTTGCATCAAACAGCATATTGACACCTGGGAATAGACT
GGGAGATCTTCTGCTCTATCTCAACATCAGCTACTAGGCACAGAGCGCCGAAGTATGTACGTGGTGGTGA
GGAAGAACACAGGATCT
>gi|5640146141gb|KF769015.1| Yellow fever virus strain 17D-204,
complete genome
                                                         SEQ ID NO: 76
GTGCTAATTGAGGTGCATTGGTCTGCAAATCGAGTTGCTAGGCAATAAACACATTTGGATTAATTTTAAT
CGTTCGTTGAGCGATTAGCAGAGAACTGACCAGAACATGTCTGGTCGTAAAGCTCAGGGAAAAACCCTGG
GCGTCAATATGGTACGACGAGGAGTTCGCTCCTTGTCAAACAAAATAAAACAAAAAACAAAACAAATTGG
AAACAGACCTGGACCTTCAAGAGGTGTTCAAGGATTTATCTTTTTCTTTTTGTTCAACATTTTGACTGGA
AAAAAGATCACAGCCCACCTAAAGAGGTTGTGGAAAATGCTGGACCCAAGACAAGGCTTGGCTGTTCTAA
GGAAAGTCAAGAGAGTGGTGGCCAGTTTGATGAGAGGATTGTCCTCAAGGAAACGCCGTTCCCATGATGT
TCTGACTGTGCAATTCCTAATTTTGGGAATGCTGTTGATGACGGGTGGAGTGACCTTGGTGCGGAAAAAC
AGATGGTTGCTCCTAAATGTGACATCTGAGGACCTCGGGAAACATTCTCTGTGGGCACAGGCAACTGCA
CAACAAACATTTTGGAAGCCAAGTACTGGTGCCCAGACTCAATGGAATACAACTGTCCCAATCTCAGTCC
AAGAGAGGAGCCAGATGACATTGATTGCTGGTGCTATGGGGTGGAAAACGTTAGAGTCGCATATGGTAAG
TGTGACTCAGCAGGCAGGTCTAGGAGGTCAAGAAGGGCCATTGACTTGCCTACGCATGAAAACCATGGTT
```

-continued

```
TGAAGACCCGGCAAGAAAAATGGATGACTGGAAGAATGGGTGAAAGGCAACTCCAAAAGATTGAGAGATG
GTTCGTGAGGAACCCCTTTTTTGCAGTGACGGCTCTGACCATTGCCTACCTTGTGGGAAGCAACATGACG
CAACGAGTCGTGATTGCCCTACTGGTCTTGGCTGTTGGTCCGGCCTACTCAGCTCACTGCATTGGAATTA
CTGACAGGGATTTCATTGAGGGGGTGCATGGAGGAACTTGGGTTTCAGCTACCCTGGAGCAAGACAAGTG
TGTCACTGTTATGGCCCCTGACAAGCCTTCATTGGACATCTCACTAGAGACAGTAGCCATTGATAGACCT
GCTGAGGTGAGGAAAGTGTGTTACAATGCAGTTCTCACTCATGTGAAGATTAATGACAAGTGCCCCAGCA
CTGGAGAGGCCCACCTAGCTGAAGAGAACGAAGGGGACAATGCGTGCAAGCGCACTTATTCTGATAGAGG
CTGGGGCAATGGCTGTGGCCTATTTGGGAAAGGGAGCATTGTGGCATGCGCCAAATTCACTTGTGCCAAA
TCCATGAGTTTGTTTGAGGTTGATCAGACCAAAATTCAGTATGTCATCAGAGCACAATTGCATGTAGGGG
CCAAGCAGGAAAATTGGACTACCGACATTAAGACTCTCAAGTTTGATGCCCTGTCAGGCTCCCAGGAAGT
CGAGTTCATTGGGTATGGAAAAGCTACACTGGAATGCCAGGTGCAAACTGCGGTGGACTTTGGTAACAGT
TACATCGCTGAGATGGAAACAGAGAGCTGGATAGTGGACAGACAGTGGGCCCAGGACTTGACCCTGCCAT
GGCAGAGTGGAAGTGGCGGGGTGTGGAGAGAGATGCATCATCTTGTCGAATTTGAACCTCCGCATGCCGC
CACTATCAGAGTACTGGCCCTGGGAAACCAGGAAGGCTCCTTGAAAACAGCTCTTACTGGCGCAATGAGG
GTTACAAAGGACACAAATGACAACAACCTTTACAAACTACATGGTGGACATGTTTCTTGCAGAGTGAAAT
TGTCAGCTTTGACACTCAAGGGGACATCCTACAAAATATGCACTGACAAAATGTTTTTTGTCAAGAACCC
AACTGACACTGGCCATGGCACTGTTGTGATGCAGGTGAAAGTGTCAAAAGGAGCCCCCTGCAGGATTCCA
GTGATAGTAGCTGATGATCTTACAGCGGCAATCAATAAAGGCATTTTGGTTACAGTTAACCCCATCGCCT
CAACCAATGATGATGAAGTGCTGATTGAGGTGAACCCACCTTTTGGAGACAGCTACATTATCGTTGGGAG
AGGAGATTCACGTCTCACTTACCAGTGGCACAAAGAGGGAAGCTCAATAGGAAAGTTGTTCACTCAGACC
ATGAAAGGCGTGGAACGCCTGGCCGTCATGGGAGACACCGCCTGGGATTTCAGCTCCGCTGGAGGGTTCT
TCACTTCGGTTGGGAAAGGAATTCATACGGTGTTTGGCTCTGCCTTTCAGGGGCTATTTGGCGGCTTGAA
CTGGATAACAAAGGTCATCATGGGGCGGTACTTATATGGGTTGGCATCAACACAAGAAACATGACAATG
TCCATGAGCATGATCTTGGTAGGAGTGATCATGATGTTTTTGTCTCTAGGAGTTGGGGCGGATCAAGGAT
GCGCCATCAACTTTGGCAAGAGAGAGCTCAAGTGCGGAGATGGTATCTTCATATTTAGAGACTCTGATGA
CTGGCTGAACAAGTACTCATACTATCCAGAAGATCCTGTGAAGCTTGCATCAATAGTGAAAGCCTCTTTT
GAAGAAGGGAAGTGTGGCCTAAATTCAGTTGACTCCCTTGAGCATGAGATGTGGAGAAGCAGGGCAGATG
AGATCAATGCCATTTTTGAGGAAAACGAGGTGGACATTTCTGTTGTCGTGCAGGATCCAAAGAATGTTTA
CCAGAGAGGAACTCATCCATTTTCCAGAATTCGGGATGGTCTGCAGTATGGTTGGAAGACTTGGGGTAAG
AACCTTGTGTTCTCCCCAGGGAGGAAGAATGGAAGCTTCATCATAGATGGAAAGTCCAGGAAAGAATGCC
CGTTTTCAAACCGGGTCTGGAATTCTTTCCAGATAGAGGAGTTTGGGACGGGAGTGTTCACCACACGCGT
GTACATGGACGCAGTCTTTGAATACACCATAGACTGCGATGGATCTATCTTGGGTGCAGCGGTGAACGGA
AAAAAGAGTCCCCATGGCTCTCCAACATTTTGGATGGGAAGTCATGAAGTAAATGGGACATGGATGATCC
ACACCTTGGAGGCATTAGATTACAAGGAGTGTGAGTGGCCACTGACACATACGATTGGAACATCAGTTGA
AGAGAGTGAAATGTTCATGCCGAGATCAATCGGAGGCCCAGTTAGCTCTCACAATCATATCCCTGGATAC
AAGGTTCAGACGAACGGACCTTGGATGCAGGTACCACTAGAAGTGAAGAGAGAAGCTTGCCCAGGGACTA
GCGTGATCATTGATGGCAACTGTGATGGACGGGAAAATCAACCAGATCCACCACGGATAGCGGGAAAGT
TATTCCTGAATGGTGTTGCCGCTCCTGCACAATGCCGCCTGTGAGCTTCCATGGTAGTGATGGGTGTTGG
TATCCCATGGAAATTAGGCCAAGGAAAACGCATGAAAGCCATCTGGTGCGCTCCTGGGTTACAGCTGGAG
AAATACATGCTGTCCCTTTTGGTTTGGTGAGCATGATGATAGCAATGGAAGTGGTCCTAAGGAAAAGACA
```

-continued

```
GGGACCAAAGCAAATGTTGGTTGGAGGAGTAGTGCTCTTGGGAGCAATGCTGGTCGGGCAAGTAACTCTC

CTTGATTTGCTGAAACTCACAGTGGCTGTGGGATTGCATTTCCATGAGATGAACAATGGAGGAGACGCCA

TGTATATGGCGTTGATTGCTGCCTTTTCAATCAGACCAGGGCTGCTCATCGGCTTTGGGCTCAGGACCCT

ATGGAGCCCTCGGGAACGCCTTGTGCTGACCCTAGGAGCAGCCATGTGGAGATTGCCTTGGGTGGCGTG

ATGGGCGGCCTGTGGAAGTATCTAAATGCAGTTTCTCTCTGCATCCTGACAATAAATGCTGTTGCTTCTA

GGAAAGCATCAAATACCATCTTGCCCCTCATGGCTCTGTTGACACCTGTCACTATGGCTGAGGTGAGACT

TGCCGCAATGTTCTTTTGTGCCGTGGTTATCATAGGGGTCCTTCACCAGAATTTCAAGGACACCTCCATG

CAGAAGACTATACCTCTGGTGGCCCTCACACTCACATCTTACCTGGGCTTGACACAACCTTTTTTGGGCC

TGTGTGCATTTCTGGCAACCCGCATATTTGGGCGAAGGAGTATCCCAGTGAATGAGGCACTCGCAGCAGC

TGGTCTAGTGGGAGTGCTGGCAGGACTGGCTTTTCAGGAGATGGAGAACTTCCTTGGTCCGATTGCAGTT

GGAGGACTCCTGATGATGCTGGTTAGCGTGGCTGGGAGGGTGGATGGGCTAGAGCTCAAGAAGCTTGGTG

AAGTTTCATGGGAAGAGGAGGCGGAGATCAGCGGGAGTTCCGCCCGCTATGATGTGGCACTCAGTGAACA

AGGGGAGTTCAAGCTGCTTTCTGAAGAGAAAGTGCCATGGGACCAGGTTGTGATGACCTCGCTGGCCTTG

GTTGGGGCTGCCCTCCATCCATTTGCTCTTCTGCTGGTCCTTGCTGGGTGGCTGTTTCATGTCAGGGGAG

CTAGGAGAAGTGGGGATGTCTTGTGGGATATTCCCACTCCTAAGATCATCGAGGAATGTGAACATCTGGA

GGATGGGATTTATGGCATATTCCAGTCAACCTTCTTGGGGGCCTCCCAGCGAGGAGTGGGAGTGGCACAG

GGAGGGGTGTTCCACACAATGTGGCATGTCACAAGAGGAGCTTTCCTTGTCAGGAATGGCAAGAAGTTGA

TTCCATCTTGGGCTTCAGTAAAGGAAGACCTTGTCGCCTATGGTGGCTCATGGAAGTTGGAAGGCAGATG

GGATGGAGAGGAAGAGGTCCAGTTGATCGCGGCTGTTCCAGGAAAGAACGTGGTCAACGTCCAGACAAAA

CCGAGCTTGTTCAAAGTGAGGAATGGGGGAGAAATCGGGCTGTCGCTCTTGACTATCCGAGTGGCACTT

CAGGATCTCCTATTGTTAACAGGAACGGAGAGGTGATTGGGCTGTACGGCAATGGCATCCTTGTCGGTGA

CAACTCCTTCGTGTCCGCCATATCCCAGACTGAGGTGAAGGAAGAAGGAAAGGAGGAGCTCCAAGAGATC

CCGACAATGCTAAAGAAAGGAATGACAACTGTCCTTGATTTTCATCCTGGAGCTGGGAAGACAAGACGTT

TCCTCCCACAGATCTTGGCCGAGTGCGCACGGAGACGCTTGCGCACTCTTGTGTTGGCCCCCACCAGGGT

TGTTCTTTCTGAAATGAAGGAGGCTTTTCACGGCCTGGACGTGAAATTCCACACACAGGCTTTTTCCGCT

CACGGCAGCGGGAGAGAAGTCATTGATGCTATGTGCCATGCCACCCTAACTTACAGGATGTTGGAACCAA

CTAGGGTTGTTAACTGGGAAGTGATCATTATGGATGAAGCCCATTTTTTGGATCCAGCTAGCATAGCCGC

TAGAGGTTGGGCAGCGCACAGAGCTAGGGCAAATGAAAGTGCAACAATCTTGATGACAGCCACACCGCCT

GGGACTAGTGATGAATTTCCACATTCAAATGGTGAAATAGAAGATGTTCAAACGGACATACCCAGTGAGC

CCTGGAACACAGGGCATGACTGGATCCTGGCTGACAAAAGGCCCACGGCATGGTTCCTTCCATCCATCAG

AGCTGCAAATGTCATGGCTGCCTCTTTGCGTAAGGCTGGAAAGAGTGTGGTGGTCCTGAACAGGAAAACC

TTTGAGAGAGAATACCCCACGATAAAGCAGAAGAAACCTGACTTTATATTGGCCACTGACATAGCTGAAA

TGGGAGCCAACCTTTGCGTGGAGCGAGTGCTGGATTGCAGGACGGCTTTTAAGCCTGTGCTTGTGGATGA

AGGGAGGAAGGTGGCAATAAAAGGGCCACTTCGTATCTCCGCATCCTCTGCTGCTCAAAGGAGGGGCGC

ATTGGGAGAAATCCCAACAGAGATGGAGACTCATACTACTATTCTGAGCCTACAAGTGAAAATAATGCCC

ACCACGTCTGCTGGTTGGAGGCCTCAATGCTCTTGGACAACATGGAGGTGAGGGTGGAATGGTCGCCCC

ACTCTATGGCGTTGAAGGAACTAAAACACCAGTTTCCCCTGGTGAAATGAGACTGAGGGATGACCAGAGG

AAAGTCTTCAGAGAACTAGTGAGGAATTGTGACCTGCCCGTTTGGCTTTCGTGGCAAGTGGCCAAGGCTG

GTTTGAAGACGAATGATCGTAAGTGGTGTTTTGAAGGCCCTGAGGAACATGAGATCTTGAATGACAGCGG

TGAAACAGTGAAGTGCAGGGCTCCTGGAGGAGCAAAGAAGCCTCTGCGCCCAAGGTGGTGTGATGAAAGG

GTGTCATCTGACCAGAGTGCGCTGTCTGAATTTATTAAGTTTGCTGAAGGTAGGAGGGGAGCTGCTGAAG
```

-continued

```
TGCTAGTTGTGCTGAGTGAACTCCCTGATTTCCTGGCTAAAAAAGGTGGAGAGGCAATGGATACCATCAG

TGTGTTTCTCCACTCTGAGGAAGGCTCTAGGGCTTACCGCAATGCACTATCAATGATGCCTGAGGCAATG

ACAATAGTCATGCTGTTTATACTGGCTGGACTACTGACATCGGGAATGGTCATCTTTTTCATGTCTCCCA

AAGGCATCAGTAGAATGTCTATGGCGATGGGCACAATGGCCGGCTGTGGATATCTCATGTTCCTTGGAGG

CGTCAAACCCACTCACATCTCCTATATCATGCTCATATTCTTTGTCCTGATGGTGGTTGTGATCCCCGAG

CCAGGGCAACAAAGGTCCATCCAAGACAACCAAGTGGCATACCTCATTATTGGCATCCTGACGCTGGTTT

CAGCGGTGGCAGCCAACGAGCTAGGCATGCTGGAGAAAACCAAGAGGACCTCTTTGGGAAGAAGAACTT

AATTCCATCTAGTGCTTCACCCTGGAGTTGGCCGGATCTTGACCTGAAGCCAGGAGCTGCCTGGACAGTG

TACGTTGGCATTGTTACAATGCTCTCTCCAATGTTGCACCACTGGATCAAAGTCGAATATGGCAACCTGT

CTCTGTCTGGAATAGCCCAGTCAGCCTCAGTCCTTTCTTTCATGGACAAGGGGATACCATTCATGAAGAT

GAATATCTCGGTCATAATGCTGCTGGTCAGTGGCTGGAATTCAATAACAGTGATGCCTCTGCTCTGTGGC

ATAGGGTGCGCCATGCTCCACTGGTCTCTCATTTTACCTGGAATCAAAGCGCAGCAGTCAAAGCTTGCAC

AGAGAAGGGTGTTCCATGGCGTTGCCAAGAACCCTGTGGTTGATGGGAATCCAACAGTTGACATTGAGGA

AGCTCCTGAAATGCCTGCCCTTTATGAGAACAAACTGGCTCTATATCTCCTTCTTGCTCTCAGCCTAGCT

TCTGTTGCCATGTGCAGAACGCCCTTTTCATTGGCTGAAGGCATTGTCCTAGCATCAGCTGCCCTAGGGC

CGCTCATAGAGGGAAACACCAGCCTTCTTTGGAATGGACCCATGGCTGTCTCCATGACAGGAGTCATGAG

GGGGAATCACTATGCTTTTGTGGGAGTCATGTACAATCTATGGAAGATGAAAACTGGACGCCGGGGGAGC

GCGAATGGAAAAACTTTGGGTGAAGTCTGGAAGAGGGAACTGAATCTGTTGGACAAGCGACAGTTTGAGT

TGTATAAAAGGACCGACATTGTGGAGGTGGATCGTGATACGGCACGCAGGCATTTGGCCGAAGGGAAGGT

GGACACCGGGGTGGCGGTCTCCAGGGGGACCGCAAAGTTAAGGTGGTTCCATGAGCGTGGCTATGTCAAG

CTGGAAGGTAGGGTGATTGACCTGGGGTGTGGCCGCGGAGGCTGGTGTTACTACGCTGCTGCGCAAAAGG

AAGTGAGTGGGGTCAAAGGATTTACTCTTGGAAGAGACGGCCATGAGAAACCCATGAATGTGCAAAGTCT

GGGATGGAACATCATCACCTTCAAGGACAAAACTGATATCCACCGCCTAGAACCAGTGAAATGTGACACC

CTTTTGTGTGACATTGGAGAGTCATCATCGTCATCGGTCACAGAGGGGGAAAGGACCGTGAGAGTTCTTG

ATACTGTAGAAAAATGGCTGGCTTGTGGGGTTGACAACTTCTGTGTGAAGGTGTTAGCTCCATACATGCC

AGATGTTCTCGAGAAACTGGAATTGCTCCAAAGGAGGTTTGGCGGAACAGTGATCAGGAACCCTCTCTCC

AGGAATTCCACTCATGAAATGTACTACGTGTCTGGAGCCCGCAGCAATGTCACATTTACTGTGAACCAAA

CATCCCGCCTCCTGATGAGGAGAATGAGGCGTCCAACTGGAAAAGTGACCCTGGAGGCTGACGTCATCCT

CCCAATTGGGACACGCAGTGTTGAGACAGACAAGGGACCCCTGGACAAAGAGGCCATAGAAGAAAGGGTT

GAGAGGATAAAATCTGAGTACATGACCTCTTGGTTTTATGACAATGACAACCCCTACAGGACCTGGCACT

ACTGTGGCTCCTATGTCACAAAAACCTCAGGAAGTGCGGCGAGCATGGTAAATGGTGTTATTAAATTCT

GACATATCCATGGGACAGGATAGAGGAGGTCACAAGAATGGCAATGACTGACACAACCCCTTTTGGACAG

CAAAGAGTGTTTAAAGAAAAAGTTGACACCAGAGCAAAGGATCCACCAGCGGGAACTAGGAAGATCATGA

AAGTTGTCAACAGGTGGCTGTTCCGCCACCTGGCCAGAGAAAAGAACCCCAGACTGTGCACAAAGGAAGA

ATTTATTGCAAAAGTCCGAAGTCATGCAGCCATTGGAGCTTACCTGGAAGAACAAGAACAGTGGAAGACT

GCCAATGAGGCTGTCCAAGACCCAAAGTTCTGGGAACTGGTGGATGAAGAAAGGAAGCTGCACCAACAAG

GCAGGTGTCGGACTTGTGTGTACAACATGATGGGAAAAGAGAGAAGAAGCTGTCAGAGTTTGGGAAAGC

AAAGGGAAGCCGTGCCATATGGTATATGTGGCTGGGAGCGCGGTATCTTGAGTTTGAGGCCCTGGGATTC

CTGAATGAGGACCATTGGGCTTCCAGGGAAAACTCAGGAGGAGGAGTGGAAGGCATTGGCTTACAATACC

TAGGATATGTGATCAGAGACCTGGCTGCAATGGATGGTGGTGGATTCTACGCGGATGACACCGCTGGATG
```

-continued

GGACACGCGCATCACAGAGGCAGACCTTGATGATGAACAGGAGATCTTGAACTACATGAGCCCACATCAC

AAAAAACTGGCACAAGCAGTGATGGAAATGACATACAAGAACAAAGTGGTGAAAGTGTTGAGACCAGCCC

CAGGAGGGAAAGCCTACATGGATGTCATAAGTCGACGAGACCAGAGAGGATCCGGGCAGGTAGTGACTTA

TGCTCTGAACACCATCACCAACTTGAAAGTCCAATTGATCAGAATGGCAGAAGCAGAGATGGTGATACAT

CACCAACATGTTCAAGATTGTGATGAATCAGTTCTGACCAGGCTGGAGGCATGGCTCACTGAGCACGGAT

GTAACAGACTGAAGAGGATGGCGGTGAGTGGAGACGACTGTGTGGTCCGGCCCATCGATGACAGGTTCGG

CCTGGCCCTGTCCCATCTCAACGCCATGTCCAAGGTTAGAAAGGACATATCTGAATGGCAGCCATCAAAA

GGGTGGAATGATTGGGAGAATGTGCCCTTCTGTTCCCACCACTTCCATGAACTACAGCTGAAGGATGGCA

GGAGGATTGTGGTGCCTTGCCGAGAACAGGACGAGCTCATTGGGAGAGGAAGGGTGTCTCCAGGAAACGG

CTGGATGATCAAGGAAACAGCTTGCCTCAGCAAAGCCTATGCCAACATGTGGTCACTGATGTATTTTCAC

AAAAGGGACATGAGGCTACTGTCATTGGCTGTTTCCTCAGCTGTTCCCACCTCATGGGTTCCACAAGGAC

GCACAACATGGTCGATTCATGGGAAAGGGGAGTGGATGACCACGGAAGACATGCTTGAGGTGTGGAACAG

AGTATGGATAACCAACAACCCACACATGCAGGACAAGACAATGGTGAAAAAATGGAGAGATGTCCCTTAT

CTAACCAAGAGACAAGACAAGCTGTGCGGATCACTGATTGGAATGACCAATAGGGCCACCTGGGCCTCCC

ACATCCATTTGGTCATCCATCGTATCCGAACGCTGATTGGACAGGAGAAATACACTGACTACCTAACAGT

CATGGACAGGTATTCTGTGGATGCTGACCTGCAACTGGGTGAGCTTATCTGAAACACCATCTAACAGGAA

TAACCGGGATACAAACCACGGGTGGAGAACCGGACTCCCCACAACCTGAAACCGGGATATAAACCACGGC

TGGAGAACCGGACTCCGCACTTAAAATGAAACAGAAACCGGGATAAAAACTACGGATGGAGAACCGGACT

CCACACATTGAGACAGAAGAAGTTGTCAGCCCAGAACCCCACACGAGTTTTGCCACTGCTAAGCTGTGAG

GCAGTGCAGGCTGGGACAGCCGACCTCCAGGTTGCGAAAAACCTGGTTTCTGGGACCTCCCACCCCAGAG

TAAAAAGAACGGAGCCTCCGCTACCACCCTCCCACGTGGTGGTAGAAAGACGGGGTCTAGAGGTTAGAGG

AGACCCTCCAGGGAACAAATAGTGGGACCATATTGACGCCAGGGAAAGACCGGAGTGGTTCTCTGCTTTT

CCTCCAGAGGTCTGTGAGCACAGTTTGCTCAAGAATAAGCAGACCTTTGGATGACAAA

Attenuated Chikungunya "Delta5nsP3" sequence

SEQ ID NO: 77

GATGGCTGCGTGAGACACACGTAGCCTACCAGTTTCTTACTGCTCTACTCTGCAAAGCAAGAGATTAATA

ACCCATCATGGATCCTGTGTACGTGGACATAGACGCTGACAGCGCCTTTTTGAAGGCCCTGCAACGTGCG

TACCCCATGTTTGAGGTGGAACCAAGGCAGGTCACACCGAATGACCATGCTAATGCTAGAGCGTTCTCGC

ATCTAGCTATAAAACTAATAGAGCAGGAAATTGACCCCGACTCAACCATCCTGGATATCGGCAGTGCGCC

AGCAAGGAGGATGATGTCGGACAGGAAGTACCACTGCGTCTGCCCGATGCGCAGTGCGGAAGATCCCGAG

AGACTCGCCAATTATGCGAGAAAGCTAGCATCTGCCGCAGGAAAAGTCCTGGACAGAAACATCTCTGGAA

AGATCGGGGACTTACAAGCAGTAATGGCCGTGCCAGACACGGAGACGCCAACATTCTGCTTACACACAGA

CGTCTCATGTAGACAGAGAGCAGACGTCGCTATATACCAAGACGTCTATGCTGTACACGCACCCACGTCG

CTATACCACCAGGCGATTAAAGGGGTCCGAGTGGCGTACTGGGTTGGGTTCGACACAACCCCGTTCATGT

ACAATGCCATGGCGGGTGCCTACCCCTCATACTCGACAAACTGGGCAGATGAGCAGGTACTGAAGGCTAA

GAACATAGGATTATGTTCAACAGACCTGACGGAAGGTAGACGAGGCAAGTTGTCTATTATGAGAGGGAAA

AAGCTAAAACCGTGCGACCGTGTGCTGTTCTCAGTAGGGTCAACGCTCTACCCGGAAAGCCGCAAGCTAC

TTAAGAGCTGGCACCTGCCATCGGTGTTCCATTTAAAGGGCAAACTCAGCTTCACATGCCGCTGTGATAC

AGTGGTTTCGTGTGAGGGCTACGTCGTTAAGAGAATAACGATGAGCCCAGGCCTTTATGGAAAAACCACA

GGGTATGCGGTAACCCACCACGCAGACGGATTCCTGATGTGCAAGACTACCGACACGGTTGACGGCGAAA

GAATGTCATTCTCGGTGTGCACATACGTGCCGGCGACCATTTGTGATCAAATGACCGGCATCCTTGCTAC

AGAAGTCACGCCGGAGGATGCACAGAAGCTGTTGGTGGGGCTGAACCAGAGAATAGTGGTTAACGGCAGA

-continued

```
ACGCAACGGAATACGAACACCATGAAAAATTATCTGCTTCCCGTGGTCGCCCAAGCCTTCAGTAAGTGGG

CAAAGGAGTGCCGGAAAGACATGGAAGATGAAAAACTCCTGGGGGTCAGAGAAAGAACACTGACCTGCTG

CTGTCTATGGGCATTCAAGAAGCAGAAAACACACACGGTCTACAAGAGGCCTGATACCCAGTCAATTCAG

AAGGTTCAGGCCGAGTTTGACAGCTTTGTGGTACCGAGTCTGTGGTCGTCCGGGTTGTCAATCCCTTTGA

GGACTAGAATCAAATGGTTGTTAAGCAAGGTGCCAAAAACCGACCTGATCCCATACAGCGGAGACGCCCG

AGAAGCCCGGGACGCAGAAAAAGAAGCAGAGGAAGAACGAGAAGCAGAACTGACTCGCGAAGCCCTACCA

CCTCTACAGGCAGCACAGGAAGATGTTCAGGTCGAAATCGACGTGGAACAGCTTGAGGACAGAGCGGGCG

CAGGAATAATAGAGACTCCGAGAGGAGCTATCAAAGTTACTGCCCAACCAACAGACCACGTCGTGGGAGA

GTACCTGGTACTCTCCCCGCAGACCGTACTACGTAGCCAGAAGCTCAGTCTGATTCACGCTTTGGCGGAG

CAAGTGAAGACGTGCACGCACAACGGACGAGCAGGGAGGTATGCGGTCGAAGCGTACGACGGCCGAGTCC

TAGTGCCCTCAGGCTATGCAATCTCGCCTGAAGACTTCCAGAGTCTAAGCGAAAGCGCAACGATGGTGTA

TAACGAAAGAGAGTTCGTAAACAGAAAGCTACACCATATTGCGATGCACGGACCAGCCCTGAACACCGAC

GAAGAGTCGTATGAGCTGGTGAGGGCAGAGAGGACAGAACACGAGTACGTCTACGACGTGGATCAGAGAA

GATGCTGTAAGAAGGAAGAAGCCGCAGGACTGGTACTGGTGGGCGACTTGACTAATCCGCCCTACCACGA

ATTCGCATATGAAGGGCTAAAAATCCGCCCTGCCTGCCCATACAAAATTGCAGTCATAGGAGTCTTCGGA

GTACCGGGATCTGGCAAGTCAGCTATTATCAAGAACCTAGTTACCAGGCAGGACCTGGTGACTAGCGGAA

AGAAAGAAAACTGCCAAGAAATCACCACCGACGTGATGAGACAGAGAGGTCTAGAGATATCTGCACGTAC

GGTTGACTCGCTGCTCTTGAATGGATGCAACAGACCAGTCGACGTGTTGTACGTAGACGAGGCGTTTGCG

TGCCACTCTGGAACGCTACTTGCTTTGATCGCCTTGGTGAGACCAAGGCAGAAAGTTGTACTTTGTGGTG

ACCCGAAGCAGTGCGGCTTCTTCAATATGATGCAGATGAAAGTCAACTATAATCACAACATCTGCACCCA

AGTGTACCACAAAAGTATCTCCAGGCGGTGTACACTGCCTGTGACCGCCATTGTGTCATCGTTGCATTAC

GAAGGCAAAATGCGCACTACGAATGAGTACAACAAGCCGATTGTAGTGGACACTACAGGCTCAACAAAAC

CTGACCCTGGAGACCTCGTGTTAACGTGCTTCAGAGGGTGGGTTAAACAACTGCAAATTGACTATCGTGG

ATACGAGGTCATGACAGCAGCCGCATCCCAAGGGTTAACCAGAAAAGGAGTTTACGCAGTTAGACAAAAA

GTTAATGAAAACCCGCTCTATGCATCAACGTCAGAGCACGTCAACGTACTCCTAACGCGTACGGAAGGTA

AACTGGTATGGAAGACACTTTCCGGCGACCCGTGGATAAAGACGCTGCAGAACCCACCGAAAGGAAACTT

CAAAGCAACTATTAAGGAGTGGGAGGTGGAGCATGCATCAATAATGGCGGGCATCTGCAGTCACCAAATG

ACCTTCGATACATTCCAAAATAAAGCCAACGTTTGTTGGGCTAAGAGCTTGGTCCCTATCCTCGAAACAG

CGGGGATAAAACTAAATGATAGGCAGTGGTCTCAGATAATTCAAGCCTTCAAAGAAGACAAAGCATACTC

ACCTGAAGTAGCCCTGAATGAAATATGTACGCGCATGTATGGGGTGGATCTAGACAGCGGGCTATTTTCT

AAACCGTTGGTGTCTGTGTATTACGCGGATAACCACTGGGATAATAGGCCTGGAGGGAAAATGTTCGGAT

TTAACCCCGAGGCAGCATCCATTCTAGAAAGAAAGTATCCATTCACAAAAGGGAAGTGGAACATCAACAA

GCAGATCTGCGTGACTACCAGGAGGATAGAAGACTTTAACCCTACCACCAACATCATACCGGCCAACAGG

AGACTACCACACTCATTAGTGGCCGAACACCGCCCAGTAAAAGGGGAAAGAATGGAATGGCTGGTTAACA

AGATAAACGGCCACCACGTGCTCCTGGTCAGTGGCTATAACCTTGCACTGCCTACTAAGAGAGTCACTTG

GGTAGCGCCGTTAGGTGTCCGCGGAGCGGACTACACATACAACCTAGAGTTGGGTCTGCCAGCAACGCTT

GGTAGGTATGACCTAGTGGTCATAAACATCCACACACCTTTTCGCATACACCATTACCAACAGTGCGTCG

ACCACGCAATGAAACTGCAAATGCTCGGGGGTGACTCATTGAGACTGCTCAAACCGGGCGGCTCTCTATT

GATCAGAGCATATGGTTACGCAGATAGAACCAGTGAACGAGTCATCTGCGTATTGGGACGCAAGTTTAGA

TCGTCTAGAGCGTTGAAACCACCATGTGTCACCAGCAACACTGAGATGTTTTTCCTATTCAGCAACTTTG
```

-continued

```
ACAATGGCAGAAGGAATTTCACAACTCATGTCATGAACAATCAACTGAATGCAGCCTTCGTAGGACAGGT
CACCCGAGCAGGATGTGCACCGTCGTACCGGGTAAAACGCATGGACATCGCGAAGAACGATGAAGAGTGC
GTAGTCAACGCCGCTAACCCTCGCGGGTTACCGGGTGGCGGTGTTTGCAAGGCAGTATACAAAAAATGGC
CGGAGTCCTTTAAGAACAGTGCAACACCAGTGGGAACCGCAAAAACAGTTATGTGCGGTACGTATCCAGT
AATCCACGCTGTTGGACCAAACTTCTCTAATTATTCGGAGTCTGAAGGGGACCGGGAATTGGCAGCTGCC
TATCGAGAAGTCGCAAAGGAAGTAACTAGGCTGGGAGTAAATAGTGTAGCTATACCTCTCCTCTCCACAG
GTGTATACTCAGGAGGGAAAGACAGGCTGACCCAGTCACTGAACCACCTCTTTACAGCCATGGACTCGAC
GGATGCAGACGTGGTCATCTACTGCCGCGACAAAGAATGGGAGAAGAAAATATCTGAGGCCATACAGATG
CGGACCCAAGTAGAGCTGCTGGATGAGCACATCTCCATAGACTGCGATATTGTTCGCGTGCACCCTGACA
GCAGCTTGGCAGGCAGAAAAGGATACAGCACCACGGAAGGCGCACTGTACTCATATCTAGAAGGGACCCG
TTTTCATCAGACGGCTGTGGATATGGCGGAGATACATACTATGTGGCCAAAGCAAACAGAGGCCAATGAG
CAAGTCTGCCTATATGCCCTGGGGGAAAGTATTGAATCGATCAGGCAGAAATGCCCGGTGGATGATGCAG
ACGCATCATCTCCCCCCAAAACTGTCCCGTGCCTTTGCCGTTACGCTATGACTCCAGAACGCGTCACCCG
GCTTCGCATGAACCACGTCACAAGCATAATTGTGTGTTCTTCGTTTCCCCTCCCAAAGTACAAAATAGAA
GGAGTGCAAAAAGTCAAATGCTCTAAGGTAATGCTATTTGACCAACGTGCCATCGCGCGTAAGTCCAA
GGGCTTATAGAGGTGCCGCTGCCGGTAACCTTGCGGCCGTGTCTGATTGGGTAATGAGCACCGTACCTGT
CGCGCCGCCCAGAAGAAGGCGAGGGAGAAACCTGACTGTGACATGTGACGAGAGAGAAGGGAATATAACA
CCCATGGCTAGCGTCCGATTCTTTAGGGCAGAGCTGTGTCCGGTCGTACAAGAAACAGCGGAGACGCGTG
ACACAGCAATGTCTCTTCAGGCACCACCGAGTACCGCCACGGAACCGAATCATCCGCCGATCTCCTTCGG
AGCATCAAGCGAGACGTTCCCCATTACATTTGGGGACTTCAACGAAGGAGAAATCGAAAGCTTGTCTTCT
GAGCTACTAACTTTCGGAGACTTCTTACCAGGAGAAGTGGATGACTTGACAGACAGCGACTGGTCCACGT
GCTCAGACACGGACGACGAGTTAAGACTAGACAGGGCAGGTGGGTATATATTCTCGTCGGACACCGGTCC
AGGTCATTTACAACAGAAGTCAGTACGCCAGTCAGTGCTGCCGGTGAACACCCTGGAGGAAGTCCACGAG
GAGAAGTGTTACCCACCTAAGCTGGATGAAGCAAAGGAGCAACTATTACTTAAGAAACTCCAGGAGAGTG
CATCCATGGCCAACAGAAGCAGGTATCAGTCGCGCAAAGTAGAAAACATGAAAGCAGCAATCATCCAGAG
ACTAAAGAGAGGCTGTAGACTATACTTAATGTCAGAGACCCCAAAAGTCCCTACTTACCGGACTACATAT
CCGGCGCCTGTGTACTCGCCTCCGATCAACGTCCGATTGTCCAATCCCGAGTCCGCAGTGGCAGCATGCA
ATGAGTTCTTAGCTAGAAACTATCCAACTGTCTCATCATACCAAATTACCGACGAGTATGATGCATATCT
AGACATGGTGGACGGGTCGGAGAGTTGCCTGGACCGAGCGACATTCAATCCGTCAAAACTCAGGAGCTAC
CCGAAACAGCACGCTTACCACGCGCCCTCCATCAGAAGCGCTGTACCGTCCCCATTCCAGAACACACTAC
AGAATGTACTGGCAGCAGCCACGAAAAGAAACTGCAACGTCACACAGATGAGGGAATTACCCACTTTGGA
CTCAGCAGTATTCAACGTGGAGTGTTTCAAAAAATTCGCATGCAACCAAGAATACTGGGAAGAATTTGCT
GCCAGCCCTATTAGGATAACAACTGAGAATTTAGCAACCTATGTTACTAAACTAAAAGGGCAAAAGCAG
CAGCGCTATTCGCAAAAACCCATAATCTACTGCCACTACAGGAAGTACCAATGGATAGGTTCACAGTAGA
TATGAAAAGGGACGTAAAGGTGACTCCTGGTACAAAGCATACAGAGGAAAGACCTAAGGTGCAGGTTATA
CAGGCGGCTGAACCCTTGGCGACAGCATACCTATGTGGGATTCACAGAGAGCTGGTTAGGAGGCTGAACG
CCGTCCTCCTACCCAATGTACATACACTATTTGACATGTCTGCCGAGGATTTCGATGCCATCATAGCCGC
ACACTTTAAGCCAGGAGACACTGTTTTGGAAACGGACATAGCCTCCTTTGATAAGAGCCAAGATGATTCA
CTTGCGCTTACTGCTTTGATGCTGTTAGAGGATTTAGGGGTGGATCACTCCCTGCTGGACTTGATAGAGG
CTGCTTTCGGAGAGATTTCCAGCTGTCACCTACCGACAGGTACGCGCTTCAAGTTCGGCGCCATGATGAA
ATCAGGTATGTTCCTAACTCTGTTCGTCAACACATTGTTAAACATCACCATCGCCAGCCGAGTGCTGGAA
```

-continued

```
GATCGTCTGACAAAATCCGCGTGCGCGGCCTTCATCGGCGACGACAACATAATACATGGAGTCGTCTCCG
ATGAATTGATGGCAGCCAGATGTGCCACTTGGATGAACATGGAAGTGAAGATCATAGATGCAGTTGTATC
CTTGAAAGCCCCTTACTTTTGTGGAGGGTTTATACTGCACGATACTGTGACAGGAACAGCTTGCAGAGTG
GCAGACCCGCTAAAAAGGCTTTTTAAACTGGGCAAACCGCTAGCGGCAGGTGACGAACAAGATGAAGATA
GAAGACGAGCGCTGGCTGACGAAGTGATCAGATGGCAACGAACAGGGCTAATTGATGAGCTGGAGAAAGC
GGTATACTCTAGGTACGAAGTGCAGGGTATATCAGTTGTGGTAATGTCCATGGCCACCTTTGCAAGCTCC
AGATCCAACTTCGAGAAGCTCAGAGGACCCGTCATAACTTTGTACGGCGGTCCTAAATAGGTACGCACTA
CAGCTACCTATTTTGCAGAAGCCGACAGCAAGTATCTAAACACTAATCAGCTACAATGGAGTTCATCCCA
ACCCAAACTTTTTACAATAGGAGGTACCAGCCTCGACCCTGGACTCCGCGCCCTACTATCCAAGTCATCA
GGCCCAGACCGCGCCCTCAGAGGCAAGCTGGGCAACTTGCCCAGCTGATCTCAGCAGTTAATAAACTGAC
AATGCGCGCGGTACCACAACAGAAGCCACGCAGGAATCGGAAGAATAAGAAGCAAAAGCAAAACAACAG
GCGCCACAAAACAACACAAATCAAAAGAAGCAGCCACCTAAAAAGAAACCGGCTCAAAAGAAAAAGAAGC
CGGGCCGCAGAGAGGATGTGCATGAAAATCGAAAATGATTGTATTTTCGAAGTCAAGCACGAAGGTAA
GGTAACAGGTTACGCGTGCCTGGTGGGGACAAAGTAATGAAACCAGCACACGTAAAGGGGACCATCGAT
AACGCGGACCTGGCCAAACTGGCCTTTAAGCGGTCATCTAAGTATGACCTTGAATGCGCGCAGATACCCG
TGCACATGAAGTCCGACGCTTCGAAGTTCACCCATGAGAAACCGGAGGGGTACTACAACTGGCACCACGG
AGCAGTACAGTACTCAGGAGGCCGGTTCACCATCCCTACAGGTGCTGGCAAACCAGGGACAGCGGCAGA
CCGATCTTCGACAACAAGGGACGCGTGGTGGCCATAGTCTTAGGAGGAGCTAATGAAGGAGCCCGTACAG
CCCTCTCGGTGGTGACCTGGAATAAAGACATTGTCACTAAAATCACCCCCGAGGGGGCCGAAGAGTGGAG
TCTTGCCATCCCAGTTATGTGCCTGTTGGCAAACACCACGTTCCCTGCTCCCAGCCCCTTGCACGCCC
TGCTGCTACGAAAAGGAACCGGAGGAAACCCTACGCATGCTTGAGGACAACGTCATGAGACCTGGGTACT
ATCAGCTGCTACAAGCATCCTTAACATGTTCTCCCCACCGCCAGCGACGCAGCACCAAGGACAACTTCAA
TGTCTATAAAGCCACAAGACCATACTTAGCTCACTGTCCCGACTGTGGAGAAGGGCACTCGTGCCATAGT
CCCGTAGCACTAGAACGCATCAGAAATGAAGCGACAGACGGGACGCTGAAAATCCAGGTCTCCTTGCAAA
TCGGAATAAAGACGGATGACAGCCACGATTGGACCAAGCTGCGTTATATGGACAACCACATGCCAGCAGA
CGCAGAGAGGGCGGGGCTATTTGTAAGAACATCAGCACCGTGTACGATTACTGGAACAATGGGACACTTC
ATCCTGGCCCGATGTCCAAAAGGGGAAACTCTGACGGTGGGATTCACTGACAGTAGGAAGATTAGTCACT
CATGTACGCACCCATTTCACCACGACCCTCCTGTGATAGGTCGGGAAAAATTCCATTCCCGACCGCAGCA
CGGTAAAGAGCTACCTTGCAGCACGTACGTGCAGAGCACCGCCGCAACTACCGAGGAGATAGAGGTACAC
ATGCCCCCAGACACCCCTGATCGCACATTAATGTCACAACAGTCCGGCAACGTAAAGATCACAGTCAATG
GCCAGACGGTGCGGTACAAGTGTAATTGCGGTGGCTCAAATGAAGGACTAACAACTACAGACAAAGTGAT
TAATAACTGCAAGGTTGATCAATGTCATGCCGCGGTCACCAATCACAAAAAGTGGCAGTATAACTCCCCT
CTGGTCCCGCGTAATGCTGAACTTGGGGACCGAAAAGGAAAAATTCACATCCCGTTTCCGCTGGCAAATG
TAACATGCAGGGTGCCTAAAGCAAGGAACCCCACCGTGACGTACGGGAAAAACCAAGTCATCATGCTACT
GTATCCTGACCACCCAACACTCCTGTCCTACCGGAATATGGGAGAAGAACCAAACTATCAAGAAGAGTGG
GTGATGCATAAGAAGGAAGTCGTGCTAACCGTGCCGACTGAAGGGCTCGAGGTCACGTGGGCAACAACG
AGCCGTATAAGTATTGGCCGCAGTTATCTACAAACGGTACAGCCCATGGCCACCCGCATGAGATAATTCT
GTATTATTATGAGCTGTACCCCACTATGACTGTAGTAGTTGTGTCAGTGGCCACGTTCATACTCCTGTCG
ATGGTGGGTATGGCAGCGGGGATGTGCATGTGTGCACGACGCAGATGCATCACACCGTATGAACTGACAC
CAGGAGCTACCGTCCCTTTCCTGCTTAGCCTAATATGCTGCATCAGAACAGCTAAAGCGGCCACATACCA
```

-continued

AGAGGCTGCGATATACCTGTGGAACGAGCAGCAACCTTTGTTTTGGCTACAAGCCCTTATTCCGCTGGCA
GCCCTGATTGTTCTATGCAACTGTCTGAGACTCTTACCATGCTGCTGTAAAACGTTGGCTTTTTTAGCCG
TAATGAGCGTCGGTGCCCACACTGTGAGCGCGTACGAACACGTAACAGTGATCCCGAACACGGTGGGAGT
ACCGTATAAGACTCTAGTCAATAGACCTGGCTACAGCCCCATGGTATTGGAGATGGAACTACTGTCAGTC
ACTTTGGAGCCAACACTATCGCTTGATTACATCACGTGCGAGTACAAAACCGTCATCCCGTCTCCGTACG
TGAAGTGCTGCGGTACAGCAGAGTGCAAGGACAAAAACCTACCTGACTACAGCTGTAAGGTCTTCACCGG
CGTCTACCCATTTATGTGGGGCGGCGCCTACTGCTTCTGCGACGCTGAAAACACGCAGTTGAGCGAAGCA
CACGTGGAGAAGTCCGAATCATGCAAAACAGAATTTGCATCAGCATACAGGGCTCATACCGCATCTGCAT
CAGCTAAGCTCCGCGTCCTTTACCAAGGAAATAACATCACTGTAACTGCCTATGCAAACGGCGACCATGC
CGTCACAGTTAAGGACGCCAAATTCATTGTGGGGCCAATGTCTTCAGCCTGGACACCTTTCGACAACAAA
ATTGTGGTGTACAAAGGTGACGTCTATAACATGGACTACCCGCCCTTTGGCGCAGGAAGACCAGGACAAT
TTGGCGATATCCAAAGTCGCACACCTGAGAGTAAAGACGTCTATGCTAATACACAACTGGTACTGCAGAG
ACCGGCTGTGGGTACGGTACACGTGCCATACTCTCAGGCACCATCTGGCTTTAAGTATTGGCTAAAAGAA
CGCGGGGCGTCGCTGCAGCACACAGCACCATTTGGCTGCCAAATAGCAACAAACCCGGTAAGAGCGGTGA
ACTGCGCCGTAGGGAACATGCCCATCTCCATCGACATACCGGAAGCGGCCTTCACTAGGGTCGTCGACGC
GCCCTCTTTAACGGACATGTCGTGCGAGGTACCAGCCTGCACCCATTCCTCAGACTTTGGGGGCGTCGCC
ATTATTAAATATGCAGCCAGCAAGAAAGGCAAGTGTGCGGTGCATTCGATGACTAACGCCGTCACTATTC
GGGAAGCTGAGATAGAAGTTGAAGGGAATTCTCAGCTGCAAATCTCTTTCTCGACGGCCTTAGCCAGCGC
CGAATTCCGCGTACAAGTCTGTTCTACACAAGTACACTGTGCAGCCGAGTGCCACCCCCCGAAGGACCAC
ATAGTCAACTACCCGGCGTCACATACCACCCTCGGGGTCCAGGACATCTCCGCTACGGCGATGTCATGGG
TGCAGAAGATCACGGGAGGTGTGGGACTGGTTGTTGCTGTTGCCGCACTGATTCTAATCGTGGTGCTATG
CGTGTCGTTCAGCAGGCACTAACTTGACAATTAAGTATGAAGGTATATGTGTCCCCTAAGAGACACACTG
TACATAGCAAATAATCTATAGATCAAAGGGCTACGCAACCCCTGAATAGTAACAAAATACAAAATCACTA
AAAATTATAAAAACAGAAAAATACATAAATAGGTATACGTGTCCCCTAAGAGACACATTGTATGTAGGTG
ATAAGTATAGATCAAAGGGCCGAATAACCCCTGAATAGTAACAAAATATGAAAATCAATAAAAATCATAA
AATAGAAAAACCATAAACAGAAGTAGTTCAAAGGGCTATAAAACCCCTGAATAGTAACAAAACATAAAAT
TAATAAAAATCAAATGAATACCATAATTGGCAAACGGAAGAGATGTAGGTACTTAAGCTTCCTAAAAGCA
GCCGAACTCACTTTGAGAAGTAGGCATAGCATACCGAACTCTTCCACGATTCTCCGAACCCACAGGGACG
TAGGAGATGTTATTTTGTTTTTAATATTTCAAAAAAAAAAAAAAAAAAAAAAA

ZIKV Sequence H/PF/2013 as sequenced

SEQ ID NO: 78

CAGACTGCGACAGTTCGAGTTTGAAGCGAAAGCTAGCAACAGTATCAACAGGTTTTATTTTGGATTTGGA
AACGAGAGTTTCTGGTCATGAAAAACCCAAAAAAGAAATCCGGAGGATTCCGGATTGTCAATATGCTAAA
ACGCGGAGTAGCCCGTGTGAGCCCCTTTGGGGGCTTGAAGAGGCTGCCAGCCGGACTTCTGCTGGGTCAT
GGGCCCATCAGGATGGTCTTGGCGATTCTAGCCTTTTTGAGATTCACGGCAATCAAGCCATCACTGGGTC
TCATCAATAGATGGGGTTCAGTGGGGAAAAAAGAGGCTATGGAAATAATAAAGAAGTTCAAGAAAGATCT
GGCTGCCATGCTGAGAATAATCAATGCTAGGAAGGAGAAGAAGAGACGAGGCGCAGATACTAGTGTCGGA
ATTGTTGGCCTCCTGCTGACCACAGCTATGGCAGCGGAGGTCACTAGACGTGGGAGTGCATACTATATGT
ACTTGGACAGAAACGACGCTGGGGAGGCCATATCTTTTCCAACCACATTGGGGATGAATAAGTGTTATAT
ACAGATCATGGATCTTGGACACATGTGTGATGCCACCATGAGCTATGAATGCCCTATGCTGGATGAGGGG
GTGGAACCAGATGACGTCGATTGTTGGTGCAACACGACGTCAACTTGGGTTGTGTACGGAACCTGCCATC
ACAAAAAAGGTGAAGCACGGAGATCTAGAAGAGCTGTGACGCTCCCCTCCCATTCCACTAGGAAGCTGCA

-continued

```
AACGCGGTCGCAAACCTGGTTGGAATCAAGAGAATACACAAAGCACTTGATTAGAGTCGAAAATTGGATA

TTCAGGAACCCTGGCTTCGCGTTAGCAGCAGCTGCCATCGCTTGGCTTTTGGGAAGCTCAACGAGCCAAA

AAGTCATATACTTGGTCATGATACTGCTGATTGCCCCGGCATACAGCATCAGGTGCATAGGAGTCAGCAA

TAGGGACTTTGTGGAAGGTATGTCAGGTGGGACTTGGGTTGATGTTGTCTTGGAACATGGAGGTTGTGTC

ACCGTAATGGCACAGGACAAACCGACTGTCGACATAGAGCTGGTTACAACAACAGTCAGCAACATGGCGG

AGGTAAGATCCTACTGCTATGAGGCATCAATATCGGACATGGCTTCGGACAGCCGCTGCCCAACACAAGG

TGAAGCCTACCTTGACAAGCAATCAGACACTCAATATGTCTGCAAAAGAACGTTAGTGGACAGAGGCTGG

GGAAATGGATGTGGACTTTTTGGCAAAGGGAGCCTGGTGACATGCGCTAAGTTTGCATGCTCCAAGAAAA

TGACCGGGAAGAGCATCCAGCCAGAGAATCTGGAGTACCGGATAATGCTGTCAGTTCATGGCTCCCAGCA

CAGTGGGATGATCGTTAATGACACAGGACATGAAACTGATGAGAATAGAGCGAAGGTTGAGATAACGCCC

AATTCACCAAGAGCCGAAGCCACCCTGGGGGGTTTTGGAAGCCTAGGACTTGATTGTGAACCGAGGACAG

GCCTTGACTTTTCAGATTTGTATTACTTGACTATGAATAACAAGCACTGGTTGGTTCACAAGGAGTGGTT

CCACGACATTCCATTACCTTGGCACGCTGGGGCAGACACCGGAACTCCACACTGGAACAACAAAGAAGCA

CTGGTAGAGTTCAAGGACGCACATGCCAAAAGGCAAACTGTCGTGGTTCTAGGGAGTCAAGAAGGAGCAG

TTCACACGGCCCTTGCTGGAGCTCTGGAGGCTGAGATGGATGGTCCAAAGGCAAGGCTGTCCTCTGGCCA

CTTGAAATGTCGCCTGAAAATGGATAAACTTAGATTGAAGGGCGTGTCATACTCCTTGTGTACCGCAGCG

TTCACATTCACCAAGATCCCGGCTGAAACACTGCACGGGACAGTCACAGTGGAGGTACAGTACGCAGGGA

CAGATGGACCTTGCAAGGTTCCAGCTCAGATGGCGGTGGACATGCAAACTCTGACCCCAGTTGGGAGGTT

GATAACCGCTAACCCCGTAATCACTGAAAGCACTGAGAACTCTAAGATGATGCTGGAACTTGATCCACCA

TTTGGGGACTCTTACATTGTCATAGGAGTCGGGGAGAAGAAGATCACCCACCACTGGCACAGGAGTGGCA

GCACCATTGGAAAAGCATTTGAAGCCACTGTGAGAGGTGCCAAGAGAATGGCAGTCTTGGGAGACACAGC

CTGGGACTTTGGATCAGTTGGAGGCGCTCTCAACTCATTGGGCAAGGGCATCCATCAAATTTTTGGAGCA

GCTTTCAAATCATTGTTTGGAGGAATGTCCTGGTTCTCACAAATTCTCATTGGAACGTTGCTGATGTGGT

TGGGTCTGAACACAAAGAATGGATCTATTTCCCTTATGTGCTTGGCCTTAGGGGAGTGTTGATCTTCTT

ATCCACAGCTGTCTCTGCTGATGTGGGGTGCTCGGTGGACTTCTCAAAGAAGGAGACGAGATGCGGTACA

GGGGTGTTCGTCTATAACGACGTTGAAGCCTGGAGGGACAGGTACAAGTACCATCCTGACTCCCCCCGTA

GATTGGCAGCAGCAGTCAAGCAAGCCTGGAAGATGGTATCTGTGGGATCTCCTCTGTTTCAAGAATGGA

AAACATCATGTGGAGATCAGTAGAAGGGGAGCTCAACGCAATCCTGGAAGAGAATGGAGTTCAACTGACG

GTCGTTGTGGGATCTGTAAAAAACCCCATGTGGAGAGGTCCACAGAGATTGCCCGTGCCTGTGAACGAGC

TGCCCCACGGCTGGAAGGCTTGGGGGAAATCGTACTTCGTCAGAGCAGCAAAGACAAATAACAGCTTTGT

CGTGGATGGTGACACACTGAAGGAATGCCCACTCAAACATAGAGCATGGAACAGCTTTCTTGTGGAGGAT

CATGGGTTCGGGGTATTTCACACTAGTGTCTGGCTCAAGGTTAGAGAAGATTATTCATTAGAGTGTGATC

CAGCCGTTATTGGAACAGCTGTTAAGGGAAAGGAGGCTGTACACAGTGATCTAGGCTACTGGATTGAGAG

TGAGAAGAATGACACATGGAGGCTGAAGAGGGCCCATCTGATCGAGATGAAAACATGTGAATGGCCAAAG

TCCCACACATTGTGGACAGATGGAATAGAAGAGAGTGATCTGATCATACCCAAGTCTTTAGCTGGGCCAC

TCAGCCATCACAATACCAGAGAGGGCTACAGGACCCAAATGAAAGGGCCATGGCACAGTGAAGAGCTTGA

AATTCGGTTTGAGGAATGCCCAGGCACTAAGGTCCACGTGGAGGAAACATGTGGAACAAGAGGACCATCT

CTGAGATCAACCACTGCAAGCGGAAGGGTGATCGAGGAATGGTGCTGCAGGGAGTGCACAATGCCCCCAC

TGTCGTTCCGGGCTAAAGATGGCTGTTGGTATGGAATGGAGATAAGGCCCAGGAAAGAACCAGAAAGTAA

CTTAGTAAGGTCAATGGTGACTGCAGGATCAACTGATCACATGGATCACTTCTCCCTTGGAGTGCTTGTG
```

-continued
ATTCTGCTCATGGTGCAGGAAGGGCTGAAGAAGAGAATGACCACAAAGATCATCATAAGCACATCGATGG

CAGTGCTGGTAGCTATGATCCTGGGAGGATTTTCAATGAGTGACCTGGCTAAGCTTGCAATTTTGATGGG

TGCCACCTTCGCGGAAATGAACACTGGAGGAGATGTAGCTCATCTGGCGCTGATAGCGGCATTCAAAGTC

AGACCAGCGTTGCTGGTATCTTTCATCTTCAGAGCTAATTGGACACCCCGTGAAAGCATGCTGCTGGCCT

TGGCCTCGTGTCTTTTGCAAACTGCGATCTCCGCCTTGGAAGGCGACCTGATGGTTCTCATCAATGGTTT

TGCTTTGGCCTGGTTGGCAATACGAGCGATGGTTGTTCCACGCACTGATAACATCACCTTGGCAATCCTG

GCTGCTCTGACACCACTGGCCCGGGGCACACTGCTTGTGGCGTGGAGAGCAGGCCTTGCTACTTGCGGGG

GGTTTATGCTCCTCTCTCTGAAGGGAAAAGGCAGTGTGAAGAAGAACTTACCATTTGTCATGGCCCTGGG

ACTAACCGCTGTGAGGCTGGTCGACCCCATCAACGTGGTGGGACTGCTGTTGCTCACAAGGAGTGGGAAG

CGGAGCTGGCCCCCTAGCGAAGTACTCACAGCTGTTGGCCTGATATGCGCATTGGCTGGAGGGTTCGCCA

AGGCAGATATAGAGATGGCTGGGCCCATGGCCGCGGTCGGTCTGCTAATTGTCAGTTACGTGGTCTCAGG

AAAGAGTGTGGACATGTACATTGAAAGAGCAGGTGACATCACATGGGAAAAAGATGCGGAAGTCACTGGA

AACAGTCCCCGGCTCGATGTGGCGCTAGATGAGAGTGGTGATTTCTCCCTGGTGGAGGATGACGGTCCCC

CCATGAGAGAGATCATACTCAAGGTGGTCCTGATGACCATCTGTGGCATGAACCCAATAGCCATACCCTT

TGCAGCTGGAGCGTGGTACGTATACGTGAAGACTGGAAAAAGGAGTGGTGCTCTATGGGATGTGCCTGCT

CCCAAGGAAGTAAAAAAGGGGGAGACCACAGATGGAGTGTACAGAGTAATGACTCGTAGACTGCTAGGTT

CAACACAAGTTGGAGTGGGAGTTATGCAAGAGGGGGTCTTTCACACTATGTGGCACGTCACAAAAGGATC

CGCGCTGAGAAGCGGTGAAGGGAGACTTGATCCATACTGGGGAGATGTCAAGCAGGATCTGGTGTCATAC

TGTGGTCCATGGAAGCTAGATGCCGCCTGGGACGGGCACAGCGAGGTGCAGCTCTTGGCCGTGCCCCCCG

GAGAGAGAGCGAGGAACATCCAGACTCTGCCCGGAATATTTAAGACAAAGGATGGGACATTGGAGCGGT

TGCGCTGGATTACCCAGCAGGAACTTCAGGATCTCCAATCCTAGACAAGTGTGGGAGAGTGATAGGACTT

TATGGCAATGGGGTCGTGATCAAAAATGGGAGTTATGTTAGTGCCATCACCCAAGGGAGGAGGGAGGAAG

AGACTCCTGTTGAGTGCTTCGAGCCTTCGATGCTGAAGAAGAAGCAGCTAACTGTCTTAGACTTGCATCC

TGGAGCTGGGAAAACCAGGAGAGTTCTTCCTGAAATAGTCCGTGAAGCCATAAAAACAAGACTCCGTACT

GTGATCTTAGCTCCAACCAGGGTTGTCGCTGCTGAAATGGAGGAAGCCCTTAGAGGGCTTCCAGTGCGTT

ATATGACAACAGCAGTCAATGTCACCCACTCTGGAACAGAAATCGTCGACTTAATGTGCCATGCCACCTT

CACTTCACGTCTACTACAGCCAATCAGAGTCCCCAACTATAATCTGTATATTATGGATGAGGCCCACTTC

ACAGATCCCTCAAGTATAGCAGCAAGAGGATACATTTCAACAAGGGTTGAGATGGGCGAGGCGGCTGCCA

TCTTCATGACCGCCACGCCACCAGGAACCCGTGACGCATTTCCGGACTCCAACTCACCAATTATGGACAC

CGAAGTGGAAGTCCCAGAGAGAGCCTGGAGCTCAGGCTTTGATTGGGTGACGGATCATTCTGGAAAAACA

GTTTGGTTTGTTCCAAGCGTGAGGAACGGCAATGAGATCGCAGCTTGTCTGACAAAGGCTGGAAAACGGG

TCATACAGCTCAGCAGAAAGACTTTTGAGACAGAGTTCCAGAAAACAAAACATCAAGAGTGGGACTTTGT

CGTGACAACTGACATTTCAGAGATGGGCGCCAACTTTAAAGCTGACCGTGTCATAGATTCCAGGAGATGC

CTAAAGCCGGTCATACTTGATGGCGAGAGAGTCATTCTGGCTGGACCCATGCCTGTCACACATGCCAGCG

CTGCCCAGAGGAGGGGCGCATAGGCAGGAATCCCAACAAACCTGGAGATGAGTATCTGTATGGAGGTGG

GTGCGCAGAGACTGACGAAGACCATGCACACTGGCTTGAAGCAAGAATGCTCCTTGACAATATTTACCTC

CAAGATGGCCTCATAGCCTCGCTCTATCGACCTGAGGCCGACAAAGTAGCAGCCATTGAGGGAGAGTTCA

AGCTTAGGACGGAGCAAAGCAAGACCTTTGTGGAACTCATGAAAAGAGGAGATCTTCCTGTTTGGCTGGC

CTATCAGGTTGCATCTGCCGGAATAACCTACACAGATAGAAGATGGTGCTTTGATGGCACGACCAACAAC

ACCATAATGGAAGACAGTGTGCCGGCAGAGGTGTGGACCAGACACGAGAGAAAAGAGTGCTCAAACCGA

GGTGGATGGACGCCAGAGTTTGTTCAGATCATGCGGCCCTGAAGTCATTCAAGGAGTTTGCCGCTGGGAA

-continued

```
AAGAGGAGCGGCTTTTGGAGTGATGGAAGCCCTGGGAACACTGCCAGGACACATGACAGAGAGATTCCAG

GAAGCCATTGACAACCTCGCTGTGCTCATGCGGGCAGAGACTGGAAGCAGGCCTTACAAAGCCGCGGCGG

CCCAATTGCCGGAGACCCTAGAGACCATTATGCTTTTGGGGTTGCTGGGAACAGTCTCGCTGGGAATCTT

TTTCGTCTTGATGAGGAACAAGGGCATAGGGAAGATGGGCTTTGGAATGGTGACTCTTGGGGCCAGCGCA

TGGCTCATGTGGCTCTCGGAAATTGAGCCAGCCAGAATTGCATGTGTCCTCATTGTTGTGTTCCTATTGC

TGGTGGTGCTCATACCTGAGCCAGAAAAGCAAAGATCTCCCCAGGACAACCAAATGGCAATCATCATCAT

GGTAGCAGTAGGTCTTCTGGGCTTGATTACCGCCAATGAACTCGGATGGTTGGAGAGAACAAAGAGTGAC

CTAAGCCATCTAATGGGAAGGAGAGAGGAGGGGGCAACCATAGGATTCTCAATGGACATTGACCTGCGGC

CAGCCTCAGCTTGGGCCATCTATGCTGCCTTGACAACTTTCATTACCCCAGCCGTCCAACATGCAGTGAC

CACTTCATACAACAACTACTCCTTAATGGCGATGGCCACGCAAGCTGGAGTGTTGTTTGGTATGGGCAAA

GGGATGCCATTCTACGCATGGGACTTTGGAGTCCCGCTGCTAATGATAGGTTGCTACTCACAATTAACAC

CCCTGACCCTAATAGTGGCCATCATTTTGCTCGTGGCGCACTACATGTACTTGATCCCAGGGCTGCAGGC

AGCAGCTGCGCGTGCTGCCCAGAAGAGAACGGCAGCTGGCATCATGAAGAACCCTGTTGTGGATGGAATA

GTGGTGACTGACATTGACACAATGACAATTGACCCCCAAGTGGAGAAAAAGATGGGACAGGTGCTACTCA

TAGCAGTAGCCGTCTCCAGCGCCATACTGTCGCGGACCGCCTGGGGGTGGGGGAGGCTGGGCCCTGAT

CACAGCGGCAACTTCCACTTTGTGGGAAGGCTCTCCGAACAAGTACTGGAACTCCTCTACAGCCACTTCA

CTGTGTAACATTTTTAGGGGAAGTTACTTGGCTGGAGCTTCTCTAATCTACACAGTAACAAGAAACGCTG

GCTTGGTCAAGAGACGTGGGGGTGAACAGGAGAGACCCTGGGAGAGAAATGGAAGGCCCGCTTGAACCA

GATGTCGGCCCTGGAGTTCTACTCCTACAAAAAGTCAGGCATCACCGAGGTGTGCAGAGAAGAGGCCCGC

CGCGCCCTCAAGGACGGTGTGGCAACGGGAGGCCATGCTGTGTCCCGAGGAAGTGCAAAGCTGAGATGGT

TGGTGGAGCGGGGATACCTGCAGCCCTATGGAAAGGTCATTGATCTTGGATGTGGCAGAGGGGCTGGAG

TTACTACGCCGCCACCATCCGCAAAGTTCAAGAAGTGAAAGGATACACAAAAGGAGGCCCTGGTCATGAA

GAACCCATGTTGGTGCAAAGCTATGGGTGGAACATAGTCCGTCTTAAGAGTGGGGTGGACGTCTTTCATA

TGGCGGCTGAGCCGTGTGACACGTTGCTGTGTGACATAGGTGAGTCATCATCTAGTCCTGAAGTGGAAGA

AGCACGGACGCTCAGAGTCCTCTCCATGGTGGGGGATTGGCTTGAAAAAAGACCAGGAGCCTTTTGTATA

AAAGTGTTGTGCCCATACACCAGCACTATGATGGAAACCCTGGAGCGACTGCAGCGTAGGTATGGGGGAG

GACTGGTCAGAGTGCCACTCTCCCGCAACTCTACACATGAGATGTACTGGGTCTCTGGAGCGAAAAGCAA

CACCATAAAAAGTGTGTCCACCACGAGCCAGCTCCTCTTGGGGCGCATGGACGGGCCCAGGAGGCCAGTG

AAATATGAGGAGGATGTGAATCTCGGCTCTGGCACGCGGGCTGTGGTAAGCTGCGCTGAAGCTCCCAACA

TGAAGATCATTGGTAACCGCATTGAAAGGATCCGCAGTGAGCACGCGGAAACGTGGTTCTTTGACGAGAA

CCACCCATATAGGACATGGGCTTACCATGGAAGCTATGAGGCCCCCACACAAGGGTCAGCGTCCTCTCTA

ATAAACGGGGTTGTCAGGCTCCTGTCAAAACCCTGGGATGTGGTGACTGGAGTCACAGGAATAGCCATGA

CCGACACCACACCGTATGGTCAGCAAAGAGTTTTCAAGGAAAAAGTGGACACTAGGGTGCCAGACCCCCA

AGAAGGCACTCGTCAGGTTATGAGCATGGTCTCTTCCTGGTTGTGGAAAGAGCTAGGCAAACACAAACGG

CCACGAGTCTGTACCAAAGAAGAGTTCATCAACAAGGTTCGTAGCAATGCAGCATTAGGGGCAATATTTG

AAGAGGAAAAAGAGTGGAAGACTGCAGTGGAAGCTGTGAACGATCCAAGGTTCTGGGCTCTAGTGGACAA

GGAAAGAGAGCACCACCTGAGAGGAGAGTGCCAGAGTTGTGTGTACAACATGATGGGAAAAAGAGAAAAG

AAACAAGGGGAATTTGGAAAGGCCAAGGGCAGCCGCGCCATCTGGTATATGTGGCTAGGGGCTAGATTTC

TAGAGTTCGAAGCCCTTGGATTCTTGAACGAGGATCACTGGATGGGGAGAGAGAACTCAGGAGGTGGTGT

TGAAGGGCTGGATTACAAAGACTCGGATATGTCCTAGAAGAGATGAGTCGCATACCAGGAGGAAGGATG
```

-continued

```
TATGCAGATGACACTGCTGGCTGGGACACCCGCATCAGCAGGTTTGATCTGGAGAATGAAGCTCTAATCA

CCAACCAAATGGAGAAAGGGCACAGGGCCTTGGCATTGGCCATAATCAAGTACACATACCAAAACAAAGT

GGTAAAGGTCCTTAGACCAGCTGAAAAAGGGAAGACAGTTATGGACATTATTTCGAGACAAGACCAAAGG

GGGAGCGGACAAGTTGTCACTTACGCTCTTAACACATTTACCAACCTAGTGGTGCAACTCATTCGGAATA

TGGAGGCTGAGGAAGTTCTAGAGATGCAAGACTTGTGGCTGCTGCGGAGGTCAGAGAAAGTGACCAACTG

GTTGCAGAGCAACGGATGGATAGGCTCAAACGAATGGCAGTCAGTGGAGATGATTGCGTTGTGAAGCCA

ATTGATGATAGGTTTGCACATGCCCTCAGGTTCTTGAATGATATGGGAAAAGTTAGGAAGGACACACAAG

AGTGGAAACCCTCAACTGGATGGGACAACTGGGAAGAAGTTCCGTTTTGCTCCCACCACTTCAACAAGCT

CCATCTCAAGGACGGGAGGTCCATTGTGGTTCCCTGCCGCCACCAAGATGAACTGATTGGCCGGGCCCGC

GTCTCTCCAGGGGCGGGATGGAGCATCCGGGAGACTGCTTGCCTAGCAAAATCATATGCGCAAATGTGGC

AGCTCCTTTATTTCCACAGAAGGGACCTCCGACTGATGGCCAATGCCATTTGTTCATCTGTGCCAGTTGA

CTGGGTTCCAACTGGGAGAACTACCTGGTCAATCCATGGAAAGGGAGAATGGATGACCACTGAAGACATG

CTTGTGGTGTGGAACAGAGTGTGGATTGAGGAGAACGACCACATGGAAGACAAGACCCCAGTTACGAAAT

GGACAGACATTCCCTATTTGGGAAAAAGGGAAGACTTGTGGTGTGGATCTCTCATAGGGCACAGACCGCG

CACCACCTGGGCTGAGAACATTAAAAACACAGTCAACATGGTGCGCAGGATCATAGGTGATGAAGAAAG

TACATGGACTACCTATCCACCCAAGTTCGCTACTTGGGTGAAGAAGGGTCTACACCTGGAGTGCTGTAAG

CACCAATCTTAGTGTTGTCAGGCCTGCTAGTCAGCCACAGCTTGGGGAAAGCTGTGCAGCCTGTGACCCC

CCCAGGAGAAGCTGGGAAACCAAGCCTATAGTCAGGCCGAGAACGCCATGGCACCGAAGAAGCCATGCTG

CCTGTGAGCCCCTCAGAGGACACTGAGTCAAAAAACCCCACGCGCTTGGAGGCGCAGGATGGGAAAAGAA

GGTGGCGACCTTCCCCACCCTTCAATCTGGGGCCTGAACTGGAGATCAGCTGTGGATCTCCAGAAGAGGG

ACTAGTGGTTAGAGGAGACCCCCCGGAAAACGCAAAACAGCATATTGACGCTGGGAAAGACCAGAGACTC

CATGAGTTTCCACCACGCTGGCCGCCAGGCACAGATCGCCGAATAGCGGCGGCCGGTGTGGGG
```

AHZ13508.1, Zika virus polyprotein from Polynesian outbreak (H/PF/2013)
SEQ ID NO: 79

MKNPKKKSGGFRIVNMLKRGVARVSPFGGLKRLPAGLLLGHGPIRMVLAILAFLRFTAIKPSLGLINRWGS

VGKKEAMEIIKKFKKDLAAMLRIINARKEKKRRGADTSVGIVGLLLTTAMAAEVTRRGSAYYMYLDRNDA

GEAISFPTTLGMNKCYIQIMDLGHMCDATMSYECPMLDEGVEPDDVDCWCNTTSTWVVYGTCHHKKGEAR

RSRRAVTLPSHSTRKLQTRSQTWLESREYTKHLIRVENWIFRNPGFALAAAAIAWLLGSSTSQKVIYLVM

ILLIAPAYSIRCIGVSNRDFVEGMSGGTWVDVVLEHGGCVTVMAQDKPTVDIELVTTTVSNMAEVRSYCY

EASISDMASDSRCPTQGEAYLDKQSDTQYVCKRTLVDRGWGNGCGLFGKGSLVTCAKFACSKKMTGKSIQ

PENLEYRIMLSVHGSQHSGMIVNDTGHETDENRAKVEITPNSPRAEATLGGFGSLGLDCEPRTGLDFSDL

YYLTMNNKHWLVHKEWFHDIPLPWHAGADTGTPHWNNKEALVEFKDAHAKRQTVVVLGSQEGAVHTALAG

ALEAEMDGAKGRLSSGHLKCRLKMDKLRLKGVSYSLCTAAFTFTKIPAETLHGTVTVEVQYAGTDGPCKV

PAQMAVDMQTLTPVGRLITANPVITESTENSKMMLELDPPFGDSYIVIGVGEKKITHHWHRSGSTIGKAF

EATVRGAKRMAVLGDTAWDFGSVGGALNSLGKGIHQIFGAAFKSLFGGMSWFSQILIGTLLMWLGLNTKN

GSISLMCLALGGVLIFLSTAVSADVGCSVDFSKKETRCGTGVFVYNDVEAWRDRYKYHPDSPRRLAAAVK

QAWEDGICGISSVSRMENIMWRSVEGELNAILEENGVQLTVVVGSVKNPMWRGPQRLPVPVNELPHGWKA

WGKSYFVRAAKTNNSFVVDGDTLKECPLKHRAWNSFLVEDHGFGVFHTSVWLKVREDYSLECDPAVIGTA

VKGKEAVHSDLGYWIESEKNDTWRLKRAHLIEMKTCEWPKSHTLWTDGIEESDLIIPKSLAGPLSHHNTR

EGYRTQMKGPWHSEELEIRFEECPGTKVHVEETCGTRGPSLRSTTASGRVIEEWCCRECTMPPLSFRAKD

GCWYGMEIRPRKEPESNLVRSMVTAGSTDHMDHFSLGVLVILLMVQEGLKKRMTTKIIISTSMAVLVAMI

LGGFSMSDLAKLAILMGATFAEMNTGGDVAHLALIAAFKVRPALLVSFIFRANWTPRESMLLALASCLLQ

-continued

TAISALEGDLMVLINGFALAWLAIRAMVVPRTDNITLAILAALTPLARGTLLVAWRAGLATCGGFMLLSL

KGKGSVKKNLPFVMALGLTAVRLVDPINVVGLLLLTRSGKRSWPPSEVLTAVGLICALAGGFAKADIEMA

GPMAAVGLLIVSYVVSGKSVDMYIERAGDITWEKDAEVTGNSPRLDVALDESGDFSLVEDDGPPMREIIL

KWLMTICGMNPIAIPFAAGAWYVYVKTGKRSGALWDVPAPKEVKKGETTDGVYRVMTRRLLGSTQVGVGV

MQEGVFHTMWHVTKGSALRSGEGRLDPYWGDVKQDLVSYCGPWKLDAAWDGHSEVQLLAVPPGERARNIQ

TLPGIFKTKDGDIGAVALDYPAGTSGSPILDKCGRVIGLYGNGVVIKNGSYVSAITQGRREEETPVECFE

PSMLKKKQLTVLDLHPGAGKTRRVLPEIVREAIKTRLRTVILAPTRVVAAEMEEALRGLPVRYMTTAVNV

THSGTEIVDLMCHATFTSRLLQPIRVPNYNLYIMDEAHFTDPSSIAARGYISTRVEMGEAAAIFMTATPP

GTRDAFPDSNSPIMDTEVEVPERAWSSGFDWVTDHSGKTVWFVPSVRNGNEIAACLTKAGKRVIQLSRKT

FETEFQKTKHQEWDFVVTTDISEMGANFKADRVIDSRRCLKPVILDGERVILAGPMPVTHASAAQRRGRI

GRNPNKPGDEYLYGGGCAETDEDHAHWLEARMLLDNIYLQDGLIASLYRPEADKVAAIEGEFKLRTEQRK

TFVELMKRGDLPVWLAYQVASAGITYTDRRWCFDGTTNNTIMEDSVPAEVWTRHGEKRVLKPRWMDARVC

SDHAALKSFKEFAAGKRGAAFGVMEALGTLPGHMTERFQEAIDNLAVLMRAETGSRPYKAAAAQLPETLE

TIMLLGLLGTVSLGIFFVLMRNKGIGKMGFGMVTLGASAWLMWLSEIEPARIACVLIVVFLLLVVLIPEP

EKQRSPQDNQMAIIIMVAVGLLGLITANELGWLERTKSDLSHLMGRREEGATIGFSMDIDLRPASAWAIY

AALTTFITPAVQHAVTTSYNNYSLMAMATQAGVLFGMGKGMPFYAWDFGVPLLMIGCYSQLTPLTLIVAI

ILLVAHYMYLIPGLQAAAARAAQKRTAAGIMKNPVVDGIVVTDIDTMTIDPQVEKKMGQVLLIAVAVSSA

ILSRTAWGWGEAGALITAATSTLWEGSPNKYWNSSTATSLCNIFRGSYLAGASLIYTVTRNAGLVKRRGG

GTGETLGEKWKARLNQMSALEFYSYKKSGITEVCREEARRALKDGVATGGHAVSRGSAKLRWLVERGYLQ

PYGKVIDLGCGRGGWSYYAATIRKVQEVKGYTKGGPGHEEPMLVQSYGWNIVRLKSGVDVFHMAAEPCDT

LLCDIGESSSSPEVEEARTLRVLSMVGDWLEKRPGAFCIKVLCPYTSTMMETLERLQRRYGGGLVRVPLS

RNSTHEMYWVSGAKSNTIKSVSTTSQLLLGRMDGPRRPVKYEEDVNLGSGTRAVVSCAEAPNMKIIGNRI

ERIRSEHAETWFFDENHPYRTWAYHGSYEAPTQGSASSLINGVVRLLSKPWDVVTGVTGIAMTDTTPYGQ

QRVFKEKVDTRVPDPQEGTRQVMSMVSSWLWKELGKHKRPRVCTKEEFINKVRSNAALGAIFEEEKEWKT

AVEAVNDPRFWALVDKEREHHLRGECQSCVYNMMGKREKKQGEFGKAKGSRAIWYMWLGARFLEFEALGF

LNEDHWMGRENSGGGVEGLGLQRLGYVLEEMSRIPGGRMYADDTAGWDTRISRFDLENEALITNQMEKGH

RALALAIIKYTYQNKVVKVLRPAEKGKTVMDIISRQDQRGSGQVVTYALNTFTNLVVQLIRNMEAEEVLE

MQDLWLLRRSEKVTNWLQSNGWDRLKRMAVSGDDCVVKPIDDRFAHALRFLNDMGKVRKDTQEWKPSTGW

DNWEEVPFCSHHFNKLHLKDGRSIVVPCRHQDELIGRARVSPGAGWSIRETACLAKSYAQMWQLLYFHRR

DLRLMANAICSSVPVDWVPTGRTTWSIHGKGEWMTTEDMLVVWNRVWIEENDHMEDKTPVTKWTDIPYLG

KREDLWCGSLIGHRPRTTWAENIKNTVNMVRRIIGDEEKYMDYLSTQVRYLGEEGSTPGVL

9320_Zika_PF_1F
                                          SEQ ID NO: 80
ttaggatCcGTTGTTGATCTGTGTGAAT 9321_Zika_PF_1R
                                          SEQ ID NO: 81
taactcgagCGTACACAACCCAAGTT 9322_Zika_PF_2F
                                          SEQ ID NO: 82
ttaggatccTCACTAGACGTGGGAGTG 9323_Zika_PF_2R
                                          SEQ ID NO: 83
taactcgagAAGCCATGTCYGATATTGAT -continued

| | |
|---|---|
| 9324_Zika_PF_3F<br>ttaggatccGCATACAGCATCAGGTG | SEQ ID NO: 84 |
| 9325_Zika_PF_3R<br>taactcgagTGTGGAGTTCCGGTGTCT | SEQ ID NO: 85 |
| 9326_Zika_PF_4F<br>ttaggatccGAATAGAGCGAARGTTGAGATA | SEQ ID NO: 86 |
| 9327_Zika_PF_4R<br>taactcgAGTGGTGGGTGATCTTCTTCT | SEQ ID NO: 87 |
| 9328_Zika_PF_5F<br>ttaggatcCAGTCACAGTGGAGGTACAGTAC | SEQ ID NO: 88 |
| 9329_Zika_PF_5R<br>taactcgagCRCAGATACCATCTTCCC | SEQ ID NO: 89 |
| 9330_Zika_PF_6F<br>ttaggatCCCTTATGTGCTTGGCCTTAG | SEQ ID NO: 90 |
| 9331_Zika_PF_6R<br>taactcgagTCTTCAGCCTCCATGTG | SEQ ID NO: 91 |
| 9332_Zika_PF_7F<br>ttaggatccAATGCCCACTCAAACATAGA | SEQ ID NO: 92 |
| 9333_Zika_PF_7R<br>taactcgagTCATTCTCTTCTTCAGCCCTT | SEQ ID NO: 93 |
| 9334_Zika_PF_8F<br>ttaggatccAAGGGTGATCGAGGAAT | SEQ ID NO: 94 |
| 9335_Zika_PF_8R<br>taactcgagTTCCCTTCAGAGAGAGGAGC | SEQ ID NO: 95 |
| 9336_Zika_PF_9F<br>ttaggatccTCTTTTGCAAACTGCGATC | SEQ ID NO: 96 |
| 9337_Zika_PF_9R<br>taactcgagTCCAGCTGCAAAGGGTAT | SEQ ID NO: 97 |
| 9338_Zika_PF_10F<br>ttaggatccGTGTGGACATGTACATTGA | SEQ ID NO: 98 |
| 9339_Zika_PF_10R<br>taactcgagCCCATTGCCATAAAGTC | SEQ ID NO: 99 |
| 9340_Zika_PF_11F<br>ttaggatccTCATACTGTGGTCCATGGA | SEQ ID NO: 100 |
| 9341_Zika_PF_11R<br>taactcgagGCCCATCTCAACCCTTG | SEQ ID NO: 101 |
| 9342_Zika_PF_12F<br>ttaggatccTAGAGGGCTTCCAGTGC | SEQ ID NO: 102 |
| 9343_Zika_PF_12R<br>taactcgAGATACTCATCTCCAGGTTTGTTG | SEQ ID NO: 103 |

| | |
|---|---|
| 9344_Zika_PF_13F<br>ttaggatccGAAAACAAAACATCAAGAGTG | SEQ ID NO: 104 |
| 9345_Zika_PF_13R<br>taactcgagGAATCTCTCTGTCATGTGTCCT | SEQ ID NO: 105 |
| 9346_Zika_PF_14F<br>ttaggatccTTGATGGCACGACCAAC | SEQ ID NO: 106 |
| 9347_Zika_PF_14R<br>ttaggatccGTTGTTGATCTGTGTGAAT | SEQ ID NO: 107 |
| 9348_Zika_PF_15F<br>taactcgagCAGGTCAATGTCCATTG | SEQ ID NO: 108 |
| 9349_Zika_PF_15R<br>ttaggatccTGTTGTGTTCCTATTGCTGGT | SEQ ID NO: 109 |
| 9350_Zika_PF_16F<br>taactcgaGTGATCAGRGCCCCAGC | SEQ ID NO: 110 |
| 9351_Zika_PF_16R<br>ttaggatccTGCTGCCCAGAAGAGAA | SEQ ID NO: 111 |
| 9352_Zika_PF_17F<br>taactcgaGCACCAACAYGGGTTCTT | SEQ ID NO: 112 |
| 9353_Zika_PF_17R<br>ttaggatcCTCAAGGACGGTGTGGC | SEQ ID NO: 113 |
| 9354_Zika_PF_18F<br>taactcgagCAATGATCTTCATGTTGGG | SEQ ID NO: 114 |
| 9355_Zika_PF_18R<br>ttaggatccTATGGGGAGGACTGGT | SEQ ID NO: 115 |
| 9356_Zika_PF_19F<br>taactcGAGCCCAGAACCTTGGATC | SEQ ID NO: 116 |
| 9357_Zika_PF_19R<br>ttaggatcCAGACCCCCAAGAAGGC | SEQ ID NO: 117 |
| 9358_Zika_PF_20F<br>taactcgagCCCCTTTGGTCTTGTCT | SEQ ID NO: 118 |
| 9359_Zika_PF_20R<br>ttaggatccAGGAAGGATGTATGCAGATG | SEQ ID NO: 119 |
| 9360_Zika_PF_21F<br>taactcgagACATTTGCGCATATGATTTTG | SEQ ID NO: 120 |
| 9361_Zika_PF_21R<br>ttaggatccAGGAAGGACACACAAGAGT | SEQ ID NO: 121 |
| 9362_Zika_PF_22F<br>taactcgagACAGGCTGCACAGCTTT | SEQ ID NO: 122 |
| 9363_Zika_PF_22R<br>ttaggatccTCTCTCATAGGGCACAGAC | SEQ ID NO: 123 |

In some embodiments, the Zika virus has a polyprotein, including an envelope (E) protein, with an amino acid sequence provided by any one of SEQ ID NO: 14-69 or 78. In some embodiments, the polyprotein or E protein sequence is at least 80%, 81%, 82%, 83%, 84%, 85%, 86%, 87%, 88%, 89%, 90%, 91%, 92%. 93%, 94%, 95%, 96%, 97%, 98%, 99%, 99.5%, 99.6%, 99.7%, 99.8% or 99.9% identical to any one of SEQ ID NOs: 2-69 or 78.

The terms "identical" or percent "identity" in the context of two or more nucleic acids or amino acid sequences refer to two or more sequences or subsequences that are the same. Two sequences are "substantially identical" if two sequences have a specified percentage of amino acid residues or nucleotides that are the same (e.g., at least 80%, 85%, 90%, 95%, 96%, 97%, 98%, or 99% identity) over a specified region or over the entire sequence, when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length. In some embodiments, the identity exists over the length of a protein, such as the E protein.

For sequence comparison, typically one sequence acts as a reference sequence, to which test sequences are compared. Methods of alignment of sequences for comparison are well known in the art. See, e.g., by the local homology algorithm of Smith and Waterman (1970) Adv. Appl. Math. 2:482c, by the homology alignment algorithm of Needleman and Wunsch, J. Mol. Biol. 48:443, 1970, by the search for similarity method of Pearson and Lipman Proc. Natl. Acad. Sci. USA 85:2444, 1988, by computerized implementations of these algorithms (GAP, BESTFIT, FASTA, Jalview and TFASTA in the Wisconsin Genetics Software Package, Genetics Computer Group. 575 Science Dr., Madison. WI), by multi sequence alignment implementation using e.g. CLUSTALW (Larkin et al., (2007). Bioinformatics, 23, 2947-2948.) or MAFFT (Katoh & Toh 2008 Briefings in Bioinformatics 9:286-298), or by manual alignment and visual inspection (see. e.g., Brent et al., Current Protocols in Molecular Biology, John Wiley & Sons, Inc. (Ringbou ed., 2003)). Two examples of algorithms that are suitable for determining percent sequence identity and sequence similarity are the BLAST and BLAST 2.0 algorithms, which are described in Altschul et al., Nuc. Acids Res. 25:3389-3402, 1977 and Altschul et al., J. Mol. Biol. 215:403-410, 1990, respectively.

EXAMPLES

Example 1: Development of a Purification Process for Live Attenuated Chikungunya Virus Vaccine Produced in Vero Cells A downstream process was developed for the purification of infectious Chikungunya virus particles whereby non-infectious virus particles and aggregates are removed by the addition of protamine sulphate. The unexpected and novel purification properties of protamine sulphate (PS) were evaluated in purification processes for Chikungunya Virus (ChikV) as follows:

A downstream purification process for the attenuated Chikungunya virus mutant "Δ5nsP3" (as described by Hallengärd et al., 2014, supra and provided by SEQ ID NO: 77) produced under standard cell culture conditions in Vero cells was developed. The attenuated Δ5nsP3 Chikungunya virus was derived from the strain LR2006-OPY1, the complete genome of which is provided herein as SEQ ID NO: 72. Briefly, the downstream process consists of crude harvest filtration followed by concentration and diafiltration on a tangential flow filtration (TFF) system. Host cell DNA and host cell proteins were reduced by precipitation with protamine sulphate and by batch adsorption, respectively. Sucrose density gradient centrifugation was done as a final polishing step. Out of 16 roller bottles $1\times10^{12}$ total PFU were purified with an overall DSP process yield of 10-15% (~1 log 10 TCID50 loss). Sucrose gradient pool samples were characterized with regard to product-related impurities, such as hcDNA, HCP and endotoxins and met safety criteria.

Harvest of Vero Cell Culture Medium Containing ChikV Δ5nsP3

ChikV Δ5nsP3 was grown on Vero cells in roller bottles. A first harvest was performed after 24 hours post infection (hpi; day 1 harvest) and stored at 2-8° C. until further processing. After the first harvest, fresh medium was added and the roller bottles were returned to the incubator. A second harvest was done after 48 hours post infection (day 2 harvest) and stored at 2-8° C.

Filtration of Crude Cell Culture Harvest

At both harvest timepoints, the crude harvest was immediately filtered using a 0.2 µm filter capsule (GE ULTA™ CG, 2 inch). The filtered harvest after 48 hpi was pooled together with the 24 hpi harvest and the pooled filtered harvest material was immediately further processed by ultrafiltration.

Purification of ChikV Δ5nsP3 by Tangential Flow Filtration (TFF)

The pooled filtered harvest material was further processed by tangential flow filtration (TFF) in order to concentrate the harvest, reduce host cell proteins and replace the depleted cell culture medium with a defined buffer system (buffer exchange). A Millipore TFF system (Millipore Pellicon II mini membrane holder) equipped with a 100 kDa cutoff PES membrane module (Pellicon2 Biomax, 1000 cm$^2$) was used for concentration and buffer exchange. A Pellicon2 Biomax membrane module was mounted on the Pellicon II mini filter holder and the device was connected to a peristaltic pump. The system was first rinsed with ultra-pure water and then sanitized by recirculation of 0.1 M NaOH for 60 min. In case the system was not used immediately, it was stored in 0.1 M NaOH until use. Prior to use the system was rinsed with 1 L of RO-water followed by buffer A until the permeate pH value was constant at pH 7.4±0.2.

Adjustment of the ChikV Δ5nsP3 Harvest (pH, Salt)

The pooled filtered harvest material was adjusted to a final concentration of 25 mM Tris and 150 mM NaCl using stock solutions of both components (see Table 1). This adjustment was done to increase buffering capacity and to reduce unspecific adsorption to the membrane. The necessary volumes of stock solutions D (1 M Tris, pH 7.4) and E (4.5 M NaCl) were calculated as follows:

Volume of stock solution D (1 M Tris, pH 7.4) added to pooled harvest=Volume of pooled filtered harvest/40

Volume of stock solution E (4.5 M NaCl) added to pooled harvest=Volume of pooled filtered harvest/30

Example: 4 L harvest obtained from 20 RB (850 cm$^2$) would require addition of 100 mL stock solution D (1 M Tris, pH 7.4) and 133 mL stock solution E (4.5 M NaCl).

The calculated volumes of stock solution D and Buffer E were added to the pooled filtered harvest under gentle stirring. The adjusted harvest was then stirred using a magnetic stirrer for 5 minutes at room temperature.

Concentration and Diafiltration of the ChikV Δ5nsP3 Harvest by TFF

In a first step, the adjusted harvest material was concentrated approximately 10 fold. The feed flowrate was approximately 220 mL/min. The transmembrane flux at a transmembrane pressure of approximately 0.6 bar was in the range of 90±5 mL/min per 1000 cm$^2$ membrane. After concentration, the cell culture medium was exchanged against 25 mM Tris, 150 mM NaCl, pH 7.5, by continuous diafiltration with 6 volume exchanges. The diafiltration buffer was supplied to the feed vessel from a measuring cylinder by a second peristaltic pump set to a flowrate of approximately 90 mL/min. Minor flowrate adjustments of the second peristaltic pump in the range of ±10 mL/min were done manually to ensure a constant volume of harvest in the feed vessel. After 6 volume exchanges, diafiltration was stopped. The liquid remaining in the membrane module was recovered by pumping the module empty with air.

Sucrose Addition to Diafiltrated ChikV Δ5nsP3 Material

After diafiltration, sucrose stock solution H (50% (w/w) sucrose solution) was added to the diafiltrated material to achieve a final sucrose concentration of 10% (w/w). The volume of buffer H was calculated as follows:

Volume of stock solution H added (mL)=Volume (mL) of diafiltrated ChikV material×0.25 (dilution factor=1:4) (i.e., final sucrose concentration is 10%)

Example: 400 mL diafiltrated ChikV solution would require addition of 100 mL stock solution H (50% sucrose).

The calculated volume of solution H was added to the diafiltrated ChikV Δ5nsP3 material under gentle stirring and the solution was then stirred using a magnetic stirrer for a further 5 minutes at room temperature. (At this stage of the process the material can be either immediately further processed or stored frozen (←−65° C., hold step).)

DNA Reduction by Protamine Sulphate Precipitation

A DNA precipitation step using protamine sulphate (PS) was performed to reduce hcDNA. Protamine sulphate stock solution L (50 mg/mL PS in PBS) was added to the diafiltrated ChikV Δ5nsP3 material to a final nominal concentration of ~1.6 mg/mL. The necessary volume of stock solution L was calculated as follows:

Volume of stock solution L (50 mg/mL PS) added=Volume of diafiltrated ChikV Δ5nsP3 material in 10% sucrose/31

Example: 500 mL diafiltrated ChikV Δ5nsP3 solution in 10% sucrose would require addition of 16 mL stock solution L (50 mg/mL PS in PBS).

The protamine sulphate stock solution was added while stirring the ChikV Δ5nsP3 material using a magnetic stirrer followed by incubation at 2-8° C. for 30 minutes. After incubation, the precipitate was not removed. The material was immediately further processed by batch adsorption with Capto™ Core 700 chromatography media.

Batch Adsorption with Capto™ Core 700

To reduce HCPs, a batch adsorption step with Capto™ Core 700 (CC700) chromatography medium was performed after DNA precipitation. CC700 slurry (50% slurry in buffer A) was added directly to the protamine sulphate treated material. The required slurry volume was determined based on the volume of Δ5nsP3 ChikV harvest material (d1+d2) and was calculated as follows:

Volume of CC700 slurry added to PS-treated concentrated harvest (mL)=Volume of Δ5nsP3 ChikV harvest material (mL)×0.02 (dilution factor=1:50) (i.e., final concentration of CC700 is 1%)

After slurry addition, the material was incubated at 4° C. for 15 minutes under constant agitation using a magnetic stirrer. After incubation, the CC700 solid matter was allowed to settle by gravity for 10 minutes. The Δ5nsP3 ChikV material was then removed from the top of the solution in order to avoid blocking of the filter by the CaptoCore particles. The remaining CaptoCore particles and the DNA precipitate were then removed from the solution by filtration using a 0.2 μm Mini Kleenpak EKV filter capsule (Pall). The resulting filtrate was further processed by sucrose density gradient centrifugation.

Sucrose Density Gradient Centrifugation

Sucrose density gradient centrifugation (SGC) was used for final concentration and polishing of the Δ5nsP3 ChikV material. The Δ5nsP3 ChikV material was loaded on top of a solution consisting of three layers of sucrose with different densities. The three sucrose layers were selected based on a preliminary study which showed the formation of a linear sucrose gradient and good separation of the virus particles from residual contaminants. The optimal volumes of the sucrose solutions were determined empirically. The volumes of individual layers for a centrifugation at 500 mL scale are shown in Table 3.

TABLE 3

Sucrose concentrations and volumes (500 mL scale)

| Solution | Volume (mL) |
| --- | --- |
| Harvest with 10% sucrose | 360 |
| 15% sucrose | 40 |
| 35% sucrose | 40 |
| 50% sucrose | 60 |
| Total volume | 500 |

Preparation of the Sucrose Gradient

Figure 12A:
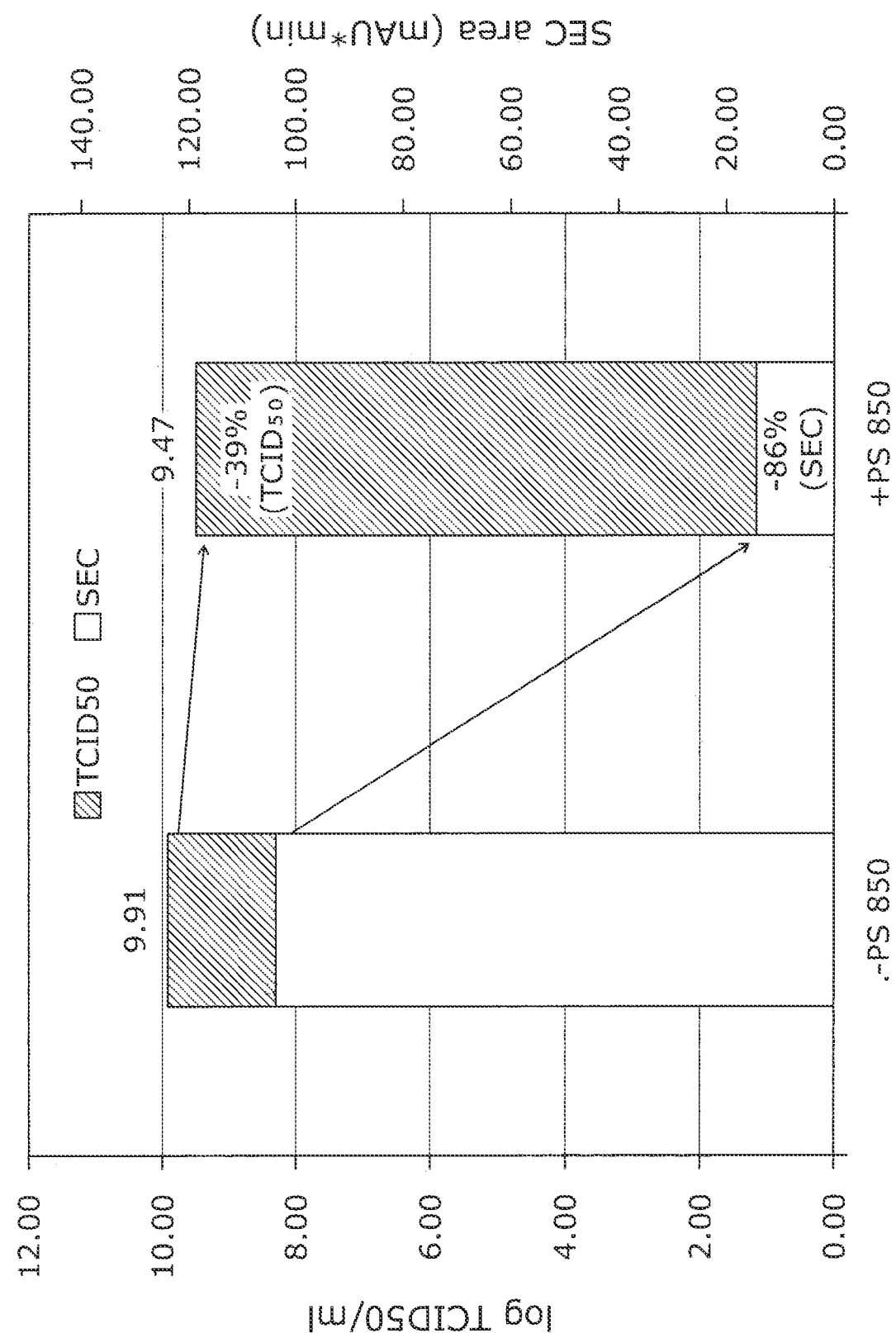
FIGS. 12A-12B: SEC area (mAU*min; right axis) and TCID$_{50}$ results (log TCID50/mL; left axis) of attenuated Δ5nsP3 ChikV production harvests before and after PS treatment. The grey portions of the bars indicate large losses in SEC area following PS treatment, but no corresponding change in the total number of infectious particles (indicated by black portions of the bars) (FIG. 12A); SEC profile of virus preparation before and after PS addition, showing a complete removal of large size virus aggregates by PS treatment as well as a reduction in host cell proteins (HCP) and LMW impurities (FIG. 12B).
Figure 12B:
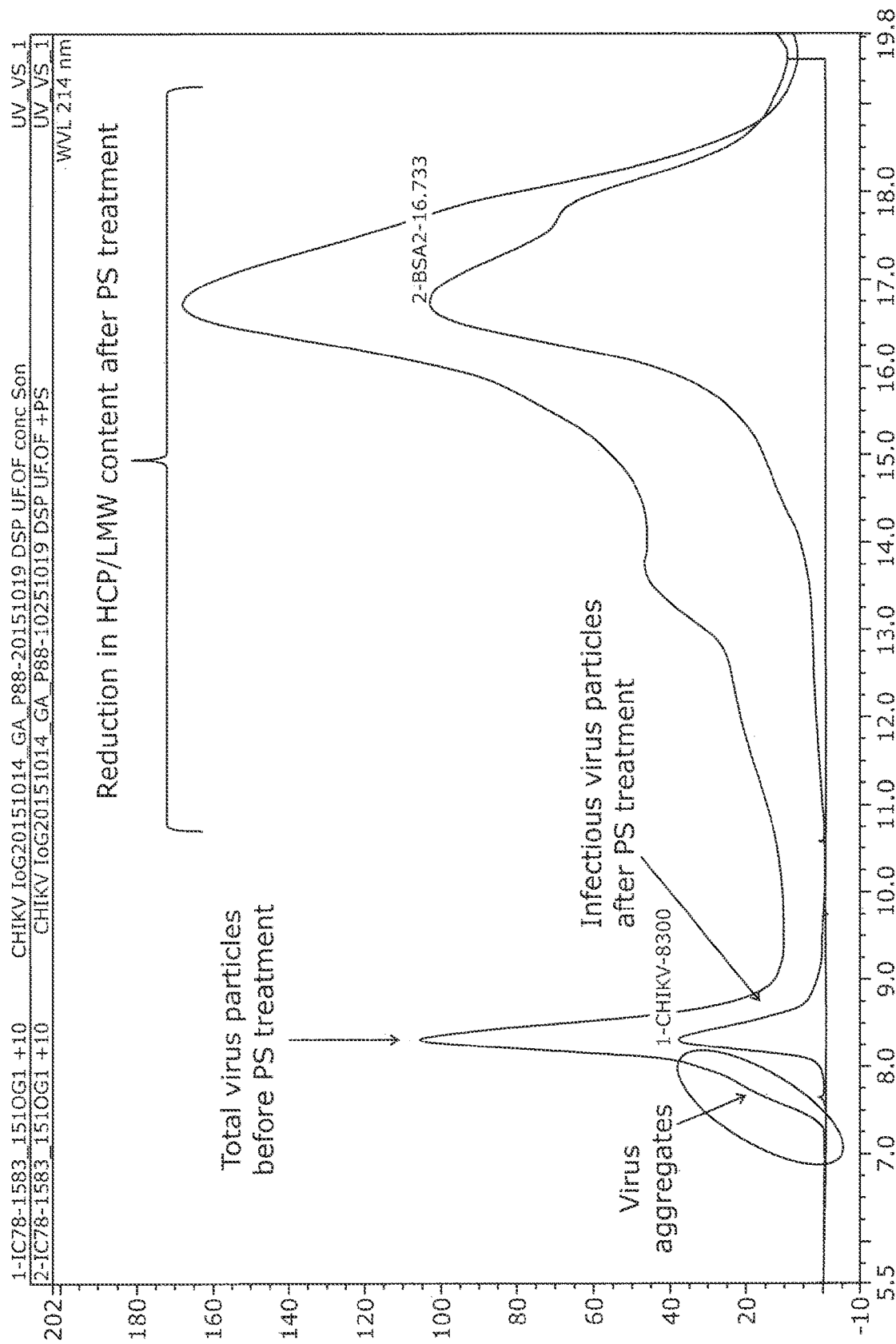
Figure 13:
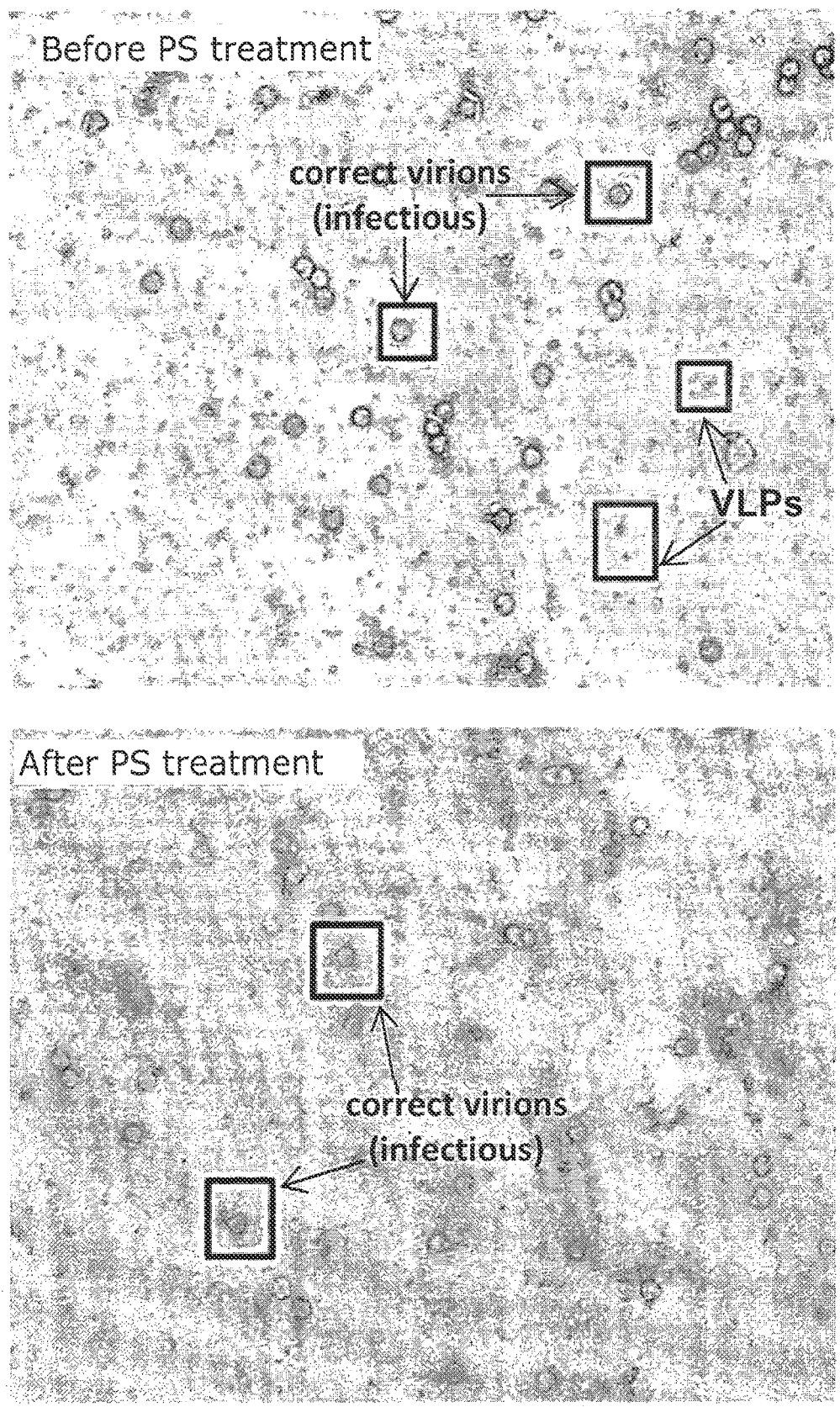
FIG. 13: Electron micrographs of attenuated Δ5nsP3 ChikV harvest before and after PS treatment.

The sucrose gradient bottles (500 mL) were prepared by underlaying the individual sucrose layers. A 3.5 mm ID plastic tube was attached to 60 cm of peristaltic pump tubing. The plastic tube was mounted on a laboratory stand using a clamp and placed into the centrifuge bottle. The nozzle of the plastic tube was placed at the bottom of the bottle. Using a peristaltic pump set to a flow rate of 25 mL per minute, the Δ5nsP3 ChikV material and the sucrose solutions were pumped into the cylinder. A measuring cylinder was used as a feed vessel. The first solution pumped was the Δ5nsP3 ChikV material as it had the lowest density (10% sucrose (w/w)). Following the addition of the Δ5nsP3 ChikV material, the sucrose solutions were pumped in ascending order starting with the lowest (15%), followed by the 35% sucrose solution and finishing with the highest density sucrose solution (50%). After all sucrose solutions were transferred, the plastic tubing was carefully removed in order not to disturb the layers. An illustration of a completed gradient is shown in FIG. 14.

Centrifugation

Prior to centrifugation a Beckman Avanti JXN-26 centrifuge equipped with rotor Beckman 10.500 was pre-cooled to 4° C. The prepared SG bottles were carefully transferred into the pre-cooled (4° C.) rotor so as to not to disturb the sucrose layers. The bottles were centrifuged at 10,000 rpm (~18,500 rcf) at 4° C. for 17-20 hours. (In case a different centrifuge system with a different rotor would be used, the necessary speed and centrifugation times would need to be calculated based on the k-factor in order to achieve comparable centrifugation efficiency.)

Sucrose Gradient Harvest

Harvesting of the sucrose gradient following centrifugation was done manually using a peristaltic pump. A 3.5 mm ID plastic tube attached to 60 cm of peristaltic pump tubing was used for harvesting the sucrose gradient. The 500 mL bottle containing the centrifuged gradient was mounted onto a laboratory stand in a tilted position (~12°) using a clamp. The plastic tubing was then placed into the bottle touching the bottom edge of the bottle and was fastened in position using a clamp. This resulted in a small gap of 1-2 mm between the tubing inlet and the bottom of the bottle (see FIG. 14). Using a peristaltic pump set to a flow rate of 60 mL per minute, the gradient was harvested and manually split into 5 mL fractions. A third of the bottle volume was harvested and the rest was discarded. The fractions were immediately tested by measuring UV absorbance in a plate reader as described below.

Analysis of Fractions by UV Absorbance and SEC-HPLC

UV absorbance measurement was used as primary method for analysis of the sucrose gradient fractions. Absorbance at 214, 280 and 260 nm was tested immediately after fractionation was completed. Briefly, a 100 μL sample of each fraction was transferred into a 96 well plate and absorbance at 214, 260 and 280 nm was measured using a plate reader. The absorbance values were plotted against the fraction number. A representative profile is shown in FIG. 11A. The Δ5nsP3 ChikV containing fractions were indicated by a peak in all three measured wavelengths (FIG. 11A, grey shaded area). The presence of impurities was indicated by an increase of the UV214 signal after the main peak. The fractions comprising the main peak were pooled from the peak start to the valley of the 214 nm curve. This method can be used as single method for pooling Δ5nsP3 ChikV fractions.

After identification of the virus containing fractions, the respective fractions were pooled. Pooling criteria for SGC fractions were based on UV 260 nm data, e.g. start of pooling at ~10% of peak maximum, end of pooling at ~30% of peak maximum. (Final pooling criteria at a manufacturing scale may need to be determined empirically.) The sucrose gradient pool was either stored at <−65° C. or immediately further formulated to drug substance (DS).

Size Exclusion Chromatography

The final pooled SGC fractions containing purified infectious Δ5nsP3 ChikV particles were analyzed for purity by SEC-HPLC. In brief, SEC was performed as follows: a Superose 6 10/300 Increase column (GE Healthcare) equilibrated with PBS+250 mM NaCl, pH 7.4 at 1 ml/min and 25° C., was used to detect ChikV particles at 214 nm detection wavelength in the pooled samples. SEC-HPLC is a semi-quantitative (relative yield) and qualitative (purity) method that separates intact virus particles from virus aggregates and host cell proteins (HCPs). The method cannot distinguish between infectious and non-infectious virus particles due to their identical retention time.

As shown in FIG. 11B, there were two defined peaks identified by SEC: the Δ5nsP3 ChikV peak and a peak corresponding to buffer components. The SGC step yield based on SEC-HPLC data for pooled fractions F6-F11 was estimated at ~70%. The final purity of the Δ5nsP3 ChikV SGC pool, based on SEC-HPLC analysis, was estimated at >95%.

SDS-PAGE and Silver Stain

SDS-PAGE silver stain was performed in order to qualitatively assess sample purity throughout the purification process from the first crude harvest through SGC. Briefly, ChikV process samples analyzed by SDS-PAGE/silver stain were diluted 1:1.33 with LDS buffer and were heated to 70° C. for 5 minutes. The samples were loaded onto 4-12% Bis-Tris Gels (NuPAGE). Silver staining was done using the Silver Express staining kit (Invitrogen).

A silver-stained gel of a representative ChikV Δ5nsP3 purification is shown in FIG. 11C. The viral proteins E1, E2 and C are marked on the right-hand side of the gel. The final SGC pool (fraction 7-fraction 11) is shown in lane 12. Note that a defined HCP band migrating between ChikV protein E2 and C still appears after CaptoCore700 treatment that has been identified as a single band in SDS-PAGE. This impurity is removed by sucrose gradient centrifugation, but can still be seen in fractions 13 and 14 (corresponding to lanes 14 and 15 of FIG. 11C).

Enrichment of Infectious Δ5nsP3 ChikV Particles by PS Treatment

Although generally used as a method of removing contaminating hcDNA, it was observed in the course of the present invention that PS treatment also removes virus aggregates and HCPs. Size exclusion chromatography (SEC-HPLC, as described above) was used throughout the purification process to determine the purity of the ChikV virus relative to impurities which also generate UV absorption.

As can be seen in FIG. 12B, treatment with PS reduces not only host cell proteins and low molecular weight contaminants of the Δ5nsP3 ChikV preparation, but also reduces the SEC area corresponding to virus products, including aggregates as indicated. A surprising finding, however, was that even a reduction of the total SEC area by 86% (in a representative experiment shown in FIG. 12A, grey portion of bars) did not result in a concomitant reduction in infectious virus particles as measured by TCID50 (FIG. 12A, left axis). Instead, even though a large percentage of virus particles were removed by PS treatment, the majority of infectious particles remained. This observation indicates that PS treatment selectively enriches infectious virus particles from a larger pool of total virus particles present in the crude harvest.

TCID50 was performed to quantify infectious virus particles during the course of the purification process and to assign an active virus titer to final drug substance and drug product samples. Briefly, Vero cells were seeded at $2 \times 10^4$ cells per well in 100 μL medium (EMEM with 2 mM L-Glutamine+5 FBS+1% antibiotic/antimycotic) in 96-well TC-treated flat-bottom plates and incubated overnight at 35° C./5% $CO_2$. On day two, Vero cell monolayers were infected by adding 100 μL of 1:10 serial dilutions of test samples to each of quintuplicate wells seeded with Vero cells and incubated at 35° C./5% $CO_2$. On day seven, plaques were counted by visualization under a microscope. The TCID50 was calculated according to the Reed & Münch endpoint calculation method (Reed, L. J.; Muench, H. (1938) A simple method of estimating fifty percent endpoints, The American Journal of Hygiene 27: 493-497).

Furthermore, electron microscopy of Δ5nsP3 ChikV samples before and after PS treatment showed that not only large aggregates but also smaller non-infectious virus-like particles (essentially not fully assembled particles lacking the RNA genome) were effectively removed by PS (FIG. 13).

This enrichment of infectious virus particles was also observed when analyzing day one and day two crude harvests separately. As presented in Table 4, the SEC area (total virus particles) of the day 1 harvest remains roughly the same after PS treatment; whereas a large decrease in virus peak area is seen for the day 2 harvest after PS treatment. This observation was confirmed by MALLS analysis of the virus preparation, wherein it was seen that a higher percentage of virus particles were of the correct size following PS treatment. Similarly to the results shown in FIG. 12, day 1 and day 2 harvests showed no reduction in infectious particles as measured by TCID50 following PS treatment, indicating that mainly non-infectious, immature and/or aggregated virus particles are removed during the PS treatment and infectious particles are enriched in the preparation.

The PS-treated samples were further purified by sucrose gradient centrifugation (see FIG. 14 for a schematic preparation of an optimized sucrose gradient). An optimal sucrose gradient was determined experimentally as shown in FIG. 15. Results of the further purification of PS-treated ChikV on the optimized sucrose gradient of the invention are shown in FIG. 15D.

TABLE 4

Overview of the process of Δ5nsP3 ChikV purification as described in Example 1. SEC-MALLS analysis of harvests before and after PS treatment shows the removal of larger virus particles (aggregates), an effect that is particularly pronounced for day 2 harvests.

| | | MALLS | | Infectious |
|---|---|---|---|---|
| | SEC Area [mAU*min] | Total particles/ mL | % correct size (20-40 nm) | particles TCID50 log 10 |
| Harvest 1 (H1) | 57 | 1.17E+11 | 49% | 10.2 |
| H1 + protamine sulphate | 53 | 1.33E+11 | 81% | 10.0 |
| Harvest 2 (H2) | 36 | 4.60E+09 | 3% | 7.9 |
| H2 + protamine sulphate | 2 | 8.80E+09 | 59% | 7.9 |

TABLE 4-continued

Overview of the process of Δ5nsP3 ChikV purification as described in Example 1. SEC-MALLS analysis of harvests before and after PS treatment shows the removal of larger virus particles (aggregates), an effect that is particularly pronounced for day 2 harvests.

| | | MALLS | | Infectious |
|---|---|---|---|---|
| | SEC Area [mAU*min] | Total particles/ mL | % correct size (20-40 nm) | particles TCID50 log 10 |
| Combined Harvests (C) | 67 | 2.60E+10 | 14% | 9.9 |
| C + protamine sulphate | 24 | 8.00E+10 | 72% | 10.1 |

Finally, an overview of the relative amounts of Δ5nsP3 ChikV particles and other components as measured by SEC-HPLC at various steps throughout the entire virus purification process from crude harvest (a) to the final SGC purified pool is presented in FIG. 16. In sum, not only are the vast majority of contaminants and undesired products removed by the process, infectious ChikV particles are highly purified. As shown by the previously presented data, the final preparation is a highly enriched preparation of infectious ChikV particles.

Drug Substance (DS) Formulation

The pooled SGC fractions are diluted with DS formulation buffer M (10 mM Tris, 5% Sucrose (w/w), 1% (10 mg/mL) rHSA, pH 7.4±0.2). The final target volume of DS should be in the range of approximately 2 L. Based on current data the estimated range of the dilution factor might be 1:20 to 1:50.

Final DS Sterile Filtration

The final DS was filtered under aseptic conditions in a laminar flow hood using a sterility grade 0.2 µm syringe filter (e.g. 0.2 µm Mini Kleenpak EKV filter capsule with 220 $cm^2$ filter surface, Pall).

Quantification of Host Cell DNA (hcDNA) Host Cell Protein (HCP) and Endotoxin The residual host cell DNA content of the sucrose gradient pool samples was determined by using the qPCR based assay. The DNA content in SGC pool was determined to be <0.002 ng/mL. The presence of residual host cell protein (HCP) from Vero cells was determined by ELISA. Residual host cell proteins present in the sucrose gradient pool samples were quantified using the Vero Cell HCP ELISA kit (Cygnus, F500). The residual host cell protein content in SGC pool was determined to be <200 ng/mL.

Endotoxin content of the SGC pool and DS was measured by Endosafe®-PTS™ system (Charles River). The system uses Limulus Amembocyte Lysate (LAL) reagents by a kinetic chromogenic methodology to measure color intensity directly related to the endotoxin content in a sample. Each cartridge contains precise amounts of a licensed LAL reagent, chromogenic substrate and an endotoxin control standard. Samples were diluted 1:100 in WFI. The SGC Pool F7-F11 was determined to be <5.00 EU/mL; likewise, the Drug Substance was also determined to have <5.00 EU/mL.

The following specifications for impurities in final Drug product were proposed: hcDNA <10 ng/dose; Endotoxins <50 EU/dose; HCP <200 ng/dose. These residual specifications would already be met in the highly concentrated SGC pool (~10 log TCID50/mL), which provides a high margin of safety considering the high dilution factor of SGC pool to final DP of >1:1000.

Figure 18:
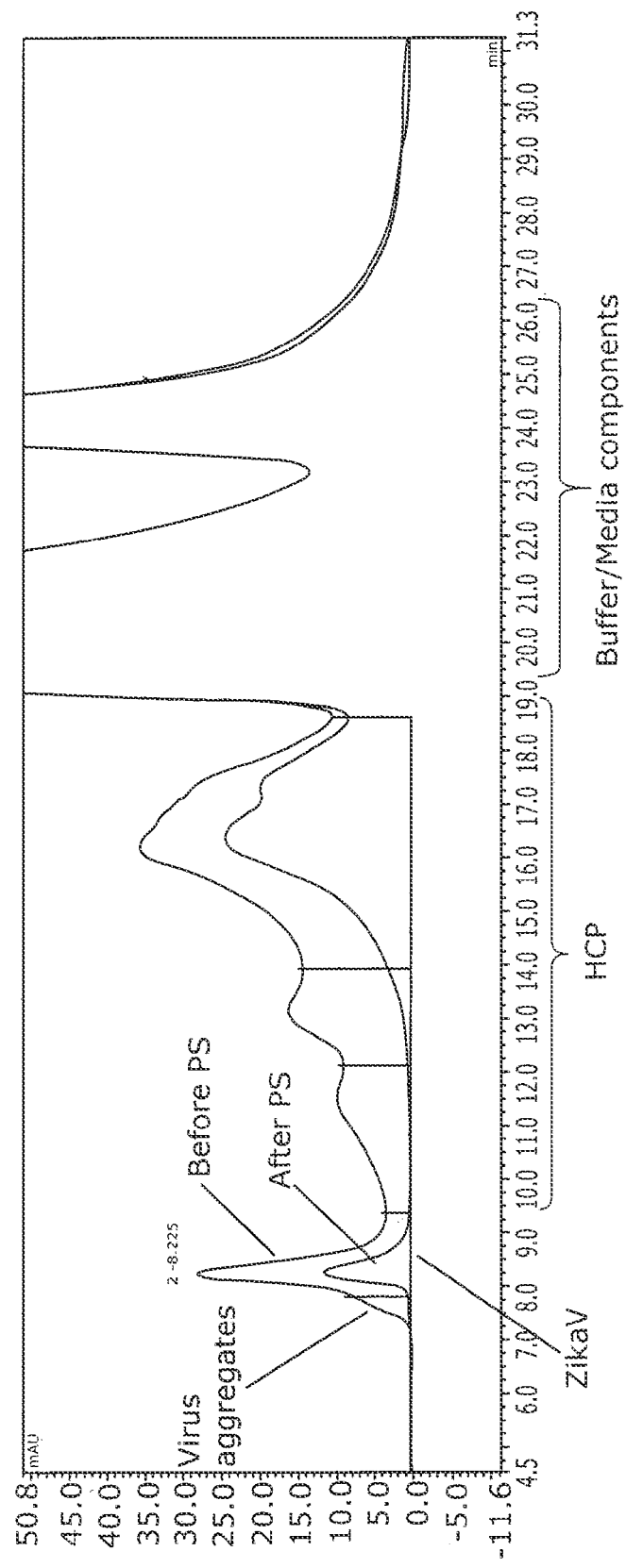
Figure 19:
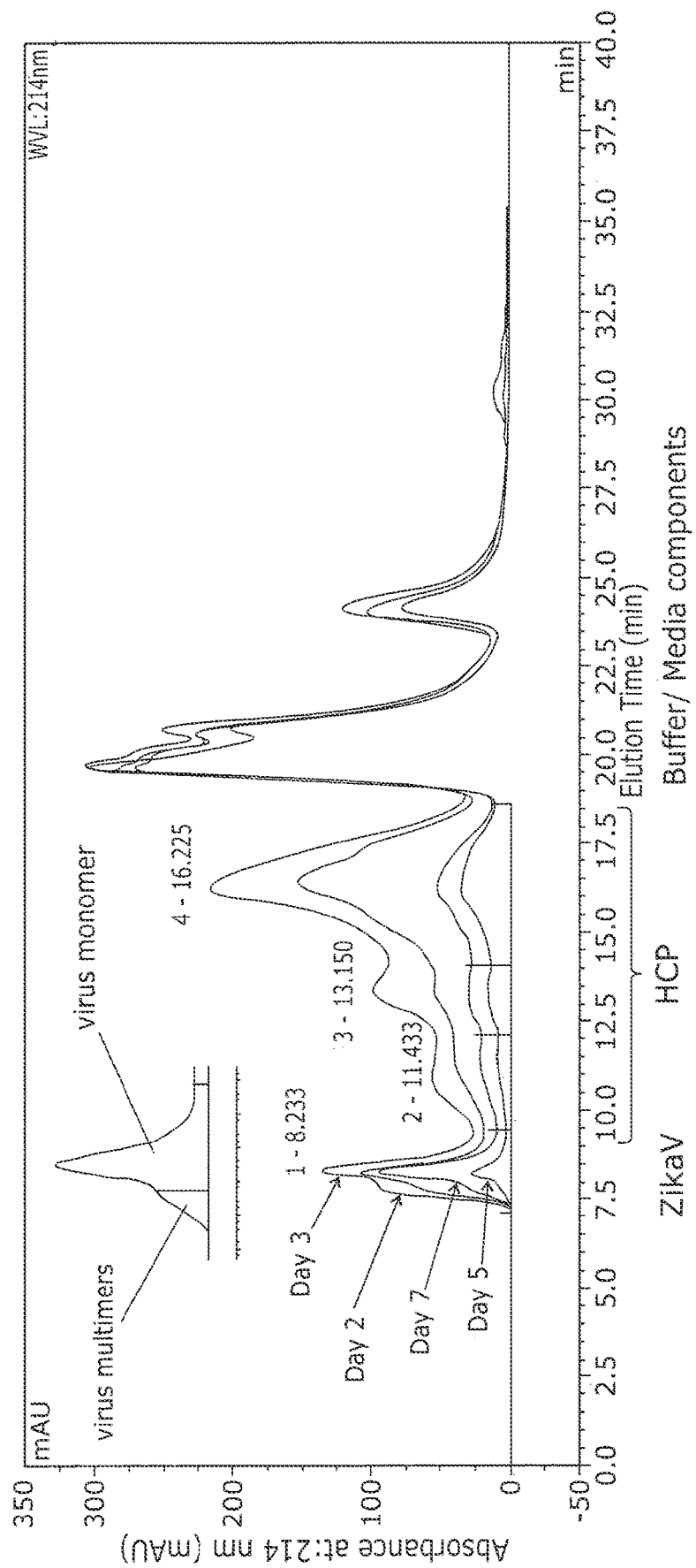
Figure 20:
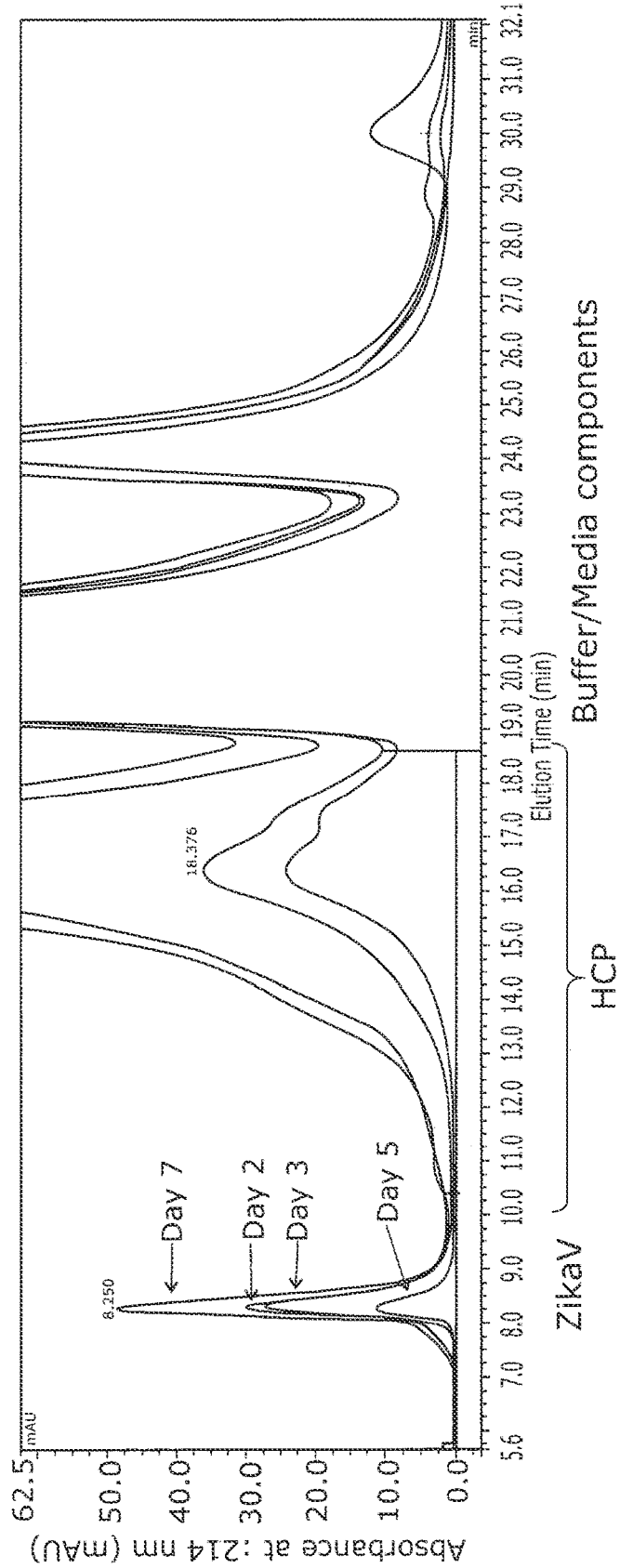
Figure 20:
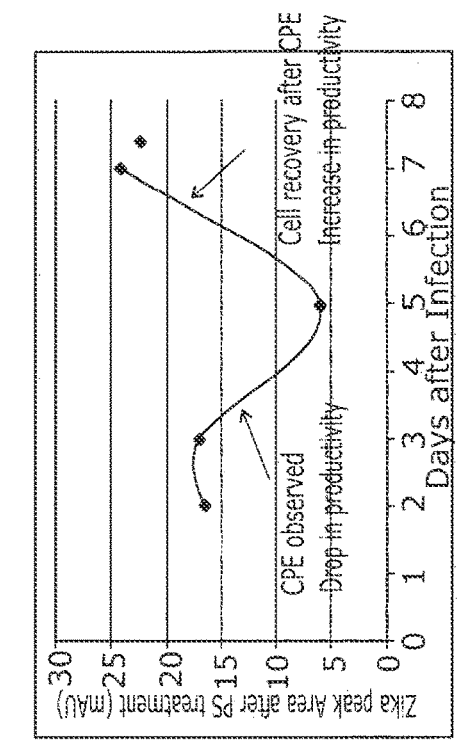

Example 2: Production of a Zika Drug Substance Suitable for Application as a Vaccine in Humans and Animals Materials and Methods For the production of ZikaV the JEV process platform (Srivastava et al., Vaccine 19 (2001) 4557-4565; U.S. Pat. No. 6,309,650B1) was used as a basis Small changes of certain process steps were adapted to ZikaV properties and to improve purity. A short summary of the process steps is outlined below (see also FIGS. 17A and B). Briefly, the unexpected and novel purification properties of protamine sulphate (PS) were evaluated in purification processes for Zika Virus similarly as found above. Again non-infectious virus particle aggregates, HCP and other LMW impurities were removed by PS precipitation as shown by removal of aggregate shoulder in SEC-HPLC and no loss of infectious virus titer by PS treatment (FIG. 18). Further optimization of the Zika purification protocol is provided below.

Upstream

Roller Bottle based Vero cell expansion (25×850 cm2 CellBind):
5% $CO_2$, 35° C., MEM+2 mM L-Glutamine+10% FBS
Infection with ZikaV research Master Seed Bank (rMSB) at MOI 0.01
Virus Production without serum
5% $CO_2$, 35° C., MEM+2 mM L-Glutamine
Multiple harvests (days 2, 3, 5 and 7) with re-feed
Sterile filtration of harvests and storage at 2-8° C. until further processing Downstream Pooling of harvests and concentration by ultrafiltration (100 kDa)
Stabilization of concentrated harvest (Tris/10% sucrose) for storage if required (−80° C.)
Removal of hcDNA by Protamine Sulphate (2 mg/mL)
Sucrose Gradient Purification (optimized three layered gradient)
Formaldehyde Inactivation (0.02%, 22° C., 10 days), neutralization with Na-metabisulfite
Dilution to DS antigen target content and formulation with Aluminium hydroxide (0.5 mg Al/mL)

Zika Virus Strain H/PF/2013 was originally isolated from a 51-year-old woman (accession number KJ776791.1, also SEQ ID NO: 13 herein) from French Polynesia. A sample was obtained from the European Virus Archive (EVAg; Ref-SKU: 001v-EVA1545). Based on this material, a research master seed bank (rMSB) was prepared on Vero cells as the cell substrate and the genomic sequence was checked by sequencing. Because the genomic sequence at the 5' and 3'flanking sequences of Zika virus strain H/PF/2013 was unknown, primers for sequencing were designed in those regions based on other Zika virus strains whereas the internal primers were designed from the published sequence (SEQ ID NOs: 80 to 123, see also Table A). The sequence obtained from the rMSB by use of these primers is provided by SEQ ID NO: 78. There was 100% overlap of the sequence with the published sequence of Zika Virus Strain H/PF/2013 (SEQ ID NO: 13). However, we sequenced additional regions 5' (an additional 40 bp) and 3 (an additional 160 bp) represented in SEQ ID NO: 78. In a preferred embodiment, the Zika virus of the invention comprises SEQ ID NO: 78. The genomic RNA is somewhat longer than the sequence according to SEQ ID NO: 78 (perhaps an additional 200 bp). Additionally, a Zika virus adapted to a host cell such as e.g. Vero cells may be expected to contain one or more mutations. For these reasons, the Zika virus of the current invention comprises the sequence of SEQ ID NO: 78 or, preferably, a sequence with at least 95%, 96%, 97%, 98%, or at least 99% sequence identity to the sequence provided by SEQ ID NO: 78. Furthermore, because the viral genome is likely to contain even further flanking regions to SEQ ID NO: 78; in one embodiment, the Zika virus of the invention contains the sequence of SEQ ID NO: 78 and optionally further comprises extensions at the 5' and/or 3' ends of at least 10, at least 20, at least 30, at least 40, at least 50, at least 60, at least 70, at least 80, at least 90, at least 100, at least 110, at least 120 or at least 130 nucleotides. In a preferred embodiment, the Zika virus comprises at least the coding sequence for the entire polyprotein of Zika Virus Strain H/PF/2013 of the invention i.e. the amino acid sequence of SEQ ID NO: 79 or a polyprotein with at least 95%, 96%, 97%, 98%, or at least 99% sequence identity to the sequence provided by SEQ ID NO: 79. Furthermore, the Zika virus comprises at least the coding sequence for the E-protein of Zika Virus Strain H/PF/2013 of the invention SEQ ID NO: 47 or an E-protein thereof with at least 95%, 96%, 97%, 98%, or at least 99% sequence identity to the sequence provided by SEQ ID NO: 47.

Virus Growth on Vero Cells

Vero cells were grown in Eagle's minimal essential medium (EMEM) containing 10% fetal bovine serum (FBS). Roller bottle cultures of Vero cell monolayers were infected with Zika Virus Strain H/PF/2013 at a multiplicity of infection (moi) of 0.01 plaque forming units (pfu) per cell. After 2 hours of virus adsorption, the cultures were washed 3 times with PBS and fed with EMEM without FBS and incubated at +35° C. with 5% $CO_2$. Infected Vero cell cultures were incubated until the virus titer reaches a desired level.

The culture medium was harvested at days 2, 3, 5 and 7 and were pooled from those harvest days and then centrifuged in a standard centrifuge. The supernatants were then filtered. Virus culture supernatants were concentrated by TFF ultrafiltration to remove cell culture media components and to reduce batch volume.

Evaluation of Harvest Procedure

The current JEV harvest process has scheduled harvests on days 3, 5, 7 and 9 post infection. To mimic the JEV process roller bottles were infected with ZIKV bank P4-FBS at an MOI of 0.01 in infection medium (MEM with 2% FBS+2 mM L-glutamine) for 2 hours. After removing the inoculum the cells were washed twice with PBS and 200 mL production medium (MEM+2 mM L-glutamine) was added.

After taking a sample on day 2 the first virus harvest was conducted on day 3 after infection. At this point significantly higher CPE could be observed compared to cells where virus was removed on day 2. Plaque assay analysis showed that the viral titers on day 2 were in the same range as for the standard harvesting schedule. However, starting with the day 3 harvest, the observed titers were significantly lower correlating with the increased CPE observed compared to the standard harvest schedule. On day 5 post infection no more living cells could be observed at all and the experiment was terminated with a final day 5 harvest.

TABLE 5

The calculated titers per plaque assay are summarized in the list below.

| | Log 10 PFU/mL |
|---|---|
| sample day 2 | 7.02 |
| harvest day 3 | 6.66 |
| harvest day 5 | 6.26 |

Figure 14:
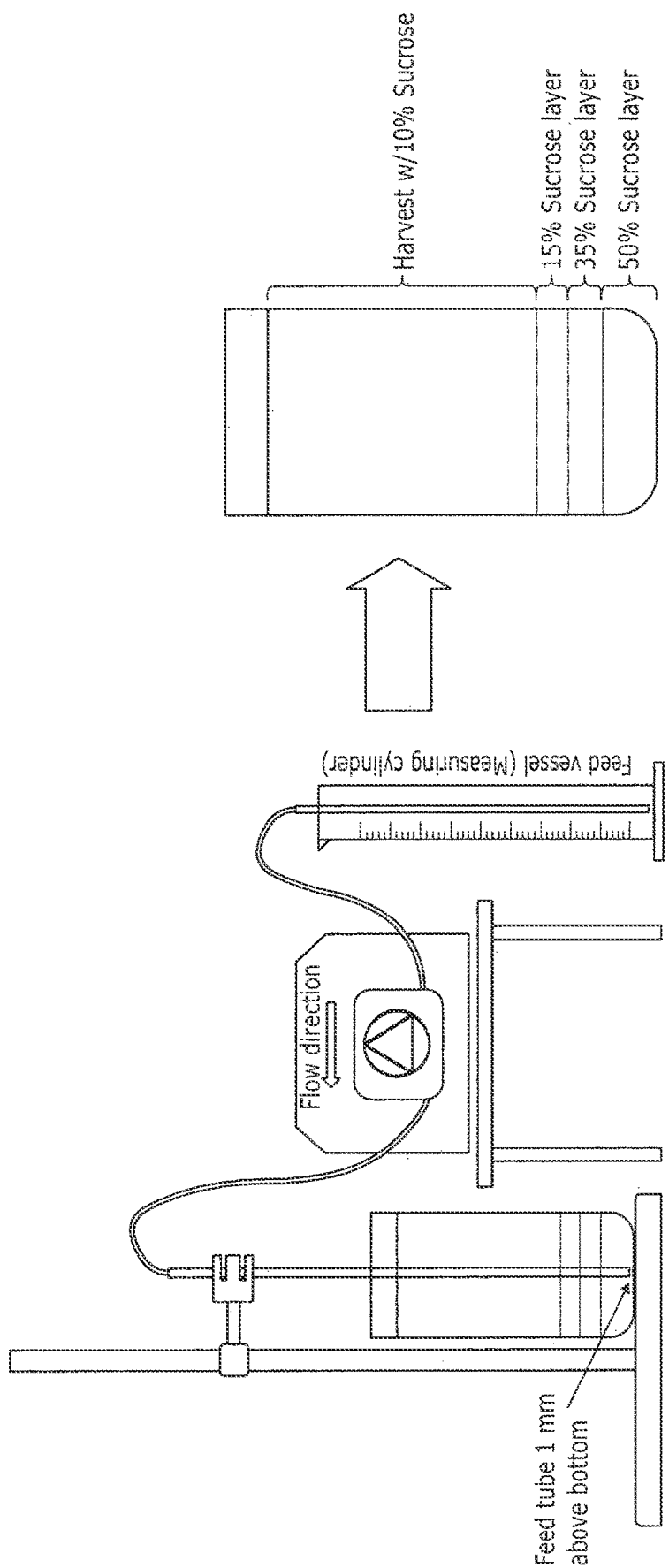
FIG. 14: Preparation of the sucrose gradient.
Figure 15A:
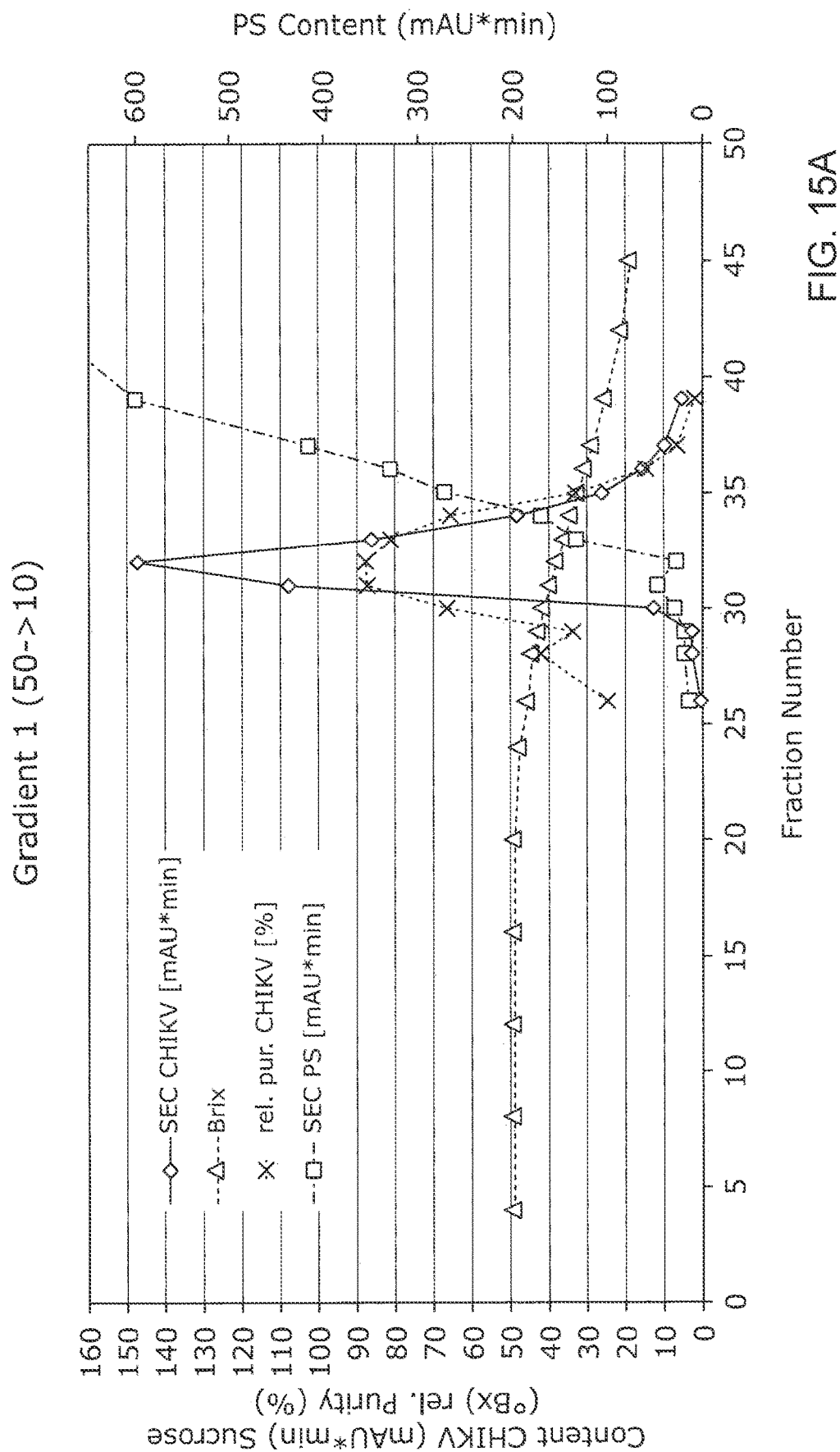
FIGS. 15A-15D: Comparison of four different sucrose gradient centrifugation experiments performed to empirically determine the optimal combination of sucrose layers for CHIKV purification. The CHIKV content in the gradient fractions was determined by SEC. The sucrose content in the gradient fractions was determined by refractometry (comparing the value of the refractive index of the sucrose solution to that of sucrose standard curve the concentration of sucrose solution can be determined with good accuracy, this is also referred to as "Brix" scale that is calibrated to give the percentage (w/w) of sucrose dissolved in water, i.e. "° Bx"). Protamine sulphate (PS) was determined by SEC. PS is separated within the sucrose gradient alongside host cell derived residual contaminants and was therefore used to assess the quality of CHIKV separation from residual contaminants in the tested gradients.
Figure 15B:
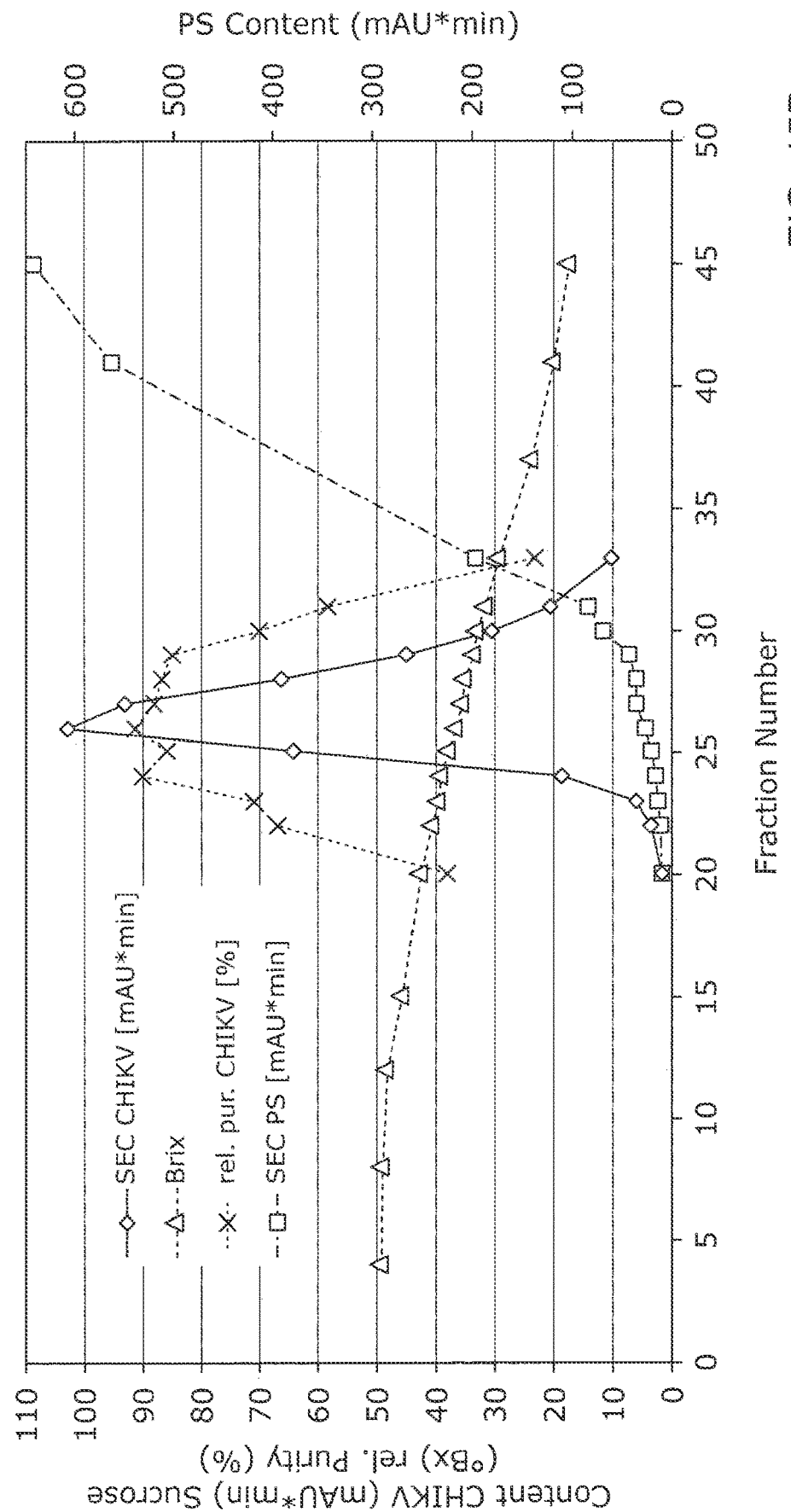
Figure 15C:
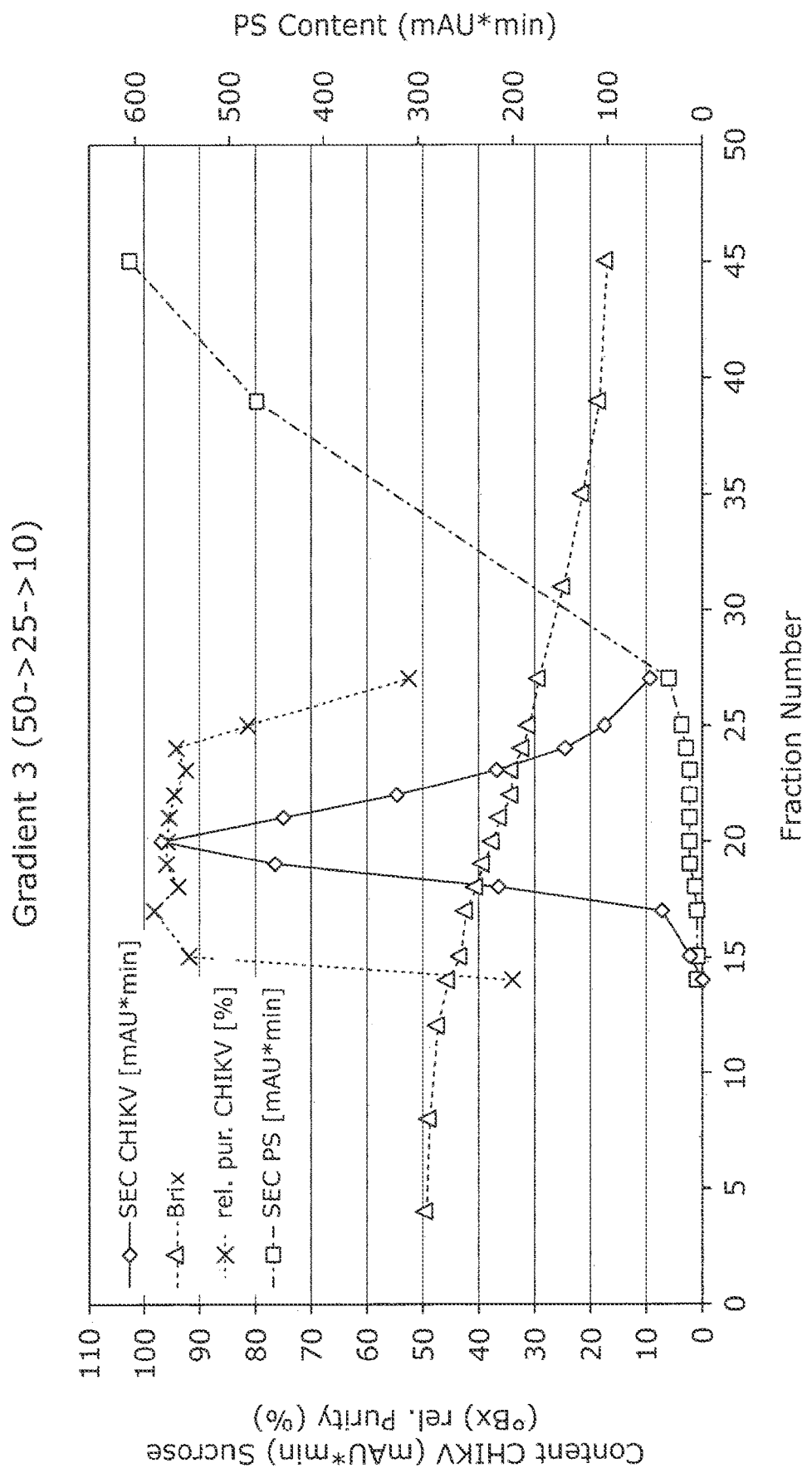
Figure 15D:
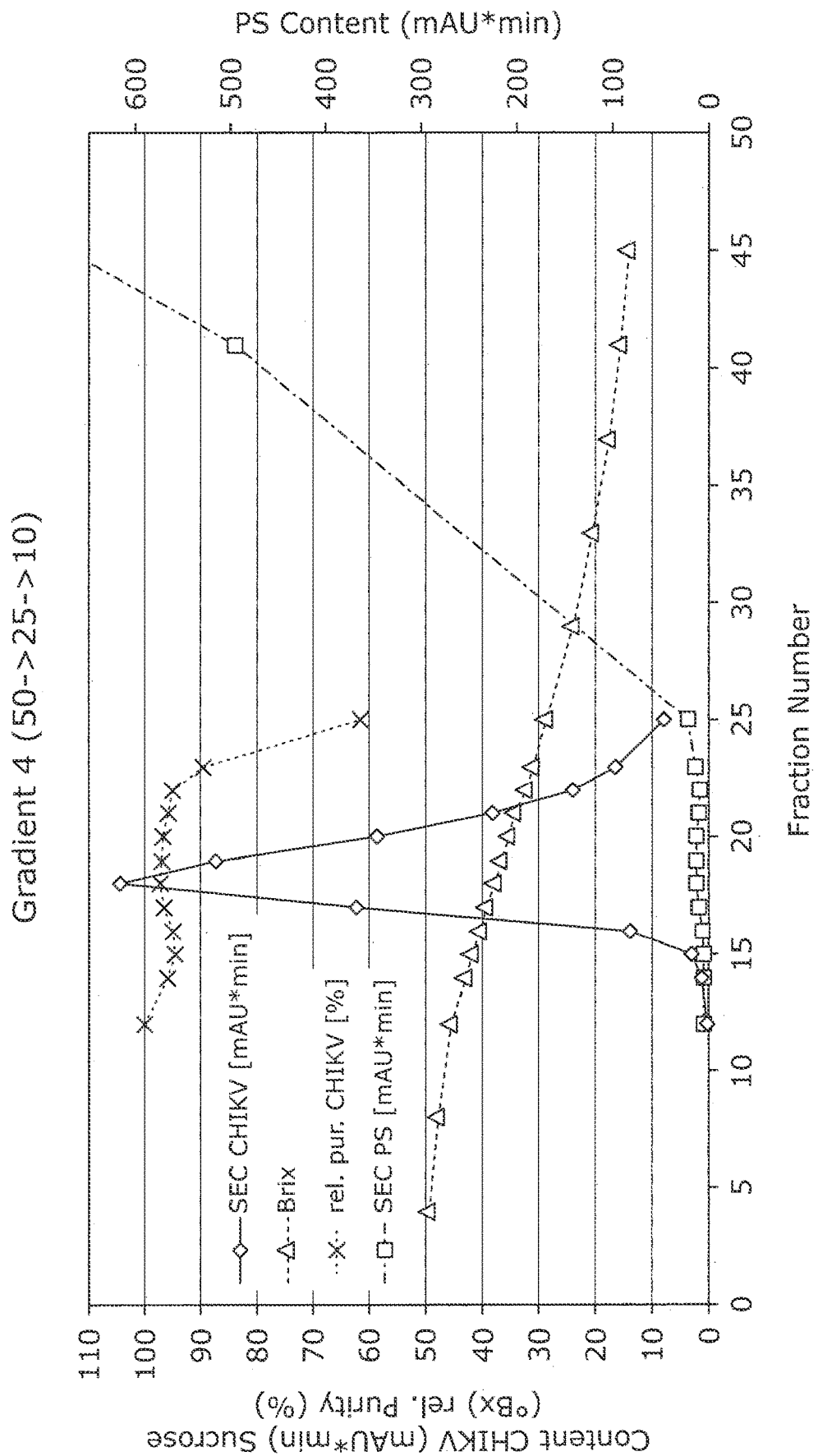
Figure 23:
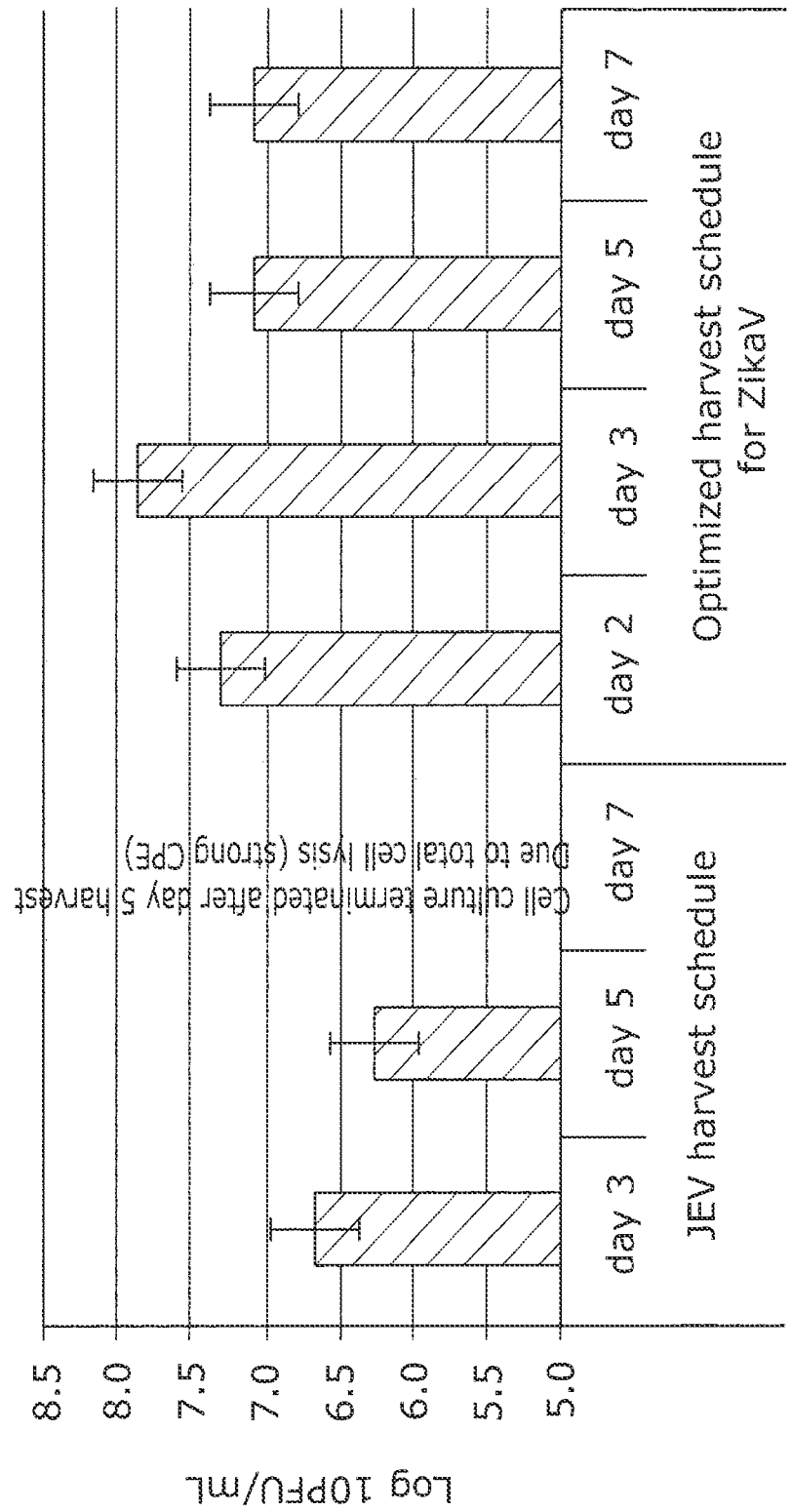

This finding led to an optimized harvest schedule to better control of CPE and allow additional harvest day 5 and 7, see FIG. 23. For both harvest days the optimized ZikaV protocol yield significant higher virus titers compared to the modified protocol showing that the time of the first harvest is crucial for production yields. Additionally first harvesting at day 3 results in maximum 2 harvest points whereas first harvesting at day 2 allows for 4 harvest points further increasing the yield gain.

Downstream Purification of Zika Virus

The purification process was carried out at room temperature (18-22° C.) unless stated otherwise. Virus purification started with concentration of filtered combined harvest using 100 kDa cut-off TFF ultrafiltration modules to remove cell culture media components and reduce batch volume. After concentration, the pooled filtered harvest material was adjusted to a final concentration of 25 mM Tris pH 7.5 and 10% sucrose (w/w) using stock solution of both components (see FIG. 19 for SEC-HPLC of different harvests prior to PS treatment). This allowed for freezing the concentrated harvest at <−65° C. if required.

Host cell DNA and protein reduction as well reduction of non-infectious virus aggregates in the concentrated material was achieved by precipitation with protamine sulphate (2 mg/mL) followed by sucrose density centrifugation (2-8° C.) as final polishing step (see FIG. 20 for SEC-HPLC of different harvests post PS treatment). The purification process was designed to be completed within 2 working days with SGC starting on end of day 1 followed by fractionation and SDS-PAGE analysis on day 2. The sucrose gradient fractions were stored at 2-8° C. during the SDS-PAGE analysis (Silver staining) to identify the pure fractions containing ZikaV (see FIG. 21). After pooling the relevant fractions, the pool was diluted and inactivated by Formalin After pooling the relevant fractions of sucrose gradient centrifugation, the pool was diluted 1:3 in PBS and inactivated by Formalin (0.02% v/v, 200 ppm). Fractions were subjected to analysis by SDS-PAGE.

Effect of PS Treatment on Virus Recovery

Samples of individual 30× concentrated harvests days 2, 3, 5 and 7 were analysed before (FIG. 19) and after PS (FIG. 20) treatment by SEC-HPLC and plaque assay. SEC-HPLC was used for determination of relative total ZikaV content (active+inactive) expressed as peak area, whereas the rel. ZikaV peak purity is given as relative content of virus monomer population to total virus peak. Plaque assay states the content of total active virus particles in each sample. Experimental results are summarized in Table 1. The virus peak recovery by SEC-HPLC was only between 12 to 36% with peak purity after PS treatment in the range of >90% (no virus aggregates detected). The recovery of active virus particles by plaque assay was all >100% (130-700%, range within the variability of the assay) showing that no active virus particles were lost during PS treatment. These results show that during PS treatment only non-infective (immature and/or aggregated virus) particles were removed.

TABLE 6

ZikaV recovery by SEC-HPLC and plaque assay before and after PS treatment.

SEC-HPLC

| | Peak area mAU*min | | | rel. virus |
|---|---|---|---|---|
| Harvest day | 30x conc | 30x + PS | SEC Recovery (%) | monomer content after PS (%) |
| Day 2 | 101.36 | 18.63 | 18 | 89% |
| Day 3 | 144.51 | 17.48 | 12 | 90% |
| Day 5 | 19.97 | 5.92 | 30 | 96% |
| Day 7 | 68.80 | 24.43 | 36 | 99% |

Plaque Assay

| | PFU/mL | | |
|---|---|---|---|
| Harvest day | 30x conc | 30x + PS | Plaque Recovery (%) |
| Day 2 | 3E+08 | 5E+08 | 179 |
| Day 3 | 2E+08 | 4E+08 | 193 |
| Day 5 | 1E+08 | 9E+08 | 700 |
| Day 7 | 3E+08 | 4E+08 | 132 |

Sucrose Gradient Centrifugation

The PS treated harvest was split in two parts and loaded on two centrifuge bottles.

Sucrose density gradient centrifugation (SGC) was used for final concentration and polishing of the ZikaV material. The ZikaV PS treated concentrated harvest was loaded on top of a solution consisting of three layers of sucrose with different densities. The three sucrose layers were selected based on a preliminary study which showed the formation of a linear sucrose gradient and complete separation of the virus particles from residual contaminants as demonstrated for ChikV (FIG. 15D). The optimal volumes of the sucrose solutions were determined empirically. The volumes of individual layers for a centrifugation in 100 mL bottle scale are shown in Table 2.

TABLE 7

Individual layers/volumes for a centrifugation in bottle.

| Solution | Volume (mL) |
|---|---|
| PS treated harvest in 10% sucrose (L) | 40 |
| 15% sucrose (J) | 15 |
| 35% sucrose (I) | 15 |
| 50% sucrose (H) | 20 |
| Total volume | 90 |

The sucrose gradient bottles were prepared by stratifying the individual sucrose layers. A plastic tube was attached to peristaltic pump tubing. The plastic tube was mounted on a laboratory stand using a clamp and placed into the centrifuge bottle. The nozzle of the plastic tube was touching the bottom of the bottle. Using a peristaltic pump the ZikaV material and the sucrose solutions were pumped into the cylinder. A measuring cylinder was used as feed vessel. The first solution pumped was the ZikaV material as it represented the solution of lowest density (10% sucrose (w/w)). After the ZikaV material the sucrose solutions were pumped in ascending order starting with the 15 (w/w) solution J, followed by 35% sucrose solution I and finishing with the highest density sucrose solution H (50% (w/w)). The described setup is shown in FIG. 14. After all sucrose solutions were transferred the plastic tubing was carefully removed in order not to disturb the layers.

Prior to centrifugation the centrifuge was pre-cooled to 4° C. The prepared SG bottles were carefully transferred into the pre-cooled rotor. (Note: Sudden movement of the bottles during transfer to the rotor must be avoided in order not to disturb the sucrose layers.) The bottles were centrifuged at ~11.000 RCF max at 4° C. for at least 20 hours, no brake/deceleration activated. In case a different centrifuge system with a different rotor is used the necessary speed and centrifugation times need to be calculated based on the k-factor in order to achieve comparable centrifugation efficiency.

Harvesting of the sucrose gradient was done manually using a peristaltic pump. A plastic tube attached to peristaltic pump tubing was used for harvesting the sucrose gradient. The bottle containing the gradient was mounted onto a laboratory stand in a tilted position (~12°) using a clamp. The plastic tubing was then placed into the bottle touching the bottom edge of the bottle and was fastened in position using a clamp. This resulted in a small gap of 1-2 mm between the tubing inlet and the bottom of the bottle (see FIG. 14).

Figure 21:
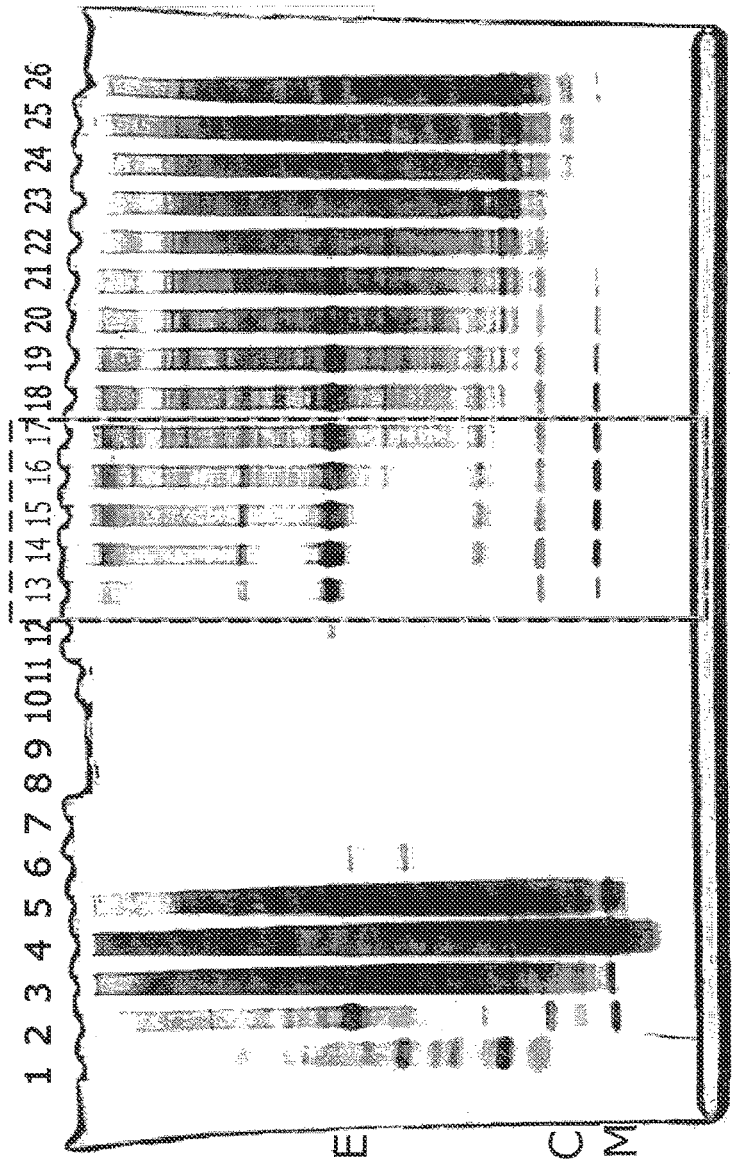

Using a peristaltic pump set to a flow rate of 30 mL per minute the gradient was harvested and manually split into 2 mL fractions. A total number of 32 fractions per bottle were harvested (~64 mL) and the remaining volume was discarded. The fractions were immediately tested by SDS-PAGE/silver stain to identify the virus containing fractions with sufficient high purity. Representative SDS-PAGE is shown in FIG. 21. Fraction 10-14 were pooled and further processed.

The purified viral solution was inactivated by incubation with 0.02% formaldehyde over a period of ten days in a 22° C. controlled-temperature incubator. The formaldehyde is neutralized by addition of sodium metabisulphite on the tenth day.

The sucrose gradient pool (~17 mL after sampling) was further diluted 3-fold with PBS to a final volume of 51 mL in a PETG container. A volume of 1% formaldehyde (10,000 ppm) solution equivalent to 1/50 of the final volume of the pre-formaldehyde pool was added to this pool resulting in an effective concentration of 200 ppm. The formaldehyde-treated solution was mixed on a magnetic stirrer for 10 minutes. After sampling, the formaldehyde-treated viral solution was placed within a cooled incubator at 22° C.±2° C. On Day 5 post addition of formaldehyde, the formaldehyde-treated viral solution was filtered through a 0.2 µm filter and then placed in the incubator at 22° C.±2° C. again. On Day 10, after removing the 10-Day inactivation final sample, a volume of 1% (of the weight of the final formaldehyde-treated viral solution) of 200 mM-sodium metabisulphite solution (2 mM final concentration) was aseptically transferred into the PETG container containing the formaldehyde-treated viral solution. After mixing for 5 minutes on a magnetic stirrer, the neutralized inactivated viral solution is held at room temperature (20 to 25° C.) for a minimum of 30 minutes. After sampling, the neutralized inactivated viral solution is stored at 5° C.±3° C. until further processing.

Inactivation by Formaldehyde

Critical parameters for this step are final formalin concentration, temperature, mixing and transfer into a new container. A preliminary acceptance criterion for maximum pfu/mL (determined by plaque assay) has been set on the diluted pool pre formaldehyde treatment.

The quality of the neutralized inactivated viral solution was monitored by the following parameters: Plaque assay on Day 10, SEC-HPLC, SDS-PAGE/Western Blot.

Interestingly, SEC-HPLC analysis of samples taken during the inactivation period followed by neutralization with bisulfite showed more or less constant peak area throughout the inactivation period.

This is in contrast to JEV where losses of viral particles up to 60% are observed using the process disclosed by Srivastava et al. Vaccine 19 (2001) 4557-4565. In a scale-down model the viral losses were even much higher due to surface/area ratio at smaller scale and high losses due to unspecific adsorption. Differences of the ZikaV inactivation experiment and JEV inactivation were noticed as follows:

A) Much higher purity of ZikaV SGP pool with regard to residual PS (<2 µg/mL) compared to JEV. The 3-fold ZikaV inactivated sample contained therefore <<1 µg/mL of residual PS. Commercial JEV SGP pool contains on average ~120 µg/mL (up to 152 µg/mL possible). The average dilution to inactivation solution of ~14-fold results in a residual PS content up to ~11 µg/mL. It may be that higher amount of residual PS could cause virus precipitation due to cross-linking/reaction with formalin.

B) ZikaV inactivation sample contained ~10% sucrose (3-fold dilution of SGP pool containing ~30-35% sucrose). Sucrose might have stabilizing effect of viral ZikaV particles during treatment with formalin.

Dilution to DS and Formulation with Aluminium Hydroxide (DP)

Figure 22:
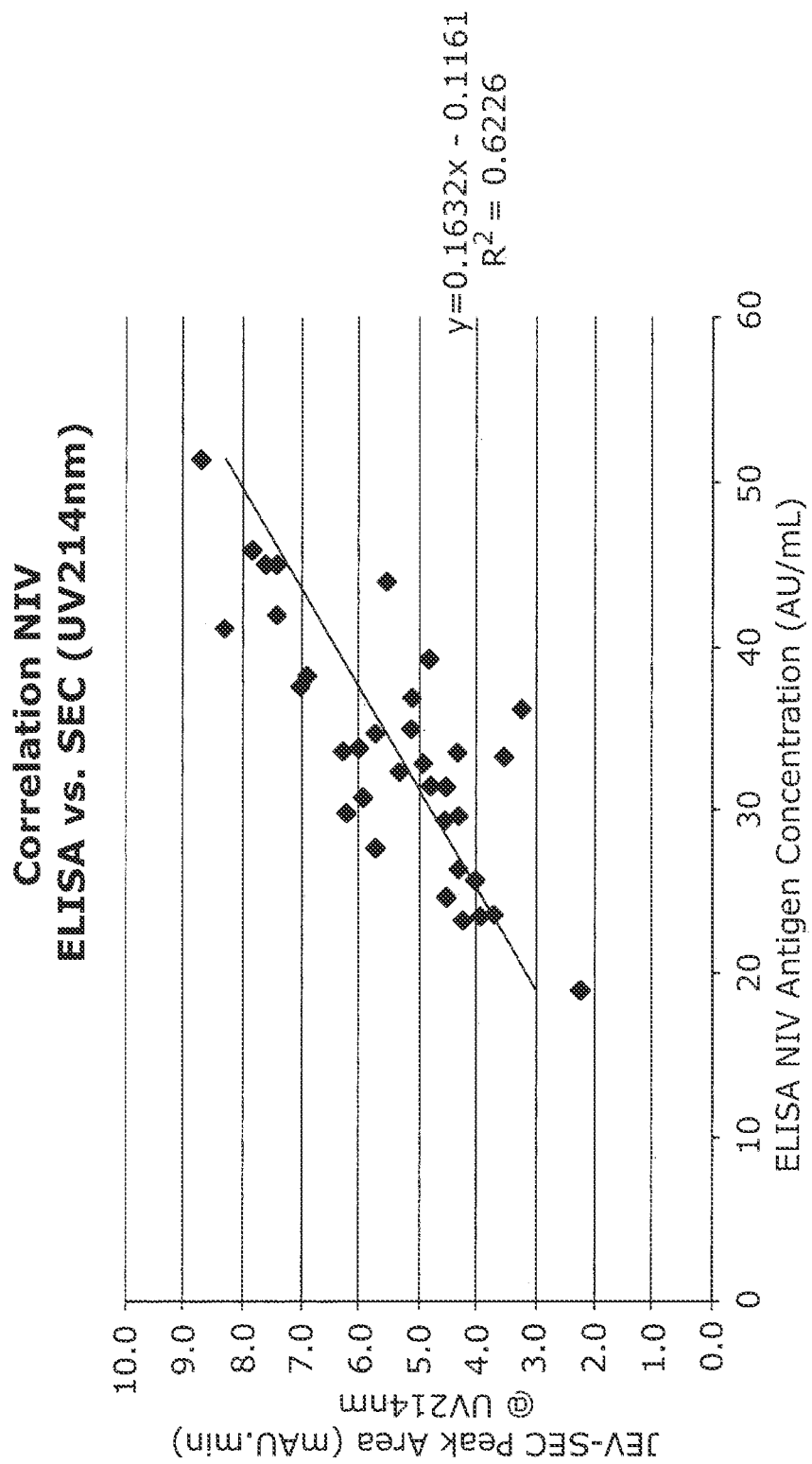

For preparation of ZikaV drug substance used in mouse potency assay an antigen content (expressed as total viral particles or SEC peak area) of 5 times higher compared to Ixiaro was targeted. The basis for determination of antigen content was SEC-HPLC. Briefly, a Superose 6 10/300 Increase column (GE Healthcare) equilibrated with PBS+ 250 mM NaCl, pH 7.4 at 1 ml/min and 25° C., was used to detect ZikaV at 214 nm detection wavelength in harvest samples and throughout the downstream process. In the current JEV process the antigen content in NIV is determined by a specific ELISA. A good correlation was observed between antigen content determined by ELISA and SEC-HPLC. On average, the antigen content in commercial NIV samples is in the range of 33 AU/mL corresponding to ~5.2 mAU JEV peak area, see FIG. 22.

ZikaV NIV day 10 (Zika peak ~36 mAU, analysed on Waters HPLC/Superose6 Increase column) was diluted with PBS to a target of 6.3 (~5.7× dilution). Aluminium hydroxide was added to a final concentration of 0.5 mg/mL Aluminium (1/20 v/v Alum 2% stock solution added) to prepare ZikaV Drug Product (DP). The DP was gently mixed for 5 min. An aliquot of the DP was removed, Alum sedimented by centrifugation and the clear supernatant analysed by SEC-HPLC. No ZikaV peak was detected in the supernatant indicating complete adsorption (estimated as >95%) of viral particles on the mineral adjuvant. Formulated ZikaV DP was stored at 2-8° C.

The impurity profile of the inactivated Zika virus DS is comparable to the profile of JEV DS with the exception of a lower PS content (Table 8).

TABLE 8

Determination of impurity profile in Zika and JEV DS samples:

|  | Specification (JEV DS) | JEV | Zika |
|---|---|---|---|
| HCP (ng/mL) | <100<br>LOQ 12 ng/mL | <LOQ | <LOQ |
| DNA (pg/mL) | <200<br>LOQ 40 pg/mL | <40 | <40 |
| Aggregates by SEC-MALLS (%) | Not specified, part of characterization<br>LOQ 5% | <LOQ | <LOQ |
| PS (µg/mL) | Specification only at SGP pool to demonstrate consistent process performance (19-152 µg/mL), *PS content in DS calculated based on PS content in SGP pool (~100 µg/mL) and average dilution factor (~28x) to DS; LOQ 2 µg/mL | ~4* | <<LOQ |

*Typical PS impurity in a JEV sample produced in accordance with protocol disclosed in Srivastava et al. Vaccine 19 (2001) 4557-4565.

SEC-MALLS Results

Figure 24:
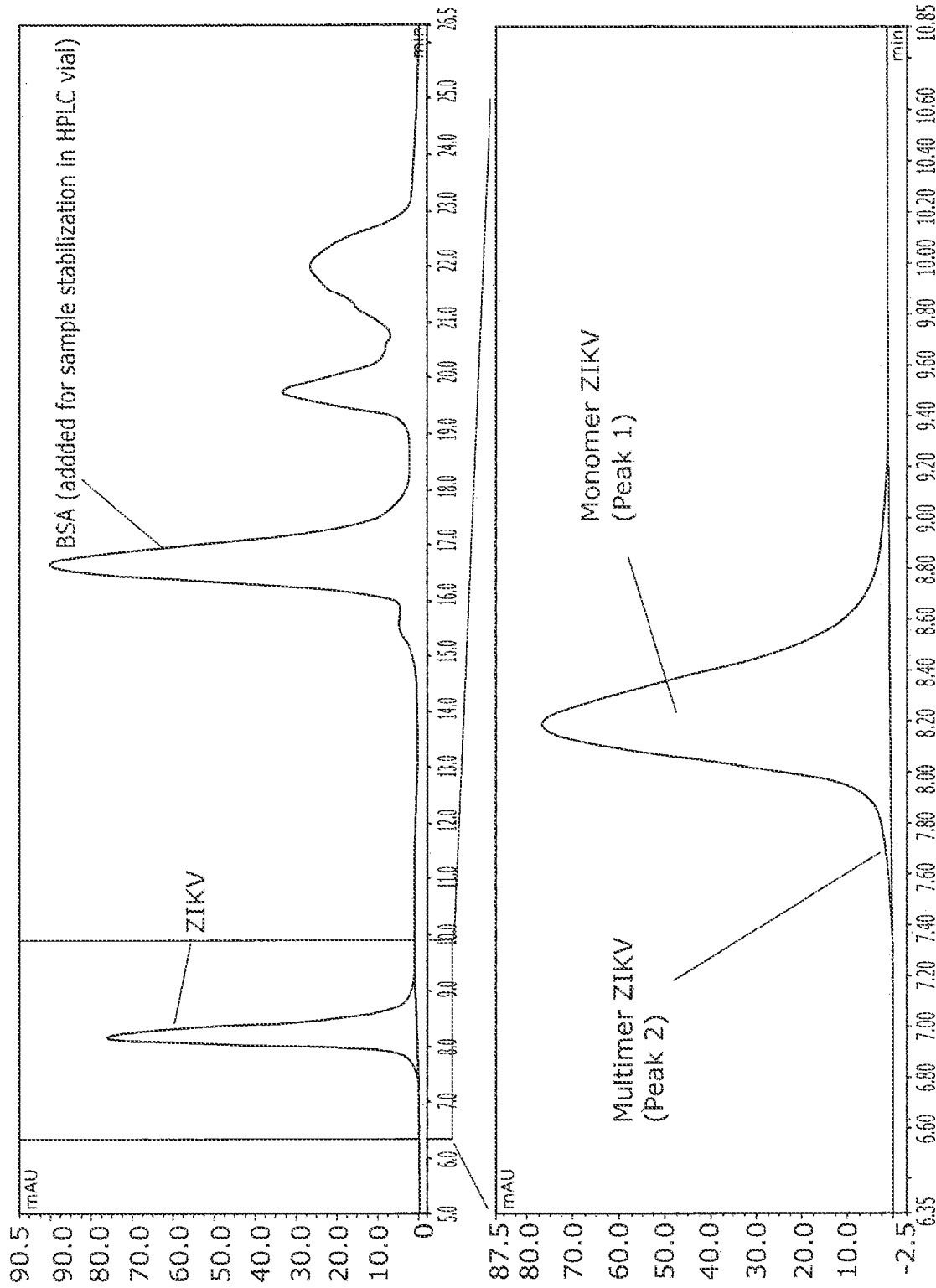

A representative SEC-HPLC elution profile of ZikaV NIV at 214 nm detection wave length is shown in FIG. 24. Note that BSA (50 µg/mL) was added to the sample to minimize losses in HPLC glass vial due to unspecific surface adsorption. ZikaV monomer content was estimated as ~98% with a multimer content of ~2%.

Figure 25:
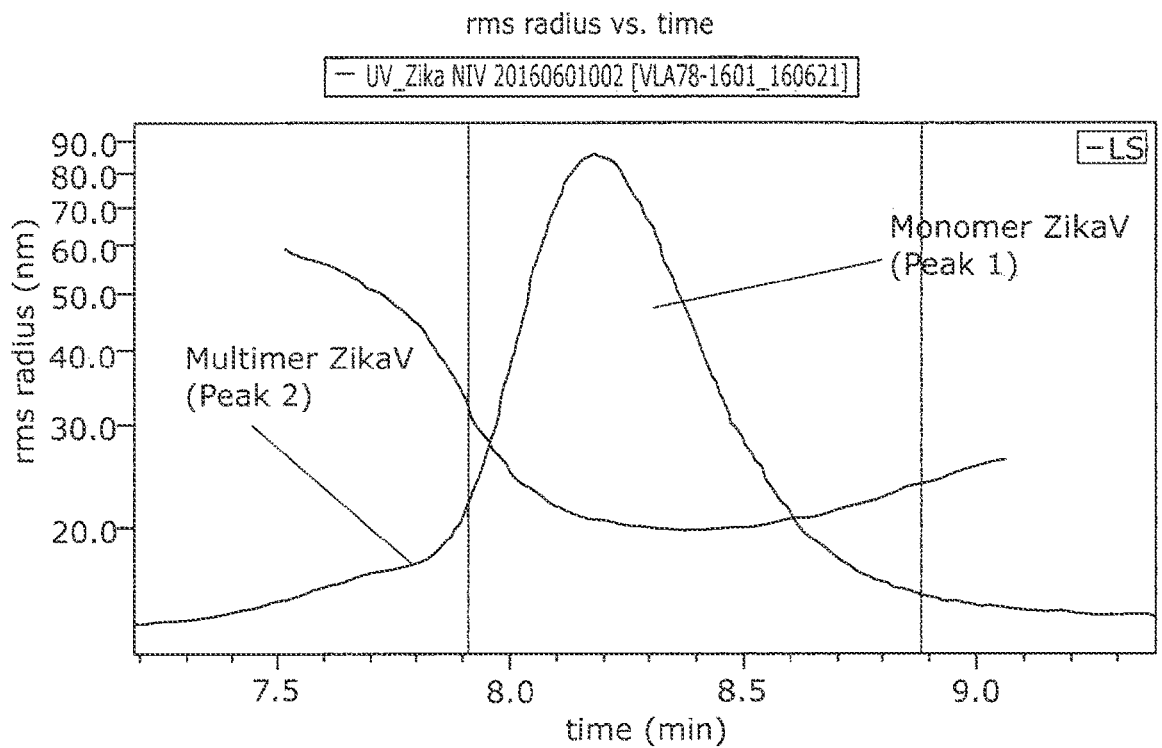
Figure 26:
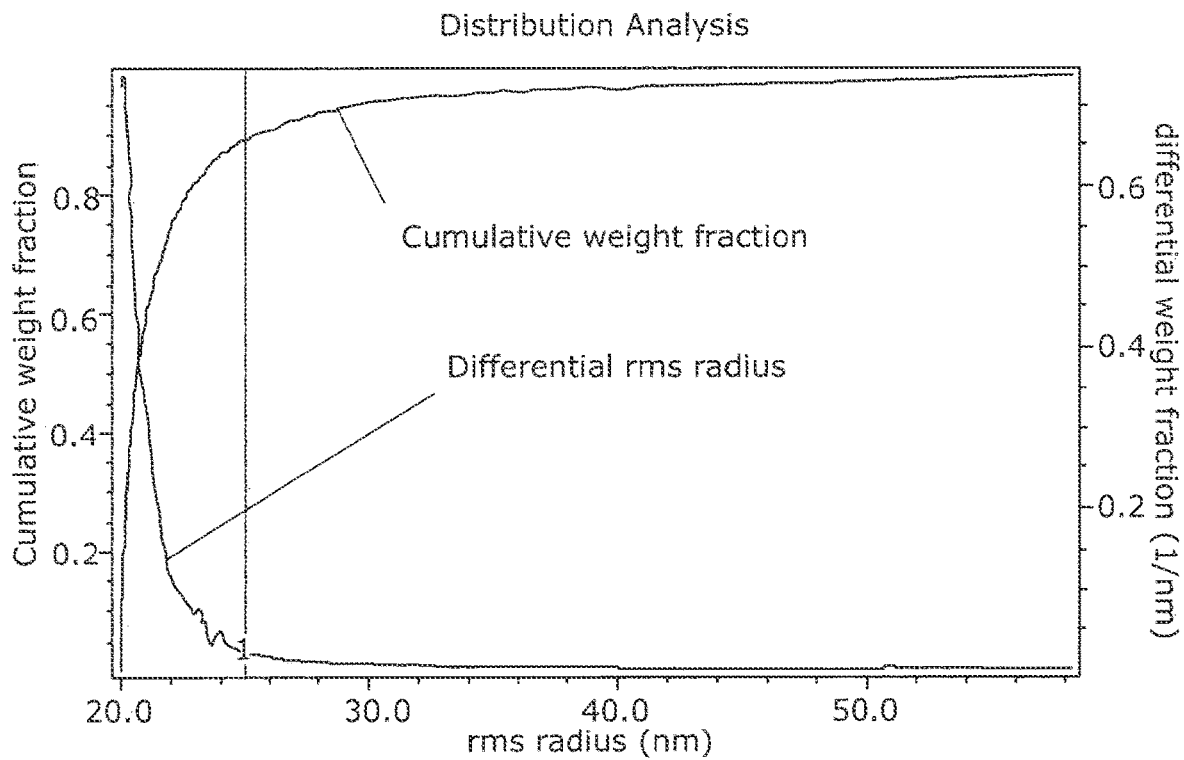

SEC-MALLS analysis (FIG. 25) of the sample confirmed the radius Rz of the monomer ZikaV population peak 1 as 21.6 nm and ~49 nm for the multimer peak 2. Cumulative particle size distribution showed that 89% of all viral particles are within a radius range between 18 to 25 nm (FIG. 26).

Results confirm purity and homogeneity of ZikaV NIV.

Viral Titer by Plaque Assay

TABLE 9

Active ZikaV pfus were quantified by plaque assay throughout the process.

| Sample | Pfu/mL |
|---|---|
| Harvest day 2 (filtered) | $6.4 \times 10^7$ |
| Harvest day 3 (filtered) | $1.0 \times 10^8$ |
| Harvest day 5 (filtered) | $1.5 \times 10^8$ |
| Harvest day 7 (filtered) | $1.1 \times 10^8$ |
| PS treated harvest 300x concentrate (=SGP load) | $9.0 \times 10^8$ |
| SGP pool | $8.9 \times 10^8$ |
| Inactivation start (SGP pool 1:3 diluted) | $3.4 \times 10^8$ |
| Inactivation day 5 | <LOD |
| Inactivation day 10 | <LOD |

Comparison of PS and Benzonase on Process Performance

A direct comparison of DNA removal method of concentrated ZikaV harvest pool was done. One aliquot was treated with PS (2 mg/mL, 15 min at room temperature), the other aliquot was treated with Benzonase (50 U/mL, 2 mM MgCl2, 4 h RT, 48 h 2-8° C.). Both samples were further purified by sucrose gradient as described in this report. Interestingly, the Benzonase treated samples did not yield any pure fractions after sucrose gradient centrifugation of the treated ZikaV harvest. In those fractions where the specific virus bands were detected, a high amount of host cell protein was detected throughout the collected fractions.

The PS treated material resulted in pure ZikaV containing fractions as expected. This finding may suggest that PS is not only effective for DNA removal by precipitation; in addition it improves the recovery of virus particles in the gradient by disrupting interaction of DNA (fragments) and virus particles. Benzonase treatment does not remove DNA, it only results in its fragmentation. Residual DNA fragments might still interact with virus particles and residual HCPs resulting in cross-contamination and co-purification in the sucrose gradient. Pooled SGP fractions were also analysed by SEC-HPLC. Although a large peak was detected, SDS-PAGE confirmed that this sample was highly contaminated with HCPs. A large peak might be detected at UV214 and 280 nm after SEC-HPLC analysis due to possible interaction of HCPs with large virus particles, changing the UV absorbance.

Immunogenicity of Vero Grown Zika Virus

Immunization of Mice

Prior to immunization, groups of ten 6-week-old female CD1 mice were bled via vena facialis and pre-immune sera were prepared. One intraperitoneal immunizations of 200 μL were administered. A dose titration (12 μg, 3 μg, 1 μg, 0.33 μg, 0.11 μg, 0.037 μg and 0.012 μg, equivalent to the protein amount in IXIARO) of inactivated Zika virus formulated with aluminium hydroxide (Al(OH)3) at a final concentration of 0.7%. Three weeks after immunization, blood was collected and immune sera were prepared. All animal experiments were conducted in accordance with Austrian law (BGB1 Nr. 501/1989) and approved by "Magistratsabteilung 58".

Plaque Reduction Neutralization Test (PRNT)

Twelve well plates were used for PRNT. Each well was seeded with 1 mL medium containing $4\times10^5$ Vero cells and incubated 35° C. with 5% CO2 overnight. Pools of heat inactivated sera from each dose group were tested in triplicate. The target viruses (H/PF/2013 (SEQ ID NO: 13) or MR766 (SEQ ID NO: 11)) were diluted to 100 pfu/165 μL.

Equal volumes of target virus and serum dilution were incubated at 35° C. with 5% $CO_2$ for 1 hour. The cell culture medium was aspirated from the Vero cells and 330 µL of the mixture target virus/serum dilution were added to each well and the plates were rocked back and forth 5 times before incubating for 2 hours at 35° C. with 5% $CO_2$. To each well 1 mL of a 2% methylcellulose solution containing EMEM and nutrients was added, the plates were then incubated for 5 days at 35° C. with 5% $CO_2$ before staining the cells for 1 hour with crystal violet/5% formaldehyde and subsequently washed 3 times with deionized water. The plates were air dried and the numbers of plaques in each well were manually counted.

Results

Figure 27:
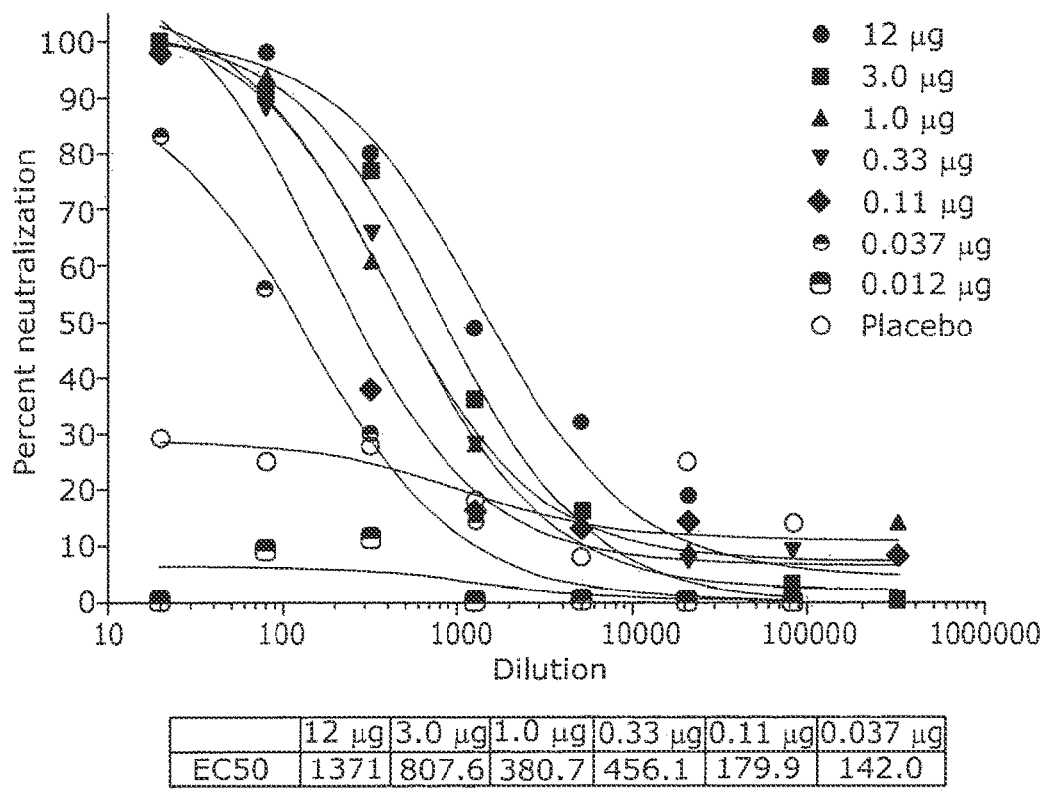
Figure 28:
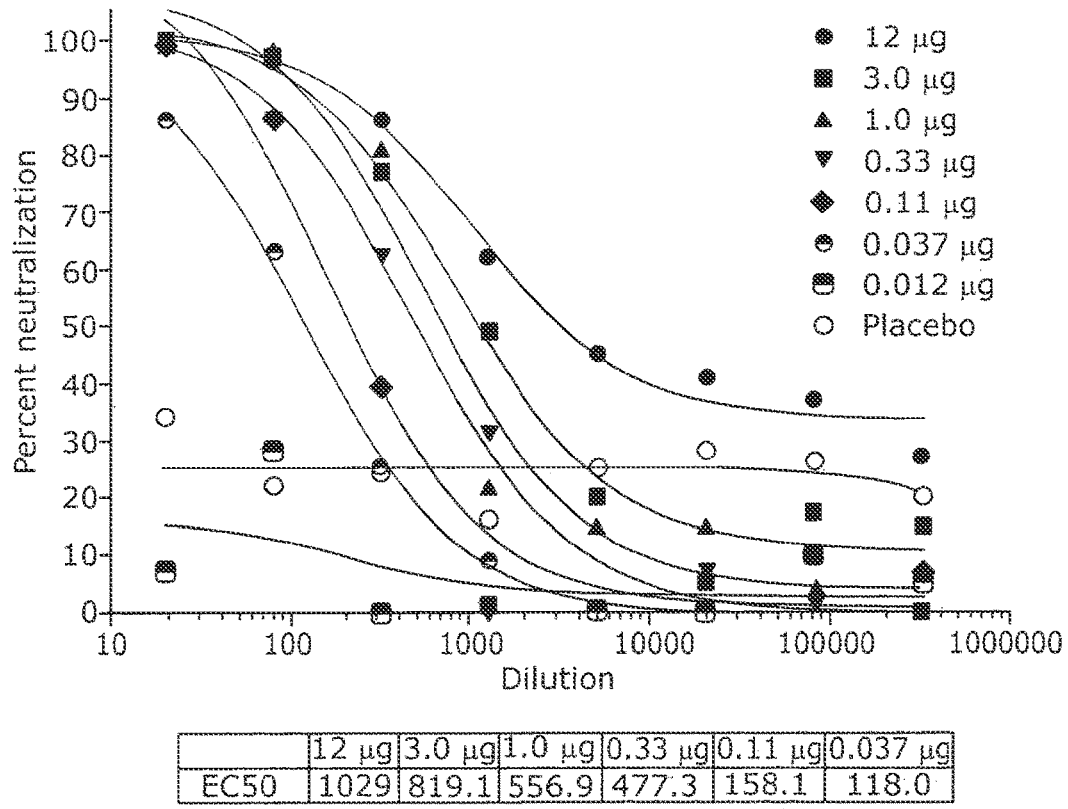

Neutralization was observed with serum pools from mice immunized with inactivated Zika virus vaccine (H/PF/2013) down to 37 ng (dosing equivalent to the amount protein in IXIARO®) against Zika viruses of both the Asian (H/PF/2013) and African (MR766) lineages (FIGS. 27 and 28, respectively). Complete inhibition was seen at the 1:20 serum dilution with an immunization dose down to 110 ng (dosing equivalent to the amount protein in IXIARO®). The neutralization of both the Asian (H/PF/2013) and African (MR766) lineages of the Zika virus was equivalent, which indicates high cross-neutralization between different Zika virus strains of the inactivated Zika virus vaccine (H/PF/2013).

Another neutralization assay was performed using the microneutralization assay as described by Larocca, et al. (2016, Nature doi:10.1038/nature18952). It was found that the inactivated Zika virus of the current invention had an MN50 (microneutralization) titer of 90 at 1 µg of inactivated purified virus.

Further methods: The immunogenicity of inactivated Zika virus preparations is assessed using a mouse model of Zika infection. Groups of adult mice are immunized subcutaneously (s.c.) with 500, 50, or 5 ng of inactivated Zika virus with adjuvant (e.g. aluminium hydroxide with or without IC31®), or without adjuvant. An additional group of mice receive PBS as a negative control. Each group is administered the indicated inoculum at t=0 and in some cases also at three or four weeks later (t=3/4). Beginning approximately three weeks after administration of the last immunization, serum samples are obtained from each of the mice at regular intervals. The serum samples are tested for the presence of neutralizing antibodies using PRNT.

The in vivo protective efficacy of the inactivated Zika virus preparations is also assessed using a mouse model of Zika infection, i.e. IFN-alpha/beta receptor knock-out mice (A129) (see e.g. Dowall et al., 4, Mar. 2016, http://dx.doi.org/10.1101/042358) or blocking of the IFN-alpha/beta receptor by administration of anti-IFN-alpha/beta receptor monoclonal antibodies to C57BL/6 or BALB/c mice (see e.g. Pinto et al., 7, Dec. 2011, DOI: 10.1371/journal.ppat.1002407). For protection assays, groups of 10 three- to eight-weeks-old A129, C57BL/6 of BALB/c mice are inoculated subcutaneously in the hindquarters with inactivated Zika virus with adjuvant (aluminium hydroxide) or without adjuvant at t=0. Age-matched controls are inoculated with PBS or non-specific antigens in alum. Mice are optionally boosted with a second administration of the indicated inoculation three to four weeks later. The mice are then challenged subcutaneously at three to eight weeks post immunization by inoculation with a deadly dose of live Zika virus. One day prior to challenge of C57BL/6 and BALB/c mice, they are passively administered (intraperitoneally) anti-IFN-alpha/beta receptor monoclonal antibodies. Challenged mice are monitored daily for morbidity and mortality for up to twenty-one days. Another alternative is to challenge intracranially adult vaccinated/non-vaccinated adult mice and observe protection.

It is expected that the Zika virus produced by the process of the invention will provide very similar functional readouts in in vitro, in vivo and finally human trials as the currently licensed JEV vaccine in the EU and US and elsewhere, IXIARO®. The dosage may alter but due to the very similar impurity profile and almost identical manufacture, a very similar efficacy and safety result will be expected as was determined for the currently licensed JEV vaccine (licensed in the EU and US and elsewhere).

Discussion & Conclusion

The existing manufacturing platform for production of inactivated JEV vaccine IXIARO® was used as a basis for a manufacturing feasibility study of inactivated ZikaV vaccine candidate (Asian strain H/PF/2013). The virus was produced on Vero cells cultivated in roller bottles. The virus was purified by PS treatment followed by an optimized sucrose gradient. Inactivation was done by formalin treat (0.02%, 10 days at 22° C.). For exploratory immunization studies in mice, a DP formulated with Alum was prepared with an estimated 5-fold higher virus particle content compared to IXIARO®, the commercial JEV Vaccine. The impurity profile of the DS met all criteria as defined in the specification for IXIARO®, the commercial JEV vaccine. The neutralization of both the Asian (H/PF/2013) and African (MR766) lineages of the Zika virus was equivalent, which indicates high cross-neutralization between different Zika virus strains of the inactivated Zika virus vaccine (H/PF/2013).

The in vivo data regarding immunogenicity of the inactivated Zika virus vaccine of the current invention indicates that the virus is surprisingly potently immunogenic and also highly cross-protective (very similar immunogenicity in African and Asian strains). Data indicate that immunogenicity was higher than the recently reported inactivated Zika virus vaccine candidate (Larocca, et. al, 2016, supra.). Inactivated viruses are among the safest vaccines and especially preferred for deliver to populations where safety is especially concerning, such as pregnant women, children and immunocompromised individuals, which makes the herein disclosed inactivated Zika virus particularly suitable. Obtaining a high titer of inactivated virus is a challenge in the field. The herein disclosed process for purifying inactivated Zika virus results in not only a high yield, but also a very pure drug substance.

Figure 29:
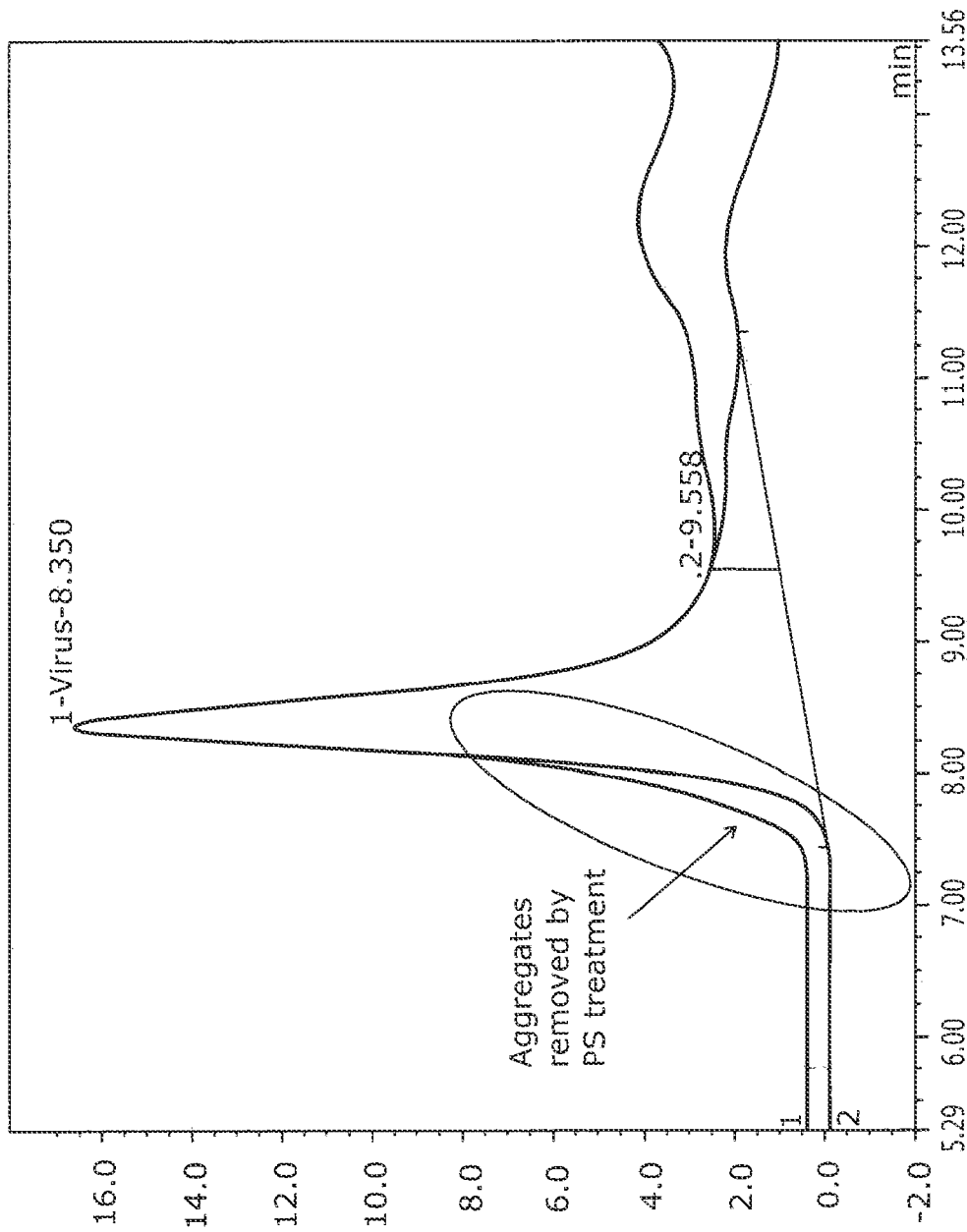

Example 3: Development of a Purification Process for Yellow Fever Virus Vaccine Produced in Vero Cells A downstream process was developed for the purification of infectious yellow fever virus particles whereby host cell nucleic acids, non-infectious virus particles and aggregates are removed by the addition of protamine sulphate as described in Examples 1 and 2. The unexpected and novel purification properties of protamine sulphate (PS) were evaluated in purification processes for yellow fever (YF) as follows:

As before the treatment of YF-harvest with PS significantly reduces the amount of aggregates as seen with SEC for two vaccine strains currently in development (FIG. 29).

Further more detailed aspects of the invention:

A1. A process of purification of infectious alphavirus particles, preferably Chikungunya virus particles, comprising the steps of:
   a) providing a crude harvest (a) comprising virus particles and impurities, wherein the impurities are generated from growing said virus particles on a cell substrate;
   b) reducing impurities from the crude harvest (a) by precipitation with an agent comprising a protamine salt, preferably a protamine sulphate, even more preferably a recombinant protamine sulphate, to obtain a virus preparation (b);
   c) contacting the virus preparation (b) with (i) a solid-phase matrix packed in a column comprising a ligand-activated core and an inactive shell comprising pores, wherein the molecular weight cut off of the pores excludes the virus particles from entering the ligand-activated core, and wherein a molecule smaller than the molecular weight cut-off of the pores can enter the ligand-activated core and collecting the virus particles to obtain a virus preparation (d), or (ii) a solid-phase matrix comprising a ligand-activated core and an inactive shell comprising pores, wherein the molecular weight cut off of the pores excludes the virus particles from entering the ligand-activated core, and wherein a molecule smaller than the molecular weight cut-off of the pores can enter the ligand-activated core and separating the solid-phase matrix from the virus particles by filtration to produce a virus preparation (c); and
   d) further purifying the virus preparation (c) by sucrose density gradient centrifugation to obtain a virus preparation (d) comprising the infectious virus particles, wherein the residual host cell DNA of the virus preparation (d) is less than 100 ng/mL and the residual host cell protein of the final virus preparation (d) is less than 1 µg/mL.

A2. The process of A1, wherein the residual host cell DNA of the virus preparation (d) is less than 10 ng/mL and the residual host cell protein of the final virus preparation (d) is less than 100 ng/mL.

A3. The process of A1 or A2, wherein the crude harvest (a) comprising virus particles and impurities is subjected to one or more pre-purification step(s) prior to step (b).

A4. The process of any one of A1 to A3, wherein the one or more pre-purification step(s) comprises
   a) filtration using a filter having a pore size equal to or less than 0.2 µm; and/or
   b) digestion of host cell genomic DNA by enzymatic treatment; and/or
   c) ultra/diafiltration using a hollow fiber membrane having a pore size equal to or greater than 300 kDa, preferably equal to or greater than 100 kDa.

A5. The process of any one of A1 to A4, wherein the concentration of protamine sulphate is 1 to 2 mg/ml, more preferably 1.2 to 1.8 mg/ml, more preferably 1.4 to 1.6 mg/ml, most preferably 1.6 mg/ml.

A6. The process of any one of A1 to A5, wherein the molecule entering the core of the solid-phase matrix has a molecular weight less than 700 kDa.

A7. The process of any one of A1 to A6, wherein the ligand of the ligand-activated core of the solid-phase matrix is capable of binding the molecule that enters the ligand-activated core via cationic-, anionic-, hydrophobic- or mixed interactions.

A8. The process of any one of A1 to A7, wherein the ligand of the ligand-activated core of the solid-phase matrix is octylamine.

A9. The process of any one of A1 to A8, wherein the solid-phase matrix is used as a slurry and at a final concentration between 0.5% (v/v) and 10% (v/v), preferably 0.6%, 0.7%, 0.9%, 1%, 2%, 3%, 4%, 5%, 6%, 7%, 8%, 9%, 10%, most preferably 1%.

A10. The process of any one of A1 to A9, wherein the solid-phase matrix is incubated with the protamine-treated virus preparation (b) at refrigerated temperatures (2° C. to 8° C.) with a stirring for at least 10 minutes, preferably 15 minutes, 30 minutes or 1 hour, most preferably 15 minutes.

A11. The process of any one of A1 to A10, wherein the enrichment of infectious virus particles in the final virus preparation relative to total virus products in the crude harvest (a) is in the range from at least 50% to 95%, preferably at least 80%.

A12. The process of any one A1 to A11, wherein the filtration of step (c) of preferred aspect 1 is performed using a filter having a pore size equal to or less than 1 µm, preferably 0.2 µm.

A13. The process of any one of A1 to A12, wherein the residual impurity of the final virus preparation is less than 10%.

A14. The process of any one of A1 to A13, wherein the virus is propagated in a cell line selected from the group consisting of an EB66 cell line, a Vero cell line, a Vero-αHis cell line, a HeLa cell line, a HeLa-S3 cell line, a 293 cell line, a PC12 cell line, a CHO cell line, a 3T3 cell line, a PerC6 cell line, a MDSK cell line, a chicken embryonic fibroblast cell line, a duck cell line, and a diploid avian cell line.

A15. The process of A14, wherein said cell line is a Vero cell line.

A16. The process of any one of A1 to A15, wherein the Chikungunya virus is a live virus, an attenuated live virus, a chimeric virus, a modified live virus, or a recombinant live virus.

A17. The process of any one of A1 to A16, wherein the Chikungunya virus is the Δ5nsP3 attenuated mutant or an immunogenic variant thereof.

A18. The process of any one of A1 to A17, wherein said process resulting in final virus preparation (d) is followed by an inactivation step, wherein the virus is inactivated preferably by formaldehyde.

A19. Use of the process according to any one of A1 to A18 for manufacturing a composition for immunization against a Chikungunya virus infection.

A20. The use according to A19, wherein the composition for immunization against a Chikungunya virus infection is a vaccine.

A21. A composition comprising the virus particles obtainable by the process of any one of A1 to A18 for treating and/or preventing a Chikungunya virus infection.

N1. A process of purification of infectious alphavirus particles, preferably Chikungunya virus particles, comprising the steps of:
   (a) providing a crude harvest (a) comprising virus particles and impurities, wherein the impurities are generated from growing said virus particles on a cell substrate;
   (b) reducing impurities from the crude harvest (a) by precipitation with an agent comprising a protamine salt, preferably a protamine sulphate, even more preferably a recombinant protamine sulphate, to obtain a virus preparation (b);

(c) contacting the virus preparation (b) with (i) a solid-phase matrix packed in a column comprising a ligand-activated core and an inactive shell comprising pores, wherein the molecular weight cut off of the pores excludes the virus particles from entering the ligand-activated core, and wherein a molecule smaller than the molecular weight cut-off of the pores can enter the ligand-activated core and collecting the virus particles to obtain a virus preparation (d), or (11) a solid-phase matrix comprising a ligand-activated core and an inactive shell comprising pores, wherein the molecular weight cut off of the pores excludes the virus particles from entering the ligand-activated core, and wherein a molecule smaller than the molecular weight cut-off of the pores can enter the ligand-activated core and separating the solid-phase matrix from the virus particles by filtration to produce a virus preparation (c); and (d) further purifying the virus preparation (c) by sucrose density gradient centrifugation to obtain a virus preparation (d) comprising the infectious virus particles, wherein the residual host cell DNA of the virus preparation (d) is less than 100 ng/mL and the residual host cell protein of the final virus preparation (d) is less than 1 µg/mL.

N2. The process of N1, wherein the residual host cell DNA of the virus preparation (d) is less than 10 ng/mL and the residual host cell protein of the final virus preparation (d) is less than 100 ng/mL.

N3. The process of N1 or 2, wherein the crude harvest (a) comprising virus particles and impurities is subjected to one or more pre-purification step(s) prior to step (b).

N4. The process of any one of N1 to 3, wherein the one or more pre-purification step(s) comprises
  (a) filtration using a filter having a pore size equal to or less than 0.2 µm; and/or
  (b) digestion of host cell genomic DNA by enzymatic treatment; and/or
  (c) ultra/diafiltration using a hollow fiber membrane having a pore size equal to or greater than 300 kDa, preferably equal to or greater than 100 kDa.

N5. The process of any one of N1 to 4, wherein the concentration of protamine sulphate is 1 to 2 mg/ml, more preferably 1.2 to 1.8 mg/ml, more preferably 1.4 to 1.6 mg/ml, most preferably 1.6 mg/ml.

N6. The process of any one of N1 to 5, wherein the molecule entering the core of the solid-phase matrix has a molecular weight less than 700 kDa.

N7. The process of any one of N1 to 6, wherein the ligand of the ligand-activated core of the solid-phase matrix is capable of binding the molecule that enters the ligand-activated core via cationic-, anionic-, hydrophobic- or mixed interactions.

N8. The process of any one of N1 to 7, wherein the ligand of the ligand-activated core of the solid-phase matrix is octylamine.

N9. The process of any one of N1 to 8, wherein the solid-phase matrix is used as a slurry and at a final concentration between 0.5% (v/v) and 10% (v/v), preferably 0.6%, 0.7%, 0.9%, 1%, 2%, 3%, 4%, 5%, 6%, 7%, 8%, 9%, 10%, most preferably 1%.

N10. The process of any one of N1 to 9, wherein the solid-phase matrix is incubated with the protamine-treated virus preparation (b) at refrigerated temperatures (2° C. to 8° C.) with a stirring for at least 10 minutes, preferably 15 minutes, 30 minutes or 1 hour, most preferably 15 minutes.

N11. The process of any one of N1 to 10, wherein the enrichment of infectious virus particles in the final virus preparation relative to total virus products in the crude harvest (a) is in the range from at least 50% to 95%, preferably at least 80%.

N12. The process of any one of N1 to 11, wherein the filtration of step (c) of N1 is performed using a filter having a pore size equal to or less than 1 µm, preferably 0.2 µm.

N13. The process of any one of N1 to 12, wherein the residual impurity of the final virus preparation is less than 10%.

N14. The process of any one of N1 to 13, wherein the virus is propagated in a cell line selected from the group consisting of an EB66 cell line, a Vero cell line, a Vero-αHis cell line, a HeLa cell line, a HeLa-S3 cell line, a 293 cell line, a PC12 cell line, a CHO cell line, a 3T3 cell line, a PerC6 cell line, a MDSK cell line, a chicken embryonic fibroblast cell line, a duck cell line, and a diploid avian cell line.

N15. The process of N14, wherein said cell line is a Vero cell line.

N16. The process of any one of N1 to 15, wherein the Chikungunya virus is a live virus, an attenuated live virus, a chimeric virus, a modified live virus, or a recombinant live virus.

N17. The process of any one of N1 to 16, wherein the Chikungunya virus is the Δ5nsP3 attenuated mutant or an immunogenic variant thereof.

N18. The process of any one of N1 to 17, wherein said process resulting in final virus preparation (d) is followed by an inactivation step, wherein the virus is inactivated preferably by formaldehyde.

N19. Use of the process according to any one of N1 to 18 for manufacturing a composition for immunization against a Chikungunya virus infection.

N20. The use according to N19, wherein the composition for immunization against a Chikungunya virus infection is a vaccine.

N21. A composition comprising the virus particles obtainable by the process of any one of N1 to 18 for treating and/or preventing a Chikungunya virus infection.

P1. A Zika virus vaccine comprising an optimally inactivated Zika virus particle, wherein the Zika virus particle is able to seroconvert a subject that is administered the Zika virus vaccine with at least a 70% probability.

P2. The Zika virus vaccine of P1, wherein the Zika virus particle is able to seroconvert the subject that is administered the Zika virus vaccine with at least a 80%, 85%, 90%, or 95% probability, preferably a 80% probability.

P3. The vaccine of P1 or 2, wherein the Zika virus particle has a RNA genome corresponding to the DNA sequence provided by any one of the nucleic acid sequences of SEQ ID NOs: 2-13, or a variant nucleic acid sequence that is at least 88% identical to any one of SEQ ID NOs: 2-13 and able to pack a virulent Zika virus.

P4. The vaccine of any one of P1-3, wherein the Zika virus particle has an E protein selected from the amino acid sequences provided by any one of SEQ ID NOs: 14-69, or a variant amino acid sequence that is at least 95% identical to any one of SEQ ID NOs: 14-69 and able to pack a virulent Zika virus.

P5. The vaccine of any one of P1-4, wherein the Zika virus is inactivated by chemical inactivation, thermal inactivation, pH inactivation, or UV inactivation.

P6. The vaccine of P5, wherein the chemical inactivation comprises contacting the Zika virus with a chemical inactivation agent for longer than is required to completely inactivate the Zika virus as measured by plaque assay.

P7. The vaccine of P6, wherein the chemical inactivation comprises contacting the Zika virus with formaldehyde.

P8. The vaccine of P7, wherein the formaldehyde inactivation comprises contacting the Zika virus with formaldehyde for between 2-10 days.

P9. The vaccine of any one of P5-8, wherein the chemical activation is performed at about +4° C. or about +22° C.

P10. The vaccine of any one of P1-9, further comprising an adjuvant.

P11. The vaccine of P10, wherein the adjuvant is an aluminum salt adjuvant.

P12. The vaccine of P11, wherein the aluminum salt adjuvant is aluminium hydroxide or aluminium phosphate salt.

P13. The vaccine of any one of P10-12, wherein the vaccine comprises or further comprises an adjuvant comprising a peptide and a deoxyinosine-containing immunostimulatory oligodeoxynucleic acid molecule (I-ODN).

P14. The vaccine of P13, wherein the peptide comprises the sequence KLKLSKLK (SEQ ID NO: 71) and the I-ODN comprises oligo-d(IC)13 (SEQ ID NO: 70).

P15. The vaccine of any one of P1-14, further comprising one or more pharmaceutically acceptable excipient.

Q1. A process of purification of infectious virus particles, comprising the steps of:
 (a) providing a crude harvest (a) comprising virus particles and impurities, wherein the impurities are generated from growing said virus particles on a cell substrate;
 (b) reducing impurities from the crude harvest (a) by precipitation with an agent comprising protamine, preferably a protamine salt, more preferably a protamine sulphate, even more preferably a recombinant protamine sulphate, to obtain a virus preparation (b);
 (c) further purifying the virus preparation (b) by an optimized sucrose density gradient centrifugation, wherein the optimized sucrose gradient is provided such that the protamine can be completely or almost completely separated from the virus fraction; and wherein the protamine concentration is reduced by this step to the extent that the protamine concentration in the final drug substance is below 1 µg/ml, preferably below 0.5 µg/mL, more preferably below 0.1 µg/mL, most preferably below 0.05 µg/mL.

Q2. The process of Q2, wherein the virus particles are selected from the group consisting of flaviviruses, e.g. yellow fever virus or Zika virus and alphaviruses, e.g. Chikungunya.

Q3. The process of Q1 or Q2, additionally comprising the step of:
 (d) a solid-phase matrix packed in a column comprising a ligand-activated core and an inactive shell comprising pores, wherein the molecular weight cut off of the pores excludes the virus particles from entering the ligand-activated core, and wherein a molecule smaller than the molecular weight cutoff of the pores can enter the ligand-activated core and collecting the virus particles.

Q4. The process of any of Q1 to 3, wherein the residual host cell DNA of the virus preparation (c) is less than 10 ng/mL and the residual host cell protein of the final virus preparation (c) is less than 100 ng/mL.

Q5. The process of any of Q1 to 4, wherein the crude harvest (a) comprising virus particles and impurities is subjected to one or more pre-purification step(s) prior to step (b).

Q6. The process of Q5, wherein the one or more pre-purification step(s) comprises
 (a) filtration using a filter having a pore size equal to or less than 0.2 µm; and/or
 (b) digestion of host cell genomic DNA by enzymatic treatment; and/or
 (c) ultra/diafiltration using a hollow fiber membrane having a pore size equal to or greater than 300 kDa, preferably equal to or greater than 100 kDa.

Q7. The process of any one of Q1 to 6, wherein the concentration of protamine sulphate is 0.5 to 3 mg/ml, more preferably 1 to 2 mg/ml, more preferably 1.2 to 1.8 mg/ml, more preferably 1.4 to 1.6 mg/ml, most preferably 1.6 mg/ml or 2 mg/ml.

Q8. The process of any one of Q1 to 7, wherein the enrichment of infectious virus particles in the virus preparation (c) or any final virus preparation relative to total virus products in the crude harvest (a) is in the range from at least 50% to 95%, preferably at least 80%.

Q9. The process of any one of Q5 to 8, wherein the one or more pre-purification step(s) prior to step (b) of any of Q5 to 8 is performed using a filter having a pore size equal to or less than 1 µm, preferably 0.2 µm.

Q10. The process of any one of Q1 to 9, wherein the residual impurity of the virus preparation (c) is less than 10%.

Q11. The process of any one of Q1 to 10, wherein the virus is propagated in a cell line selected from the group consisting of an EB66 cell line, a Vero cell line, a Vero-αHis cell line, a HeLa cell line, a HeLa-S3 cell line, a 293 cell line, a PC12 cell line, a CHO cell line, a 3T3 cell line, a PerC6 cell line, a MDSK cell line, a chicken embryonic fibroblast cell line, a duck cell line, and a diploid avian cell line.

Q12. The process of Q11, wherein said cell line is a Vero cell line.

Q13. The process of any one of Q1 to 12, wherein the infectious virus particles is an infectious Zika virus particle that is a live virus, an attenuated live virus, a chimeric virus, a modified live virus, or a recombinant live virus.

Q14. The process of any one of Q1 to 13, wherein the Zika virus is a Zika virus strain of the Asian lineage or an immunogenic variant thereof.

Q15. The process of any one of Q1 to 14, wherein said process resulting in final virus preparation (c) or (d) is followed by an inactivation step, wherein the virus is inactivated preferably by formaldehyde.

Q16. Use of the process according to any one of Q1 to 15 for manufacturing a composition for immunization against a virus infection.

Q17. The use according to Q16, wherein the composition for immunization against a virus infection is an infection caused by a group of viruses consisting of yellow fever virus, Chikungunya virus and Zika virus.

Q18. A composition comprising the virus particles obtainable or obtained by the process of any one of Q1 to 17 for treating and/or preventing an infection, such as e.g. a Zika virus infection.

Q19. A Zika virus vaccine comprising an inactivated Zika virus particle grown on vero cells, wherein the Zika virus particle is able to seroconvert a subject that is administered the Zika virus vaccine with at least a 70% probability and comprises minor amounts of protamine sulphate, preferably below the detection limit.

Q20. The Zika virus vaccine of Q19, wherein the Zika virus particle is able to seroconvert the subject that is administered the Zika virus vaccine with at least a 80%, 85%, 90%, or 95% probability, preferably a 80% probability.

Q21. The vaccine of Q19 or 20, wherein the Zika virus particle has a RNA genome corresponding to the DNA sequence provided by any one of the nucleic acid sequences of SEQ ID NOs: 2-13, or a variant nucleic acid sequence that is at least 88% identical to any one of SEQ ID NOs: 2-13 and able to pack a virulent Zika virus.

Q22. The vaccine of any one of Q19, 20 and 21, wherein the Zika virus particle has an E protein selected from the amino acid sequences provided by any one of SEQ ID NOs: 14-69, or a variant amino acid sequence that is at least 95% identical to any one of SEQ ID NOs: 14-69 and able to pack a virulent Zika virus.

Q23. The vaccine of any one of Q19, 20 to 22, wherein the Zika virus obtained by culturing on Vero cells is purified by protamine sulfate precipitation and sucrose gradient centrifugation.

Q24. The vaccine of Q23, wherein the sucrose gradient centrifugation is an optimized sucrose gradient centrifugation.

Q25. The vaccine of Q24, wherein the optimized sucrose gradient centrifugation comprises a virus comprising fraction in a 10% (w/w) sucrose solution and three layers of sucrose with different densities, i.e. a first sucrose solution with 15% (w/w) sucrose solution, a second sucrose solution with 35% (w/w) sucrose solution, and a third sucrose solution with a 50% (w/w) sucrose solution.

Q26. The vaccine of any one of Q19, 20 to 25, wherein the Zika virus is inactivated by chemical inactivation, thermal inactivation, pH inactivation, or UV inactivation.

Q27. The vaccine of Q26, wherein the chemical inactivation comprises contacting the Zika virus with a chemical inactivation agent for longer than is required to completely inactivate the Zika virus as measured by plaque assay.

Q28. The vaccine of Q27, wherein the chemical inactivation comprises contacting the Zika virus with formaldehyde.

Q29. The vaccine of Q28, wherein the formaldehyde inactivation comprises contacting the Zika virus with formaldehyde for between 2-10 days.

Q30. The vaccine of any one of Q27-29, wherein the chemical activation is performed at about +4° C. or about +22° C.

Q31. The vaccine of any one of Q19 to 30, further comprising an adjuvant.

Q32. The vaccine of Q31, wherein the adjuvant is an aluminum salt adjuvant.

Q33. The vaccine of Q32, wherein the aluminum salt adjuvant is aluminium hydroxide or aluminium phosphate salt.

Q34. The vaccine of Q32, wherein the aluminum salt adjuvant is aluminium hydroxide with less than 1.25 ppb Cu based on the final pharmaceutical composition comprising the Zika virus, preferably the inactivated Zika virus.

Q35. The vaccine of any one of Q19 to 34, further comprising one or more pharmaceutically acceptable excipient.

R1. Use of protamine, preferably a protamine salt, to separate infectious and non-infectious virus particles, host cell proteins and/or undefined low molecular weight materials.

R2. A process of purification of infectious virus particles, comprising the steps of:
(a) providing a crude harvest (a) comprising virus particles and impurities, wherein the impurities are generated from growing said virus particles on a cell substrate;
(b) reducing impurities from the crude harvest (a) by precipitation with an agent comprising protamine, preferably a protamine salt, more preferably a protamine sulphate, even more preferably a recombinant protamine sulphate, to obtain a virus preparation (b), wherein the enrichment of infectious virus particles in the virus preparation (b) relative to total virus products in the crude harvest (a) is in the range from at least 50% to 95%, preferably at least 80%.

R3. The use of R1 or the process of R2, wherein the virus particles are selected from the group consisting of flaviviruses, e.g. yellow fever virus or Zika virus and alphaviruses, e.g. Chikungunya.

R4. A process of purification of infectious virus particles, comprising the steps of:
(a) providing a crude harvest (a) comprising virus particles and impurities, wherein the impurities are generated from growing said virus particles on a cell substrate;
(b) reducing impurities from the crude harvest (a) by precipitation with an agent comprising protamine, preferably a protamine salt, more preferably a protamine sulphate, even more preferably a recombinant protamine sulphate, to obtain a virus preparation (b);
(c) further purifying the virus preparation (b) by one or more size exclusion methods such as (i) a sucrose density gradient centrifugation, (11) a solid-phase matrix packed in a column comprising a ligand-activated core and an inactive shell comprising pores, wherein the molecular weight cut off of the pores excludes the virus particles from entering the ligand-activated core, and wherein a molecule smaller than the molecular weight cutoff of the pores can enter the ligand-activated core and collecting the virus particles, and/or (iii) size exclusion chromatography to obtain a virus preparation (c) comprising the infectious virus particles, wherein the residual host cell DNA of the virus preparation (c) is less than 100 ng/mL and the residual host cell protein and the residual aggregates of infectious virus particles of the final virus preparation (c) is less than 1 m/mL.

R5. The process of R4, wherein the residual host cell DNA of the virus preparation (c) is less than 10 ng/mL and the residual host cell protein of the final virus preparation (c) is less than 100 ng/mL.

R6. The process of any of R2 to 5, wherein the crude harvest (a) comprising virus particles and impurities is subjected to one or more pre-purification step(s) prior to step (b).

R7. The process of R6, wherein the one or more pre-purification step(s) comprises
(a) filtration using a filter having a pore size equal to or less than 0.2 µm; and/or
(b) digestion of host cell genomic DNA by enzymatic treatment; and/or
(c) ultra/diafiltration using a hollow fiber membrane having a pore size equal to or greater than 300 kDa, preferably equal to or greater than 100 kDa.

R8. The process of any one of R2 to 7, wherein the concentration of protamine sulphate is 0.5 to 3 mg/ml, more preferably 1 to 2 mg/ml, more preferably 1.2 to 1.8 mg/ml, more preferably 1.4 to 1.6 mg/ml, most preferably 1.6 mg/ml.

R9. The process of any one of R2 to 8, wherein the enrichment of infectious virus particles in the virus preparation (c) or any final virus preparation relative to total virus products in the crude harvest (a) is in the range from at least 50% to 95%, preferably at least 80%.

R10. The process of any one of R6 to 9, wherein the one or more pre-purification step(s) prior to step (b) of any of R6 to 9 is performed using a filter having a pore size equal to or less than 1 μm, preferably 0.2 μm.

R11. The process of any one of R2 to 10, wherein the residual impurity of the virus preparation (c) is less than 10%.

R12. The process of any one of R2 to 11, wherein the virus is propagated in a cell line selected from the group consisting of an EB66 cell line, a Vero cell line, a Vero-αHis cell line, a HeLa cell line, a HeLa-S3 cell line, a 293 cell line, a PC12 cell line, a CHO cell line, a 3T3 cell line, a PerC6 cell line, a MDSK cell line, a chicken embryonic fibroblast cell line, a duck cell line, and a diploid avian cell line.

R13. The process of R12, wherein said cell line is a Vero cell line.

R14. The process of any one of R2 to 13, wherein the Zika virus is a live virus, an attenuated live virus, a chimeric virus, a modified live virus, or a recombinant live virus.

R15. The process of any one of R2 to 14, wherein the Zika virus is a Zika virus strain of the Asian lineage or an immunogenic variant thereof.

R16. The process of any one of R2 to 15, wherein said process resulting in final virus preparation (c) is followed by an inactivation step, wherein the virus is inactivated preferably by formaldehyde.

R17. Use of the process according to any one of R1 to 16 for manufacturing a composition for immunization against a virus infection.

R18. The use according to R17, wherein the composition for immunization against a virus infection is an infection caused by a group of viruses consisting of yellow fever virus, Chikungunya virus and Zika virus.

R19. A composition comprising the virus particles obtainable or obtained by the process of any one of R2 to 16 for treating and/or preventing an infection.

What is claimed is:

1. A method for separating infectious virus particles from non-infectious virus particles comprising precipitating the non-infectious virus particles with protamine, wherein the virus particles are selected from the group consisting of Paramyxoviridae, Orthomyxoviridae, Flaviviridae, Filoviridae, Arenaviridae, Rhabdoviridae, Togaviridae and Coronaviridae, and wherein the virus particles are not Zika virus particles.

2. The method according to claim 1, wherein said protamine precipitation also facilitates the separation of infectious virus particles from host cell proteins and/or low molecular weight materials.

3. A method for purifying infectious virus particles, comprising the steps of i) providing a crude harvest (a) comprising infectious virus particles, non-infectious virus particles, and impurities, wherein the impurities are generated from growing said virus particles on a cell substrate;

ii) contacting said crude harvest (a) with an agent comprising protamine to obtain a virus preparation (b) comprising infectious virus particles, wherein the enrichment of infectious virus particles in the virus preparation (b) relative to total virus particles in the crude harvest (a) is in the range of at least 50% to 95%, wherein the virus particles are selected from the group consisting of Paramyxoviridae, Orthomyxoviridae, Flaviviridae, Filoviridae, Arenaviridae, Rhabdoviridae, Togaviridae and Coronaviridae, and wherein the virus particles are not Zika virus particles.

4. The method according to claim 3, wherein said virus preparation (b) is further purified by one or more size exclusion methods selected from i) sucrose density gradient centrifugation, ii) a solid-phase matrix packed in a column comprising a ligand-activated core and an inactive shell comprising pores, wherein the pores comprise a molecular weight cut-off that excludes the virus particles from entering the ligand-activated core, and wherein a molecule smaller than the molecular weight cut-off of the pores can enter the ligand-activated core, and iii) size exclusion chromatography;

to obtain a final virus preparation (c) comprising the infectious virus particles, less than 100 ng/ml residual host cell DNA, less than 1 μg/mL residual host cell protein, and less than 1 μg/mL virus particle aggregates.

5. The method according to claim 4, wherein the final virus preparation (c) comprises less than 10 ng/mL residual host cell DNA and less than 100 ng/ml residual host cell protein.

6. The method according to claim 3, wherein said crude harvest (a) is subjected to one or more pre-purification step(s) prior to step ii), wherein the one or more pre-purification step(s) comprise a) filtration using a filter having a pore size equal to or less than 0.2 μm, b) digestion of host cell genomic DNA by enzymatic treatment, and c) ultra/diafiltration using a hollow fiber membrane having a pore size equal to or greater than 100 kDa.

7. The method according to claim 3, wherein the concentration of protamine is between 0.5 mg/mL and 3 mg/mL.

8. The method according to claim 4, wherein the infectious virus particles in said final virus preparation (c) are enriched by at least 50% to 95% relative to total virus particles in crude harvest (a).

9. The method according to claim 4, wherein said virus preparation (c) comprises less than 10% impurities.

10. The method according to claim 3, wherein said infectious virus particles are propagated in a cell line selected from the group consisting of an EB66 cell line, a Vero cell line, a Vero-αHis cell line, a HeLa cell line, a HeLa-S3 cell line, a 293 cell line, a PC12 cell line, a CHO cell line, a 3T3 cell line, a PerC6 cell line, an MDSK cell line, a chicken embryonic fibroblast cell line, a duck cell line, and a diploid avian cell line.

11. The method according to claim 3, wherein said infectious virus particles are selected from the group consisting of a live virus, an attenuated live virus, a chimeric virus, a modified live virus, and a recombinant live virus.

12. The method according to claim 4, further comprising a step iv) comprising inactivating the virus preparation (c).

13. The method according to claim 12, wherein said inactivating step iv) is performed using formaldehyde.

14. The method according to claim 3, where said protamine is selected from the group comprising a protamine salt, a protamine sulphate, and a recombinant protamine sulphate.

* * * * *

SEQUENCE LISTING

```
Sequence total quantity: 123
SEQ ID NO: 1            moltype = AA  length = 32
FEATURE                 Location/Qualifiers
REGION                  1..32
                        note = synthetic peptide
source                  1..32
                        mol_type = protein
                        organism = synthetic construct
SEQUENCE: 1
PRRRRSSSRP VRRRRRPRVS RRRRRRGGRR RR                                 32

SEQ ID NO: 2            moltype = DNA  length = 10676
FEATURE                 Location/Qualifiers
source                  1..10676
                        mol_type = other DNA
                        organism = Zika virus
SEQUENCE: 2
gttgttactg ttgctgactc agactgcgac agttcgagtt tgaagcgaaa gctagcaaca   60
gtatcaacag gttttatttg gatttggaaa cgagagtttc tggtcatgaa aaacccaaaa   120
aagaaatccg gaggattccg gattgtcaat atgctaaaac gcggagtagc ccgtgtgagc   180
ccctttgggg gcttgaagag gctgccagcc ggacttctgc tgggtcatgg gcccatcagg   240
atggtcttgg caattctagc cttttttgaga ttcacggcaa tcaagccatc actgggtctc   300
atcaatagat ggggttcagt ggggaaaaaa gaggctatgg aaataataaa gaagttcaag   360
aaagatctgg ctgccatgct gagaataatc aatgctagga aggagaagaa gagacggggc   420
gcagatacta gtgtcggaat tgttggcctc ctgctgacca cagctatggc agcggaggtc   480
actagacgtg ggagtgcata ctatatgtac ttggacagaa acgatgctgg ggaggccata   540
tctttttccaa ccacattggg gatgaataag tgttatatac agatcatgga tcttggacac   600
atgtgtgatg ccaccatgag ctatgaatgc cctatgctgg atgaggggt ggaaccagat   660
gacgtcgatt gttggtgcaa cacgacgtca acttgggttg tgtacggaac ctgccatcac   720
aaaaaaggtg aagcacggag atctagaaga gctgtgacgc tccctccca ttccactagg   780
aagctgcaaa cgcggtcgca aacctggttg gaatcaagag aatacacaaa gcacttgatt   840
agagtcgaaa attggatatt caggaaccct ggcttcgcgt tagcagcagc tgccatcgct   900
tggcttttgg gaagctcaac gagccaaaaa gtcatatact tggtcatgat actgctgatt   960
gccccggcat acagcatcag gtgcatagga gtcagcaata gggactttgt ggaaggtatg  1020
tcaggtggga cttgggttga tattgtcttg gaacatggaa gttgtgtcac cgtaatggca  1080
caggacaaac cgactgtcga catagagctg gttacaacaa cagtcagcaa catggcgag   1140
gtaagatcct actgctatga ggcatcaata tcagacatgg cttcggacag ccgctgccca  1200
acacaaggtg aagcctacct tgacaagcaa tcagacactc aatatgtctg caaaagaacg  1260
ttagtgacga gagctgggg aaatgatgt ggacttttg gcaaagggag tctggtgaca   1320
tgcgctaagt ttgcatgctc caagaaaatg accgggaaga gcatccagcc agagaatctg  1380
gagtaccgga taatgctgtc agttcatggc tcccagcaca gtgggatgat cgttaatgac  1440
acaggacatg aaactgatga gaatagacg aaggttgaga taacgcccaa ttcaccaaga  1500
gccgaagcca ccctggggg ttttgaagcc ctaggacttg attgtgaacc gaggacaggc  1560
cttgacttttt cagatttgta ttacttgact atgaataaca agcactggtt ggttcacaag  1620
gagtggttcc acgacattcc attaccttgg cacgctgggg cagacaccgg aactccacac  1680
tggaacaaca agaagcact ggtagagttc aaggacgcac atgccaaaag gcaaactgtc  1740
gtggttctag ggagtcaaga aggagcagtt cacacggccc ttgctggagc tctggaggct  1800
gagatggatg gtgcaaaggg aagctgtcc tctggccact tgaaatgtcg cctgaaaatg  1860
gataaactta gattgaaggg cgtgtcatac tccttgtgta ccgcagcgtt cacattcacc  1920
aagatcccgg ctgaaacact gcacgggaca gtcacagtgg aggtacagta cgcagggaca  1980
gatggacctt gcaaggttcc agctcagatg gcggtggaca tgcaaactct gaccccagtt  2040
gggaggttga taaccgctaa ccccgtaatc actgaaagca ctgagaactc taagatgatg  2100
ctggaacttg atccaccatt tggggactct tacattgtca taggagtcgg ggagaagaag  2160
```

```
atcacccacc actggcacag gagtggcagc accattggaa aagcatttga agccactgtg    2220
agaggtgcca agagaatggc agtcttggga gacacagcct gggactttgg atcagttgga    2280
ggcgctctca actcattggg caagggcatc catcaaattt ttggagcagc tttcaaatca    2340
ttgtttggag gaatgtcctg gttctcacaa attctcattg gaacgttgct gatgtggttg    2400
ggtctgaaca caaagaatgg atctatttcc cttatgtgct tggccttagg gggagtgttg    2460
atcttcttat ccacagccgt ctctgctgat gtggggtgct cggtggactt ctcaaagaag    2520
gagacgagat gcggtacagg ggtgttcgtc tataacgacg ttgaagcctg gagggacagg    2580
tacaagtacc atcctgactc cccccgtaga ttggcagcag cagtcaagca agcctgggaa    2640
gatggtatct gcgggatctc ctctgtttca agaatggaaa acatcatgtg gagatcagta    2700
gaagggggagc tcaacgcaat cctggaagag aatggagttc aactgacggt cgttgtggga    2760
tctgtaaaaa accccatgtg gagaggtcca cagagattgc ccgtgcctgt gaacgagctg    2820
ccccacggct ggaaggcttg ggggaaatcg cacttcgtca gagcagcaaa gacaaataac    2880
agctttgtcg tggatggtga cacactgaag gaatgcccac tcaaacatag agcatggaac    2940
agctttcttg tggaggatca tgggttcggg gtatttcaca ctagtgtctg gctcaaggtt    3000
agagaagatt attcattaga gtgtgatcca gccgttattg gaacagctgt taaggcaaag    3060
gaggctgtac acagtgatct aggctactgg attgagagtg agaagaatga cacatggagg    3120
ctgaagaggg cccatctgat cgagatgaaa acatgtgaat ggcaaagtc ccacacattg    3180
tggacaggag gaatagaaga gagtgatctg atcataccca agtctttagc tgggccactc    3240
agccatcaca ataccagaga gggctacagg acccaaatga aagggccatg gcacagtgaa    3300
gagcttgaaa ttcggtttga ggaatgccca ggcactaagg tccacgtgga ggaaacatgt    3360
ggaacaagag gaccatctct gagatcaacc actgcaagcg gaagggtgat cgaggaatgg    3420
tgctgcaggg agtgcacaat gccccccactg tcgttccggg ctaaagatgg ctgttggtat    3480
ggaatggaga taaggcccag gaaagaacca gaaagcaact tagtaaggtc aatggtgact    3540
gcaggatcaa ctgatcacat ggatcacttc tcccttggag tgcttgtgat tctgctcatg    3600
gtgcaggaag ggctgaagaa gagaatgacc acaaagatca tcataagcac atcaatggca    3660
gtgctggtag ctatgatcct gggaggattt caatgagtg acctggctaa gcttgcaatt    3720
ttgatgggtg ccaccttcgc ggaaatgaac actggaggag atgtagctca tctggcgctg    3780
atagcggcat tcaaagtcag accagcgttg ctggtatctt tcatcttcag agctaattgg    3840
acaccccgtg aaagcatgct gctggccttg cctcgtgtc ttttgcaaac tgcgatctcc    3900
gccttggaag gcgacctgat ggttctcatc aatggttttg ctttggcctg gttggcaata    3960
cgagcgatgg ttgttccacg cactgataac atccaccttgg caatcctggc tgctctgaca    4020
ccactggccc ggggcacact gcttgtggcg tggagagcag gccttgctac ttgcgggggg    4080
tttatgctcc tctctctgaa gggaaaggc agtgtgaaga gaacttacc atttgtcatg    4140
gccctgggac taaccgctgt gaggctggtc gacccatca acgtggtggg gctgctgttg    4200
ctcacaagga gtgggaagcg gagctggccc cctagcgaag tactcacagc tgttggcctg    4260
atatgcgcat tggctggagg gttcgccaag gcagatatag agatggctgg gcccatggcc    4320
gcggtcggtc tgctaattgt cagttacgtg gtctcaggaa agagtgtgga catgtacatt    4380
gaaagagcag gtgacatcac atgggaaaaa gatgcggaag tcactggaaa cagtccccgg    4440
ctcgatgtgg cgctagatga gagtggtgat ttctccctgg tggaggatga cggtccccc    4500
atgagagaga tcatactcaa ggtggtcctg atgaccatct gtggcatgaa cccaatagcc    4560
ataccctttg cagctggagc gtggtacgta tacgtgaaga ctggaaaaag gagtggtgct    4620
ctatgggatg tgcctgctcc caaggaagta aaaaaggggg agaccacaga tggagtgtac    4680
agagtaatga ctcgtagact gctaggttca acacaagttg gagtggggaat tatgcaagag    4740
gggtctttc acactatgtg gcacgtcaca aaaggatccg cgctgagaag cggtgaaggg    4800
agacttgatc catactgggg agatgtcaag caggatctgg tgtcatactg tggtccatgg    4860
aagctagatg ccgcctggga cgggcacagc gaggtgcagc tcttggccgt gccccccgga    4920
gagagagcga ggaacatcca gactctgccc ggaatattta agacaaagga tggggacatt    4980
ggagcggttg cgctggatta cccagcagga acttcaggat ctccaatcct agacaagtgt    5040
gggagagtga taggacttta tggcaatggg gtcgtgatca aaaatgggag ttatgttagt    5100
gccatcaccc aagggaggag ggaggaagag actcctgttg agtgcttcga gccttcgatg    5160
ctgaagaaga agcagctaac tgtcttagac ttgcatcctg gagctgggaa aaccaggaga    5220
gttcttcctg aaatagtccg tgaagccata aaaacaagac tccgtactgt gatcttagct    5280
ccaaccaggg ttgtcgctgc tgaaatggag gaagcccta gagggcttcc agtgcgttat    5340
atgacaacag cagtcaatgt cacccactct ggaacagaaa tcgtcgactt aatgtgccat    5400
gccaccttca cttcacgtct actacagcca atcagagtcc caactataa tctgtatatt    5460
atggatgagg cccacttcac agatcccctca agtatagcag caagaggata catttcaaca    5520
agggttgaga tgggcgaggc ggctgccatc ttcatgaccg ccacgccacc aggaacccgt    5580
gacgcatttc cggactccaa ctcaccaatt atggacaccg aagtggaagt cccagagaga    5640
gcctggagct caggcctttga ttgggtgacg gattattctg gaaaaacagt ttggtttgtt    5700
ccaagcgtga ggaacggcaa tgagatcgca gcttgtctga caaaggctgg aaaacgggtc    5760
atacagctca gcagaaagac ttttgagaca gagttccaga aaacaaaaca tcaagagtgg    5820
gactttgtcg tgacaactga catttcagag atggcgcca actttaaagc tgaccgtgtc    5880
atagattcca ggagatgcct aaagccggtc atacttgatg gcgagagagt cattctggct    5940
ggacccatgc ctgtcacaca tgccagcgct gcccagagga ggggcgcat aggcaggaat    6000
cccaacaaac ctggagatga gtatctgtat ggaggtgggt gcgcagagac tgacgaagac    6060
catgcacact ggcttgaagc aagaatgctc cttgacaata tttacctcca agatggcctc    6120
atagcctcgc tctatcgacc tgaggccgac aaagtagcag ccattgaggg agagttcaag    6180
cttaggacgg agcaaaggaa gacctttgtg gaactcatga agagggata tcttcctgtt    6240
tggctggcct atcaggttgc atctgccgga ataacctaca gatagaag atggtgctt    6300
gatggcacga ccaacaacac cataatgaa gacagtgtgc cggcagaggt gtggaccaga    6360
cacggagaga aaagagtgct caaaccgagg tggatgacg ccagagtttg ttcagatcat    6420
gcggccctga gtcattcaa ggagtttgcc gctgggaaaa aggagcggc ttttggagtg    6480
atggaagccc tgggaacact gccaggacac atgacagaga gattccagga agccattgac    6540
aacctgctca tgcatcgcg ggcagagact ggaagcaggc cttacaaagc cgcgcggc    6600
caattgccgg agaccctaga gaccattatg ctttttgggt tgctgggaac agtctcgctg    6660
ggaatctttt tcgtcttgat gaggaacaag ggcataggga agatgggctt ggaatggtg    6720
actcttgggg ccagcgcatg gctcatgtgg ctctcggaaa ttgagccagc cagaattgca    6780
tgtgtcctca ttgttgtgtt cctattgctg gtggtgctca tacctgagcc agaaaagcaa    6840
agatctcccc aggacaacca aatggcaatc atcatcatgg tagcagtagg tcttctgggc    6900
```

```
ttgattaccg ccaatgaact cggatggttg gagagaacaa agagtgacct aagccatcta  6960
atgggaagga gagaggaggg ggcaaccatg ggattctcaa tggacattga cctgcgccca  7020
gcctcagctt gggccatcta tgctgccttg acaactttca ttaccccagc cgtccaacat  7080
gcagtgacca cttcatacaa caactactcc ttaatggcga tggccacgca agctggagtg  7140
ttgttttggta tgggcaaagg gatgccattc tacgcatggg actttggagg cccgctgcta  7200
atgataggtt gctactcaca attaacgccc ctgaccctaa tagtgggcat cattttgctc  7260
gtggcgcact acatgtactt gatcccaggg ctgcaggcag cagctgcgcg tgctgcccag  7320
aagagaacgg cagctggcat catgaagaac cctgttgtgg atggaatagt ggtgactgac  7380
attgacacaa tgacaattga cccccaagtg gagaaaaaga tgggacaggt gctactcatg  7440
gcagtagccg tctccagcgc catactgtcg cggacccgcc tggggtgggg ggaggctatg  7500
gccctgatca cagccgcaac ttccactttg tgggaaggct ctccgaacaa gtactggaac  7560
tcctctacag ccacttcact gtgtaacatt tttaggggaa gttacttggc tggagcttct  7620
ctaatctaca cagtaacaag aaacgctggc ttggtcaaga cgtgggggg tggaacagga  7680
gagaccctgg gagagaaatg gaaggcccgc ttgaaccaga tgtcggccct ggagttctac  7740
tcctacaaaa agtcaggcat caccgagtg tgcagagaa aggcccgccg cgccctcaag  7800
gacggtgtgg caacgggagg ccatgctgtg tcccgaggaa gtgcaaagct gagatggttg  7860
gtggagcggg gatacctgca gccctatgga aaggtcattg atcttggatg tggcagaggg  7920
ggctggagtt actacgccgc caccatccgc aaagttcaag aagtgaaagg atacacaaaa  7980
ggaggccctg gtcatgaaga acccgtgttg gtgcaaagct atgggtggaa catagtccgt  8040
cttaagagtg gggtggacgt ctttcatatg gcggctgagc cgtgtgacac gttgctgtgt  8100
gacataggtg agtcatcatc tagtcctgaa gtggaagaag cacggacgct cagagtcctc  8160
tccatggtgg gggattggct tgaaaaaaga ccaggagcct tttgtataaa agtgttgtgc  8220
ccatacacca gcactatgat ggaaaccctg agcgactgc agcgtaggta tgggggagga  8280
ctggtcagag tgccactctc ccgcaactct acacatgaga tgtactgggt ctctggagcg  8340
aaaagcaaca ccataaaaag tgtgtccacc acgagccagc tcctcttggg gcgcatggac  8400
gggcctagga ggcagtgaa atatgaggag gatgtgaatc tcggctctgg gacgcgggct  8460
gtggtaagct gcgctgaagc tcccaacatg aagatcattg gtaaccgcat tgaaaggatc  8520
cgcagtgagc acgcggaaac gtggttcttt gacgagaacc acccatatag gacatgggct  8580
taccatggaa gctatgaggc ccccacacaa gggtcagcgt cctctctaat aaacggggtt  8640
gtcaggctcc tgtcaaaacc ctgggatgtg gtgactggga tcacaggaat agccatgacc  8700
gacaccacac cgtatggtca gcaaagagtt ttcaaggaaa aagtggacac tagggtgcca  8760
gaccccaag aaggtactcg tcaggttatg agcatggtct cttcctggtt gtggaaagag  8820
ctaggcaaac acaaacggcc acgagtctgt accaagaag agttcatcaa caaggttcgt  8880
agcaatgcag cattagggc aatatttgaa gaggaaaaag agtggaagac tgcagtggaa  8940
gctgtgaacg atccaaggtt ctgggctcta gtggcaaaga aagagagca ccacctgaga  9000
ggagagtgcc agagttgtgt gtacaacatg atgggaaaa gagaaagaa acaagggaa  9060
tttgaaaagg ccaagggcag ccgcgccatc tggtatatgt ggctagggc tagatttcta  9120
gagttcgaag cccttggatt cttgaacgag atcactggga tggggagaga gaactcagga  9180
ggtggttgtt aagggctggg attacaaaga ctcggatatg tcctagaaga gatgagtcga  9240
ataccaggag gaaggatgta tgcagatgac actgctggct gggacacccg catcagcagg  9300
tttgatctgg agaatgaagc tctaatcacc aaccaaatgg agaaagggca cagggccttg  9360
gcattggcca taatcaagta cacataccaa aacaaagtgt taaggtcct tagaccagct  9420
gaaaaaggga aaacagttat ggacattatt tcgagacgaa accaaagggg gagcggacaa  9480
gttgtcactt acgctcttaa cacatttacc aacctagtgg tgcaactcat tcggaatatg  9540
gaggctgagg aagtcctaga gatgcaagac ttgtggctgc tgcggaggtc agagaaagtg  9600
accaactggt tgcagagcaa cggatgggat aggctcaaac gaatggcagt cagtggagat  9660
gattcgttg tgaagccaat tgatgatagg tttgcacatg ccctcagtt cttgaatgat  9720
atgggaaaag ttaggaagga cacacaagag tggaaaccct caactgatg gacaactgga  9780
gaagaagttc cgttttgctc ccaccactcc aacaagctcc atctcaagga cgggaggtcc  9840
attgtggttc cctgccgcca ccaagatgaa ctgattggcc gggcccgcgt ctctccaggg  9900
gcgggatgga gcatccggga gactgcttgc ctagcaaaat catatgcgca aatgtggcag  9960
ctcctttatt tccacagaag ggacctccga ctgatggcca atgccatttg ttcatctgtg 10020
ccagttgact gggttccaac tgggagaact acctggtcaa tccatggaaa gggagaatgg 10080
atgaccactg aagacatgct tgtggtgtgg aacagagtgt ggattgagga gaacgaccac 10140
atggaagaca agacccccagt tacgaaatgg acagacattc cctatttggg aaaaagggaa 10200
gacttgtggt gtgatctct cataggcac agaccgcga ccacctgggc tgagaacatt 10260
aaaaacacag tcaacatggt gcgcaggatc ataggtgatg aagaaagta catggactac 10320
ctatccaccc aagttcgcta cttgggtgaa gaggggctcta cacctggagt gctgtaagca 10380
ccaatcttaa tgttgtcagg cctgctagtc agccacagct tggggaaagc tgtgcagcct 10440
gtgaccccc caggagaagc tgggaaacca agcctatagt caggccgaga acgcatggc 10500
acggaagaag ccatgctgcc tgtgagcccc tcagaggaca ctgagtcaaa aaccccacg 10560
cgcttggagg cgcaggatgg gaaaagaagg tggcgacctt ccccacccctt caatctgggg 10620
cctgaactgg agatcagctg tggatctcca gaagagggac tagtggttag aggaga     10676

SEQ ID NO: 3        moltype = DNA  length = 10793
FEATURE             Location/Qualifiers
source              1..10793
                    mol_type = unassigned DNA
                    organism = Zika virus
SEQUENCE: 3
ccaatctgtg aatcagactg cgacagttcg agtttgaagc gaaagctagc aacagtatca   60
acaggtttta ttttggattt ggaaacgaga gtttctggtc atgaaaaacc caaaaaagaa  120
atccggagga ttccggattg tcaatatgct aaaacgcgga gtagcccgtg tgagcccctt  180
tgggggcttg aagaggctgc cagccggact tctgctgggt catgggccca tcaggatggt  240
cttggcgatt ctagcctttt tgagattcac ggcaatcaag ccatcactgg gtctcatcaa  300
tagatggggt tcagtgggga aaaaagaggc tatggaaata ataaagaagt tcaagaaaga  360
tctggctgcc atgctgagaa taatcaatgc caggaaggag aagaagagac gaggcgcaga  420
tactagtgtc ggaatcgttg gcctcctgct gaccacagct atggcagcgg aggtcactag  480
acgtgggagt gcatactata tgtacttgga cagaaacgat gctggggagg ccatatcttt  540
```

```
tccaaccaca ttggggatga ataagtgtta tatacagatc atggatcttg gacacatgtg    600
tgatgccacc atgagctatg aatgccctat gctggatgag ggggtggaac cagatgacgt    660
cgattgttgg tgcaacacga cgtcaacttg ggttgtgtac ggaacctgcc atcacaaaaa    720
aggtgaagca cggagatcta aaagagctgt gacgctcccc tcccattcca ctaggaagct    780
gcaaacgcgg tcgcaaacct ggttggaatc aagagaatac acaaagcact tgattagagt    840
cgaaaattgg atattcagga acctggcttc gcgttagca gcagctgcca tcgcttggct     900
tttgggaagc tcaacgagcc aaaaagtcat atacttggtc atgatactgc tgattgcccc    960
ggcatacagc atcaggtgca taggagtcag caataggac tttgtggaag gtatgtcagg    1020
tgggacttgg gttgatgttg tcttggaaca tgggggttgt gtcaccgtaa tggcacagga   1080
caaaccgact gtcgacatag agctggttac aacaacagtc agcaacatgg cggaggtaag   1140
atcctactgc tatgaggcat caatatcaga catggcttcg gacagccgct gcccaacaca   1200
aggtgaagcc taccttgaca agcaatcaga cactcaatat gtctgcaaaa gaacgttagt   1260
ggacagaggc tggggaaatg gatgtggact ttttggcaaa gggagcctgg tgacatgcgc   1320
taagtttgca tgctccaaga aaatgaccgg gaagagcatc cagccagaga atctggagta   1380
ccggataatg ctgtcagttc atggctccca gcacagtggg atgatcgtta atgcacagg    1440
acatgaaact gatgagaata gagcgaaggt tgagataacg cccaattcac caagagccga   1500
agccaccctg gggggttttg gaagcttagg acttgattgt gaaccgagga caggccttga   1560
cttttcagat ttgtattact tgactatgaa taacaagcac tggttggttc acaaggagtg   1620
gttccacgac attccattac cttggcacgc tggggcagaa accggaactc cacactggaa   1680
caacaaagaa gcactggtag agttcaagga cgcacatgcc aaaaggcaaa ctgtcgtggt   1740
tctagggact caagaaggag cagttcacac ggcccttgct ggagctctgg aggctgagat   1800
ggatggtgca aagggaaggc tgtcctctgg ccacttgaaa tgtcgcctga aaatggataa   1860
acttagattg aagggcgtgt cactctcctt gtgtaccgca gcgttcacat tcaccaagat   1920
cccggctgaa acactgcacg ggacagtcac agtggaggta cagtacgcag ggacagatgg   1980
accttgcaag gttccagctc agatggcggt ggacatgcaa actctgaccc cagttgggag   2040
gttgataacc gctaaccccg taatcactga aagcactgag aactctaaga tgatgctgga   2100
acttgatcca ccatttgggg actcttacat tgtcatagga gtcgggaga agaagatcac    2160
ccaccactgg cacaggagtg gcagcaccat tggaaaagca tttgaagcca ctgtgagagg   2220
tgccaagaga atggcagtct gggagacac agcctggac tttggatcag ttggaggcgc    2280
tctcaactca ttgggcaagg gcatccatca aattttgac gcagctttca aatcattgt    2340
tggaggaatg tcctggttct cacaaattct cattggaacg ttgctgatgt ggttgggtct   2400
gaacacaaag aatggatcta tttccttat gtgcttggcc ttaggggag tgttgatctt    2460
cttatccaca gccgtctctg ctgatgtggg gtgctcggtg gacttctcaa gaaggagac    2520
gagatgtggt acagggtgt tcgtctataa cgacgttgaa gcctggaggg acaggtacaa   2580
gtaccatcct gactctcccc gtagattggc agcagcagtc aagcaagcct gggaagatgg   2640
tatctgcggg atctcctctg tttcaagaat ggaaaacatc atgtggagat cagtagaagg   2700
ggagcttaac gcaatcctgg aagagaatgg agttcaactg acggtcgttg tgggatctgt   2760
aaaaaacccc atgtggagag gtccacagag attgcccgtg cctgtgaacg agctgcccca   2820
cggctggaag gcttggggga aatcgtactt cgtcagagca gcaaagacaa ataacagctt   2880
tgtcgtggat ggtgacacac tgaaggaatg cccactcaaa catagagcat ggaacagctt   2940
tcttgtggag gatcatgggt tcggggtatt tcacactagt gtctggctca aggttagaga   3000
agattattca ttagagtgtg atccagccgt tattggaaca gctgttaagg gaaggaggc    3060
tgtacacagt gatctaggct actgattga gagtgagaag aatgacacat ggaggctgaa   3120
gagggcccat ctgatcgaga tgaaaacatg tgaatggcca aagtcccaca cattgtggac   3180
agatgccaata aagagagtg atctgatcat acccaagtct ttagctgggc cactcagcca   3240
tcacaatacc agagagggct acaggaccca aatgaaaggg ccatggcaca gtgaagagct   3300
tgaaattcgg tttgaggaat gcccaggcac taaggtccac ggtgaggaaa catgtggaac   3360
aagaggacca tctctgagat caaccactgc aagcggaagg gtgatcgagg aatggtgctg   3420
cagggagtgc acaatgcccc cactgtcgtt ccgggctaaa gatggctgtt ggtatggaat   3480
ggagataagg cccaggaaag aaccagaaag caacttagta aggtcaatgg tgactgcagg   3540
atcaactgat cacatggatc acttctccct tggagtgctt gtgattctgc tcatggtgca   3600
ggaagggctg aagaagagaa tgaccacaaa gatcatcata agcacatcaa tggcagtgct   3660
ggtagctatg atcctgggag gatttttcaat gagtgacctg gctaagcttg caattttgat   3720
gggtgccacc ttcgcggaaa tgaacactgg aggagatgta gctcatcgg cgctgatagc    3780
ggcattcaaa gtcagaccag cgttgctggt atctttcatc ttcagagcta attggacacc   3840
ccgtgaaagc atgctgctgg ccttggcctc gtgttttttg caaactgcga tctccgcctt   3900
ggaaggcgac ctgatggttc tcatcaatgg ttttgctttg gctggttgg caatacgagc    3960
gatggttgtt ccacgcactg acaacatcac cttggcaatc ctgctgctc tgacaccact    4020
ggcccggggc acactgcttg tggcgtggag agcaggcctt gctacttgcg gggggttttat   4080
gctcctctct ctgaagggaa aaggcagtgt gaagaagaac ttaccatttg tcatggccct   4140
gggactaacc gctgtgaggc tggtcgaccc catcaacgtg gtgggactgc tgttgctcac   4200
aaggagtggg aagcggagct ggcccctag cgaagtactc acagctgttg gcctgatatg   4260
cgcattggct ggagggttcg ccaaggcaga tatagagatg gctgggccca tggccgcggt   4320
cggtctgcta attgtcagtt acgtggtctc aggaaagagt gtggacatgt acattgaaag   4380
agcaggtgac atcacatggg aaaaagatgc ggaagtcact ggaaacagtc cccgcctga    4440
tgtggcgcta gatgagagtg tgacttctc cctggtggag gatgacgtc cccccatgag   4500
agagatcata ctcaaggtgg tcctgatgac catctgtgc atgaaccaa tagccatacc    4560
ctttgcagct ggagcgtgt acgtatacgt gaagactgga aaaaggagtg gtgtctatg    4620
ggatgtgcct gctcccaagg aagtaaaaaa ggggagacc acagatggag tgtacagagt   4680
aatgactcgt agactgctag gttcaacaca agttggagtg ggagttatgc aagagggggt   4740
ctttcacact atgtggcacg tcacaaaagg atccgcgctg agaagcggtg aagggagact   4800
tgatccatac tgggggatg tcaagcagga tctggtgtca tactgggtc atgtgaagct    4860
agatgccgcc tgggacgggc acagcgaggt gcagctcttg gccgtgcccc ccggagagag   4920
agcgaggaac atccagactc tgccccgaat atttaagaca aaggatgggg acattggaag   4980
ggttgcgctg gattcccag caggaacttc aggatctcca atcctagaca agtgtgggag   5040
agtgatagga cttatggca atgggtcgt gataaaaaat gggagttatg ttagtgccat   5100
cacccaaggg aggagggagg aagagactcc tgttgagtgc ttcgagcctt cgatgctgaa   5160
gaagaagcag ctaactgtct tagacttgca tcctggagct gggaaaacca ggagagttct   5220
tcctgaaata gtccgtgaag ccataaaaac aagactccgt actgtgatct tagctccaac   5280
```

```
cagggttgtc gctgctgaaa tggaggaagc ccttagaggg cttccagtgc gttatatgac   5340
aacagcagtc aatgtcaccc actctggaac agaaatcgtc gacttaatgt gccatgccac   5400
cttcacttca cgtctactac agccaatcag agtccccaac tataatctgt atattatgga   5460
tgaggcccac ttcacagatc cctcaagcat agcagcaaga ggatacattt caacaagggt   5520
tgagatgggc gaggcggctg ccatcttcat gaccgccacg ccaccaggaa cccgtgacgc   5580
atttccggac tccaactcac caattatgga caccgaagtg gaagtccag agagagcctg    5640
gagctcaggc tttgattggg tgacggatca ttctggaaaa acagtttggt ttgttccaag   5700
cgtgaggaac ggcaatgaga tcgcagcttg tctgacaaag gctggaaaac gggtcataca   5760
gctcagcaga aagactttg agacagagtt ccagaaaaca aaacatcaag agtgggactt    5820
tgtcgtgaca actgacactt cagagatggg cgccaacttt aaagctgacc gtgtcataga   5880
ttccaggaga tgcctaaagc cggtcatact tgatggcgag agagtcattc tggctggacc   5940
catgcctgtc acacatgcca gcgctgccca gaggagggg cgcataggca ggaatcccaa    6000
caaacctgga gatgagtacc tgtatggagg tgggtgcgca gagactgacg aagaccatgc   6060
acactggctt gaagcaagaa tgctccttga caatatttac ctccaagatg gcctcatagc   6120
ctcgctctat cgacctgagg ccgacaaagt agcagccatt gagggagagt tcaagcttag   6180
gacggagcaa aggaagacct ttgtggaact catgaaaaga ggagatcttc ctgtttggct   6240
ggcctatcag gttgcatctg ccggaataac ctacacagat agaagatggt gctttgatgg   6300
cacgaccaac aacaccataa tggaagacag tgtgccggca gaggtgtgga ccagacacgg   6360
agagaaaaga gtgctcaaac cgaggtggat ggacgccaga gtttgttcag atcatgcggc   6420
cctgaagtca ttcaaggagt ttgccgctgg gaaaagagga gcggcttttg gagtgatgga   6480
agccctggga acactgccag gacacatgac agagagattc caggaagcca ttgacaacct   6540
cgctgtgctc atgcgggcag agactggaag caggcccttac aaagccgcgg ggcccaatt   6600
gccgagacc ctagagacca ttatgctttt ggggttgctg ggaacagtct cgctgggaat    6660
ctttttcgtc ttgatgagga acaagggcat agggaagatg ggctttggaa tggtgactct   6720
tggggccagc gcatggctca tgtggctctc ggaaattgag ccagcagaa ttgcatgtgt    6780
cctcattgtt gtgttcctat tgctgattgg gctcatacct gagccagaaa agcaaagatc   6840
tccccaggac aaccaaatgg caatcatcat catgtagtcca gtaggtcttc tgggcttgat   6900
taccgccaat gaactcggat ggttggagag aacaaagagt gacctaagcc atctaatggg   6960
aaggagagag gaggggggcaa ccataggatt ctcaatggac attgacctgc ggccagcctc   7020
agcttgggcc atctatgctg ccttgacaac tttcattacc ccagccgtcc aacatgcagt   7080
gaccacttca tacaacaact actccttaat ggcgatggcc acgcaagctg gagtgttgtt   7140
tggtatgggc aaagggatgc cattctacgc atgggactttt ggagtccgc tgctaatgat   7200
aggttgctac tcacaattaa caccctgac cctaatagtg gccatcattt tgctcgtggc   7260
gcactacatg tacttgatcc cagggctgca ggcagcagct gcgcgtgctg cccagaagag   7320
aacggcagct ggcatcatga aaaccgtg tgtggatgga atagtggtga ctgacattga     7380
cacaatgaca attgacccc aagtggagaa aaagatggga caggtgctac tcatagcagt    7440
agccgtctcc agcgccatac tgtcgcggac cgcctggggg tggggggagg ctgggggcct   7500
gatcacagcc gcaacttcca ctttgtggga aggctctccg aacaagtact ggaactcctc   7560
tacagccact tcactgtgta acattttag gggaagttac ttggctggag cttctctaat   7620
ctacacagta acaagaaacg ctggcttggt caagagacgt ggggtggaa caggagagac    7680
cctgggagag aaatgtgaagg cccgcttgaa ccagatgtcg gccctggagt tctactccta   7740
caaaaagtca ggcatcaccg aggtgtgcag agaagaggcc cgccgcgccc tcaaggacgg   7800
tgtggcaacg ggaggccatg ctgtgtcccg aggaagtgca gggttggtgga gttggtggga   7860
gcggggatac ctgcagccct atggaaaggt cattgatctt ggatgtggca gaggggctg    7920
gagttactac gccgccacca tccgcaaagt tcaagaagtg aaaggataca caaaaggagg   7980
ccctggtcat gaagaacccg tgttggtgca aagctatggg tggaacatag tccgtcttaa   8040
gagtggggta gacgtctttc atatggcggc tgagccgtgt gacacgttgc tgtgtgacat   8100
aggtgagtca tcatctagtc ctgaagtgga agaagcacgg acgctcagag tcctctccat   8160
ggtgggggat tggcttgaaa aaagaccagg agccttttgc ataaaagtgt tgtgcccata   8220
caccagcact atgatggaaa ccctggacgc actgcagcgt aggtatgggg gaggactggt   8280
cagagtgcca ctctcccgca actctacaca tgagatgtac tgggtctctg gagcgaaaag   8340
caacaccata aaaagtgtgt ccaccacgag ccagctcctc ttggggcgca tggacgggcc   8400
taggaggcca gtgaaatatg aggaggatgt gaatctcggc tctggcacgc gggctgtggt   8460
aagctgcgct gaagctccca catgaagat cattggtaac cgcattgaaa ggatccgcag    8520
tgagcacgcg gaaacgtggt tctttgacga aaaccaccca tataggaacat gggcttacca   8580
tggaagctat gtggccccca cacaagggtc agcgtcctct ctaataaacg gggttgtcag   8640
gctcctgtca aaaccctggg atgtggtgac tggagtcaca ggaatagcca tgaccgacac   8700
cacaccgtat ggtcagcaaa gagttttcaa ggaaaaagtg gacactaggg tgccagaccc   8760
ccaagaaggc actcgtcagg ttatgacgat ggtctcttcc tggttgtgga aagagctagg   8820
caaaacacaaa cgaccacgag tctgtaccaa agaagagttc atcaacaagg ttcgtagcaa   8880
tgcagcatta ggggcaatat ttgaagagga aaaagagtg aagactgcag tggaagctgt    8940
gaacgatcca aaggttctggg ctctagtgga caaggaaaga gagcaccacc tgagaggaga   9000
gtgccagagt tgtgtgtaca acatgatggg aaaaagagaa aagaaacaag gggaatttgg   9060
aaaggccaag ggcagccgcg ccatctgtta tatgtggcct agcactttct ctaagcttt    9120
cgaagccctt ggattcttga acgaggatca ctggatgggg agagaaaact caggaggtgg   9180
tgttgaaggg ctgggattac aaagactcgg atatgtccta aagagatga gtcgcatacc    9240
aggaggaagg atgtatgcag atgacactgc tggctgggac acccgcatca gcaggtttga   9300
tctggagaat gaagctctaa tcaccaacca aatggagaaa gggcacaggg ccttggcatt   9360
ggccataatc aagtacacat accaaaacaa agtggtaaag gtccttagac cagctgaaaa   9420
agggaaaaca gttatggaca ttatttcgag acaagaccaa aggggtagcg gacaagttgt   9480
cacttacgct cttaacacat ttaccaacct agtggtgcaa ctcattcgga atatggaggc   9540
tgaggaagtt ctagagatgc aagacttgtg gctgctgcgg aggtcagaga agtgaccaa    9600
ctggttgcag agcaacggat gggataggct caaacgaatg gcagtcagtg gagatgattg   9660
cgttgtgaag ccaattgatg ataggtttgc acatgccctc aggttcttga atgatatggg   9720
aaaagttagg aaggacacac aagagtgaaa accctcaact ggatgggaca actgggaaga   9780
agttccgttt tgctcccacc acttcaacaa gctccatctc aaggacggga ggtccattgt   9840
ggttccctgc cgccaccaag atgaactgat ggccgggcc cgcgtctctc caggggcggg   9900
atggagcatc cgggagactg cttgcctagc aaaatcatat gcgcaaatgt ggcagctcct   9960
ttatttccac agaagggacc tccgactgat ggccaatgcc atttgttcat ctgtgccagt  10020
```

```
tgactgggtt ccaactggga gaactacctg gtcaatccat ggaaaggag aatggatgac    10080
cactgaagac atgcttgtgg tgtgaacag agtgtggatt gaggagaacg accacatgga    10140
agacaagacc ccagttacga aatggacaga cattccctat ttgggaaaaa gggaagactt    10200
gtggtgtgga tctctcatag ggcacagacc gcgcaccacc tgggctgaga acattaaaaa    10260
tacagtcaac atggtgcgca ggatcatagg tgatgaagaa aagtacatgg actacctatc    10320
cacccaagtt cgctacttgg gtgaagaagg gtctacacct ggagtgctgt gagcaccaat    10380
cttaatgttg tcaggcctgc tagtcagcca cagcttgggg aaagctgtgc agcctgtgac    10440
ccctccagga gaagctgggt aaccaagcct atagtcaggc cgagaacgcc atggcacgga    10500
agaagccatg ctgcctgtga gcccctcaga ggactgag tcaaaaaacc ccacgcgctt    10560
ggaggcgcag gatgggaaaa gaaggtggcg accttcccca cccttcaatc tggggcctga    10620
actggagatc agctgtggat ctccagaaga gggactagtg gttagaggag acccccccgga    10680
aaacgcaaaa cagcatattg acgctgggaa agaccagaga ctccatgagt ttccaccacg    10740
ctggccgcca ggcacagatc gccgaatagc ggcggccggt gtggggaaat cca         10793

SEQ ID NO: 4              moltype = DNA  length = 10675
FEATURE                   Location/Qualifiers
source                    1..10675
                          mol_type = unassigned DNA
                          organism = Zika virus
SEQUENCE: 4
gttgttgatc tgtgtgaatc agactgcgac agttcgagtt tgaagcgaaa gctagcaaca    60
gtatcaacag gttttatttt ggatttgaa acgagagttt ctggtcatga aaaacccaaa    120
aaagaaatcc ggaggattcc ggattgtcaa tatgctaaaa cgcggagtag cccgtgtgag    180
cccctttggg ggcttgaaga ggctgccagc cggacttctg ctgggtcatg ggcccatcag    240
gatggtcttg gcgattctag ccttttgag attcacggca atcaagccat cactgggtct    300
catcaataga tgggttcag tggggaaaaa agaggctagg gaaacaataa agaagttcaa    360
gaaagatctg gctgccatgc tgagaataat caatgctagg aaggagaaga gagacgagg    420
cgcagatact agtgtcggaa ttgttggcct cctgctgacc acagctatgg cagcggaggt    480
cactagacgt gggagtgcat actatatgta cttggacaga aacgatgctg gggaggccat    540
atcttttcca accacattgg ggatgaataa gtgttatata cagatcatgg atcttggaca    600
catgtgtgat gccaccatga gctatgaatg ccctatgctg gatgaggggg tggaaccaga    660
tgacgtcgat tgttggtgca acacgacgtc aacttgggtt gtgtacgaa cctgccatca    720
caaaaaggt gaagcacgga gatctagaag agctgtgacg ctcccctccc attccaccag    780
gaagctgcaa acgcggtcgc aaacctggtt ggaatcacaa gaatacacaa agcacttgat    840
tagagtcgaa aattggatat tcaggaaccc tggcttcgcg ttagcagcag ctgccatcgc    900
ttggcttttg ggaagctcaa cgagccaaaa agtcatatac ttggtcatga tactgctgat    960
tgccccggca tacagcatca ggtgcatagg agtcagcaat agggactttg tggaaggtat    1020
gtcaggtggg acttgggttg atgttgtctt ggaacatgga ggttgtgtca ccgtaatggc    1080
acaggacaaa ccgactgtcg acatagagct ggttacaaca acatcagca acatggcgga    1140
ggtaagatcc tactgctatg aggcatcaat atcagacatg gcttctgaca gccgctgccc    1200
aacacaaggt gaagcctacc ttgacaagca atcagacact caatatgtct gcaaaagaac    1260
gttagtggac agaggctggg gaaatggatg tggactttt ggcaagggga gcctggtgac    1320
atgcgctaag tttgcatgct ccaagaaaat gaccgggaag agcatccgac agagaatct    1380
ggagtaccgg ataatgctgt cagttcatg ctcccagcac agtgggatga tcgttaatga    1440
cacaggacat gaaactgatg agaatagagc gaaagttgag ataacgccca attcaccgag    1500
agccgaagcc accctggggg gttttggaag cctaggactt gattgtgaac cgaggacagg    1560
ccttgacttt tcagatttgt attacttgac tatgaataac aagcactggt tggttcacaa    1620
ggagtggttc cacgacattc cattaccttg gcacgctggg gcagacaccg gaactccaca    1680
ctggaacaac aaaagaagca ctgtagagtt caaggacgca catgccaaaa ggcaaactgt    1740
cgtggttcta gggagtcaag aaggagcagt tcacacggcc cttgctggag ctctggaggc    1800
tgagatggat ggtgcaaagg gaaggctgtc ctctggccaa ttgaaatgtc gcctgaaaat    1860
ggataaactt agattgaagg gcgtgtcata ctccttgtgt actgcagcgt tcacattcac    1920
caagatcccg gctgaaacac tgcacggac agtcacagtg gaggtacagt acgcagggac    1980
agatggacct tgcaaggttc cagctcagat ggcggtggca atgcaaactc tgacccccagt    2040
tgggaggttg ataaccgcta accccgtaat cactgaaagc actgagaact ctaagatgat    2100
gctggaactt gatccaccat ttggggactc ttacattgtc ataggagtcg gggagaagaa    2160
gatcacccac cactggcaca ggagtggcag caccattgga aaagcatttg aagccactgt    2220
gagaggtgcc aagagaatgg cagtcttggg agacacagcc tggacttg gatcagttgg    2280
aggcgctctc aactcattgg gcaaggcat ccatcaaatt tttggagcag ctttcaaatc    2340
attgtttgga ggaatgtcct ggttctcaca aattctcatt ggaacgttgc tgatgtggtt    2400
gggtctgaac acaaagaatg gatctatttc ccttatgtgc ttggcttag ggggagtgtt    2460
gatcttctta tccacagccg tctctgctga tgtggggtgc tcggtggact ctcaaagaa    2520
gggagacgaga tgcggtacag gggtgttcgt ctataacgac gttgaagcct ggagggacag    2580
gtacaagtac catcctgact cccccgtag attggcagca gcagtcaagc aagcctggga    2640
agatggtatc tgcgggatct cctctgtttc aagaatgaa acatcatgt ggagatcagt    2700
agaaggggag ctcaacgcaa tcctggaaga gaatggagtt caactgacgg tcgttgtggg    2760
atctgtaaaa accccatgt ggaaggtcc acagagattg cccgtgcctg tgaacgagct    2820
gccccacggc tggaaggctt gggggaaatc gtatttcgtc agacagcaa agacaaataa    2880
cagctttgtc gtggatgtg acacactgaa ggaatgccca ctcaaacata gagcatgaa    2940
cagctttctt gtgaggatc atgggttcgg ggtatttcac actagtgtct ggctcaaggt    3000
tagagaagat tattcattag agtgtgatcc agccgttatt ggaacagctg ttaagggaaa    3060
ggaggctgta cacagtgatc taggctactg gattgagagt gagaagaatg acacatggag    3120
gctgaagagg gcccatctga tcgagatgaa acatgtgaa tggccaaagt cccacacatt    3180
gtggacagat ggaatagaag agagtgatct gatcataccc aagtctttag ctgggcccact    3240
cagccatcac aataccagag agggctacag gacccaaatg aaagggccat ggcacagtga    3300
agagcttgaa attcggttg aggaatgccc aggcactaag gtccacgtgg aggaaacatg    3360
tggaacaaga ggaccatctc tgagatcaac cactgcaagc ggaagggtga tcgaggaatg    3420
gtgctgcagg gagtgcacaa tgcccccact gtcgttccgg gctaaagatg gctgttggta    3480
tggaatggag ataaggccca ggaaagaacc agaaagcaac ttagtaaggt caatggtgac    3540
```

```
tgcaggatca actgatcaca tggaccactt ctcccttgga gtgcttgtga tcctgctcat    3600
ggtgcaggaa gggctgaaga agagaatgac cacaaagatc atcataagca catcaatggc    3660
agtgctggta gctatgatcc tgggaggatt ttcaatgagt gacctggcta agcttgcaat    3720
tttgatgggt gccaccttcg cggaaatgaa cactggagga gatgtagctc atctggcgct    3780
gatagcggca ttcaaagtca gaccagcgtt gctggtatct ttcatcttca gagctaattg    3840
gacacccgt gaaagcatgc tgctggcctt ggcctcgtgt cttttgcaaa ctgcgatctc     3900
cgccttggaa ggcgacctga tggttctcat caatggtttt gctttggcct ggttggcaat    3960
acgagcgatg gttgttccac gcactgataa catcaccttg gcaatcctgg ctgctctgac    4020
accactggcc cggggcacac tgcttgtggc gtggagagca ggcctgctca cttgcgggg    4080
gtttatgctc ctctctctga agggaaaagg cagtgtgaag aagaacttac catttgtcat    4140
ggccctggga ctaaccgctg tgaggctggt cgacccatc aacgtggtgg gactgctgtt     4200
gctcacaagg agtgggaagc ggagctggcc cctagcgaa gtactcacag ctgttggcct     4260
gatatgcgca ttggctggag ggttcgccaa ggcagatata gagatggctg ggcccatggc    4320
cgcggtcggt ctgctaattg tcagttacgt ggtctcagga aagagtgtgg acatgtacat    4380
tgaaagagca ggtgacatca catgggaaaa agatgcggaa gtcactggaa acagtccccg    4440
gctcgatgtg gcgctagatg agagtggtga tttctccctg gtggaggatg acggtccccc    4500
catgagagag atcatactca aggtggtcct gatgaccatc tgtggcatga cccaatagc    4560
catacccttt gcagctggag cgtggtacgt atacgtgaag actggaaaaa ggagtggtgc    4620
tctatgggat gtgcctgctc ccaaggaagt aaaaaagggg gagaccacag atggagtgta    4680
cagagtaatg actcgtagac tgctaggttc aacacaagtt ggagtgggag ttatgcaaga    4740
ggggtcttt cacactatgt ggcacgtcac aaaaggatcc gcgctgagaa gcggtgaagg    4800
gagacttgat ccatactggg gagatgtcaa gcaggatctg gtgtcatact gtggtccatg    4860
gaagctagat gccgcctggg atgggcacag cgaggtgcag ctcttggccg tgccccccgg    4920
agagagagcg aggaacatcc agactctgcc cggaatattt aagacaaagg atggggacat    4980
tggagcggtt gcgctggatt acccagcagg aacttcagga tctccaatcc tagacaagtg    5040
tgggagagtg ataggacttt ggcaatgg ggtcgtgatc aaaaacggga gttatgttag     5100
tgccatcacc caaggaggga gggaggaaga gactcctgtt gagtgcttcg agccctcgat    5160
gctgaagaag aagcagctaa ctgtcttaga cttgcatcct ggagctggga aaaccaggag    5220
agttcttcct gaaatagtcc gtgaagccat aaaaacaaga ctccgtactg tgatcttagc    5280
tccaaccagg gttgtcgctg ctgaaatgga ggaggccttc cagggcttgc cagtgcgtta    5340
tatgacaaca gcagtcaatg tcacccactc tggaacagaa atcgtcgact taatgtgcca    5400
tgccaccttc acttcacgtc tactacagcc aatcagagtc cccaactata atctgtatat    5460
tatggatgag gcccacttca cagatccctc aagtatagca gcaagaggat acatttcaac    5520
aagggttgag atgggcgagg cggctgccat cttcatgacc gccacgccac caggaaccgg    5580
tgacgcattt ccggactcca actcaccaat tatggacacc gaagtggaag tccagagag    5640
agcctggagc tcaggctttg attgggtgac ggatcattct ggaaaaacag tttggtttgt    5700
tccaagcgtg aggaacggca atgagatcgc agcttgtctg acaaaggctg gaaaacgggt    5760
catacagctc agcagaaaga cttttgagac agagttccag aaaacaaaac atcaagagtg    5820
ggacttttgc gtgacaactg acatttcaga gatgggcgcc aacttcaaag ctgaccgtgt    5880
catagattcc aggagatgcc taaagccggt catacttgat ggcgagagag tcattctggc    5940
tggacccatg cctgtcacac atgccagcgc tgcccagagg aggggcgca taggcaggaa    6000
tcccaacaaa cctggagatg agtatctgta tggaggtggg tgcgcagaga ctgacgaaga    6060
ccatgcacac tggcttgaag caagaatgct ccttgacaat atttacctcc aagatggcct    6120
catagcctcg ctctatcgac ctgaggccga caaagtagca gccattgagg gagagttcaa    6180
gcttaggacg gagcaaagga agaccttgt ggaactcatg aaaagaggag atcttcctgt     6240
ttggctggcc tatcaggttg catctgccgg aataacctac acagatagaa gatggtgctt    6300
tgatgcacg accaacaaca ccataatgga agacagtgtc ccggcagagt gtgaccag      6360
acacggagag aaaagagtgc tcaaaccgag gtgatggaa gccagagttt gttcagatca    6420
tgcggccctg aagtcattca aggagttgc cgctgggaaa agaggagcgg cttttggagt    6480
gatggaagcc ctgggaacac tgccaggaca catgacagag agattccagg aagccattga    6540
caacctgct gtgctcatgc gggcagagac tggaagcagg ccttacaaag ccgcggcgg    6600
ccaattgccg gagaccctag agaccataat gcttttgggg ttgctgggaa cagtctcgct    6660
gggaatcttc ttcgtcttga tgaggaacaa gggcataggg aagatgggct ttggaatggt    6720
gactcttggg gccagcgcat ggctcatgtg gctctcggaa attgagccag ccagaattgc    6780
atgtgcctc attgttgtgt tcctattgct ggtggtctc ataccgagc cagaaaagca      6840
aagatctccc caggacaacc aaatggcaat catcatcatg gtagcagtag gtcttctggg    6900
cttgattacc gccaatgaac tcggatggtt ggagagaaca aagagtgacc taagccatct    6960
aatgggaagg agagaggagg ggcaaccat aggattctca atggacattg acctgcggcc    7020
agcctcagct tgggccatct atgctgcctt gacaactttc attaccccag ccgtccaaca    7080
tgcagtgacc acctcataca acaactactc cttaatggcg atggccacg aagctgagt     7140
gttgtttggc atgggcaaag gatgccattc tacgcatgg gactttgag tcccgctgct     7200
aatgataggt tgctactcac aattaacacc cctgaccca atagtggcca tcattttgct    7260
cgtggcgcac tacatgtact tgatcccagg gctgcaggca gcagctgcgc gtgctgccca    7320
gaagagaacg agctggcca tcatgaagaa ccctgttgtg gatgggaatag tggtgactga    7380
cattgacaca atgacaattg accccccaagt ggagaaaaag atgggacagg tgctactcat    7440
agcagtagcc gtctccagcg ccatactgtc ccgaccgcc tggggtggg gggaggctgg     7500
ggctctgatc acagccgcaa cttccacttt gtgggaaggc tctccgaaca agtactgaa    7560
ctcctctaca gccacttcac tgtgtaacat ttttagggga agttacttgg ctggagcttc    7620
tctaatctac acagtaacaa gaaacgctgg cttggtcaga agacgtgggg gtggaacagg    7680
agagaccctg ggagagaaat ggaaggcccg cttgaaccag atgtcggccc tggagttcta    7740
ctcctacaaa aagtcaggca tcaccgaggt gtgcagagaa gaggccgcc gcgccctcaa    7800
ggacggtgtg gcaacgggag ccatgcgtgt gtcccgagga agtgcaaagc tgagatggt    7860
ggtggagcgg ggatacctgc agcccatgg aaaggtcatt gatcttggat gtggcagagg    7920
gggctgaagt tactacgtcg ccaccatccg caagtcaa gaagtgaaag gatcacaaa     7980
aggaggccc ggtcatgaag aacccgtgtt ggtgcaaagc tatgggtgga acatagtccg    8040
tcttaagagt ggggtggacg tctttcatat ggccgctgag ccgtgtgaca cgttgctgtg    8100
tgacatagg gagtcatcat ctagtcctga agtggaagaa gcacggacgc tcagagtcct    8160
ctccatggtg ggggattggc ttgaaaaaag accaggagc ttttgtataa aagtgttgtg    8220
cccatacacc agcactatga tggaaaccct ggagcgactg cagcgtaggt atgggggagg    8280
```

```
actggtcaga gtgccactct cccgcaactc tacacatgag atgtactggg tctctggagc   8340
gaaaagcaac accataaaaa gtgtgtccac cacgagccag ctcctcttgg ggcgcatgga   8400
cgggcctagg aggccagtga aatatgagga ggatgtgaat ctcggctctg gcacgcgggc   8460
tgtggtaagc tgcgctgaag ctcccaacat gaagatcatt ggtaaccgca ttgaaaggat   8520
ccgcagtgag cacgcggaaa cgtggttctt tgacgagaac cacccatata ggacatgggc   8580
ttaccatgga agctatgagg cccccacaca agggtcagcg tcctctctaa taaacggggt   8640
tgtcaggctc ctgtcaaaac cctgggatgt ggtgactgga gtcacaggaa tagccatgac   8700
cgacaccaca ccgtatggtc agcaaagagt tttcaaggaa aaagtggaca ctagggtgcc   8760
agaccccaa gaaggcactc gtcaggttat gagcatggtc tcttcctggt tgtgaaaga   8820
gctaggcaaa cacaaacggc cacgagtctg caccaaagaa gagttcatca acaaggttcg   8880
tagcaatgca gcattagggg caatatttga agaggaaaaa gagtggaaga ctgcagtgga   8940
agctgtgaac gatccaaggt tctgggctct agtggacaag gaaagagagc accacctgag   9000
aggagagtgc cagagctgtg tgtacaacat gatgggaaaa agaaaaaga aacaagggga   9060
atttgaaaag gccaagggca gccgcgccat ctggtatatg tggctagggg ctagatttct   9120
agagttcgaa gcccttggat tcttgaacga ggatcactgg atggggagag agaactcagg   9180
aggtggtgtt gaagggctgg gattacaaag actcggatat gtcctagaag atgagtcg    9240
tataccagga ggaaggatgt atgcagatga cactgctggc tgggacaccc gcattagcag   9300
gtttgatctg gagaatgaag ctctaatcac caaccaaatg gagaaaggc acgggccttt   9360
ggcattggcc ataatcaagt acacatacca aaacaaagtg gtaaaggtcc ttagaccagc   9420
tgaaaaaggg aaaacagtta tggacattat ttcgagacaa gaccaaaggg ggagcggaca   9480
agttgtcact tacgctctta acacatttac caacctagtg gtgcaactca ttcggaatat   9540
ggaggctgag gaagttctag agatgcaaga cttgtggctg ctgagaggtg cagagaaagt   9600
gaccaactgg ttgcagagca acggatggga taggctcaaa cgaatggcag tcagtggaga   9660
tgattgcgtt gtgaagccaa ttgatgatag gtttgcacat gccctcaggt tcttgaatga   9720
tatgggaaaa gttaggaagg acacacaaga gtggaaaccc tcaactggat gggacaactg   9780
ggaagaagtt ccgttttgct cccaccactt caacaagctc catctcaagg acgggaggtc   9840
cattgtggtt ccctgccgcc accaagatga actgattggc cgggcccgcg tctctccagg   9900
ggcgggatgg agcatccggg agactgcttg cctagcaaaa tcatatgcgc aaatgtggca   9960
gctcctttat ttccacagaa gggacctccg actgatggcc aatgccattt gttcatctgt  10020
gccagttgac tgggttccaa ctgggagaac tacctggtca atccatggaa agggagaatg  10080
gatgaccact gaagacatgc ttgtggtgtg aacagagtg tggattgagg agaaccacca  10140
catgaagac aagaccccag ttacgaaatg gacagacatt ccctatttgg gaaaagggga  10200
agacttgtgt gtgtggatctc tcatagggca cagaccgcgc accacctggg ctgagaacat  10260
taaaaacaca gtcaactgg tgcgcaggat cataggtgat gaagaaagt acatggacta  10320
cctatccacc caagttcgct acttgggtga agagggtct acacctggag tgctgtaagc  10380
accaatctta atgttgtcag gcctgctagt cagccacagc ttggggaaag ctgtgcagcc  10440
tgtgaccccc caggagaag ctgggaaacc aagcctatag tcaggccgag aacgccatgg  10500
cacggaagaa gccatgctgc ctgtgagccc ctcaggagac actgagtcaa aaacccccac  10560
gcgcttggag gcgcaggatg ggaaaagaag gtggcgacct tccccaccct tcaatctggg  10620
gcctgaactg gagatcagct gtggatctcc agaagaggga ctagtggtta gagga       10675

SEQ ID NO: 5        moltype = DNA  length = 10676
FEATURE             Location/Qualifiers
source              1..10676
                    mol_type = unassigned DNA
                    organism = Zika virus
SEQUENCE: 5
gttgttactg ttgctgactc agactgcgac agttcgagtt tgaagcgaaa gctagcaaca     60
gtatcaacag gttttatttg gatttggaaa cgagagtttc tggtcatgaa aaacccaaaa    120
aagaaatccg gaggattccg gattgtcaat atgctaaaac gcggagtagc ccgtgtgagc    180
cccttttgggg gcttgaagag gctgccagcc ggacttctgt tgggtcatgg gcccatcagg    240
atggtcttgg caattctagc cttttttgaga ttcacggcaa tcaagccatc actgggtctc    300
atcaatagat ggggttcagt ggggaaaaaa gaggctatgg aaataataaa gaagttcaag    360
aaagatctgc tgccatgct gagaataatc aatgctagga aggagaagaa gagacgaggc    420
gcagatacta gtgtcggaat tgttggcctc ctgctgacaa cagctatggc agcggaggtc    480
actagacgtg ggagtgcata ctatatgtac ttggacagaa acgatgctgg ggaggccata    540
tcttttccaa ccacattggg gatgaataag tgttatatac agatcatgga tcttggacac    600
atgtgtgatg ccaccatgag ctatgaatgc cctatgctgg atgaggggt ggaaccagat    660
gacgtcgatt gttggtgcaa cacgacgtca acttgggttg tgtacggaac ctgccatcac    720
aaaaaaggtg aagcacggag atctagaaga gctgtgacgc tcccctccca ttccactagg    780
aagctgcaaa cgcggtcgca aacctggttg gaatcaagaa aatacacaaa gcacttgatt    840
agagtcgaaa attggatatt caggaaccct ggcttcgcgt tagcagcagc tgccatcgct    900
tggcttttgg gaagctcaac gagccaaaaa gtcatatact tggtcatgat actgctgatt    960
gccccggcat acagcaata gtgcatagga gtcagcatca gggactttgt ggaaggtatg   1020
tcaggtggga cttgggttga tgttgtcttg aacatggagg gttgtgtcac cgtaatgca   1080
caggacaaac gactgtcga catagagctg gttacaacaa cagtcagcaa catggcggag   1140
gtaagatcct actgctatga ggcatcaata tcagacatgg cttcggacag ccgctgccca   1200
acacaaggtg aagcctacct tgacaagcaa tcagacactc aatatgtctg caaaagaacg   1260
ttagtggaca gaggctgggg aaatggatgt ggactttttg gcaaagggag tctggtgaca   1320
tgcgctaagt ttgcatgctc caagaaaatg accgggaaga catccagcc agagaatctg   1380
gagtaccgga taatgctgtc agttcatggc tcccagcaca gtgggatgat cgttaatgac   1440
acaggacatg aaactgatga aatagagcg aaggttgaga taacgcccaa ttcaccaaga   1500
gccgaagcca cctgggggg ttttggaagc ctaggactta ttgtgaacc gaggacaggc   1560
cttgactttt cagatttgta ttacttgact atgaataaca agactggtt ggttcacaag   1620
gagtggttta acgacattcc attaccttgg cacgctgggg cagacaccgg aactccacac   1680
tggaacaaca agaagcact ggtagagttc aaggacgcac atgccaaaag gcaaactgtc   1740
gtggttctag ggagtcaaga aggagcagtt cacacggccc ttgctggagc tctgaggct   1800
gagatggatg gtgcaaaggg aaggctgtcc tctggccact tgaaatgtcg cctgaaatg   1860
gataaactta gattgaaggg cgtgtcatac tccttgtgta ccgcagcgtt cacattcacc   1920
```

```
aagatcccgg ctgaaacact gcacgggaca gtcacagtgg aggtacagta cgcagggaca   1980
gatggacctt gcaaggttcc agctcagatg gcggtggaca tgcaaactct gaccccagtt   2040
gggaggttga taaccgctaa ccccgtaatc actgaaagca ctgagaactc taagatgatg   2100
ctggaacttg atccaccatt tggggactct tacattgtca taggagtcgg ggagaagaag   2160
atcacccacc actggcacag gagtggcagc accattggaa aagcatttga agccactgtg   2220
agaggtgcca agagaatggc agtcttggga gacacagcct gggactttgg atcagttgga   2280
ggcgctctca actcattggg caagggcatc catcaaattt ttggagcagc tttcaaatca   2340
ttgtttggag gaatgtcctg gttctcacaa attctcattg gaacgttgct gatgtggttg   2400
ggtctgaaca caaagaatgg atctatttcc cttatgtgct tggccttagg gggagtgttg   2460
atcttcttat ccacagccgt ctctgctgat gtggggtgct cggtggactt ctcaaagaag   2520
gagacgagat gcggtacagg ggtgttcgtc tataacgacg ttgaagcctg gagggacagg   2580
tacaagtacc atcctgactc cccccgtaga ttggcagcag cagtcaagca agcctgggaa   2640
gatggtatct gcgggatctc ctctgtttca agaatggaaa acatgcatgtg gagatcagta   2700
gaagggggagc tcaacgcaat cctggaagag aatggagttc aactgacgtc cgttgtggga   2760
tctgtaaaaa accccatgtg gagaggtcca cagagattgc ccgtgcctgt gaacgagctg   2820
ccccacggct ggaaggcttg ggggaaatcg cacttcgtca gagcagcaaa gacaaataac   2880
agctttgtcg tggatggtga cactctgaag gaatgcccac tcaaacatag agcatggaac   2940
agctttcttg tggaggatca tgggttcggg tgatttcaca ctagtgtctg gctcaaggtt   3000
agagaagatt attcattaga gtgtgatcca gccgttattg gaacagctgt taagggaaag   3060
gaggctgtac acagtgatct aggctactgg attgagagtg agaagaatga cacatggagg   3120
ctgaagaggg cccatctgat cgagatgaaa acatgtgaat ggccaaagtc ccacacattg   3180
tggacagatg gaatagaaga gagtgatctg atcatacca agtcttttagc tgggccactc   3240
agccatcaca ataccagaga gggctacagg acccaaatga aagggccatg gcacagtgaa   3300
gagcttgaaa ttcggtttga ggaatgccca ggcactaagg tccacgtgga ggaaacatgt   3360
ggaacaagag gaccatctct gagatcaacc actgcaagcg gaagggtgat cgaggaatgg   3420
tgctgcagga gtgcacaat gccccactc tcgttccggg ctaaagatgg ctgttggtat   3480
ggaatggaga taaggcccag gaaagaacca gaaagcaact tagtaaggtc aatggtgact   3540
gcaggatcaa ctgatcacat ggatcacttc tcccttggag tgcttgtgat tctgctcatg   3600
gtgcaggaag ggctgaagaa gagaatgacc acaaagatca tcataagcac atcaatggca   3660
gtgctggtag ctatgatcct gggaggattt caatgagtg acctggctaa gcttgcaatt   3720
ttgatgggtg ccaccttcgc ggaaatgaac actggaggag atgtagctca tctggcgctg   3780
atagcggcat tcaaagtcag accagcgttg ctggtatctt tcatcttcag agctaattgg   3840
acaccccgtg aaagcatgct gctggccttg gcctcgtgtc ttttgcaaac tgcgatctcc   3900
gccttggaag gcgacctgat ggttctcatc aatggttttg ctttggcctg gttggcaata   3960
cgagcgatgt ttgttccacg cactgataac atcaccttgg caatcctggc tgctctgaca   4020
ccactggccc ggggcacact gcttgtggcg tggagagcag gccttgctac ttgcggggg   4080
tttatgctcc tctctctgaa gggaaaaggc agtgtgaaga gaacttacc atttgtcatg   4140
gccctgggac taacgctgt gaggctggtc gaccccatca acgtggtggg gctgctgttg   4200
ctcacaagga gtgggaagcg gagctggccc cctagcgaag tactcacagc tgttggcctg   4260
atatgcgcat tggctggagg gttcgccaag gcagatatag agatggctgg gcccatggcc   4320
gcggtcggtc tgctaattgt cagttacgtg gtctcaggaa agagtgtgga catgtacatt   4380
gaaagagcag gtgacatcac atgggaaaaa gatgcggaag tcactggaaa cagtcccccgg   4440
ctcgatgtgg cgctagatga gagtggtgat ttctccctgg tggaggatga cggtccccccc   4500
atgagagaga tcatactcaa ggtggtcctg atgaccatct gtggcatgaa cccaatagcc   4560
atacccttg cagctggagc gtggtacgta tacgtgaaga ctggaaaaag gagtggtgct   4620
ctatgggatg tgcctgctcc caaggaagta aaaaaggggg agaccacaga tggagtgtac   4680
agagtaatga ctcgtagact gctaggttca acacaagttg gagtgggaat tatgcaagag   4740
ggggtctttc acactatgtg gcacgtcaca aaaggatccg cgctgagaag cggtgaaggg   4800
agacttgatc catactgggg agatgtcaag caggatctgg tgtcatactg tggtccatgg   4860
aagctagatg ccgcctggga cgggcacagc gaggtgcagc tcttggccgt gccccccgga   4920
gagagagcga ggaacatcca gactctgccc ggaatattta agacaaagga tggggacatt   4980
ggagcggttg cgctggatta cccagcagga acttcaggat ctccaatcct agacaagtgt   5040
gggagagtga taggactta tggcaatggg gtcgtgatca aaaatgggag ttatgttagt   5100
gccatcaccc aagggaggag ggaggaagag actcctgttg agtgcttcga gccttcgatg   5160
ctgaagaaga agcagctaac tgtcttagac ttgcatcctg gagctgggaa aaccaggaga   5220
gttcttcctg aaatagtccg tgaagccata aaacaagac tccgtactgt gatcttagct   5280
ccaaccaggg ttgtcgctgc tgaaatggag gaagcccta gagggcttcc agtgcgttat   5340
atgacaacag cagtcaatgt cacccactct ggaacagaaa tcgtcgactt aatgtgccat   5400
gccaccttca cttcacgtct actacagcca atcagagtcc ccaactataa tctgtatatt   5460
atggatgagg cccacttcac agatccctca gtatagcag caagaggata catttcaaca   5520
agggttgaga tgggcgaggc ggctgccatc ttcatgaccg ccacgccacc aggaaccgt   5580
gacgcatttc cggactccaa ctcaccaatt atggacaccg aagtgaagt cccagagaga   5640
gcctggagct caggctttga ttgggtgacg gattattctg gaaaaacagt ttggtttgtt   5700
ccaagcgtga ggaacggcaa tgagatcgca gcttgtctga caaaggctgg aaaacgggtc   5760
atacagctca gcagaaagac ttttgagaca gagttccaga aaacaaaaca tcaagagtgg   5820
gactttgtcg tgacaactga catttcagag atgggcgcca actttaaagc tgaccgtgtc   5880
atagattcca ggagatgcct aaagccggtc tacttgatg cgagagagt cattctggct   5940
ggacccatgc ctgtcacaca tgccagcgct gcccagagga gggcgcat aggcaggaat   6000
cccaacaaac ctggagatga gtatctgtat ggagtgggt gcgcagagac tgacgaagac   6060
catgcacact ggcttgaagc aagaatgctc cttgacaata tttacctcca agatggcctc   6120
atagcctcgc tctatcgacc tgaggccgac aaagtagcac ccattgaggg agagttcaag   6180
cttaggacgg agcaaaggaa gacctttgtg gaactcatga aaagaggaga tcttcctgtt   6240
tggctggcct atcaggttgc atctgccgga ataacctaca cagatagaag atggtgcttt   6300
gatggcaaca ccaacaacac cataatggaa gacagtgtgc cggcagaggt gtggaccaga   6360
cacggagaga aaagagtgct caaaccgagg tggatggacg ccagagtttg ttcagatcat   6420
gcggccctga gtcattcaa ggagtttgcc gctgggaaaa gaggagcggc ttttggagtg   6480
atggaagccc tgggaacact gccaggacac atgacagaga gattccagga agccattgac   6540
aacctcgctg tgctcatgcg ggcagagact ggaagcaggc cttacaaagc cgcggcggcc   6600
caattgccgg agacccctaga gaccattatg ctttttgggt tgctgggaac agtctcgctg   6660
```

```
ggaatctttt tcgtcttgat gaggaacaag ggcatagggga agatgggctt tggaatggtg  6720
actcttgggg ccagcgcatg gctcatgtgg ctctcggaaa ttgagccagc cagaattgca  6780
tgtgtcctca ttgttgtgtt cctattgctg gtggtgctca tacctgagcc agaaaagcaa  6840
agatctcccc aggacaacca aatggcaatc atcatcatgg tagcagtagg tcttctgggc  6900
ttgattaccg ccaatgaact cggatggttg gagagaacaa agagtgacct aagccatcta  6960
atgggaagga gagaggaggg ggcaaccatg ggattctcaa tggacattga cctgcgccca  7020
gcctcagctt gggccatcta tgctgccttg acaactttca ttaccccagc cgtccaacat  7080
gcagtgacca cttcatacaa caactactcc ttaatggcga tggccacgca agctggagtg  7140
ttgttggta tgggcaaagg gatgccattc tacgcatgga acttggagt cccgctgcta  7200
atgataggtt gctactcaca attaacgccc ctgacccta tagtgccat cattttgctc  7260
gtggcgcact acatgtactt gatcccaggg ctgcaggcag cagctgcgcg tgctgcccag  7320
aagagaacgg cagctggcat catgaagaac cctgttgtgg atggaatagt ggtgactgac  7380
attgacacaa tgacaattga ccccccaagtg agaaaaaga tgggacaggt gctactcatg  7440
gcagtagccg tctccagcgc catactgtcg cggaccgcct ggggtggg ggaggctgg  7500
gccctgatca cagccgcaac ttccactttg tgggaaggct ctccgaacaa gtactgggac  7560
tcctctacag ccacttcact gtgtaacatt tttaggggga gttacttggc tggagcttct  7620
ctaatctaca cagtaacaag aaacgctggc ttggtcaaga acgtgggg tggaacagga  7680
gagaccctgg gagagaaatg gaaggcccgc ttgaaccaga tgtcggccct ggagttctac  7740
tcctacaaaa agtcaggcat caccgaggtg tgcagagaa aggcccgccg cgcccctcaag  7800
gacggtgtgg caacggggag ccatgctgtg tcccgaggaa gtgcaaagct gagatggttg  7860
gtggagcggg gatacctgca gccctatgga aaggtcattg atcttggatg tggcagaggg  7920
ggctggagtt actacgccgc caccatccgc aaagttcaag agttgaaagg atacacaaaa  7980
ggaggccctg gtcatgaaga acccgtgttg gtgcaaagct atgggtggaa catagtccgt  8040
cttaagagtg gggtggacgt cttttcatatg gcggctgagc cgtgtgacac gttgctgtgt  8100
gacataggtg agtcatcatc tagtcctgaa gtggaagaag cacggacgct cagagtcctc  8160
tccatggtgg gggattggct tgaaaaaaga ccaggacct ttttgtataaa agtgttgtgc  8220
ccatacacca gcactatgat ggaaaccctg gagcgactgc agcgtaggta tggggagga  8280
ctggtcagag tgccactctc ccgcaactct acacatgaga tgtactgggt ctctggagcg  8340
aaaagcaaca ccataaaag tgtgtccacc acgagccagc tcctcttggg gcgcatggac  8400
gggcctagga ggccagtgaa atatgaggag gatgtgaatc tcggctctgg cacgcgggct  8460
gtggtaagct cgcgctgaagc tcccaacatg aagatcattg gtaaccgcat tgaaaggatc  8520
cgcagtgagc acgcggaaac gtggttcttt gacgagaacc acccatatag gacatgggct  8580
taccatggaa gctatgaggc ccccacacaa gggtcagcgt cctctctaat aaacggggtt  8640
gtcaggctcc tgtcaaaacc ctgggatgtg gtgactggag tcacaggaat agccatgacc  8700
gacaccacac cgtatggtca gcaaagagtt ttcaaggaca aagtggacac taggtgcca  8760
gaccccaag aaggcactcg tcaggttatg agcatggtct cttcctggtt gtggaaagag  8820
ctaggcaaac acaaacggcc acgagtctgt accaagaag agttcatcaa caaggttcgt  8880
agcaatgcag cattaggggc aatatttgaa gaggaaaaag agtggaagac tgcagtggaa  8940
gctgtgaacg atccaaggtt ctgggctcta gtggacagaa aagagagca ccaccctgaga  9000
ggagagtgcc agagttgtgt gtacaacatg atgggaaaaa gagaaaagaa acaaggggaa  9060
tttgaaagg ccaagggcag ccgcgccatc tggtatatgt ggctagggc tagatttcta  9120
gagttcgaag cccttggatt cttgaacgag atcactgga tggggagaga gaactcagga  9180
ggtggttga aagggctggg attacaaaga ctcgatatg tcctagaaga gatgagtcgc  9240
ataccaggag gaaggatgta tgcagatgac actgctggct gggacaccccg catcagcagg  9300
tttgatctgg agaatgaagc tctaatcacc aaccaaatgg agaaagggca cagggccttg  9360
gcattggcca taatcaagta cacataccaa aacaaagtgt taaaggtcct tagaccagct  9420
gaaaaaggga agacagttat ggacattatt gccaaaagggg gagcggacaa  9480
gttgtcactt acgctcttaa cacatttacc aacctagtgg tgcaactcat tcggaatatg  9540
gaggctgagg aagttctaga gatgcaagac ttgtggctgc tgcggaggtc agagaaagtg  9600
accaactggt tgcagagcaa cggatgggat aggctcaaac gaatggcagt cagtggagat  9660
gattcgttg tgaagccaat tgatgatagg tttgcacatg ccctcaggtt cttgaatgat  9720
atggggaaaag ttaggaagga cacacaagag tggaaaccct caactggatg ggacaactgg  9780
gaagaagttc cgtttttgctc ccaccacttc aacaagctcc atctcaagga cgggaggtcc  9840
attgtggttc cctgccgcca ccaagatgaa ctgattggcc gggccccgcgt ctctccaggg  9900
gcgggatgga gcatccggga gactgcttgc ctagcaaaat catatgcgca aatgtggcag  9960
ctcctttatt tccacagaag ggacctccga ctgatggcca atgccatttg ttcatctgtg 10020
ccagttgact gggttccaac tgggagaact acctggtcaa tccatggaaa gggagaatgg 10080
atgaccactg aagacatgct tgtggtgtgg aacagagtgt ggattgagga aacgaccac 10140
atggaagaca agacccccagt tacgaaatgg acagacattc cctatttggg aaaagggaa 10200
gacttgtggt gtgatctct catagggcac agaccgcgca ccacctgggc tgagaacatt 10260
aaaaacacag tcaacatggt gcgcaggatc ataggtgatg aagaaagta catggactac 10320
ctatccaccc aagttcgcta cttgggtgaa agggtcta cacctggagt gctgtaagca 10380
ccaatcttaa tgttgtcagg cctgctagtc agccacagct ggggaaagc tgtgcagcct 10440
gtgaccccc caggagaagc tgggaaacca agcctatgt caggccgaga acgccatggca 10500
acggaagaag ccatgctgcc tgtgagcccc tcagaggaca ctgagtcaaa aaccccacg 10560
cgcttggagg cgcaggatgg aaaagaaggg tggcgacctt ccccaccctt caatctgggg 10620
cctgaactgg agatcagctg tggatctcca aagagggac tagtggttag aggaga     10676

SEQ ID NO: 6         moltype = DNA   length = 10808
FEATURE              Location/Qualifiers
source               1..10808
                     mol_type = unassigned DNA
                     organism = Zika virus
SEQUENCE: 6
agttgttgat ctgtgtgaat cagactgcga cagttcgagt ttgaagcgaa agctagcaac   60
agtatcaaca ggttttattt tggatttgga acgagagttc tctggtcatg aaaaacccaa  120
aaaagaaatc cggaggattc cggattgtca atatgctaaa acgcggagta gcccgtgtga  180
gccccttgg gggcttgaag aggctgccag ccggacttct gctgggtcat gggcccatca  240
ggatggtctt ggcaattcta gccttttga gattcacggc aatcaagcca tcactgggtc  300
```

```
tcatcaatag atggggttca gtggggaaaa aagaggctat ggaaataata aagaagttca   360
agaaagatct ggctgccatg ctgagaataa tcaatgctag gaaggagaag aagagacgag   420
gcgcagatac tagtgtcgga attgttggcc tcctgctgac cacagctatg cagcggagg    480
tcactagacg tgggagtgca tactatatgt acttggacag aaacgatgct ggggaggcca   540
tatcttttcc aaccacattg gggatgaata agtgttatat acagatcagt gatcttggac   600
acatgtgtga tgccaccatg agctatgaat gccctatgct ggatgagggg gtggaaccga   660
atgacgtcga ttgttggtgc aacacgacgt caacttgggt tgtgtacgga acctgccatc   720
acaaaaaagg tgaagcacgg agatctagaa gagctgtgac gctcccctcc cattccacta   780
ggaagctgca aacgcggtcg caaacctggt tggaatcaag agaatacaca aagcacttga   840
ttagagtcga aaattggata ttcaggaacc ctggcttcgc gttagcagca gctgccatcg   900
cttggctttt gggaagctca acgagccaaa aagtcatata cttggtcatg atactgctga   960
ttgccccggc atacagcatc aggtgcatag gagtcagcaa tagggacttt gtggaaggta  1020
tgtcaggtgg gacttgggtt gatgttgtct tggaacatgg aggttgtgtc accgtaatgg  1080
cacaggacaa accgactgtc gacatagagc tggttacaac aacagtcagc aacatggcag  1140
aggtaagatc ctactgctat gaggcatcaa tatcagacat ggcttcggac agccgctgcc  1200
caacacaagg tgaagcctac cttgacaagc aatcagacac tcaatatgtc tgcaaaagaa  1260
cgttagtgga cagaggctgg ggaaatggat gtggactttt tggcaagggg agcctggtga  1320
catgcgctaa gtttgcatgc tccaagaaaa tgaccggaag gagcatccag ccagagaatc  1380
tggagtaccg gataatgctg tcagttcatg gctcccagca cagtgggatg atcgttaatg  1440
acacaggaca tgaaactgat gagaatagag cgaaggttga gataacgccc aattcaccaa  1500
gagccgaagc cacccctgggg ggttttggaa gcctaggact tgattgtgaa ccgaggacag  1560
gccttgactt ttcagatttg tattacttga ctatgaataa caagcactgg ttggtccaca  1620
aggagtggtt ccacgacatt ccattacctt ggcacgctgg ggcagacacc ggaactccac  1680
actgaaacaa caaagaagca ctggtagagt tcaaggacgc acatgccaaa aggcaaactg  1740
tcgtggttct agggagtcaa gaaggagcag ttcacacggc ccttgctgga gctctggagg  1800
ctgagatgga tggtgcaaag gaaaggctgt cctctgcaca cttgaaatgt cgcctgaaaa  1860
tggataaact tagattgaag ggcgtgtcat actccttgtg taccgcagcg ttcacattca  1920
ccaagatccc ggctgaaaca ctgcacggga cagtcacagt ggaggtacag tacgcaggga  1980
cagatggacc ttgcaaggtt ccagctcaga tggcggtgga catgcaaact ctgacccccag  2040
tgggaggtt gataaccgct aacccccgtaa tcactgaaag cactgagaac tctaagatga  2100
tgctggaact tgatccacca tttgggggact cttacattgt cataggagtc ggggagaaga  2160
agatcaccca ccactggcac aggagtggca gcaccattgg aaaagcatttt gaagccactg  2220
tgagaggtgc caagagaatg gcagtcttgg gagacacagc ctgggactttt ggatcagttg  2280
gaggcgctct caactcattg ggcaagggca tccatcaaat ttttggagca gctttcaaat  2340
cattgtttgg aggaatgtcc tggttctcac aaatcctcat tggaacgttg ctgatgtgat  2400
tgggtctgaa cacaaagaat ggatctattt ccctatgtg cttggcctta gggggagtgt  2460
tgatcttctt atccacagcc gtctctgctg atgtgggggtg ctcggtggac ttctcaaaga  2520
aggagacgag atgcggtaca ggggtgttcg tctataacga cgttgaagcc tggagggaca  2580
ggtacaagta ccatcctgac tcccccccgta gattggcagc agcagtcaag caagcctggg  2640
aagatggtat ctgcgggatc tcctctgttt caagaatgga gaacatcatg tggagatcag  2700
tagaagggga gctcaacgca atcttggaag agaatggagt tcaactgacg gtcgttgtgg  2760
gatctgtaaa aaaccccatg tggagaggtc cacagagatt gcccgtgcct gtgaacgagc  2820
tgccccacgg ctgaaaggct tgggggaaat cgtacttcgt cagagcagca aagacaaata  2880
acagctttgt cgtggatggt gacacactga aggaatgccc actcgaacat agagcatgga  2940
acagcttttct tgtggaggat catggggttcg gggtatttca cactagtgtc tggctcaagg  3000
ttagagaaga ttattcatta gagtgtgatc cagccgttat tggaacagct gttaaaggga  3060
aggaggctgt acacagtgat ctaggctact ggattgagaa tgagaagaat gacacatgga  3120
ggctgaagag ggcccatcta atcgagatga aaacatgtga atggccaaag tcccacacat  3180
tgtgggcaga tggaatagaa gagagtgatc tgatcattcc caagtctttta gctgggccac  3240
tcagccatca caataccaga gagggctaca ggacccaaat gaaagggcca tggcacagtg  3300
aagagcttga aattcggttt gaggaatgcc cgggcactaa ggtccacgtg gaggaaacat  3360
gtggaacaag aggaccatct ctgagatcaa ccactgcaag cggaagggtg atcgaggaat  3420
ggtgctgcag ggagtgcaca atgccccac tgtcgttccg ggctaaagat ggctgttggt  3480
atggaatgga gataaggccc aggaaagaac cagaaagcaa cttagtaagg tcagtggtga  3540
ctgcaggatc aactgatcac atggatcact tctccctttgg agtgctttgt gattctgctca  3600
tggtcagga agggctgaag aagagaatga ccacaaagat catcataagc acatcaatga  3660
cagtgctggt agctatgatc ctgggaggat tttcaatgag tgacctggct aagcttgcaa  3720
ttttgatggg cgccaccttc gcggaaatga acactggagg agatgtagct catctggcgc  3780
tgatagcggc attcaaagtc agaccagcgt tgctggtatc tttcatcttc agagctaatt  3840
ggacaccccg tgaaagcatg ctgctggcct tggcctcgtg tcttttgcaa actgcgatct  3900
ccgccttgga aggcgacctg atggttctca tcaatggttt tgctttggcc tggttggcaa  3960
tacgagcgat ggttgttcca cgcactgata acatcacctt ggcaatcctg ctgctctga   4020
caccactggc ccgggggcaca ctgcttgtgg cgtggagagc aggccttgct acttgcgggg  4080
ggtttatgct cctctctctg aagggaaaag gcagtgtgaa gaagaactta ccatttgtca  4140
tggccctggg actaaccgct gtgaggctgg tcgacccccat caacgtggtg ggactgctgt  4200
tgctcacaag gagtgggaag cggagctgcc ccctagcga agtactcaca gctgttggcc  4260
tgatatgcgc attggctgga gggttcgcca aggcagatat agagatggct gggcccatgg  4320
ccgcggtcgg tctgctaatt gtcagttacg tggtctcagg aaagagtgtg gacatgtaca  4380
ttgaaagage aggtgacatc acatgggaaa aagatgcgga agtcactgga aacagtcccc  4440
ggctcgatgt ggcgctagat gagagtggtg atttctccct ggtggaggat gacggtcccc  4500
ccatgagaga gatcatactc aaggtggtcc tgatgaccat ctgtggcatg aacccaatag  4560
ccatacccct tgcagctgga gcgtggtacg tatacgtgaa gactgaaaaa aggagtggtg  4620
ctctatggga tgtgcctgct cccaaggaag taaaaaaggg ggagaccaca gatggagtgt  4680
acagataat gactcgtaga ctgctaggtt caacagatgg agtggggatt gttatgcaag  4740
agggggtctt tcacactatg tggcacgtca caaaaggatc cgcgctgaga agcggtgaag  4800
ggagacttga tccatactgg ggagatgtca agcaggatct ggtgtcatac tgtggtccat  4860
ggaagctaga tgccgcctgg gacgggcaca gcgaggtgca gctcttggcc gtgccccccg  4920
gagagagagc gaggaacatc cagactctgc ccggaatatt taagacaaag gatggggaca  4980
ttggagcggt tgcgctggat tacccagcag gaacttcagg atctccaatc ctagacaagt  5040
```

```
gtgggagagt gataggactt tatggcaatg gggtcgtgat caaaaatggg agttatgtta    5100
gtgccatcac ccaagggagg agggaggaag agactcctgt tgagtgcttc gagccttcga    5160
tgctgaagaa gaagcagcta actgtcttag acttgcatcc tggagctggg aaaaccagga    5220
gagttcttcc tgaaatagtc cgtgaagcca taaaaacaag actccgtact gtgatcttag    5280
ctccaaccag ggttgtcgct gctgaaatgg aggaagcctt tagagggctt ccagtgcgtt    5340
atatgacaac agcagtcaat gtcacccact ctggaacaga aatcgtcgac ttaatgtgcc    5400
atgccacctt cacttcacgt ctactacagc caatcagagt ccccaactat aatctgtata    5460
ttatggatga ggcccacttc acagatccct caagtatagc agcaagagga tacatttcaa    5520
caagggttga gatgggcgag gcggctgcca tcttcatgac cgccacgcca ccaggaaccc    5580
gtgacgcatt tccggactcc aactcaccaa ttatggacac cgaagtggaa gtcccagaga    5640
gagcctggag ctcaggcttt gattgggtga cggatcattc tggaaaaaca gtttggtttg    5700
ttccaagcgt gaggaacggc aatgagatcg cagcttgtct gacaaaggct ggaaaacggg    5760
tcatacagct cagcagaaag acttttgaga cagagttcca gaaaacaaaa catcaagagt    5820
gggactttgt cgtgacaact gacatttcag agatgggtgc caactttaaa gctgaccgtg    5880
tcatagattc caggagatgc ctaaagccgg tcatacttga tggcgagaga gtcatttggg    5940
ctggacccat gcctgtcaca catgccagcg ctgcccagag gagggggcgc ataggcagga    6000
atcccaacaa acctggagat gagtatctgt atggaggtgg gtgcgcagag actgacgaag    6060
accatgcaca ctggcttgaa gcaagaatgc tccttgacaa tatttacctc caagatggcc    6120
tcatagcctc gctctatcga cctgaggccg acaaagtagc agccattgag ggagagttca    6180
agcttaggac ggagcaaagg aagacctttg tggaactcat gaaaagagga gatcttcctg    6240
tttggctggc ctatcaggtt gcatctgccg gaataaccta cacagataga agatggtgct    6300
ttgatggcac gaccaacaac accataatgg aagacagtgt gccggcagag gtgtggacca    6360
gacacggaga gaaaagagtg ctcaaaccga ggtggatgga cgccagagtt tgttcagatc    6420
atgcggccct gaagtcattc aaggagtttg ccgctgggaa aagaggagcg gcttttggag    6480
tgatggaagc cctgggaaca ctgccaggac acatgacaga gagattccag gaagccattg    6540
acaacctcgc tgtgctcatg cgggcagaga ctggaagcag gccttacaaa gccgcggccg    6600
cccaattgcc ggagacccta gagaccatta tgcttttggg gttgctggga acagtctcgc    6660
tgggaatctt tttcgtcttg atgaggaaca aagggcatag gaagatgggc tttgaaatgg    6720
tgactcttgg ggccagcgca tggctcatgt ggctctcgga aattgagcca gccagaattg    6780
catgtgtcct cattgttgtg ttcctattgc tggtggtgct catacctgag ccagaaaagc    6840
aaagatctcc ccaggacaac caaatggcaa tcatcatcat ggtagcagta ggtcttctgg    6900
gcttgattac cgccaatgaa ctcggatggt tggagagaac aaagagtgac ctaagccatc    6960
taatgggaag gagagaggag ggagcaacca taggattctc aatggacatt gacctgcggc    7020
cagcctcagc ttgggccatc tatgctgcct tgacaacttt cattaccccca gccgtccaac    7080
atgcagtgac cacttcatac aacaactact ccttaatggc gatggccacg caagctggaa    7140
tgttgtttgg tatgggcaaa gggatgccat tctacgcatg ggacttctgga gtcccgctgc    7200
taatgatagg ttgctactca caattaacac ccctgaccct aatagtggcc atcattttgc    7260
tcgtggcgca ctacatgtac ttgatcccag ggctgcaggc agcagctgcg cgtgctgccc    7320
agaagagaac ggcagctggc atcatgaaga acctgttgt ggattggaata gtggtgactg    7380
acattgacac aatgacaatt gaccccccaag tggagaaaaa gatgggacag gtgctactca    7440
tagcagtagc agtctccagc gccatactgt cgcggaccgc ctgggggtgg ggagggctgg    7500
gggccctgat cacagccgca acttccactt tgtgggaagg ctctccgaac aagtactgga    7560
actcctctac agccacttca ctgtgtaaca ttttaggg aagttacttg gctgagctt       7620
ctctaatcta catagtaaca agaaacgctg gcttggtcaa gagacgtggg ggtgaacag    7680
gagagaccct gggagagaaa tggaaggcc cgcttgaacca gatgtcggcc ctggagttct    7740
actcctacaa aaagtcaggc atcaccgagg tgtgcagaga gaggcccgc cgcgccctca    7800
aggatggtgt ggcaacggga ggccatgctg tgtcccgagg aagtgcaaag ctgagatggt    7860
tggtggagcg gggatacctg cagcccctatg gaaaggtcat tgatcttgga tgtggcagag    7920
ggggctggag ttactacgcc gccaccatcc gcaaagttca agaagtgaaa ggatacacaa    7980
aaggaggccc tggtcatgaa gaacccgtgt tggtgcaaag ctatgggtgg aacatagtcc    8040
gtcttaagag tggggtggac gtctttcata tggccggctga gccgtgtgac acgttcgtgg    8100
gtgacatagg tgagtcatca tctagtcctg aagtggaaga agcacggacg ctcagatgcc    8160
tctccatggt gggggattgg cttgaaaaaa gaccaggagc cttttgtata aaagtgttgt    8220
gcccatacac cagcactatg atggaaaccc tggagcgact gcagcgtagg tatggggag    8280
gactggtcag agtgccactc tcccgcaact ctacacatga gatgtactgg gtctctggag    8340
cgaaaagcaa caccataaaa agtgtgtcca ccacgagcca gctcctcttg gggcgcatgg    8400
acgggcctag gaggccagtg aaatatgagg aggatgtgaa tctcggctct ggcacgcggg    8460
ctgtggtaag ctgcgctgaa gctcccaaca tgaagatcat tggtaaccgc attgaaagga    8520
tccgcagtga gcacgcggaa acgtggttct ttgacgagaa ccacccatat aggacatggg    8580
cttaccatgg aagctatgag gcccccacac aagggtcagc gtcctctcta ataaacggg    8640
ttgtcaggct cctgtcaaaa ccctgggatg tggtgactgg agtcacagga atagccatga    8700
ccgacaccac accgtatggt cagcaaagag ttttcaagga aaaagtggac actagggtgc    8760
cagaccccca agaaggcact cgtcaggtta tgagcatggt ctcttcctgg ttgtggaaag    8820
agctaggcaa acacaaacgg ccacgagtct gtaccaaaga agattcatc aacaaggttc    8880
gtagcaatgc agcattaggg gcaatatttg aagagaaaga agattggaag actgcagtg    8940
aagctgtgaa cgatccaagg ttctgggctc tagtggacaa ggaaagagag caccacctga    9000
gaggagagtg ccagagttgt gtgtacaaca tgatgggaaa aagagaaaag aaacaagggg    9060
aatttggaaa ggccaagggc agccgcgcca tctggtatat gtggcttggg ctagatttc    9120
tagagttcga agcccttgga ttcttgaacg aggatcactg gatggggaga gaaactcag    9180
gaggtggtgt tgaagggctg ggattacaaa gactcggata tgtcctagaa gagatgagtc    9240
gcataccagg aggaaggatg tatgcagatg acactgctgg ctgggacacc cgcatcagca    9300
ggtcgatctg ggaatgaa gctctaatca ccaaccaaat ggaaagg catgggcct    9360
tggcattggc cataatcaag tacacatacc aaaacaagt ggtaaggtc cttagaccag    9420
ctgaaaaagg aaaaactgt atggaacagt tttcgagaca agaccaaagg gggagcggac    9480
aagttgtcac ttcgctctt aacacattta ccaaacctagt ggtgcaactc attcggaata    9540
tggaggctga ggaagttcta gagatgcaag acttgtggct gctgcggagg tcagagaaag    9600
tgaccaactg gttgcagagc aacgatgggg ataggctcaa cgaatgca gtcagtggag    9660
atgattgcgt tgtgaagcca attgatgata ggtttgcaca tgccctcagg ttcttgaatg    9720
atatgggaaa agttaggaag gacacacaag agtggaaacc ctcaactgga tgggacaact    9780
```

-continued

```
gggaagaagt tccgttttgc tcccaccact tcaacaagct ccatctcaag gacgggaggt    9840
ccattgtggt tccctgccgc caccaagatg aactgattgg ccgggcccgc gtctctccag    9900
gggcgggatg gagcatccgg gagactgctt gcctagcaaa atcatatgcg caaatgtggc    9960
agctccttta tttccacaga agggacctcc gactgatggc caatgccatt tgttcatctg   10020
tgccagttga ctgggttcca actgggagaa ctacctggtc aatccatgca aagggagaat   10080
ggatgaccac tgaagacatg cttgtggtgt ggaacagagt gtggattgag gagaacgacc   10140
acatggaaga caagacccca gttacgaaat ggacagacat tccctatttg ggaaaagggg   10200
aagacttgtg tgtggatctc tcataggggc acagaccgcg caccacctgg gctgagaaca   10260
ttaaaaacac agtcaacatg gtgcgcagga tcataggtga tgaagaaaag tacatggact   10320
acctatccac ccaagttcgc tacttgggtg aagaaggggtc tacacctgga gtgctgtaag   10380
caccaatctt aatgttgtca ggcctgctag tcagccacag cttggggaaa gctgtgcagc   10440
ctgtgacccc cccaggagaa gctgggaaac caagcctata gtcaggccga aacgccatg    10500
gcacggaaga agccatgctg cctgtgagcc cctcaggaga cactgagtca aaaaccccca   10560
tgcgcttgga ggcgcaggat gggaaaagaa ggtggcgacc ttcccccacc ttcaatctgg   10620
ggcctgaact ggagatcagc tgtggatctc cagaagaggg actagtggtt agaggagacc   10680
ccccggaaaa cgcaaaacag catattgacg ctgggaaaga ccagagactc catgagtttc   10740
caccacgctg gccgccaggc acagatcgcc gaatagcggc ggccggtgtg gggaaatcca   10800
tgggtctt                                                            10808

SEQ ID NO: 7        moltype = DNA  length = 10807
FEATURE             Location/Qualifiers
source              1..10807
                    mol_type = unassigned DNA
                    organism = Zika virus
SEQUENCE: 7
agttgttgat ctgtgtgaat cagactgcga cagttcgagt ttgaagcgaa agctagcaac     60
agtatcaaca ggttttattt tggatttgga aacgagagtt tctggtcatg aaaaacccaa    120
aaaagaaatc cggaggattc cggattgtca atatgctaaa acgcggagta gcccgtgtga    180
gcccctttgg gggcttgaag aggctgccag ccggacttct gctgggtcat gggcccatca    240
ggatggtctt ggcgattcta gccttttga gattcacggc aatcaagcca tcactgggtc    300
tcatcaatag atggggttca gtgggaaaaa aagaggctat ggaataataa aagaagttca    360
agaaagatct ggctgccatg ctgagaataa tcaatgctag gaaggagaag aagagacgag    420
gcacagatac tagtgtcgga attgttggcc tcctgctgac cacagctatg gcagcggagg    480
tcactagacg tgggagtgca tactatatgt acttggacaa aagcgatgct ggggaggcca    540
tatctttttcc aaccacactg gggatgaata agtgttatat acagatcatg gatcttggac    600
acatgtgtga tgccaccatg agctatgaat gccctatgct ggatgagggg gtagaaccag    660
atgacgtcga ttgttggtgc aacacgacgt caacttgggt tgtgtacgga acctgccatc    720
acaaaaaagg tgaagcacgg agatccagaa gagctgtgac gctccctcc cattccacta    780
ggaagctgca aacggttcg cagacctggt tggaatcaag agaatacaca aagcacttga    840
ttagagtcga aaattggata ttcaggaacc ctggcttcgc gttagcagca gctgccatcg    900
cttggctttt gggaagctca acgagccaaa aagtcatata cttggtcatg atactgctga    960
ttgcccccggc atacagcatc aggtgcatag gagtcagtaa tagggacttt gtggaaggta   1020
tgtcaggtgg gacttgggtt gatgttgtct tggaacatgg aggttgtgtc accgtaagtg   1080
cacaggacaa accgactgtc gacatagagc tggttacaac aacagtcagc aacatgcggg   1140
aggtaagatc ctactgctat gaggcatcaa tatcggacat ggcttcggac agccgctgcc   1200
caacacaagg tgaagcctac cttgacaagc aatcagacac tcaatatgtc tgcaaaagaa   1260
cgttagtgga cagaggctgg ggaaatggat gtggactttt tggcaaaggg agcctggtga   1320
catgcgctaa gtttgcatgc tccaagaaaa tgaccgggaa gagcatccag ccagagaatc   1380
tggagtaccg gataatgctg tcagttcatg gctcccagca cagtgggatg atcgttaatg   1440
acacaggaca tgaaactgat gagaatagag cgaaggttga gataacgccc aattcaccaa   1500
gagccgaagc cacccctggg ggttttgaaa gcctaggact tgattgtgaa ccgaggacag   1560
gccttgactt ttcagatttg tattacttga ctatgaacaa caagcactgg ttggttcaca   1620
aggagtggtt ccacgacatt ccattacctt ggcacactgg ggcagacacc ggaactccac   1680
actgaacaa caaagaagca ctggtagagt tcaaggacgc acatgccaaa aggcaaactg   1740
tcgtggttct agggagtcaa gaaggagcag ttcacacgcc ccttgctgga gtctctggagg   1800
ctgagatgga tggtgcaaag ggaaggctgt cctctggcca cttgaaatgt cgcctgaaaa   1860
tggataaact tagattgaag ggcgtgtcat actccttgtg taccgcagcg ttcacattca   1920
ccaagatccc ggctgaaaca ctgcacggga cagtcacagt ggaggtacag tacgcaggga   1980
cagatggacc ttgcaaggtt ccagctcaga tggcggtgga catgcaaact ctgacccag   2040
ttgggagggtt gataaccgct aaccccgtaa tcactgagaac tctaagatga   2100
tgctggaact tgatccacca tttgggactc ttacattgt cataggagtc ggggagaaga   2160
agatcaccca ccactggcac aggagtggca gcaccattgg aaaagcattt gaagccactg   2220
tgagaggtgc aagagaatg gcagtcttgg gagacacagc ctgggactttt ggatcagttg   2280
gaggcgttct taactcattg gcaagggca tccatcaat ttttggagca gcttttcaat   2340
cattgttgg aggaatgtcc tggttctcac aaattctcat tggaacgttg ctgatgtggt   2400
tgggtctgaa tacaaagaat ggatctattt cccttatgtg cttggcctta ggggagtgt   2460
tgatcttctt atccacagcc gtctccgctg atgtgggtgt ctcggtggac ttctcaagaa   2520
aggaaacgag atgcggtaca ggggtgttcg tctataacga cgttgaagcc tggagggaca   2580
ggtacaagta ccatcctgac tcccctcgta gttggcagc agtagtcaag caagcctggga   2640
aagatggtat ctgtgggatc tcctctgttt caagaatgga aaacatcatg tggagatcag   2700
tagaagggga gctcaacgca atcctggaag agaatgagt tcaactacg gtcgttgtgg   2760
gatctgtaaa aaaccccatg tggagaggtc cacagagatt gccgtgcct gtgaacgagc   2820
tgccccacgg ctggaaggct tggggaaaat cgtacttcgt cagagcagca aagacaaata   2880
acagcttttg cgtggatggt gacactgctga aggaatgcc actcaaacat agagcatgga   2940
acagctttct tgtggaggat catgggttcg gggtatttca cactagtgtc tggctcaagg   3000
ttagagaaga ttattcacta gagtgtgatc cagccgtcat ggaacagct gttaaggga   3060
aggaggctgt acagtgtgat ctaggctact ggattgagag tgagaagac acacatgga   3120
ggctgaggag ggcccacctg atcgagatga aacatgtga atggcaaag tcccacacat   3180
tgtggacaga tggaatagaa gagagtgatc tgatcatacc caagtcttta gctgggcccac   3240
```

```
tcagccatca caacaccaga gagggctaca ggacccaaat gaaagggcca tggcacagtg   3300
aagagcttga aattcggttt gaggaatgcc caggcactaa ggtccacgtg gaggaaacat   3360
gtggaacaag aggaccatct ctgagatcaa ccactgcaag cggaagggtg atcgaggaat   3420
ggtgctgcag ggagtgcaca atgcccccac tgtcgttccg ggctaaagat ggctgttggt   3480
atggaatgga gataaggccc aggaaagaac cagaaagtaa cttagtaagg tcaatggtga   3540
ctgcaggatc aactgatcac atggatcact tttcccttgg agtgcttgtg attctgctca   3600
tggtgcagga agggctgaag aagagaatga ccacaaagat catcataagc acatcaatgg   3660
cagtgctggt agctatgatc ctgggaggat tttcaatgag tgatctggct aagcttgcaa   3720
ttttgatggg tgccacctt gcggaaatga acactggagg agatgtagct catctggctg    3780
tggtagcggc attcaaagtc agaccagcgt tgctggtatc tttcatcttc agagctaatt   3840
ggacaccccg tgaaagcatg ctgctggcct tggcctcgtg tcttttgcaa actgcgatct   3900
ccgccttgga aggcgacctg atggttctca tcaatggttt tgctttggcc tggttggcaa   3960
tacgagcgat ggttgttcca cgcactgaca atatcacctt ggcaatcctg gctgctctga   4020
caccactggc ccggggcaca ctgcttgtgg cgtggaggag aggccttgct acttgcgggg   4080
ggttcatgct cctctctctg aaggggaaag gcagtgtgaa gaagaactta ccatttgtca   4140
tggccctggg actaaccgct gtgaggctgg tcgaccccat caacgtggtg ggactgctgt   4200
tgctcacaag gagtgggaag cggagctggc ccctagcga agtactcaca gctgttggcc    4260
tgatatgcgc attggctgga gggttcgcca aggcagatat agagatggct gggcccatgg   4320
ccgcggtcgg tctgctaatt gtcagttacg tggtctcagg aaagagtgtg gacatgtaca   4380
ttgaaagagc aggtgacatc acatgggaaa agatgcggaa agttactgga aacagtcccc   4440
ggctcgatgt ggcactagat gagagtggtg atttctccct ggtggaggat gacggtcccc   4500
ccatgagaga gatcatactc aaagtggtcc tgatgaccat ctgtggcatg aacccaatag   4560
ccatacccett tgcagctgga gcgtggtacg tatacgtgaa aactggaaaa aggagtggtg   4620
ctctatggga tgtgcctgct cccaaggaag taaaaagggg ggagaccaca gatggagtgt   4680
acagagtaat gactcgtaga ctgctaggtt caacacaagt tggagtggga gttatgcaag   4740
aggggtctt tcacactatg tggcatgtca caaaaggatc cgcgctgaga acggtgaag    4800
ggagacttga tccatactgg ggagatgtca agcaggatct ggtgtcatac tgtggtccat   4860
ggaagctaga tgccgcctgg gacgggcaca gcgaggtgca gctcttggcc gtgccccccg   4920
gagagagagc gaggaacatc cagactctgc cggaatatt taagcaaag gatgggggaca    4980
ttggagcggt tgcgctggac tatccagcag gaacttcagg atctccaatc ctagacaagt   5040
gtgggagagt gataggactc tatggcaatg gggtcgtgat caagaatggg agttatgtca   5100
gtgccatcac ccaagggagg agggaggaag agactcctgt tgagtgcttc gagccttcga   5160
tgctgaagaa gaagcagcta actgtcttag acttgcatcc tggagctggg aaaaccagga   5220
gagttcttcc tgaaatagtc cgtgaagcca taaaaacgag actccgtact gtgatcttag   5280
ctccaaccag ggttgtcgct gctgaaatgg aggaagcctc tagagggctt ccagtgcgtt   5340
atatgacaac agcagtcaat gtcacccatt ctgggacaga aatcgttgac ttaatgtgcc   5400
atgccacctt cacttcacgt ctactacagc caatcagagt ccccaactat aatctgtata   5460
ttatggatga ggcccacttc acagatccct caagtatagc agcaagagga tacatttcaa    5520
caagggtga gatgggcgag gcagctgcca tcttcatgac cgccacgcca ccaggaaccc   5580
gtgacgcatt cccggactcc aactcaccaa ttatggacac cgaagtggaa gtcccagaga   5640
gagcctggag ctcaggcttt gattgggtga cggatcattc tggaaaaaca gtttggtttg    5700
tcccaagcgt gaggaacggc aatgagatcg cagcttgtct gacaaaggct ggaaaacggg   5760
tcatacagct cagcagaaag acttttgaga cagagttcca gaaaacaaaa catcaagagt   5820
gggacttcgt cgtgacaact gacatttcag agatgggcgc caactttaaa gctgaccgtg   5880
tcatagattc caggagatgc ctaaagccgg tcatacttga tggcgagaga gtcattctgg   5940
ctggacccat gcctgtcaca catgccagcg ctgcccagag gaggggcgc ataggcagga    6000
atcccaacaa acctggagat gagtatctgt atgggggtgg gtgcgcagag actgatgaag   6060
accatgcaca ctggcttgaa gcaagaatgc tccttgacaa tatttacctc caagatggcc   6120
tcatagcctc gctctatcga cctgaggccg acaaagtagc agccattgag ggagagttca   6180
agcttaggac ggagcaaagg aagacctttg tggaactcat gaaaagagga gatcttcctg   6240
tttggctggc ctatcaggtt gcatctgccg gaataaccta cacagataga agatggtgct   6300
ttgatggcat gaccaacaac accataatgg aagacagtgt gccggcagag gtgtggacca   6360
gacacgagaa gaaagagtgc tcaaaccga ggtggatgga cgccagagtt tgttcagatc    6420
atgcggccct gaagtcattc aaggagtttg ccgctgggaa aagaggagcg cttttggag    6480
tgatggaagc cctgggaaca tgccaggac acatgacgga gagattccag gaagccattg   6540
acaacctcgc tgtgctcatg cgggcagaga ctgaagcag gccttacaaa gccgcggcgg   6600
cccaattgcc ggagaccta gagaccatta tgcttttggg gttgctggga acagtctcgc    6660
tgggaatctt tttcgtcttg atgcggaaca agggcatagg gaagatgggc tttgaatgg    6720
tgactcttgg ggccagcgca tggctcatgt ggctctcgga aattgagcca gccagaattg   6780
catgcgtcct cattgttgtg ttcctattgc tggtggtgct cataccatga gccagaaaagc   6840
aaagatcccc ccaggacaac caaatggcaa tcatcatcat ggtagcagta ggtcttctgg   6900
gcttgattac cgccaatgaa ctcggatggt tggagagaac aaaagtgac ctaagccatc    6960
taatgggaag gagagaggag ggggcaacca taggattctc aatggacatt gacctgcggc   7020
cagcctcgc ctgggccatc tatgctgccc tgacaacttt cattacccca gccgtccaac    7080
atgcagtgac cacttcatac aacaactact ccttaatggc gatggccacg caagctggag   7140
tgttgtttgg tatgggcaaa gggatgccat tctacgcatg gacttttga gtcccgctgc    7200
taatgatagg ttgctactca caattaacac ccctgacct aatagtggct atcatttgc    7260
tcgtggcgca ctacatgtac ttgatcccag gctgcaggc agcagctgcg cgtgctgccc   7320
agaagagaac ggcagctggc atcatgaaga accctgttgt ggataatgtg gtgactgact   7380
acattgacac aatgactatt gaccccccaa gtggagaaaa gatgggacag tgctactca    7440
tagcagtagc cgtctccagc gccatactgt cgcggaccgc ctgggggtgg ggggaagctg   7500
gggccctgat cacagctgca acttccactt tgtgggaagg ctctccgaac aagtactgga   7560
actcctctac agccacttca ctgtgcaaca tttttaggg aagttacttg gctggagctt   7620
ctctaatcta cacagtaaca agaaacgctg cttggtcaa gacgtggg ggtgggaacag    7680
gagagaccct gggagagaaa tggaaggccc gcttgaacca gatgcggcc ctggagttct    7740
actcctacaa aaagtcaggc atcaccgagg tgtcagaga gaggcccgc cgcgccctca    7800
aggacgtgt ggcaacggga ggccatgctg tgtcccgagg aagtgcaaag ctgagatggt   7860
tggtggagcg gggatacctg cagccctatg gaaaggtcat tgatcttgga tgtggcagag   7920
ggggctggag ttactacgcc gccaccatcc gcaaagttca agaagtgaaa ggatacacaa   7980
```

```
aaggaggccc tggtcatgaa gaacccatgt tggtgcaaag ctatgggtgg aacatagtcc    8040
gtcttaagag tggggtggac gtctttcata tggcggctga gccgtgtgac acgttgctgt    8100
gtgacatagg tgagtcatca tctagtcctg aagtggaaga agcacggacg ctcagagtcc    8160
tctccatggt gggggattgg cttgaaaaaa gaccaggagc cttttgtgta aaagtgttgt    8220
gcccatacac cagcactatg atggaaaccc tggagcgact gcagcgtagg tatgggggag    8280
gactggtcag agtgccactc tcccgcaact ctacacatga gatgtactgg gtctctggag    8340
cgaaaagcaa caccataaaa agtgtgtcca ccacgagcca gctcctcttg gggcgcatgg    8400
acgggcccag gaggccagtg aaatatgagg aggatgtgaa tctcggctct ggcacgcggg    8460
ctgtggtaag ctgcgctgaa gctcccaaca tgaagatcat tggtaaccgc attgaaagga    8520
tccgcagtga gcacgcggaa acgtggttct ttgacgagaa ccacccatat aggacatggg    8580
cttaccatgg aagctatgag gcccctacac aagggtcagc gtcctctcta ataaacgggg    8640
ttgtcaggct cctgtcaaaa ccctgggatg tggtgactgg agtcacagga atagccatga    8700
ccgacaccac accgtatggt cagcaaagag ttttcaagga aaaagtggac accagggtgc    8760
cagaccccca agaaggcact cgtcaggtta tgagcatggt ctcttcctgg ttgtggaaag    8820
agctaggcaa acacaaacgg ccacgagtct gtaccaaaga agagttcatc aacaaggttc    8880
gtagcaatgc agcattaggg gcaatatttg aagaggaaaa agagtggaag accgcagtgg    8940
aagctgtgaa cgatccaagg ttctgggctc tagtggacaa ggaaagagag caccacctga    9000
gaggagagtg ccagagctgt gtgtacaaca tgatggaaa aagagaaaag aaacaagggg    9060
aatttggaaa ggccaagggc agccgcgcca tctggtatat gtggctaggg gctagatttc    9120
tagagttcga agcccttgga ttcttaaatg aggatcactg gatggggaga gagaactcag    9180
gaggtggtgt tgaagggctg ggattacaaa gactcggata tgtcctagaa gagatgagtc    9240
gcataccagg aggaaggatg tatgcagatg acactggtga ctgggacacc cgcatcagca    9300
ggtttgatct ggagaatgaa gctttaatca ccaaccaaat ggagaaaggg cacagggcct    9360
tagcattggc cataatcaag tacacatacc aaaacaaagt ggtaaggtc cttagaccag    9420
ctgaaaaagg gaagacagtt atggacatta tttcaagaca agaccaaagg gggagcggac    9480
aagttgtcac ttacgctctt aacacattta ccaacctagt ggtgcaactc attcggaata    9540
tggaggctga ggaagttcta gagatgcaag acttgtggct gctgcggagg tcagagaaag    9600
tgaccaactg gttgcagagc aacggatggg ataggctcaa acgaatgca gtcagtggag    9660
atgattgcgt tgtgaagcca attgatgata ggtttgcaca tgccctcagg ttcttgaatg    9720
atatgggaag agttaggaag gacacacaag agtggaaacc ctcaactgtc tgggacaact    9780
gggaagaagt tccgttttgt tcccaccact tcaacaagct ccatctcaag gacgggaggt    9840
ccattgtggt tccctgccgc caccaagatg aactgattgg ccgggccgt gtctctccag    9900
gggcgggatg gagcatccgg gagactgctt gcctagcaaa gtcatatgcg caaatgtggc    9960
agctccttta tttccacaga agggacctcc gactgatgc caatgccatc tgttcatctg    10020
tgccagttga ctgggttcca actgggagaa ctacctggtc aatccatgaa aaggagaat    10080
ggatgaccac tgaagacatg cttgtggtgt ggaacagagt gtggattgag gagaacgacc    10140
acatggaaga caagcccca gttacgaaat ggacagacat tccctatctg ggaaaaaggg    10200
aagacttgtg gtgtggatct ctcatagggc acagaccgcg caccacctgg gctgagaaca    10260
ttaaaaacac agtcaacatg gtgcgcagga tcataggtga tgaagaaaag tacatggact    10320
acctatccac ccaagttcgc tacttgggtg aagaagggtc tacacctgga gtgctataag    10380
caccaatctt agtgttgtca ggcctgctag tcagccacag cttggggaaa gctgtgcagc    10440
ctgtgacccc cccaggagag gctgggaaac aagcccata gtcaggccga aacgccatg    10500
gcacggaaga agccatgctg cctgtgagcc cctcagagga cactgagtca aaaaacccca    10560
cgcgcttgga ggcgcaggat gggaaaagaa ggtggcgacc ttcccacccc ttcaatctgg    10620
ggcctgaact ggagatcagc tgtggatctc cagaagaggg actagtggtt agaggagacc    10680
cccggaaaa cgcaaaacag catattgacg ctgggaaaga ccagagactc catgagtttc    10740
caccacgctg gccgccaggc acagatcgcc gaatagcggg gccggtgtg gggaaatcca    10800
tgggtct                                                             10807

SEQ ID NO: 8           moltype = DNA  length = 10807
FEATURE                Location/Qualifiers
source                 1..10807
                       mol_type = unassigned DNA
                       organism = Zika virus
SEQUENCE: 8
agttgttgat ctgtgtgaat cagactgcga cagttcgagt ttgaagcgaa agctagcaac      60
agtatcaaca ggttttattt tggatttgga acgagagtt tctggtcatg aaaaacccaa     120
aaagaaatc cggaggattc cggattgtca atatgctaaa acgcggagta gcccgtgtga     180
gccccttggg gggcttgaag aggctgccag ccggacttc gctgggccat gggcccatca     240
ggatggtctt ggcgataca gccttttga gattcacgac aatcaagcca tcactgggtc     300
tcatcaatag atggggttca gtggggaaaa aagaggctat ggaataata aagaagttca     360
agaaagatct ggctgccatg ctgagaataa tcaatgctag gaaggagaag aagagacgag     420
gcgcagatac tagcgtcgga attgttggcc tcctcctgac cacagccatg gcagtagagg     480
tcactagacg tgggagtgca tactatatgt acttggacag aagcgatgct gggggaagca     540
tatctttttc aaccacactg gggatgaata agtgttacat caaatcatg gatcttggac     600
acatgtgtga tgccaccatg agctatgaat gccctatgtt ggatgagggg gtagaaccag     660
atgacgtcga ttgctggtgc aacacgacat caacttgggt tgtgtatgga acctgccacc     720
acaaaaaagg tgaagcacgg agatctagaa gagctgtgac gctccctcc cattccacta     780
ggaagctgca aacgcgtcg cagacctggt tggaatcaag agaatacaca aagcacctta     840
ttagagttga aaattggata ttcaggaacc ctgcttcgc gttagcagca gctgtcatcg     900
cttggctttt gggaagttca acgagccaaa aagtcatata tctggtcatg atactgctga     960
ttgccccggc atacagcatc aggtgcatag gagtcagcaa tagggacttt gtggaaggta    1020
tgtcaggtgg gacttgggtt gatgttgtct ggaacatgg aggttgtgtt accgtaatgg    1080
cacaggcaa accgactgtc gacatagagc tggttacaac aacagatgg gccctgatga    1140
aggtaagatc ctactgctat gaggcatcaa tatcggatat ggcttcgac agccgctgcc    1200
caacacaagg tgaggcctac cttgacaagc agtcagacac tcaatatgtc tgcaaaagaa    1260
cgttagtgga cagaggctgg ggaaatggat gtggacttttt tggcaagggg agcctggtga    1320
catgcgctaa gtttgcatgc tccaagaaaa tgaccgggaa gagcatccag ccagagaatc    1380
tggagtaccg gataatgctg tcagttcatg gctcccagca cagtgggatg atcgttaatg    1440
```

```
acacaggaca tgaaactgat gagaatagag cgaaggttga gataacgccc aattcaccaa  1500
gagccgaagc caccctgggg ggttttggga gcctaggact tgattgtgaa ccgaggacag  1560
gccttgactt ttcagatttg tattacctga ctatgaataa caagcactgg ttggttcaca  1620
aggagtggtt ccacgacatt ccattacctt ggcatgctgg ggcagacact ggaactccac  1680
attggaacaa caaagaagca ctggtagagt tcaaggacgc acatgcaaaa aggcaaactg  1740
tcgtggttct agggagtcaa gaaggagcag ttcacacggc ccttgctgga gctctggagg  1800
ctgagatgga tggagccaag ggaaggctgt cctctggcca cttgaaatgt cgcctgaaaa  1860
tggataaact tagattgaag ggcgtgtcat actccttgtg cactgcagcg ttcacattca  1920
ccaagatccc ggctgaaaca ctgcacggga cagtcacagt ggaggtacag tacgcaggga  1980
cagatggacc ttgcaaggtt ccagctcaga tggcggtgga tatgcaaact ctgaccccag  2040
ttgggaggtt gataaccgct aaccctgtaa tcactgaaag caccgagaac tctaagatga  2100
tgctggaact tgatccacca tttggggact cttacattgt cataggagtc ggggagaaga  2160
agatcaccca tcactggcac aggagtggca gcaccattgg aaaagcattt gaagccactg  2220
tgagaggtgc caagagaatg gcagtcttgg gagacacagc ctggacttt ggatcagttg  2280
ggggtgctct caactcattg ggcaagggca tccatcaaat ttttggagca gctttcaaat  2340
cattgttcgg aggaatgtcc tggttctcac aaattctcat tggaacgttg ctggtgtggt  2400
tgggtctgaa tacaaagaat ggatctattt cccttacgtg cttggcctta gggggagtgt  2460
tgatcttctt atccacagcc gtttctgctg atgtggggtg ctcggtggac ttctcaaaga  2520
aggaaacgag atgcggtaca ggggtgttcg tctataacga cgttgaagcc tggagggaca  2580
ggtacaagta ccatcctgac tcccctcgta gattggcagc agcagtcaag caagcctggg  2640
aagatgggat ctgtgggatc tcctctgtct caagaatgga aaacatcatg tggagatcag  2700
tagaagggga gctcaacgca atcctggaag agaatggaat tcaactgacg gtcgttgttg  2760
gatctgtaaa aaaccccatg tggagaggtc cacagagatt gcccgtgcct gtgaacgagc  2820
tgccccacgg ctgaaggct tgggggaaat cgtacttcgt cagagcagca aagacaaata  2880
acagctttgt cgtggatggt gacacactga aggaatgccc actcaaacat agagcatgga  2940
acagctttct tgtggaggat catgggtttg gggtatttca cactagtgtc tggctcaagg  3000
ttagagaaga ttattcatta gagtgtgatc cagccgtcat tggaacagct gctaagggaa  3060
aggaggctgt gcacagcgat ctaggctact ggattgagag tgagaagaac gacacatgga  3120
ggctgaagag ggcccacctg atcgagatga aaacatgtga atggccaaag tcccacacat  3180
tgtggagtaa tggagtagaa gaaagtgatc tgatcatacc caagtcttta gctgggccac  3240
tcagccatca caacaccaga gagggctaca ggactcaaat gaaagggcca tggcacagtg  3300
aagagcttga aattcggttt gaggaatgcc caggcactaa ggtccacgtg gaggaaacat  3360
gtgggacaag gaggaccatcc ctgagatcaa ccactgcaag cggaagggtg atcgaggaat  3420
ggtgctgcag ggaatgcaca atgccccac tgtcgttccg agctaaagat ggctgttggt  3480
atggaatgga gataaggccc aggaaagaac cagaagtaa cttagtaagg tcaatggctg  3540
ctgcaggatc aactgatcac atggatcact tctctcttgg agtgcttgtg attttgctca  3600
tggtgcagga agggctgaag aagagaatga ccacaaagat catcataagc acatcaatgg  3660
cagtgctggt agccatgatc ctgggaggat tttcaatgag tgacctggct aagcttgcaa  3720
ttttaggtgg tgccaccttc gcggaaatga acactggagg agatgtagct catttgggcg  3780
tgatagcggc attcaaagtc agacctgcgt tgctggtatc tttcatcttc agagctaatt  3840
ggacaccccg tgagagcatg ctgctggcct tggcctcgtg tcttctgcaa actgcgatct  3900
ccgccttgga aggcgacctg atggttctca tcaatgggtt tgctttggcc tggttggcaa  3960
tacgacggat ggttgttcca cgcactgaca acatcacctt ggcaatcctg gctgctctga  4020
caccactggc ccggggcaca ctgcttgtgg cgtggagagc aggccttgct acttgcgggg  4080
ggttcatgct cctctctctg aaggggaaag gcagtgtgaa gaagaaccta ccatttgtca  4140
tggccttggg actaactgct gtgaggctgg tcgaccccat caacgtggtg ggactgctgt  4200
tgctcacaag gagtgggaag cggagcctgg ccctagtga agtactcaca gctgttggcc  4260
tgatatgcgc attggctgga gggttcgcca aggcggatat agagactggct gggcccatgt  4320
ccgcggtcgg tctgctaatt gtcagttacg tggtctcagg aaagagtgtg gacatgtaca  4380
ttgaaagagc aggtgacatc acatgggaaa agatgcggaa aatcactgga aacagtccccс  4440
ggctcgatgt ggcactagat gagagtggtg atttctccct agtggaggat gatgtccac  4500
ccatgagaga gatcatactc aaagtggtcc tgatgaccat ctgcggcatg aacccaatag  4560
ccataccctt tgcagctgga gcgtggtacg tgtatgtgaa gactgaaaa aggagtggtg  4620
ctctatggga tgtgcctgct cccaaggaag taaaaagggg ggagaccaca gatggagtgt  4680
acagagtaat gactcgtaga ctgcttggtt caacacaagt tggagtggga gtcatgcaag  4740
aggggggtctt ccacactatg tggcacgtca caaaaggatc cgcgctgaga agcggtgaag  4800
ggagacttga tccatactgg ggagatgtca gcaggatct ggtgtcatac tgtggtccgt  4860
ggaagctaga cgccgcctgg gacgggcaca gcgaggtgca gctcttggcc gtgcccccccg  4920
gagagagagc gaggaacatc cagactctgc ccggaacatt taagacaaag gatggggaca  4980
ttgggagcgt tgcgctggac tacccagcag gaacttcagg atcctccaatc ctagacaagt  5040
gtgggagagt gataggactc tatggtaatg gggtcgtgat aaaaaatggg agttatgtta  5100
gtgccatcac ccaagggagg agggaggaag agactcctgt tgagtgcttc gagccttcga  5160
tgctgaagaa gaagcagcta actgtcttag acctgcatcc tggagccggg aaaaccagga  5220
gagttcttcc tgaaatagtc cgtgaagcca taaaacaag actccgtact gtgatcttag  5280
ctccaaccag ggtcgtcgct gctgaaatgg aggaagccct tagagggctt ccagttcgtt  5340
atatgacaac agcagtcaat gtcacccatt ctgggacaga aatcgttgac ttaatgtgcc  5400
atgctacctt cacttcacgc ctactacaac caatcagagt ccccaactat aatttgtata  5460
ttatggatga ggcccacttc acagatcct caagtatgc agcaagagga tacatttcaa  5520
caagggttga gatgggcgag gcgctgcca tcttcatgac cgccacgccc ccaggaaccc  5580
gtgacgcatt cccggactcc aactcaccaa ttatggacac cgaggtggaa gtcccagaga  5640
gagcctggag cacaggcttt gattgggtga cggatcattc tgggaaaaca gtctggtttg  5700
ttccaagcgt gaggaacggc aatgagatcg cagcttgtct gacaaaggct ggaaaacggg  5760
tcatacagct cagcagaaag actttgaga cagagttcca gaaaacgaaa atcaagagt  5820
gggacttcgt cgtgacaacc gacatttcag agatggggcc caacttaaa gctgaccgtg  5880
tcatagattc caggagatgc ttaaagccgg tcatacttga tggcgagaga gtcattttgg  5940
ctggacccat gcctgtcaca catgccagcg ctgctcagag gagggggcgc ataggcagga  6000
atcccaacaa acctggagat gagtatctgt atggaggtgg tgcgcagaga actgatgaag  6060
atcacgcaca ctggcttgaa gcaagaatgc ttcttgacaa catttacctc caagatgcc  6120
tcatagcttc gctctatcga cctgaggccg acaaagtagc agctattgag ggagagttca  6180
```

```
agcttaggac ggagcaaagg aagacctttg tggaactcat gaaaagagga gatcttccgg   6240
tttggttggc ctatcaggtt gcatctgccg gaataaccta cacagataga agatggtgct   6300
ttgatggcat gaccaacaac accataatgg aagacagtgt gccggcagag gtgtggacca   6360
gatacggaga gaaaagagtg ctcaaaccga ggtggatgga cgccagagtt tgttcagatc   6420
atgcggccct gaagtcattc aaagagtttg ccgctgggaa aagaggagcg gccttggag   6480
tgatagaagc cctgggaaca ctgccaggac acatgacaga gagattccag gaagccattg   6540
acaacctcgc tgtgctcatg cgggcagaga ctggaagcag gccttacaaa gccgcggcgg   6600
cccaattgcc ggagacccta gagaccatta tgcttttggg gttgctggga acagtctcgc   6660
tgggaatctt tttcgtcttg atgcggaaca agggcatggg gaagatgggc tttggaatgg   6720
tgactcttgg ggccagcgca tggcttatgt ggctctcgga aattgagcca gccagaattg   6780
catgtgtcct cattgtcgtg ttcctattgc tggtggtgct cataccgag ccagaaaagc   6840
aaagatctcc tcaggacaac caaatggcaa tcatcatcat ggtagcagtg ggtcttctgg   6900
gcttgattac cgccaatgaa ctcggatggt tggagaaac aaaaagtgac ctaagccatc   6960
taatgggaag gagagaggag ggggcaacca caggattctc aatggacatt gacctggcc   7020
cagcctcagc ttgggctatc tatgctgctc tgacaacttt catcaccca gccgtccaac   7080
atgcggtgac cacttcatac aacaactact ccttaatggc gatggccacg caagctgggg   7140
tgttgtttgg tatgggcaaa gggatgccat tctacgcatg ggactttgga gtcccgctgc   7200
taatgatggg ttgctactca caattaacac ctctgacct aatagtgacc atcattttgc   7260
tcgtggcgca ctacatgtac ttgatcccag ggctgcaggc agcagctgcg cgggctgccc   7320
agaagagaac ggcagctggc atcatgaaga accctgttgt ggatgaaata gtggtgactg   7380
acattgacac aatgacaatt gaccccccaag tggaaaaaaa gatggggcag gtgctactca   7440
tagcagtagc cgtctccagc gccatactgt cgcggaccgc ctgggggtgg ggaggaggcctg   7500
gggccctgat cacagctgca acttccaccc tgtgggaagg ctctccgaac aagtactgga   7560
actcctccac agccacttca ctgtgtaaca tttttagggg aagttacttg gctggagctt   7620
ctctaatcta cacagtaaca agaaacgctg cttggtcaa gagacgtggg ggtggaacgg   7680
gagagaccct gggagagaaa tggaaggccc cctgacacaa gatgtcggcc ctggagttct   7740
actcctacaa aaagtcaggc atcaccgagg tgtgcagaga agaggccgc cgtgccctca   7800
aggacggtgt ggcaacagga ggccatgctg tgtcccgagg aagtgcaaag cttagatggc   7860
tggtggagag aggatacctg cagccctatg gaaaggtcat tgatcttgga tgtggcagag   7920
ggggctggag ttactatgcc gccaccatcc gcaaagttca ggaagtgaaa ggatacacaa   7980
aaggaggccc tggtcatgaa gaacccatgt tggtgcaaag ctatgggtgg aacatagtcc   8040
gtcttaagag tggggtggac gtctttcaca tggcggctga gccgtgtgac actttgctgt   8100
gtgatatagg tgagtcatca tctagtcctg aagtggaaga agcacggacg ctcagagtcc   8160
tctccatggt ggggattggg cttgaaaaaa gaccaggagc cttttgtata aaagtgttgt   8220
gcccatacac cagcactatg atggaaaccc tggagcgact gcagctagg tatgggggag   8280
gactggtcag ggtgccactc tcccgcaact ctacacatga gatgtactgg gtctctggag   8340
cgaaaagcaa caccataaaa agtgtgtcca ccacgagcca gctcctcttg gggcgcatgg   8400
acgggcccag gaggccagtg aaatatgagg aggatgtgaa tctcggctct ggcacgcggg   8460
ctgtgtaag ctgcgctgaa gctcccaaca tgaagatcat tggtaaccgc attgagagga   8520
tccgcagtga gcacgcggaa acgtggttct ttgacgagaa ccaccatat aggacatggg   8580
cttaccatga aagctatgag gcccctacac aagggtcagc gtcctctcta ataaacgggg   8640
ttgtcaggct cctgtcaaaa ccctgggatg tggtgactgg agtcacagga atagccatga   8700
ctgacaccac accgtatggt cagcaaagga tttcaagga aaaagtggac actagggtgc   8760
cagacccca agaaggcact cgtcaggtta tgagcatggt ctcttcctgg ttatggaagg   8820
agctaggcaa acacaaacgg ccacgagtct gtaccaaaga agagttcatc aacaaggttc   8880
gtagcaatgc agcattaggg gcaatatttg aagaggaaaa agagtggaag actgcagtgg   8940
aagctgtgaa tgatccaagg ttctgggctc tagtggacaa ggaaagagag catcacctga   9000
gaggagagtg tcagagctgt gtgtacaaca tgatgggaaa aagagaaaag aaacaagggg   9060
aatttggaaa ggccaagggc agccgcgcca tctggtatat gtggctaggg gctagattcc   9120
tagagttcga agcccttgga ttcttgaatg aggatcattg gatggggaga gagaattcag   9180
gaggtgtgt tgaaggactg ggattacaaa gactcggata tgtcctagaa gagatgagtc   9240
gcataccagg aggaaggatg tatgcagatg atactgctgg ctgggacacc cgcatcagca   9300
ggtttgatct ggagaatgaa gctctaatca ccaaccaaat ggagaaaggg cacagggcct   9360
tggcattggc cataatcaag tacacatacc aaaacaaagt ggtaaggtc cttagaccag   9420
ctgaaaaggg gaagacagtt atggacatta tttcaagaca agaccaaaag ggggagcggac   9480
aagttgtcac ttacgctctt aatacattca ccaacctggt ggtgcagctc attcggaata   9540
tggaggctga ggaagttcta gagatgcaag acttgtggct gctgcggagg ccagagaaag   9600
tgaccaactg gttgcaaagc aacggatggg ataggctcaa aagaatggca gtcagtggag   9660
atgattgcgt tgtgaaacca attgatgata ggtttgcaca tgccctcagg ttcttgaatg   9720
atatgggaaa agttaggaag gacacacaag agtggaaacc ctcaactgga tgggacaact   9780
gggaagaagt tccgttttgc tcccaccact tcaacaaact ccatcttaag gacgggaggt   9840
ccattgtggt tccctgccgc caccaagatg aactgattgg ccgagcccgc gtatcaccag   9900
gggcgggatg gagcatccgg gagactgctt gcctagcaaa atcatatgcg caaatgtggc   9960
agctccttta tttccacaga agggacctcc gactgatgc catcgccatt tgttcatctg  10020
tgccagttga ttgggttcca actgggagaa ctacctggtc aatccatgca agggagaat  10080
ggatgaccac tgaagacatg cttgtggtat ggaacagagt gtggattgag gaaaacgacc  10140
acatggaaga caagaccccca gttacaaaat ggacagacat tccctatttg ggaaaaagag  10200
aagacttgtg gtgtggatct ctcataggc acagaccgcg tactacctgg gctgagaaca  10260
tcaaaaatac agtcaacatg atgcgcagga tcataggtga tgaaaaaag tacatggact  10320
acctatccac ccaggttcgc tacttgggtg aagaagggtc cacactggac gtgctgtaag  10380
caccaatctt agtgttgtca ggcctgctag tcagccacag cttggggaaa gctgtgcagc  10440
ctgtgacccc cccaggagaa gctggaaac caagcctata gtcaggccga gaacgccatg  10500
gcacggaaga agccatgctg cctgtgagcc cctcagggga cactgagtca aaaaacccca  10560
cgcgcttgga ggcgcaggat gggaaaagaa ggtggcgacc ttcccacccc ttcaatctg   10620
ggcctgaact ggagatcagc tgtggatctc cagaagaggg actagtggtt agaggagacc  10680
ccccggaaaa cgcaaaacag catattgacg ctgggaaaga ccagactc catgagtttc   10740
caccacgctg gccgccaggc acagatcgcc gaatagcggc ggccggtgtg ggaaatcca   10800
tgggtct                                                           10807
```

| SEQ ID NO: 9 | moltype = DNA length = 10648 |
|---|---|
| FEATURE | Location/Qualifiers |
| source | 1..10648 |
| | mol_type = unassigned DNA |
| | organism = Zika virus |

SEQUENCE: 9

```
gacagttcga gtttgaagcg aaagctagca acagtatcaa caggttttat ttggatttgg    60
aaacgagagt ttctggtcat gaaaaaccca aaaagaaat  ccggaggatt ccggattgtc   120
aatatgctaa aacgcggagt agcccgtgtg agcccctttg ggggcttgaa gaggctgcca   180
gccggacttc tgctgggtca tgggcccatc aggatggtct tggcgattct agccttttg   240
agattcacgg caatcaagcc atcactgggt ctcatcaata gatgggggttc agtgggaaaa   300
aaagaggcta tggaaataat aaagaagttc aagaaagatc tggctgccat gctgagaata   360
atcaatgcta ggaaggagaa gaagagacga ggcgcagata ctagtgtcgg aattgttggc   420
ctccctgctga ccacagctat ggcagcggag gtcactagac gtgggagtgc atactatatg   480
tacttggaca gaaacgatgc tggggaggcc atatctttc  caaccacatt ggggatgaat   540
aagtgttata tacagatcat ggatcttgga cacatgtgtg atgccaccat gagctatgaa   600
tgccctatgc tggatgaggg ggtggaacca gatgacgtcg attgttggtg caacacgacg   660
tcaacttggg ttgtgtacgg aacctgccat cacaaaaaag gtgaagcacg gagatctaga   720
agagctgtga cgctccccctc ccattccact aggaagctgc aaacgcggtc gcaaacctgg   780
ttggaatcaa gagaatacac aaagcacttg attagagtcg aaaattggat attcaggaac   840
cctggcttcg cgttagcagc agctgccatc gcttggcttt tgggaagctc aacgagccaa   900
aaagtcatat acttggtcat gatactgctg attgccccga gctacagcag caggtgcata   960
ggagtcagca ataggggactt tgtggaaggt atgtcaggtg ggacctgggt tgatgttgtc  1020
ttggaacatg gaggttgtgt caccgtaatg gcacaggaca aaccgactgt cgacatagag  1080
ctggttacaa caacagtcag caacatgcg  gaggtaagat cctactgcta tgaggcatca  1140
atatcagaca tggcttcgga cagccgctgc ccaaacacaag gtgaagccta ccttgacaag  1200
caatcagaca ctcaatatgt ctgcaaaaga acgttagtgg acagaggctg gggaaatgga  1260
tgtggactttt ttggcaaagg gagcctggtg acatgcgcta agtttgcatg ctccaagaaa  1320
atgaccggga gagcatcca gccagagaat ctggagtacc ggataatgct gtcagttcat  1380
ggctcccagc acagtgggat gattgttaat gacacagag atgaaactga tgagaataga  1440
gcgaaagttg agataacgcc caattcacca agagccgaag ccaccctggg gggttttgga  1500
agcctaggac ttgattgtga accgaggaca ggccttgact tttcagattt gtattacttg  1560
actatgaata caagcactg  gttggttcac aaggagtggt tccacgacat tccattacct  1620
tggcacgctg gggcagacac cggaactcca cactggaaca acaaagaagc actgatctag  1680
ttcaaggacg cacatgccaa aaggcaaact gtcgtggttc tagggagtca agaaggagca  1740
gttcacacgg cccttgctgg agctctggag gctgagatgg atggtgcaaa ggggaaggctca  1800
tcctctggcc acttgaaatg tcgcctgaaa atggataaac ttagattgaa gggcgtgtca  1860
tactccttgt gtactgcagc gttcacatc  accaagatcc cggctgaaac actgcacggg  1920
acagtcacag tggaggtaca tacgcaggg  acagatgagc cttgcaaggt tccagctcag  1980
atggcggtgg acatgcaaac tctgacccca gttggggaggt tgataaccgc taaccccgta  2040
atcactgaaa gcactgagaa ctcaagatg  atgctgggaac ttgatccacc atttggggac  2100
tcttacattg tcataggagt cgggggaagaag aagatcaccc accactggca caggagtggc  2160
agcaccattg gaaaagcatt tgaagccact gtgagggtgc ccaagagaat cagcagtcttg  2220
ggagacacag cctgggactt tggatcagtt ggaggcgctc tcaactcatt gggcaagggc  2280
atccatcaaa ttttttggagc agctttcaaa tcattgtttg gaggaatgtc ctggttctca  2340
caaattctca ttgaacgtt  gctgatgtgg ttgggtctga acacaaagaa tggatctatt  2400
tcccttatgt gcttggcctt agggggagtg ttgatcttct tatccacagc cgtctctgct  2460
gatgtggggt gctcggtgga cttctcaaag aaggagacga gatgcggtac aggggtgttc  2520
gtctataacg acgttgaagc ctgaggacac aggtacaagt accatcctga ctcccccgt   2580
agattggcag cagcagtcaa gcaagcctgg gaagatggta tctgcgggat ctcctctgtt  2640
tcaagaatgg aaaacatcat gtggagatca gtagaaggg  agctcaacgc aatcctgtgg  2700
gagaatggag ttcaactgac ggtcgttgtg ggatctgtaa aaaacccca  gtggagaggt  2760
ccacagagat tgcccgtgcc tgtgaacgag ctgccccacg gctggaaggc ttgggggaaa  2820
tcgtacttcg tcagagcagc aaagacaaat aacagctttg tcgtggatgg tgacacactg  2880
aaggaatgcc cactcaaaca tagacatggg aacagcttc  ttgtgggagga tcatgggttc  2940
ggggtatttc acactagtgt ctggctcaag gttagagaag attattcatt agagtgtgat  3000
ccagccgtta ttggaacagc tgttaaggga aaggaggctg tacacagtga tctaggctac  3060
tggattgaga gtgagaagaa tgacacatgg aggctgaaga ggcccatct  gatcgagatg  3120
aaaacatgtg aatggccaaa gtcccacaca ttgtggcaga atggaataga agagagtgat  3180
ctgatcatac ccaagtcttt agctgggcca gtcagccatc acaataccag agagggctac  3240
aggacccaaa tgaaagggcc atggcacagt gaagagcttg aaattcggtt tgaggaatgc  3300
ccaggcacta aggtccacgt ggaggaaaca tgtggaacaa gaggaccatc tctgagatca  3360
accactgcaa gcgcaagggt gatcgaggaa tggtgctgca gggagtgcac aatgcccca  3420
ctgtcgttcc gggctaaaga tggctgttgg tatgaaatgga agataaggcc aggaaagaa  3480
ccagaaagca acttagtaag gtcaatggtg actgcaggat caactgatca catgaccac   3540
ttctcccttg gagtgcttgt gattctgctc atggtgcagg aagggctgaa gaagagaatg  3600
accacaaaga tcatcataag cacatcaatg gcagtgctgg tagctatgat cctgggagga  3660
ttttcaatga gtgacctggc taagcttgca attttgatgg gtgccacctt cgcggaaatg  3720
aacactggag gagatgtagc tcatctggcg ctgatagcg  cattcaaagt cagaccagcg  3780
ttgctggtat cttcatcttt cagagctaat tggacacccc gtgaaagcat gctgctggcc  3840
ttggcctcgt gtcttttgca aactgcgatc tccgccttgg aaggcgacct gatggttctc  3900
atcaatggtt ttgctttggc ctggttgca atacgagcga tggttgttcc acgcactgat  3960
aacatcacct tggcaatcct ggctgctctg acaccactgg ccccgggcac actgcttgtg  4020
gcgtggagag gaggctgtgc tacttgcggg gggtttatgc tcctctctct gaagggaaaa  4080
ggcagtgtga agaagaactt accatttgtc atgcccctgg gactaaccgc tgtgaggctg  4140
gtcgaccccca tcaacgtggt gggactgctg ttgctcacaa ggagtgggaa gcggagctgg  4200
cccccctagcc aagtactcac agctgttggc ctgatatgcg cattggctgg agggttcgcc  4260
aaggcagata tagagatggc tgggcccatg gccgcggtcg gtctgctaat tgtcagttac  4320
gtggtctcag gaaagagtgt ggacatgtac attgaaagag caggtgacat cacatgggaa  4380
```

```
aaagatgcgg aagtcactgg aaacagtccc cggctcgatg tggcgctaga tgagagtggt 4440
gatttctccc tggtggagga tgacggtccc cccatgagag agatcatact caaggtggtc 4500
ctgatgacca tctgtggcat gaacccaata gccatacect ttgcagctgg agcgtggtac 4560
gtatacgtga agactggaaa aaggagtggt gctctatggg atgtgcctgc tcccaaggaa 4620
gtaaaaaagg gggagaccac agatggagtg tacagagtaa tgactcgtag actgctaggt 4680
tcaacacaag ttggagtggg agttatgcaa gagggggtct ttcacactat gtggcacgtc 4740
acaaaaggat ccgcgctgag aagcggtgaa gggagacttg atccatactg gggagatgtc 4800
aagcaggatc tggtgtcata ctgtggtcca tggaagctag atgccgcctg ggacgggcac 4860
agcgaggtgc agctcttggc cgtgccccccc ggagagagag cgaggaacat ccagactctg 4920
cccggaatat ttaagacaaa ggatggggac attggacgg ttgcgctgga ttacccagca 4980
ggaacttcag gatctccaat cctagacaag tgtgggagag tgataggact ttatggcaat 5040
ggggtcgtga tcaaaatgg gagttatgtt agtgccatca cccaagggag gagggaggaa 5100
gagactcctg ttgagtgctt cgagccttcg atgctgaaga agaagcagct aactgtctta 5160
gacttgcatc ctggagctgg gaaaaccagg agagttcttc ctgaaatagt ccgtgaagcc 5220
ataaaaacaa gactccgtac tgtgatctta gctccaacca gggttgtcgc tgctgaaatg 5280
gaggaggccc ttagagggct tccagtgcgt tatatgacaa cagcagtcaa tgtcacccac 5340
tctgaacag aaatcgtcga cttaatgtgc catgccacct tcacttcacg tctactacag 5400
ccaatcagag tccccaacta taatctgtat attatggatg aggccacctt cacagatccc 5460
tcaagtatag cagcaagagg atacatttca acaaggggtg agatgggcga ggcggctgcc 5520
atcttcatga ccgccacgcc accaggaacc cgtgacgcat ttccggactc caactcacca 5580
attatgggaca ccgaagtgga agtcccagag agagcctgga gctcaggctt tgattgggtg 5640
acggatcatt ctgaaaaaac agtttggttt gttccaagcg tggaaacgg caatgagatc 5700
gcagcttgtc tgacaaaggc tggaaaacgg gtcatacagc tcagcagaaa gacttttgag 5760
acagagttcc agaaaacaaa acatcaagag tgggactttg tcgtgacaac tgacatttca 5820
gagatgggcg ccaactttaa agctgaccgt gtcatagatt ccaggagatg cctaaagccg 5880
gtcatacttg atggcgagag agtcattctg gctggaccca tgcctgtcac acatgccagt 5940
gctgcccaga ggaggggggcg cataggcagg aatcccaaca aacctggaga tgagtatctg 6000
tatgagggtg ggtgcgcaga gactgacgaa gaccatgcac actggcttga agcaagaatg 6060
ctccttgaca atatttacct ccaagatggc ctcatagcct cgctctatcg acctgaggcc 6120
gacaaagtag cagccattga gggagagttc aagcttagga gggagcaaag gaagaccttt 6180
gtggaactca tgaaaagagg agatcttcct gttttgctgg cctatcaggt tgcatctgcc 6240
ggaataacct acacagatag aagatggtgc tttgatggca cgaccaacaa caccataatg 6300
gaagacagtg tgccggcaga ggtgtggacc agacacggag agaaagagt gctcaaaccg 6360
aggtggatgg acgccagagt ttgttcagat catgcggccc tgaagtcatt caaggagttt 6420
gccgctggga aagaggagc ggcttttgga gtgatggaag ccctgggaac actgccagga 6480
cacatgacag agagattcca ggaagccatt gacaacctcg ctgtgctcat gcgggcagag 6540
actgaagca ggccttacaa agccgcggcg gcccaattgc cggagaccct agagaccatt 6600
atgctttttg ggttgctggg aacagtctcg ctgggaatct tcttcgtctt gatgaggaac 6660
aagggcatag ggaagatggg cttttggaatg gtgactcttg gggccagcgc atggctcatg 6720
tggctctcgg aaattgagcc agccagaatt gcatgtgtcc tcattgttgt gtttctattg 6780
ctggtggtgc tcatacctga gccagaaaag caaagatctc cccaggacaa ccaaatggca 6840
atcatcatca tggtagcagt aggtcttctg ggcttgatta ccgccaatga actcggatgg 6900
ttggagagaa caaagagtga cctaagccat ctaatggaga gaggagggccaacc 6960
ataggattct caatggacat tgacctgcgg ccagcctcag cttgggccat ctatgctgcc 7020
ttgacaactt tcattacccc agccgtccaa catgcagtga ccacttcata caacaactac 7080
tccttaatgg cgatggccac gcaagctgga gtgttgtttg gtatgggcaa agggatgcca 7140
ttctacgcat gggacttgg agtcccgctg ctaatgatag gttgctactc acaattaaca 7200
cccctgaccc taatagtggc catcattttg ctcgtggcgc actacatgta cttgatccca 7260
gggctgcagg cagcagctgc gcgtgctgcc cagaagagaa cggcagctgg catcatgaag 7320
aaccctgttg tggatggaat agtggtgact gacattgaca caatgacaat tgaccccaa 7380
gtggagaaaa agatgggaca ggtgctcatc atagcagtag ccgtctccag cgccatactg 7440
tcgcggaccg cctgggggtg gggggaggct ggggccctga tcacagccgc aacttccact 7500
ttgtgggaag gctctccgaa caagtactgg aactcctcta cagccacttc actgtgtaac 7560
atttttaggg gaagttactt ggctggagct tctctaatct acacagtaac aagaaacgct 7620
ggcttggtca agagacgtgg gggtggaaca ggagagaccc tgggagagaa atggaaggcc 7680
cgcttgaacc agatgtcggc cctggagttc tactcctaca aaaagtcagg catcaccgga 7740
gtgtgcagaa agagggccg ccgcgccctc aaggacggtg tggcaacggg aggccatgct 7800
gtgtcccgag gaagtgcaaa gctgagatgg ttggtggagc ggggatacct gcagccctat 7860
ggaaaggtca ttgatcttgg atgtggcaga ggggctgga gttactacgc cgccaccatc 7920
cgcaaagttc aagaagtgaa aggatacaca aaggcaggct ctggtcatga agaaccgtg 7980
ttggtgcaaa gctatgggtg gaacatagtc cgtcttaaga gtgggtgga cgtctttcat 8040
atggcggctg agccgtgtga cacgttgctg tgtgacatag tgagtcatc atctagtcct 8100
gaagtggaag aagcacggac gctcagagtc ctctccatgg tgggggattg gcttgaaaaa 8160
agaccaggag cctttttgtat aaaggtgttg tgcccataca ccagcacatt gatggaaacc 8220
ctggagcgac tgcagcgtag gtatgggga ggactggtca gagtgccact ctcccgcaac 8280
tctacacatg agatgtattg ggtctctgga gcgaaaagca acaccataaa aagtgtgtcc 8340
accacgagcc agctcctctt ggggcgcatg gacgggccta ggaggccagt gaaatatgag 8400
gaggatgtga atctcggctc tggcacgcgg gctgtgtaa gctgcgctga agctcccaac 8460
atgaagatca ttggtaaccg cattgaaagg atccgcagtg agcacgcgga aacgtggttc 8520
tttgacgaga accacccata taggacatgg gcttaccatg gaagctatga ggccccaca 8580
caagggtcag cgtcctctct aataaacggg ttgtcaggc tcctgtcaaa accctgggat 8640
gtggtgactg agtcacagg aatagccatg accgacacca caccgtatgg tcagcaaaga 8700
gttttcaagg aaaagtgga cactagggtg ccagacccc aagaaggcac tcgtcaggtt 8760
atgagcatgg tctcttcctg gttgtggaaa gagctaggca acacaaacg gccacgagtc 8820
tgtaccaaag aagagttcat caacaaggtt cgtagcaatg cagcattagg caatatttt 8880
gaagaggaaa aagagtggaa gactcagtg gaagctgtga acgatccaag gttctgggct 8940
ctagtggata aggaaagaga gcaccacctg agaggagagt gccagagttg tgtgtacaac 9000
atgatggaa aagagaaaaa gaaacaaggg gaatttggaa aggccaaggg cagccgccgcc 9060
atctggtata tgtggctagg ggctagattt ctagagttcg aagcccttgg attcttgaac 9120
```

-continued

```
gaggatcact ggatggggag agagaactca ggaggtggtg ttgaagggct gggattacaa    9180
agactcggat atgtcctaga agagatgagt cgtataccag gaggaaggat gtatgcagat    9240
gacactgctg gctgggacac ccgcatcagc aggtttgatc tggagaatga agctctaatc    9300
accaaccaaa tggaaaaagg gcacagggcc ttggcattgg ccataatcaa gtacacatac    9360
caaaacaaag tggtaaaggt ccttagacca gctgaaaaag ggaaaacagt tatggacatt    9420
atttcgagac aagaccaaag ggggagcgga caagttgtca cttacgctct taacacattt    9480
accaacctag tggtgcaact cattcggaat atggaggctg aggaagttct agagatgcaa    9540
gacttgtggc tgctgcggag gtcagagaaa gtgaccaact ggttgcagag caacggatgg    9600
gataggctca aacgaatggc agtcagtgga gatgattgcg ttgtgaagcc aattgatgat    9660
aggtttgcac atgccctcag gttcttgaat gatatgggaa aagttaggaa ggacacacaa    9720
gagtggaaac cctcaactgg atgggacaac tgggaagaag ttccgttttg ctcccaccac    9780
ttcaacaagc tccatctcaa ggacggggag tccattgtgg ttccctgccg ccaccaagat    9840
gaactgattg gccgggcccg cgtctctcca ggggcggat ggagcatccg ggagactgct    9900
tgcctagcaa aatcatatgc gcaaatgtgg cagctccttt atttccacag aagggacctc    9960
cgactgatgg ccaatgccat ttgttcatct gtgccagttg actgggttcc aactgggaga    10020
actacctggt caatccatgg aaaggggaga tggatgacca ctgaagacat gcttgtggtg    10080
tggaacagag tgtggattga ggagaacgac cacatggaag acaagacccc agttacgaaa    10140
tggacagaca tcccctattt gggaaaaagg gaagacttgg ctgtggatc tctcatgggg    10200
cacagaccgc gcaccacctg ggctgagaac attaaaaaca cagtcaacat ggtgcgcagg    10260
atcataggtg atgaagaaaa gtacatggac tacctatcca cccaagttcg ctacttgggt    10320
gaagaaggg ctacacctgg agtgctgtaa gcaccagtgt taatgttgtc aggcctgcta    10380
gtcagccaca gcttgggaaa agctgtcgag cctgtgaccc cccaggaga agctgggaaa    10440
ccaagcctat agtcaggccg agaacgccat ggcacggaag aagccatgct cctgtgagc    10500
ccctcagagg acactgagtc aaaaaacccc acgcgcttgg aggcgcagga tgggaaagaa    10560
aggtggcgac cttccccacc cttcaatctg gggcctgaac tggagatcag ctgtggatct    10620
ccagaagagg gactagtggt tagaggag                                      10648
```

```
SEQ ID NO: 10          moltype = DNA   length = 10676
FEATURE                Location/Qualifiers
source                 1..10676
                       mol_type = unassigned DNA
                       organism = Zika virus
SEQUENCE: 10
gttgttactg ttgctgactc agactgcgac agttcgagtt tgaagcgaaa gctagcaaca      60
gtatcaacag gttttatttg gatttggaaa cgagagtttc tggtcatgaa aaacccaaaa     120
aagaaatccg gaggattccg gattgtcaat atgctaaaac gcggagtagc ccgtgtgagc     180
ccctttgggg gcttgaagag gctgccagcc ggacttctgc tgggtcatgg gcccatcagg     240
atggtcttgg caattctagc ctttttgaga ttcacggcaa tcaagccatc actgggtctc     300
atcaatagat gggggttcgt ggggaaaaaa gatgctatgg aaataataaa gaagttcaag     360
aaagatctgg ctgccatgct gagaataatc aatgctagga aggagaagaa gagacgaggc     420
gcagatacta gtgtcggaat tgttggcctc ctgctgacca cagctatggc agcggaggtc     480
actagacgtg ggagtgcata ctatatgtac ttggacagaa acgatgctgg ggaggccata     540
tctttttccaa ccacattggg gatgaataag tgttatatac agatcatgga tcttggacaa     600
atgtgtgatg ccaccatgag ctatgaatgc cctatgctgg atgaggggt ggaaccagat     660
gacgtcgatt gttggtgcaa cacgacgtca acttgggttg tgtacggaac ctgccatcac     720
aaaaaaggtg aagcacggag atctagaaga gctgtgacgc tcccttccca ttccactagg     780
aagctgcaaa cgcggtcgca aacctggttg gaatcaagag aatacacaaa gcacttgatt     840
agagtcgaaa attggatatt caggaaccct ggcttcgcgt tagcagcagc tgccatcgct     900
tggcttttgg gaagctcaac gagccaaaaa gtcatatact tggtcatgat actgctgatt     960
gccccggcat acagcatcag gtgcatagga gtcagcaata gggactttgt ggaaggtatg    1020
tcaggtggga cttgggttga tgttgtcttg gaacatggaa gttgtgtcac cgcaatgcga    1080
caggacaaac cgactgtcga catagagctg gttacaacaa cagtcagcaa catggcggag    1140
gtaagatcct actgctatga ggcatcaata tcagacatgg cttcggacag ccgctgccca    1200
acacaaggtg aagcctacct tgacaagcaa tcagacactc aatatgtttg caaaagaacg    1260
ttagtggaca gaggctgggg aaatggatgt ggacttttg gcaaagggag tctggtgaca    1320
tgcgctaagt ttgcatgctc caagaaaatg accgggaaga gcatccagcc agagaatctg    1380
gagtaccgga taatgctgtc agttcatgc tcccagcaca gtgggatgct cgttaatgac    1440
acaggacatg aaactgatga gaatagacg aaggttgaga taacgcccaa tccaccaga    1500
gccgaagcca cctgggggg ttttggaagc ctaggacttg attgtgaacc gagggacagg    1560
cttgactttt cagatttgta ttacttgact atgaataaca gcactggtt ggctcacaag    1620
gagtggttcc acgacattcc attaccttgg cacgctgggg cagccaccgg aactccacac    1680
tggaacaaca agaagcact ggtagagttc aaggacgcac atgccaaaag gcaaactgtc    1740
gtggttctag ggagtcaaga aggagcagtt cacacgcccc ttgctggagc tctgaggct    1800
gagatgagtg gtcaaagggt aagctgtcc tctgccact tgaaatgtcg tctgaaaatg    1860
gataaactta gattgaaggg cgtgtcatac tccttgtgta ccgcagcgtt cacattcacc    1920
aagatcccgg ctgaaacagt ggacgggaca gtcacagtgg agggacagta cggagggaca    1980
gatggacctt gcaaggttcc agctcagatg gcggtggaca tgcagactct gaccccagtt    2040
gggaggttga taaccgctaa ccccgtaatc actgaaagca ctgagaactc taagatgatg    2100
ctggaacttg atccaccatt tggggactct tacattgtca ggagtcgg ggagaagaag    2160
atcacccacc actggcacag gagtggcagc accattggaa aagcatttga agccactgtg    2220
agaggtgcca agagaatggc agtcttggga gacacagcct gggactttgg atcagttgga    2280
ggcgctctca actcattggg caagggcatc atcaaatta ttggagcagc tttcaaatca    2340
ttgtttggag gaatgtcctg gttctcacaa attctcattg gacgttgct gatgtggttg    2400
ggtctgaaca caaagaatgg atctatttcc ctatgtgta tggcccttag gggagtgttg    2460
atcttcttat ccacagcgt ctcaggtggt gtgggtgct cggtggactt ctcaaagaag    2520
gagacgagat gcggtacagg ggtgttcgtc tataacgatg ttgaagcctg agggacagg    2580
tacaagtacc atcctgactc cccccgtaga ttggcagcag cagtcaagca agcctgggaa    2640
gatggtatct gcgggatctc ctctgttca agaatgaaa acatcatgtg gagatcagta    2700
gaaggggagc tcaacgcaat cctggaagag aatggagttc aactgacggt cgttgtggga    2760
```

```
tctgtaaaaa accccatgtg gagaggtcca cagagattgc ccgtgcctgt gaacgagctg    2820
ccccacggct ggaaggcttg ggggaaatcg tacttcgtca gagcagcaaa gacaaataac    2880
agctttgtcg tggatggtga cacactgaag gaatgcccac tcaaacatag agcatggaac    2940
agctttcttg tggaggatca tgggttcggg gtatttcaca ctagtgtctg gctcaaggtt    3000
agagaagact attggttaga gtgtgatcca gccgttattg gaacagctgt taagggaaag    3060
gaggctgtac acagtgatct aggctactgg attgagagtg agaagaatga cacatggtgg    3120
ctgaagaggg cccatctgat cgagatgaaa acatgtgaat ggccaaagtc ccacacattg    3180
tggacagatg gaatagaaga gagtgatctg atcatacccc agtctttagc tgggccactc    3240
agccatcaca atgccagaga gggctacagg acccaaatga aagggccatg gcacagtgaa    3300
gagcttgaaa ttcggtttga ggaatgccca ggcactaagg tccacgtgga ggaaacatgt    3360
ggaacaagag gaccatctct gagatcaacc actgcaagcg gaagggtgat cgaggaatgg    3420
tgctccaggg agtgcacaat gcccccactg tccttccagg ctaaagatgg ctgttggtat    3480
ggaatggaga taaggcccag gaaagaacca gaaagcaact tagtaaggtc aatggtgact    3540
gcaggatcaa ctgatcacat ggatcacttc tcccttgtga tgcttgtgat tctgctcatg    3600
gtgcaggaag ggctgaagaa gagaatgacc acaaagatca tcataagcac atcaatggca    3660
gtgctggtag ctatgatcct gggaggattt tcaatgagtg acctggctaa gcttgcaatt    3720
ttgatgggtg ccaccttcgc ggaaatgaac actggaggag atgtagctca tctggcgctg    3780
atagcggcat tcaaagtcag accagcgttg tcggtatctt tcatcttcag agctaattgg    3840
acaccccgtg aaagcatgct gctggccttg gcctcgtgtc ttttgcaaac tgcgatctcc    3900
gccttggaag gcgacctgat ggttctcatc aatggttttg ctttggcctg gttggcaata    3960
cgagcgatgg ttgttccacg cactgataac atcaccttag caatcctggc tgctctgaca    4020
ccactggccc ggggcacact gcttgtggcg tggagacagg gcctgctac ttgcgggggg    4080
tttatgctcc tctctctgaa gggaaaaggc agtgtgaaga agaacttacc atttgtcatg    4140
gccctggac taaccgctgt gaggctggtc gaccccatca acgtggtggg actgctgttg    4200
ctcacaagga gtgggaagcg gagctggccc cctagcgaag tactcacagc tgttggcctg    4260
atatgcgcat tggctggagg gttcgccaag gcagatatag agatgggtgg gcccatggcc    4320
gcggtcggtc tgctaattgt cagttacgtg gtctcaggaa agagtgtgga catgtacatt    4380
gaaagagcag gtgacatcac atgggaaaaa gatgcggaag tcactggaaa cagtcccgg    4440
ctcgatgtgg cgctagatga gagtggtgat ttctccctgg tggaggatga cggtcccccc    4500
atgagagaa tcatactcaa ggtggtcctg atgaccatct gtggcatgaa cccaataggc    4560
atacccttg cagctggagc gtggtacgta tacgtgaaga ctggaaaaag gagtggtgct    4620
ctatgggatg tgcctgctcc caaggaagta aaaaaggggg agaccacaga tggagtgtac    4680
agagtaatga ctcgcagact gctaggttca acacaagttg gagtgggagt tatgcaagag    4740
ggggtctttc acactatgtg gcacgtcaca aaaggatccg cgctgagaag cggtgaaggg    4800
agacttgatc catactgggg agatgtcaag caggatctgg tgtcatactg tggtccatgg    4860
aagctagatg ccgcctggga cgggcacagc gaggtcagc tcttggccgt gccccccgga    4920
gagagagcga ggaacatcca gactctgccc ggaatattta agacaaagga tgggacatt    4980
ggagcggttg cactggatta cccagcagga acttcaggat ctccaatcct agacaagtgt    5040
gggagagtga taggactttta tggcaatggg gtcgtgatca aaatgggag ttatgttagt    5100
gccatcaccc aagggaggag ggaggaagag actcctgttg agtgcttcga gccttcgatg    5160
ctgaagaaga agcagctaac tgtcttagac ttgcatcctg gagctgggaa aaccaggaga    5220
gttcttcctg aaatagtccg tgaagccata aaaacaagac tccgtactgt gatcttggct    5280
ccaaccaggg ttgtcgctgc tgaaatggaa gaggcccta agtgcgttat                5340
atgacaacag cagtcaatgt cacccactct ggaacagaaa tcgtcgactt aatgtgccat    5400
gccaccttca cttcacgtct actacagcca attagagtcc caactataa tctgtatatt    5460
atggatgagg cccacttcac agatcccctca agtatagcag caagaggata catttcaaca    5520
agggttgaga tgggcgaggc ggctgccatc ttcatgaccg ccacgccacc aggaacccgt    5580
gacgcatttc cggactccaa ctcaccaatt atggacaccg aagtggaagt cccagagaga    5640
gcctggagct caggctttga ttgggtgacg gagtattctg gaaaaacagt ttggtttgtt    5700
ccacgcgtga ggaacggcaa tgagatcgca gcttgtctga caaaggctgg aaaacgggtc    5760
atacagctca gcagaaagac ttttgacaca gagttccaga aaacaaaaca tcaagagtgg    5820
gactttgtcg tgacaactga catttcagag atgggcgcca actttaaagc tgaccgtgtc    5880
atagattcca ggagatgcct aaagccggtc atacttggtg gcgagagagt cattctggct    5940
ggacccatgc ctgtcacaca tgccagcgct gcccagagga ggggcgcat aggcaggaat    6000
cccaacaaac ctgagatga gtatctgtat ggaggtggtc gagcagagac tgacgaagac    6060
catgcacact ggcttgaagc aagaatgctc cttgacaata tttacctcca agatggcctc    6120
atagcctcgc tctatcgacc tgaggccgac aaagtagcag ccattgaggg agagttcaag    6180
cttaggacga agcaaaggaa gacctttgtg gaactcatga aaagaggaga tcttcctgtt    6240
tggctggcct atcaggttgc atctgccgga ataacctaca cagatagaag atggtgcttt    6300
gatgcacga ccaacaacac cataatgaa gacagtgtgc cggcagaggt gtggaccaga    6360
cacgagaga aaagagtgct caaaccgagg tggatgacg ccagagtttg ttcagatcat    6420
gcggccctga agtcattcaa ggagtttgcc gctgggaaaa gaggagcggc ttttggagtg    6480
atggaagccc tgggaacact gccaggacac atgacagaga gattccagga agccattgac    6540
aacctgctc tgctcatgcg ggcagaact ggaagcgaac cttacaaagc cgtcggggtg    6600
caattgccgg agaccctaga gaccattatg cttttgggt tgctgggaac agtctcgctg    6660
ggaatctttt tcgtcttgat gaggaacaag gcataggga agatgggctt tggaatggtg    6720
actcttgggg ccagcgcatg gctcatgtgg ctctcggaaa ttgagccagc cagaattgca    6780
tgtgtcctca ttgttgtgtt cctattgctg gtggtgctca tacctgagcc agaaaagcaa    6840
agatctcccc aggacaacca aatggccatc atcatcgta tagcactagg tcttctgtgg    6900
ttgattaccg ccaatgaact cggatggttg gagagaacaa agagtgacct aagccatcta    6960
atgggaagga gagaggaggg ggcaaccatg ggattctcaa tggacattga cctgcggcca    7020
gcctcagctt gggccatcta tgcaccttg acatctttca ttaccccagc cgtccaacat    7080
gcagtgacca cttcatacaa caactactcc ttaatgcgca tggccacgca agctggagtg    7140
ttgtttggga tgggcaaagg atgccattc acgcatggt actttgggct cgctgtagct    7200
atgataggtt gctactcaca attaacgccc ctgaccctaa tagtggccat cattttctct    7260
gtggcgcact acatgtactt gatcccaggg ctgcaggcag cagctgcgcg tgctgcccag    7320
aagagaacga cagctggcat catgaagaac cctgttgtgg agggaatagt ggtgactgac    7380
attgacacaa tgacaattga ccccccaagtg gagaaaaaga tgggacaggt gctactcatg    7440
gcagtagccg tctccagcgc catactgtcg aggaccgcct gggggtgggg ggaggctggg    7500
```

```
gccctgatca cagccgcaac ttccactttg tgggaaggct ctccgaacaa gtactggaac    7560
tcctctacag ccacctcact gtgtaacatt tttaggggaa gttacttggc tggagcttct    7620
ctaatctaca cagtaacaag aaacgctggc ttggtcaaga gacgtggggg tggaacagga    7680
gagaccctgg gagagaaatg gaaggccgc ttgaaccaga tgtcggccct ggagttctac    7740
tcctacaaaa agtcaggcat caccgaggtg tgcagagaag aggcccgccg cgcccctcaag   7800
gacggtgtgg caacgggagg ccatgctgtg tcccgaggaa gtgcaaagct gagatggttg    7860
gtggagcggg gatacctgca gcccatggaa aaggtcattg atcttggatg tggcagaggg    7920
ggctggagtt actacgccgc caccatccgc aaagttcaag aagtgaaagg atacacaaaa    7980
ggaggccctg gtcatgaaga acccgtgttg gtgcaaagct atgggtggaa catagtccgt    8040
cttaagagtg gggtggacgt cttcatatg gcggctgagc cgtgtgacac gttgctgtgt    8100
gacataggtg agtcatcatc tagtcctgaa gtggaagaag cacggacgct cagagtcctc    8160
tccatggtgg gggattggct tgaaaaaaga ccaggagcct tttgtataaa agtgttgtgc    8220
ccatacacca gcactatgat ggaaaccctg gagcgactgc agcgtaggta tggggaggaa   8280
ctggtcagag tgccactctc ccgcaactct acacatgaga tgtactgggt ctctggagcg    8340
aaaagcaaca ccataaaag tgtgtccacc acgagccagc tcctcttggg gcgcatggac    8400
gggcctagga ggccagtgaa atatgaggag gatgtgaatc tcggctctgg cacgcgggct    8460
gtggtaagct gcgctgaagc tcccaacatg aagatcattg gtaaccgcat tgaaaggatc    8520
cgcgctgaga aagcggaaac gtggttcttt gacgagaacc acccatatag gacatggcct    8580
taccatggaa gctatgatgc cgccacacaa gggtcagcgt cctctctaat aaacggggtt    8640
gtcaggctcc tgtcaaaacc ctgggatgtg tgactggag tcacaggaat agccatgacc    8700
gacaccacac cgtatggtca gcaaagagtt ttcaaggaaa agtgacacac tagggtgcca    8760
gaccccaag aaggcactcg tcaggtttatg agcatgtct cttcctggtt gtggaaagag    8820
ctaggcaaac acaaacgcc acgagtctgt accaagaag agttcatcaa caaggttcgt    8880
agcaatgcag cattaggggc aatatttgaa gaggaaaaag agtggaagac tgcagtggaa    8940
gctgtgaacg atccaaggtt ctgggctcta gtggacaagg aaagagagca ccacctgaga    9000
ggagagtgcc agagttgtgt gtacatcaca atgggaaaca gagaaagaa acaagggaa    9060
tttgaaaagg ccaagggcag ccgcgccatc tggtatatgt ggctaggggc tagatttcta    9120
gagttcgaag cccttggatt cttgaacgag atcactggaa tggggagaga gaactcagga    9180
ggtggtgttg aagggctggg attacaaaga ctcgatatg tcctagaaga gatgagtcgc    9240
ataccaggag gaaggatgta tgcagatgac actgctgctg gggacacccg catcagcagg    9300
tttgatctgg agaatgaagc tctaatcacc aaccaaatgg agaagggca cagggccttg    9360
gcattggcca taatcaagta cacataccaa aacaaagtgg taaaggtcct tagaccagct    9420
gaaaagggga agacagttat ggacattatt tcgagacaag accaagggg gagcggacaa    9480
gttgtcactt acgctctcaa cacatttacc aacctagtgg tgcaactcat tcggaatatg    9540
gaggctgagg aagttctaga gatgcaagac ttgtggctgc tgcggaggtc agagaaagtg    9600
accaactggt tgcagagcaa cggatgggat aggctcaaac gaatggcggt cagtggagat    9660
gattgcgttg tgaaaccaat tgatgatagg tttgcacatg ccctcaggtt cttgaatgat    9720
atgggaaaag ttaggaagga cacacaagag tggaaaccct caactggatg ggacaactgg    9780
gaagaagttc ccttctgctc ccaccacttc aacaagctcc atctcaagga cggagggtcc    9840
attgtggttc cctgccgcca ccaagatgaa ctgattggcc gggcccgcgt ctctccaggg    9900
gcgggatgga gcatccggga gactgcttgc ctagcaaaat catatgcgca aatgtggcag    9960
ctcctttatt tccacagaag ggacctccga ctgatggcca atgccatttg ttcatctgtg   10020
ccagttgact gggttccaac tgggagaact acctggtcaa tccatgaaa gggagaatgg   10080
atgaccactg aagacatgct tgtgcgctgg aacagagtgt ggattgagga aacgaccac    10140
atggaagaca gaccccagt cacgaaatgg acagacattc cctatttggg aaaagggaa    10200
gacttgtggt gtggatctct catagggcac agaccgcgca ccacctgggc tgagaacatt   10260
aaaaacacag tcaacatggt gcgcaggatc ataggtgatg aagaaaagta catggactac   10320
ctatccaccc aagttcgcta cttgggtgaa aagggtcta cacctggagt gctgtaagca   10380
ccaatcttaa tgttgtcagg cctgctagtc agccacagct tggggaaagc tgtgcagcct   10440
gtgaccccc caggagaagc tgggaaacca agcctatagt caggccgaga acgccatggc   10500
acggaagaag ccatgctgcc tgtgagcccc tcagaggaca ctgagtcaaa aaaccccacg   10560
cgcttggagg cgcaggatgg gaaaagaagg tggcgacctt ccccacccctt caatctgggg   10620
cctgaactgg agatcagctg tggatctcca gaagagggac tagtggttag aggaga        10676

SEQ ID NO: 11          moltype = DNA   length = 10807
FEATURE                Location/Qualifiers
source                 1..10807
                       mol_type = unassigned DNA
                       organism = Zika virus
SEQUENCE: 11
agttgttgat ctgtgtgagt cagactgcga cagttcgagt ctgaagcgag agctaacaac      60
agtatcaaca ggtttaattt ggatttggaa acgagagttt ctggtcatga aaacccaaa     120
gaagaaatcc ggaggattcc ggattgtcaa tatgctaaaa cgcggagtag cccgtgtaaa     180
cccctctggg ggtttgaaga ggttgccagc cggacttctg gacccatcag                240
aatggttttg gcgatactag ccttttttgag atttacagca atcaagccat cactgggcct     300
tatcaacaga tggggttccg tggggaaaaa agaggctatg gaaataataa agaagttcaa     360
gaaagatctt gctgccatgt tgagaataat caatgctagg aaagagagga gagacgtgg     420
cgcagacacc agcatcggaa tcattggcct cctgctgact acagatggg cagcagagat     480
cactagacgc gggagtgcac actacatgta cttggatagg agcgatgccg ggaaggccan     540
ttcgtttgct accacattgg gagtgaacaa gtgccacgta cagatcatgg acctcggca     600
catgtgtgac gccaccatga gttatgagtg ccctatgctg gatgagggag tggaaccaga     660
tgatgtcgat tgctggtgca acacgacatc aacttgggtt gtgtacgaa cctgtcatca     720
caaaaaggt gaggcacggc gatctagaag agccgtgacg ctcccttctc actctacaag     780
gaagttgcaa acgcggtcgc agatcgtgtt agaatacaga agcactttgat                840
caaggttgaa aactggatat tcaggaaccc cgggttgcg ctagtggccg ttgccattgc     900
ctggcttttg ggaagctcga cgagccaaaa agtcatatac ttggtcatga tactgctgat     960
tgccccggca tacagtatca ggtgcattgg agtcagcaat agagacttcg tggagggcat    1020
gtcaggtggg acctggggttg atgttgtctt ggaacatgga ggctgcgtta ccgtgatggc    1080
acaggacaag ccaacagttg acatagagtt ggtcacgacg acgttagta acatggccga    1140
```

```
ggtaagatcc tattgctacg aggcatcgat atcggacatg gcttcggaca gtcgttgccc   1200
aacacaaggt gaagcctacc ttgacaagca atcagacact caatatgtct gcaaaagaac   1260
attagtggac agaggttggg gaaacggttg tggactttt ggcaaaggga gcttggtgac    1320
atgtgccaag tttacgtgtt ctaagaagat gaccgggaag agcattcaac cggaaaatct   1380
ggagtatcgg ataatgctat cagtgcatgg ctcccagcat agcgggatga ctgtcaatga   1440
tataggatat gaaactgacg aaaatagagc gaaagtcgag gttacgccta attcaccaag   1500
agcggaagca accttgggag gctttggaag cttaggactt gactgtgaac caaggacagg   1560
ccttgactt tcagatctgt attacctgac catgaacaat aagcattggt tggtgcacaa    1620
agagtggttt catgacatcc cattgccttg gcatgctggg gcagacactg gaactccaca   1680
ctggaacaac aaagaggcat tggtagaatt caaggatgcc cacgccaaga ggcaaaccgt   1740
cgtcgttctg gggagccagg aaggagccgt tcacacggct ctcgctggag ctctagaggc   1800
tgagatggat ggtgcaaagg gaaagctgtt ctctggccat ttgaaatgcc gcctaaaaat   1860
ggacaagctt agattgaagg gcgtgtcata ttccttgtgc actgcggcat tcacattcac   1920
caaggtccca gctgaaacac tgcatgaac agtcacagtg gaggtgcagt atgcagggac    1980
agatggaccc tgcaagatcc cagtccagat ggcggtggaa atgcagaccc tgaccccagt   2040
tggaaggctg ataaccgcca accccgtgat tactgaaagc actgagaact caaagatgat   2100
gttggagctt gacccaccat ttggggattc ttacattgtc ataggagttg gggacaagaa   2160
aatcacccac cactggcata ggagtggtag caccatcgga aagcatttg aggccactgt    2220
gagaggcgcc aagagaatgg cagtcctggg ggatacagcc tgggacttcg gatcagtcgg   2280
gggtgtgttc aactcactgg gtaagggcat tcaccagatt tttggagcag ccttcaaatc   2340
actgtttgga ggaatgtcct ggttctcaca gatcctcata ggcacgctgc tagtgtggtt   2400
aggtttgaac acaaagaatg gatctatctc cctcacatgc cttgccctgg gggagtgat    2460
gatcttcctc tccacggctg tttctgctga cgtggggtgc tcagtggact tctcaaaaaa   2520
ggaaacgaga tgtggcacgg gggtattcat ctataatgat gttgaagcct ggagggaccg   2580
gtacaagtac catcctgact ccccccgcag attggcagca gcagtcaagc aggcctggga   2640
agagggatc tgtgggatct catccgtttc aagaatgaaa aacatcatgt gcgaaatcagt    2700
agaagggagg ctcaatgcta cctagaggga aatggagtt caactgacag ttgttgtggg    2760
atctgtaaaa aaccccatgt ggagaggtcc acaaagattg ccagtgcctg tgaatgagct   2820
gccccatggc tggaaagcct gggggaaatc gtattttgtt agggcggcaa agaccaacaa   2880
cagttttgtt gtcgacggtg acacactgga ggaatgtccg cttgagcaca gagcatggaa   2940
tagttttctt gtggaggatc acgggtttgg agtcttccac accagtgtct ggctttaaggt  3000
cagagaagat tactcattag aatgtgaccc agccgtcata ggaacagctg ttaagggaag   3060
ggaggccgcg cacagtgatc tgggctattg gattgaaagt gaaaagaatg acacatggag   3120
gctgaagagg gcccacctga ttgagatgaa aacatgtgaa tggccaaagt ctcacacatt   3180
gtggacagat ggagtagaag aaaagtgatct tatcatacccc aagtctttag ctggtccact  3240
cagccaccac aacaccagag agggttacag aacccaagtg aaagggccat ggcacagtga   3300
agagcttgaa atccggtttg aggaatgtcc aggcaccaag gttacgtgg aggagacatg    3360
cggaactaga ggaccatctc tgagatcaac tactgcaagt ggaagggtca ttgaggaatg   3420
gtgctgtagg gaatgcacaa tgcccccact atcgtttcga gcaaaaagacg gctgctggta   3480
tggaatggag ataaggccca ggaaagaacc agagagcaac ttagtgaggt caatggtgac   3540
agcggggtca accgatcata tggaccactt ctctcttgga gtgcttgtga ttctactcat   3600
ggtgcaggag gggttgaaga agagaatgac cacaaagatc atcatgagca catcaatggc   3660
agtgctggta gtcatgatct tggaggatt ttcaatgagt gacctggcca agcttgtgat    3720
cctgatgggt gctactttcg cagaaatgaa cactggagga gatgtagctc acttggcatt   3780
ggtagcggca tttaaagtca gaccagcctt gctggtctcc ttcattttca gagccaattg   3840
gacacccgt gagagcatgc tgctagccct ggcttcgtgt cttctgcaaa ctgcgatctc     3900
tgctcttgaa ggtgacttga tggtcctcat taatggattt ggcttggct ggttggcaat    3960
tcgagcaatg gccgtgccac gcactgacaa catcgctcta ccaatcttgg ctgctctaac   4020
accactagct cgaggcacac tgctcgtggc atggagagcg gcctggcta cttgtggagg    4080
gatcatgctc ctctccctga agggaaagg tagtgtgaag aagaacctgc catttgtcat    4140
ggcctggga ttgacagctg tgagggtagt agacccatt aatgtggtag gactactgtt     4200
actcacaagg agtgggaagc ggagctggcc ccctagtgaa gttctcacag ccgttgcct    4260
gatatgtgca ctgccggag ggttttgccaa ggcagacatt gagatggctg gacccatggc   4320
tgcagtaggc ttgctaattg tcagctatgt ggtctcggga aagagtgtgg acatgtacat   4380
tgaaagagca ggtgacatca catgggaaaa ggacgcggaa gtcactggaa acagtcctcg   4440
gcttgacgtg gcactggatg agagtggtga tttctcctg gtagaggaag atggtccacc    4500
catgagagag atcatactta aggtggtcct gatggcatc tgtggcatga cccaatagc     4560
tatccttt gctgcaggag cgtggtatgt gtatgtgaag actgggaaaa ggagtggcgc     4620
cctctgggac gtgcctgctc ccaaagaagt gaagaaagga gagaccacag atggagtgta   4680
cagagtgatg actcgcgac tgctaggttc aacacaggtt ggagtgggag tcatgcaaga   4740
gggagtcttc cacaccatgt ggcacgttac aaaaggagcc gcactgagga gcggtgaggg   4800
aagacttgat ccatactggg gggatgtcaa gcaggacttg gtgtcatact gtgggcctta   4860
gaagttggat gcagcttggg atggactcag cgaggtacga cttttggccg tacctcccgg   4920
agagaggcc agaaacattc agaccctgcc tggaatattc aagacaaagg acgggatgcat  4980
cggagcagtt gctctggact accctgcagg gacctcagga tctccgatcc tagacaaatg   5040
tggaagagtg ataggactct atggcaatgg ggttgtgatc aagaatgaa gctatgttag    5100
tgctataacc cagggaaaga gggaggagga gactccggtt gaatgtttcg aaccctcgat   5160
gctgaagaag aagcagcctaa ctgtcttgga tctgcatcca ggaccggaa aaaccaggag   5220
agttcttcct gaaatagtcc gtgaagccat aaaaagaga ctccgacag tgatcttggc    5280
accaactagg gttgtcgctg ctgagatgga ggaggccttg agaggacttc cggtgcgtta   5340
catgacaaca gcagtcaacg tcacccattc gggacagaa atcgttgatt tgatgtgcca    5400
tgccactttc acttcacgct tactacaacc catcagagtc cctaattaca atctctacat   5460
catggatgaa gcccacttca cagacccctc aagtatagct gcaagaggat atatatcaac   5520
aaggggtgaa atgggcgagg cggctgccat ttttatgact gccaccaccc caggaaccg    5580
tgatgcgtttt cctgactcta actcaccaat catggacaca gaagtgcaag tcccagagag   5640
agcctgagc tcaggctttg attgggtgac agaccattct gggaaacag tttgttcgt     5700
tccaagcgtg agaacggaa atgaaatcgc agcctgtctg acaaaggctg aaagcgggt     5760
catacagctc agcaggaaga cttttgagac agaatttcag aaaacaaaaa atcaagagtg   5820
ggacttttgtc ataacaactg acatctcaga gatgggcgcc aacttcaagg ctgaccgggt  5880
```

```
catagactct aggagatgcc taaaaccagt catacttgat ggtgagagag tcatcttggc   5940
tgggcccatg cctgtcacgc atgctagtgc tgctcagagg agaggacgta taggcaggaa   6000
ccctaacaaa cctggagatg agtacatgta tggaggtggg tgtgcagaga ctgatgaagg   6060
ccatgcacac tggcttgaag caagaatgct tcttgacaac atctacctcc aggatggcct   6120
catagcctcg ctctatcggc ctgaggccga taaggtagcc gccattgagg gagagtttaa   6180
gctgaggaca gagcaaagga agaccttcgt ggaactcatg aagagaggag accttcccgt   6240
ctggctagcc tatcaggttg catctgccgg aataacttac acagacagaa gatggtgctt   6300
tgatggcaca accaacaaca ccataatgga agacagcgta ccagcagagg tgtggacaaa   6360
gtatggagag aagagagtgc tcaaaccgag atggatggat gctagggtct gttcagacca   6420
tgcggccctg aagtcgttca aagaattcgc cgctggaaaa agaggagcgg ctttgggagt   6480
aatggaggcc ctgggaacac tgccaggaca catgacagag aggtttcagg aagccattga   6540
caacctcgcc gtgctcatgc gagcagagac tggaagcagg ccttataagg cagcggcagc   6600
ccaactgccg gagaccctag agaccattat gctcttaggt ttgctgggaa cagtttcact   6660
ggggatcttc ttcgtcttga tgcggaataa gggcatcggg aagtaggct ttggaatggt   6720
aaccctgggg gccagtgcat ggctcatgtg gctttcggaa attgaaccag ccagaattgc   6780
atgtgtcctc attgttgtgt ttttattact ggtggtgctc atacccgagc cagagaagca   6840
aagatctccc caagataacc agatggcaat tatcatcatg gtggcagtgg gccttctagg   6900
tttgataact gcaaacgaac ttggatggct ggaaagaaca aaaaatgaca tagctcatct   6960
aatgggaagg agagaagaag gagcaaccat gggattctca atggacattg atctgcggcc   7020
agcctccgcc tgggctatct atgccgcatt gacaactctc atcaccccag ctgtccaaca   7080
tgcggtaacc acttcataca caactactc cttaatggcg atgccacac aagctggagt   7140
gctgttttggc atgggcaaag ggatgccatt ttatgcatgg gaccttggag tcccgctgct   7200
aatgatgggt tgctattcac aattaacacc cctgactctg atagtagcta tcattctgct   7260
tgtggcgcac tacatgtact tgatcccagg cctacaagcg gcagcagcgc gtgctgccca   7320
gaaaaggaca gcagctggca tcatgaagaa tcccgttgtg gatggaatag tggtaactga   7380
cattgacaca atgacaatag ccccccaggt ggagaagaag atgggaacag tgttactcat   7440
agcagtagcc atctccagtg ctgtgctgct gcgaccgcc tggggatggg gggaggctgg   7500
agctctgatc acagcagcga cctccaccttgtgggaaggc tctccaaaca aatactggaa   7560
ctcctctaca gccacctcac tgtgcaacat cttcagagga agctatctgg caggagcttc   7620
ccttatctat acagtgacga gaaacgctgg cctggttaag agacgtggag gtgggacggg   7680
agagactctg ggagagaagt ggaaagctcg tctgaatcag atgtcggccc tggagttcta   7740
ctcttataaa aagtcaggta tcactgaagt gtgtagagag gaggctcgcc gtgccctcaa   7800
ggatggagtg gccacaggag gacatgccgt atcccgggga agtgcaaagc tcagatggtt   7860
ggtggagaga ggatatctgc agccctatgg gaaggttgtt gacctcggat gtggcagagg   7920
gggctggagc tattatgccg ccaccatccg caaagtgcag gaggtgagag gatacacaaa   7980
gggaggtccc ggtcatgaag aacccatgct ggtgcaaagc tatgggtgga acatagttcg   8040
tctcaagagt ggagtggacg tcttccacat ggcggctgag ccgtgtgaca ctctgctgtg   8100
tgacataggt gagtcatcat ctagtcctga agtggaagag acacgaacac tcagagtgct   8160
ctctatgtg ggggactggc ttgaaaaaag accaggggcc ttctgtataa aggtgctgtg   8220
cccatacacc agcactatga tggaaaccat ggagcgactg caacgtaggc atgggggagg   8280
attagtcaga gtgccattgt ctcgcaactc cacacatgag atgtactggg tctctgggc   8340
aaaagagcaac atcataaaaa gtgtgtccac cacaagtcag ctcctcctgg gacgcatgga   8400
tggcccccagg aggccagtga aatatgagga ggatgtgaac ctcggtcgg gtacacgagg   8460
tgtggcaagc tgtgctgagg ctcctaacat gaaaatcatc ggcaggcgca ttgagagaat   8520
ccgcaatgaa catgcagaaa catggtttct tgatgaaaac cacccataca ggacatgggc   8580
ctaccatggg agctacgaag ccccccacgca aggatcagcc tcttccctcg tgaacggggt   8640
tgttagactc ctgtcaaagc cttgggacgt ggtgactgga gttacaggaa tagccatgac   8700
tgacaccaca ccatacgcc aacaaagagt cttcaaagaa aaagtggaca ccagggtgcc   8760
agatccccaa gaaggcactc gccaggtaat gaacatagtc tcttcctggc tgtgaagga   8820
gctggggaaa cgcaagcggc cacgcgtctg caccaaagaa gagtttatca acaaggtgcg   8880
cagcaatgca gcactgggag caatatttga agaggaaaa gaatgaaga cggctgtgga   8940
agctgtgaat gatccaaggt tttgggccct agtggatagg gagagagaac caccctgag   9000
aggagagtgt cacagctgtg tgtacaacat gatgggaaaa agagaaaaga agcaaggaga   9060
gttcgggaaa gcaaaaggta gccgcgccat ctggtacatg tggttgggag ccagattctt   9120
ggagttttgaa gcccttggat tcttgaacga ggaccattgg atgggaaaga aaactcagg   9180
aggtggagtc gaagggttag gattgcaaag acttggatac attctagaag aaatgaatcg   9240
ggcaccagga ggaaagatgt acgcagatga cactgctggc tgggacaccc gcattagtaa   9300
gtttgatctg gagaatgaag ctctgattac caaccaaatg gaggaagggc acagaactct   9360
ggcgttggcc gtgattaaat acacatacca aaacaaagtg gtgaaggttc tcagaccagc   9420
tgaaaaggga agaaaacagtta tggacatcat ttcaagacaa gaccagagga gggactgaca   9480
agttgtcact tatgctctca acacattcac caacttggtg gtgcagctta tccggaacat   9540
ggaagctgag gaagtgttag agatgcaaga cttatggttg ttgaggaagc cagagaaagt   9600
gaccagatgg ttgcagagca atggatggga tagactcaaa cgaatggcgg tcagtggaga   9660
tgactgcgtt gtgaagccaa tcgatgatag gtttgcacat gccctcaggt tcttgaattga   9720
catgggaaaa gttaggaaag acacacagga gtgaaaccc tcgactggat ggagcaattg   9780
ggaagaagtc ccgttctgct cccaccacctt caacaagctg tacctcaagg atgggagatc   9840
cattgtggtc ccttgccgcc accaagatga actgattggc cgagctcgcg tctcaccagg   9900
ggcaggatgg agcatccggg agactgcctg tcttgcaaaa tcatatgcgc agatgtggca   9960
gctcctttat ttccacagaa gagacttccg actgatgact aatgccattt gctcggctgt  10020
gccagttgac tgggtaccaa ctgggagaac cacctggtca atccatgaa gggagaatg  10080
gatgaccact gaggacatgc tcatggtgtg aatagagtg tggattgagg agacgacca  10140
tatgaggac aagactcctg taacaaaatg gacagacatt ccctatctag aaaagggga  10200
ggacttatgg tgtggatccc ttataggcca cagacccgc accacttggg ctgaaaacat  10260
caaagacaa gtcaacatgg tgcgcagat cataggtgat gaagaaaagt acatggacta  10320
tctatccacc caagtccgct acttgggtga ggaagggtcc acaccggag tgttgtaagc  10380
accaatttta gtgttgtcag gcctgctagt cagccacagt ttggggaaag ctgtgcagcc  10440
tgtaaccccc ccaggagaag ctgggaaacc aagctcatag tcaggccgag aacgccatgg  10500
cacggaagaa gccatgctgc ctgtgagccc tcagaggac actgagtcaa aaaacccac  10560
gcgcttgaa gcgcaggatg ggaaaagaag gtggcgacct tccccaccct tcaatctggg  10620
```

```
gcctgaactg gagactagct gtgaatctcc agcagaggga ctagtggtta gaggagaccc    10680
cccggaaaac gcaaaacagc atattgacgc tgggaaagac cagagactcc atgagtttcc    10740
accacgctgg ccgccaggca cagatcgccg aacagcggcg gccggtgtgg ggaaatccat    10800
ggtttct                                                              10807
```

| SEQ ID NO: 12 | moltype = DNA   length = 10794 |
|---|---|
| FEATURE | Location/Qualifiers |
| source | 1..10794 |
| | mol_type = unassigned DNA |
| | organism = Zika virus |

SEQUENCE: 12

```
agttgttgat ctgtgtgagt cagactgcga cagttcgagt ctgaagcgag agctaacaac      60
agtatcaaca ggtttaattt ggatttggaa acgagagttt ctggtcatga aaaacccaa     120
agaagaaatc cggaggatcc ggattgtcaa tatgctaaaa cgcggagtag cccgtgtaaa     180
cccccttgga ggtttaagga ggttgccagc cggacttctg ctgggtcatg gacccatcag     240
aatggttttg gcgatactag cctttttgag atttacagca atcaagccat cactgggcct     300
tatcaacaga tggggttccg tggggaaaaa agaggctatg gaaataataa agaagttcaa     360
gaaagatctt gctgccatgt tgagaataat caatgctagg aaagagagga agacgtgg      420
cgcagacacc agcatcggaa tcattggcct cctgctgact acagccatgg cagcagagat     480
cactagacgc gggagtgcat actacatgta cttggatagg agcgatgccg ggaaggccat     540
ttcgtttgct accacattgg gagtgaacaa gtgccacgta cagatcatgg acctcgggca     600
catgtgtgac gccaccatga gttatgagtg ccctatgctg gatgagggag tggaaccaga     660
tgatgtcgat tgctggtgca acacgacatc aacttgggtt gtgtacggaa cctgtcatca     720
caaaaaggt gaggcacggc gatctagaag agccgtgacg ctcccttctc actctacaag     780
gaagttgcaa acgcggtcgc agacctggtt agaatcaaga gaatacacga agcacttgat     840
caaggttgaa aactggatat tcaggaaccc cgggtttgcc ctagtggccg ttgccattgc     900
ctggcttttg ggaagctcga cgagccaaaa agtcatatac ttggtcatga tactgctgat     960
tgccccggca tacagtatca ggtgcattgg agtcagcaat agagacttcg tggagggcat    1020
gtcaggtggg acctggggtg atgttgtctt ggaacatgga ggctgcgtta ccgtgatggc    1080
acaggacaag ccaacagtcg acatagagtt ggtcacgacg acggttagta acatggccga    1140
ggtaagatcc tattgctacg aggcatcgat atcggacatg gcttcggaca gtcgttgccc    1200
aacacaaggt gaagcctacc ttgacaagca atcagacact caatatgtct gcaaaagaac    1260
attagtggac agaggttggg gaaacggttg tggactttt ggcaagggga gcttggtgac    1320
atgtgccaag tttacgtgtt ctaagaagat gaccgggaag agcattcaac ggaaaatct    1380
ggagtatcgg ataatgctat cagtgcatgg ctcccagcat agcgggatga ttggatatga    1440
aactgacgaa gatagagcga agtcgaggt tacgcctaat tcaccaagag cggaagcaac    1500
cttgggaggc tttggaagct taggacttga ctgtgaacca aggacaggcc ttgactttc    1560
agatctgtat tacctgacca tgaacaataa gcattggttg gtgcacaaag agtggtttca    1620
tgcatccca ttgccttggc atgctgggc agacaccgga actccacact ggaacaacaa    1680
agaggcattg gtagaattca aggatgccca cgccaagagg caaaccgtcg tcgttctggg    1740
gagccaggaa ggagccgttc acacggctct cgctggagct ctagaggctg agatggatgg    1800
tgcaaaggga aggctgttct ctggccattt gaaatgccgc ctaaaatgg acaagcttag    1860
attgaagggc gtgtcatatt ccttgtgcac tgcggcattc acattcacca aggtcccagc    1920
tgaaacactg catggaacag tcacagtgga ggtgcagtat gcagggacag atggaccctg    1980
caagatccca gtccagatgg cggtggacat gcagaccctg acccagttg aaggctgat    2040
aaccgccaac cccgtgatta ctgaaagcac tgagaactca aagatgatgt tggagcttga    2100
cccaccattt ggggattctt acattgtcat aggagttggg gacaagaaaa tcaccccaca    2160
ctggcatagg agtggtagca ccatcggaaa ggcattgag gccactgtga gaggcgccaa    2220
gagaatggca gtcctgggg atacagccct ggacttcgga tcagtcgggg gtgtgttcaa    2280
ctcactgggt aagggcattc accagatttt tggagcagcc ttcaaatcac tgtttggagg    2340
aatgtcctgg ttctcacaga tcctcatagg cacgctgcta gtgtggttag gtttgaacac    2400
aaagaatgga tctatctccc tcacatgctt ggccctgggg ggagtgatga tcttcctctc    2460
cacggctgtt tctgctgacg tggggtgctc agtggacttc tcaaaaaagg aaacgagatg    2520
tggcacgggg gtattcatct ataatgatgt tgaagcctgg agggaccggt acaagtacca    2580
tcctgactcc ccccgcagat tggcagcagc agtcaagcag gcctgggaag aggggatctg    2640
tgggatctca tccgtttcaa gaatggaaaa catcatgtgg aaatcagtag aaggggagct    2700
caatgctatc ctagaggaga tggagttca actgacagtt gttgtgggat ctgtaaaaaa    2760
ccccatgtgg agaggtccac aaagattgcc agtgcctgtg aatgagctgc cccatgctgt    2820
gaaagcctgg gggaaatcgt attttgttag ggcggcaaag accaacaaca gttttgttgt    2880
cgacggtgac acactgaagg aatgtccgct tgagcacaga gcatggaata gttttcttgt    2940
ggaggatcac gggtttggag tcttccacac cagtgtctgg cttaaggtca gagaagatta    3000
ctcattagaa tgtgacccag ccgtcatagg aacagctgtt aagggaaggg aggccgcgca    3060
cagtgatctg ggctattgga ttgaaaagtga aagaatgac acatggaggc tgaagagggc    3120
ccacctgatt gagatgaaaa catgtgaatg gccaaagtct cacacattgt ggactgatgg    3180
agtagaagaa agtgatctta tcataccaa gtctttagct ggtccactca gccaccacaa    3240
caccagagag ggttacagaa cccaagtgaa agggccatgg cacagtgaag gcttgaaat    3300
ccggtttgag gaatgtccag gcaccaaggt tacgtggag agacatgcg gaactagagg    3360
accatctctg agatcaacta ctgccagtgg aagggtcatt gaggaatgat gctgtaggga    3420
atgcacaatg ccccccactat cgtttcgagc aaaagacggc tgctggtatg gaatggaat    3480
aaggcccagg aaagaaccag agagcaactt agtgaggtca atggtgacag cggggtcaac    3540
cgatcatatg gaccacttct ctctggagt gcttgtgatt ctactcatgg tgcaggaggg    3600
gttgaagaag agaatgacca caaagatcat catgagcaca tcaatggcag tgctggtagt    3660
catgatcttg ggaggatttt caatgagtga cctggccaag cttgtgatcc tgatgggtgc    3720
tactttgca gaaatgaaca ctggaggaga tgtcgcattg tagccattt    3780
taaagtcaga ccagccttgc tggtctcctt catttcaga gccaattgga caccccgtga    3840
gagcatgctg ctagccctgg cttcgtgtct tctgcaaact gcgatcctg ctcttgaagg    3900
tgacttgatg gtcctcatta tggatttgc tttggcctgg ttggcaattc gagcaatggc    3960
cgtgccacgc actgacaaca tcgctctacc aatcttggct gctctaacac cactagctcg    4020
aggcacactg ctcgtggcat ggagagcggg cctggcatct tgtggaggga tcatgctcct    4080
```

```
ctccctgaaa gggaaaggta gtgtgaagaa gaacctgcca tttgtcatgg ccctgggatt   4140
gacagctgtg agggtagtag acccctattaa tgtggtagga ctactgttac tcacaaggag   4200
tgggaagcgg agctggcccc ctagtgaagt tctcacagcc gttggcctga tatgtgcact   4260
ggccggaggg tttgccaagg cagacattga gatggctgga cccatggctg cagtaggctt   4320
gctaattgtc agctatgtgg tctcgggaaa gagtgtggac atgtacattg aaagagcagg   4380
tgacatcaca tgggaaaagg acgcggaagt cactggaaac agtcctcggc ttgacgtggc   4440
actggatgag agtggtgact tctccttggt agaggaagat ggtccaccca tgagagagat   4500
catactcaag gtggtcctga tggccatctg tggcatgaac ccaatagcta tacctttgc    4560
tgcaggagcg tggtatgtgt atgtgaagac tgggaaaagg agtggcgccc tctgggacgt   4620
gcctgctccc aaagaagtga agaaaggaga gaccacagat ggagtgtaca gagtgatgac   4680
tcgcagactg ctaggttcaa cacaggttgg agtgggagtc atgaagagg gagtcttcca    4740
caccatgtgg cacgttacaa aaggagccgc actgaggagc ggtgagggaa gacttgatcc   4800
atactgggg gatgtcaagc aggacttggt gtcatactgt gggccttgga agttggatgc    4860
agcttgggat ggactcagcg aggtacagct tttggccgta cctcccggag agagggccag   4920
aaacattcag accctgcctg gaatattcaa gacaaaggac ggggacatcg gagcagttgc    4980
tctggactac cctgcaggga cctcaggatc tccgatccta gacaaatgtg gaagagtgat   5040
aggactctat ggcaatgggg ttgtgatcaa gaatggaagc tatgttagtg ctataaccca   5100
gggaaagagg gaggaggaa ctccggttga atgtttcgaa ccctcgatgc tgaagaagaa    5160
gcagctaact gtcttggatc tgcatccagg agccggaaaa accaggagag ttcttcctga   5220
aatagtccgt gaagccataa aaagagact ccggacagtg atcttggcac caactagggt    5280
tgtcgctgct gagatggagg aggccttgag aggacttccg gtgcgttaca tgacaacagc   5340
agtcaacgtc accccattctg ggacagaaat cgttgatttg atgtgccatg ccactttcac   5400
ttcacgctta ctacaaccca tcagagtccc taattacaat ctcaacatca tggatgaagc   5460
ccacttcaca gaccctcaa gtatagctgc aagaggatac atatcaacaa gggttgaaat    5520
gggcgaggcg gctgccattt tatgactgc cacaccacca ggaacccgtg atgcgtttcc    5580
tgactctaac tcaccaatca tggacacaga agtggaagtc ccagagagag cctgagctc    5640
aggctttgat tgggtgacag accattctg gaaaacagtt tggttcgttc caagcgtgag    5700
aaacggaaat gaaatcgcag cctgtctgac aaaggctgga aagcgggtca tacagctcag   5760
caggaagact tttgagacag aatttcagaa aacaaaaaat caagagtggg actttgtcat    5820
aacaactgac atctcagaga tgggcgccaa cttcaaggct gaccgggtca tagactctag   5880
gagatgccta aaaccagtca tacttgatgg tgagagagtc atcttggctg gcccatgcc   5940
tgtcacgcat gctagtgctg ctcagaggag aggacgtata gcaggaacc ctaacaaacc    6000
tggagatgag tacatgtatg gaggtgggtg tgcagagact gatgaaggcc atgcacactg   6060
gcttgaagca agaatgcttc ttgacaacat ctacctccag ggaccttca tagcctcgct   6120
ctatcggcct gaggccgata aggtagccgc cattgaggga gagtttaagc tgaggacaga   6180
gcaaaggaag acettcgtgg aactcatgaa gagaggagac cttcccgtct ggctagccta    6240
tcaggttgca tctgccggaa taacttacac agacagaaga tggtgctttg atggcacaac   6300
caacaacacc ataatggaag acagtgtacc agcagaggtt tggacaaagt atggagagaa   6360
gagagtgctc aaaccgagat ggatggatgc tagggtctgt tcagaccatg cggccctgaa   6420
gtcgttcaaa gaattcgccg ctggaaaaag aggagcggct ttgggagtaa tggaggccct   6480
gggaacactg ccaggacaca tgacagagag gtttcaggaa gccattgaca acctcgccgt   6540
gctcatgcga gcagagactg gaagcaggcc ttataaggca gcgcagccc aactgccgga    6600
gaccctagag accattatgc tcttaggttt gctgggaaca gttcactgg ggatcttctt    6660
cgtcttgatg cggaataagg gcatcggaaa gatgggcttt ggaatggtaa ccctggggc    6720
cagtgcatgg ctcatgtggc tttcggaaat tgaaccagcc agaattgcat gtgtcctcat    6780
tgttgtgttt ttattactgg tggtgctcat acccgagcca gagaagcaaa gatctcccca    6840
agataaccag atggcaatta tcatcatggt ggcagtgggc cttctaggtt tgataactgc    6900
aaacgaactt ggatggctgg aaagaacaaa aaatgacata gctcatctaa tgggaaggag    6960
agaagaagga gcaaccatgg gattctcaat ggacattgat ctgcggccag cctccgcctg    7020
ggctatctat gccgcattga caactctcat caccccagct gtccaacatg cggtaaccac    7080
ttcatacaac aactactcct taatgcatgt ggccacacaa gctggagtgc tgtttggat    7140
gggcaaaggg atgccatttta tgcatgggga ccttggagtc ccgctgctaa tgatgggttg   7200
ctattcacaa ttaacacccc tgactctgat agtagctatc attctgcttg tggcgcacta   7260
catgtacttg atcccaggcc tacaagcggc agcagcgcgt gctgcccaga aaggacagc    7320
agctgcatc atgaagaatc ccgttgtgga tggatgg gtaactgaca ttgacacaat    7380
gacaatagac ccccaggtgg agaagaagat gggacaagtg ttactcatag cagtagccat    7440
ctccagtgct gtgctgctgc ggaccgcctg gggatggggg gaggctggag ctctgatcac    7500
agcagcgacc tccaccttgt gggaaggctc tccaaacaaa tactgaact cctctacagc    7560
cacctcactg tgcaacatct tcagaggaag ctatctggca ggacttccc ttatctatac    7620
agtgacgaga aacgctggcc tggttaagag acgtggaggt gggacgggaga agactctgga    7680
agagaagtgg aaagctcgtc tgaatcagat gtcggccctg gagttctact cttataaaaa    7740
gtcaggtatc actgaagtgt gtagagagga ggctcgccgt gccctcaagg atggagtggc   7800
cacaggagga catgccgtat cccggggaag tgcaaagatc agatggttgg aggagagagg    7860
atatctgcag ccctatggga aggttgttga cctcggagtg ggcagaggg gctggagcta    7920
ttatgccgcc accatccgca agtgcagga ggtgagagga tacacaaagg aggtcccgg    7980
tcatgaagaa cccatgctgg tgcaaagcta gggtggaac atagttcgtc tcaagagtgg   8040
agtggacgtc ttccacatgg cggctgagcc gtgtgacact ctgctgtgtg acataggtga    8100
gtcatcatct agtcctgaag tggaagagac acgaacactc agagtgctct ctatggtggg   8160
ggactggctt gaaaaagac caggggcctt ctgtataaag gtgctgtgcc catacaccag    8220
cactatgatg gaaaccatgg agcgactgca acgtaggcat ggggaggat tagtcagagt   8280
gccattgtgt cgcaactcca cacatgagat tgtactgggtc tctggggcaa agagcaacat   8340
cataaaaagt gtgtccacca caagtcagct cctcctggga cgcatggatg ccccaggag    8400
gccagtgaaa tatgaggagg atgtgaacct cggctcgggt acacgagctg tggcaagctg   8460
tgctgctgcc cttaactga aaatcatcgg caggcgcatt gagagaatcc gcaatgaaca    8520
tgcagaaaca tggttttctg atgaaaacca cccatacagg acatgggcct accatggag    8580
ctacgaagcc cccacgcaag gatcagcgtt ttccctcgtg aacggggttg ttagactcct    8640
gtcaaagcct ggggacgtgg tgactggagt tacaggaata gccatgactg acaccacacc    8700
atacggccaa caaagagtct tcaaagaaaa agtggacacc agggtgccag atccccaaga    8760
aggcactcgc caggtaatga acatagtctc ttcctggctg tggaaggagc tggggaaacg    8820
```

```
caagcggcca cgcgtctgca ccaaagaaga gtttatcaac aaggtgcgca gcaatgcagc    8880
actgggagca atatttgaag aggaaaaaga atgaagacg gctgtggaag ctgtgaatga     8940
tccaaggttt tgggccctag tggatagga gagagaacac cacctgagag gagagtgtca    9000
cagctgtgtg tacaacatga tgggaaaaag agaaaagaag caaggagagt tcgggaaagc    9060
aaaaggtagc cgcgccatct ggtacatgtg gttgggagcc agattcttgg agtttgaagc    9120
ccttggattc ttgaacgagg accattggat gggaagagaa aactcaggag gtggagtcga    9180
agggttagga ttgcaaagac ttggatacat tctagaagaa atgaatcggg caccaggagg    9240
aaagatgtac gcagatgaca ctgctggctg ggacacccgc attagtaagt ttgatctgga    9300
gaatgaagct ctgattacca accaaatgga ggaagggcac agaactctgg cgttggccgt    9360
gattaaaatac acataccaaa acaaagtggt gaaggttctc agaccagctg aaggaggaaa    9420
aacagttatg gacatcattt caagacaaga ccagagaggg agtggacaag ttgtcactta    9480
tgctctcaac acattcacca acttggtggt gcagcttatc cggaacatgg aagctgagga    9540
agtgttagag atgcaagact tatggttgtt gaggaagcca gagaaagtga ccagatggtt    9600
gcagagcaat ggatgggata gactcaaacg aatggccgtc agtggagatg actgcgttgt    9660
gaagccaatc gatgataggt ttgcacatgc cctcaggttc ttgaatgaca tgggaaaagt    9720
taggaaagac acacaggagt ggaaaccctc gactggatgg agcaattggg aagaagtccc    9780
gttctgctcc caccacttca acaagctgta cctcaaggat gggagatcca ttgtggtccc    9840
ttgccgccac caagatgaac tgattggccg agctcgcgtc tcaccagggg caggatggga    9900
catccgggag actgcctgtc ttgcaaaatc atatgcgcag atgtggcagc tcctttattt    9960
ccacagaaga gaccttcgac tgatggctaa tgccatttgc tcggctgtgc cagttgactg   10020
ggtaccaact gggagaacca cctggtcaat ccatggaaag ggagaatgga tgaccactga   10080
ggacatgctc atggtgtgga ataagtgtgt gattgaggag aacgaccata tgtgaggacaa   10140
gactcctgta acaaaatgga cagacattcc ctatctagga aaaagggagg acttatggtg   10200
tggatccctt ataggcaca gaccccgcac cacttgggct gaaaacatca agacacagt    10260
caacatggtg cgcaggatca taggtgatga agaaaagtac atggactatc tatccaccca   10320
agtccgctac ttgggtgagg aaggtccaa acccggagtg ttgtaagcac caattttagt   10380
gttgtcaggc ctgctagtca gccacagttt ggggaaagct gtgcagcctg taaccccccc   10440
aggagaagct gggaaaccaa gctcatagtc aggccgagaa cgccatggca cggaagaagc   10500
catgctgcct gtgagcccct cagaggacac tgagtcaaaa accccacgc gcttggaagc    10560
gcaggatggg aaaagaaggt ggcgaccttc cccaccctc aatctggggc ctgaactgga   10620
gactagctgt gaatctccag cagagggact agtggttaga ggagaccccc cggaaaacgc   10680
aaaacagcat attgactgg gaaagaccag agactccatg agtttccacc acgctggccg   10740
ccaggcacag atcgccgaac ttcggcggcc ggtgtgggga aatccatggt ttct         10794

SEQ ID NO: 13           moltype = DNA length = 10617
FEATURE                 Location/Qualifiers
source                  1..10617
                        mol_type = unassigned DNA
                        organism = Zika virus
SEQUENCE: 13
agtatcaaca ggttttattt tggatttgga aacgagagtt tctggtcatg aaaaacccaa      60
aaaagaaatc cggaggattc cggattgtca atatgctaaa acgcggagta gcccgtgtga    120
gcccctttgg gggcttgaag aggctgccag ccggacttct gctgggtcat gggcccatca    180
ggatggtctt ggcgattcta gccttttga gattcacggc aatcaagcca tcactgggtc    240
tcatcaatag atggggttca gtggggaaaa aagaggctat ggaataata aagaagttca    300
agaaagatct ggctgccatg ctgagaataa tcaatgctag gaaggagaag aagagacgag    360
gcgcagatac tagtgtcgga attgttggcc tcctgctgac cacagctgca gcagcggagg    420
tcactagacg tgggagtgca tactatatgt acttggacag aaacgacgct ggggaggcca    480
tatcttttcc aaccacattg gggatgaata agtgttatat acagatcatg gatcttggac    540
acatgtgtga tgccaccatg agctatgaat gccctatgct ggatgagggg gtggaaccag    600
atgacgtcga ttgttggtgc aacacgacgt caacttggtg tgtacgaca acctgccaca    660
acaaaaaagg tgaagcacgg agatctagaa gagctgtgac gctcccctcc cattccacta    720
ggaagctgca aacgcggtcg caaacctggt tggaatcaag agaatacaca aagcacttga    780
ttagagtcga aaattggata ttcaggaacc ctggcttcgc gttagcagca gctgccatcg    840
cttggctttt gggaagctca acgagccaaa aagtcatata cttggtcatg atactgctga    900
ttgccccggc atacagcatc aggtgcatag gagtcagcaa tagggacttt gtggaaggta    960
tgtcaggtgg gacttgggtt gatgttgtct tggaacatgg aggttgtgtc accgtaatgg   1020
cacaggacaa accgactgtc gacatagagc tggttacaac aacagtcagc aacatggcgg   1080
aggtaagatc ctactgctat gaggcatcaa tatcggacat ggcttcggac agcgctgcc   1140
caacacaagg tgaagcctac cttgacaagc aatcagacac tcaatatgtc tgcaaaagaa   1200
cgttagtgga cagaggctgg ggaaatggat gtggactttt tggcaaaggg agcctggtga   1260
catgcgctaa gtttgcatgc tccaagaaaa tgaccgggaa gagcatccag ccagagaatc   1320
tggagtaccg gataatgctg tcagttcatg gctcccagca cagtgggatg atcgttaatg   1380
acacagaca tgaaactgat gagaatagag cgaaggttga gataacgccc aattcaccaa   1440
gagccgaagc caccctgggg ggttttgaa gcctaggact tgattgtgaa ccgaggacag   1500
gccttgactt tcagatttg tattacttga ctatgaataa caagcactgg ttggttcaca   1560
aggagtggt ccacgacatt ccattacctt ggcacgctgg ggcagacacc ggaactccac   1620
actggaacaa caaagaagca ctggtagagt tcaaggacgc acatgccaaa aggcaaactg   1680
tcgtggttct agggagtcaa gaaggagcag ttcacacgc ccttgctgga gctctggagg   1740
ctgagatgga tggtgcaaag ggaaggctgt cctctggcca cttgaaatgt cgcctgaaaa   1800
tggataaact tagattgaag ggcgtgtcat actccttgtg taccgcagcg ttcacattca   1860
ccaagatccc ggctgaaaca ctgcacggga cagtcacagt ggaggtacag tacgcaggga   1920
cagatggacc ttgcaaggtt ccagctcaga tggcggtgga catgcaaact ctgacccag   1980
tgggaaggtt gataaccgct aaccccgtca tcactgagaac tcaagatga   2040
tgctgaaact tgatcaacca tttgggactc ttacattgt cataggagtc ggggagaaga   2100
agatcacccca ccactggcac aggagtggca gcaccattgg aaaagcattt gaagccactg   2160
tgagaggtgc caagagaatg gcagtcttgg gagacacagc tgggactttt ggatcagttg   2220
gaggcgctct caactcattg ggcaagggca tccatcaaat ttttgagca gctttcaat   2280
cattgtttgg aggaatgtcc tggttctcac aaattctcat tggaacgttg ctgatgtggt   2340
```

```
tgggtctgaa cacaaagaat ggatctattt cccttatgtg cttggcctta gggggagtgt    2400
tgatcttctt atccacagct gtctctgctg atgtggggtg ctcggtggac ttctcaaaga    2460
aggagacgag atgcggtaca ggggtgttcg tctataacga cgttgaagcc tggagggaca    2520
ggtacaagta ccatcctgac tcccccgta gattggcagc agcagtcaag caagcctggg     2580
aagatggtat ctgtgggatc tcctctgttt caagaatgga aaacatcatc tggagatcag    2640
tagaagggga gctcaacgca atcctggaag agaatggagt tcaactgacg gtcgttgtgg    2700
gatctgtaaa aaccccatg tggagaggtc cacagagatt gcccgtgcct gtgaacgagc     2760
tgccccacgg ctggaaggct ggggggaaat cgtacttcgt cagagcagca aagacaaata    2820
acagctttgt cgtggatggt gacacactga aggaatgccc actcaaacat agagcatgga    2880
acagcttttct tgtggaggat catgggttcg gggtatttca cactagtgtc tggctcaagg   2940
ttagagaaga ttattcatta gagtgtgatc cagccgttat tggaacagct gttaagggaa    3000
aggaggctgt acacagtgat ctaggctact ggattgagag tgagaagaat gacacatgga    3060
ggctgaagag ggcccatctg atcgagatga aacatgtga atggccaaag tcccacacat     3120
tgtggacaga tggaatagaa gagagtgatc tgatcatacc caagtcttta gctgggccac    3180
tcagccatca caataccaga gagggctaca ggacccaaat gaaagggcca tggcacagtg    3240
aagagcttga aattcggttt gaggaatgcc caggcactaa ggtccacgtg gaggaaacat    3300
gtggaacaag gaggaccatct ctgagatcaa ccactgcaag cggaagggtg atcgaggaat   3360
ggtgctgcag ggagtgcaca atgccccac tgtcgttccg ggctaaagat ggctgttggt     3420
atggaatgga gataaggccc aggaaagaac cagaaagtaa cttagtaagg tcaatggtga    3480
ctgcaggatc aactgatcac atggatcact tctcccttgg agtgcttgtg attctgctca    3540
tggtgcagga agggctgaag aagagaatga ccacaaagat catcataagc acatcgatgg    3600
cagtgctggt agctatgatc ctggaggat tttcaatgag tgacctgact gacttgcaa     3660
ttttgatggg tgccaccttc gcggaaatga acactggagg agatgtagct catctggcgc   3720
tgatagcggc attcaaagtc agaccagcgt tgctggtatc tttcatcttc agagctaatt    3780
ggacaccccg tgaaagcatg ctgctggcct tggcctcgtg tcttttgcaa actgcgatct    3840
ccgccttgga aggcgacctg atggttctca tcaatgtttt tgctttgccc tggttggcaa    3900
tacgagcgat ggttgttcca cgcactgata acatcacctt ggcaatcctg gctgctctga    3960
caccactggc ccgggacaca ctgcttgtgg cgtggagagc aggccttgct acttgcgggg   4020
ggtttatgct cctctctctg aagggaaaag gcagtgtgaa gaagaactta ccatttgtca    4080
tggccctggg actaaccgct gtgaggctgg tcgaccccat caacgtggtg ggactgctga    4140
tgctcacaag gagtgggaag cggagctgg cccctagcga agtactcaca gctgttggcc    4200
tgatatcgc attggctgga gggttcgcca aggcagatat agagatggct gggcccatgg     4260
ccgcggtcgg tctgctaatt gtcagttacg tggtctcagg aaagagtgtg acatgtaca     4320
ttgaaagagc aggtgacatc acatgggaaa aagatgcgga agtcactgga aacagtgtta    4380
ggctcgatgt ggcgctagat gagagtggtg atttctccct ggtggaggat gacgtcccc     4440
ccatgagaga gatcatactc aaggtggtcc tgatgaccat ctgtggcatg aacccaatag    4500
ccataccctt tgcagctgga gcgtggtacg tatacgtgaa gactggaaaa aggagtggtg    4560
ctctatggga tgtgcctgct cccaaggaag taaaaaggg ggagaccaca gatggagtgt     4620
acagagtaat gactcgtaga ctgctaggtt caacacaagt tggagtggga gttatgcaag    4680
agggggtctt tcacactatg tggcacgtca caaaaggatc cgcgctgaga agcggtgaag    4740
ggagacttga tccatactgg ggagatgtca agcaggatct ggtgtcatac tgtggtccat    4800
ggaagctaga tgccgcctgg gacgggcaca gcgaggtgca gctcttggcc gtgcccccg     4860
gagagagagc gaggaacatc cagactctgc ccggaatatt taagacaaag gatggggaca    4920
ttggagcggt tgcgctggat tacccagcag gaacttcagg atctccaatc ctagacaagt    4980
gtgggagagt gataggactt tatggcaatg gggtcgtgat caaaaatggg agttatgtta    5040
gtgccatcac ccaaggagg agggaggaag agactcctgt tgagtgcttc gagccttcga    5100
tgctgaagaa gaagcagcta actgtcttag acttgcatcc tggagctggg aaaaccagga    5160
gagttcttcc tgaaatagtc cgtgaagcca taaaacaag actccgtact gtgatcttag     5220
ctccaaccag ggttgtcgct gctgaaatgg aggaagccct tagagggctt ccagtgcgtt    5280
atatgacaac agcagtcaat gtcacccact ctggaacaga aatcgtcgac ttaatgtgcc    5340
atgccacctt cacttcacgt ctactacagc caatcagagt cccaaactat aatctgtata    5400
ttatggatga ggcccacttc acagatcct caagtatagc agcaagagga tacatttcaa    5460
caagggttga gatggcgag gcggctgcca tcttcatgac cgccacgcca ccaggaaccc     5520
gtgacgcatt tccggactcc aactcaccaa ttatggacac cgaagtggaa gtcccagaga    5580
gagcctggag ctcaggcttt gattgggtga cggatcattc tggaaaaaca gtttggtttg    5640
ttccaagcgt gaggaacggc aatgagatcg cagcttgtct gacaaaggct ggaaaacggg    5700
tcatacagct cagcagaaag acttttgaga cagagttcca gaaaacaaaa catcaagagt    5760
gggactttgt cgtgacaact gacatttcag agatgggcgc caactttaaa gctgaccgtg    5820
tcatagattc caggagatgc ctaaagccgg tcatacttga tggcgagaga gtcattctgg    5880
ctggacccat gcctgtcaca catgccagcg ctgcccagag gaggggcgc ataggcagga    5940
atcccaacaa acctggagat gagtatctgt atggaggtgg gtgcgcagag actgacgaag    6000
accatgcaca ctggcttgaa gcaagaatgc tccttgacaa tatttacctc caagatggcc    6060
tcatagcctc gctctatcga cctgaggccg acaaagtagc agccattgag ggagagttca    6120
agcttaggac ggagcaaagg aagaccttt tggaactcat gaaagagga gatcttcctg    6180
tttggctggc ctatcaggtt gcatctgccg gaataaccta cacagataga agatggtgct    6240
ttgatggcac accaacaac accataatgg aagacagtgt gccggcagag gtgtggacca    6300
gacacgagag aaaagagtg ctcaaaccga ggtggatgga cgccagagtt tgttcagatc     6360
atgcggccct gaagtcattc aaggagtttg ccgctggaa aagaggagcg gcttttgagg    6420
tgatggaagc cctgggaaca cctggagac acatgacgga agattccag gaagccattg    6480
acaacctcgc tgtgctcatg cgggcagaga ctgaagcag gccttacaaa gccgcggcgg    6540
cccaattgcc ggagaccta gagaccatta tgctttggg gttgctggga acagtctcgc    6600
tgggaatctt tttcgtcttg atgaggaaca agggcatagg gaagatggc tttgaatgg     6660
tgactcttgg ggcagcgca tggctcatgt ggctctcgga aattgagcca gccagaattg    6720
catgtgtcct cattgttgtg ttcctattgc tggtggtgct cataccaggag ccagaaaagc   6780
aaagatctcc ccaggacaac caaatgcaa tcatcatcat ggtagcagta ggtcttctgg    6840
gcttgattac cgccaatgaa ctcggatggt tggagaaac aaagagtgac ctaagccatc    6900
taatgggaag agagagaggag ggggcaacca taggattctc aatggacatt gacctgcggc  6960
cagcctcagc ttgggccatc tatgctgcct tgacaacttt cattaccca gccgtccaac    7020
atgcagtgac cacttcatac aacaactact ccttaatggc gatggccacg caagctggag    7080
```

```
tgttgtttgg tatgggcaaa gggatgccat tctacgcatg ggactttgga gtcccgctgc  7140
taatgatagg ttgctactca caattaacac ccctgaccct aatagtggcc atcattttgc  7200
tcgtggcgca ctacatgtac ttgatcccag ggctgcaggc agcagctgcg cgtgctgccc  7260
agaagagaac ggcagctggc atcatgaaga accctgttgt ggatggaata gtggtgactg  7320
acattgacac aatgacaatt gaccccccaag tggagaaaaa gatgggacag gtgctactca  7380
tagcagtagc cgtctccagc gccatactgt cgcggaccgc ctgggggtgg ggggaggctg  7440
gggccctgat cacagcggca acttccactt tgtgggaagg ctctccgaac aagtactgga  7500
actcctctac agccacttca ctgtgtaaca ttttttagggg aagttacttg gctggagctt  7560
ctctaatcta cacagtaaca agaaacgctg gcttggtcaa gagacgtggg ggtggaacag  7620
gagagaccct gggagagaaa tggaaggccc gcttgaacca gatgtcggcc ctggagttct  7680
actcctacaa aaagtcaggc atcaccgagg tgtgcagaga agaggcccgc cgcgccctca  7740
aggacggtgt ggcaacggga ggccatgctg tgtcccgagg aagtgcaaag ctgagatggt  7800
tggtggagcg gggatacctg cagccctatg gaaaggtcat tgatcttgga tgtggcagag  7860
ggggctggag ttactacgcc gccaccatcc gcaaagttca agaagtgaaa ggatacacaa  7920
aaggaggccc tggtcatgaa gaaccatgtg tggtgcaaag ctatgggtgg aacatagtcc  7980
gtcttaagag tggggtggac gtctttcata tggcggctga gccgtgtgac acgttgctgt  8040
gtgacatagg tgagtcatca tctagtcctg aagtggaaga agcacggacg ctcagagtcc  8100
tctccatggt gggggattgg cttgaaaaaa gaccaggagc cttttgtata aaagtgttgt  8160
gcccatacac cagcactatg atggaaaccc tggagcgact gcagcgtagg tatgggggag  8220
gactggtcag agtgccactc tcccgcaact ctacacatga gatgtactgg gtctctggag  8280
cgaaaagcaa caccataaaa agtgtgtcca ccacgagcca gctcctcttg gggcgcatgg  8340
acgggccagg gaggccagtg aaatatgagg aggatgtgaa tctcggctct ggcacgcggg  8400
ctgtggtaag ctgcgctgaa gctcccaaca tgaagatcat tggtaaccgc attgaaagga  8460
tccgcagtga gcacgcggaa acgtggttct tgacgagaaa ccaccccatat aggacatggg  8520
cttaccatgg aagctatgag gcccccacac aagggtcagc gtcctctcta ataaacgggg  8580
ttgtcaggct cctgtcaaaa ccctgggatg tggtgactgg agtcacagga atagccatga  8640
ccgacaccac accgtatggt cagcaaaagag ttttcaagga aaaagtggac actagggtgc  8700
cagacccca agaaggcact cgtcaggtta tgagcatggt ctcttcctgg ttgtggaaag  8760
agctaggcaa acacaaacgg ccacgagtct gtaccaaaga agagttcatc aacaaggttc  8820
gtagcaatgc agcattaggg gcaatatttg aagaggaaaa agagtggaag actgcagtgg  8880
aagctgtgaa cgatccaagg ttctgggctc tagtggacaa ggaaagagag caccacctga  8940
gaggagagtg ccagagttgt gtgtacaaca tgatgggaaa aagagaaaag aaacagggg  9000
aatttggaaa ggccaagggc agccgcgcca tctggtatat gtggctaggg gctagatttc  9060
tagagttcga agcccttgga ttcttgaacg aggatcactg gatggggaga gagaactcag  9120
gaggtggtgt tgaagggctg gattacaaag actcggata tgtcctagaa gagatgagtc  9180
gcataccagg aggaaggatg tatgcagatg acactgctgg ctgggacacc cgcatcagca  9240
ggtttgatct ggagaatgaa gctctaatca ccaaccaaat ggagaaaggg cacagggcct  9300
tggcattgga cataatcaag tacacataccc aaaacaaagt ggtaaaggtc cttagaccag  9360
ctgaaaaagg gaagacagtt atggacatta tttcgagaca agaccaaagg gggagcggac  9420
aagttgtcac ttacgctctt aacacattta ccaacctagt ggtgcaactc attcggaata  9480
tggaggctga ggaagttcta gagatgcaag acttgtggct gctgcggagg tcagagaaag  9540
tgaccaactg gttgcagagc aacggatggg ataggctcaa acgaatggca gtcagtggag  9600
atgattcgt tgtgaagcca attgatgata ggttttgcaca gtgccctcag ttcttgaatg  9660
atatgggaaa agttaggaag gacacacaag agtggaaacc ctcaactgga tgggacaact  9720
gggaagaagt tccgttttgc tcccaccact tcaacaagct ccatctcaag gacgggaggt  9780
ccattgtggt tccctgccgc caccaagatg aactgattgg ccgggccgc gtctctccag  9840
gggcgggatg gagcatccgg gagactgctt gcctagcaaa atcatatgcg caaatgtggc  9900
agctccttta tttccacaga agggacctcc gactgatgac caatgccatt tgttcatctg  9960
tgccagttga ctgggttcca actgggagaa ctacctggtc aatccataag aagggagaat  10020
ggatgaccac tgaagacatg cttgtggtgt ggaacagagt gtggattgag agaacgacc  10080
acatggaaga caagacccca gttacgaaat ggacagacat tccctatttg ggaaaaaggg  10140
aagacttgtg gtgtggatct ctcataggc acagaccgcg caccacctgg gctgagaaca  10200
ttaaaaacac agtcaacatg gtgcgacaga tcataggtga tgaagaaaag tacatggact  10260
acctatccac ccaagttcgc tacttgggtg aagaaggtc tacacctgga gtgctgtaag  10320
caccaatctt agtgttgtca ggcctgctag tcagccacag cttggggaaa gctgtgcagc  10380
ctgtgacccc cccaggagaa gctgggaaac caagcctata gtcaggccga gaacgccatg  10440
gcacggaaga gccatgctg cctgtgagcc cctcaggaga cactgagtca aaaaccccca  10500
cgcgcttgga ggcgcaggat gggaaaagaa ggtggcgacc ttccccaccc ttcaatctgg  10560
ggcctgaact ggagatcagc tgtggatctc cagaagaggg actagtggtt agaggag     10617
```

SEQ ID NO: 14          moltype = AA  length = 498
FEATURE                Location/Qualifiers
source                 1..498
                       mol_type = protein
                       organism = Zika virus
SEQUENCE: 14
IRCIGVSNRD FVEGMSGGTW VDVVLEHGGC VTVMAQDKPT VDIELVTTTV SNMAEVRSYC    60
YEASISDMAS DSRCPTQGEA YLDKQSDTQY VCKRTLVDRG WGNGCGLFGK GSLVTCAKFT   120
CSKKMTGKSI QPENLEYRIM LSVHGSQHSG MIVNDENRAK VEVTPNSPRA EATLGGFGSL   180
GLDCEPRTGL DFSDLYYLTM NNKHWLVHKE WFHDIPLPWH AGADTGTPHW NNKEALVEFK   240
DAHAKRQTVV VLGSQEGAVH TALAGALEAE MDGAKGRLFS GHLKCRLKMD KLRLKGVSYS   300
LCTAAFTFTK VPAETLHGTV TVEVQYAGTD GPCKVPAQMA VDMQTLTPVG RLITANPVIT   360
ESTENSKMML ELDPPFGDSY IVIGVGDKKI THHWHRSGST IGKAFEATVR GAKRMAVLGD   420
TAWDFGSVGG VFNSLKGIH QIFGAAFKSL FGGMSWFSQI LIGTLLVWLG LNTKNGSISL    480
TCLALGGVMI FLSTAVSA                                                 498

```
SEQ ID NO: 15          moltype = AA  length = 498
FEATURE                Location/Qualifiers
source                 1..498
                       mol_type = protein
                       organism = Zika virus
SEQUENCE: 15
IRCIGVSNRD FVEGMSGGTW VDVVLEHGGC VTVMAQDKPT VDIELVTTTV SNMAEVRSYC  60
YEASISDMAS DSRCPTQGEA YLDKQSDTQY VCKRTLVDRG WGNGCGLFGK GSLVTCAKFT  120
CSKKMTGKSI QPENLEYRIM LSVHGSQHSG MIVNDENRAK VEVTPNSPRA EATLGGFGSL  180
GLDCEPRTGL DFSDLYYLTM NNKHWLVHKE WFHDIPLPWH SGADTETPHW NNKEALVEFK  240
DAHAKRQTVV VLGSQEGAVH TALAGALEAE MDGAKGRLSS GHLKCRLKMD KLRLKGVSYS  300
LCTAAFTFTK VPAETLHGTV TVEVQYAGRD GPCKVPAQMA VDMQTLTPVG RLITANPVIT  360
ESTENSKMML ELDPPFGDSY IVIGVGDKKI THHWHRSGSI IGKAFEATVR GAKRMAVLGD  420
TAWDFGSVGG VFNSLGKGIH QIFGAAFKSL FGGMSWFSQI LIGTLLVWLG LNTKNGSISL  480
TCLALGGVMI FLSTAVSA                                               498

SEQ ID NO: 16          moltype = AA  length = 504
FEATURE                Location/Qualifiers
REGION                 156..162
                       note = misc_feature - X=any amino acid
source                 1..504
                       mol_type = protein
                       organism = Zika virus
SEQUENCE: 16
IRCIGVSNRD FVEGMSGGTW VDVVLEHGGC VTVMAQDKPT VDIELVTTTV SNMAEVRSYC  60
YEASISDMAS DSRCPTQGEA YLDKQSDTQY VCKRTLVDRG WGNGCGLFGK GSLVTCAKFT  120
CSKKMTGKSI QPENLEYRIM LSVHGSQHSG MIVNDXXXXX XXNRAEVEVT PNSPRAEATL  180
GGFGSLGLDC EPRTGLDFSD LYYLTMNNKH WLVHKEWFHD IPLPWHAGAD TGTPHWNNKE  240
ALVEFKDAHA KRQTVVVLGS QEGAVHTALA GALEAEMDGA KGRLFSGHLK CRLKMDKLRL  300
KGVSYSLCTA AFTFTKVPAE TLHGTVTVEV QYAGTDGPCK VPAQMAVDMQ TLTPVGRLIT  360
ANPVITESTE NSKMMLELDP PFGDSYIVIG VGDKKITHHW HRSGSTIGKA FEATVRGAKR  420
MAVLGDTAWD FGSVGGVFNS LGKGIHQIFG AAFKSLFGGM SWFSQILIGT LLVWLGLNTK  480
NGSISLTCLA LGGVMIFLST AVSA                                        504

SEQ ID NO: 17          moltype = AA  length = 504
FEATURE                Location/Qualifiers
REGION                 152..156
                       note = misc_feature - X=any amino acid
source                 1..504
                       mol_type = protein
                       organism = Zika virus
SEQUENCE: 17
IRCIGVSNRD FVEGMSGGTW VDVVLEHGGC VTVMAQDKPT VDIELVTTTV SNMAEVRSYC  60
YEASISDMAS DSRCPTQGEA YLDKQSDTQY VCKRTLVDRG WGNGCGLFGK GSLVTCAKFT  120
CSKKMTGKSI QPENLEYRIM LSVHGSQHSG MXXXXXGHET DENRAKVEVT PNSPRAEATL  180
GGFGSLGLDC EPRTGLDFSD LYYLTMNNKH RLVRKEWFHD IPLPWHAGAD TGTPHWNNKE  240
ALVEFKDAHA KRQTVVVLGS QEGAVHTALA GALEAEMDGA KGRLFSGHLK CRLKMDKLRL  300
KGVSYSLCTA AFTFTKVPAE TLHGTVTVEV QYAGTDGPCK VPAQMAVDMQ TLTPVGRLIT  360
ANPVITESTE NSKMMLELDP PFGDSYIVIG VGDKKITHHW LKKGSSIGKA FEATVRGAKR  420
MAVLGDTAWD FGSVGGVFNS LGKGVHQIFG AAFKSLFGGM SWFSQILIGT LLVWLGLNTK  480
NGSISLTCLA LGGVMIFLST AVSA                                        504

SEQ ID NO: 18          moltype = AA  length = 504
FEATURE                Location/Qualifiers
source                 1..504
                       mol_type = protein
                       organism = Zika virus
SEQUENCE: 18
IRCIGVSNRD FVEGMSGGTW VDVVLEHGGC VTVMAQDKPT VDIELVTTTV SNMAEVRSYC  60
YEASISDMAS DSRCPTQGEA YLDKQSDTQY VCKRTLVDRG WGNGCGLFGK GSLVTCAKFT  120
CSKKMTGKSI QPENLEYRIM LSVHGSQHSG MIVNDIGHET DENRAKVEVT PNSPRAEATL  180
GGFGSLGLDC EPRTGLDFSD LYYLTMNNKH WLVHKEWFHD IPLPWHAGAD TGTPHWNNKE  240
ALVEFKDAHA KRQTVVVLGS QEGAVHTALA GALEAEMDGA KGRLFSGHLK CRLKMDKLRL  300
KGVSYSLCTA AFTFTKVPAE TLHGTVTVEV QYAGTDGPCK VPAQMAVDMQ TLTPVGRLIT  360
ANPVITESTE NSKMMLELDP PFGDSYIVIG VGDKKITHHW HRSGSTIGKA FEATVRGAKR  420
MAVLGDTAWD FGSVGGVFNS LGKGIHQIFG AAFKSLFGGM SWFSQILIGT LLVWLGLNTK  480
NGSISLTCLA LGGVMIFLST AVSA                                        504

SEQ ID NO: 19          moltype = AA  length = 504
FEATURE                Location/Qualifiers
source                 1..504
                       mol_type = protein
                       organism = Zika virus
SEQUENCE: 19
IRCIGVSNRD FVEGMSGGTW VDVVLEHGGC VTVMAQDKPT VDIELVTTTV SNMAEVRSYC  60
YEASISDMAS DSRCPTQGEA YLDKQSDTQY VCKRTLVDRG WGNGCGLFGK GSLVTCAKFT  120
CSKKMTGKSI QPENLEYRIM LSVHGSQHSG MIVNDIGHET DENRAKVEVT PNSPRAEATL  180
GGFGSLGLDC EPRTGLDFSD LYYLTMNNKH WLVHKEWFHD IPLPWHAGAD TGTPHWNNKE  240
```

```
ALVEFKDAHA KRQTVVVLGS QEGAVHTALA GALEAEMDGA KGRLFSGHLK CRLKMDKLRL    300
KGVSYSLCTA AFTFTKVPAE TLHGTVTVEV QYAGTDGPCK VPAQMAVDMQ TLTPVGRLIT    360
ANPVITESTE NSKMMLELDP PFGDSYIVIG VGDKKITHHW HRSGSTIGKA FEATVRGAKR    420
MAVLGDTAWD FGSVGGVFNS LGKGIHQIFG AAFKSLFGGM SWFSQILIGT LLVWLGLNTK    480
NGSISLTCLA LGGVMIFLST AVSA                                          504

SEQ ID NO: 20           moltype = AA  length = 504
FEATURE                 Location/Qualifiers
source                  1..504
                        mol_type = protein
                        organism = Zika virus
SEQUENCE: 20
IRCIGVSNRD FVEGMSGGTW VDVVLEHGGC VTVMAQDKPT VDIELVTTTV SNMAEVRSYC     60
YEASISDMAS DSRCPTQGEA YLDKQSDTQY VCKRTLVDRG WGNGCGLFGK GSLVTCAKFT    120
CSKKMTGKSI QPENLEYRIM LSVHGSQHSG MIVNDIGHET DENRAKVEVT PNSPRAEATL    180
GGFGSLGLDC EPRTGLDFSD LYYLTMNNKH WLVHKEWFHD IPLPWHAGAD TGTPHWNNKE    240
ALVEFKDAHA KRQTVVVLGS QEGAVHTALA GALEAEMDGA KGRLFSGHLK CRLKMDKLRL    300
KGVSYSLCTA AFTFTKVPAE TLHGTVTVEV QYAGTDGPCK VPAQMAVDMQ TLTPVGRLIT    360
ANPVITESTE NSKMMLELDP PFGDSYIVIG VGDKKITHHW HRSGSTIGKA FEATVRGAKR    420
MAVLGDTAWD FGSVGGVFNS LGKGIHQIFG AAFKSLFGGM SWFSQILIGT LLVWLGLNTK    480
NGSISLTCLA LGGVMIFLST AVSA                                          504

SEQ ID NO: 21           moltype = AA  length = 504
FEATURE                 Location/Qualifiers
source                  1..504
                        mol_type = protein
                        organism = Zika virus
SEQUENCE: 21
IRCIGVSNRD FVEGMSGGTW VDVVLEHGGC VTVMAQDKPT VDIELVTTTV SNMAEVRSYC     60
YEASISDMAS DSRCPTQGEA YLDKQSDTQY VCKRTLVDRG WGNGCGLFGK GSLVTCAKFT    120
CSKKMTGKSI QPENLEYRIM LSVHGSQHSG MIVNDIGHET DENRAKVEVT PNSPRAEATL    180
GGFGSLGLDC EPRTGLDFSD LYYLTMNNKH WLVHKEWFHD IPLPWHAGAD TGTPHWNNKE    240
ALVEFKDAHA KRQTVVVLGS QEGAVHTALA GALEAEMDGA KGRLFSGHLK CRLKMDKLRL    300
KGVSYSLCTA AFTFTKVPAE TLHGTVTVEV QYAGTDGPCK VPAQMAVDMQ TLTPVGRLIT    360
ANPVITESTE NSKMMLELDP PFGDSYIVIG VGDKKITHHW HRSGSTIGKA FEATVRGAKR    420
MAVLGDTAWD FGSVGGVFNS LGKGIHQIFG AAFKSLFGGM SWFSQILIGT LLVWLGLNTK    480
NGSISLTCLA LGGVMIFLST AVSA                                          504

SEQ ID NO: 22           moltype = AA  length = 504
FEATURE                 Location/Qualifiers
source                  1..504
                        mol_type = protein
                        organism = Zika virus
SEQUENCE: 22
IRCIGVSNRD FVEGMSGGTW VDVVLEHGGC VTVMAQDKPT VDIELVTTTV SNMAEVRSYC     60
YEASISDMAS DSRCPTQGEA YLDKQSDTQY VCKRTLVDRG WGNGCGLFGK GSLVTCAKFT    120
CSKKMTGKSI QPENLEYRIM LSVHGSQHSG MIVNDTGHET DENRAKVEVT PNSPRAEATL    180
GGFGSLGLDC EPRTGLDFSD LYYLTMNNKH WLVHKEWFHD IPLPWHAGAD TGTPHWNNKE    240
ALVEFKDAHA KRQTVVVLGS QEGAVHTALA GALEAEMDGA KGRLFSGHLK CRLKMDKLRL    300
KGVSYSLCTA AFTFTKVPAE TLHGTVTVEV QYAGTDGPCK VPAQMAVDMQ TLTPVGRLIT    360
ANPVITESTE NSKMMLELDP PFGDSYIVIG VGDKKITHHW HRSGSTIGKA FEATVRGAKR    420
MAVLGDTAWD FGSVGGVFNS LGKGIHQIFG AAFKSLFGGM SWFSQILIGT LLVWLGLNTK    480
NGSISLTCLA LGGVMIFLST AVSA                                          504

SEQ ID NO: 23           moltype = AA  length = 504
FEATURE                 Location/Qualifiers
source                  1..504
                        mol_type = protein
                        organism = Zika virus
SEQUENCE: 23
IRCIGVSNRD FVEGMSGGTW VDVVLEHGGC VTVMAQDKPT VDIELVTTTV SNMAEVRSYC     60
YEASISDMAS DSRCPTQGEA YLDKQSDTQY VCKRTLVDRG WGNGCGLFGK GSLVTCAKFT    120
CSKKMTGKSI QPENLEYRIM LSVHGSQHSG MTVNDIGHET DENRAKVEVT PNSPRAEATL    180
GGFGSLGLDC EPRTGLDFSD LYYLTMNNKH WLVHKEWFHD IPLPWHAGAD TGTPHWNNKE    240
ALVEFKDAHA KRQTVVVLGS QEGAVHTALA GALEAEMDGA KGKLFSGHLK CRLKMDKLRL    300
KGVSYSLCTA AFTFTKVPAE TLHGTVTVEV QYAGTDGPCK IPVQMAVDMQ TLTPVGRLIT    360
ANPVITESTE NSKMMLELDP PFGDSYIVIG VGDKKITHHW HRSGSTIGKA FEATVRGAKR    420
MAVLGDTAWD FGSVGGVFNS LGKGIHQIFG AAFKSLFGGM SWFSQILIGT LLVWLGLNTK    480
NGSISLTCLA LGGVMIFLST AVSA                                          504

SEQ ID NO: 24           moltype = AA  length = 504
FEATURE                 Location/Qualifiers
source                  1..504
                        mol_type = protein
                        organism = Zika virus
SEQUENCE: 24
IRCIGVSNRD FVEGMSGGTW VDVVLEHGGC VTVMAQDKPT VDIELVTTTV SNMAEVRSYC     60
YEASISDMAS DSRCPTQGEA YLDKQSDTQY VCKRTLVDRG WGNGCGLFGK GSLVTCAKFT    120
CSKKMTGKSI QPENLEYRIM LSVHGSQHSG MTVNDIGYET DENRAKVEVT PNSPRAEATL    180
```

```
GGFGSLGLDC EPRTGLDFSD LYYLTMNNKH WLVHKEWFHD IPLPWHAGAD TGTPHWNNKE    240
ALVEFKDAHA KRQTVVVLGS QEGAVHTALA GALEAEMDGA KGKLFSGHLK CRLKMDKLRL    300
KGVSYSLCTA AFTFTKVPAE TLHGTVTVEV QYAGTDGPCK IPVQMAVDMQ TLTPVGRLIT    360
ANPVITESTE NSKMMLELDP PFGDSYIVIG VGDKKITHHW HRSGSTIGKA FEATVRGAKR    420
MAVLGDTAWD FGSVGGVFNS LGKGIHQIFG AAFKSLFGGM SWFSQILIGT LLVWLGLNTK    480
NGSISLTCLA LGGVMIFLST AVSA                                          504

SEQ ID NO: 25           moltype = AA  length = 504
FEATURE                 Location/Qualifiers
source                  1..504
                        mol_type = protein
                        organism = Zika virus
SEQUENCE: 25
IRCIGVSNRD FVEGMSGGTW VDVVLEHGGC VTVMAQDKPT VDIELVTTTV SNMAEVRSYC     60
YEASISDMAS DSRCPTQGEA YLDKQSDTQY VCKRTLVDRG WGNGCGLFGK GSLVTCAKFT    120
CSKKMTGKSI QPENLEYRIM LSVHGSQHSG MIVNDTGYET DENRAKVEVT PNSPRAEATL    180
GGFGSLGLDC EPRTGLDFSD LYYLTMNNKH WLVHKEWFHD IPLPWHAGAD TGTPHWNNKE    240
ALVEFKDAHA KRQTVVVLGS QEGAVHTALA GALEAEMDGA KGKLFSGHLK CRLKMDKLRL    300
KGVSYSLCTA AFTFTKVPAE TLHGTVTVEV QYAGTDGPCK IPVQMAVDMQ TLTPVGRLIT    360
ANPVITESTE NSKMMLELDP PFGDSYIVIG VGDKKITHHW HRSGSTIGKA FEATVRGAKR    420
MAVLGDTAWD FGSVGGVFNS LGKGIHQIFG AAFKSLFGGM SWFSQILIGT LLVWLGLNTK    480
NGSISLTCLA LGGVMIFLST AVSA                                          504

SEQ ID NO: 26           moltype = AA  length = 504
FEATURE                 Location/Qualifiers
source                  1..504
                        mol_type = protein
                        organism = Zika virus
SEQUENCE: 26
IRCIGVSNRD FVEGMSGGTW VDVVLEHGGC VTVMAQDKPT VDIELVTTTV SNMAEVRSYC     60
YEASISDMAS DSRCPTQGEA YLDKQSDTQY VCKRTLVDRG WGNGCGLFGK GSLVTCAKFT    120
CSKKMTGKSI QPENLEYRIM LSVHGSQHSG MIVNDIGHET DENRAKVEVT PNSPRAEATL    180
GGFGSLGLDC EPRTGLDFSD LYYLTMNNKH WLVHKEWFHD IPLPWHAGAD TGTPHWNNKE    240
ALVEFKDAHA KRQTVVVLGS QEGAVHTALA GALEAEMDGA KGRLFSGHLK CRLKMDKLRL    300
KGVSYSLCTA VCTAAKVPAE TLHGTVTVEV QYAGTDGPCK VPAQMAVDMQ TLTPVGRLIT    360
ANPVITESTE NSKMMLELDP PFGDSYIVIG VGDKKITHHW HRSGSTIGKA FEATVRGAKR    420
MAVLGDTAWD FGSVGGVFNS LGKGIHQIFG AAFKSLFGGM SWFSQILIGT LLVWLGLNTK    480
NGSISLTCLA LGGVMIFLST AVSA                                          504

SEQ ID NO: 27           moltype = AA  length = 500
FEATURE                 Location/Qualifiers
source                  1..500
                        mol_type = protein
                        organism = Zika virus
SEQUENCE: 27
IRCIGVSNRD FVEGMSGGTW VDVVLEHGGC VTVMAQDKPT VDIELVTTTV SNMAEVRSYC     60
YEASISDMAS DSRCPTQGEA YLDKQSDTQY VCKRTLVDRG WGNGCGLFGK GSLVTCAKFT    120
CSKKMTGKSI QPENLEYRIM LSVHGSQHSG MIGYETDEDR AKVEVTPNSP RAEATLGGFG    180
SLGLDCEPRT GLDFSDLYYL TMNNKHWLVH KEWFHDIPLP WHAGADTGTP HWNNKEALVE    240
FKDAHAKRQT VVVLGSQEGA VHTALAGALE AEMDGAKGRL FSGHLKCRLK MDKLRLKGVS    300
YSLCTAAFTF TKVPAETLHG TVTVEVQYAG TDGPCKIPVQ MAVDMQTLTP VGRLITANPV    360
ITESTENSKM MLELDPPFGD SYIVIGVGDK KITHHWRSG STIGKAFEAT VRGAKRMAVL     420
GDTAWDFGSV GGVFNSLGKG IHQIFGAAFK SLFGGMSWFS QILIGTLLVW LGLNTKNGSI    480
SLTCLALGGV MIFLSTAVSA                                               500

SEQ ID NO: 28           moltype = AA  length = 500
FEATURE                 Location/Qualifiers
source                  1..500
                        mol_type = protein
                        organism = Zika virus
SEQUENCE: 28
IRCIGVSNRD FVEGMSGGTW VDVVLEHGGC VTVMAQDKPT VDIELVTTTV SNMAEVRSYC     60
YEASISDMAS DSRCPTQGEA YLDKQSDTQY VCKRTLVDRG WGNGCGLFGK GSLVTCAKFT    120
CSKKMTGKSI QPENLEYRIM LSVHGSQHSG MIGYETDEDR AKVEVTPNSP RAEATLGGFG    180
SLGLDCEPRT GLDFSDLYYL TMNNKHWLVH KEWFHDIPLP WHAGADTGTP HWNNKEALVE    240
FKDAHAKRQT VVVLGSQEGA VHTALAGALE AEMDGAKGRL FSGHLKCRLK MDKLRLKGVS    300
YSLCTAAFTF TKVPAETLHG TVTVEVQYAG TDGPCKIPVQ MAVDMQTLTP VGRLITANPV    360
ITESTENSKM MLELDPPFGD SYIVIGVGDK KITHHWRSG STIGKAFEAT VRGAKRMAVL     420
GDTAWDFGSV GGVFNSLGKG IHQIFGAAFK SLFGGMSWFS QILIGTLLVW LGLNTKNGSI    480
SLTCLALGGV MIFLSTAVSA                                               500

SEQ ID NO: 29           moltype = AA  length = 500
FEATURE                 Location/Qualifiers
source                  1..500
                        mol_type = protein
                        organism = Zika virus
SEQUENCE: 29
IRCIGVSNRD FVEGMSGGTW VDVVLEHGGC VTVMAQDKPT VDIELVTTTV SNMAEVRSYC     60
YEASISDMAS DSRCPTQGEA YLDKQSDTQY VCKRTLVDRG WGNGCGLFGK GSLVTCAKFT    120
```

```
CSKKMTGKSI QPENLEYRIM LSVHGSQHSG MIGYETEDDR AKVEVTPNSP RAEATLGGFG  180
SLGLDCEPRT GLDFSDLYYL TMNNKHWLVH KEWFHDIPLP WHAGADTGTP HWNNKEALVE  240
FKDAHAKRQT VVVLGSQEGA VHTALAGALE AEMDGAKGRL FSGHLKCRLK MDKLRLKGVS  300
YSLCTAAFTF TKVPAETLHG TVTVEVQYAG TDGPCKIPVQ MAVDMQTLTP VGRLITANPV  360
ITESTENSKM MLELDPPFGD SYIVIGVGDK KITHHWHRSG STIGKAFEAT VRGAKRMAVL  420
GDTAWDFGSV GGVFNSLGKG IHQIFGAAFK SLFGGMSWFS QILIGTLLVW LGLNTKNGSI  480
SLTCLALGGV MIFLSTAVSA                                             500

SEQ ID NO: 30            moltype = AA   length = 504
FEATURE                  Location/Qualifiers
source                   1..504
                         mol_type = protein
                         organism = Zika virus
SEQUENCE: 30
IRCIGVSNRD FVEGMSGGTW VDVVLEHGGC VTVMAQDKPT VDIELVTTTV SNMAEVRSYC   60
YEASISDMAS DSRCPTQGEA YLDKQSDTQY VCKRTLVDRG WGNGCGLFGK GSLVTCAKFA  120
CSKKMTGKSI QPENLEYRIM LSVHGSQHSG MIVNDTGHET DENRAKVEIT PNSPRAEATL  180
GGFGSLGLDC EPRTGLDFSD LYYLTMNNKH WLVHKEWFHD IPLPWHTGAD TGTPHWNNKE  240
ALVEFKDAHA KRQTVVVLGS QEGAVHTALA GALEAEMDGA KGRLSSGHLK CRLKMDKLRL  300
KGVSYSLCTA AFTFTKIPAE TLHGTVTVEV QYAGTDGPCK VPAQMAVDMQ TLTPVGRLIT  360
ANPVITEGTE NSKMMLELDP PFGDSYIVIG VGEKKITHHW HRSGSTIGKA FEATVRGAKR  420
MAVLGDTAWD FGSVGGVLNS LGKGIHQIFG AAFKSLFGGM SWFSQILIGT LLMWLGLNTK  480
NGSISLMCLA LGGVLIFLST AVSA                                        504

SEQ ID NO: 31            moltype = AA   length = 504
FEATURE                  Location/Qualifiers
source                   1..504
                         mol_type = protein
                         organism = Zika virus
SEQUENCE: 31
IRCIGVSNRD FVEGMSGGTW VDVVLEHGGC VTVMAQDKPT VDIELVTTTV SNMAEVRSYC   60
YEASISDMAS DSRCPTQGEA YLDKQSDTQY VCKRTLVDRG WGNGCGLFGK GSLVTCAKFA  120
CSKKMTGKSI QPENLEYRIM LSVHGSQHSG MIVNDTGHET DENRAKVEIT PNSPRAEATL  180
GGFGSLGLDC EPRTGLDFSD LYYLTMNNKH WLVHKEWFHD IPLPWHTGAD TGTPHWNNKE  240
ALVEFKDAHA KRQTVVVLGS QEGAVHTALA GALEAEMDGA KGRLSSGHLK CRLKMDKLRL  300
KGVSYSLCTA AFTFTKIPAE TLHGTVTVEV QYAGTDGPCK VPAQMAVDMQ TLTPVGRLIT  360
ANPVITEGTE NSKMMLELDP PFGDSYIVIG VGEKKITHHW HRSGSTIGKA FEATVRGAKR  420
MAVLGDTAWD FGSVGGVLNS LGKGIHQIFG AAFKSLFGGM SWFSQILIGT LLMWLGLNTK  480
NGSISLMCLA LGGVLIFLST AVSA                                        504

SEQ ID NO: 32            moltype = AA   length = 504
FEATURE                  Location/Qualifiers
source                   1..504
                         mol_type = protein
                         organism = Zika virus
SEQUENCE: 32
IRCIGVSNRD FVEGMSGGTW VDVVLEHGGC VTVMAQDKPT VDIELVTTTV SNMAEVRSYC   60
YEASISDMAS DSRCPTQGEA YLDKQSDTQY VCKRTLVDRG WGNGCGLFGK GSLVTCAKFA  120
CSKKMTGKSI QPENLEYRIM LSVHGSQHSG MIVNDTGHET DENRAKVEIT PNSPRAEATL  180
GGFGSLGLDC EPRTGLDFSD LYYLTMNNKH WLVHKEWFHD IPLPWHAGAD TGTPHWNNKE  240
ALVEFKDAHA KRQTVVVLGS QEGAVHTALA GALEAEMDGA KGRLSSGHLK CRLKMDKLRL  300
KGVSYSLCTA AFTFTKIPAE TLHGTVTVEV QYAGTDGPCK VPAQMAVDMQ TLTPVGRLIT  360
ANPVITESTE NSKMMLELDP PFGDSYIVIG VGEKKITHHW HRSGSTIGKA FEATVRGAKR  420
MAVLGDTAWD FGSVGGALNS LGKGIHQIFG AAFKSLFGGM SWFSQILIGT LLMWLGLNTK  480
NGSISLMCLA LGGVLIFLST AVSA                                        504

SEQ ID NO: 33            moltype = AA   length = 504
FEATURE                  Location/Qualifiers
source                   1..504
                         mol_type = protein
                         organism = Zika virus
SEQUENCE: 33
IRCIGVSNRD FVEGMSGGTW VDVVLEHGGC VTVMAQDKPT VDIELVTTTV SNMAEVRSYC   60
YEASISDMAS DSRCPTQGEA YLDKQSDTQY VCKRTLVDRG WGNGCGLFGK GSLVTCAKFA  120
CSKKMTGKSI QPENLEYRIM LSVHGSQHSG MIVNDTGHET DENRAKVEIT PNSPRAEATL  180
GGFGSLGLDC EPRTGLDFSD LYYLTMNNKH WLVHKEWFHD IPLPWHAGAD TGTPHWNNKE  240
ALVEFKDAHA KRQTVVVLGS QEGAVHTALA GALEAEMDGA KGRLSSGHLK CRLKMDKLRL  300
KGVSYSLCTA AFTFTKIPAE TLHGTVTVEV QYAGTDGPCK VPAQMAVDMQ TLTPVGRLIT  360
ANPVITESTE NSKMMLELDP PFGDSYIVIG VGEKKITHHW HRSGSTIGKA FEATVRGAKR  420
MAVLGDTAWD FGSVGGALNS LGKGIHQIFG AAFKSLFGGM SWFSQILIGT LLMWLGLNTK  480
NGSISLMCLA LGGVLIFLST AVSA                                        504

SEQ ID NO: 34            moltype = AA   length = 504
FEATURE                  Location/Qualifiers
source                   1..504
                         mol_type = protein
                         organism = Zika virus
```

```
SEQUENCE: 34
IRCIGVSNRD FVEGMSGGTW VDVVLEHGGC VTVMAQDKPT VDIELVTTTV SNMAEVRSYC    60
YEASISDMAS DSRCPTQGEA YLDKQSDTQY VCKRTLVDRG WGNGCGLFGK GSLVTCAKFA   120
CSKKMTGKSI QPENLEYRIM LSVHGSQHSG MIVNDTGHET DENRAKVEIT PNSPRAEATL   180
GGFGSLGLDC EPRTGLDFSD LYYLTMNNKH WLVHKEWFHD IPLPWHAGAD TGTPHWNNKE   240
ALVEFKDAHA KRQTVVVLGS QEGAVHTALA GALEAEMDGA KGRLSSGHLK CRLKMDKLRL   300
KGVSYSLCTA AFTFTKIPAE TLHGTVTVEV QYAGTDGPCK VPAQMAVDMQ TLTPVGRLIT   360
ANPVITESTE NSKMMLELDP PFGDSYIVIG VGEKKITHHW HRSGSTIGKA FEATVRGAKR   420
MAVLGDTAWD FGSVGGALNS LGKGIHQIFG AAFKSLFGGM SWFSQILIGT LLMWLGLNTK   480
NGSISLMCLA LGGVLIFLST AVSA                                         504

SEQ ID NO: 35          moltype = AA   length = 504
FEATURE                Location/Qualifiers
source                 1..504
                       mol_type = protein
                       organism = Zika virus
SEQUENCE: 35
IRCIGVSNRD FVEGMSGGTW VDVVLEHGGC VTVMAQDKPT VDIELVTTTV SNMAEVRSYC    60
YEASISDMAS DSRCPTQGEA YLDKQSDTQY VCKRTLVDRG WGNGCGLFGK GSLVTCAKFA   120
CSKKMTGKSI QPENLEYRIM LSVHGSQHSG MIVNDTGHET DENRAKVEIT PNSPRAEATL   180
GGFGSLGLDC EPRTGLDFSD LYYLTMNNKH WLVHKEWFHD IPLPWHAGAD TGTPHWNNKE   240
ALVEFKDAHA KRQTVVVLGS QEGAVHTALA GALEAEMDGA KGRLSSGHLK CRLKMDKLRL   300
KGVSYSLCTA AFTFTKIPAE TLHGTVTVEV QYAGTDGPCK VPAQMAVDMQ TLTPVGRLIT   360
ANPVITESTE NSKMMLELDP PFGDSYIVIG VGEKKITHHW HRSGSTIGKA FEATVRGAKR   420
MAVLGDTAWD FGSVGGALNS LGKGIHQIFG AAFKSLFGGM SWFSQILIGT LLMWLGLNTK   480
NGSISLMCLA LGGVLIFLST AVSA                                         504

SEQ ID NO: 36          moltype = AA   length = 504
FEATURE                Location/Qualifiers
source                 1..504
                       mol_type = protein
                       organism = Zika virus
SEQUENCE: 36
IRCIGVSNRD FVEGMSGGTW VDVVLEHGGC VTVMAQDKPT VDIELVTTTV SNMAEVRSYC    60
YEASISDMAS DSRCPTQGEA YLDKQSDTQY VCKRTLVDRG WGNGCGLFGK GSLVTCAKFA   120
CSKKMTGKSI QPENLEYRIM LSVHGSQHSG MIVNDTGHET DENRAKVEIT PNSPRAEATL   180
GGFGSLGLDC EPRTGLDFSD LYYLTMNNKH WLVHKEWFHD IPLPWHAGAD TGTPHWNNKE   240
ALVEFKDAHA KRQTVVVLGS QEGAVHTALA GALEAEMDGA KGRLSSGHLK CRLKMDKLRL   300
KGVSYSLCTA AFTFTKIPAE TLHGTVTVEV QYAGTDGPCK VPAQMAVDMQ TLTPVGRLIT   360
ANPVITESTE NSKMMLELDP PFGDSYIVIG VGEKKITHHW HRSGSTIGKA FEATVRGAKR   420
MAVLGDTAWD FGSVGGALNS LGKGIHQIFG AAFKSLFGGM SWFSQILIGT LLMWLGLNTK   480
NGSISLMCLA LGGVLIFLST AVSA                                         504

SEQ ID NO: 37          moltype = AA   length = 504
FEATURE                Location/Qualifiers
source                 1..504
                       mol_type = protein
                       organism = Zika virus
SEQUENCE: 37
IRCIGVSNRD FVEGMSGGTW VDVVLEHGGC VTVMAQDKPT VDIELVTTTV SNMAEVRSYC    60
YEASISDMAS DSRCPTQGEA YLDKQSDTQY VCKRTLVDRG WGNGCGLFGK GSLVTCAKFA   120
CSKKMTGKSI QPENLEYRIM LSVHGSQHSG MIVNDTGHET DENRAKVEIT PNSPRAEATL   180
GGFGSLGLDC EPRTGLDFSD LYYLTMNNKH WLVHKEWFHD IPLPWHAGAD TGTPHWNNKE   240
ALVEFKDAHA KRQTVVVLGS QEGAVHTALA GALEAEMDGA KGRLSSGHLK CRLKMDKLRL   300
KGVSYSLCTA AFTFTKIPAE TLHGTVTVEV QYAGTDGPCK VPAQMAVDMQ TLTPVGRLIT   360
ANPVITESTE NSKMMLELDP PFGDSYIVIG VGEKKITHHW HRSGSTIGKA FEATVRGAKR   420
MAVLGDTAWD FGSVGGALNS LGKGIHQIFG AAFKSLFGGM SWFSQILIGT LLMWLGLNTK   480
NGSISLMCLA LGGVLIFLST AVSA                                         504

SEQ ID NO: 38          moltype = AA   length = 504
FEATURE                Location/Qualifiers
source                 1..504
                       mol_type = protein
                       organism = Zika virus
SEQUENCE: 38
IRCIGVSNRD FVEGMSGGTW VDVVLEHGGC VTVMAQDKPT VDIELVTTTV SNMAEVRSYC    60
YEASISDMAS DSRCPTQGEA YLDKQSDTQY VCKRTLVDRG WGNGCGLFGK GSLVTCAKFA   120
CSKKMTGKSI QPENLEYRIM LSVHGSQHSG MIVNDTGHET DENRAKVEIT PNSPRAEATL   180
GGFGSLGLDC EPRTGLDFSD LYYLTMNNKH WLVHKEWFHD IPLPWHAGAD TGTPHWNNKE   240
ALVEFKDAHA KRQTVVVLGS QEGAVHTALA GALEAEMDGA KGRLSSGHLK CRLKMDKLRL   300
KGVSYSLCTA AFTFTKIPAE TLHGTVTVEV QYAGTDGPCK VPAQMAVDMQ TLTPVGRLIT   360
ANPVITESTE NSKMMLELDP PFGDSYIVIG VGEKKITHHW HRSGSTIGKA FEATVRGAKR   420
MAVLGDTAWD FGSVGGALNS LGKGIHQIFG AAFKSLFGGM SWFSQILIGT LLMWLGLNTK   480
NGSISLMCLA LGGVLIFLST AVSA                                         504
```

```
SEQ ID NO: 39           moltype = AA  length = 504
FEATURE                 Location/Qualifiers
source                  1..504
                        mol_type = protein
                        organism = Zika virus
SEQUENCE: 39
IRCIGVSNRD FVEGMSGGTW VDVVLEHGGC VTVMAQDKPT VDIELVTTTV SNMAEVRSYC   60
YEASISDMAS DSRCPTQGEA YLDKQSDTQY VCKRTLVDRG WGNGCGLFGK GSLVTCAKFA  120
CSKKMTGKSI QPENLEYRIM LSVHGSQHSG MIVNDTGHET DENRAKVEIT PNSPRAEATL  180
GGFGSLGLDC EPRTGLDFSD LYYLTMNNKH WLVHKEWFHD IPLPWHAGAD TGTPHWNNKE  240
ALVEFKDAHA KRQTVVVLGS QEGAVHTALA GALEAEMDGA KGRLSSGHLK CRLKMDKLRL  300
KGVSYSLCTA AFTFTKIPAE TLHGTVTVEV QYAGTDGPCK VPAQMAVDMQ TLTPVGRLIT  360
ANPVITESTE NSKMMLELDP PFGDSYIVIG VGEKKITHHW HRSGSTIGKA FEATVRGAKR  420
MAVLGDTAWD FGSVGGALNS LGKGIHQIFG AAFKSLFGGM SWFSQILIGT LLMWLGLNTK  480
NGSISLMCLA LGGVLIFLST AVSA                                        504

SEQ ID NO: 40           moltype = AA  length = 504
FEATURE                 Location/Qualifiers
source                  1..504
                        mol_type = protein
                        organism = Zika virus
SEQUENCE: 40
IRCIGVSNRD FVEGMSGGTW VDVVLEHGGC VTVMAQDKPT VDIELVTTTV SNMAEVRSYC   60
YEASISDMAS DSRCPTQGEA YLDKQSDTQY VCKRTLVDRG WGNGCGLFGK GSLVTCAKFA  120
CSKKMTGKSI QPENLEYRIM LSVHGSQHSG MIVNDTGHET DENRAKVEIT PNSPRAEATL  180
GGFGSLGLDC EPRTGLDFSD LYYLTMNNKH WLVHKEWFHD IPLPWHAGAD TGTPHWNNKE  240
ALVEFKDAHA KRQTVVVLGS QEGAVHTALA GALEAEMDGA KGRLSSGHLK CRLKMDKLRL  300
KGVSYSLCTA AFTFTKIPAE TLHGTVTVEV QYAGTDGPCK VPAQMAVDMQ TLTPVGRLIT  360
ANPVITESTE NSKMMLELDP PFGDSYIVIG VGEKKITHHW HRSGSTIGKA FEATVRGAKR  420
MAVLGDTAWD FGSVGGALNS LGKGIHQIFG AAFKSLFGGM SWFSQILIGT LLMWLGLNTK  480
NGSISLMCLA LGGVLIFLST AVSA                                        504

SEQ ID NO: 41           moltype = AA  length = 504
FEATURE                 Location/Qualifiers
source                  1..504
                        mol_type = protein
                        organism = Zika virus
SEQUENCE: 41
IRCIGVSNRD FVEGMSGGTW VDVVLEHGGC VTVMAQDKPT VDIELVTTTV SNMAEVRSYC   60
YEASISDMAS DSRCPTQGEA YLDKQSDTQY VCKRTLVDRG WGNGCGLFGK GSLVTCAKFA  120
CSKKMTGKSI QPENLEYRIM LSVHGSQHSG MIVNDTGHET DENRAKVEIT PNSPRAEATL  180
GGFGSLGLDC EPRTGLDFSD LYYLTMNNKH WLVHKEWFHD IPLPWHAGAD TGTPHWNNKE  240
ALVEFKDAHA KRQTVVVLGS QEGAVHTALA GALEAEMDGA KGRLSSGHLK CRLKMDKLRL  300
KGVSYSLCTA AFTFTKIPAE TLHGTVTVEV QYAGTDGPCK VPAQMAVDMQ TLTPVGRLIT  360
ANPVITESTE NSKMMLELDP PFGDSYIVIG VGEKKITHHW HRSGSTIGKA FEATVRGAKR  420
MAVLGDTAWD FGSVGGALNS LGKGIHQIFG AAFKSLFGGM SWFSQILIGT LLMWLGLNTK  480
NGSISLMCLA LGGVLIFLST AVSA                                        504

SEQ ID NO: 42           moltype = AA  length = 504
FEATURE                 Location/Qualifiers
source                  1..504
                        mol_type = protein
                        organism = Zika virus
SEQUENCE: 42
IRCIGVSNRD FVEGMSGGTW VDVVLEHGGC VTVMAQDKPT VDIELVTTTV SNMAEVRSYC   60
YEASISDMAS DSRCPTQGEA YLDKQSDTQY VCKRTLVDRG WGNGCGLFGK GSLVTCAKFA  120
CSKKMTGKSI QPENLEYRIM LSVHGSQHSG MIVNDTGHET DENRAKVEIT PNSPRAEATL  180
GGFGSLGLDC EPRTGLDFSD LYYLTMNNKH WLVHKEWFHD IPLPWHAGAD TGTPHWNNKE  240
ALVEFKDAHA KRQTVVVLGS QEGAVHTALA GALEAEMDGA KGRLSSGHLK CRLKMDKLRL  300
KGVSYSLCTA AFTFTKIPAE TLHGTVTVEV QYAGTDGPCK VPAQMAVDMQ TLTPVGRLIT  360
ANPVITESTE NSKMMLELDP PFGDSYIVIG VGEKKITHHW HRSGSTIGKA FEATVRGAKR  420
MAVLGDTAWD FGSVGGALNS LGKGIHQIFG AAFKSLFGGM SWFSQILIGT LLMWLGLNTK  480
NGSISLMCLA LGGVLIFLST AVSA                                        504

SEQ ID NO: 43           moltype = AA  length = 504
FEATURE                 Location/Qualifiers
source                  1..504
                        mol_type = protein
                        organism = Zika virus
SEQUENCE: 43
IRCIGVSNRD FVEGMSGGTW VDVVLEHGGC VTVMAQDKPT VDIELVTTTV SNMAEVRSYC   60
YEASISDMAS DSRCPTQGEA YLDKQSDTQY VCKRTLVDRG WGNGCGLFGK GSLVTCAKFA  120
CSKKMTGKSI QPENLEYRIM LSVHGSQHSG MIVNDTGHET DENRAKVEIT PNSPRAEATL  180
GGFGSLGLDC EPRTGLDFSD LYYLTMNNKH WLVHKEWFHD IPLPWHAGAD TGTPHWNNKE  240
ALVEFKDAHA KRQTVVVLGS QEGAVHTALA GALEAEMDGA KGRLSSGHLK CRLKMDKLRL  300
KGVSYSLCTA AFTFTKIPAE TLHGTVTVEV QYAGTDGPCK VPAQMAVDMQ TLTPVGRLIT  360
```

```
ANPVITESTE NSKMMLELDP PFGDSYIVIG VGEKKITHHW HRSGSTIGKA FEATVRGAKR   420
MAVLGDTAWD FGSVGGALNS LGKGIHQIFG AAFKSLFGGM SWFSQILIGT LLMWLGLNTK   480
NGSISLMCLA LGGVLIFLST AVSA                                          504

SEQ ID NO: 44           moltype = AA  length = 504
FEATURE                 Location/Qualifiers
source                  1..504
                        mol_type = protein
                        organism = Zika virus
SEQUENCE: 44
IRCIGVSNRD FVEGMSGGTW VDVVLEHGGC VTVMAQDKPT VDIELVTTTV SNMAEVRSYC   60
YEASISDMAS DSRCPTQGEA YLDKQSDTQY VCKRTLVDRG WGNGCGLFGK GSLVTCAKFA   120
CSKKMTGKSI QPENLEYRIM LSVHGSQHSG MIVNDTGHET DENRAKVEIT PNSPRAEATL   180
GGFGSLGLDC EPRTGLDFSD LYYLTMNNKH WLVHKEWFHD IPLPWHAGAD TGTPHWNNKE   240
ALVEFKDAHA KRQTVVVLGS QEGAVHTALA GALEAEMDGA KGRLSSGHLK CRLKMDKLRL   300
KGVSYSLCTA AFTFTKIPAE TLHGTVTVEV QYAGTDGPCK VPAQMAVDMQ TLTPVGRLIT   360
ANPVITESTE NSKMMLELDP PFGDSYIVIG VGEKKITHHW HRSGSTIGKA FEATVRGAKR   420
MAVLGDTAWD FGSVGGALNS LGKGIHQIFG AAFKSLFGGM SWFSQILIGT LLMWLGLNTK   480
NGSISLMCLA LGGVLIFLST AVSA                                          504

SEQ ID NO: 45           moltype = AA  length = 504
FEATURE                 Location/Qualifiers
source                  1..504
                        mol_type = protein
                        organism = Zika virus
SEQUENCE: 45
IRCIGVSNRD FVEGMSGGTW VDVVLEHGGC VTVMAQDKPT VDIELVTTTV SNMAEVRSYC   60
YEASISDMAS DSRCPTQGEA YLDKQSDTQY VCKRTLVDRG WGNGCGLFGK GSLVTCAKFA   120
CSKKMTGKSI QPENLEYRIM LSVHGSQHSG MIVNDTGHET DENRAKVEIT PNSPRAEATL   180
GGFGSLGLDC EPRTGLDFSD LYYLTMNNKH WLVHKEWFHD IPLPWHAGAD TGTPHWNNKE   240
ALVEFKDAHA KRQTVVVLGS QEGAVHTALA GALEAEMDGA KGRLSSGHLK CRLKMDKLRL   300
KGVSYSLCTA AFTFTKIPAE TLHGTVTVEV QYAGTDGPCK VPAQMAVDMQ TLTPVGRLIT   360
ANPVITESTE NSKMMLELDP PFGDSYIVIG VGEKKITHHW HRSGSTIGKA FEATVRGAKR   420
MAVLGDTAWD FGSVGGALNS LGKGIHQIFG AAFKSLFGGM SWFSQILIGT LLMWLGLNTK   480
NGSISLMCLA LGGVLIFLST AVSA                                          504

SEQ ID NO: 46           moltype = AA  length = 504
FEATURE                 Location/Qualifiers
source                  1..504
                        mol_type = protein
                        organism = Zika virus
SEQUENCE: 46
IRCIGVSNRD FVEGMSGGTW VDVVLEHGGC VTVMAQDKPT VDIELVTTTV SNMAEVRSYC   60
YEASISDMAS DSRCPTQGEA YLDKQSDTQY VCKRTLVDRG WGNGCGLFGK GSLVTCAKFA   120
CSKKMTGKSI QPENLEYRIM LSVHGSQHSG MIVNDTGHET DENRAKVEIT PNSPRAEATL   180
GGFGSLGLDC EPRTGLDFSD LYYLTMNNKH WLVHKEWFHD IPLPWHAGAD TGTPHWNNKE   240
ALVEFKDAHA KRQTVVVLGS QEGAVHTALA GALEAEMDGA KGRLSSGHLK CRLKMDKLRL   300
KGVSYSLCTA AFTFTKIPAE TLHGTVTVEV QYAGTDGPCK VPAQMAVDMQ TLTPVGRLIT   360
ANPVITESTE NSKMMLELDP PFGDSYIVIG VGEKKITHHW HRSGSTIGKA FEATVRGAKR   420
MAVLGDTAWD FGSVGGALNS LGKGIHQIFG AAFKSLFGGM SWFSQILIGT LLMWLGLNTK   480
NGSISLMCLA LGGVLIFLST AVSA                                          504

SEQ ID NO: 47           moltype = AA  length = 504
FEATURE                 Location/Qualifiers
source                  1..504
                        mol_type = protein
                        organism = Zika virus
SEQUENCE: 47
IRCIGVSNRD FVEGMSGGTW VDVVLEHGGC VTVMAQDKPT VDIELVTTTV SNMAEVRSYC   60
YEASISDMAS DSRCPTQGEA YLDKQSDTQY VCKRTLVDRG WGNGCGLFGK GSLVTCAKFA   120
CSKKMTGKSI QPENLEYRIM LSVHGSQHSG MIVNDTGHET DENRAKVEIT PNSPRAEATL   180
GGFGSLGLDC EPRTGLDFSD LYYLTMNNKH WLVHKEWFHD IPLPWHAGAD TGTPHWNNKE   240
ALVEFKDAHA KRQTVVVLGS QEGAVHTALA GALEAEMDGA KGRLSSGHLK CRLKMDKLRL   300
KGVSYSLCTA AFTFTKIPAE TLHGTVTVEV QYAGTDGPCK VPAQMAVDMQ TLTPVGRLIT   360
ANPVITESTE NSKMMLELDP PFGDSYIVIG VGEKKITHHW HRSGSTIGKA FEATVRGAKR   420
MAVLGDTAWD FGSVGGALNS LGKGIHQIFG AAFKSLFGGM SWFSQILIGT LLMWLGLNTK   480
NGSISLMCLA LGGVLIFLST AVSA                                          504

SEQ ID NO: 48           moltype = AA  length = 504
FEATURE                 Location/Qualifiers
source                  1..504
                        mol_type = protein
                        organism = Zika virus
SEQUENCE: 48
IRCIGVSNRD FVEGMSGGTW VDVVLEHGGC VTVMAQDKPT VDIELVTTTV SNMAEVRSYC   60
YEASISDMAS DSRCPTQGEA YLDKQSDTQY VCKRTLVDRG WGNGCGLFGK GSLVTCAKFA   120
CSKKMTGKSI QPENLEYRIM LSVHGSQHSG MIVNDTGHET DENRAKVEIT PNSPRAEATL   180
GGFGSLGLDC EPRTGLDFSD LYYLTMNNKH WLVHKEWFHD IPLPWHAGAD TGTPHWNNKE   240
ALVEFKDAHA KRQTVVVLGS QEGAVHTALA GALEAEMDGA KGRLSSGHLK CRLKMDKLRL   300
```

```
KGVSYSLCTA AFTFTKIPAE TLHGTVTVEV QYAGTDGPCK VPAQMAVDMQ TLTPVGRLIT    360
ANPVITESTE NSKMMLELDP PFGDSYIVIG VGEKKITHHW HRSGSTIGKA FEATVRGAKR    420
MAVLGDTAWD FGSVGGALNS LGKGIHQIFG AAFKSLFGGM SWFSQILIGT LLMWLGLNTK    480
NGSISLMCLA LGGVLIFLST AVSA                                          504

SEQ ID NO: 49           moltype = AA  length = 504
FEATURE                 Location/Qualifiers
source                  1..504
                        mol_type = protein
                        organism = Zika virus
SEQUENCE: 49
IRCIGVSNRD FVEGMSGGTW VDIVLEHGGC VTVMAQDKPT VDIELVTTTV SNMAEVRSYC     60
YEASISDMAS DSRCPTQGEA YLDKQSDTQY VCKRTLVDRG WGNGCGLFGK GSLVTCAKFA    120
CSKKMTGKSI QPENLEYRIM LSVHGSQHSG MIVNDTGHET DENRAKVEIT PNSPRAEATL    180
GGFGSLGLDC EPRTGLDFSD LYYLTMNNKH WLVHKEWFHD IPLPWHAGAD TGTPHWNNKE    240
ALVEFKDAHA KRQTVVVLGS QEGAVHTALA GALEAEMDGA KGRLSSGHLK CRLKMDKLRL    300
KGVSYSLCTA AFTFTKIPAE TLHGTVTVEV QYAGTDGPCK VPAQMAVDMQ TLTPVGRLIT    360
ANPVITESTE NSKMMLELDP PFGDSYIVIG VGEKKITHHW HRSGSTIGKA FEATVRGAKR    420
MAVLGDTAWD FGSVGGALNS LGKGIHQIFG AAFKSLFGGM SWFSQILIGT LLMWLGLNTK    480
NGSISLMCLA LGGVLIFLST AVSA                                          504

SEQ ID NO: 50           moltype = AA  length = 504
FEATURE                 Location/Qualifiers
source                  1..504
                        mol_type = protein
                        organism = Zika virus
SEQUENCE: 50
IRCIGVSNRD FVEGMSGGTW VDIVLEHGGC VTVMAQDKPT VDIELVTTTV SNMAEVRSYC     60
YEASISDMAS DSRCPTQGEA YLDKQSDTQY VCKRTLVDRG WGNGCGLFGK GSLVTCAKFA    120
CSKKMTGKSI QPENLEYRIM LSVHGSQHSG MIVNDTGHET DENRAKVEIT PNSPRAEATL    180
GGFGSLGLDC EPRTGLDFSD LYYLTMNNKH WLVHKEWFHD IPLPWHAGAD TGTPHWNNKE    240
ALVEFKDAHA KRQTVVVLGS QEGAVHTALA GALEAEMDGA KGRLSSGHLK CRLKMDKLRL    300
KGVSYSLCTA AFTFTKIPAE TLHGTVTVEV QYAGTDGPCK VPAQMAVDMQ TLTPVGRLIT    360
ANPVITESTE NSKMMLELDP PFGDSYIVIG VGEKKITHHW HRSGSTIGKA FEATVRGAKR    420
MAVLGDTAWD FGSVGGALNS LGKGIHQIFG AAFKSLFGGM SWFSQILIGT LLMWLGLNTK    480
NGSISLMCLA LGGVLIFLST AVSA                                          504

SEQ ID NO: 51           moltype = AA  length = 504
FEATURE                 Location/Qualifiers
source                  1..504
                        mol_type = protein
                        organism = Zika virus
SEQUENCE: 51
IRCIGVSNRD FVEGMSGGTW VDVVLEHGGC VTVMAQDKPT VDIELVTTTV SNMAEIRSYC     60
YEASISDMAS DSRCPTQGEA YLDKQSDTQY VCKRTLVDRG WGNGCGLFGK GSLVTCAKFA    120
CSKKMTGKSI QPENLEYRIM LSVHGSQHSG MIVNDTGHET DENRAKVEIT PNSPRAEATL    180
GGFGSLGLDC EPRTGLDFSD LYYLTMNNKH WLVHKEWFHD IPLPWHAGAD TGTPHWNNKE    240
ALVEFKDAHA KRQTVVVLGS QEGAVHTALA GALEAEMDGA KGRLSSGHLK CRLKMDKLRL    300
KGVSYSLCTA AFTFTKIPAE TLHGTVTVEV QYAGTDGPCK VPAQMAVDMQ TLTPVGRLIT    360
ANPVITESTE NSKMMLELDP PFGDSYIVIG VGEKKITHHW HRSGSTIGKA FEATVRGAKR    420
MAVLGDTAWD FGSVGGALNS LGKGIHQIFG AAFKSLFGGM SWFSQILIGT LLMWLGLNTK    480
NGSISLMCLA LGGVLIFLST AVSA                                          504

SEQ ID NO: 52           moltype = AA  length = 504
FEATURE                 Location/Qualifiers
source                  1..504
                        mol_type = protein
                        organism = Zika virus
SEQUENCE: 52
IRCIGVSNRD FVEGMSGGTW VDVVLEHGGC VTVMAQDKPT VDIELVTTTV SNMAEVRSYC     60
YEASISDMAS DSRCPTQGEA YLDKQSDTQY VCKRTLVDRG WGNGCGLFGK GSLVTCAKFA    120
CSKKMTGKSI QPENLEYRIM LSVHGSQHSG MIVNDTGHET DENRAKVEIT PNSPRAEATL    180
GGFGSLGLDC EPRTGLDFSD LYYLTMNNKH WLVHKEWFHD IPLPWHAGAD TGTPHWNNKE    240
ALVEFKDAHA KRQTVVVLGT QEGAVHTALA GALEAEMDGA KGRLSSGHLK CRLKMDKLRL    300
KGVSYSLCTA AFTFTKIPAE TLHGTVTVEV QYAGTDGPCK VPAQMAVDMQ TLTPVGRLIT    360
ANPVITESTE NSKMMLELDP PFGDSYIVIG VGEKKITHHW HRSGSTIGKA FEATVRGAKR    420
MAVLGDTAWD FGSVGGALNS LGKGIHQIFG AAFKSLFGGM SWFSQILIGT LLMWLGLNTK    480
NGSISLMCLA LGGVLIFLST AVSA                                          504

SEQ ID NO: 53           moltype = AA  length = 504
FEATURE                 Location/Qualifiers
source                  1..504
                        mol_type = protein
                        organism = Zika virus
SEQUENCE: 53
IRCIGVSNRD FVEGMSGGTW VDVVLEHGGC VTVMAQDKPT VDIELVTTTV SNMAEVRSYC     60
YEASISDMAS DSRCPTQGEA YLDKQSDTQY VCKRTLVDRG WGNGCGLFGK GSLVTCAKFA    120
CSKKMTGKSI QPENLEYRIM LSVHGSQHSG MIVNDTGHET DENRAKVEIT PNSPRAEATL    180
GGFGSLGLDC EPRTGLDFSD LYYLTMNNKH WLVHKEWFHD IPLPWHAGAD TGTPHWNNKE    240
```

```
ALVEFKDAHA KRQTVVVLGT QEGAVHTALA GALEAEMDGA KGRLSSGHLK CRLKMDKLRL    300
KGVSYSLCTA AFTFTKIPAE TLHGTVTVEV QYAGTDGPCK VPAQMAVDMQ TLTPVGRLIT    360
ANPVITESTE NSKMMLELDP PFGDSYIVIG VGEKKITHHW HRSGSTIGKA FEATVRGAKR    420
MAVLGDTAWD FGSVGGALNS LGKGIHQIFG AAFKSLFGGM SWFSQILIGT LLMWLGLNTK    480
NGSISLMCLA LGGVLIFLST AVSA                                          504

SEQ ID NO: 54         moltype = AA  length = 504
FEATURE               Location/Qualifiers
source                1..504
                      mol_type = protein
                      organism = Zika virus
SEQUENCE: 54
IRCIGVSNRD FVEGMSGGTW VDVVLEHGGC VTVMAQDKPT VDIELVTTTV SNMAEVRSYC    60
YEASISDMAS DSRCPTQGEA YLDKQSDTQY VCKRTLVDRG WGNGCGLFGK GSLVTCAKFA    120
CSKKMTGKSI QPENLEYRIM LSVHGSQHSG MIVNDTGHET DENRAKVEIT PNSPRAEATL    180
GGFGSLGLDC EPRTGLDFSD LYYLTMNNKH WLVHKEWFHD IPLPWHAGAD TGTPHWNNKE    240
ALVEFKDAHA KRQTVVVLGS QEGAVHTALA GALEAEMDGA KGRLSSGHLK CRLKMDKLRL    300
KGVSYSLCTA AFTFTKIPAE TLHGTVTVEV QYAGTDGPCK VPAQMAVDMQ TLTPVGRLIT    360
ANPVITESTE NSKMMLELDP PFGDSYIVIG VGEKKITHHW HRSGSTIGKA FEATVRGARR    420
MAVLGDTAWD FGSVGGALNS LGKGIHQIFG AAFKSLFGGM SWFSQILIGT LLMWLGLNTK    480
NGSISLMCLA LGGVLIFLST AVSA                                          504

SEQ ID NO: 55         moltype = AA  length = 504
FEATURE               Location/Qualifiers
source                1..504
                      mol_type = protein
                      organism = Zika virus
SEQUENCE: 55
IRCIGVSNRD FVEGMSGGTW VDVVLEHGGC VTVMAQDKPT VDIELVTTTV SNMAEVRSYC    60
YEASISDMAS DSRCPTQGEA YLDKQSDTQY VCKRTLVDRG WGNGCGLFGK GSLVTCAKFA    120
CSKKMTGKSI QPENLEYRIM LSVHGSQHSG MIVNDTGHET DENRAKVEIT PNSPRAEATL    180
GGFGSLGLDC EPRTGLDFSD LYYLTMNNKH WLVHKEWFHD IPLPWHAGAD TGTPHWNNKE    240
ALVEFKDAHA KRQTVVVLGS QEGAVHTALA GALEAEMDGA KGRLSSGHLK CRLKMDKLRL    300
KGVSYSLCTA AFTFTKIPAE TLHGTVTVEV QYAGTDGPCK VPAQMAVDMQ TLTPVGRLIT    360
ANPVITESTE NSKMMLELDP PFGDSYIVIG VGEKKITHHW HRSGSTIGKA FEATVRGAKR    420
MAVLGDTAWD FGSVGGALNS LGKGIHQIFG AAFKSLFGGM SWFSQILIGT LLVWLGLNTK    480
NGSISLMCLA LGGVLIFLST AVSA                                          504

SEQ ID NO: 56         moltype = AA  length = 504
FEATURE               Location/Qualifiers
source                1..504
                      mol_type = protein
                      organism = Zika virus
SEQUENCE: 56
IRCIGVSNRD FVEGMSGGTW VDVVLEHGGC VTVMAQDKPT VDIELVTTTV SNMAEVRSYC    60
YEASISDMAS DSRCPTQGEA YLDKQSDTQY VCKRTLVDRG WGNGCGLFGK GSLVTCAKFA    120
CSKKMTGKSI QPENLEYRIM LSVHGSQHSG MIVNDTGHET DENRAKVEIT PNSPRAEATL    180
GGFGSLGLDC EPRTGLDFSD LYYLTMNNKH WLVHKEWFHD IPLPWHAGAD TGTPHWNNKE    240
ALVEFKDAHA KRQTVVVLGS QEGAVHTALA GALEAEMDGA KGRLSSGHLK CRLKMDKLRL    300
KGVSYSLCTA AFTFTKIPAE TLHGTVTVEV QYAGTDGPCK VPAQMAVDMQ TLTPVGRLIT    360
ANPVITESTE NSKMMLELDP PFGDSYIVIG VGEKKITHHW HRSGSTIGKA FEATVRGAKR    420
MAVLGDTAWD FGSVGGALNS LGKGIHQIFG AAFKSLFGGM SWFSQILIGT LLMWLGLNAK    480
NGSISLMCLA LGGVLIFLST AVSA                                          504

SEQ ID NO: 57         moltype = AA  length = 504
FEATURE               Location/Qualifiers
source                1..504
                      mol_type = protein
                      organism = Zika virus
SEQUENCE: 57
IRCIGVSNRD FVEGMSGGTW VDVVLEHGGC VTVMAQDKPT VDIELVTTTV SNMAEVRSYC    60
YEASISDMAS DSRCPTQGEA YLDKQSDTQY VCKRTLVDRG WGNGCGLFGK GSLVTCAKFA    120
CSKKMTGKSI QPENLEYRIM LSVHGSQHSG MIVNDTGHET DENRAKVEIT PNSPRAEATL    180
GGFGSLGLDC EPRTGLDFSD LYYLTMNNKH WLVHKEWFHD IPLPWHAGAD TGTPHWNNKE    240
ALVEFKDAHA KRQTVVVLGS QEGAVHTALA GALEAEMDGA KGRLSSGHLK CRLKMDKLRL    300
KGVSYSLCTA AFTFTKIPAE TLHGTVTVEV QYAGTDGPCK VPAQMAVDMQ TLTPVGRLIT    360
ANPVITESTE NSKMMLELDP PFGDSYIVIG VGEKKITHHW HRSGSTIGKA FEATVRGAKR    420
MAVLGDTAWD FGSVGGALNS LGKGIHQIFG AAFKSLFGGM SWFSQILIGT LLMWLGLNAK    480
NGSISLMCLA LGGVLIFLST AVSA                                          504

SEQ ID NO: 58         moltype = AA  length = 504
FEATURE               Location/Qualifiers
source                1..504
                      mol_type = protein
                      organism = Zika virus
SEQUENCE: 58
IRCIGVSNRD FVEGMSGGTW VDVVLEHGGC VTVMAQDKPT VDIELVTTTV SNMAEVRSYC    60
YEASISDMAS DSRCPTQGEA YLDKQSDTQY VCKRTLVDRG WGNGCGLFGK GSLVTCAKFA    120
CSKKMTGKSI QPENLEYRIM LSVHGSQHSG MIVNDTGHET DENRAKVEIT PNSPRAEATL    180
```

```
GGFGSLGLDC EPRTGLDFSD LYYLTMNNKH WLVHKEWFHD IPLPWHAGAD TGTPHWNNKE    240
ALVEFKDAHA KRQTVVVLGS QEGAVHTALA GALEAEMDGA KGRLSSGHLK CRLKMDKLRL    300
KGVSYSLCTA AFTFTKIPAE TLHGTVTVEV QYAGTDGPCK VPAQMAVDTQ TLTPVGRLIT    360
ANPVITESTE NSKMMLELDP PFGDSYIVIG VGEKKITHHW HRSGSTIGKA FEATVRGAKR    420
MAVLGDTAWD FGSVGGALNS LGKGIHQIFG AAFKSLFGGM SWFSQILIGT LLMWLGLNTK    480
NGSISLMCLA LGGVLIFLST AVSA                                          504

SEQ ID NO: 59          moltype = AA  length = 504
FEATURE                Location/Qualifiers
source                 1..504
                       mol_type = protein
                       organism = Zika virus
SEQUENCE: 59
IRCIGVSNRD FVEGMSGGTW VDVVLEHGGC VTVMAQDKPT VDIELVTTTV SNMAEVRSYC     60
YEASISDMAS DSRCPTQGEA YLDKQSDTQY VCKRTLVDRG WGNGCGLFGK GSLVTCAKFA    120
CSKKMTGKSI QPENLEYRIM LSVHGSQHSG MIVNGTGHET DENRAKVEIT PNSPRAEATL    180
GGFGSLGLDC EPRTGLDFSD LYYLTMNNKH WLVHKEWFHD IPLPWHAGAD TGTPHWNNKE    240
ALVEFKDAHA KRQTVVVLGS QEGAVHTALA GALEAEMDGA KGRLSSGHLK CRLKMDKLRL    300
KGVSYSLCTA AFTFTKIPAE TLHGTVTVEV QYAGTDGPCK VPAQMAVDMQ TLTPVGRLIT    360
ANPVITESTE NSKMMLELDP PFGDSYIVIG VGEKKITHHW HRSGSTIGKA FEATVRGAKR    420
MAVLGDTAWD FGSVGGALNS LGKGIHQIFG AAFKSLFGGM SWFSQILIGT LLMWLGLNTK    480
NGSISLMCLA LGGVLIFLST AVSA                                          504

SEQ ID NO: 60          moltype = AA  length = 504
FEATURE                Location/Qualifiers
source                 1..504
                       mol_type = protein
                       organism = Zika virus
SEQUENCE: 60
IRCIGVSNRD FVEGMSGGTW VDVVLEHGGC VTVMAQDKPT VDIELVTTTV SNMAEVRSYC     60
YEASISDMAS DSRCPTQGEA YLDKQSDTQY VCKRTLVDRG WGNGCGLFGK GSLVTCAKFA    120
CSKKMTGKSI QPENLEYRIM LSVHGSQHSG MIVNDTGHET DENRAKVEIT PNSPRAEATL    180
GGFGSLGLDC EPRTGLDFSD LYYLTMNNKH WLVHKEWFHD IPLPWHAGAD TGTPHWNNKE    240
ALVEFKDAHA KRQTVVVLGS QEGAVHTALA GALEAEMDGA KGRLSSGHLK CRLKMDKLRL    300
KGVSYSLCTA AFTFTKIPAE TLHGTVTVEV QYAGTDGPCK VLAQMAVDMQ TLTPVGRLIT    360
ANPVITESTE NSKMMLELDP PFGDSYIVIG VGEKKITHHW HRSGSTIGKA FEATVRGAKR    420
MAVLGDTAWD FGSVGGALNS LGKGIHQIFG AAFKSLFGGM SWFSQILIGT LLMWLGLNTK    480
NGSISLMCLA LGGVLIFLST AVSA                                          504

SEQ ID NO: 61          moltype = AA  length = 504
FEATURE                Location/Qualifiers
source                 1..504
                       mol_type = protein
                       organism = Zika virus
SEQUENCE: 61
IRCIGVSNRD FVEGMSGGTW VDVVLEHGGC VTVMAQDKPA VDIELVTTTV SNMAEVRSYC     60
YEASISDMAS DSRCPTQGEA YLDKQSDTQY VCKRTLVDRG WGNGCGLFGK GSLVTCAKFA    120
CSKKMTGKSI QPENLEYRIM LSVHGSQHSG MIVNDTGHET DENRAKVEIT PNSPRAEATL    180
GGFGSLGLDC EPRTGLDFSD LYYLTMNNKH WLVHKEWFHD IPLPWHAGAD TGTPHWNNKE    240
ALVEFKDAHA KRQTVVVLGS QEGAVHTALA GALEAEMDGA KGRLSSGHLK CRLKMDKLRL    300
KGVSYSLCTA AFTFTKIPAE TLHGTVTVEV QYAGTDGPCK VPAQMAVDMQ TLTPVGRLIT    360
ANPVITESTE NSKMMLELDP PFGDSYIVIG VGEKKITHHW HRSGSTIGKA FEATVRGAKR    420
MAVLGDTAWD FGSVGGALNS LGKGIHQIFG AAFKSLFGGM SWFSQILIGT LLVWLGLNTK    480
NGSISLTCLA LGGVLIFLST AVSA                                          504

SEQ ID NO: 62          moltype = AA  length = 504
FEATURE                Location/Qualifiers
source                 1..504
                       mol_type = protein
                       organism = Zika virus
SEQUENCE: 62
IRCIGVSNRD FVEGMSGGTW VDVVLEHGGC VTVMAQDKPT VDIELVTTTV SNMAEVRSYC     60
YEASISDMAS DSRCPTQGEA YLDKQSDTQY VCKRTLVDRG WGNGCGLFGK GSLVTCAKFA    120
CSKKMTGKSI QPENLEYRIM LSVHGSQHSG MIVNDTGHET DENRAKVEIT PNSPRAEATL    180
GGFGSLGLDC EPRTGLDFSD LYYLTMNNKH WLVHKEWFHD IPLPWHAGAD TGTPHWNNKE    240
ALVEFKDAHA KRQTVVVLGS QEGAVHTALA GALEAEMDGA KGRLSSGHLK CRLKMDKLRL    300
KGVSYSLCTA AFTFTKIPAE TLHGTVTVEV QYAGTDGPCK VPAQMAVDMQ TLTPVGRLIT    360
ANPVITESTE NSKMMLELDP PFGDSYIVIG VGEKKITHHW HRSGSTIGKA FEATVRGAKR    420
MAVLGDTAWD FGSVGGALNS LGKGIHQIFG AAFKSLFGGM SWFSQILIGT LLVWLGLNTK    480
NGSISLTCLA LGGVLIFLST AVSA                                          504

SEQ ID NO: 63          moltype = AA  length = 504
FEATURE                Location/Qualifiers
source                 1..504
                       mol_type = protein
                       organism = Zika virus
SEQUENCE: 63
IRCIGVSNRD FVEGMSGGTW VDVVLEHGGC VTVMAQDKPT VDIELVTTTV SNMAEVRSYC     60
YEASISDMAS DSRCPTQGEA YLDKQSDTQY VCKRTLVDRG WGNGCGLFGK GSLVTCAKFA    120
```

```
CSKKMTGKSI QPENLEYRIM LSVHGSQHSG MIVN

```
SEQUENCE: 68
ISCIGVSNRD LVEGMSGGTW VDVVLEHGGC VTEMAQDKPT VDIELVTMTV SNMAEVRSYC    60
YEASLSDMAS ASRCPTQGEP SLDKQSDTQS VCKRTLGDRG WGNGCGIFGK GSLVTCSKFT   120
CCKKMPGKSI QPENLEYRIM LPVHGSQHSG MIVNDIGHET DENRAKVEVT PNSPRAEATL   180
GGFGSLGLDC EPRTGLDFSD LYYLTMNNKH WLVHKEWPHD IPLPWHAGAD TGTPHWNNKE   240
ALVEFKDAHA KRQTVVVLGS QEGAVHTALA GALEAEMDGA KGRLFSGHLK CRLKMDKLRL   300
KGVSYSLCTA AFTFTKVPAE TLHGTVTVEV QSAGTDGPCK VPAQMAVDMQ TLTPVGRLIT   360
ANPVITESTE NSKMMLELDP PFGDSYIVIG VGDKKITHHW HRSGSTIGKA FEATVRGAKR   420
MAVLGDTAWD FGSVGGVFNS LGKGIHQIFG AAFKSLFGGM SWFSQILIGT LLVWLGLNTK   480
NGSISLTCLA LGGVMIFLST AVSA                                         504

SEQ ID NO: 69           moltype = AA   length = 498
FEATURE                 Location/Qualifiers
source                  1..498
                        mol_type = protein
                        organism = Zika virus
SEQUENCE: 69
IRCIGVSNRD FVEGMSGGTW VDVVLEHGGC VTVMAQDKPT VDIELVTTTV SNMAEVRSYC    60
YEASISDMAS DSRCPTQGEA YLDKQSDTQY VCKRTLVDRG WGNGCGLFGK GSLVTCAKFT   120
CSKKMTGKSI QPENLEYRIM LSVHGSQHSG MIVNDENRAK VEVTPNSPRA EATLGGFGSL   180
GLDCEPRTGL DFSDLYYLTM NNKHWLVHKE WFHDIPLPWH AGADTGTPHW NNKEALVEFK   240
DAHAKRQTVV VLGSQEGAVH TALAGALEAE MDGAKGRLFS GHLKCRLKMD KLRLKGVSYS   300
LCTAAFTFTK VPAETLHGTV TVEVQYAGTD GPCKVPAQMA VDMQTLTPVG RLITANPVIT   360
ESTENSKMML ELDPPFGDSY IVIGVGDKKI THHWHRSGST IGKAFEATVR GAKRMAVLGD   420
TAWDFGSVGG VFNSLGKGIH QIFGAAFKSL FGGMSWFSQI LIGTLLVWLG LNTKNGSISL   480
TCLALGGVMI FLSTAVSA                                                498

SEQ ID NO: 70           moltype = DNA   length = 26
FEATURE                 Location/Qualifiers
misc_feature            1..26
                        note = synthetic polynucleotide
misc_feature            1..26
                        note = n=inosine
source                  1..26
                        mol_type = other DNA
                        organism = synthetic construct
SEQUENCE: 70
ncncncnc ncncncncnc ncncnc                                          26

SEQ ID NO: 71           moltype = AA   length = 11
FEATURE                 Location/Qualifiers
REGION                  1..11
                        note = synthetic peptide
source                  1..11
                        mol_type = protein
                        organism = synthetic construct
SEQUENCE: 71
KLKLLLLLKL K                                                        11

SEQ ID NO: 72           moltype = DNA   length = 11840
FEATURE                 Location/Qualifiers
source                  1..11840
                        mol_type = genomic DNA
                        organism = Chikungunya virus
SEQUENCE: 72
atggctgcgt gagacacacg tagcctacca gtttcttact gctctactct gcaaagcaag    60
agattaataa cccatcatgg atcctgtgta cgtggacata gacgctgaca gcgccttttt   120
gaaggccctg caacgtgcgt accccatgtt tgaggtggaa ccaaggcagg tcacaccgaa   180
tgaccatgct aatgctagag cgttctcgca tctagctata aaactaatag agcaggaaat   240
tgaccccgac tcaaccatcc tggatatcgg cagtgcgcca gcaaggagga tgatgtcgga   300
caggaagtac cactgcgtct gcccgatgcg cagtgcggaa gatcccgaga gactcgccaa   360
ttatgcgaga aagctagcat ctgccgcagg aaaagtcctg gacagaaaca tctctggaaa   420
gatcgggac ttacaagcag taatggccgt gccagacacg agacgccaa cattctgctt    480
acacacagac gtctcatgta gacagagagc agacgtcgct atataccaag acgtctatgc   540
tgtacacgca cccacgtcgc tataccacca ggcgattaaa ggggtccgag tggcgtactg   600
ggttgggttc gacacaaccc cgttcatgta caatgccatg gcgggtgcct accccctcata   660
ctcgacaaac tgggcagatg agcaggtact gaaggctaag aacataggat tatgttcaac   720
agacctgacg gaaggtagac gaggcaagtt gtctattatg agagggaaaa agctaaaagc   780
gtgcgaccgt gtgctcgttct cagtagggtc aacgctctac ccggaaagcc gcaagctact   840
taagagctgg caccttgccat cggtgttcca tttaaagggc aaactcagct tcacatgccg   900
ctgtgataca gtggtttcgt gtgagggcta cgtcgttaag agaataacga tgagcccagg   960
cctttatgga aaaaccacag ggtatgcggt aacccaccac gcagacggat tcctgatgtg  1020
caagactacc gacacggttg acggcgaaag artgtcattc tcggtgtgca catacgtgcc  1080
ggcgaccatt tgtgatcaaa tgaccggcat ccttgctaca ccggaggatg ccaaggaact  1140
acagaagctg ttggtgggc tgaaccagag aatagtggtt aacggcagaa cgcaacggaa  1200
tacgaacacc atgaaaaatt atctgcttcc cgtggtcgcc caagcttca gtaagtgggc  1260
aaaggagtgc cggaaagaca tggaagatga aaactcctg gggtcagag aagaacact   1320
gacctgctgc tgtctatggg cattcaagaa gcagaaaca cacacggtct acaagaggcc   1380
tgatacccag tcaattcaga aggttcaggc cgagtttgac agctttgtgg taccgagtct  1440
```

```
gtggtcgtcc gggttgtcaa tcccttgag gactagaatc aaatggttgt taagcaaggt  1500
gccaaaaacc gacctgatcc catacagcgg agacgcccga gaagcccggg acgcagaaaa  1560
agaagcagag gaagaacgag aagcagaact gactcgcgaa gccctaccac ctctacaggc  1620
agcacaggaa gatgttcagg tcgaaatcga cgtggaacag cttgaggaca gagcgggcgc  1680
aggaataata gagactccga gaggagctat caaagttact gcccaaccaa cagaccacgt  1740
cgtgggagag tacctggtac tctccccgca gaccgtacta cgtagccaga agctcagtct  1800
gattcacgct ttggcggagc aagtgaagac gtgcacgcac aacggacgag cagggaggta  1860
tgcggtcgaa gcgtacgacg gccgagtcct agtgccctca ggctatgcaa tctcgcctga  1920
agacttccag agtctaagcg aaagcgcaac gatggtgtat aacgaaagag agttcgtaaa  1980
cagaaagcta caccatattg cgatgcacgg accagcccty aacaccgacg aagagtcgta  2040
tgagctggtg agggcagaga ggacagaaca cgagtacgtc tacgacgtgg atcagagaag  2100
atgctgtaag aaggaagaag ccgcaggact ggtactggtg ggcgacttga ctaatccgcc  2160
ctaccacgaa ttcgcatatg aagggctaaa aatccgccct gcctgcccat acaaaaattgc  2220
agtcataaga gtcttcggag taccgggatc tggcaagtca gctattatca agaacctagt  2280
taccaggcag gacctggtga ctagcggaaa gaaagaaaac tgccaagaaa tcaccaccga  2340
cgtgatgaga cagagaggtc tagagatatc tgcacgtacg gttgactcgc tgctcttgaa  2400
tggatgcaac agaccagtcg acgtgttgta cgtagacgag gcgtttgcgt gccactctgg  2460
aacgctactt gctttgatcg ccttggtgag accaaggcag aaagttgtac tttgtggtga  2520
cccgaagcag tgcggcttct tcaatatgat gcagatgaaa gtcaactata atcacaacat  2580
ctgcacccaa gtgtaccaca aaagtatctc caggcggtgt acactgcctg tgaccgccat  2640
tgtgtcatcg ttgcattacg aaggcaaaat gcgcactacg aatgagtaca caagccgat  2700
tgtagtggac actacaggct caacaaaacc tgaccctgga gacctcgtgt taacgtgctt  2760
cagagggtgg gttaaacaac tgcaaattga ctatcgtgga tacgaggtca tgacagcagc  2820
cgcatcccaa gggttaacca gaaaggagt ttacgcagtt agacaaaaag ttaatgaaaa  2880
cccgctctat gcatcaacgt cagagcacgt caacgtactc ctaacgcgta cggaaggtaa  2940
actggtatgg aagacacttt ccggcgaccc gtggataaga acgctgcaga acccaccgga  3000
aggaaacttc aaagcaacta ttaaggagtg ggaggtggaa catgcatcaa taatgccggg  3060
catctgcagt caccaaatga ccttcgatac attccaaaat aaagccaacg tttgttggc  3120
taagagcttg gtccctatcc tcgaaacagc gggataaaa ctaaatgata ggcagtggtc  3180
tcagataatt caagccttca aagaagacaa agcatactca cctgaagtag ccctgaatga  3240
aatatgtacg cgcatgtatg gggtggatct agacagcggg ctattttcta aaccgttggt  3300
gtctgtgtat tacgcggata accactggga taataggcct ggaggaaaa tgttcggatt  3360
taaccccgag gcagcatcca ttctagaaag aaagtatcca ttcacaaag ggaagtggaa  3420
catcaacaag cagatctgcg tgactaccag gaggatagaa gactttaacc ctaccaccaa  3480
catcataccg gccaacagga gactaccaca ctcattagtg gccgaacacc gcccagtaaa  3540
aggggaaaga atggaatggc tggttaacaa gataaacggc caccacgtgc tcctggtcag  3600
tggctataac cttgcactgc ctactaagag agtcacttgg gtagcgccgt taggtgtccg  3660
cggagcggac tacacataca acctagagtt gggtctgcca gcaacgcttg gtaggtatga  3720
cctagtggtc ataaacatcc acacaccttt tcgcatacac cattaccaac agtgcgtcga  3780
ccacgcaatg aaactgcaaa tgctcggggg tgactcattg agactgctca aaccgggcgg  3840
ctctctattg atcagagcat atggttacgc agatagaacc agtgaacgag tcatctgcgt  3900
attgggacgc aagtttagat cgtctagagc gttgaaacca ccatgtgtca ccagcaacac  3960
tgagatgttt ttcctattca gcaactttga caatggcaga aggaattcca caactcatgt  4020
catgaacaat caactgaatg cagccttcgt aggacaggtc acccgagcag gatgtgcacc  4080
gtcgtaccgg gtaaaacgca tggacatcgc gaagaacgat gaagagtgcg tagtcaacgc  4140
cgctaaccct cgcgggttac cgggtgrcgg tgtttgcaag gcagtataca aaaatggcc  4200
ggagtccttt aagaacagtg caacaccagt gggaaccgca aaaacagtta tgtgcggtac  4260
gtatccagta atccacgctg ttggaccaaa cttctctaat tattcggagt ctgaagggaa  4320
ccgggaattg gcagctgcct atcgagaagt cgcaaaggaa gtaactaggc tgggagtaaa  4380
tagtgtagct ataccctctc tctccacagg tgtatactca ggaggaaag acaggctgac  4440
ccagtcactg aaccacctct ttacagccat ggactcgacg gatgcagacg tggtcatcta  4500
ctgccgcgac aaagaatggg agaagaaaat atctgaggcc atacagatgc ggacccaagt  4560
agagctgctg gatgagcaca tctccataga ctgcgatatt gttcgcgtgc accctgacag  4620
cagcttggca ggcagaaaag gatacagcac cacggaaggc gcactgtact catatctaga  4680
agggaccgt tttcatcaga cggctgtgga tatggcggga acatatacta tgtggccaaa  4740
gcaaacagag gccaatgagc aagtctgcct atatgccctg ggggaaagta ttgaatcgat  4800
caggcagaaa tgcccggtgg atgatgcaga cgcatcatct ccccccaaaa ctgtcccgtg  4860
cctttgccgt tacgctatga ctccagaacg cgtcacccgg cttcgcatga accacgtcac  4920
aagcataatt gtgtgttctt cgtttcccct cccaaagtac aaaatagaag gagtgcaaaa  4980
agtcaaatgc tctaaggtaa tgctatttga ccacaacgtg ccatcgcgcg taagtccaag  5040
ggaatataka tcttcccagg agtctgcaca ggaggcgagt acaatcacgt cactgacgca  5100
tagtcaattc gacctaagcg ttgatggcga gatactgccc gtcccgtcag acctggatgc  5160
tgacgcccca gccctagaac cagcactaga cgacgggcg acacacacgc tgccatccac  5220
aaccggaaac cttgcgccg tgtctgattg ggtaatgagc accgtacctg tcgcgccgcc  5280
cagaagaagg cgagggagaa acctgactgt gacatgtgac gagagagaag gaatataac  5340
acccatggct agcgtccgat tcttttagggc agagctgtgt ccggtcgtac aagaaacagc  5400
gggagacgcgt gacacagcaa tgtctcttca ggcaccaccg agtaccgcca cggaaccgaa  5460
tcatccgccg atctccttcg gagccatcaag cgagacgttc cccattacat ttgggggactt  5520
caacgaagga gaaatcgaaa gcttgtcttc tgagctacta actttcggag acttcttacc  5580
aggagaagtg gatgacttga cagacagcga ctggtccacg tgctcagaca cggacgacga  5640
gttatgacta gacagggcag gtgggtatat atttctcgtcg acaccggtc caggtcattt  5700
acaacagaag tcagtacgcc agtcagtgct gccggtgaac ccctggagg aagtccacga  5760
ggagaagtgt taccccaccta agctggatga agcaaaggag caactattac ttaagaaact  5820
ccaggagaag gcatcatgg ccaacagaag caggtcatg tcgcgcaaag tagaaaacat  5880
gaaagcagca atcatccaga gactaaagag aggctgtaga ctatacttaa tgtcagagac  5940
cccaaaagtc cctacttacc ggactacata tccggcgcct gtgtactcgc ctccgatcaa  6000
cgtccgattg tccaatcccg agtccgcagt ggcagcatgc aatgagttct tagctagaaa  6060
ctatccaact gtctcatcat accaaattac cgacgagtat gatgcatatc tagacatggt  6120
ggacgggtcg gagagttgcc tggaccgagc gacattcaat ccgtcaaaac tcaggagcta  6180
```

```
cccgaaacag cacgcttacc acgcgccctc catcagaagc gctgtaccgt ccccattcca  6240
gaacacacta cagaatgtac tggcagcagc cacgaaaaga aactgcaacg tcacacagat  6300
gagggaatta cccactttgg actcagcagt attcaacgtg gagtgtttca aaaaattcgc  6360
atgcaaccaa gaatactggg aagaatttgc tgccagccct attaggataa caactgagaa  6420
tttagcaacc tatgttacta aactaaaagg gccaaaagca gcagcgctat tcgcaaaaac  6480
ccataatcta ctgccactac aggaagtacc aatggatagg ttcacagtag atatgaaaag  6540
ggacgtaaag gtgactcctg gtacaaagca tacagaggaa agacctaagg tgcaggttat  6600
acaggcggct gaacccttgg cgacagcata cctatgtggg attcacagag agctggttag  6660
gaggctgaac gccgtcctcc tacccaatgt acatacacta tttgacatgt ctgccgagga  6720
tttcgatgcc atcatagccg cacactttaa gccaggagac actgtttttgg aaacggacat  6780
agcctccttt gataagagcc aagatgattc acttgcgctt actgtcttga tgctgttaga  6840
ggatttaggg gtggatcact ccctgctgga cttgatagag gctgctttcg gagagatttc  6900
cagctgtcac ctaccgacag gtacgcgctt caagttcggc gccatgatga aatcaggtat  6960
gttcctaact ctgttcgtca acacattgtt aaacatcacc atcgccagcc gagtgctgga  7020
agatcgtctg acaaaatccg cgtgcgcggc cttcatcggc gacgacaaca taatacatgg  7080
agtcgtctcc gatgaattga tggcagccag atgtgccact tggatgaaca tggaagtgaa  7140
gatcatagat gcagttgtat ccttgaaagc cccttacttt tgtggagggt ttatactgca  7200
cgatactgtg acaggaacag cttgcagagt ggcagacccg ctaaaaaggc ttttttaaact  7260
gggcaaaccg ctagcggcag gtgacgaaca agatgaagat agaagacgag cgctggctga  7320
cgaagtgatc agatggcaac gaacagggct aattgatgag ctggagaaag cggtatactc  7380
taggtacgaa gtgcagggta tatcagttgt ggtaatgtcc atggccacct ttgcaagctc  7440
cagatccaac ttcgagaagc tcagaggacc cgtcataact ttgtacggcg gtcctaaata  7500
ggtacgcact acagctacct attttgcaga agccgacagc aagtatctaa acactaatca  7560
gctacaatgg agttcatccc aacccaaact ttttacaata ggaggtacca gcctcgaccc  7620
tggactccgc gccctactat ccaagtcatc aggcccagac cgcgccctca gaggcaagct  7680
gggcaacttg cccagctgat ctcagcagtt aataaactga caatgcgcgc ggtaccccaa  7740
cagaagccac gcaggaatcg gaagaataag aagcaaaagc aaaaacaaca ggcgccacaa  7800
aacaacacaa atcaaaagaa gcagccacct aaaaagaaac cggctcaaaa gaaaaagaag  7860
ccgggccgca gagagaggat gtgcatgaaa atcgaaaatg attgtatttt cgaagtcaag  7920
cacgaaggta aggtaacagg ttacgcgtgc ctggtggggg acaaagtaat gaaccagca   7980
cacgtaaagg ggaccatcga taacgcggac ctgaccaaac tggcctttaa gcgtcatct   8040
aagtatgacc ttgaatgcgc gcagatacco gtgcacatga agtccgacgc ttcgaagttc  8100
acccatgaga aaccggaggg gtactacaac tggcaccacg gagcagtaca gtactcagga  8160
ggccggttca ccatccctac aggtgctggc aaaccagggg acgcggcag accgatcttc  8220
gacaacaagg gacgcgtggt ggccatagtc ttaggaggag ctaatgaagg agccccgtaca 8280
gccctctcgg tggtgacctg gaataaagac attgtcacta aaatcaccc cgaggggccc   8340
gaagagtgga gtcttgccat cccagttatg tgcctgttgg caaacaccac gttccctgc   8400
tcccagcccc cttgcacgcc ctgctgctac gaaaaggaac cggaggaaac cctacgcatg  8460
cttgaggaca acgtcatgag acctgggtac tatcagctgc tacaagcatc cttaactgat  8520
tctccccacc gccagcgacg cagcaccaag gacaacttca atgtctataa agccacaaga  8580
ccatacttag ctcactgtcc cgactgtgga gaagggcact cgtgccatag tcccgtagca  8640
ctagaacgca tcagaaatga agcgacagac gggacgctga aaatccaggt ctccttgcaa  8700
atcggaataa agacggatga cagccacgat tggaccaagc tgcgttatat ggacaaccat  8760
atgccagcag acgcagagag ggcgggcta tttgtaagaa catcagcacc gtgtacgatt  8820
actgaacaa tgggacactt catcctggcc cgatgtccaa aagggaaac tctgacggtg   8880
ggattcactg acagtaggaa gattagtcac tcatgtacgc acccatttca ccacgaccct   8940
cctgtgatag gtcgggaaaa attccattcc cgaccgcagc acgtaaaga gctaccttgc   9000
agcacgtacg tgcagagcac cgccgcaact accgaggaga tagaggtaca catgcccca   9060
gacacccctg atcgcacatt aatgtcacaa cagtccggca acgtaaagat cacagtcaat  9120
ggccagacgg tgcggtacaa gtgtaattgc ggtggctcaa atgaaggact aacaactaca  9180
gacaaaggta ttaataactg caaggttgat caatgtcatg ccgcggtcac caatcacaa   9240
aagtggcagt ataactcccc tctggtcccg cgtaatgctg aacttgggga ccgaaaagga  9300
aaaattcaca tcccgtttcc gctggcaaat gtaacatgca gggtgcctaa agcaaggaac  9360
cccaccgtga cgtacgggaa aaaccaagtc atcatgctac tgtatcctga ccacccaaca  9420
ctcctgtcct accggaatat gggagaagaa ccaaactatc aagaagagtg ggtgatgcat  9480
aagaaggaag tcgtgctaac cgtgccgact gaagggctcg aggtcacgtg gggcaacaac  9540
gagccgtata agtattggcc gcagttatct acaaacggta cagcccatgg ccaccccgcat 9600
gagataattc tgtattatta tgagctgtac cccactatga ctgtagtagt tgtgtcagtg  9660
gccacgttca tactcctgtc gatggtgggt atggcagcgg gatgtgcat gtgtgacga   9720
cgcagatgca tcacaccgta tgaactgaca ccaggagcta ccgtccctt cctgcttagc  9780
ctaatatgct gcatcagaac agctaaagcg gccacatacc aagaggctgc gatatcctg   9840
tggaacgagc agcaaccttt gttttggcta caagcccta ttccgctggc agccctgatt  9900
gttctatgca actgtctgag actcttacca tgctgctgta aaacgttggc ttttttagcc  9960
gtaatgagcg tcggtgccca cactgtgagc gcgtacgaac acgtaacagt gatccgcaat 10020
acggtgggag taccgtataa gactctagtc aatagacctg gctacagccc catggtattg 10080
gagatggaac tactgtcagt cactttggag ccaaacacta tcgcttgatta catcacgtgc 10140
gagtacaaaa ccgtcatccc gtctccgtac gtgaagtgct gcggtacagc agagtgcaag 10200
gacaaaaacc tacctgacta cagctgtgaag gtcttcaccg cgtctaccg attatgtgg 10260
ggcggcgcct actgcttctg cgacgctgaa aacacggact tgagcgaagc acacgtgga  10320
aagtccgaat catgcaaaac agaatttgca tcagctcacta gggctcatac cgcatctgca 10380
tcagctaagc tccgcgtcct ttaccaagga aataacatca ctgtaactgc ctatgcaaac 10440
ggcgaccatg ccgtcacagt taaggacgcc aaattcattg tgggccaat gtcttcagcc 10500
tggacaccctt tcgacaacaa aattgtgtgt acaaaggtg acgtcatata catggactac 10560
ccgccctttg gcgcaggaag accaggacaa tttggagaca tccaaagtcg caccctgga 10620
agtaaagacg tctatgctaa tacacaactg gtactgcaga gaccggctgt gggtacggta 10680
cacgtgccat actctcaggc accatctggc tttaagtatt ggctaaaaga acgcggggcg 10740
tcgctgcagc acacagcacc atttggctgc caaatagcaa caaacccggt aagagcggtg 10800
aactgcgccg tagggaacat gcccatctcc atcgacatac cggaagcggc cttcactagg 10860
gtcgtcgacg cgccctcttt aacggacatg tcgtgcgagg taccagcctg cacccattcc 10920
```

-continued

```
tcagactttg ggggcgtcgc cattattaaa tatgcagcca gcaagaaagg caagtgtgcg   10980
gtgcattcga tgactaacgc cgtcactatt cgggaagctg agatagaagt tgaagggaat   11040
tctcagctgc aaatctcttt ctcgacggcc ttagccagcg ccgaattccg cgtacaagtc   11100
tgttctacac aagtacactg tgcagccgag tgccacccc cgaaggacca catagtcaac    11160
tacccggcgt cacataccac cctcggggtc caggacatct ccgctacggc gatgtcatgg   11220
gtgcagaaga tcacgggagg tgtgggactg gttgttgctg ttgccgcact gattctaatc   11280
gtggtgctat gcgtgtcgtt cagcaggcac taacttgaca attaagtatg aaggtatatg   11340
tgtcccctaa gagacacact gtacatagca aataatctat agatcaaagg ctacgcaac    11400
ccctgaatag taacaaaata caaaatcact aaaaattata aaaacagaaa aatacataaa   11460
taggtatacg tgtcccctaa gagacacatt gtatgtaggt gataagtata gatcaaaggg   11520
ccgaataacc cctgaatagt aacaaaatat gaaaatcaat aaaaatcata aatagaaaa    11580
accataaaca gaagtagttc aaagggctat aaaaccctg aatagtaaca aaacataaaa    11640
ttaataaaaa tcaaatgaat accataattg gcaaacggaa gagatgtagg tacttaagct   11700
tcctaaaagc agccgaactc actttgagaa gtaggcatag cataccgaac tcttccacga   11760
ttctccgaac ccacagggac gtaggagatg ttattttgtt tttaatattt caaaaaaaaa   11820
aaaaaaaaaa aaaaaaaaaa                                                11840

SEQ ID NO: 73          moltype = DNA  length = 10863
FEATURE                Location/Qualifiers
source                 1..10863
                       mol_type = genomic DNA
                       organism = Japanese encephalitis virus
SEQUENCE: 73
tttaaacagt tttttagaac ggaagataac catgactaaa aaaccaggag ggcccggtaa     60
aaaccgggct atcaatatgc tgaaacgcgg cctaccccgc gtattcccac tagtgggagt    120
gaagagggta gtaatgagct tgttggacgg cagagggcca gtacgtttcg tgctggctct   180
tatcacgttc ttcaagttta cagcattagc cccgaccaag gcgcttttag ccgatggaa    240
agcagtggaa aagagtgtgg caatgaaaca tcttactagt ttcaaacgag aacttggaac    300
actcattgac gccgtgaaca gcggggcag aaagcaaaac aaaagaggag gaaatgaagg     360
ctcaatcatg tggctcgcga gcttggcagt tgtcatagct tgtgcaggag ccatgaagtt    420
gtcgaatttc caggggaagc ttttgatgac catcaacaac acggacattg cagacgttat    480
cgtgattccc acctcaaag gagagaacag atgctgggtc cggcaatcg acgtcggcta     540
catgtgtgag gacactatca cgtacgaatg tcctaagctt accatgggca atgatccaga    600
ggatgtggat tgctggtgtg acaaccaaga agtcacgtc caatatggac ggtcacgtc     660
gaccaggcat tccaagcgaa gcaggagatc cgtgtcgtc caaacacatg ggagagttc    720
actagtgaat aaaaagagg cttggctgga ttcaacgaaa gccacacgat atctcatgaa   780
aactgagaac tggatcataa ggaatcctgg ctatgctttc ctggcggcgg tacttggctg   840
gatgcttggc agtaacaacg gtcaacgcgt ggtatttacc atcctcctgc tgttggtcgc    900
tccggcttac agttttaatt gtctggggaat gggcaatcgt gacttcatag aaggagccag    960
tggagccact tgggtggact tggtgctaga aggagatagc tgcttgacaa tcatggcaaa   1020
cgacaaacca acattggacg tccgcatgat taacatcgaa gctagccaac ttgctgaggt   1080
cagaagttac tgctatcatg cttcagtcac tgacatctcg acggtggctc ggtgcccac    1140
gactggagaa gcccacaacg agaagcgagc tgatagtagc tatgtgtgca aacaaggctt   1200
cactgaccgt gggtgggca acggatgtgg actttcggg aagggaagca ttgacacatg    1260
tgcaaaattc tcctgcacca gtaaagcgat tgggagaaca atccagccag aaaacatcaa   1320
atacgaagtt ggcatttttg tgcatggaac caccacttcg gaaaaccatg ggaattattc    1380
agcgcaagtt ggggcgtcc aggcggcaaa gtttacagta acaccccaatg ctccttcgat    1440
aaccctcaaa cttggtgact acggagaagt cacactggac tgtgagccaa ggagtggact    1500
gaacactgaa gcgttttacg tcatgaccgt ggggtcaaag tcatttctgg tccatagggaa  1560
gtggtttcat gacctcgctc tcccctggac gtcccttcg agcacagcgt ggagaaacag    1620
agaactcctc atggaatttg aaggggcgca gccacacaaa cagtccgttg ttgctcttgg   1680
gtcacaggaa ggaggcctcc atcaggcgtt ggcaggagcc atcgtggtgg agtactcaag    1740
ctcagtgaag ttaacatcag gccacctgaa atgtaggctg aaaatggaca aactggctct   1800
gaaaggcaca acctatggca tgtgtacaga aaaattctcg ttcgcgaaaa atccggcgga   1860
cactggtcac ggaacagttg tcattgaact ctcctactct gggagtgatg gccctgcaa    1920
aattccgatt gttttccgtt cgagcctcaa tgacatgacc cccgttgggc ggctggtgac   1980
agtgaacccc ttcgtcgcga cttccagtgc caactcaaag gtgctggtcg agatggaacc   2040
cccttcgga gactcctaca tcgtagttgg aaggggagac aagcagatca ccaccattg   2100
gcacaaagct ggaagcgcgc tgggcaaggc cttttcaca actttgaagg gagctcaaag   2160
actggcagcg ttgggcgaca cagcctgga ctttggctct attggagggg tcttcaactc    2220
cataggaaaa gccgttcacc aagtgtttgg tggtgccttc agaacactct tgggggaat    2280
gtcttggatc acacaaggc taatgggtgc cctactgctc tggatgggcg tcaacgcacg    2340
agaccgatca attgctttgg ccttcttagc cacagggggt gtgctcgtgt tcttagcgac    2400
caatgtgcat gctgacactg gatgtgccat tgacatcaca agaaagagaa tgatggtgg    2460
aagtggcatc ttcgtgcaca acgacgtgga agcctgggtg gataggtata aatatttgcc    2520
agaaacgccc gatcctag cgaagatcgt ccacaaagcg cacaaggaag gcgtgtgcgg    2580
agtcagatct gtcactagac tggagcacca aatgtggaa gccgtacggg acgaattgaa    2640
cgtcctgctc aaagagaatg cagtggacct cagtgtggtt gtgaacaagc ccgtgggaag   2700
atatcgctca gccccttaaac gcctatccat gacgcaagag aagtttgaaa tgggctgaa    2760
agcatggga aaaagcattc tctttgcccc ggaattggct aactccacat tgtcgtaga    2820
tggacctgag acaaggaat gccctgatga gcacagagct tggaacagca tgcaaatcga    2880
agacttcggc tttggcatca catcaacccg tgtgtggctg aaaattagag aggagcac     2940
tgacgagtgt gatggagcga tcataggcac ggctgtcaaa ggacatgtgg cagtccatag   3000
tgacttgtcg tactgattg agagtcgcta caacgacaca tggaaacttg agagggcgt     3060
cttggagag gtcaaatctt gcacttggcc agagacacac ccctttggg agatgatgt    3120
tgaggaaagt gaactcatca ttcgcacac catagccgga ccaaaagca agcacaatcg    3180
gagggaaggg tataagacac aaaaccaggg accttgggat gagaatgca tagtcttgga   3240
ctttgattat tgcccaggga caaaagtcac cattacagag gattgtggca agagaggccc   3300
ttcggtcaga accactactg acagtggaaa gttgatcact gactggtgct gtcgcagttg   3360
```

```
ctcccttccg cccctacgat tccggacaga aaatggctgc tggtacggaa tggaaatcag  3420
acctgttagg catgatgaaa caacactcgt cagatcacag gttgatgctt tcaatggtga  3480
aatggttgac ccttttcagc tgggccttct ggtgatgttt ctggccaccc aggaggtcct  3540
tcgcaagagg tggacggcca gattgaccat tcctgcggtt ttgggggccc tacttgtgct  3600
gatgcttggg ggcatcactt acactgattt ggcgaggtat gtggtgctag tcgctgctgc  3660
tttcgcagag gccaacagtg gaggagacgt cctgcacctt gctttgattg ccgtttttaa  3720
gatccaacca gcatttctag tgatgaacat gcttagcacg agatggacga accaagaaaa  3780
cgtggttctg gtcctagggg ctgccttttt ccaattggcc tcagtagatc tgcaaatagg  3840
agtccacgga atcctgaatg ccgccgctat agcatggatg attgtccgag cgatcacctt  3900
ccccacaacc tcctccgtca ccatgccagt cttagcgctt ctaactccgg ggatgagggc  3960
tctataccta gacacttaca gaatcatcct cctcgtcata gggatttgct ccctgctgca  4020
cgagaggaaa aagaccatgg caaaaaagaa aggagctgta ctcttgggct tagcgctcac  4080
atccactgga tggttctcgc ccaccactat agctgccgga ctaatggtct gcaacccaaa  4140
caagaagaga gggtggccag ctactgagtt tttgtccgga gttggattga tgtttgccat  4200
cgtaggtggt ttggccgagt tggatattga atccatgtca ataccccttca tgctggcagg  4260
tctcatggca gtgtcctacg tggtgtcagg aaaagcaaca gatatgtggc ttgaacgggc  4320
cgccgacatc agctgggaga tggatgctgc aatcacagga agcagtcgga ggctggatgt  4380
gaaactggat gatgacgagg attttcactt gattgatgat cccggtgttc catggaaggt  4440
ctgggtcctg cgcatgtctt gcattggctt agccgccctc acgccttggg ccatcgttcc  4500
cgccgctttc ggttattggc tcactttaaa aacaacaaaa agaggggcg tgttttggga  4560
cacgccatcc ccaaaacctt gctcaaaagg agacaccact acaggagtct accgaattat  4620
ggctagaggg attcttggca cttaccaggc cggcgtcgga gtcatgtacg agaatgtttt  4680
ccacacacta tggcacacaa ctagaggagc agccattatg agtgagaag gaaaattgac  4740
gccatactgg ggtagtgtga gagaagaccg catagcttac ggaggcccat ggaggtttga  4800
ccgaaaatgg aatggaacag atgacgtgca agtgatcgtg gtagaaccgg ggaaggctgc  4860
agtaaacatc cagacaaaac caggagtgtt tcggactccc ttcggggagg ttggggctgc  4920
tagtctggat tacccgcgag gaacatccgg ctcacccatt ctggattcca atggagacat  4980
tataggccta tacggcaatg gagttgagct tggcgatggc tcatacgtca gcgccatcgt  5040
gcagggtgac cgtcaggagg aaccagtccc agaagcttac ccccaaaca tgttgagaaa  5100
gagacagatg actgtgctag atttgcaccc tggttcaggg aaaaccagga aaattctgcc  5160
acaaataatt aaggacgcta tccagcagcg cctaagaaca gctgtgttgg caccgacgcg  5220
ggtggtagca gcagaaatgg cagaagcttt gagagggctc ccagtacgat atcaaacttc  5280
agcagtgcag agagagcacc aagggaatga aatagtggat gtgatgtgcc acgccactct  5340
gacccataga ctgatgtcac cgaacagagt gcccaactac aacctatttg tcatggatga  5400
agctcatttc accgaccag cagtatagc cgcacgagga tacattgcta ccaaggtgga  5460
attaggggag gcagcagcca tctttatgac agcgacccg cctggaacca cggatccttt  5520
tcctgactca aatgccccaa tccatgattt gcaagatgag ataccagaca gggcatggag  5580
cagtggatac gaatggatca cagaatatgc gggtaaaacc gtgtggtttg tggcgagcgt  5640
aaaaatgggg aatgagattg caatgtgcct ccaaagagcg gggaaaaagg tcatccaact  5700
caaccgcaag tcctatgaca cagaatacc aaaatgtaag aatggagact gggattttgt  5760
cattaccacc gacatctctg aaatgggggc caacttcggt gcgagcaggg tcatcgactg  5820
tagaaagagc gtgaaaccca ccatcttaga agagggagaa ggcagagtca tcctcggaaa  5880
cccatctccc ataaccagtg caagcgcagc tcaacggagg gcagagtag gcagaaaccc  5940
caaccaagtt ggagatgaat accactatgg ggggctacc agtgaagatg acagtaacct  6000
agcccattgg acagaggcaa agatcatgtt agacaacata cacatgccca atggactggt  6060
ggcccagctc tatggaccag agagggaaaa ggctttcaca atggatggcg aataccgtct  6120
cagaggtgaa gaaaagaaaa acttcttaga gctgcttaga acggctgacc tcccggtgtg  6180
gctggcctac aagtggcgt ccaatgcat tcagtacacc gacagaaagt ggtgttttga  6240
tgggcccgcgt acgaatgcca tactggagga caacaccgag gtagagatag tcaccccggat  6300
gggtgagagg aaaatcctca gccgagatg gcttgatgca agagtttatg cagatcacca  6360
agccctcaag tggttcaaag actttgcagc agggaagaga tcagccgtta gcttcataga  6420
ggtgctcggt cgcatgcctg agcatttcat gggaaagacg cgggaagctt tagacaccat  6480
gtacttggtt gcaacggctg agaaaggtgg gaaagcacac cgaatggctc tcgaagagct  6540
gccagatgca ctgaaaacca tcacacttat tgtcgccatt actgtgatga caggaggatt  6600
cttcctacta atgatgcagc gaaaggtat agggaagatg ggtcttggag ctctagtgct  6660
cacgctagct accttcttcc tgtgggcggc agaggttcct ggaaccaaaa tagcagggac  6720
cctgctgatc gccctgctgc tgatggtggt tctcatccca gaaccggaaa acagaggtc  6780
acagacagat aaccaactgg cggtgtttct catctgtgtc ttgaccgtgg ttggagtggt  6840
ggcagcaaac gagtacggga tgctagaaaa aaccaaagca gatctcaaga gcatgtttgg  6900
cggaaagacg caggcatcag gactgactgg attgccaagc atggcactgg acctgcgtcc  6960
agccacagcc tggcactgt atggggggag cacagtcgtg ctaaccctc ttctgaagca  7020
cctgatcacg tcggaatacg tcaccacatc gctagcctca attaactcac aagctggctc  7080
attattcgtc ttgccacgag gcgtgccttt taccgaccta gacttgaccg ttggcctcgt  7140
cttccttggc tgttgggtc aaatcaccct ccaaacgttt ctgacagcca tggttctggc  7200
gacacttcac tatgggtaca tgctcccctg atggcaagca gaagcactca gggctgccca  7260
gagaaggaca gcgctggaa taatgaagaa tgccgttgtt gacggaatgg tcgccactga  7320
tgtgcctgaa ctgaaagga ctactcctct gatgcaaaag aaagtcggac aggtgctcct  7380
catagggta agcgtggcag cgttcctcgt caacccctaat gtcaccactg tgagagaagc  7440
aggggtgttg gtgacgccg ctactgagagc aatggagcca gtgccgtttg  7500
gaattccacc acagccacgg gactctgcca tgtcatgcga ggtagtacc tggctggagg  7560
ctccattgct tggactctca tcaagaacgc tgataagccc tccttgaaaa ggggaaggcc  7620
tgggggcagg acgctagggg agcagtgaa ggaaaaacta aatgccatga gcagagaaga  7680
gttttttaaa taccggagag aggccataat cgaggtggac cgcactgaag cacgcagggc  7740
cagacgtgaa aataacatag tgggaggaca tccggtttcg cggcctcag caaaactccg  7800
ttggctcgtg gagaaaggat ttgtctcgcc aataggaaaa gtcattgatc tagggtgtgg  7860
gcgtggagga tggagctact acgcagcaac cctgaagaag gtccaggaag tcagaggata  7920
cacgaaaggt gggcgggac atgaagaacc gatgctcatg cagagctacg gctgaacct  7980
ggtctccctg aagagtggag tggacgtgtt ttacaaacct tcagagccca gtgacaccct  8040
gttctgtgac ataggggaat cctccccaag tccagaagta gaagaacaac gcacactacg  8100
```

```
cgtcctagag atgacatctg actggttgca ccgaggacct agagagttct gcattaaagt   8160
tctctgccct tacatgccca aggttataga aaaaatggaa gttctgcagc gccgcttcgg   8220
aggtgggcta gtgcgtctcc ccctgtcccg aaactccaat cacgagatgt attgggttag   8280
tggagccgct ggcaatgtgg tgcacgctgt gaacatgacc agccaggtac tactggggcg   8340
aatggatcgc acagtgtgga gagggccaaa gtatgaggaa gatgtcaacc tagggagcgg   8400
aacaagagcc gtgggaaagg gagaagtcca tagcaatcag gagaaaatca agaagagaat   8460
ccagaagctt aaagaagaat tcgccacaac gtggcacaaa gaccctgagc atccataccg   8520
cacttggaca taccacggaa gctatgaagt gaaggctact ggctcagcca gctctctcgt   8580
caacggagtg gtgaagctca tgagcaaacc ttgggacgcc attgccaacg tcaccaccat   8640
ggccatgact gacaccaccc cttttggaca gcaaagagtt ttcaaggaga agttgacac   8700
gaaggctcct gagccaccag ctggagccaa ggaagtgctc aacgagacca ccaactggct   8760
gtgggcccac ttgtcacggg aaaaaagacc ccgcttgtgc accaaggaag aattcataaa   8820
gaaagtcaac agcaacgcgg ctcttggagc agtgttcgct gaacagaatc aatggagcac   8880
ggcgcgtgag gctgtggatg acccgcggtt ttgggagaga gttgatgaag agagggaaaa   8940
ccatctgcga ggagagtgtc acacatgtat ctacaacatg atgggaaaaa gagaagaaga   9000
gcctggagag tttggaaaag ctaaaggaag cagggccatt tggttcatgt ggcttggagc   9060
acggtatcta gagtttgaag cttttgggtt cctgaatgaa gaccattggc tgagccgaga   9120
gaattcagga ggtggagtgg aaggctcagg cgtccaaaag ctgggataca tcctccgtga   9180
catagcagga aagcaaggag ggaaaatgta cgctgatgat accgccgggt gggacactag   9240
aattaccaga actgatttag aaaatgaagc taaggtactg gagctcctag acggtgaaca   9300
ccgcatgctc gcccgagcca taattgaact gacttacagg cacaaagtgg tcaaggtcat   9360
gagacctgca gcagaaggaa agaccgtgat ggacgtgata tcaagagaag atcaaagggg   9420
gagtggacag gtggtcactt atgctcttaa cactttcacg aacatcgctg tccagctcgt   9480
caggctgatg gaggctgagg gggtcattgg accacaacac ttggaacagc tacctaggaa   9540
aaacaagata gctgtcagga cctggctctt tgagaatgga gaggagagag tgaccaggat   9600
ggcgatcagc ggagacgact gtgtcgtcaa gccgctggac acagattcg ccacagccct   9660
ccacttcctc aacgcaatgt caaaggtcag aaaagacatc caggaatgga gccttcgca   9720
tggctggcac gattggcagc aagttcccct ctgctctaac cattttcagg agattgtgat   9780
gaaagatgga aggagtatag ttgtcccgtg cagaggacag gatgagctga taggcagggc   9840
tcgcatctct ccaggagctg gatggaatgt gaaggacaca gcttgcctgg ccaaagcata   9900
tgcacagatg tggcactcc tatacttcca tcgcagggac ttgcgtctca tggcaaatgc   9960
gatttgctca gcagtgccag tggattgggt gcccacaggc aggacatcct ggtcaataca   10020
ctcgaaagga gagtggatga ccacggaaga catgctgcag gtctggaaca gagtctggat   10080
tgaagaaaat gaatggatga tggacaagac tccaatcaca agctggacag acgttccgta   10140
tgtgggaaag cgtgaggaca tctggtgtgg cagcctcatc ggaacgcgat ccagagcaac   10200
ctgggctgag aacatctatg cggcgataaa ccaggttaga gctgtcattg ggaaagaaaa   10260
ttatgttgac tacatgacct cactcaggag atacgaagac gtcttgatcc aggaagacag   10320
ggtcatctag tgtgatttaa ggtagaaaag tagactatgt aaataatgta aatgagaaaa   10380
tgcatgcata tggagtcagg ccagcaaaag ctgccaccgg ggtcactgg  10440
cctgcgtctc agtccagga ggactgggtt aacaaatctg acaacagaaa gtgagaagc   10500
cctcagaacc gtctcggaag taggtccctg ctcactggaa gttgaaagac caacgtcagg   10560
ccacaaattt gtgccactcc gctagggagt gcggcctgcg cagccccagg aggactgggt   10620
taccaaagcc gttgaggccc ccacggccca agcctcgtct aggatgcaat agcgaggtg   10680
taaggactag aggttagagg agaccccgtg gaaacaacaa catgcggccc aagcccctc   10740
gaagctgtag aggaggtgga aggactagag gttagaggag accccgcatt tgcatcaaac   10800
agcatattga cacctgggaa tagactggga gatcttctgc tctatctcaa catcagctac   10860
tag                                                                 10863
```

| SEQ ID NO: 74 | moltype = DNA length = 10977 |
|---|---|
| FEATURE | Location/Qualifiers |
| source | 1..10977 |
| | mol_type = genomic DNA |
| | organism = Japanese encephalitis virus |

SEQUENCE: 74
```
agaagtttat ctgtgtgaac ttcttggctt agtatcgtag agaagaatcg agagattagt   60
gcagtttaaa cagttttta gaacggaaga taaccatgac taaaaaacca ggagggcccg   120
gtaaaaaccg ggctatcaat atgctgaaac gcggcctacc ccgcgtattc ccactagtgg   180
gagtgaagag ggtagtaatg agcttgttgg acggcagagg gccagtacgt ttcgtgctgc   240
ctcttatcac gttcttcaag tttacagcat tagccccgac caaggcgctt tcaggccgat   300
ggaaagcagt ggaaaagagt gtggcaatga aacatcttac tagtttcaaa cgagaacttg   360
gaacactcat tgacgccgtg aacaagcggg gcagaaagca aaacaaaaga ggaggaaatg   420
aaggctcaat catgtggctc gcgagcttgg cagttgtcat agcttgtgca ggagccatga   480
agttgtcgaa tttccagggg aagcttttga tgaccatcaa caacacgac attgcagacg   540
ttatcgtgat tccacctca aaaggagaga acagtgcgtg ggtccgggca atcgacgtgg   600
gctacatgtg tgaggacact atcacgtacg aatgtcctaa gcttaccatg gcaatgatc   660
cagaggatgt ggattgctgg tgtgacaacc aagaagtcta cgtccaatat ggacggtgca   720
cgcggaccag gcattccaag cgaagcagga tccgtgtc ggtccaaaca catggggaga   780
gttcactagt gaataaaaaa gaggcttggc tggattcaac gaaagccaca cgatatctca   840
tgaaactgga gaactggatc ataaggaatc ctggctatgc tttcctggcg gcggtacttg   900
gctggatgct tggcagtaac aacggtcaac gcgtggtatt taccatcctc ctgctgttgg   960
tcgctccggc ttacagtttt aattgtctgg gaatgggcaa tcgtgacttc atagaaggag  1020
ccagtggagc cacttgggtg gacttggtgc tagaaggaga cagctgcttg acaatcatg   1080
caaacgacaa accaaccattg gacgtccgca tgattaacat cgaagctagc caacttgctg  1140
aggttactga ttactgctat catgcttcag tcactagaat ctgacggtg gtcggttcg   1200
ccacgactgt agaagcccac aacgagaagc gagctgatag tagctatgtg tgcaaacaag  1260
gcttcactga ccgtgggtgg ggcaacggat tggatttttt cgggaaggga agcattgaca  1320
catgtgcaaa attctcctgc accagtaaag cgattgggaa acaatccag ccagaaaaca  1380
tcaaatacaa agttggcatt tttgtgcatg gaaccaccac ttcggaaaac catggggaatt  1440
attcagcgca agttggggcg tcccaggcgg caaagttac agtaacaccc aatgctcctt  1500
```

```
cggtagccct caaacttggt gactacgag aagtcacact ggactgtgag ccaaggagtg   1560
gactgaacac tgaagcgttt tacgtcatga ccgtggggtc aaagtcattt ctggtccata   1620
gggagtggtt tcatgacctc gctctcccct ggacgtcccc ttcgagcaca gcgtggagaa   1680
acagagaact cctcatggaa tttgaagggg cgcacgccac aaaacagtcc gttgttgctc   1740
ttgggtcaca ggaaggaggc ctccatcatg cgttggcagg agccatcgtg gtggagtact   1800
caagctcagt gatgttaaca tcaggccacc tgaaatgtag gctgaaaatg gacaaactgg   1860
ctctgaaagg cacaacctat ggcatgtgta cagaaaaatt ctcgttcgcg aaaaatccgg   1920
tggacactgg tcacggaaca gttgtcattg aactctccta ctctgggagt gatggcccct   1980
gcaaaattcc gattgtttcc gttgcgagcc tcaatgacat gacccccgtt gggcggctgg   2040
tgacagtgaa ccccttcgtc gcgacttcca gtgccaactc aaaggtgctg gtcgagatgg   2100
aaccccccctt cggagactcc tacatcgtag ttggaagggg agacaagcag atcaaccacc   2160
attggcacaa agctggaagc acgctgggca aggccttttc aacaactttg aagggagctc   2220
aaagactggc agcgttgggc gacacagcct gggactttgg ctctattgga ggggtcttca   2280
actccatagg aagagccgtt caccaagtgt ttggtggtgc cttcagaaca ctcttttggg   2340
gaatgtcttg gatcacacaa gggctaatgg tgccctact gctctggatg ggcgtcaacg   2400
cacgagaccc atcaattgct ttggccttct tagccacagg aggtgtgctc gtgttcttag   2460
cgaccaatgt gcatgctgac actggatgtg ccattgacat cacaagaaaa gagatgagat   2520
gtggaagtgg catcttcgtg cacaacgacg tggaagcctg ggtggatagg tataaatatt   2580
tgccagaaac gcccagatcc ctagcgaaga tcgtccacaa agcgcacaag gaaggcgtgt   2640
gcggagtcag atctgtcact agactggagc accaaatgtg gaagccgta agggacgaat   2700
tgaacgtcct gctcaaagag aatgcagtgg acctcagtgt ggttgtgaac aagcccgtgg   2760
gaagatatcg ctcagcccct aaacgcctat ccatgacgca aggaagttt gaaatgggct   2820
ggaaagcatg gggaaaaagc atcctctttg ccccggaatt ggctaactcc acatttgtcg   2880
tagatggacc tgagacaaag gaatgccctg atgagcacag agcttggaac agcatgcaaa   2940
tcgaagactt cggcttggc atcacatcaa cccgtgtgtg gctgaaaatt agagaggaga   3000
gcactgacga gtgtgatgga gcgatcatag gcacggctgt caaaggacat ggtgcagtcc   3060
atagtgactt gtcgtactgg attgagagtc gctacaacga cacatggaaa cttgagaggg   3120
cagtctttgg agaggtcaaa tcttgcactt ggccagagac acacacccctt tggggagatg   3180
atgttgagga aagtgaactc atcattccgc acaccatagc cggaccaaaa agcaagcaca   3240
atcggaggga agggtataag acacaaaacc agggaccttg ggatgagaat ggcatagtcct   3300
tggactttga ttattgccca gggacaaaag tcaccattac agaggattgt agcaagagag   3360
gcccttcggt cagaaccact actgacagtg gaaagttgat cactgactgg tgctgtcgca   3420
gttgctccct tccgccccta cgattccgga cagaaaatgg ctgctggtac ggaatggaaa   3480
tcagacctgt tatgcatgat gaaacaacac tcgtcagatc acaggttcat gctttcaaag   3540
gtgaaatgat tgacccttttt cagctgggcc ttctggtgat gtttctggcc acccaggaag   3600
tccttcgcaa gaggtggacg gccagattga ccattcctgc ggttttgggg gtcctacttg   3660
tgctgatgct tgggggtatc acttacactg atttggcgag gtatgtggtg ctagtcgctg   3720
ctgctttcgc agaggccaac agtggaggag acgtcctgca ccttgctttg attgctgttt   3780
ttaagatcca accagcattt ttagtgatga acatgcttag cacgagatgg acgaaccaag   3840
aaaacgtggt tctggtccta ggggctgcct ttttccaatt ggcctcagta gatctgcaaa   3900
taggagtcca cggaatcctg aatgccgcg ctatagcatg gatgattgtc cgagcgatca   3960
ccttcccccac aacctcctcc gtcaccatgc cagtcttagc gcttctaact ccggggatga   4020
gggtctctata cctagacact tacagaatca tcctcctcgt cataggggatt tgctccctgc   4080
tgcacgagag gaaaaagacc atggcgaaaa agaaggacgt tgtactcttg ggcttagcgc   4140
tcacatccac tggatggttc tcgcccacca ctatagctgc cggactaatg gtctgcaacc   4200
caaacaagaa gagagggtgg ccagctactg agttttttgtc ggcagttgga ttgatgtttg   4260
ccatcgtagg tggtttggcc gagttggaa ttgaatccat gtcaataccc ttcatgctgg   4320
caggtctcat ggcagtgtcc tacgtggtgt caggaaaagc aacagatatg tggcttgaac   4380
gggccgccga catcagctgg gatatgggtg ctgcaatcac aggaagcagt cggaggctgg   4440
atgtgaaact ggatgatgac ggagattttc acttgattga tgatcccggt gttccatgga   4500
aggtctggt cctgcgcatg tcttgcattg gcttagccgc cctcacgcct tgggccatcg   4560
ttcccgccgc tttcgttat tggctcactt taaaaacaac aaaaagaggg ggcgtgtttt   4620
gggcacgcc atcccaaaa ccttgctcaa aaggagacac cactcagga gtctaccgaa   4680
ttatggctag agggattctt ggcacttacc aggccggcgt cggagtcatg tacgagaatg   4740
ttttccacac actatggcac acaactagag gagcagccat tgtgagtgga gaaggaaaat   4800
tgacgccata ctggggtagt gtgaagaaag accgcatagc ttacgaggc ccatggaggt   4860
ttgaccgaaa atgaatgga acagatacg tgcaagtgat cgtggtagaa ccggggaagg   4920
gcgcagtaaa catccagaca aaaccaggag tgtttcggac tcccttcggg gaggttgggg   4980
ctgttagtct ggattacccg cgaggaacat ccggctcacc cattctggat tccaatggag   5040
acattatagg cctatacggc aatggagttg agcttggcga tggctcatac gtcagcgcca   5100
tcgtgcaggg tgaccgtcag gaggaaccag tcccagaagc ttacacccca aacatgttga   5160
gaaagagaca gatgactgtg ctagatttgc accctggttc agggaaaacc aggaaaattc   5220
tgccacaaat aattaaggac gctatccagc agcgcctaag aacagctgtg ttggcaccga   5280
cgcgggtggt agcagcagaa atgcagaaa ctttgagagg gctccagta cgatatcaaa   5340
cttcagcagt gcagagagag caccaaggga tgaaatagt ggatgtgatg tgccacgcca   5400
ctctgaccca tagactgatg tcaccgaaca gagtgcccaa ctacaaccta tttgtcatgg   5460
atgaagctca tttcaccgac ccagccagta gccgcacg aggatacatt gctaccaagg   5520
tggaattagg ggaggcagca gccatcttta tgacagcgac cccgcctgga accacggatc   5580
cttttcctga ctcaaatgcc caatccatg atttgcaatga tgagatacca gacagggcat   5640
ggagcagtgg atacgaatgg atcacagaat atgcgggtaa aaccgtgtgg tttgtggcga   5700
gcgtaaaaat ggggaatgag attgcaatgt gcctccaaag agcggggaaa aagtcatcc   5760
aactcaaccg caagtcctat gacacagaat acccaaaatg taagaatgga gactgggatt   5820
ttgtcattac caccgcacatc tctgaaatgg gggccaactt cggtgcgagc agggtcatcg   5880
actgtagaaa gagcgtgaaa cccaccatct tagaagaggg agtcatcctcg             5940
gaaacccatc tcccataacc agtgcaagcg cagctcaacg gagggccaga gtaggcagaa   6000
acccccaatca agttggagat gaataccact atggggggc taccagtgaa gatgacagta   6060
acctagccca ttgacagag gcaaagatca tgttagacaa catacacatg cccaatggac   6120
tggtggccca gctctatgga ccagagaggg aaaaggctt cacaatggat ggcgaatacc   6180
gtctcagagg tgaagaaaag aaaaacttct tagagctgct taggacggct gacctcccgg   6240
```

```
tgtggctggc ctacaaggtg gcgtccaatg gcattcagta caccgacaga agtggtgtt   6300
ttgatgggcc gcgtacgaat gccatactgg aggacaacac cgaggtagag atagtcaccc   6360
ggatgggtga gaggaaaatc ctcaagccga gatggcttga tgcaagagtt tatgcagatc   6420
accaggccct caagtggttc aaagactttg cagcagggaa gagatcagcc gttagcttca   6480
tagaggtgct cggtcgcatg cctgagcatt tcatggaaga gacgcgggaa gctttagaca   6540
ccatgtactt ggttgcaacg gctgagaaag gtgggaaagc acaccgaatg gctctcgaag   6600
agctgccaga tgcactggaa accatcacac ttattgtcgc cattactgtg atgacaggag   6660
gattcttcct actaatgatg cagcgaaagg gtataggaa atgggtctt ggagctctag     6720
tgctcacact agctaccttc ttcctgtggg cggcagaggt tcctggaacc aaaatagcag   6780
ggaccctgct gatcgccctg ctgctgatgg tggttctcat cccagaaccg gaaaaacaga   6840
ggtcacagac agataaccaa ctgccggtgt ttctcatctg tgtcttgacc gtggttggag   6900
tggtggcagc aaacgagtac gggatgctag aaaaaaccaa agcggatctc aagagcatgt   6960
ttggcggaaa gacgcaggca tcaggactga ctggattgcc aagcatggca ctggacctgc   7020
gtccagccac agcctgggca ctgtatgggg ggagcacagt cgtgctaacc cctcttctga   7080
agcacctgat cacgtcggaa tacgtcacca catcgctagc ttcaattaac tcacaagctg   7140
gctcattatt cgtcttgcca cgaggcgtgc cttttaccga cctagacttg actgttggcc   7200
tcgtcttcct tggctgttgg ggtcaagtca ccctcacaac gtttctgaca gccatggttc   7260
tggcgacact tcactatggg tacatgtcc ctggatggca agcagaagca ctcagggctg    7320
cccagagaag gacagcggct ggaataatga agaatgccgt tgttgacgga atggtcgcca   7380
ctgatgtgcc tgaactggaa aggactactc tctgatgca aaagaaagtc ggacaggtgc    7440
tcctcatagg ggtaagcgtg gcagcgttcc tcgtcaaccc taatgtcacc actgtgagag   7500
aagcagggt gttggtgacg gcggctacgc ttactttgtg ggaccgcact gaagcacgca    7560
tttggaattc caccacagcc acgggactct gccatgtcat gcgaggtagc tacctggctg   7620
gaggctccat tgcttggact ctcatcaaga acgctgataa gccctccttg aaaagggaa    7680
ggcctggggg caggacgcta ggggagcagt ggaaggaaaa actaaatgcc atgagtagag   7740
aagagttttt taaataccgg agagaggcca taatcgaagt ggaccgcact gaagcacgca    7800
gggccagacg tgaaaataac atagtgggag gacatccggt ttcgcgaggc tcagcaaaac   7860
tccgttggct cgtggagaaa ggatttgtct cgccaatagg aaaagtcatt gatctagggt   7920
gtgggcgtgg aggatggagc tactacgcag caaccctgaa gaaggtccag gaagtcagag   7980
gatacacgaa aggtggggcg ggacatgaaa aaccgatgct catgcagagc tacggctgga   8040
acctggtctc cctgaagagt ggagtggacg tgttttacaa accttcagag cccagtgata   8100
ccctgttctg tgacataggg gaatcctccc caagtccaga agtagaagaa caacgcacac   8160
tacgcgtcct agagatgaca tctgactggt tgcaccgagg acctagagag ttctgcatta   8220
aagttctctg cccttacatg cccaaggtta tagaaaaaat ggaagttctg cagcgtcgct   8280
tcggaggtgg gctagtgcgt ctccccctgt cccgaaactc caatcacgag atgtattggg   8340
ttagtggagc cgctggcaat gtggtgcacg ctgtgaacat gaccagccag gtattactgg   8400
ggcgaatgga tcgcacagtg tggagagggc aaaagtatga ggaagatgtc aacctaggga   8460
gcggaacaag agccgtggga aagggagaag tccatagcaa tcaggagaaa atcaagaaga   8520
gaatccagaa gcttaaagaa gaattcgcca caacgtggca caaagaccct gagcatccat   8580
accgcacttg gacataccac ggaagctatg aagtgaaggc tactggctca gccagctctc   8640
tcgtcaacgg agtggtgaag ctcatgagca aaccttggga cgccattgcc aacgtcacca   8700
ccatggccat gactgacacc acccccttttg gacagcaaag agttttcaag agagaagttg   8760
acacgaaggc tcctgagcca ccagctggga ccaaggaagt gctcaacgag accaccaact   8820
ggctgtgggc ctacttgtca cgggaaaaaa gaccccgctt gtgcaccaag gaagaattca   8880
ttaagaaagt taacagcaac gcggctcttg gagcagtgtt cgctgaacag aatcaatgga   8940
gcacggcgcg tgaggctgtg gatgaccgc ggttttggga gatggttgat gaagagaggg     9000
aaaaccatct gcgaggagag tgtcacacat gtatctacaa catgatggga aaaagagaa    9060
agaagcctgg agagtttgga aaagctaaag gaagcagggc catttggttc atgtggcttg   9120
gagcacggta tctagagttt gaagcttggg ggttcctgaa tgaagaccat tggctgagcc   9180
gagagaattc aggaggtgga gtggaaggct caggcgtcca aaagctggga tacatcctcc   9240
gtgacatagc aggaaagcaa ggagggaaaa tgtacgctga tgataccgcc gggtgggaca   9300
ctagaattac cagaactgat ttagaaaatg aagctaaggt actggagctc ctagacggtg   9360
aacaccgcat gctcgcccga gccataattg aactgactta caggcacaaa gtggtcaagg   9420
tcatgagacc tgcagcagaa ggaaagaccg tgatggacgt gatatcaaga gaagatcaaa   9480
gggggagtgg acaggtggtc acttatgctc ttaacacttt cacgaacatc gctgtccagc   9540
tcgtcaggct gatggaggct gaggggtca ttggaccaca acacttggaa catctaccta    9600
ggaaaaacaa gatagctgtc aggacctggc tctttgagaa tggagaggag agagtgacca   9660
ggatggcgat cagcggagac gactgtgccg tcaaaccgct ggacgacaga ttcgccacag   9720
ccctccactt cctcaacgca atgtcaaagg tcagaaaaga catccaggaa tggaagcctt   9780
cgcatggctg gcacgattgg cagcaagttc ccttctgttc taaccatttt caggagattg   9840
tgatgaaaga tggaaggagt atagttgtcc cgtgcagagg acaggatgag ctgatagca    9900
gggctcgcat ctctcctgga gctggatgga atgtgaagga cacagcttgc ctggccaaag   9960
catatgcaca gatgtggcta ctcctatact tccatcgcag ggacttgcgt ctcatggcaa   10020
atgcgatttg ctcagcagtg ccagtagatt gggtgcccac ggcaggaaca tcctggtcaa   10080
tacactcgaa aggagagtgg atgaccacgg aagacatgct gcaggtctgg aacagagttt   10140
ggattgaaga aaatgaatgg atgatggaca agactccaat cacaagctgg acagacgttc   10200
cgtatgtggg aaagcgcgag gacatctggt gtggcagcct catcggaacg cgatccagag   10260
caacctgggc tgagaacatc tatgcggcga taaaccaggt tagagctgtc attgggaaag   10320
aaaattatgt tgactacatg acctcactca gagatacga agacgtcttg atccaggaag   10380
acagggtcat ctagtgtgat ttaaggtaga aaagtagact atgtaaacaa tgtaaatgag   10440
aaaatgcatg catatggagt caggccagca aaagctgcca ccggatactg ggtagacggt   10500
gctgcctgcg tctcagtccc aggaggactg ggttaacaaa tctgacaaca gaaagtgaga   10560
aagccctcag aaccgtctcg gaagtaggtc cctgctcact ggaagttgaa agaccaacgt   10620
caggccacaa atttgtgcca ctccgctagg gagtgcggcc tgcgcagccc caggaggact   10680
gggttaccaa agccgttgag gccccacgg cccaagcctc gtctaggatg caatagacga    10740
ggtgtaagga ctagaggtta gaggagaccc cgtggaaaca acaacatgcg gcccaagccc   10800
cctcgaagct gtagaggagg tggaaggact agaggttaga ggagacccgc catttgcatc   10860
aaacagcata ttgacacctg gaatagact gggagatctt ctgctctatc tcaacatcag   10920
ctactaggca cagagcgccg aagtatgtag ctggtggtga ggaagaacac aggatct       10977
```

```
SEQ ID NO: 75           moltype = DNA   length = 10976
FEATURE                 Location/Qualifiers
source                  1..10976
                        mol_type = genomic DNA
                        organism = Japanese encephalitis virus
SEQUENCE: 75
agaagtttat ctgtgtgaac ttcttggctt agtatcgtag agaagaatcg agagattagt   60
gcagtttaaa cagttttta gaacggaaga taaccatgac taaaaaacca ggagggcccg   120
gtaaaaaccg ggctatcaat atgctgaaac gcggcctacc ccgcgtattc ccactagtgg   180
gagtgaagag ggtagtaatg agcttgttgg acggcagagg gccagtacgt ttcgtgctgg   240
ctcttatcac gttcttcaag tttacagcat tagccccgac caaggcgctt tcaggccgat   300
ggaaagcagt ggaaaagagt gtggcaatga aacatcttac tagtttcaaa cgagaacttg   360
gaacactcat tgacgccgtg aacaagcggg gcagaaagca aacaaaaga ggaggaaatg   420
aaggctcaat catgtggctc gcgagcttgg cagttgtcat agcttgtgca ggagccatga   480
agttgtcgaa tttccagggg aagctttga tgaccatcaa caacacggac attgcagacg   540
ttatcgtgat tcccacctca aaaggagaga acagatgctg ggtccgggca atcgacgtcg   600
gctacatgtg tgaggacact atcacgtacg aatgtcctaa gcttaccatg ggcaatgatc   660
cagaggatgt ggattgctgg tgtgacaacc aagaagtcta cgtccaatat ggacggtgca   720
cgcggaccag gcattccaag cgaagcagga gatccgtgtc ggtccaaaca catggggaga   780
gttcactagt gaataaaaa gaggcttggc tggattcaac gaaagccaca cgatatctca   840
tgaaaactga gaactggatc ataaggaatc ctggctatgc tttcctggcg gcggtacttg   900
gctggatgct tggcagtaac aacggtcaac gcgtggtatt taccatcctc ctgctgttga   960
tcgctccggc ttacagtttt aattgtctgg gaatgggcaa tcgtgacttc atagaaggag  1020
ccagtggagc cacttgggtg gacttggtgc tagaaggaga cagctgcttg acaatcatgg  1080
caaacgacaa accaacattg gacgtccgca tgattaacat cgaagctagc caacttgctg  1140
aggtcagaag ttactgctat catgcttcag tcactgacat ctcgacggtg ctcggtgcc   1200
ccacgactgg agaagcccac aacgagaagc gagctgatag tagctatgtg tgcaaacaag  1260
gcttcactga ccgtgggtgg ggcaacggat gtggattttt cggaaggga agcattgaca  1320
catgtgcaaa attctcctgc accagtaaag cgattgggga aacaatccag ccagaaaaca  1380
tcaaatacaa agttggcatt tttgtgcatg gaaccaccac ttcggaaaac catgggaatt  1440
attcagcgca agttggggcg tcccaggcgg caaagtttac agtaacaccc aatgctcctt  1500
cggtagccct caaacttggt gactacgag aagtcacact ggactgtgag ccaaggagtg  1560
gactgaacac tgaagcgttt tacgtcatga ccgtggggtc aaagtcattt ctggtccata  1620
gggagtggtt tcatgacctc gctctcccct ggacgtcccc ttcgagcaca gcgtggagaa  1680
acagagaact cctcatggaa tttgaagggg cgcacgccac aaaacagtcc gttgttgctc  1740
ttgggtcaca ggaaggaggc ctccatcatg cgttggcagg agccatccgt gtggagtact  1800
caagctcagt gatgttaaca tcaggccacc tgaaatgtag gctgaaaatg gacaaactgg  1860
ctctgaaagg cacaacctat ggcatgtgta cagaaaaatt ctcgttcgcg aaaaatccgg  1920
tggacactgg tcacgaaca gttgtcattg aactctccta ctctgggagt gatgccccct  1980
gcaaaattcc gattgtttcc gttgcgagcc tcaatgacat gaccccgtt gggcggctgg  2040
tgacagtgaa cccccttcgt cgcgacttcc agtgccaactc aaaggtgctg gtcgagatgg  2100
aacccccctt cggagactcc tacatcgtag ttggaagggg agacaagcag atcaaccacc  2160
attggcacaa agctgaagc acgctgggca aggccttttc aacaactttg aagggagctc  2220
aaagactggc agcgttgggc gacacagcct gggactttgg ctctattgga ggggtcttca  2280
actccatagg aagagccgtt caccaagtgt tggtgatgc cttcagaaca ctctttgggg  2340
gaatgtcttg gatcacacaa gggctaatgg gtgcctact gctctgatgg gctgtcaacg  2400
cacgagaccg atcaattgct ttggccttct tagccacagg aggtgtgctc gtgttcttag  2460
cgaccaatgt gcatgctgac actggatgtg ccattgacat cacaagaaaa gagatgagat  2520
gtggaagtgg catcttcgtg cacaacgacg tggaagcctg ggtggatagg tataaatatt  2580
tgccagaaac gcccagatcc ctagcagaga tcgtccacaa agccacagg aaggcgtgt   2640
gcggagtcag atctgtcact agactggagc accaaatgtg ggaagccgta agggacgaat  2700
tgaacgtcct gctcaaagag aatgcagtgg acctcagtgt ggttgtgaac aagcccgtgg  2760
gaagatatcg ctcagcccct aaacgccat ccatgacgca agaagtttt gaaatgggct  2820
ggaaagcatg gggaaaaagc atcctctttg ccccggaatt ggctaactcc acatttgtcg  2880
tagatggacc tgagacaaag gaatgccctg atgagcacag agcttggaac agcatgcaaa  2940
tcgaagactt cggctttgc atcacatcaa cccgtgtgtg gctgaaaatt agagaggaga  3000
gcactgacga gtgtgatgga gcgatcatag gcacggctgt caaggacat gtggcagtcc  3060
atagtgactt gtcgtactgg attgagagtc gctacaacga cacatgaagg cttgagaggg  3120
cagtctttgg agaggtcaaa tcttgcactt ggccagagac acacaccctt tgggagatg   3180
atgttgagga aagtgaactc atcattccgc acaccatagc cggaccaaaa agcaagcaca  3240
atcggaggga agggtataag acacaaaacc agggaccttg ggatgagaat ggcatagtct  3300
tggactttga ttattgccca gggacaaaag tcaccattac agaggattgt agcaagagag  3360
gccctttcggt cagaaccact actgacagtg gaaagttgat cactgactgg tgctgtcgga  3420
gttgctcct tccgccccta cgattccgga cagaaatgct gctggtac ggaatggaaa   3480
tcagacctgt tatgcatgat gaaacaacac tcgtcagatc acaggttcat gctttcaaag  3540
gtgaaatggt tgaccctttt cagctgggcc ttctggtgat gtttctggcc acccaggaag  3600
tccttcgcaa gaggtggacg gccagattga ccattcctgc ggttttggg gtcctacttg  3660
tgctgatgct tgggggtatc acttacactg atttggcgag tgatgtcta ctagtcgctg  3720
ctgctttcgc agaggccaac agtggaggag acgtcctgca ccttgctttg attgctgttt  3780
ttaagatcca accagcatt ttagtgatga acatgcttag cacgagatgg acgaaccaag  3840
aaaacgtggt tctggtccta ggggctgcct ttttccaatt ggcctcagta gatctgcaaa  3900
taggagtcca cggaatcctg aatgccgcg ctatagcatg gatgattgtc cgagcgatca  3960
cctcccac aacctcctcc gtcaccatgc cagtcttagc gcttctaact ccggggatga  4020
gggctctata cctagacact tacagaatca tcctcctcgt catagggatt gctccctgc   4080
tgcacgagag gaaaaagacc atggcgaaaa agaaggagc tgtactcttg ggcttagcgc  4140
tcacatccac tggatggttc tcgcccacca ctatagctgc cggactaatg gtctgcaacc  4200
caaacaagaa gagagggtgg ccagctactg agttttgtc ggcagttgga ttgatgtttg  4260
ccatcgtagg tggtttggcc gagttggata ttgaatccat gtcaatacc ttcatgctgg  4320
```

```
caggtctcat ggcagtgtcc tacgtggtgt caggaaaagc aacagatatg tggcttgaac   4380
gggccgccga catcagctgg gatatgggtg ctgcaatcac aggaagcagt cggaggctgg   4440
atgtgaaact ggatgatgac ggagattttc acttcattga tgatcccggt gttccatgga   4500
aggtctgggt cctgcgcatg tcttgcattg gcttagccgc cctcacgcct tgggccatcg   4560
ttcccgccgc tttcggttat tggctcactt taaaaacaac aaaaagaggg gccgtgtttt   4620
gggacacgcc atcccaaaaa ccttgctcaa aaggagacac cactacagga gtctaccgaa   4680
ttatggctag agggattctt ggcacttacc aggccggcgt cggagtcatg tacgagaatg   4740
ttttccacac actatggcac acaactagag gagcagccat tgtgagtgga gaaggaaaat   4800
tgacgccata ctgggggtagt gtgaaagaag accgcatagc ttacggaggc ccatggaggt   4860
ttgaccgaaa atggaatgga acagatgacg tgcaagtgat cgtggtagaa ccggggaagg   4920
gcgcagtaaa catccagaca aaaccaggag tgtttcggac tcccttcggg gaggttgggg   4980
ctgttagtct ggattacccg cgaggaacat ccggctcacc cattctggat tccaatggag   5040
acattatagg cctatacggc aatggagttg agcttggcga tggctcatac gtcagcgcca   5100
tcgtgcaggg tgaccgtcag gaggaaccag tcccagaagc ttacacccca aacatgttga   5160
gaaagagaca gatgactgtg ctagatttgc accctggttc agggaaaacc aggaaaattc   5220
tgccacaaat aattaaggac gctatccagc agcgcctaag aacagctgtg ttggcaccga   5280
cgcgggtggt agcagcagaa atggcagaag ttttgagagg gctcccagta cgatatcaaa   5340
cttcagcagt gcagagagag caccaaggga tgaaatagt ggatgtgatg tgccacgcca   5400
ctctgaccca tagactgatg tcaccgaaca gagtgcccaa ctacaaccta tttgtcatgg   5460
atgaagctca tttccacgac ccagccagta tagccgcacg aggatacatt gctaccaagg   5520
tggaattagg ggaggcagca gccatctttta tgacagcgac cccgcctgga accacggatc   5580
cttttcctga ctcaaatgcc ccaatccatg atttgcaagg tgagatacca gacagggcat   5640
ggagcagtgg atacgaatgg atcacagaat atgcgggtaa aaccgtgtgg tttgtggcga   5700
gcgtaaaaat ggggaatgag attgcaatgt gcctccaaag agcggggaaa aaggtcatcc   5760
aactcaaccg caagtcctat gacacagaat acccaaaatg taagaatgga gactgggatt   5820
ttgtcattac caccgacatc tctgaaatgg gggcaactt cggtgcgagc agggtcatcg   5880
actgtagaaa gagcgtgaaa cccaccatct tagaagaggg agaaggcaga gtcatcctcg   5940
gaaacccatc tccataacc agtgcaagcg cagctcaacg gaggggcaga gtaggcagaa   6000
accccaatca agttggagat gaataccact atgggggggc taccagtgaa gatgacagta   6060
acctagccca ttgacagag gcaaagatca tgttagacaa catacacatg cccaatgac   6120
tggtggccca gctctatgga ccagagaggg aaaaggcttt cacaatggat ggcgaatacc   6180
gtctcagagg tgaagaaaag aaaaacttct tagagctgct taggacggct gacctccgg   6240
tgtggctggc ctacaaggtg gcgtccaatg gcattcagta caccgacaga aagtggtgtt   6300
ttgatgggcc gcgtacgaat gccatactgg aggacaacac cgaggtagag atagtcaccc   6360
ggatgggtga gaggaaaatc ctcaagccga gatggcttga tgcaagagtt tatgcagatc   6420
accaggccct caagtggttc aaagacttttg cagcagggaa gagatcagcc gttagcttca   6480
tagaggtgct cggtcgcatg cctgagcatt tcatgggaaa gacgcgggaa gctttagaca   6540
ccatgtactt ggttgcaacg gctgagaaag gtgggaaagc acaccgaatg gctctcgaag   6600
agctgccaga tgcactggaa accatcacac ttattgtcgc cattactgtg atgacaggag   6660
gattcttcct actaatgatg cagcgaaagg gtataggaaa gatgggtctt ggagctctag   6720
tgctcacact agctaccttc ttcctgtggg cggcagaggt tcctgaacc aaaatagcag   6780
ggaccctgct gatcgccctg ctgctgatgg tggttctcat cccagaaccg gaaaaacaga   6840
ggtcacagac agataaccaa ctggccgtgt ttctcatctg tgtcttgacc gtggttggag   6900
tggtggcagc aaacgagtac gggatgctag aaaaaaccaa agcggatctc aagagcatgt   6960
tggcggaaa gacgcaggca tcaggactga ctggattgcc aagcatggca ctggacctgc   7020
gtccagccac agcctgggca ctgtatgggg ggagcacagt cgtgctaacc cctcttctga   7080
agcacctgat cacgtcggaa tacgtcacca catcgctagc ttcaattaac tcacaagctg   7140
gctcattatt cgtcttgcca cgaggcgtgc cttttaccga cctagacttg actgttggcc   7200
tcgtcttcct tggctgttgg ggtcaagtca ccctcacaac gtttctgaca gccatggttc   7260
tggcgacact tcactatggg tacatgctcc ctggatggca agcagaagca ctcagggctg   7320
cccagacgaag gacagcggct ggaataatga aagaatgcgc tgttgacgga atggtcgcca   7380
ctgatgtgcc tgaactggaa aggactactc ctctgatgca aaagaaagtc ggacaggtgc   7440
tcctcatagg ggtaagcgtg gcagcgttcc tcgtcaaccc taatgtcacc actgtgagag   7500
aagcagggg gttggtgacg gcggctacgc ttactttgtg ggacaatgga gccagtgccg   7560
tttggaattc caccacagcc acgggactct gccatgtcat gcgaggtagc tacctggctg   7620
gaggctccat tgcttggact ctcatcaaga acgctgataa gccctccttg aaaaggggaa   7680
ggcctggggg caggacgcta ggggagcagt ggaaggaaaa actaaatgcc atgagtagag   7740
aagagttttt taaataccgg agagagggca taatcgaggt ggaccgcact gaagcacgca   7800
gggccagaag tgaaataac atagtgggag gacatccggt ttcgcgaggc tcagcaaaac   7860
tccgttggct tgtggagaaa ggatttgtct cgccaatagg aaaagtcatt gatctagggt   7920
gtgggcgtgg aggatggagc tactacgcag caacccgaa gaaggtccag gaagtcagag   7980
gatacacgaa aggtggggcg ggacatgaag aaccgatgct catgcagagc tacggctgga   8040
acctggtctc cctgaagagt ggagtggacg tgttttacaa accttcagag cccagtgata   8100
ccctgttctg tgacatagg gaatcctccc caagtccaga agtagaagaa caacgcacac   8160
tacgcgtcct agagatgaca tctgactggt tgcaccgagg acctagagaa ttctgcatta   8220
aagttctctg ccctttacatg cccaaggtta tagaaaaaat tgaagttctg cagcgccgct   8280
tcggaggtgg gctagtgcgt gtcccctgt cccgaaactc caatcacgag atgtattggg   8340
ttagtggagc cgctggcaat gtggtgcacg ctgtgaacat gaccagccag gtattactgg   8400
ggcaatgga tcgcacagtg tggagagggc caaagtggag gaagatgtc aacctaggga   8460
gcggaacaag agccgtggga aagggagaag tccatagcaa tcaggagaaa atcaagaaga   8520
gaatccagaa gcttaaagaa gaattcgcca acgtggcaa caaagaccct gagcatccat   8580
accgcacttg gacataccac ggaagctatg aagtgaaggc tactggctca gccagctctc   8640
tcgtcaacgg agtggtgaag ctcatgagca accttgggga cgccattgcc aacgtcacca   8700
ccatgagact gactgacacc accccctttg gacacgaag agttttcaag gagaaagttg   8760
acacgaaggc tcctgagcca ccagctggag ccaggaagt gctcaacgag accaccaact   8820
ggctgtgggc ctacttgtca cgggaaaaaa gaccccgctt gtgcaccaag gaagaattca   8880
ttaagaaagt taacagcaac gcggctcttg gagcagtgtt cgctgaacag aatcaatgga   8940
gcacggcgcg tgaggctgtg gatgacccgc ggttttggga gatggttgat gaagagaggg   9000
aaaaccatct gcgaggagag tgtcacacat gtatctacaa catgatggga aaagagaga   9060
```

```
agaagcctgg agagtttgga aaagctaaag gaagcagggc catttggttc atgtggcttg   9120
gagcacggta tctagagttt gaagctttgg ggttcctgaa tgaagaccat tggctgagcc   9180
gagagaattc aggaggtgga gtggaaggct caggcgtcca aaagctggga tacatcctcc   9240
gtgacatagc aggaaagcaa ggagggaaaa tgtacgctga tgataccgcc gggtgggaca   9300
ctagaattac cagaactgat ttagaaaatg aagctaaggt actggagctc ctagacggtg   9360
aacaccgcat gctcgcccga gccataattg aactgactta caggcacaaa gtggtcaagg   9420
tcatgagacc tgcagcagaa ggaaagaccg tgatggacgt gatatcaaga gaagatcaaa   9480
gggggagtga acaggtggtc acttatgctc ttaacacttt cacgaacatc gctgtccagc   9540
tcgtcaggct gatggaggct gaggggtca ttggaccaca acacttggaa catctaccta   9600
ggaaaaacaa gatagctgtc aggacctggc tctttgagaa tggagaggag agagtgacca   9660
ggatggcgat cagcggagac gactgtgccg tcaaaccgct ggacgacaga ttcgccacag   9720
ccctccactt cctcaacgca atgtcaaagg tcagaaaaga catccaggaa tggaagcctt   9780
cgcatgctg cacgattgg cagcaagttc ccttctgttc taaccatttt caggagattg   9840
tgatgaaaga tggaaggagt atagttgtcc cgtgcagagg acaggatgag ctgataggca   9900
gggctcgcat ctctccagga gctggatgga atgtgaagga cacagcttgc ctgcccaaag   9960
catatgcaca aatgtgggta ctcctatact tccaccgcag ggacttgcgt ctcatggcaa  10020
atgcgatttg ctcagcagtg ccagtagatt gggtgcccac aggcaggaca tcctggtcaa  10080
tacactcgaa aggagagtgg atgaccacgg aagacatgct gcaggtctgg aacagagttt  10140
ggattgaaga aaatgaatgg atgatggaca agactccaat cacaagctgg acagacgttc  10200
cgtatgtggg aaagcgcgag gacatctggt gtggcagcct catcggaacg cgatccagag  10260
caacctgggc tgagaacatc tatgcggcga taaccaggt tagagctgtc attgggaaag  10320
aaaattatgt tgactacatg acctcactca ggagatacga agactcttg atccaggaag  10380
acagggtcat ctagtgtgat ttaaggtaga aaagtagact atgtaaacaa tgtaaatgag  10440
aaaatgcatg catatggagt caggccagca aaagctgcca ccggatactg ggtagacggt  10500
gctgcctgcg tctcagtccc aggaggactg ggttaacaaa tctgacaaca gaaagtgaga  10560
aagccctcag aactgtctcg gaagtaggtc cctgctcact gcaagttgca agaccaacgt  10620
caggccacaa atttgtgcca ctccgctagg gagtgcggcc tgcgcagccc caggaggact  10680
gggttaccaa agccgttgag cccccacggc ccaagcctcg tctaggatgc aatagacgag  10740
gtgtaaggac tagaggttag aggagacccc gtggaaacaa caacatgcgg cccaagcccc  10800
ctcgaagctg tagaggaggt ggaaggacta gaggttagag gagaccccgc atttgcatca  10860
aacagcatat tgacacctgg gaatagactg ggagatcttc tgctctatct caacatcagc  10920
tactaggcac agagcgccga agtatgtacg tggtggtgag gaagaacaca ggatct       10976

SEQ ID NO: 76          moltype = DNA   length = 10838
FEATURE                Location/Qualifiers
source                 1..10838
                       mol_type = genomic DNA
                       organism = Yellow fever virus
SEQUENCE: 76
gtgctaattg aggtgcattg gtctgcaaat cgagttgcta ggcaataaac acatttggat     60
taattttaat cgttcgttga gcgattagca gagaactgac cagaacatgt ctggtcgtaa    120
agctcaggga aaaaccctgg gcgtcaatat ggtacgacga ggagttcgct ccttgtcaaa    180
caaaataaaa caaaaaacaa aacaaattgg aaacagacct ggaccttcaa gaggtgttca    240
aggatttatc tttttcttt tgttcaacat tttgactgga aaaagatca cagcccacct    300
aaagagggttg tggaaaatgc tggacccaag acaaggcttg gctgttctaa ggaaagtcaa    360
gagagtggtg gccagtttga tgagaggatt gtcctcaagg aaacgccgtt cccatgatgt    420
tctgactgtg caattcctaa ttttgggaat gctgttgatg gcgggtggag tgaccttggt    480
gcggaaaaac agatggttgc tcctaaatgt gacatctgag gacctcggga aaacattctc    540
tgtgggcaca gcaactgca caacaaacat tttggaagcc aagtactggt gcccagactc    600
aatgaaatac aactgtccca atctcagtcc aagagaggag ccagtgaca ttgattgctg    660
gtgctatggg gtgaaaacg ttagagtcgc atatggtaag tgtgactcag caggcaggtc    720
taggaggtca agaagggcca ttgacttgcc tacgcatgaa aaccatggtt tgaagacccg    780
gcaagaaaaa tggatgactg gaagaatggg tgaaaggcaa ctccaaaaga ttgagagatg    840
gttcgtgagg aaccccctt tgcagtgac ggctctgacc attgcctacc ttgtgggaag    900
caacatgacg caacgagtcg tgattgccct actggtcttg gctgttggcc cggcctactc    960
agctcactgc attggaatta ctgcagggg tttcattgag ggggtgcatg gaggaacttg   1020
ggtttcagct ccctggagc aagacaagtg tgtcactgtt atggccctg acaagccttc   1080
attggacatc tcactagaga cagtagccat tgatagacct gctgaggtga ggaaagtgtg   1140
ttacaatgca gttctcactc atgtgaagat taatgacaag tgccccagca ctggagaggc   1200
ccacctagct gaagagaacg aagggacaa tgcgtgcaag cgcacttatt ctgataggg   1260
ctggggcaat ggctgtggcc tatttgggaa agggagcatt gtggcatgcg ccaaattcac   1320
ttgtgccaaa tccatgagtt tgtttgaggt tgatcagacc aaaattcagt atgtcatcag   1380
agcacaattg catgtaggg ccaagcagga aaattggact accgacatta agactctcaa   1440
gtttgatgcc ctgtcaggct cccaggaagt cgagttcatt ggtatgaaa agctacact   1500
ggaatgccag gtgcaaactg cggtggactt tggtaacagt tacatcgctg agatgggaaac   1560
agagagctgg atagtggaca cacagtgggc ccaggactg accctgccat ggcagagtgg   1620
aagtggcggg gtgtggagag atgcatcata tcttgtcgaa tttgaacctc gcatgccgc   1680
cactatcaga gtactggccc tggaaacca ggaaggctcc ttgaaacag ctcttactgg   1740
cgcaatgagg gttacaaagg acacaaatga caaccaacct tacaaactac atggtgaca   1800
tgtttcttgc agagtgaaat tgtcagtttt gacactcaag gggacatcct acaaaatatg   1860
cactgacaaa atgttttttg tcaagaaccc aactgacact ggccatggca ctgttgtgat   1920
gcaggtgaaa gtgtcaaaag gagccccctg caggattcca gtgatagtag ctgatgatct   1980
tacagcggca atcaataaag gcattttggt tacagttaac cccatcgcct caaccaatga   2040
tgatgaagtg ctgattgagg tgaacccacc ttttggggga gactcatgt tcgttgggag   2100
aggagattca cgtctcactt accagtggca caaagaggga agctcaatag gaaagttgtt   2160
cactcagacc atgaaaggcg tggaacgcct ggccgtcatg ggagacacg cctgggattt   2220
cagctccgct ggagggttct tcacttcggt tgggaaagga attcatacg gtgttggctc   2280
tgcctttcag gggctatttg gcggcttgaa ctggataaca aaggtcatca gggggcggt   2340
acttatatgg gttggcatca acacaagaaa catgacaatg tccatgagca tgatcttggt   2400
```

```
aggagtgatc atgatgtttt tgtctctagg agttggggcg gatcaaggat gcgccatcaa 2460
ctttggcaag agagagctca agtgcggaga tggtatcttc atatttagag actctgatga 2520
ctggctgaac aagtactcat actatccaga agatcctgtg aagcttgcat caatagtgaa 2580
agcctctttt gaagaaggga agtgtggcct aaattcagtt gactcccttg agcatgagat 2640
gtggagaagc agggcagatg agatcaatgc cattttttgag gaaaacgagg tggacatttc 2700
tgttgtcgtg caggatccaa agaatgttta ccagagagga actcatccat tttccagaat 2760
tcgggatggt ctgcagtatg gttggaagac ttggggtaag aacctgtgt tctccccagg 2820
gaggaagaat ggaagcttca tcatagatgg aaagtccagg aaagaatgcc cgttttcaaa 2880
ccgggtctgg aattctttcc agatagagga gtttgggacg ggagtgttca ccacacgcgt 2940
gtacatggac gcagtctttg aatacaccat agactgcgat ggatctatct tgggtgcagc 3000
ggtgaacgga aaaaagagtg cccatggctc tccaacattt tggatgggaa gtcatgaagt 3060
aaatgggaca tggatgatcc acaccttgga ggcattagat tacaaggagt gtgagtggcc 3120
actgacacat acgattggaa catcagttga agagagtgaa atgttcatgc cgagatcaat 3180
cggaggccca gttagctctc acaatcatat ccctggatac aaggttcaga cgaacggacc 3240
ttggatgcag gtaccactag aagtgaagag agaagcttgc ccagggacta gcgtgatcat 3300
tgatggcaac tgtgatggac ggggaaaatc aaccagatcc accacggata gcgggaaagt 3360
tattcctgaa tggtgttgcc gctcctgcac aatgccgcct gtgagcttcc atggtagtga 3420
tgggtgttgg tatcccatgg aaattaggcc aaggaaaacg catgaaagcc atctggtgcg 3480
ctcctgggtt acagctggag aaatacatgc tgtcccttttt ggtttggtga gcatgatgat 3540
agcaatggaa gtggtcctaa ggaaaagaca gggaccaaag caaatgttgg ttggaggagt 3600
agtgctcttg ggagcaatgc tggtcgggca agtaactctc cttgatttgc tgaaactcac 3660
agtggctgtg ggattgcatt tccatgagat gaacaatgga ggagacgcca tgtatatggc 3720
gttgattgct gcctttttcaa tcagaccagg gctgctcatc ggctttgggc tcaggaccct 3780
atggagcccc cggaacgcc ttgtgctgac cctaggagca gccatggtgg agattgcctt 3840
gggtggcgtg atgggcggcc tgtggaagta tctaaatgca gtttctctct gcatcctgac 3900
aataaatgct gttgcttcta ggaaaatcat caaataccat ttgcccctca tggctctgct 3960
gacacctgtc actatggctg aggtgagact tgccgcaatg ttcttttgtg ccgtggttat 4020
catagggtc cttcaccaga atttcaagga cacctccatg cagaagacta tacctctggt 4080
ggccctcaca ctcacatctt acctgggctt gacacaacct ttttttgggcc tgtgtgcatt 4140
tctggcaacc cgcatatttg ggcgaaggag tatcccaggt aatgaggcac tcgcagcagc 4200
tggtctagtc ggagtgctgg caggactggc ttttcaggag atggagaact tccttggtcc 4260
gattgcagtt ggaggactcc tgatgatgct ggttagcgtg gctgggaggg tggatgggct 4320
agagctcaag aagcttggtg aagtttcatg ggaagaggag gcgagatca gcgggagttc 4380
cgcccgctat gatgtggcac tcagtgaaca aggggagttc aagctgcttt ctgaagaaa 4440
agtgccatgg gaccaggttg tgatgacctc gctggcctlg gttgggctg ccctccatcc 4500
atttgctctt ctgctggtcc ttgctgggtg gctgtttcat gtcaggggag ctaggagaag 4560
tggggatgtc ttgtgggata ttcccactcc taagatcatc gaggaatgtg aacatctgga 4620
ggatgggatt tatggcatat tccagtcaac cttcttgggg gcctcccagc gaggagtggg 4680
agtggcacag ggaggggtgt tccacacaat gtggcatgtc acaagaggag cttttccttgt 4740
caggaatggc aagaagttga ttccatcttg ggcttcagta aaggaagacc ttgtcgccta 4800
tggtggctca tggaagttgg aaggcagatg ggatggagag gaagaggtcc agttgatcgc 4860
ggctgttcca ggaaagaacg tggtcaacgt ccagacaaaa ccgagcttgt tcaaagtgag 4920
gaatggggga gaaatcgggg ctgtcgctct tgactatccg gctggcactt caggatctcc 4980
tattgttaac aggaacgagg aggtgattgg gctgtacggc aatggcatcc ttgtcggtga 5040
caactccttc gtgtccgcca tatcccgac tgaggtgaag gaagaggaa aggaggagct 5100
ccaagagatc ccgacaatgc taaagaaagg aatgacaact gtccttgatt ttcatcctgg 5160
agctggaaag acaagacgtt tcctcccaca gatcttgggc gagtgcgcac ggagacgctt 5220
gcgcactctt tgtgttggccc ccaccagggt tgttctttct gaaatgaagg aggcttttca 5280
cggcctggac gtgaaattcc acacacaggc ttttttccgct cacggcagcg ggagagaagt 5340
cattgatgct atgtgccatg ccaccctaac ttacaggatg ttgaaccaa ctaggggttgt 5400
taactgggga tgatcatta tggatgaagc ccatttttttg gatccagcta gcatagccgt 5460
tagaggttgg gcagcgcaca gagctagggc aaatgaaagt gcaacaatct tgatgacagc 5520
cacaccgcct gggactagtg atgaatttcc acattcaaat ggtgaaatag aagatgttca 5580
aacggacata cccagtgagc cctgaacac agggcatgac tggatcctgg ctgacaaaag 5640
gcccacggca tggttccttc catccatcag agctgcaaat gtcatgctg cctcttttgcg 5700
taaggctgaa aagagtgtgg tggtcctgaa caggaaaacc ttgagagag aataccccac 5760
gataaagcag aagaaacctg actttatatt ggccactgac atagctgaaa tgggagccaa 5820
cctttgcgtg gagcgagtgc tggattcag acggcttttt aagcctgtgc ttgtggatga 5880
agggaggaag gtggcaataa aagggccact tcgtatctcc gcatcctctg ctgctcaaag 5940
gaggggggcgc attgggaaga atcccaacag agatggagac tcatactact attctgagcc 6000
tacaagtgaa aataatgccc accacgtctg ctggttggag gcctcaatgc tcttggacaa 6060
catggaggtg aggggtggaa tggtcgcccc actctatggc gttgaaggaa ctaaaacacc 6120
agtttccccct ggtgaaatga actgagggga tgaccagagg aaagtcttca gagaactagt 6180
gaggaattgt gacctgccg tttggcttttc gtggcaagtg gccaaggctg gtttgaagac 6240
gaatgatcgt aagtggttgt ttgaaggccc tgaggaacat gagatcttga atgcagcggc 6300
tgaaacagtg aagtggcaggg ctcctggagg agcaaagaag cctctgcgcc caaggtggtg 6360
tgatgaaagg gtgtcatctg accagagtgc gctgtcgaa tttattaagt ttgctgaagg 6420
taggagggga gctgctgaag tgcttgtggt gctgagtgaa ctccctgatt tcctggctaa 6480
aaaaggtgga gaggcaatgg ataccatcag tgtgtttttcac cactctgagg aaggctctag 6540
ggcttaccgc aatgcactat caatgatgcc tgaggcaatg acaatagtca tgctgttttat 6600
actggctgga ctactgacat cgggaatggt catctttttc atgtctccca aaggcatcag 6660
tagaatgtct atggcgatgg gcacaatggc cggctgtgga tatctcatgt tccttggagg 6720
cgtcaaaccc actcacatct cctatatcat gctcatattc tttgtcctga tggtggttgt 6780
gatccccgag ccaagggcaac aaggtccat ccaagacaac aggggcat acctcattat 6840
tggcatcctg acgctggttt cagcggtggc agcaacgag ctaggcatgc tggagaaaac 6900
caaagaggac ctctttggga agaagaactt aatttccatc agtgcttcac cctggagttg 6960
gccgatcttt gacctgaagc caggagctgc ctggacagtg tacgttggca ttgttacaat 7020
gctctctcca atgttgcacc actggatcaa agtcgaatat ggcaacctgt ctctgtctgg 7080
aatagcccag tcagcctcag tccttttcttt catggacaag gggataccat tcatgaagat 7140
```

```
gaatatctcg gtcataatgc tgctggtcag tggctggaat tcaataacag tgatgcctct    7200
gctctgtggc atagggtgcg ccatgctcca ctggtctctc attttacctg gaatcaaagc    7260
gcagcagtca aagcttgcac agagaagggt gttccatggc gttgccaaga accctgtggt    7320
tgatgggaat ccaacagttg acattgagga agctcctgaa atgcctgccc tttatgagaa    7380
gaaactggct ctatatctcc ttcttgctct cagcctagct tctgttgcca tgtgcagaac    7440
gcccttttca ttggctgaag gcattgtcct agcatcagct gccctagggc cgctcataga    7500
gggaaacacc agccttcttt ggaatggacc catggctgtc tccatgacag gagtcatgag    7560
ggggaatcac tatgcttttg tgggagtcat gtacaatcta tggaagatga aaactggacg    7620
ccgggggagc gcgaatggaa aaactttggg tgaagtctgg aagagggaac tgaatctgtt    7680
ggacaagcga cagtttgagt tgtataaaag gaccgacatt gtggaggtgg atcgtgatac    7740
ggcacgcagg catttggccg aagggaaggt ggacaccggg gtggcggtct ccaggggac    7800
cgcaaagtta aggtggttcc atgagcgtgg ctatgtcaag ctggaaggta gggtgattga    7860
cctggggtgt ggccgcggag gctggtgtta ctacgctgct gcgcaaaagg aagtgagtgg    7920
ggtcaaagga tttactcttg gaagagacgg ccatgaagaa cccatgaatg tgcaaagtct    7980
gggatggaac atcatcacct tcaaggacaa aactgatatc caccgcctag aaccagtgaa    8040
atgtgacacc cttttgtgtg acattggaga gtcatcatcg tcatcggtca cagagggga    8100
aaggaccgtg agagttcttg atactgtaga aaatggctg gcttgtgggg ttgacaactt    8160
ctgtgtgaag gtgttagctc catacatgcc agatgttctc gagaaactgg aattgctcca    8220
aaggaggttt ggcggaacag tgatcaggaa ccctctctcc aggaattcca ctcatgaaat    8280
gtactacgtg tctggagccc gcagcaatgt cacatttact gtgaaccaaa catcccgcct    8340
cctgatgagg agaatgaggc gtccaactgg aaaagtgacc ctgaaggctg acgtcatcct    8400
cccaattggg acacgcagtg ttgagacaga caagggaccc tggacacaaa aggccataga    8460
agaaagggtt gagaggataa aatctgagta catgaccctc tggtttatg acaatgacaa    8520
cccctacagg acctggcact actgtggctc ctatgtcaca aaacctcag gaagtgcggc    8580
gagcatggta aatggtgtta ttaaaattct gacatatcca tgggacagga tagaggaggt    8640
cacaagagga gcaatgactg acacaacccc ttttggacag caaagagtgt ttaaagaaaa    8700
agttgacacc agagcaaagg atccaccagc gggaactagg aagatcatga agttgtcaa    8760
caggtggctg ttccgccacc tggccagaga aaagaacccc agactgtgca caaaggaaga    8820
atttattgca aaagtccgaa gtcatgcagc cattggagct tacctggaag aacaagaaca    8880
gtggaagact gccaatgagg ctgtccaaga cccaaagttc tgggaactgg tggatgaaga    8940
aaggaagctg caccaacaag gcaggtgtcg gacttgtgtg tacaacatga tgggaaaag    9000
agaagaagaag ctgtcagagt ttgggaaagc aagggaagc cgtgccatat ggtatatgtg    9060
gctgggagcg cggtatcttg agtttgaggc cctgggattc ctgaatgagg accattgggc    9120
ttccagggaa aactcaggag gaggagtgga aggcattggc ttacaatacc taggatatgt    9180
gatcagagac ctggctgcaa tggatggtgg tggattctca gcggatgaca ccgctggatg    9240
ggacacgcgc atcacagagg cagaccttga tgatgaacag gagatcttga ctcatgag    9300
cccacatcac aaaaaactgg cacaagcagt gatggaaatg acatacaaga caaagtggt    9360
gaaagtgttg agaccagccc caggaggaa agcctacatg gatgtcataa gtcgacgaga    9420
ccagagagga tccgggcagg tagtgactta tgctctgaac accatcacca ccttgaaagt    9480
ccaattgatc agaatggcag aagcagagat ggtgatacat caccaacatg ttcaagattg    9540
tgatgaatca gttctgacca ggctggaggc atggctcact gagcacggat gtaacagact    9600
gaagaggatg gcggtgagtg gagacgactg tgtggtccgg cccatcgatg acaggttcgg    9660
cctggccctg tcccatctca acgccatgtc caaggttaga aaggacatat ctgaatggca    9720
gccatcaaaa gggtggaatg attgggagaa tgtgcccttc tgttcccacc acttccatga    9780
actacagctg aaggatggca ggaggattgt ggtgccttgc cgagaacagg acgagctcat    9840
tgggagagga agggtgtctc caggaaacgg ctggatgatc aaggaaacag cttgcctcag    9900
caaagcctat gccaacatgt ggcactgat gtattttcac aaaaggaaca tgaggctact    9960
gtcattggct gtttcctcag ctgttcccac ctcatgggtt ccacaaggac gcacaacatg    10020
gtcgattcat gggaaagggg agtggatgac cacggaagac atgcttgagg tgtgaaacag    10080
agtatggata ccaacaacc cacacatgca ggacaagaca atggtgaaaa atggagaga    10140
tgtccttat ctaaccaaga gacaagacaa gctgtgcgga tcactgattg gaatgaccaa    10200
tagggccacc tgggcctccc acatccattt ggtcatccat cgtatccgaa cgctgattgc    10260
acaggagaaa tacactgact acctaacagt catggacagg tattctgtgg atgctgacct    10320
gcaactgggt gagcttatct gaaacaccat ctaacaggaa taaccgggat acaaaccacg    10380
ggtggaaac cggactcccc aaaacctgaa accgggatat aaaccacggc tggagaaccg    10440
gactccgcac ttaaaatgaa acagaaaccg ggataaaaac tacgatgga gaaccggact    10500
ccacacattg agacagaaga agttgtcagc ccagaacccc acgagtttt gccactgct    10560
aagctgtgag gcagtgcagg ctgggacagc cgacctccag gttgcgaaaa acctggtttc    10620
tgggacctcc caccccagag taaaaagaac ggagcctccg ctaccacccc cccacgtggt    10680
ggtagaaaga cgggggctag aggttagagg agaccctcca gggaacaaat agtgggacca    10740
tattgacgcc agggaaagac cggagtggtt ctctgctttt cctccagagg tctgtgagca    10800
cagtttgctc aagaataagc agacctttgg atgacaaa                           10838
SEQ ID NO: 77             moltype = DNA   length = 11674
FEATURE                   Location/Qualifiers
source                    1..11674
                          mol_type = genomic DNA
                          organism = Chikungunya virus
SEQUENCE: 77
gatggctgcg tgagacacac gtagcctacc agtttcttac tgctctactc tgcaaagcaa     60
gagattaata acccatcatg gatcctgtgt acgtggacat agacgctgac agcgcctttt    120
tgaaggccct gcaacgtgcg tacccatgt ttgaggtgga accaaggcag gtcacaccga    180
atgaccatgc taatgctaga gcgttctcgc atctagctat aaaactaata gagcaggaaa    240
ttgaccccga ctcaaccatc ctggatatcg gcagtgcgcc agcaaggagg atgatgtcgg    300
acaggaagta ccactgcgtc tgcccgatgc gcagtgcgga agatcccgag agactcgcca    360
attatgcgag aaagctagca tctgccgcag gaaaagtcct ggacagaaac atctctggaa    420
agatcgggga cttacaagca gtaatggccg tgccagacac ggagacgcca acattctgct    480
tacacacaga cgtctcatgt agacagagag cagacgtcgc tataccaa gacgtctatg    540
ctgtacacgc acccacgtcg ctataccacc aggcgattaa aggggtccga gtggcgtact    600
```

```
gggttgggtt cgacacaacc ccgttcatgt acaatgccat ggcgggtgcc taccccctcat  660
actcgacaaa ctgggcagat gagcaggtac tgaaggctaa gaacatagga ttatgttcaa  720
cagacctgac ggaaggtaga cgaggcaagt tgtctattat gagagggaaa aagctaaaac  780
cgtgcgaccg tgtgctgttc tcagtagggt caacgctcta cccggaaagc cgcaagctac  840
ttaagagctg gcacctgcca tcggtgttcc atttaaaggg caaactcagc ttcacatgcc  900
gctgtgatac agtggtttcg tgtgagggct acgtcgttaa gagaataacg atgagcccga  960
gcctttatgg aaaaaccaca gggtatgcgg taacccacca cgcagacgga ttcctgatgt 1020
gcaagactac cgacacggtt gacggcgaaa gaatgtcatt ctcggtgtgc acatacgtgc 1080
cggcgaccat ttgtgatcaa atgaccggca tccttgctac agaagtcacg ccggaggatg 1140
cacagaagct gttggtgggg ctgaaccaga gaatagtggt taacggcaga acgcaacgga 1200
atacgaacac catgaaaaat tatctgcttc ccgtggtcgc ccaagccttc agtaagtggg 1260
caaaggagtg ccgaaagac atggaagatg aaaaactcct gggggtcaga gaaagaacac 1320
tgacctgctg ctgtctatgg gcattcaaga agcagaaaac acacacggtc tacaagaggc 1380
ctgataccca gtcaattcag aaggttcagg ccgagtttga cagctttgtg gtaccgagtc 1440
tgtggtcgtc cgggttgtca atcccttga ggactagaat caaatggttg ttaagcaagg 1500
tgccaaaaac cgacctgatc ccatacagcg gagacgcccg agaagccgg gacgcagaaa 1560
aagaagcaga ggaagaacga gaagcagaac tgactcgcga agcccctacca cctctacagg 1620
cagcacagga agatgttcag gtcgaaatcg acgtggaaca gcttgaggac agagcgggcg 1680
caggaataat agagactccg agaggagcta tcaaagttac tgcccaacca acagaccacg 1740
tcgtgggaga gtacctggta ctctccccgc agaccgtact acgtagccag aagctcagtc 1800
tgattcacgc tttggcggag caagtgaaga cgtgcacgca caacgacga gcagggaggt 1860
atgcggtcga agcgtacgac ggccgagtcc tagtgccctc aggctatgca atctcgcctg 1920
aagacttcca gagtctaagc gaaagcgcaa cgatggtgta taacgaaaga gagttcgtaa 1980
acagaaagct acaccatatt gcgatgcacg gaccagccct gaacaccgac gaagagtcgt 2040
atgagctggt gagggcagag aggacagaac acgagtacgt ctacgacgtg gatcagaaa 2100
gatgctgtaa gaaggaagaa gccgcaggac tggtactggt ggcgacttg actaatccgc 2160
cctaccacga attcgcatat gaagggctaa aaatccgccc tgcctgccca tacaaaattg 2220
cagtcatagg agtcttcgga gtaccgggat ctggcaagtc agctattatc aagaacctag 2280
ttaccaggca ggacctggtg actagcgaaa agaaagaaaa ctgccaagaa atcaccaccg 2340
acgtgatgag acagagaggt ctagagatat ctgcacgtac ggttgactcg ctgctcttga 2400
atggatgcaa cagaccagtc gacgtgttgt acgtacgacga ggcgtttgcg tgccactctg 2460
gaacgctact tgctttgatc gccttggtga gaccaaggca gaaagttgta ctttgtggtg 2520
acccgaagca gtgcggcttc ttcaatatga tgcagatgaa agtcaactat aatcacaaca 2580
tctgcaccca agtgtaccac aaaagtatct ccaggcggtg tacactgcct gtgaccgcca 2640
ttgtgtcatc gttgcattac gaaggcaaa tgcgcactac gaatgagtac aacaagccga 2700
ttgtagtgga cactacaggc tcaacaaaac ctgaccctgg agacctcgtg ttaacgtgct 2760
tcagagggtg ggttaaacaa ctgcaaattg actatcgtgg atacgaggtc atgacagcag 2820
ccgcatccca agggttaacc agaaaaggag tttacgcagt tagacaaaaa gttaatgaaa 2880
acccgctcta tgcatcaacg tcagacacg tcaacgtact cctaacgcgt acggaaggta 2940
aactggtatg gaagacactt tccggcgacc cgtggataaa gacgctgcag aacccaccga 3000
aaggaaactt caaagcaact attaaggagt gggaggtgga gcatgcatca ataatggcgg 3060
gcatctgcag tcaccaaatg accttcgata cattccaaa taaagccaac gtttgttggg 3120
ctaagagctt ggtccctatc ctcgaaacag cgggataaa actaaatgat aggcagtggt 3180
ctcagataat tcaagccttc aaagaagaca aagcatactc acctgaagta gccctgaatg 3240
aaatatgtac gcgcatgtat ggggtggatc tagacagcgg gctattttct aaaccgttgg 3300
tgtctgtgta ttacgcggat aaccactggg ataataggcc tggagggaaa atgttcggat 3360
ttaaccccga ggcagcatcc attctagaaa gaaagtatcc attcacaaaa gggaagtgga 3420
acatcaacaa gcagatctgc gtgactacca ggaggataga agactttaac cctaccacca 3480
acatcatacc ggccaacagg agactaccac actcattagt ggccgaacac cgcccagtaa 3540
aaggggaaag aatggaatgg ctggttaaca agataaacgg ccaccacgtg ctcctggtca 3600
gtgctataa ccttgcactg cctactaaga gagtcacttg ggtagcgccg ttaggtgtga 3660
gcggagcgga ctacacatac aacctagagt tgggtctgcc agcaacgctt ggtaggtatg 3720
acctagtggt cataaacatc cacacacctt ttcgcataca ccattaccaa cagtgcgtcg 3780
accacgcaat gaaactgcaa atgctcgggg gtgactcatt gagactgctc aaaccggggcg 3840
gctctctatt gatcagagca tatggttacg cagatagaac cagtgaacga gtcatctgcg 3900
tattgggacg caagtttaga tcgtctagag cgttgaaacc accatgtgtc accagcaaca 3960
ctgagatgtt tttcctattc agcaactttg acaatggcag aaggaatttc acaactcatg 4020
tcatgaacaa tcaactgaat gcagccttcg taggacaggt cacccgagca ggatgtgcac 4080
cgtcgtaccg ggtaaaacgc atggacatcg cgaagaacga tgaagagtgc gtagtcaacg 4140
ccgctaaccc tcgcgggtta ccgggtggcg gtgtttgcaa ggcagtatac aaaaaatgcg 4200
cggagtcctt taagaacagt gcaacaccag tgggaaccgc aaaaacagtt atgtgcggta 4260
cgtatccagt aatccacgct gttggaccaa acttctctaa ttattcggag tctgaagggg 4320
accgggaatt ggcagctgcc tatcgagaag tcgcaaagga agtaactagg ctgggagtaa 4380
atagtgtagc tatacctctc tctccacag gtgtatactc agagggaaa gacaggctga 4440
cccagtcact gaaccacctc tttacagcca tggactcgac ggatgcagac gtggtcatct 4500
actgccgcga caaagaatgg gagaagaaaa tatctgaggc catacagatg cggacccaag 4560
tagagctgct ggatgagcac atctccatag actgcgatat tgttcgcgtg caccctgaca 4620
gcagcttggc aggcagaaaa ggatacagca ccacggaagg cgcactgtac tcatatctag 4680
aagggaccg ttttcatcag acggctgtgg atatggcgga gatacatact atgtggccaa 4740
agcaaacaga ggccaatgag caagtctgcc tatatgccct gggggaaagt attgaatcga 4800
tcaggcagaa atgccggtg gatgatgcag acgcatcatc tcccccaaa actgtcccgt 4860
gcctttgccg ttacgctatg actccagaac gcgtcacccg gcttcgcatg aaccacgtca 4920
caagcataat tgtgtgttct tcgtttcccc tcccaaagta caaatagaa gggagtgcaaa 4980
aagtcaaatg ctctaaggta atgctatttg accacaacgt gccatccgcg taagtcaa 5040
gggcttatag aggtgccgct gccggtaacc ttgcggccgt gtctgattgg gtaatgagca 5100
ccgtacctgt cgcgccgccc agaagaaggc gaggagaaa cctgactgtg acatgtgacg 5160
agagagaagg gaatataaca cccatggcta gcgtccgatt cttagggca gagctgtgtc 5220
cggtcgtaca agaaacagcg gagacgcgtg acacagcaat gtctcttcag gcaccaccga 5280
gtaccgccac ggaaccgaat catccgccga tctccttcgg agcatcaagc gagacgttcc 5340
```

```
ccattacatt tggggacttc aacgaaggag aaatcgaaag cttgtcttct gagctactaa   5400
ctttcggaga cttcttacca ggagaagtgg atgacttgac agacagcgac tggtccacgt   5460
gctcagacac ggacgacgag ttaagactag acagggcagg tgggtatata ttctcgtcgg   5520
acaccggtcc aggtcattta caacagaagt cagtacgcca gtcagtgctg ccggtgaaca   5580
ccctggagga agtccacgag gagaagtgtt acccacctaa gctggatgaa gcaaaggagc   5640
aactattact taagaaactc caggagagtg catccatggc caacagaagc aggtatcagt   5700
cgcgcaaagt agaaaacatg aaagcagcaa tcatccagag actaaagaga ggctgtagac   5760
tatacttaat gtcagagacc ccaaaagtcc ctacttaccg gactacatat ccggcgcctg   5820
tgtactcgcc tccgatcaac gtccgattgt ccaatcccga gtccgcagtg gcagcatgca   5880
atgagttctt agctagaaac tatccaactg tctcatcata ccaaattacc gacgagtatg   5940
atgcatatct agacatggtg gacgggtcgg agagttgcct ggaccgagcg acattcaatc   6000
cgtcaaaact caggagctac ccgaaacagc acgcttacca cgcgccctcc atcagaagcg   6060
ctgtaccgtc cccattccag aacacactac agaatgtact ggcagcagcc acgaaaagaa   6120
actgcaacgt cacacagatg agggaattac ccacttttgga ctcagcagta ttcaacgtgg   6180
agtgtttcaa aaaattcgca tgcaaccaag aatactggga agaatttgct gccagcccta   6240
ttaggataac aactgagaat ttagcaacct atgttactaa actaaagggg ccaaaagcag   6300
cagcgctatt cgcaaaaacc cataatctac tgccactaca ggaagtacca atggataggt   6360
tcacagtaga tatgaaaagg gacgtaaagg tgactcctgg tacaaagcat acagaggaaa   6420
gacctaaggt gcaggttata caggcggctg aaccccttggc gacagcatac ctatgtggga   6480
ttcacagaga gctggttagg aggctgaacg ccgtcctcct acccaatgta catacactat   6540
ttgacatgtc tgccgaggat ttcgatgcca tcatagccgc acactttaag ccaggagaca   6600
ctgttttgga aacggacata gcctcctttg ataagagcca aagatgattca cttgcgctta   6660
ctgctttgat gctgttagag gatttagggg tggatcactc cctgctggac ttgatagagg   6720
ctgctttcgg agagatttcc agctgtcacc taccgacagg tacgcgcttc aagttcggcg   6780
ccatgatgaa atcaggtatg ttcctaactc tgttcgtcaa cacattgtta aacatcacca   6840
tcgccagccg agtgctggaa gatcgtctga caaaatccgc gtgcgcggcc ttcatcgcgg   6900
acgacaacat aatacatgga gtcgtctccg atgaattgat ggcagccaga tgtgccactt   6960
ggatgaacat ggaagtgaag atcatagatg cagttgtatc cttgaaagcc ccttactttt   7020
gtggagggtt tatactgcac gatactgtga caggaacagc ttgcagagtg cagaccccgc   7080
taaaaaggct ttttaaactg ggcaaaccgc tagcggcagg tgccaacaa gatgaagata   7140
gaagacgagc gctggctgac gaagtgatca gatggcaacg aacagggcta attgatgagc   7200
tggagaaagc ggtatactct aggtacgaag tgcagggtat atcagttgtg gtaatgtcca   7260
tggccaccct tgcaagctcc agatccaact tcgagaagct cagaggaccc gtcataactt   7320
tgtacggcg tcctaaatag gtacgcacta cagctaccta ttttgcagaa gccgacagca   7380
agtatctaaa cactaatcag ctacaatgga gttcatccca acccaaactt tttacaatag   7440
gaggtaccag cctcgaccct ggactccgcg ccctactatc caagtcatca ggcccagacc   7500
gcgcctcag aggcaagctg ggcaacttgc ccagctgatc tcagcagtta ataaactgac   7560
aatgcgcgcg gtaccacaac agaagccacg caggaatcgg aagaataaga agcaaaagca   7620
aaaacaacag gcgccacaaa acaacacaaa tcaaaaagaag cagccaccta aaaagaaacc   7680
ggctcaaaag aaaaagaagc cgggccgcag agagaggatg tgcatgaaaa tcgaaaatga   7740
ttgtattttc gaagtcaagc acgaaggtaa ggtaacaggt tacgcgtgcc tggtggggga   7800
caaagtaatg aaaccagcac acgtaaaggg gaccatcgat aacgcggacc tggccaaact   7860
ggcctttaag cggtcatcta agtatgacct tgaatgcgca cgatacccgg tcacatgaa   7920
gtccgacgct tcgaagttca cccatgagaa accggagggg tactacaact ggcaccacgg   7980
agcagtacag tactcaggag gccggttcac catccctaca ggtgctggca aaccaggga   8040
cagcggcaga ccgatcttcg acaacaaggg acgcgtggtg gccatagtct taggaggagc   8100
taatgaaggaa gcccgtacag ccctctcggg ggtgacctgga aataaagaca ttgtcactaa   8160
aatcacccc gaggggccg aagagtggag tcttgccatc ccagttatgt gcctgttggc   8220
aaacaccacg ttccctgct cccagccccc ttgcacgcc tgctgctacg aaaaggaacc   8280
ggaggaaacc ctacgcatgc ttgaggacaa cgtcatgaga cctgggtact atcagctgct   8340
acaagcatcc ttaacatgtt ctccccaccg ccagcgcagc agcaccaagg acaacttcaa   8400
tgtctataaa gccacaagac catacttagc tcactgtccc gactgtggag aagggcactc   8460
gtgccatagt cccgtagcac tagaacgcat cagaaatgaa gcgacagacg ggacgctgaa   8520
aatccaggtc tccttgcaaa tcggaataaa gacggatgac agccacgatt ggaccaagct   8580
gcgttatatg gacaaccaca tgccagcaga cgcagagagg gcggggctat ttgtaagaac   8640
atcagcaccg tgtacgatta ctggaacaat gggacacttc atcctggccc gatgtccaaa   8700
aggggaaact ctgacggtgg gattcactga cagtaggaag attagtcact catgtacgca   8760
cccattcac cacgaccctc ctgtgatagg tcggaaaaa ttccattccc gaccgcagca   8820
cggtaaagag ctaccttgca gcacgtacgt gcagagcacc gccgcaacta ccgaggagat   8880
agaggtacac atgccccag acaccctga tcgcacatta atgtcacaac agtccggcaa   8940
cgtaaagatc acagtcaatg gccagacggt gcggtacaag tgtaattgcg gtggctcaaa   9000
tgaaggacta acaactacag acaaagtgat taataactgc aaggttgatc aatgtcatgc   9060
cgcggtcacc aatcacaaaa agtggcagta taactcccct ctggtccgc gtaatgctga   9120
acttggggac cgaaaaggaa aaattccat cccgtttccg ctggcaaatg taacatgcag   9180
ggtgcctaaa gcaaggaacc ccaccgtgac gtacgggaaa aaccaagtca tcatgctact   9240
gtatcctgac caccccaaca tcctgtccta ccggaatatg ggagaagaac caaactatca   9300
agaagagtgg gtgatgcata aagaaggtagt cgtgctaacc gtgccgactg aagggctcga   9360
ggtcacgtgg ggcaacaacg agccgtataa gtattggccg cagttatcta caaacggtac   9420
agcccatggc cacccgcact tgattattat gagctgtacc cactatgac   9480
tgtagtagtt gtgtcagtgg ccacgttcat actcctgtcg atggtggggta tggcagcggg   9540
gatgtgcatg tgtgcacgac gcagatgcat cacaccgtat gaactgacac caggagctac   9600
cgtccctttc ctgcttagcc taatatgctg catcagaaca gctaaagcgg ccacatacca   9660
agaggctgcg atatacctgt ggaacgagca gcaacccttg ttttggctac aagcccttat   9720
tccgctgcca gccctgattg ttctatgcaa ctgtctgaga ctcttaccat gctgctaa   9780
aacgttggct tttttagccg taatgagcgt cggtgccac actgtgagcg cgtacgaaca   9840
cgtaacagtg atcccgaaca cggtgggagt accgtataag actcagtca atagacctgg   9900
ctacagcccc atggtattgg agatggaact actgtcagtc actttggagc caacactatc   9960
gcttgattac atcacgtgcg agtacaaaac cgtcatcccg tctccgtacg tgaagtgctg  10020
cggtacagca gagtgcaagg acaaaaacct acctgactac agctgtaagg tcttcaccgg  10080
```

```
cgtctaccca tttatgtggg gcggcgccta ctgcttctgc gacgctgaaa cacgcagtt   10140
gagcgaagca cacgtggaga agtccgaatc atgcaaaaca gaatttgcat cagcatacag  10200
ggctcatacc gcatctgcat cagctaagct ccgcgtcctt taccaaggaa ataacatcac  10260
tgtaactgcc tatgcaaacg gcgaccatgc cgtcacagtt aaggacgcca aattcattgt  10320
ggggccaatg tcttcagcct ggacaccttt cgacaacaaa attgtggtgt acaaaggtga  10380
cgtctataac atggactacc cgcccttttgg cgcaggaaga ccaggacaat ttggcgatat  10440
ccaaagtcgc acacctgaga gtaaagacgt ctatgctaat acacaactgg tactgcagag  10500
accggctgtg ggtacggtac acgtgccata ctctcaggca ccatctgget ttaagtattg  10560
gctaaaagaa cgcggggcgt cgctgcagca cacagcaca tttggctgcc aaatagcaac  10620
aaacccggta agagcggtga actgcgccgt agggaacatg cccatctcca tcgacatacc  10680
ggaagcggcc ttcactaggg tcgtcgacgc gccctcttta acggacatga cgtgcgaggt  10740
accagcctgc acccattcct cagactttgg gggcgtcgcc attattaaat atgcagccag  10800
caagaaaggc aagtgtgcgg tgcattcgat gactaacgcc gtcactattc gggaagctga  10860
gatagaagtt gaagggaatt ctcagctgca aatctcttc tcgacgcct tagccagcgc  10920
cgaattccgc gtacaagtct gttctacaca agtacactgt gcagccgagt gccaccccc  10980
gaaggaccac atagtcaact acccggcgt acataccacc ctcggggtcc aggacatctc  11040
cgctacggcg atgtcatggg tgcagaagat cacgggaggt gtgggactgg ttgttgctgt  11100
tgccgcactg attctaatcg tggtgctatg cgtgtcgttc agcaggcact aacttgacaa  11160
ttaagtatga aggtatatgt gtcccctaag agacacactg tacatagcaa ataatctata  11220
gatcaaaggg ctacgcaacc cctgaatagt aacaaaatac aaaatcacta aaaattataa  11280
aaacagaaaa atacataaat aggtatacgt gtcccctaag agacacattg tatgtaggtg  11340
ataagtatag atcaaagggc cgaataaccc ctgaatagta acaaaatatg aaaatcaata  11400
aaaatcataa aatagaaaaa ccataaacag aagtagttca aagggctata aaaccccctga  11460
atagtaacaa aacataaaat taataaaaat caaatgaata ccataattgg caaacggaag  11520
agatgtaggt acttaagctt cctaaaagca gccgaactca ctttgagaag taggcatagc  11580
ataccgaact cttccacgat tctccgaacc cacagggacg taggagatgt tattttgttt  11640
ttaatatttc aaaaaaaaaa aaaaaaaaaa aaaa                              11674

SEQ ID NO: 78            moltype = DNA   length = 10773
FEATURE                  Location/Qualifiers
source                   1..10773
                         mol_type = genomic DNA
                         organism = Zika virus
SEQUENCE: 78
cagactgcga cagttcgagt ttgaagcgaa agctagcaac agtatcaaca ggttttattt  60
tggatttgga acgagagtt tctggtcatg aaaaacccaa aaaagaaatc cggaggattc   120
cggattgtca atatgctaaa acgcggagta gcccgtgtga gccccttgg gggcttgaag   180
aggctgccag ccggacttct gctgggtcat gggcccatca ggatggtctt ggcgattcta  240
gccttttga gattcacggc aatcaagcca tcactggtc tcatcaatag atggggttca  300
gtggggaaaa aagaggctat ggaaataata aagaagttca gaaagatct ggctgccatg  360
ctgagaataa tcaatgctag gaaggagaag aagagacgag cgcagatac tagtgtcgga  420
attgttggcc tcctgctgac cacagctatg gcagcggagt tcactagacg tgggagtgca  480
tactatatgt acttggacag aaacgacgct ggggaggcca tatcttttcc aaccacatta  540
gggatgaata agtgttatat acagatcatg gatcttggac acatgtgtga tgccaccatg  600
agctatgaat gccctatgct ggatgagggg gtggaaccag atgacgtcga ttgttggtgc  660
aacacgcgt caacttgggt tgtgtacgga acctgccatc acaaaaaagg tgaagcacgg  720
agatctagaa gagctgtgac gctcccctcc cattccacta gaaagctgca aacgcggtcg  780
caaacctggt tggaatcaag agaatacaca aagcacttga ttagagtcga aaattggata  840
tcaggaacc ctgcttcgc gttagcagca gctgccatcg cttggctttt gggaagctca  900
acgagccaaa aagtcatata cttggtcatg atactgctga ttgcccccggc atacagcatc  960
aggtgcatag gagtcagcaa tagggacttt gtggaaggta tgtcaggtgg gacttgggtt  1020
gatgttgtct tggaacatgg aggttgtgtc accgtaatgg cacaggacaa accgactgtc  1080
gacatagagc tggttacaac aacagtcaga acatgcgg aggtaagatc ctactgctat  1140
gaggcatcaa tatcggacat ggcttcggac agccgctgcc caacacaagg tgaagcctac  1200
cttgacaagc aatcagacac tcaatatgtc tgcaaaagaa cgttagtgga cagaggctgg  1260
ggaaatggat gtggactttt tggcaaaggg agcctggtga catgcgctaa gtttgcatgc  1320
tccaagaaaa tgaccgggaa gagcatccag ccagagaatc tggagtaccg gataatgctg  1380
tcagttcatg gctcccagca cagtgggatg atcgttaatg acacaggaca tgaaactgat  1440
gagaatagag cgaaggttga gataacgccc aattccacaa gagccgaagc caccctgggg  1500
ggttttggaa gcctaggact tgattgtgaa ccgaggacag gccttgactt ttcagatttg  1560
tattacttga ctatgaataa caagcactgg ttggttcaca aggagtggtt ccacgacatt  1620
ccattacctt ggcacgctgg ggcagacacc ggaactccac actggaacaa caagaagca  1680
ctggtagagt tcaaggacgc acatgccaaa aggcaaactg tcgtggttct agggagtcaa  1740
gaaggcagca ttcacacggc ccttgctgga gctctggagg ctgagatgga tggtgcaaag  1800
ggaaggctgt cctctggcca cttgaaatgt cgcctgaaaa tggataaact tagattgaag  1860
ggcgtgtcat actccttgtg taccgcagcg ttcacattca caagatccc ggctgaaaca  1920
ctgcacggga cagtcacagt ggaggtacag tacgcaggga cagatggacc ttgcaaggtt  1980
ccagctcaga tggcggtgga catgcaaact ctgacccgac ttgggaggtt gataaccgct  2040
aaccccgtaa tcactgaaag cactgagaac tctaagatga tgctggaact tgatccacca  2100
tttgggact cttacattgt cataggagtc ggggagaaga agatcaccca ccactgcac  2160
aggagtggca gcaccattgg aaaagcattt gaagccactg tgagagtgc caagagaatg  2220
gcagtcttgg gagacacagc ctgggacttt ggatcagttg gaggcgctct caactcattg  2280
ggcaagggca tccatcaaat tttttggagca gctttcaaat cattgtttgg aggaatgtcc  2340
tggttctcac aaattctcat tggaacgttg ctagtctggt tgggtctgaa cacaaagaat  2400
ggatcatattt cccttatgtg cttggcctta ggggagtgt tgatcttctt atccacagct  2460
gtctctgctg atgtggggtg ctcggtggac ttccaaga aggagacgag atgcggtaca  2520
ggggtgttcg tctataacga cgttgaagcc tgaggggaca ggtacaagta ccatcctgac  2580
tcccccgta gattggcagc agcagtcaag caagcctggg aagatggtat ctgtgggatc  2640
tcctctgttt caagaatgga aaacatcatg tggagatcag tagaagggga gctcaacgca  2700
```

```
atcctggaag agaatggagt tcaactgacg gtcgttgtgg gatctgtaaa aaacccccatg  2760
tggagaggtc cacagagatt gcccgtgcct gtgaacgagc tgccccacgg ctggaaggct  2820
tgggggaaat cgtacttcgt cagagcagca aagacaaata acagctttgt cgtggatggt  2880
gacacactga aggaatgccc actcaaacat agagcatgga acagctttct tgtggaggat  2940
catgggttcg gggtatttca cactagtgtc tggctcaagg ttagagaaga ttattcatta  3000
gagtgtgatc cagccgttat tggaacagct gttaagggaa aggaggctgt acacagtgat  3060
ctaggctact ggattgagag tgagaagaat gacacatgga ggctgaagag ggcccatctg  3120
atcgagatga aacatgtgaa atggccaaag tcccacacat tgtggacaga tggaatagaa  3180
gagagtgatc tgatcatacc caagtctttta gctgggccac tcagccatca caataccaga  3240
gagggctaca ggacccaaat gaaagggcca tggcacagtg aagagcttga aattcggttt  3300
gaggaatgcc caggcactaa ggtccacgtg gaggaaacat gtggaacaag aggaccatct  3360
ctgagatcaa ccactgcaag cggaagggtg atcgaggaat ggtgctgcag ggagtgcaca  3420
atgccccac tgtcgttccg ggctaaagat ggctgttggt atggaatgga gataaggccc  3480
aggaaagaac cagaaagtaa cttagtaagg tcaatggtga ctgcaggatc aactgatcac  3540
atggatcact tctcccttgg agtgcttgtg attctgctca tggtgcagga agggctgaag  3600
aagagaatga ccacaaagat catcataagc acatcgatgg cagtgctggt agctatgatc  3660
ctgggaggat tttcaatgag tgacctggct aagcttgcaa ttttgatggg tgccaccttc  3720
gcggaaatga actggaggg agatgtagct catctgggcg tgatagcgcc attcaaagtc  3780
agaccagcgt tgctggtatc tttcatcttc agagctaatt ggacaccccg tgaaagcatg  3840
ctgctggcct tggcctcgtg tcttttgcaa actgcgatct ccgccttgga aggcgacctg  3900
atggttctca tcaatggttt tgctttggcc tggttggcaa tacgagcgat ggttgttcca  3960
cgcactgata acatcacctt ggcaatcctg gctgctctga ccactggc ccgggggcaca  4020
ctgcttgtgg cgtggagagc aggccttgct acttgcgggg ggttttatgct cctctctctg  4080
aagggaaaag gcagtgtgaa gaagaactta ccatttgtca tggcccctggg actaaccgct  4140
gtgaggctgg tcgaccccat caacgtgtg ggactgctgt tgctcacaag gagtgggaag  4200
cggagctggc ccctagcga agtactcaca gctgttggcc tgtatatgcg attggctgga  4260
gggttcgcca aggcagatat agagatggct gggcccatgg ccgcggtcgg tctgctaatt  4320
gtcagttacg tggtctcagg aaaagagtgt gacatgtaca ttgaaagagc aggtgacatc  4380
acatgggaaa aagatgcgga agtcactgga aacagtcccc ggctcgatgt ggcgctagat  4440
gagagtggtg attctcccct ggtggaggat gacgtcccc ccatgagaga gatcatactc  4500
aaggtggtcc tgatgaccat ctgtggcatg aacccaatag ccataccctt tgcagctgga  4560
gcgtggtacg tatacgtgaa gactggaaaa aggagtggtg ctctatggga tgtgcctgct  4620
cccaaggaag taaaaagggg ggagaccaca gatggagtgt acagtaat gactcgtaga  4680
ctgctaggtt caacacaagt tggagtggga gttatgcaag aggggtctt tcacactgtt  4740
tggcacgtca caaaggatc cgcgctgaga agcggtgaag ggagacttga tccatactgg  4800
ggagatgtca agcaggatct ggtgtcatac tgtggtccat ggaagctaga tgccgcctgg  4860
gacgggcaca gcgaggtgca gctcttggcc gtgcccccg gagagagagc gaggaacatc  4920
cagactctgc ccggaatatt taagacaaag gatgggaca ttggagcggt tgcgctggat  4980
tacccagcag gaacttcagg atctccaatc ctagacaagt gtggagagt gataggactt  5040
tatggcaatg gggtcgtgat caaaaatggg agttatgtta gtgccatcac ccaagggagg  5100
agggaggaag agactcctgt tgagtgcttc gagccttcga tgctgaagaa gaagcagcta  5160
actgtcttag acttgcatcc tggagctggg aaaaccagga gagttcttcc tgaaaatgtc  5220
cgtgaagcca taaaaacaag actccgtact gtgatcttag ctccaaccag ggttgtcgct  5280
gctgaaatgg aggaagccct tagagggctt ccagtgcgtt atatgacaac agcagtcaat  5340
gtcacccact ctgaaacaga aatcgtcgac ttaatgtgcc atgccacctt cacttcacgt  5400
ctactacagc caatcagagt ccccaactat aatctgtata ttatggatga ggcccacttc  5460
acagatccct caagtatagc agcaagagga tacatttcaa caagggttga gatgggcgag  5520
gcggctgcca tcttcatgac cgccacgcca ccaggaaccc gtgacgcatt tccggactcc  5580
aactcaccaa ttatggacac cgaagtggaa gtcccagaga gagcctggag ctcaggcttt  5640
gattgggtga cggatcattc tggaaaaaca gtttggtttg ttccaagcgt gaggaacggc  5700
aatgagatcg cagcttgtct gacaaaggct ggaaaacggg tcatacagct cagcagaaag  5760
acttttgaga cagagttcca gaaaacaaaa catcaagagt gggactttgt cgtgacaact  5820
gacatttcag agatgggcgc caactttaaa gctgaccgtg tcatagattc aggagatgc  5880
ctaaagccgg tcatacttga tggcgagaga gtcattctgg ctggacccat gcctgtcaca  5940
catgccagcg ctgcccagag gaggggcgc ataggcagga atcccaacaa acctggagat  6000
gagtatctgt atggaggtgg gtgcgcagag actgacgaag accatgcaca ctggcttgaa  6060
gcaagaatgc tccttgacaa tatttacctc caagatggcc tcatagcctc gctctatcga  6120
cctgaggcca acaagtagc agccattgag ggagagttca gcttaggac ggagcaaagg  6180
aagaccttg tggaactcat gaaaagagga gatcttcctg ttttgctggc ctatcaggtt  6240
gcatctgccg gaataaccta cacagataga agatgtgtgct ttgatggcac gaccaacaac  6300
accataatgg aagacagtgt gccggcgag gtgtggacca gacacggaga gaaagagtg  6360
ctcaaaccga ggtggatgga cgccagagtt tgttcagatc atgcggccct gaagtcattc  6420
aaggagtttg ccgctgggaa aagaggagcg gcttttggag tgatgaagc cctgggaaca  6480
ctgccaggac acatgacaga gagattccag gaagccattg acaacctcgc tgtgctcatg  6540
cgggcagaga ctgaagcag gccttacaaa gccgcggcgg cccaattgcc ggagacccta  6600
gagaccatta tgcttttggg gttgctggga acagtctcgc tggaatcctt tttcgtcttg  6660
atgaggaaca aggggcatagg gaagatgggc tttgaatgg tgactcttgg ggccagcgca  6720
tggctcatgt ggctctcgga aattgagcca gccagaatg catgtgtcct cattgttgtg  6780
ttcctattgc tggtggtgct catcctgag ccagaaaagc aaagatctcc ccaggacaac  6840
caaatggcaa tcatcatcat ggtagcagta gtcttctgg gcttgattac cgccaatgaa  6900
ctcggatggt tggagagaac aaaagtgac ctaagccatc taatgggaag agagaggag  6960
ggggcaacca taggattctc aatggacatt gacctgcggc cagcctcagc tgggccatc  7020
tatgctgcct tgacaacttt cattacccca gccgtccaac atgcagtgac cacttcatac  7080
aacaactact ccttaatggc gatggccacg caagctggga tgttgtttg tatgggcaaa  7140
gggatgcca tctacgcatg ggactttgga gtcccgctgc taatgatagg ttgctactca  7200
caattaacac ccctgacct aatagtggcc atcattttgc tcgtggcgca ctacatgtac  7260
ttgatcccag gctgcaggc agcagctgcg cgtgctgccc agaagagaac ggcagctggc  7320
atcatgaaga accctgttgt ggatggaata gtggtgactg acattgacac aatgacaatt  7380
gacccccaag tggagaaaa gatgggacag gtgctactca tagcagtagc cgtctccagc  7440
```

```
gccatactgt cgcggaccgc ctggggggtgg ggggaggctg gggccctgat cacagcggca   7500
acttccactt tgtggggaagg ctctccgaac aagtactgga actcctctac agccacttca   7560
ctgtgtaaca ttttaggggg aagttacttg gctggagctt ctctaatcta cacagtaaca   7620
agaaacgctg gcttggtcaa gagacgtggg ggtggaacag gagagaccct gggagagaaa   7680
tggaaggccc gcttgaacca gatgtcggcc ctggagttct actcctacaa aaagtcaggc   7740
atcaccgagg tgtgcagaga agaggcccgc cgcgccctca aggacggtgt ggcaacggga   7800
ggccatgctg tgtcccgagg aagtgcaaag ctgagatggt tggtggagcg gggatacctg   7860
cagcccctatg gaaaggtcat tgatcttgga tgtggcagag ggggctggag ttactacgcc   7920
gccaccatcc gcaaagttca agaagtgaaa ggatacacaa aggaggccc tggtcatgaa   7980
gaacccatgt tggtgcaaag ctatgggtgg aacatagtcc gtcttaagag tggggtggac   8040
gtctttcata tggcggctga gccgtgtgac acgttgctgt gtgacatagg tgagtcatca   8100
tctagtcctg aagtggaaga agcacggacg ctcagagtcc tctccatggt gggggattgg   8160
cttgaaaaaa gaccaggagc cttttgtata aaagtgttgt gcccatacac cagcactatg   8220
atggaaaccc tggagcgact gcagcgtagg tatgggggag gactggtcag agtgccactc   8280
tcccgcaact ctacacatga gatgtactgg gtctctggag cgaaaagcaa caccataaaa   8340
agtgtgtcca ccacgagcca gctcctcttg gggcgcatgg acgggcccag gaggccagtg   8400
aaatatgagg aggatgtgaa tctcggctct ggcacgcggg ctgtggtaag ctgcgctgaa   8460
gctcccaaca tgaagatcat tggtaaccgc attgaaagga tccgcagtga gcacgcggaa   8520
acgtggttct ttgacgagaa ccacccatat aggacatggg cttaccatgg aagctatgag   8580
gcccccacac aagggtcagc gtcctctcta ataaacgggg ttgtcaggct cctgtcaaaa   8640
ccctgggatg tggtgactgg agtcacagga atagccatga ccgacaccac accgtatggt   8700
cagcaaagag ttttcaagga aaagtggac actagggtgc agacccccca agaaggcact   8760
cgtcaggtta tgagcatggt ctcttcctgg ttgtggaaag agctaggcaa acacaaacgg   8820
ccacgagtct gtaccaaaga agagttcatc aacaaggttc gtagcaatgc agcattaggg   8880
gcaatatttg aagagaaaa agagtggaag actgcagtgg aagctgtgaa cgatccaagg   8940
ttctgggctc tagtggcaca ggaaagagag caccacctga gaggagagtg ccagagttgt   9000
gtgtacaaca tgatgggaaa aagagaaaag aaacaagggg aatttggaaa ggccaagggc   9060
agccgcgcca tctggtatat gtggctaggg gctagatttc tagagttcga agcccttgga   9120
ttcttgaacg aggatcactg gatggggaga gagaactcag gaggtggtgt gaagggctg   9180
ggattacaaa gactcggata tgtcctagaa gatgagtc gcataccagg aggaaggatg   9240
tatgcagatg acactgctgg ctgggacacc cgcatcagca ggtttgatct ggagaatgaa   9300
gctctaatca ccaaccaaat ggagaaaggg cacagggcct tggcattggc cataatcaag   9360
tacacatacc aaaacaaagt ggtaaggtc cttagaccag ctgaaaaagg gaagacagtt   9420
atggacatta tttcgagaca agaccaaagg gggagcggac aagttgtcac ttacgctctt   9480
aacacatttta ccaaccttagt ggtgcaactc attcggaata tggaggctga ggaagttcta   9540
gagatgcaag acttgtggct gctgcggagg tcagagaaag tgaccaactg gttgcagagc   9600
aacgatgggg ataggctcaa acgaatgcat gtcagtggaa atgattgcgt tgtgaagcca   9660
attgatgata ggtttgcaca tgccctcagg ttcttgaatg atatgggaaa agttaggaag   9720
gacacacaag agtggaaacc ctcaactgga tgggaaact tccgttttgc               9780
tcccaccact tcaacaagct ccatctcaag gacgggaggt ccattgtggt tcctgccgc   9840
caccaagatg aactgattgg ccgggcccgc gtctctccag gggcgggatg gagcatccgg   9900
gagactgctt gcctagcaaa atcatatgcg caaatgtggc agctccttta tttccacaga   9960
agggacctcc gactgatggc caatgccatt tgttcatctg tcccagttga ctgggttcca  10020
actgggagaa ctacctggtc aatccatgga aagggagaat ggatgaccac tgaagacatg  10080
cttgtggtgt ggaacagagt gtggattgag gagaacgacc acatgaagaa caagaccccca  10140
gttacgaaat ggacagacat tccctatttg gaaaaaggg aagacttgtg tgtggatct   10200
ctcataggc acagaccgcg caccacctgg gctgagaaca ttaaaaacac agtcaacatg  10260
gtgcgcagga tcataggtga tgaagaaaag tacatggact acctatccac ccaagttcgc  10320
tacttgggtg aagaagggtc tacacctgga gtgctgtaag caccaatctt agtgttgtca  10380
ggcctgctag tcagccacag cttggggaaa gctgtgcagc ctgtgacccc cccaggaaaa  10440
gctgggaaac caagcctata gtcaggccga gaacgccatg gcacggaaga agccatgcg   10500
cctgtgagcc cctcagagga cactgagtca aaaaacccca cgcgcttgga ggcgcaggat  10560
gggaaaagaa ggtggcgacc ttccccaccc ttcaatctgg ggcctgaact ggagatcagc  10620
tgtggatctc cagaagaggg actagtggtt agaggagacc ccccgaaaaa cgcaaaacag  10680
catattgacg ctgggaaaga ccagagactc catgagtttc caccacgctg gccgccaggc  10740
acagatcgcc gaatagcggc ggccggtgtg ggg                               10773

SEQ ID NO: 79        moltype = AA  length = 3423
FEATURE              Location/Qualifiers
source               1..3423
                     mol_type = protein
                     organism = Zika virus
SEQUENCE: 79
MKNPKKKSGG FRIVNMLKRG VARVSPFGGL KRLPAGLLLG HGPIRMVLAI LAFLRFTAIK    60
PSLGLINRWG SVGKKEAMEI IKKFKKDLAA MLRIINARKE KKRRGADTSV GIVGLLLTTA   120
MAAEVTRRGS AYYMYLDRND AGEAISFPTT LGMNKCYIQI MDLGHMCDAT MSYECPMLDE   180
GVEPDDVDCW CNTTSTWVVY GTCHHKKGEA RRSRRAVTLP SHSTRKLQTR SQTWLESREY   240
TKHLIRVENW IFRNPGFALA AAAIAWLLGS STSQKVIYLV MILLIAPAYS IRCIGVSNRD   300
FVEGMSGGTW VDVVLEHGGC VTVMAQDKPT VDIELVTTTV SNMAEVRSYC YEASISDMAS   360
DSRCPTQGEA YLDKQSDTQY VCKRTLVDRG WGNGCGLFGK GSLVTCAKFA CSKKMTGKSI   420
QPENLEYRIM LSVHGSQHSG MIVNDTGHET DENRAKVEIT PNSPRAEATL GGFGSLGLDC   480
EPRTGLDFSD LYYLTMNNKH WLVHKEWFHD IPLPWHAGAD TGTPHWNNKE ALVEFKDAHA   540
KRQTVVVLGS QEGAVHTALA GALEAEMDGA KGRLSSGHLK CRLKMDKLRL KGVSYSLCTA   600
AFTFTKIPAE TLHGTVTVEV QYAGTDGPCK VPAQMAVDMQ TLTPVGRLIT ANPVITESTE   660
NSKMMLELDP PFGDSYIVIG VGEKKITHHW HRSGSTIGKA FEATVRGAKR MAVLGDTAWD   720
FGSVGGALNS LGKGIHQIFG AAFKSLFGGM SWFSQILIGT LLMWLGLNTK NGSISLMCLA   780
LGGVLIFLST AVSADVGCSV DFSKKETRCG TGVFVYNDVE AWRDRYKYHP DSPRRLAAAV   840
KQAWEDGICG ISSVSRMENI MWRSVEGELN AILEENGVQL TVVVGSVKNP MWRGPQRLPV   900
PVNELPHGWK AWGKSYFVRA AKTNNSFVVD GDTLKECPLK HRAWNSFLVE DHGFGVFHTS   960
```

```
VWLKVREDYS LECDPAVIGT AVKGKEAVHS DLGYWIESEK NDTWRLKRAH LIEMKTCEWP 1020
KSHTLWTDGI EESDLIIPKS LAGPLSHHNT REGYRTQMKG PWHSEELEIR FEECPGTKVH 1080
VEETCGTRGP SLRSTTASGR VIEEWCCREC TMPPLSFRAK DGCWYGMEIR PRKEPESNLV 1140
RSMVTAGSTD HMDHFSLGVL VILLMVQEGL KKRMTTKIII STSMAVLVAM ILGGFSMSDL 1200
AKLAILMGAT FAEMNTGGDV AHLALIAAFK VRPALLVSFI FRANWTPRES MLLALASCLL 1260
QTAISALEGD LMVLINGFAL AWLAIRAMVV PRTDNITLAI LAALTPLARG TLLVAWRAGL 1320
ATCGGFMLLS LKGKGSVKKN LPFVMALGLT AVRLVDPINV VGLLLLTRSG KRSWPPSEVL 1380
TAVGLICALA GGFAKADIEM AGPMAAVGLL IVSYVVSGKS VDMYIERAGD ITWEKDAEVT 1440
GNSPRLDVAL DESGDFSLVE DDGPPMREII LKVVLMTICG MNPIAIPPAA GAWYYVKTG 1500
KRSGALWDVP APKEVKKGET TDGVYRVMTR RLLGSTQVGV GVMQEGVFHT MWHVTKGSAL 1560
RSGEGRLDPY WGDVKQDLVS YCGPWKLDAA WDGHSEVQLL AVPPGERARN IQTLPGIFKT 1620
KDGDIGAVAL DYPAGTSGSP ILDKCGRVIG LYGNGVVIKN GSYVSAITQG RREEETPVEC 1680
FEPSMLKKKQ LTVLDLHPGA GKTRRVLPEI VREAIKTRLR TVILAPTRVV AAEMEEALRG 1740
LPVRYMTTAV NVTHSGTEIV DLMCHATFTS RLLQPIRVPN YNLYIMDEAH FTDPSSIAAR 1800
GYISTRVEMG EAAAIFMTAT PPGTRDAFPD SNSPIMDTEV EVPERAWSSG FDWVTDHSGK 1860
TVWFVPSVRN GNEIAACLTK AGKRVIQLSR KTFETEFQKT KHQEWDFVVT TDISEMGANF 1920
KADRVIDSRR CLKPVILDGE RVILAGPMPV THASAAQRRG RIGRNPNKPG DEYLYGGGCA 1980
ETDEDHAHWL EARMLLDNIY LQDGLIASLY RPEADKVAAI EGEFKLRTEQ RKTFVELMKR 2040
GDLPVWLAYQ VASAGITYTD RRWCFDGTTN NTIMEDSVPA EVWTRHGEKR VLKPRWMDAR 2100
VCSDHAALKS FKEFAAGKRG AAFGVMEALG TLPGHMTERF QEAIDNLAVL MRAETGSRPY 2160
KAAAAQLPET LETIMLLGLL GTVSLGIFFV LMRNKGIGKM GFGMVTLGAS AWMLWLSEIE 2220
PARIACVLIV VFLLLVVLIP EPEKQRSPQD NQMAIIIMVA VGLLGLITAN ELGWLERTKS 2280
DLSHLMGRRE EGATIGFSMD IDLRPASAWA IYAALTTFIT PAVQHAVTTS YNNYSLMAMA 2340
TQAGVLFGMG KGMPFYAWDF GVPLLMIGCY SQLTPLTLIV AIILLVAHYM YLIPGLQAAA 2400
ARAAQKRTAA GIMKNPVVDG IVVTDIDTMT IDPQVEKKMG QVLLIAVAVS SAILSRTAWG 2460
WGEAGALITA ATSTLWEGSP NKYWNSSTAT SLCNIFRGSY LAGASLIYTV TRNAGLVKRR 2520
GGGTGETLGE KWKARLNQMS ALEFYSYKKS GITEVCREEA RRALKDGVAT GGHAVSRGSA 2580
KLRWLVERGY LQPYGKVIDL GCGRGGWSYY AATIRKVQEV KGYTKGGPGH EEPMLVQSYG 2640
WNIVRLKSGV DVFHMAAEPC DTLLCDIGES SSPEVEEAR TLRVLSMVGD WLEKRPGAFC 2700
IKVLCPYTST MMETLERLQR RYGGGLVRVP LSRNSTHEMY WVSGAKSNTI KSVSTTSQLL 2760
LGRMDGPRRP VKYEEDVNLG SGTRAVVSCA EAPNMKIIGN RIERIRSEHA ETWFFDENHP 2820
YRTWAYHGSY EAPTQGSASS LINGVVRLLS KPWDVVTGVT GIAMTDTTPY GQQRVFKEKV 2880
DTRVPDPQEG TRQVMSMVSS WLWKELGKHK RPRVCTKEEF INKVRSNAAL GAIFEEEKEW 2940
KTAVEAVNDP RFWALVDKER EHHLRGECQS CVYNMMGKRE KKQGEFGKAK GSRAIWYMWL 3000
GARFLEFEAL GFLNEDHWMG RENSGGGVEG LGLQRLGYVL EEMSRIPGGR MYADDTAGWD 3060
TRISRFDLEN EALITNQMEK GHRALALAII KYTYQNKVVK VLRPAEKGKT VMDIISRQDQ 3120
RGSGQVVTYA LNTFTNLVVQ LIRNMEAEEV LEMQDLWLLR RSEKVTNWLQ SNGWDRLKRM 3180
AVSGDDCVVK PIDDRFAHAL RFLNDMGKVR KDTQEWKPST GWDNWEEVPF CSHHFNKLHL 3240
KDGRSIVVPC RHQDELIGRA RVSPGAGWSI RETACLAKSY AQMWQLLYFH RRDLRLMANA 3300
ICSSVPVDWV PTGRTTWSIH GKGEWMTTED MLVVWNRVWI EENDHMEDKT PVTKWTDIPY 3360
LGKREDLWCG SLIGHRPRTT WAENIKNTVN MVRRIIGDEE KYMDYLSTQV RYLGEEGSTP 3420
GVL                                                              3423

SEQ ID NO: 80            moltype = DNA  length = 28
FEATURE                  Location/Qualifiers
misc_feature             1..28
                         note = primer
source                   1..28
                         mol_type = other DNA
                         organism = synthetic construct
SEQUENCE: 80
ttaggatccg ttgttgatct gtgtgaat                                    28

SEQ ID NO: 81            moltype = DNA  length = 26
FEATURE                  Location/Qualifiers
misc_feature             1..26
                         note = primer
source                   1..26
                         mol_type = other DNA
                         organism = synthetic construct
SEQUENCE: 81
taactcgagc gtacacaacc caagtt                                      26

SEQ ID NO: 82            moltype = DNA  length = 27
FEATURE                  Location/Qualifiers
misc_feature             1..27
                         note = primer
source                   1..27
                         mol_type = other DNA
                         organism = synthetic construct
SEQUENCE: 82
ttaggatcct cactagacgt gggagtg                                     27

SEQ ID NO: 83            moltype = DNA  length = 29
FEATURE                  Location/Qualifiers
misc_feature             1..29
                         note = primer
```

```
source                  1..29
                        mol_type = other DNA
                        organism = synthetic construct
SEQUENCE: 83
taactcgaga agccatgtcy gatattgat                                              29

SEQ ID NO: 84           moltype = DNA  length = 26
FEATURE                 Location/Qualifiers
misc_feature            1..26
                        note = primer
source                  1..26
                        mol_type = other DNA
                        organism = synthetic construct
SEQUENCE: 84
ttaggatccg catacagcat caggtg                                                 26

SEQ ID NO: 85           moltype = DNA  length = 27
FEATURE                 Location/Qualifiers
misc_feature            1..27
                        note = primer
source                  1..27
                        mol_type = other DNA
                        organism = synthetic construct
SEQUENCE: 85
taactcgagt gtggagttcc ggtgtct                                                27

SEQ ID NO: 86           moltype = DNA  length = 31
FEATURE                 Location/Qualifiers
misc_feature            1..31
                        note = primer
source                  1..31
                        mol_type = other DNA
                        organism = synthetic construct
SEQUENCE: 86
ttaggatccg aatagagcga argttgagat a                                           31

SEQ ID NO: 87           moltype = DNA  length = 28
FEATURE                 Location/Qualifiers
misc_feature            1..28
                        note = primer
source                  1..28
                        mol_type = other DNA
                        organism = synthetic construct
SEQUENCE: 87
taactcgagt ggtgggtgat cttcttct                                               28

SEQ ID NO: 88           moltype = DNA  length = 31
FEATURE                 Location/Qualifiers
misc_feature            1..31
                        note = primer
source                  1..31
                        mol_type = other DNA
                        organism = synthetic construct
SEQUENCE: 88
ttaggatcca gtcacagtgg aggtacagta c                                           31

SEQ ID NO: 89           moltype = DNA  length = 27
FEATURE                 Location/Qualifiers
misc_feature            1..27
                        note = primer
source                  1..27
                        mol_type = other DNA
                        organism = synthetic construct
SEQUENCE: 89
taactcgagc rcagatacca tcttccc                                                27

SEQ ID NO: 90           moltype = DNA  length = 28
FEATURE                 Location/Qualifiers
misc_feature            1..28
                        note = primer
source                  1..28
                        mol_type = other DNA
                        organism = synthetic construct
SEQUENCE: 90
ttaggatccc ttatgtgctt ggccttag                                               28
```

```
SEQ ID NO: 91            moltype = DNA   length = 26
FEATURE                  Location/Qualifiers
misc_feature             1..26
                         note = primer
source                   1..26
                         mol_type = other DNA
                         organism = synthetic construct
SEQUENCE: 91
taactcgagt cttcagcctc catgtg                                           26

SEQ ID NO: 92            moltype = DNA   length = 29
FEATURE                  Location/Qualifiers
misc_feature             1..29
                         note = primer
source                   1..29
                         mol_type = other DNA
                         organism = synthetic construct
SEQUENCE: 92
ttaggatcca atgcccactc aaacataga                                        29

SEQ ID NO: 93            moltype = DNA   length = 30
FEATURE                  Location/Qualifiers
misc_feature             1..30
                         note = primer
source                   1..30
                         mol_type = other DNA
                         organism = synthetic construct
SEQUENCE: 93
taactcgagt cattctcttc ttcagcsctt                                       30

SEQ ID NO: 94            moltype = DNA   length = 26
FEATURE                  Location/Qualifiers
misc_feature             1..26
                         note = primer
source                   1..26
                         mol_type = other DNA
                         organism = synthetic construct
SEQUENCE: 94
ttaggatcca agggtgatcg aggaat                                           26

SEQ ID NO: 95            moltype = DNA   length = 29
FEATURE                  Location/Qualifiers
misc_feature             1..29
                         note = primer
source                   1..29
                         mol_type = other DNA
                         organism = synthetic construct
SEQUENCE: 95
taactcgagt tcccttcaga gagaggagc                                        29

SEQ ID NO: 96            moltype = DNA   length = 28
FEATURE                  Location/Qualifiers
misc_feature             1..28
                         note = primer
source                   1..28
                         mol_type = other DNA
                         organism = synthetic construct
SEQUENCE: 96
ttaggatcct cttttgcaaa ctgcgatc                                         28

SEQ ID NO: 97            moltype = DNA   length = 27
FEATURE                  Location/Qualifiers
misc_feature             1..27
                         note = primer
source                   1..27
                         mol_type = other DNA
                         organism = synthetic construct
SEQUENCE: 97
taactcgagt ccagctgcaa agggtat                                          27

SEQ ID NO: 98            moltype = DNA   length = 28
FEATURE                  Location/Qualifiers
misc_feature             1..28
                         note = primer
source                   1..28
                         mol_type = other DNA
                         organism = synthetic construct
```

```
SEQUENCE: 98
ttaggatccg tgtggacatg tacattga                                          28

SEQ ID NO: 99           moltype = DNA   length = 26
FEATURE                 Location/Qualifiers
misc_feature            1..26
                        note = primer
source                  1..26
                        mol_type = other DNA
                        organism = synthetic construct
SEQUENCE: 99
taactcgagc ccattgccat aaagtc                                            26

SEQ ID NO: 100          moltype = DNA   length = 28
FEATURE                 Location/Qualifiers
misc_feature            1..28
                        note = primer
source                  1..28
                        mol_type = other DNA
                        organism = synthetic construct
SEQUENCE: 100
ttaggatcct catactgtgg tccatgga                                          28

SEQ ID NO: 101          moltype = DNA   length = 26
FEATURE                 Location/Qualifiers
misc_feature            1..26
                        note = primer
source                  1..26
                        mol_type = other DNA
                        organism = synthetic construct
SEQUENCE: 101
taactcgagg cccatctcaa cccttg                                            26

SEQ ID NO: 102          moltype = DNA   length = 26
FEATURE                 Location/Qualifiers
misc_feature            1..26
                        note = primer
source                  1..26
                        mol_type = other DNA
                        organism = synthetic construct
SEQUENCE: 102
ttaggatcct agagggcttc cagtgc                                            26

SEQ ID NO: 103          moltype = DNA   length = 31
FEATURE                 Location/Qualifiers
misc_feature            1..31
                        note = primer
source                  1..31
                        mol_type = other DNA
                        organism = synthetic construct
SEQUENCE: 103
taactcgaga tactcatctc caggtttgtt g                                      31

SEQ ID NO: 104          moltype = DNA   length = 30
FEATURE                 Location/Qualifiers
misc_feature            1..30
                        note = primer
source                  1..30
                        mol_type = other DNA
                        organism = synthetic construct
SEQUENCE: 104
ttaggatccg aaaacaaaac atcaagagtg                                        30

SEQ ID NO: 105          moltype = DNA   length = 31
FEATURE                 Location/Qualifiers
misc_feature            1..31
                        note = primer
source                  1..31
                        mol_type = other DNA
                        organism = synthetic construct
SEQUENCE: 105
taactcgagg aatctctctg tcatgtgtcc t                                      31

SEQ ID NO: 106          moltype = DNA   length = 26
FEATURE                 Location/Qualifiers
misc_feature            1..26
                        note = primer
```

```
source                   1..26
                         mol_type = other DNA
                         organism = synthetic construct
SEQUENCE: 106
ttaggatcct tgatggcacg accaac                                              26

SEQ ID NO: 107           moltype = DNA   length = 28
FEATURE                  Location/Qualifiers
misc_feature             1..28
                         note = primer
source                   1..28
                         mol_type = other DNA
                         organism = synthetic construct
SEQUENCE: 107
ttaggatccg ttgttgatct gtgtgaat                                            28

SEQ ID NO: 108           moltype = DNA   length = 26
FEATURE                  Location/Qualifiers
misc_feature             1..26
                         note = primer
source                   1..26
                         mol_type = other DNA
                         organism = synthetic construct
SEQUENCE: 108
taactcgagc aggtcaatgt ccattg                                              26

SEQ ID NO: 109           moltype = DNA   length = 30
FEATURE                  Location/Qualifiers
misc_feature             1..30
                         note = primer
source                   1..30
                         mol_type = other DNA
                         organism = synthetic construct
SEQUENCE: 109
ttaggatcct gttgtgttcc tattgctggt                                          30

SEQ ID NO: 110           moltype = DNA   length = 25
FEATURE                  Location/Qualifiers
misc_feature             1..25
                         note = primer
source                   1..25
                         mol_type = other DNA
                         organism = synthetic construct
SEQUENCE: 110
taactcgagt gatcagrgcc ccagc                                               25

SEQ ID NO: 111           moltype = DNA   length = 26
FEATURE                  Location/Qualifiers
misc_feature             1..26
                         note = primer
source                   1..26
                         mol_type = other DNA
                         organism = synthetic construct
SEQUENCE: 111
ttaggatcct gctgcccaga agagaa                                              26

SEQ ID NO: 112           moltype = DNA   length = 26
FEATURE                  Location/Qualifiers
misc_feature             1..26
                         note = primer
source                   1..26
                         mol_type = other DNA
                         organism = synthetic construct
SEQUENCE: 112
taactcgagc accaacaygg gttctt                                              26

SEQ ID NO: 113           moltype = DNA   length = 25
FEATURE                  Location/Qualifiers
misc_feature             1..25
                         note = primer
source                   1..25
                         mol_type = other DNA
                         organism = synthetic construct
SEQUENCE: 113
ttaggatcct caaggacggt gtggc                                               25
```

```
SEQ ID NO: 114           moltype = DNA  length = 28
FEATURE                  Location/Qualifiers
misc_feature             1..28
                         note = primer
source                   1..28
                         mol_type = other DNA
                         organism = synthetic construct
SEQUENCE: 114
taactcgagc aatgatcttc atgttggg                                              28

SEQ ID NO: 115           moltype = DNA  length = 26
FEATURE                  Location/Qualifiers
misc_feature             1..26
                         note = primer
source                   1..26
                         mol_type = other DNA
                         organism = synthetic construct
SEQUENCE: 115
ttaggatcct atgggggagg actggt                                                26

SEQ ID NO: 116           moltype = DNA  length = 25
FEATURE                  Location/Qualifiers
misc_feature             1..25
                         note = primer
source                   1..25
                         mol_type = other DNA
                         organism = synthetic construct
SEQUENCE: 116
taactcgagc ccagaacctt ggatc                                                 25

SEQ ID NO: 117           moltype = DNA  length = 25
FEATURE                  Location/Qualifiers
misc_feature             1..25
                         note = primer
source                   1..25
                         mol_type = other DNA
                         organism = synthetic construct
SEQUENCE: 117
ttaggatcca gacccccaag aaggc                                                 25

SEQ ID NO: 118           moltype = DNA  length = 26
FEATURE                  Location/Qualifiers
misc_feature             1..26
                         note = primer
source                   1..26
                         mol_type = other DNA
                         organism = synthetic construct
SEQUENCE: 118
taactcgagc ccctttggtc ttgtct                                                26

SEQ ID NO: 119           moltype = DNA  length = 29
FEATURE                  Location/Qualifiers
misc_feature             1..29
                         note = primer
source                   1..29
                         mol_type = other DNA
                         organism = synthetic construct
SEQUENCE: 119
ttaggatcca ggaaggatgt atgcagatg                                             29

SEQ ID NO: 120           moltype = DNA  length = 30
FEATURE                  Location/Qualifiers
misc_feature             1..30
                         note = primer
source                   1..30
                         mol_type = other DNA
                         organism = synthetic construct
SEQUENCE: 120
taactcgaga catttgcgca tatgattttg                                            30

SEQ ID NO: 121           moltype = DNA  length = 28
FEATURE                  Location/Qualifiers
misc_feature             1..28
                         note = primer
source                   1..28
                         mol_type = other DNA
                         organism = synthetic construct
```

-continued

```
SEQUENCE: 121
ttaggatcca ggaaggacac acaagagt                                  28

SEQ ID NO: 122          moltype = DNA  length = 26
FEATURE                 Location/Qualifiers
misc_feature            1..26
                        note = primer
source                  1..26
                        mol_type = other DNA
                        organism = synthetic construct
SEQUENCE: 122
taactcgaga caggctgcac agcttt                                    26

SEQ ID NO: 123          moltype = DNA  length = 28
FEATURE                 Location/Qualifiers
misc_feature            1..28
                        note = primer
source                  1..28
                        mol_type = other DNA
                        organism = synthetic construct
SEQUENCE: 123
ttaggatcct ctctcatagg gcacagac                                  28
```